United States Patent
Yuan et al.

(10) Patent No.: US 10,526,320 B2
(45) Date of Patent: Jan. 7, 2020

(54) PYRROLIDINE DERIVATIVES AS PPAR AGONISTS

(71) Applicant: GUANGDONG RAYNOVENT BIOTECH CO., LTD., Guangdong (CN)

(72) Inventors: Zhiliang Yuan, Shanghai (CN); Chaofeng Long, Guangdong (CN); Zhigan Jiang, Shanghai (CN); Xiaoxin Chen, Guangdong (CN); Haiying He, Shanghai (CN); Xing Liu, Guangdong (CN); Xiao Zhang, Shanghai (CN); Zhiqiang Liu, Guangdong (CN); Yan Wang, Shanghai (CN); Leilei Gao, Shanghai (CN); Zhen Gong, Shanghai (CN); Jian Li, Shanghai (CN); Shuhui Chen, Shanghai (CN)

(73) Assignee: GUANGDONG RAYNOVENT BIOTECH CO., LTD., Guangdong (CN)

( * ) Notice: Subject to any disclaimer, the term of this patent is extended or adjusted under 35 U.S.C. 154(b) by 0 days.

(21) Appl. No.: 16/317,510

(22) PCT Filed: Jul. 12, 2017

(86) PCT No.: PCT/CN2017/092583
§ 371 (c)(1),
(2) Date: Jan. 11, 2019

(87) PCT Pub. No.: WO2018/010656
PCT Pub. Date: Jan. 18, 2018

(65) Prior Publication Data
US 2019/0225597 A1    Jul. 25, 2019

(30) Foreign Application Priority Data

Jul. 12, 2016   (CN) .......................... 2016 1 0547500
Feb. 17, 2017   (CN) .......................... 2017 1 0087306

(51) Int. Cl.
| | |
|---|---|
| *A61P 1/16* | (2006.01) |
| *A61P 3/06* | (2006.01) |
| *A61P 5/50* | (2006.01) |
| *A61P 9/10* | (2006.01) |
| *C07D 207/08* | (2006.01) |
| *C07D 401/12* | (2006.01) |
| *C07D 403/06* | (2006.01) |
| *C07D 403/12* | (2006.01) |
| *C07D 405/04* | (2006.01) |
| *C07D 409/06* | (2006.01) |

(52) U.S. Cl.
CPC .............. *C07D 409/06* (2013.01); *A61P 1/16* (2018.01); *A61P 3/06* (2018.01); *A61P 5/50* (2018.01); *A61P 9/10* (2018.01); *C07D 207/08* (2013.01); *C07D 403/12* (2013.01); *C07D 405/04* (2013.01); *C07D 401/12* (2013.01); *C07D 403/06* (2013.01)

(58) Field of Classification Search
CPC .. C07D 409/06; C07D 403/12; C07D 405/04; C07D 207/08; C07D 401/12; C07D 403/06; C07D 207/12; C07D 207/16; A61P 1/16; A61P 3/06; A61P 9/10; A61P 5/50; A61P 3/04; A61P 3/00; A61K 31/4025; A61K 31/40
See application file for complete search history.

(56) References Cited

FOREIGN PATENT DOCUMENTS

| WO | 0217912 A1 | 3/2002 | |
|---|---|---|---|
| WO | 2006097175 A1 | 9/2006 | |
| WO | 2007053819 A2 | 5/2007 | |
| WO | 2008068423 A2 | 6/2008 | |
| WO | WO-2016164201 A1 * | 10/2016 | ........... C07D 403/12 |
| WO | WO-2019120257 A1 * | 6/2019 | ......... A61K 31/4025 |

OTHER PUBLICATIONS

International Search Report dated Oct. 12, 2017 issued for related PCT patent app. No. PCT/CN2017092583.

\* cited by examiner

*Primary Examiner* — Amanda L Aguirre
(74) *Attorney, Agent, or Firm* — D'Ambrosio & Menon, PLLC; Usha Menon

(57) ABSTRACT

The present invention discloses a class of pyrrolidine derivatives as PPAR agonist, and their use for the treatment of some diseases of PPAR receptor-associated pathways (such as nonalcoholic steatohepatitis and concurrent fibrosis, insulin resistance, primary biliary cholangitis, dyslipidemia, hyperlipidemia, hypercholesterolemia, atherosclerosis, hypertriglyceridemia, cardiovascular disease, obesity or the like). In particular, the present invention discloses a compound represented by Formula (I) or a pharmaceutically acceptable salt thereof.

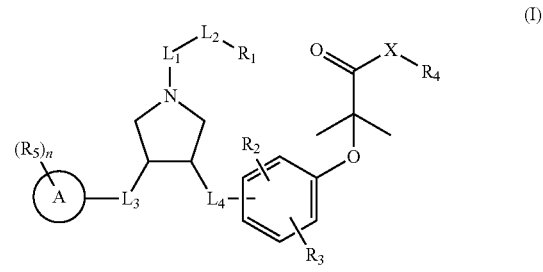

20 Claims, No Drawings

PYRROLIDINE DERIVATIVES AS PPAR AGONISTS

FIELD OF INVENTION

The present invention relates to a class of pyrrolidine derivatives as PPAR agonist, as well as their use for the treatment of some diseases related to PPAR receptor-associated pathways (such as, nonalcoholic steatohepatitis and concurrent fibrosis, insulin resistance, primary biliary cholangitis, dyslipidemia, hyperlipidemia, hypercholesterolemia, atherosclerosis, hypertriglyceridemia, cardiovascular disease, obesity, and the like). In particular, the present invention relates to a compound represented by Formula (I) or a pharmaceutically acceptable salt thereof.

BACKGROUND OF THE INVENTION

Nonalcoholic fatty liver disease (NAFLD), which is the most common liver disease in developed countries or regions, means that excess fat accumulates in the liver in a form of triglycerides (steatosis <5% of hepatocyte tissue). In addition to excess fact, patients suffering from NAFLD may be accompanied with hepatocyte injury and inflammation (fatty liver hepatitis), of which the latter is NASH (Nonalcoholic steatohepatitis). NAFLD having steatosis alone does not correlate with increased short-term morbidity or mortality, but once developed into NASH, it would increase significantly the risk of having liver cirrhosis, liver failure, and hepatocellular carcinoma (HCC). Liver cirrhosis caused by NASH is one cause leading to increasing liver transplantation. In NASH patients, the morbidity and mortality caused by liver diseases are substantially increased, and NASH is closely related to increased morbidity and mortality for cardiovascular diseases. It showed by the diagnosis of asymptomatic middle-aged male patients that 46% of patients were nonalcoholic fatty liver disease (NAFLD), and 12.2% were NASH. Most patients with NAFLD are males, old people, hypertensives and diabetics. 60-76% of diabetics have NAFLD, and 22% have NASH. The number of children with NAFLD is also growing year by year, and 38-53% of obese children have NAFLD. In China, the incidence of nonalcoholic fatty liver disease has been ranked first.

At present, there is no FDA-approved medicament for the treatment of such disease. In China, clinical therapy commonly employs liver protection medicaments such as polyene phosphatidylcholine, silymarin, ursodeoxycholic acid, glycyrrhizic acid and the like.

Peroxisome proliferator-activated receptors (PPARs), which are members of the nuclear hormone receptor superfamily, are ligand-activated transcription factors that regulate gene expression. PPARs mainly comprise three subtypes: PPAP Alpha, which is mainly expressed in brown adipose tissue, liver, heart and skeletal muscle, and plays a major role in the metabolism of bile acids, lipids and sugars; PPAP Delta, which has no obvious specific expression, and may have anti-inflammatory effect; and PPAP Gamma, which has certain effects on insulin resistance. This receptor is associated with various diseases, including dyslipidemia, hyperlipidemia, hypercholesterolemia, atherosclerosis, atherogenesis, hypertriglyceridemia, heart failure, myocardial infarction, vascular diseases, cardiovascular diseases, hypertension, obesity, inflammation, arthritis, cancer, Alzheimer's disease, skin diseases, respiratory diseases, eye disorders, IBD (irritable bowel disease), ulcerative colitis, and Crohn's disease. Since PPAR has various mechanisms beneficial to liver functions, PPAR agonists are one of the most effective potential medicaments for the treatment of fatty liver.

The following compounds are PPAR agonist compounds which have been reported in literatures.

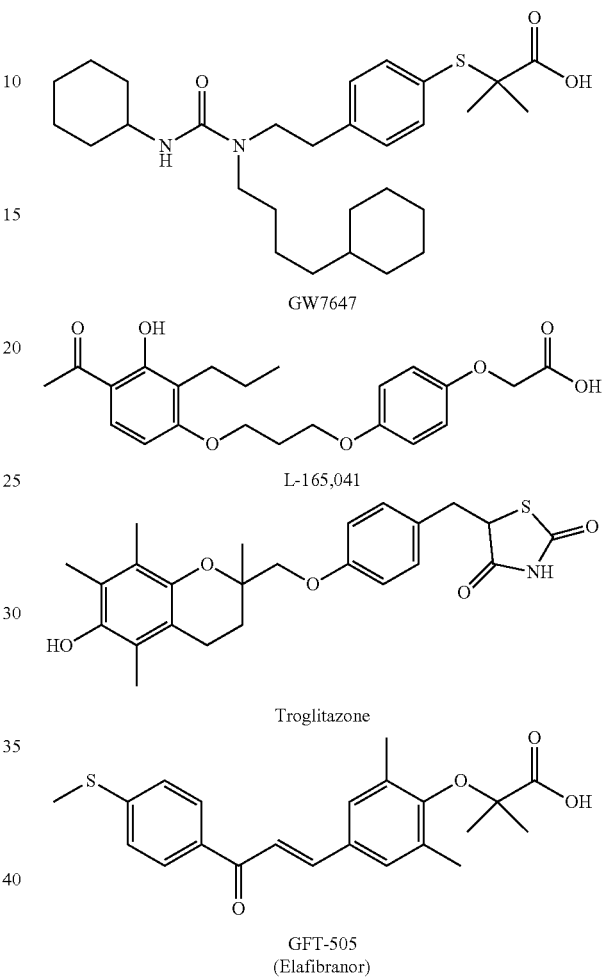

GW7647

L-165,041

Troglitazone

GFT-505
(Elafibranor)

SUMMARY OF THE INVENTION

The present invention provides a compound of Formula (I),

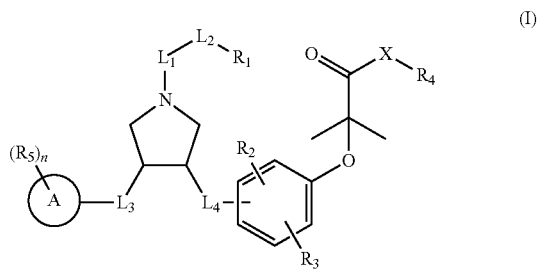

and a pharmaceutically acceptable salt thereof,
wherein:
$R_1$ is selected from H, $NH_2$, or from $C_{1-6}$ alkyl, $C_{1-6}$ heteroalkyl, $C_{3-6}$ cycloalkyl, 3-6-membered heterocycloalkyl, phenyl, and 5-6-membered heteroaryl each of which is optionally substituted with 1, 2, or 3 R;

R$_2$, R$_3$ are independently selected from H, halogen, OH, NH$_2$, or from C$_{1-3}$ alkyl optionally substituted with 1, 2, or 3 R;

X is selected from NH, O, and S;

when X is selected from O or S, R$_4$ is selected from H, or from C$_{1-6}$ alkyl optionally substituted with 1, 2, or 3 R;

when X is selected from NH, R$_4$ is selected from H, C$_{1-6}$ alkyl, or from C$_{1-6}$ alkyl-S(=O)$_2$—, —C$_{1-6}$ alkyl-S(=O)$_2$OH each of which is optionally substituted with 1, 2, or 3 R;

or, a structural unit R$_4$—X— is selected from:

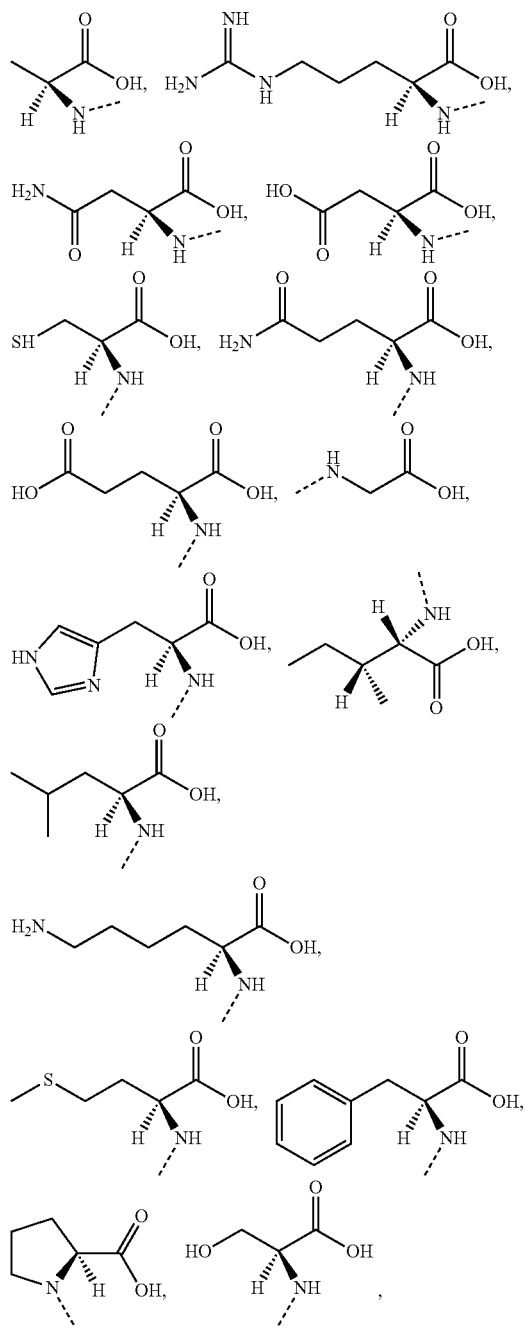

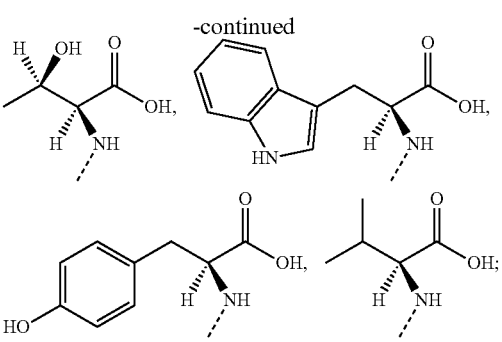

R$_5$ is selected from H, halogen, OH, NH$_2$, CN, COOH, or from C$_{1-6}$ alkyl, C$_{1-6}$ alkyl-S(=O)—, C$_{1-6}$ alkyl-S(=O)$_2$—, C$_{1-6}$ alkoxy, C$_{1-6}$ alkylthio each of which is optionally substituted with 1, 2, or 3 R group;

n is selected from 0, 1, 2 or 3;

a ring A is selected from phenyl, naphthyl, 5-6-membered heteroaryl;

L$_1$ is selected from a single bond, —C(=O)—, —O—, —NH—, —C(=O)O—, —C(=O)NH—, —S(=O)$_2$—, —S(=O)—, —(CRR)$_{1-3}$—;

L$_2$ is selected from a single bond, —(CRR)$_{1-3}$—, —C(=O)—, —O—, —S—, —NH—, —C(=O)O—, —C(=O)NH—, —S(=O)$_2$—, —S(=O)—;

L$_3$ is selected from —(CRR)—, —C(=O)—;

L$_4$ is selected from a single bond, —(CRR)$_{1-3}$—;

R is selected from H, F, Cl, Br, I, OH, CN, NH$_2$, COOH, C(=O)NH$_2$, or from C$_{1-6}$ alkyl, C$_{1-6}$ heteroalkyl each of which is optionally substituted with 1, 2, or 3 R';

R' is selected from F, Cl, Br, I, OH, CN, NH$_2$, COOH, Me, Et, CF$_3$, CHF$_2$, CH$_2$F, NHCH$_3$, N(CH$_3$)$_2$;

"hetero-" refers to a heteroatom or a heteroatomic group, and is selected from —C(=O)NH—, —NH—, —C(=NH)—, —S(=O)$_2$NH—, —S(=O) NH—, —O—, —S—, =O, =S, —O—N=, —C(=O)O—, —C(=O)—, —C(=S)—, —S(=O)—, —S(=O)$_2$— and —NHC(=O)NH—;

in any one of the cases defined above, the number of the heteroatoms or heteroatomic groups is independently selected from 1, 2 or 3.

In some embodiments of the present invention, the above R is selected from H, F, Cl, Br, I, OH, CN, NH$_2$, COOH, C(=O)NH$_2$, or from C$_{1-3}$ alkyl, C$_{1-3}$ alkoxy, C$_{1-3}$ alkylthio, C$_{1-3}$ alkylamino, N,N'-di(C$_{1-3}$ alkyl)amino each of which is optionally substituted with 1, 2, or 3 R'.

In some embodiments of the present invention, the above R is selected from H, F, Cl, Br, I, OH, CN, NH$_2$, COOH, C(=O)NH$_2$, Me, CF$_3$, CHF$_2$, CH$_2$F,

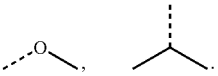

In some embodiments of the present invention, the above R$_1$ is selected from H, NH$_2$, or from C$_{1-6}$ alkyl, cyclopentyl, azetidinyl, pyrrolidinyl, tetrahydrothienyl, tetrahydrofuranyl, piperidyl, morpholinyl, piperazinyl, phenyl, pyrazolyl, pyridyl, cyclohexyl each of which is optionally substituted with 1, 2, or 3 R.

In some embodiments of the present invention, the above R$_1$ is selected from H, NH$_2$, or from Me, Et,

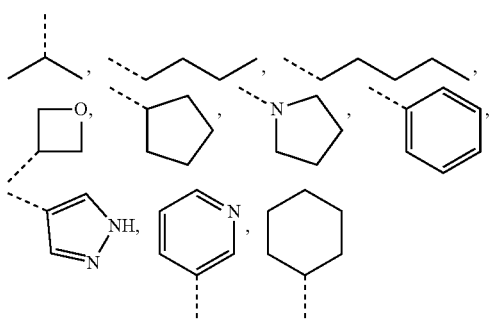

each of which is optionally substituted with 1, 2, or 3 R.

In some embodiments of the present invention, the above $R_1$ is selected from H, $NH_2$, Me, Et,

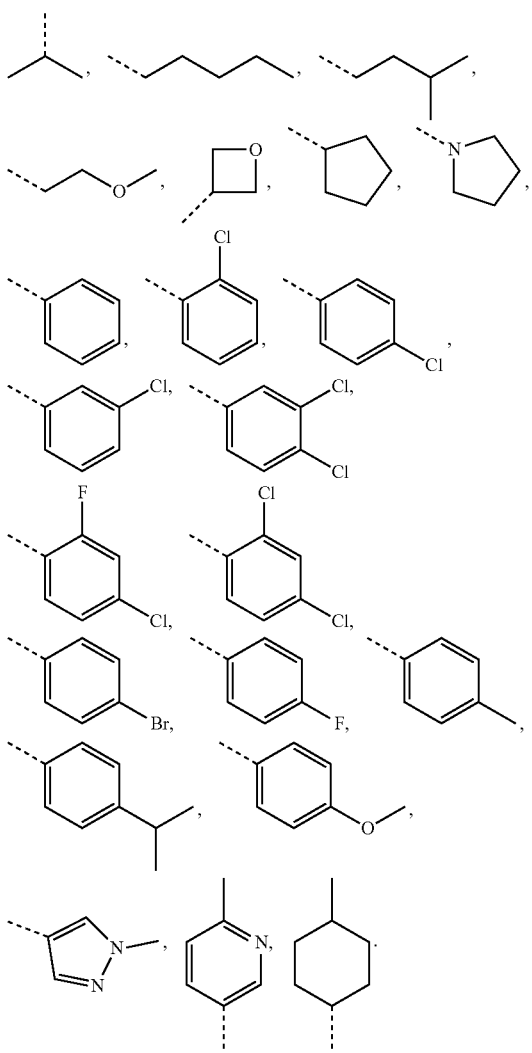

In some embodiments of the present invention, the above $R_2$, $R_3$ are independently selected from H, F, Cl, Br, I, OH, $NH_2$, or from Me, Et each of which is optionally substituted with 1, 2, or 3 R.

In some embodiments of the present invention, the above $R_2$, $R_3$ are independently selected from H, F, Cl, Br, I, OH, $NH_2$, Me, Et.

In some embodiments of the present invention, when X is selected from O or S as described above, $R_4$ is selected from H, or from Me, Et,

each of which is optionally substituted with 1, 2, or 3 R.

In some embodiments of the present invention, when X is selected from 0 or S as described above, $R_4$ is selected from H, Me, Et,

In some embodiments of the present invention, when X is selected from NH as described above, $R_4$ is selected from H, $C_{1-4}$ alkyl, or from $C_{1-4}$ alkyl-S(=O)$_2$—, —$C_{1-3}$ alkyl-S(=O)$_2$OH each of which is optionally substituted with 1, 2, or 3 R.

In some embodiments of the present invention, when X is selected from NH as described above, $R_4$ is selected from H, Me, Et,

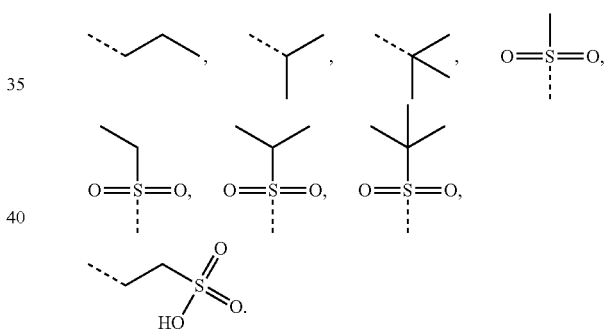

In some embodiments of the present invention, the above $R_5$ is selected from H, F, Cl, Br, I, OH, $NH_2$, CN, COOH, or from Me, Et,

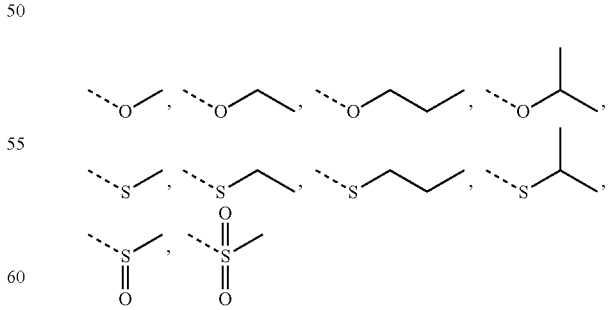

each of which is optionally substituted with 1, 2, or 3 R.

In some embodiments of the present invention, the above $R_5$ is selected from H, F, Cl, Br, I, OH, $NH_2$, CN, COOH, $CF_3$,

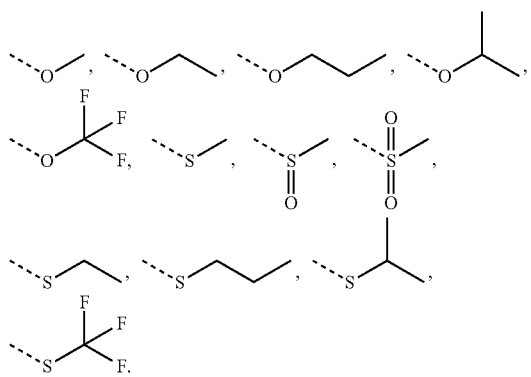

In some embodiments of the present invention, the above structural unit

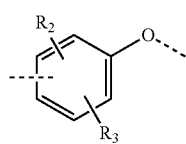

is selected from;

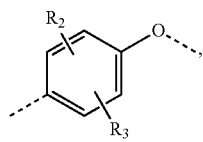 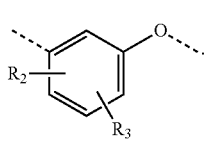

In some embodiments of the present invention, the above structural unit

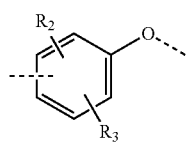

is selected from:

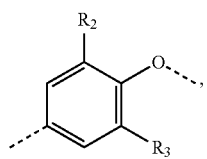 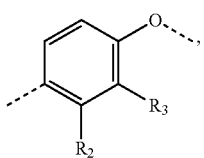

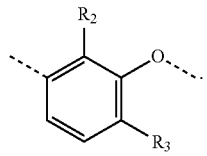

In some embodiments of the present invention, the above structural unit

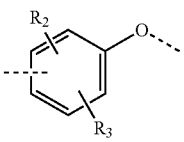

is selected from:

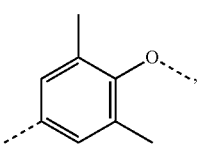 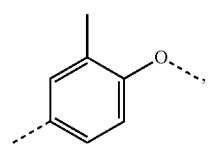

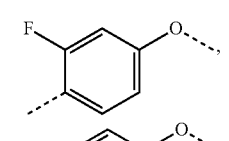

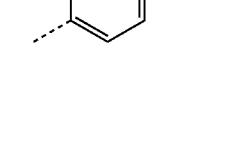

In some embodiments of the present invention, the above ring A is selected from: phenyl, naphthyl, pyridyl, pyrimidyl, pyrazinyl, pyridazinyl, thienyl, pyrazolyl, imidazolyl, oxazolyl, thiazolyl, isoxazolyl, isothiazolyl.

In some embodiments of the present invention, the above structural unit

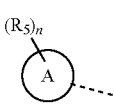

is selected from:

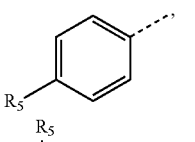 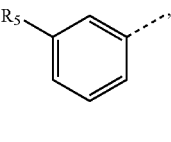

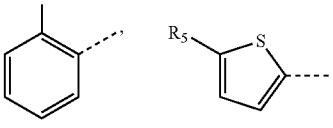

In some embodiments of the present invention, the above structural unit

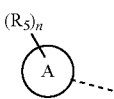

is selected from

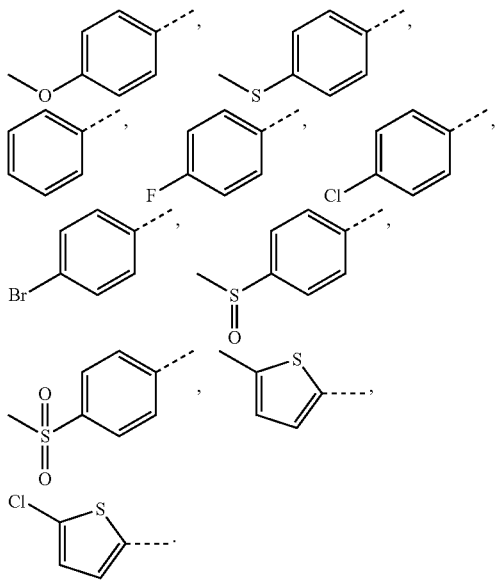

In some embodiments of the present invention, the above $L_2$ is selected from a single bond, —$CH_2$—, —$CH_2CH_2$—, —C(=O)—, —O—, —S—, —NH—, —C(=O)O—, —C(=O)NH—, —S(=O)$_2$—, —S(=O)—.

In some embodiments of the present invention, the above $L_3$ is selected from —$CH_2$—, —C(=O)—.

In some embodiments of the present invention, the above structural unit -$L_1$-$L_2$- is selected from: a single bond, —$CH_2$—, —C(=O)—, —S(=O)$_2$—, —C(=O)O—, —C(=O)NH—, —C(=O)—$CH_2$—, —C(=O)O—$CH_2$—, —$CH_2CH_2O$—.

In some embodiments of the present invention, the above $L_4$ is selected from a single bond, —$CH_2$—, —$CH_2CH_2$—.

In some embodiments of the present invention, the above R is selected from H, F, Cl, Br, I, OH, CN, $NH_2$, COOH, C(=O)$NH_2$, or from $C_{1-3}$ alkyl, $C_{1-3}$ alkoxy, $C_{1-3}$ alkylthio, $C_{1-3}$ alkylamino, N,N'-di($C_{1-3}$ alkyl)amino each of which is optionally substituted with 1, 2, or 3 R', and other variables are as defined above.

In some embodiments of the present invention, the above R is selected from H, F, Cl, Br, I, OH, CN, $NH_2$, COOH, C(=O)$NH_2$, Me, $CF_3$, $CHF_2$, $CH_2F$,

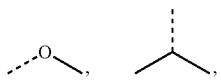

and other variables are as defined above.

In some embodiments of the present invention, the above $R_1$ is selected from H, $NH_2$, or from $C_{1-6}$ alkyl, cyclopentyl, azetidinyl, pyrrolidinyl, tetrahydrothienyl, tetrahydrofuranyl, piperidyl, morpholinyl, piperazinyl, phenyl, pyrazolyl, pyridyl, cyclohexyl each of which is optionally substituted with 1, 2, or 3 R, and other variables are as defined above.

In some embodiments of the present invention, the above $R_1$ is selected from H, $NH_2$, or from Me, Et,

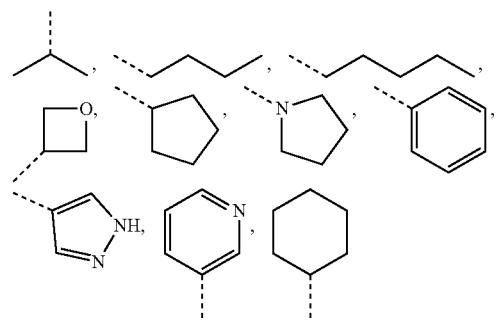

each of which is optionally substituted with 1, 2, or 3 R, and other variables are as defined above.

In some embodiments of the present invention, the above $R_1$ is selected from H, $NH_2$, Me, Et,

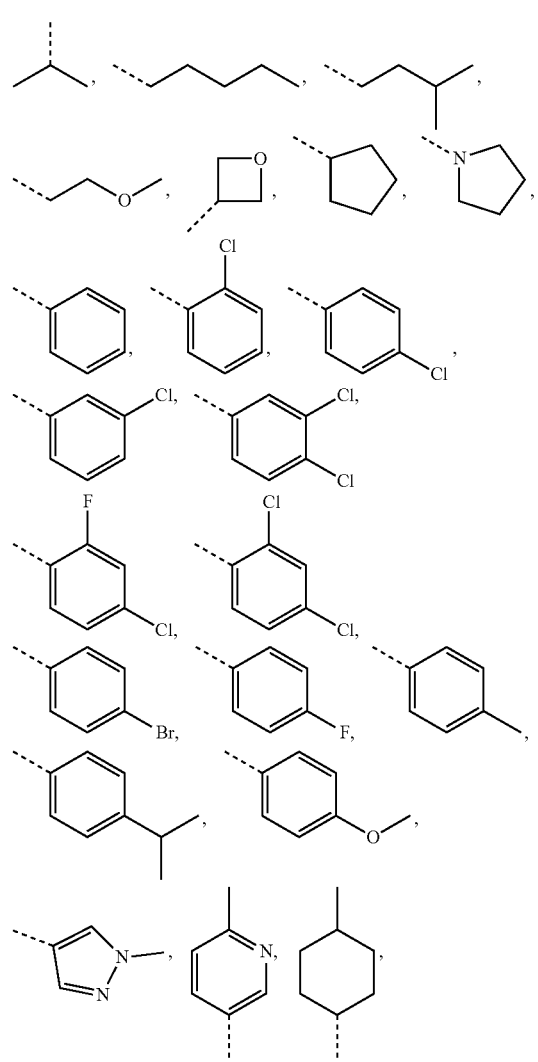

and other variables are as defined above.

In some embodiments of the present invention, the above $R_2$, $R_3$ are independently selected from H, F, Cl, Br, I, OH, $NH_2$, or from Me, Et each of which is optionally substituted with 1, 2, or 3 R, and other variables are as defined above.

In some embodiments of the present invention, the above R$_2$, R$_3$ are independently selected from H, F, Cl, Br, I, OH, NH$_2$, Me, Et, and other variables are as defined above.

In some embodiments of the present invention, when X is selected from O or S as described above, R$_4$ is selected from H, or from Me, Et,

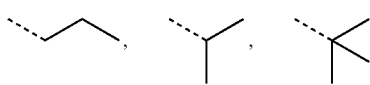

each of which is optionally substituted with 1, 2, or 3 R, and other variables are as defined above.

In some embodiments of the present invention, when X is selected from 0 or S as described above, R$_4$ is selected from H, Me, Et,

and other variables are as defined above.

In some embodiments of the present invention, when X is selected from NH as described above, R$_4$ is selected from H, C$_{1-4}$ alkyl, or from C$_{1-4}$ alkyl-S(=O)$_2$—, —C$_{1-3}$ alkyl-S(=O)$_2$OH each of which is optionally substituted with 1, 2, or 3 R, and other variables are as defined above.

In some embodiments of the present invention, when X is selected from NH as described above, R$_4$ is selected from H, Me, Et,

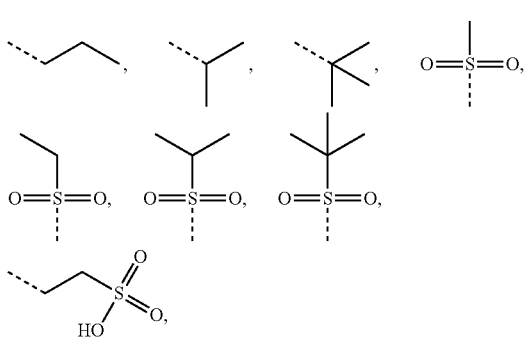

and other variables are as defined above.

In some embodiments of the present invention, the above R$_5$ is selected from H, F, Cl, Br, I, OH, NH$_2$, CN, COOH, or from Me, Et,

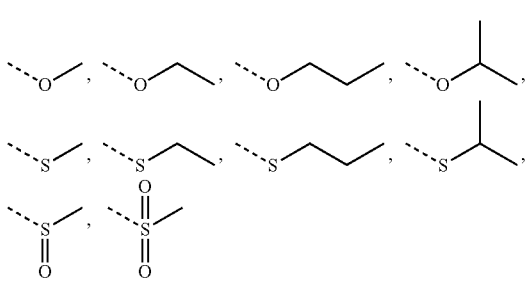

each of which is optionally substituted with 1, 2, or 3 R, and other variables are as defined above.

In some embodiments of the present invention, the above R$_5$ is selected from H, F, Cl, Br, I, OH, NH$_2$, CN, COOH, CF$_3$,

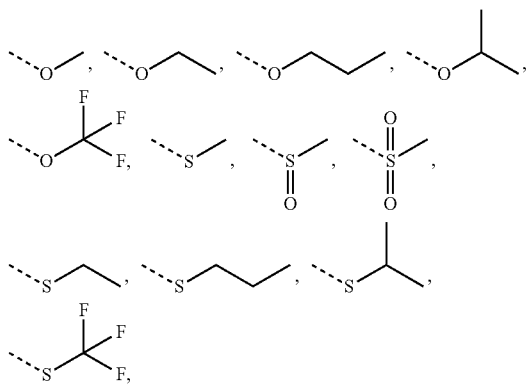

and other variables are as defined above.

In some embodiments of the present invention, the above structural unit

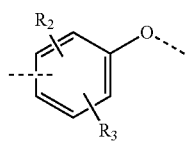

is selected:

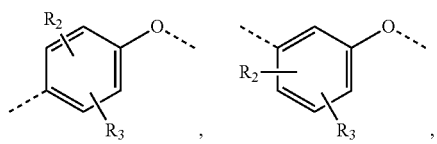

and other variables are as defined above.

In some embodiments of the present invention, the above structural unit

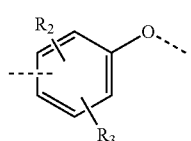

is selected from:

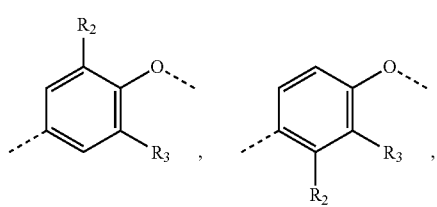

-continued

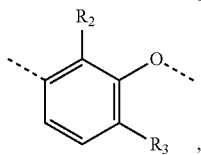

and other variables are as defined above.

In some embodiments of the present invention, the above structural unit

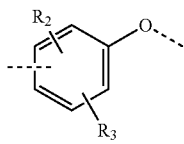

is selected from:

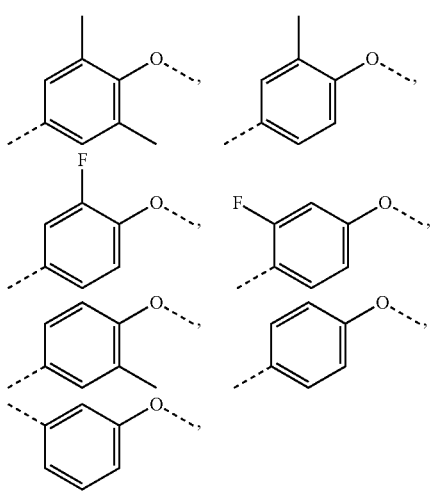

and other variables are as defined above.

In some embodiments of the present invention, the above ring A is selected from: phenyl, naphthyl, pyridyl, pyrimidyl, pyrazinyl, pyridazinyl, thienyl, pyrazolyl, imidazolyl, oxazolyl, thiazolyl, isoxazolyl, isothiazolyl, and other variables are as defined above.

In some embodiments of the present invention, the above structural unit

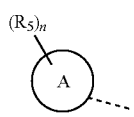

is selected from:

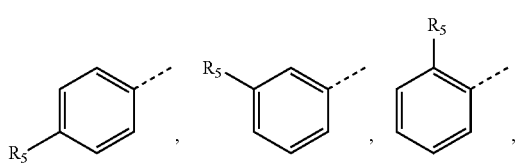

-continued

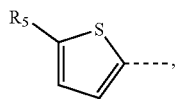

and other variables are as defined above.

In some embodiments of the present invention, the above structural unit

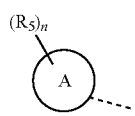

is selected from

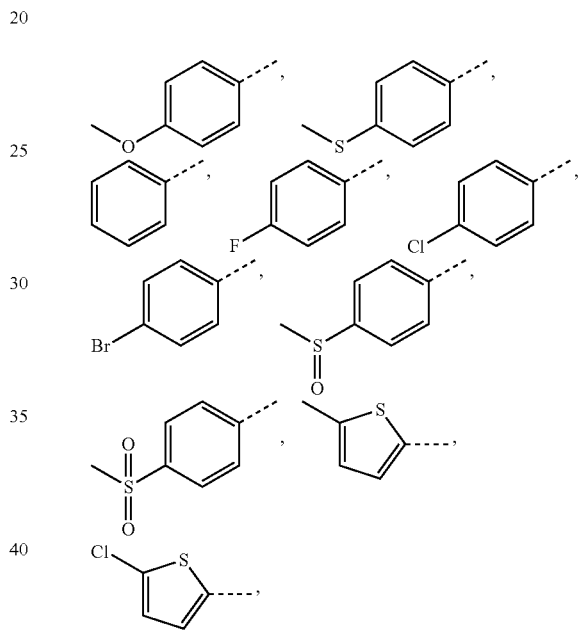

and other variables are as defined above.

In some embodiments of the present invention, the above $L_2$ is selected from a single bond, —$CH_2$—, —$CH_2CH_2$—, —C(=O)—, —O—, —S—, —NH—, —C(=O)O—, —C(=O)NH—, —S(=O)$_2$—, —S(=O)—, and other variables are as defined above.

In some embodiments of the present invention, the above $L_3$ is selected from —$CH_2$—, —C(=O)—, and other variables are as defined above.

In some embodiments of the present invention, the above structural unit -$L_1$-$L_2$- is selected from: a single bond, —$CH_2$—, —C(=O)—, —S(=O)$_2$—, —C(=O)O—, —C(=O)NH—, —C(=O)—$CH_2$—, —C(=O)O—$CH_2$—, and other variables are as defined above.

In some embodiments of the present invention, the above $L_4$ is selected from a single bond, —$CH_2$—, —$CH_2CH_2$—, and other variables are as defined above.

In some embodiments of the present invention, the above compound or pharmaceutically acceptable salt thereof, which is selected from:

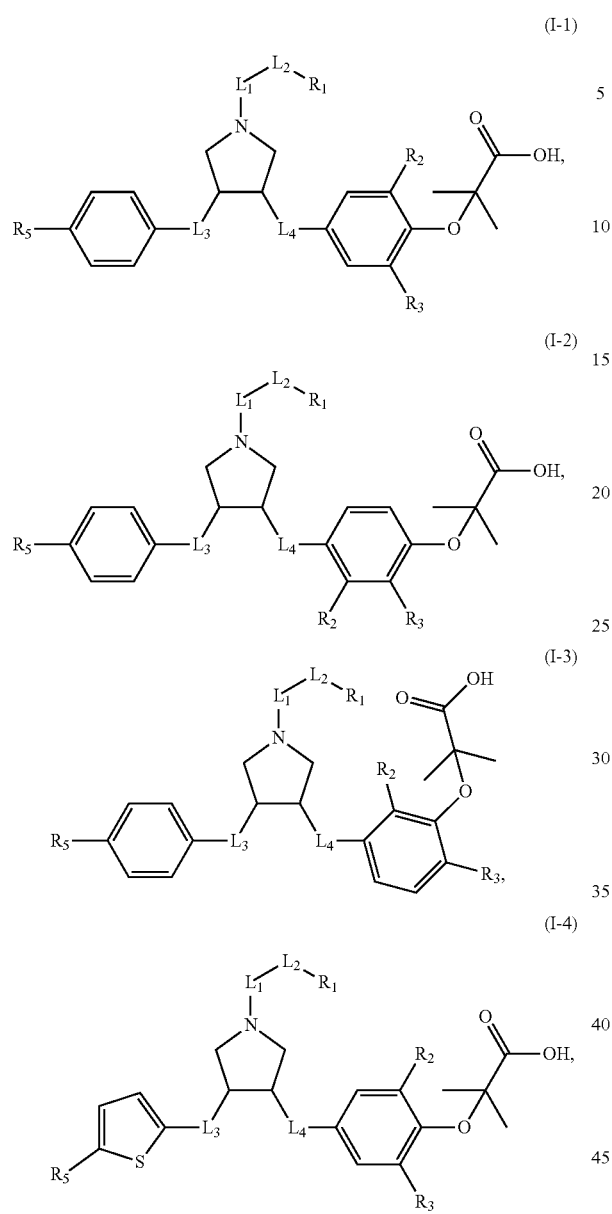
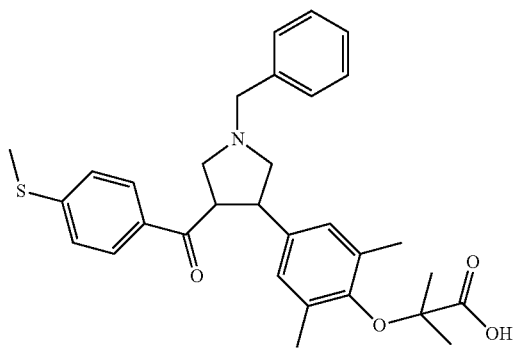
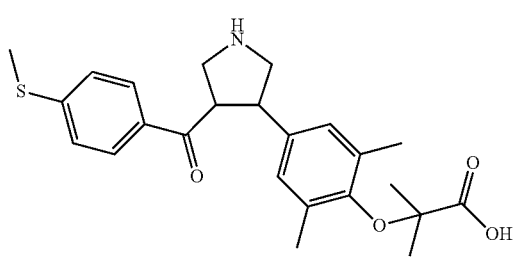
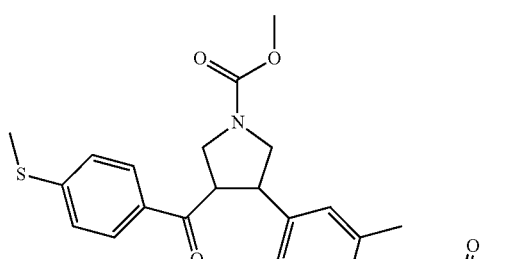
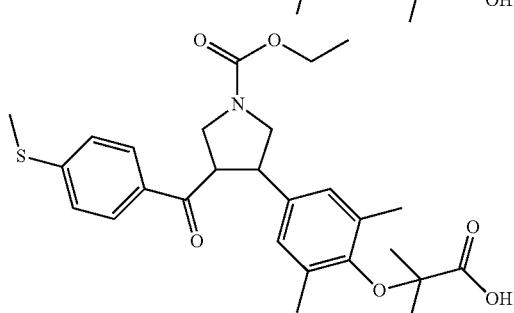
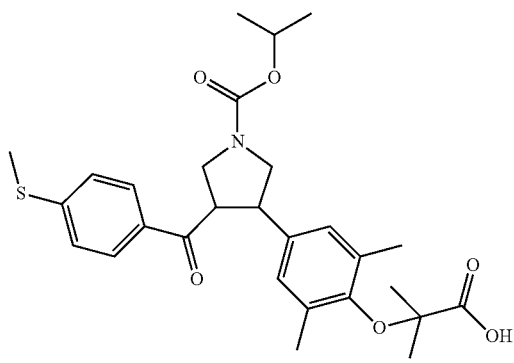
wherein R₁, R₂, R₃, R₅, L₁, L₂, L₃, L₄ are as defined above.
The present invention further provides a compound which is represented by a formula selected from:
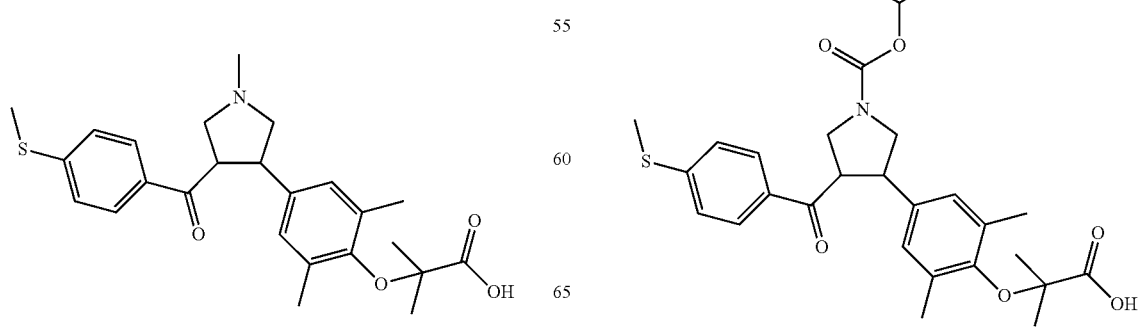

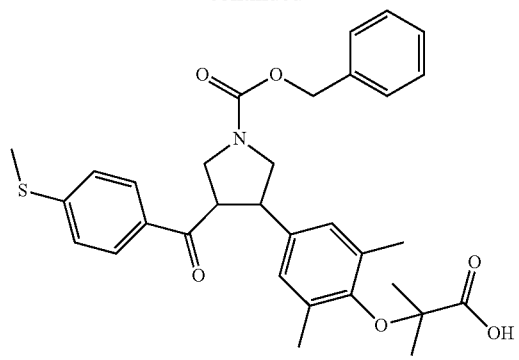
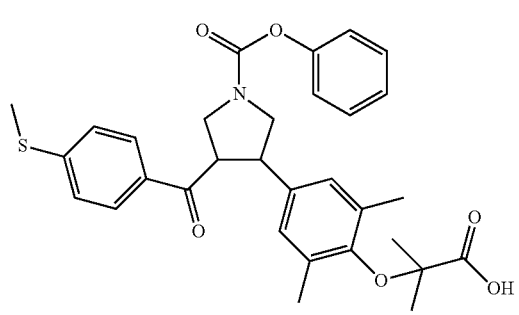
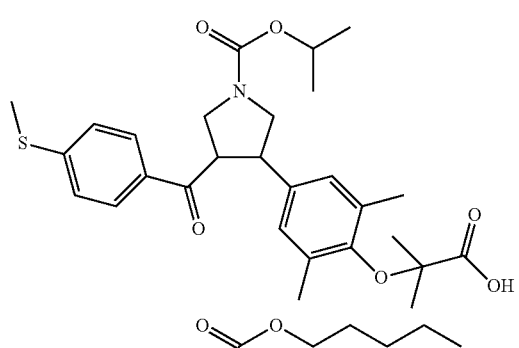
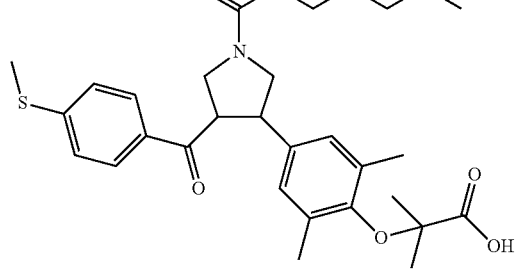
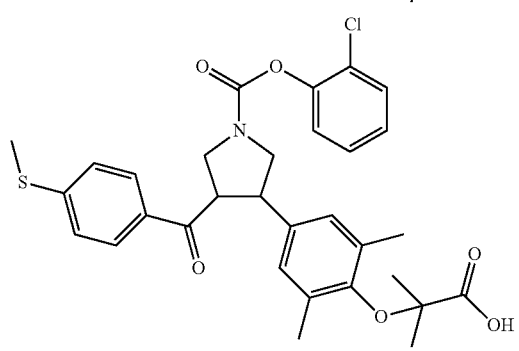
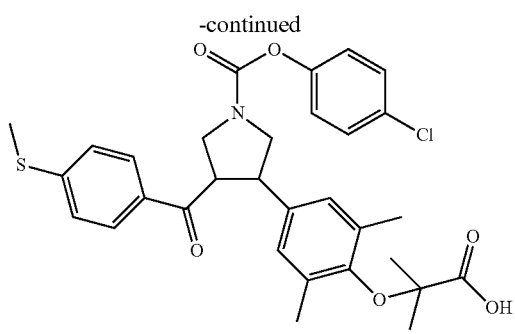
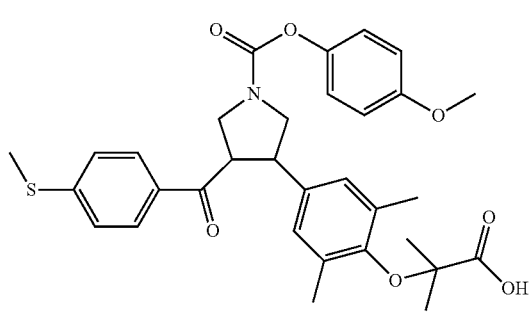
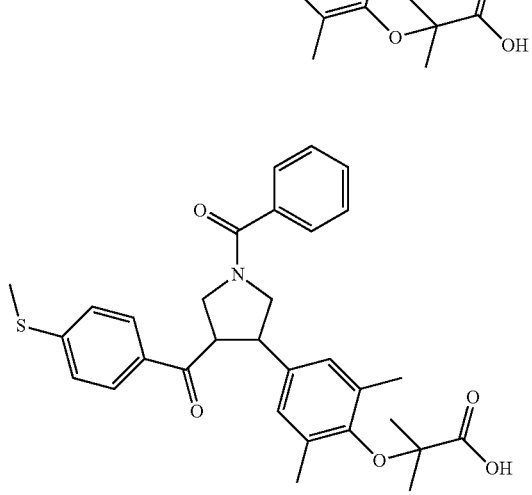
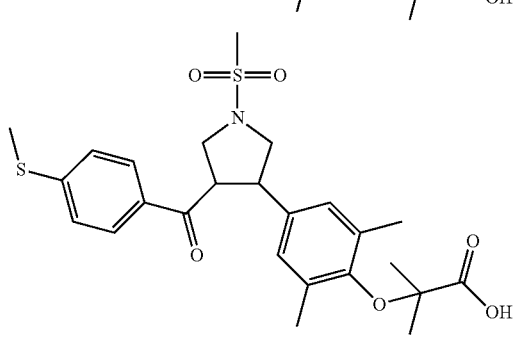
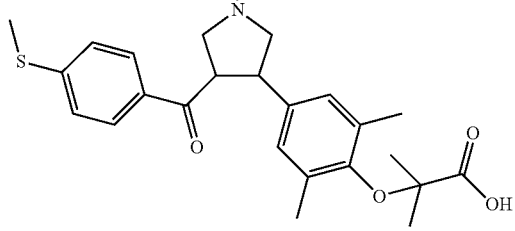

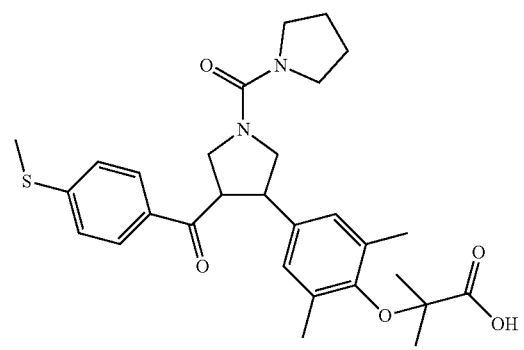
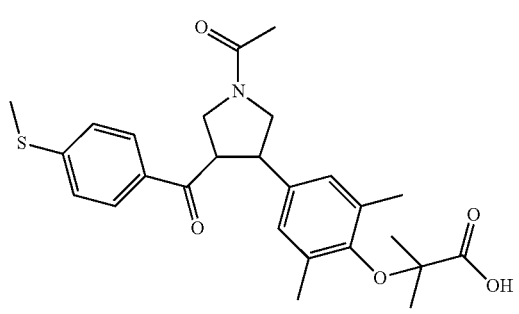
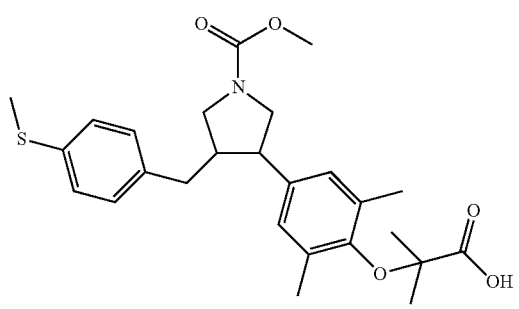
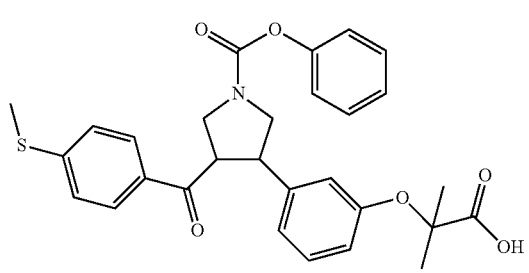
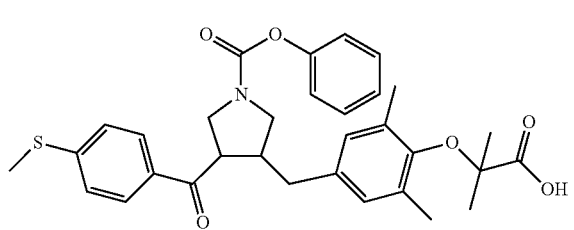
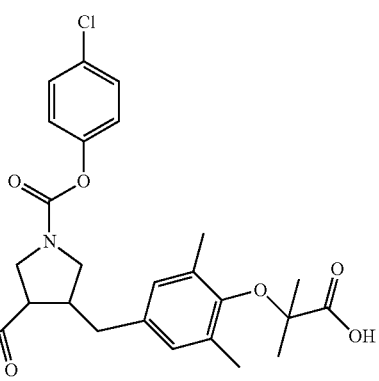
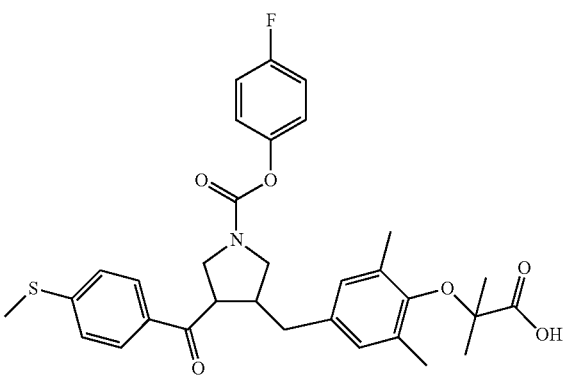
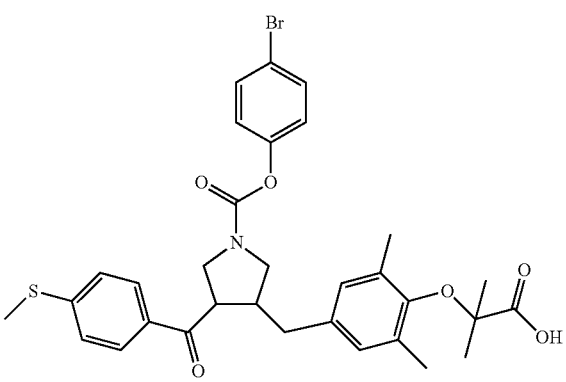
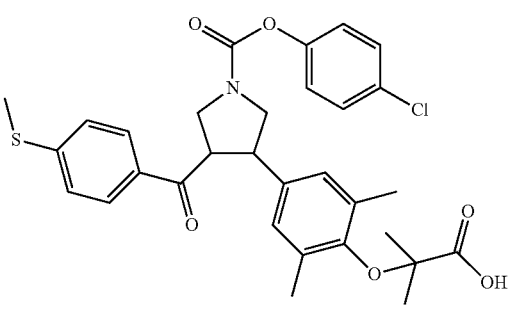
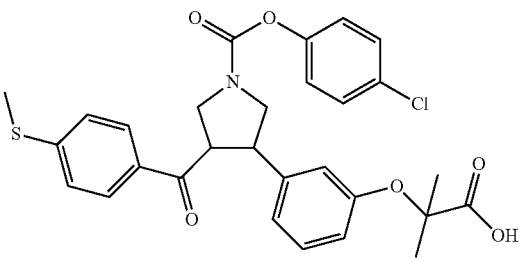

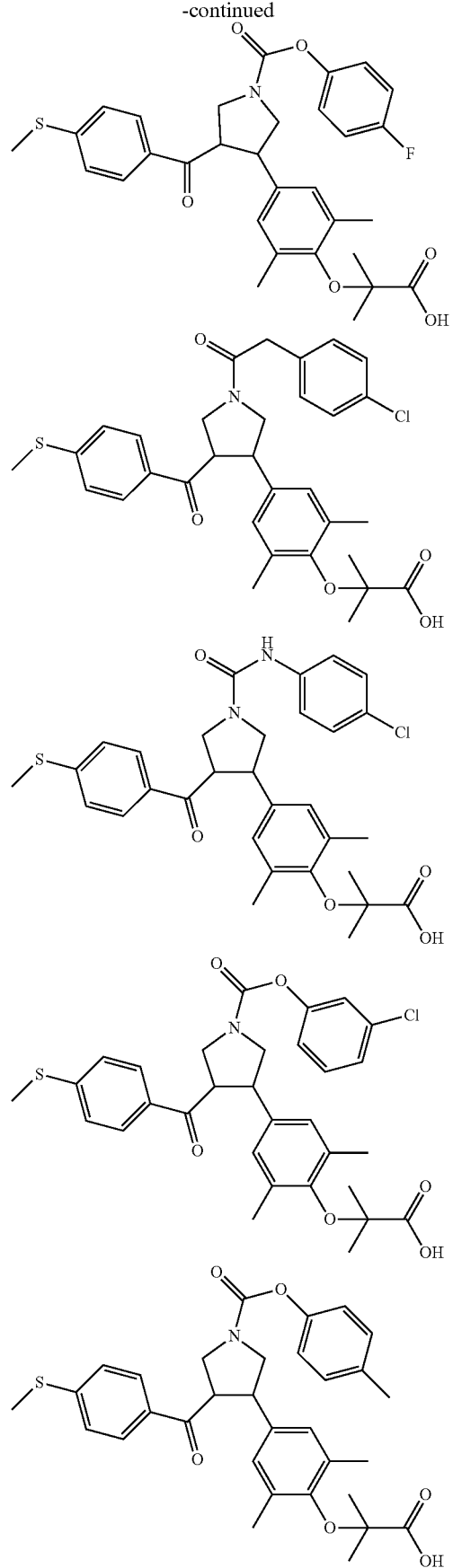
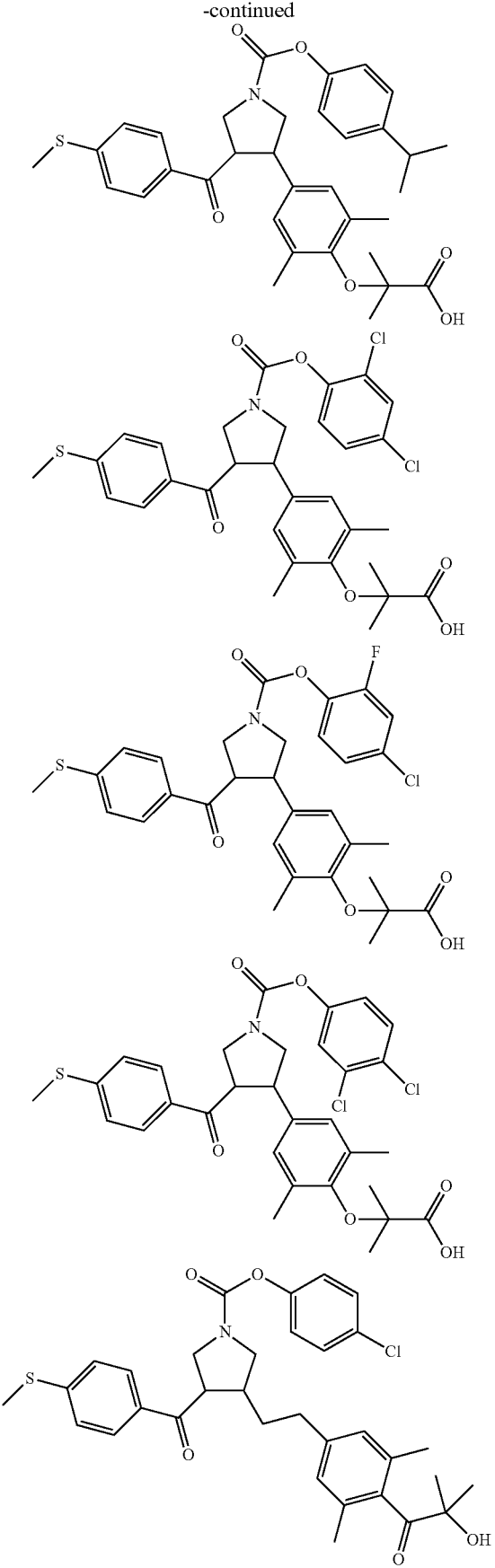

-continued
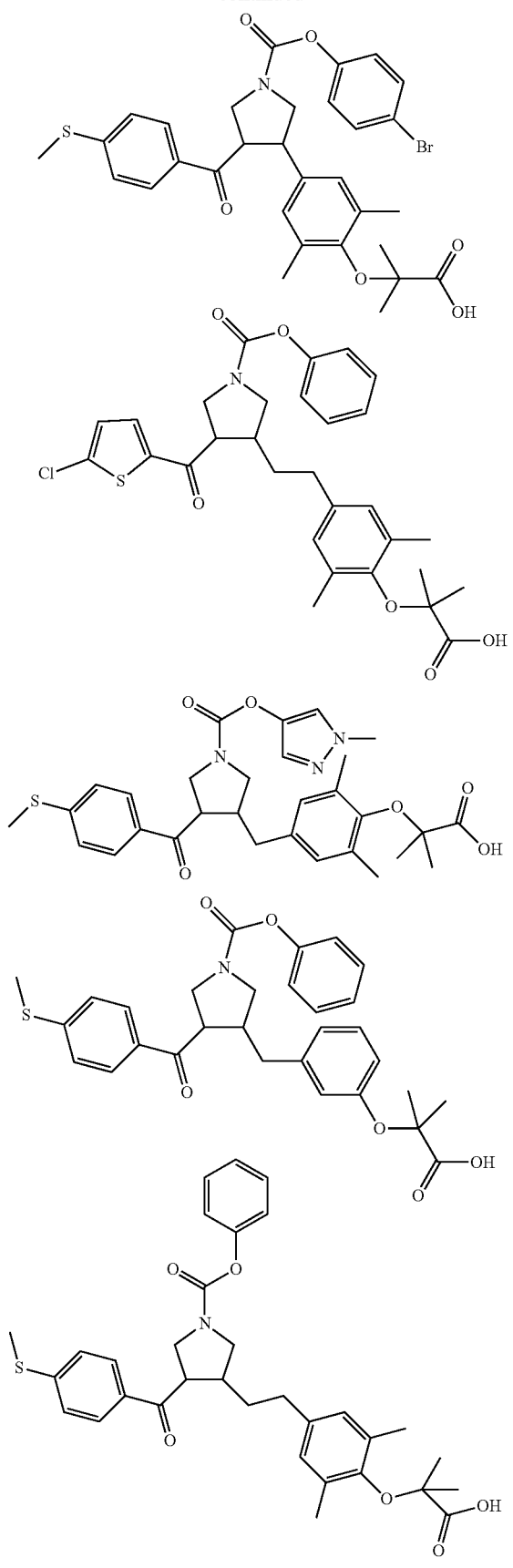
-continued
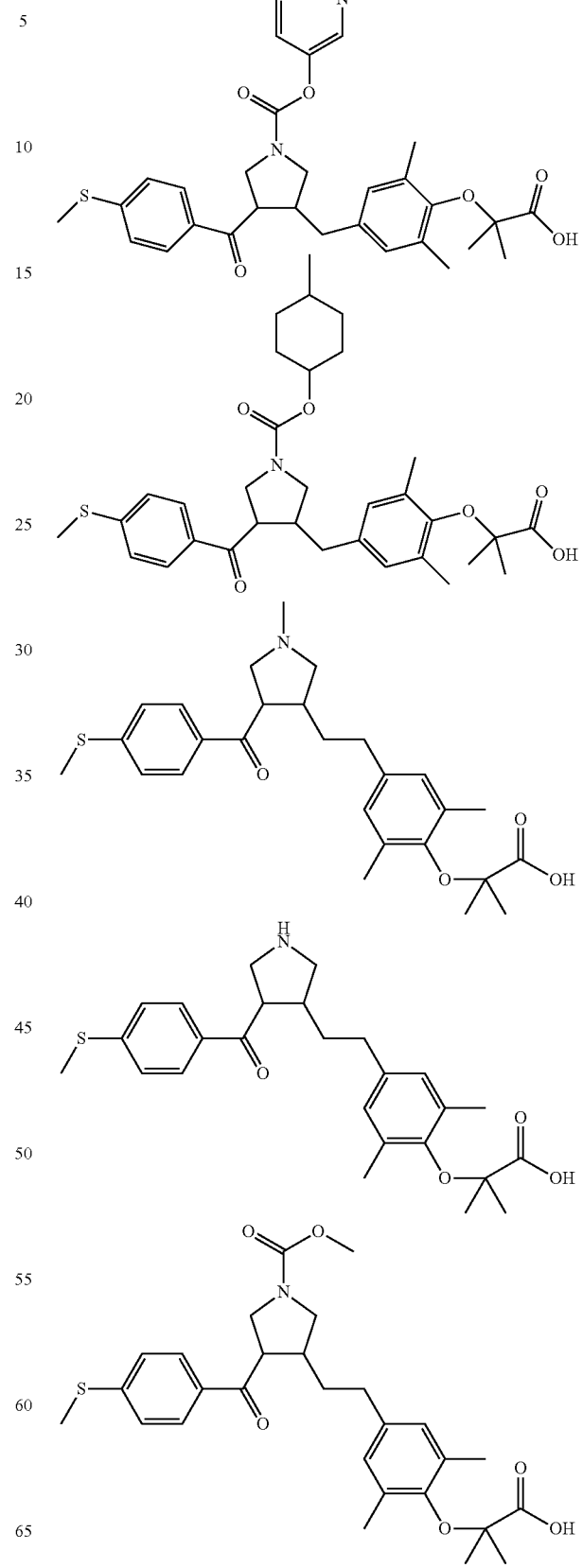

25
-continued
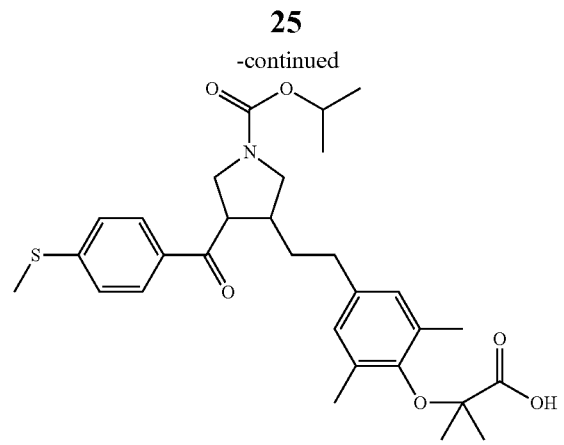
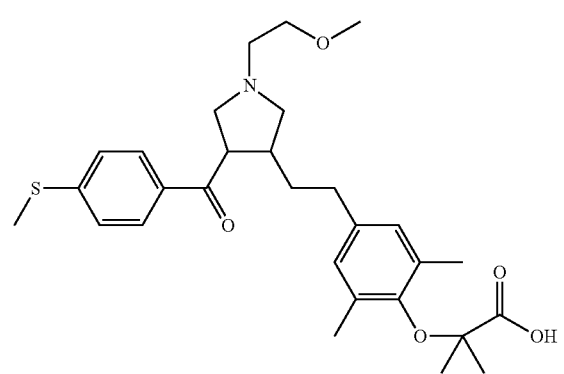
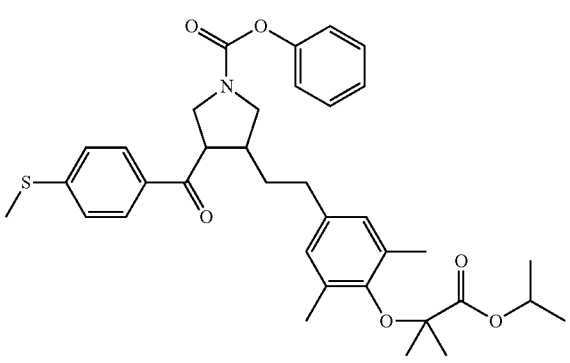
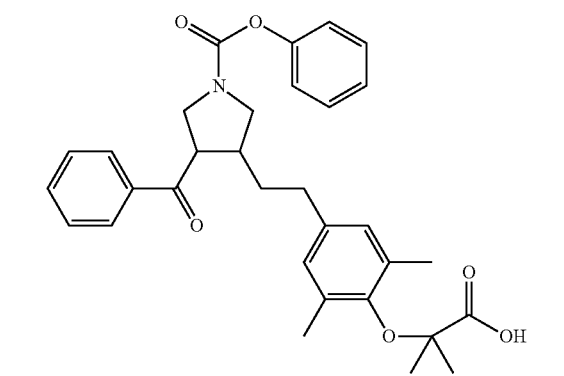
26
-continued
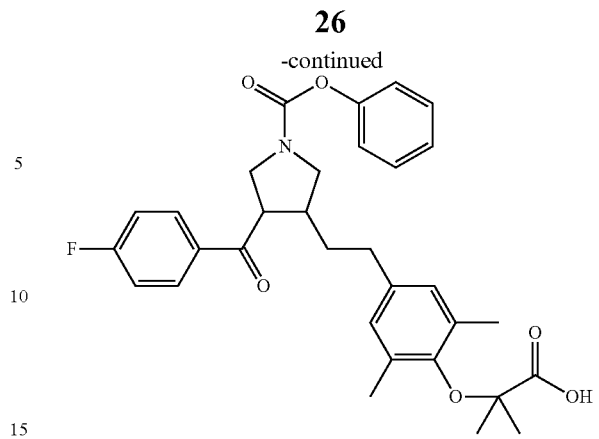
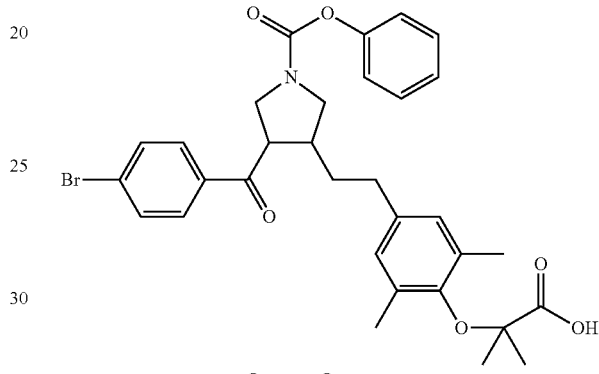
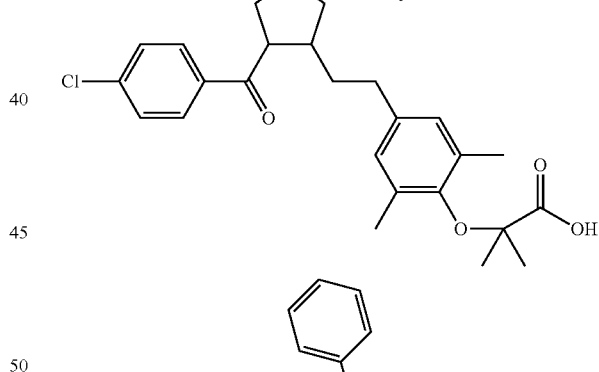
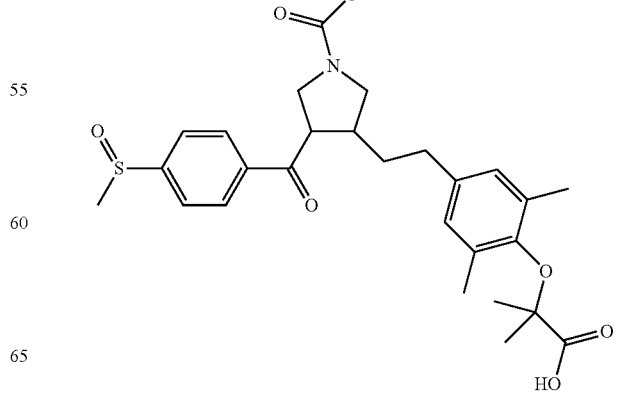

27
-continued
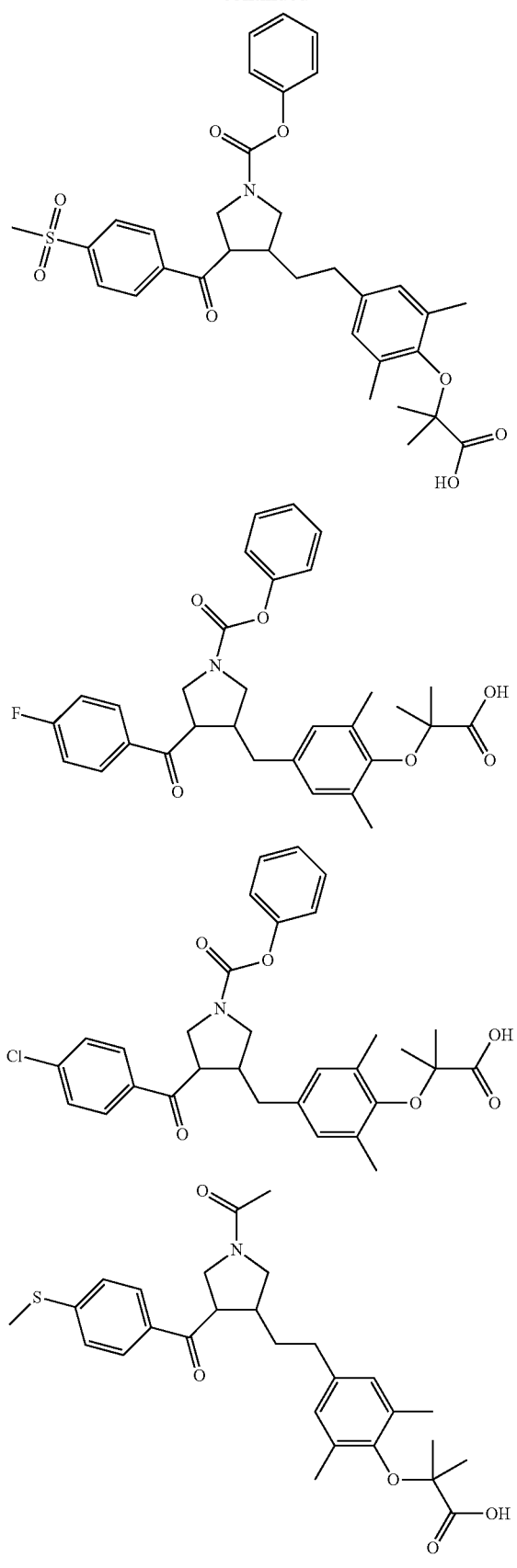
28
-continued
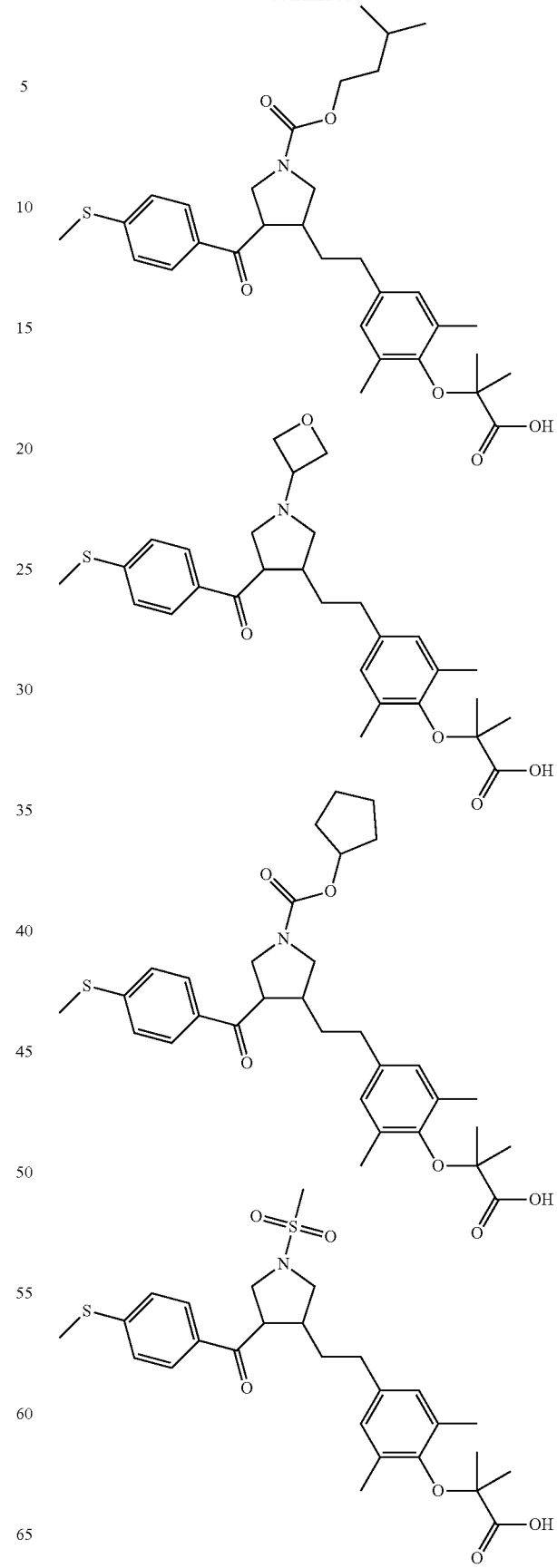

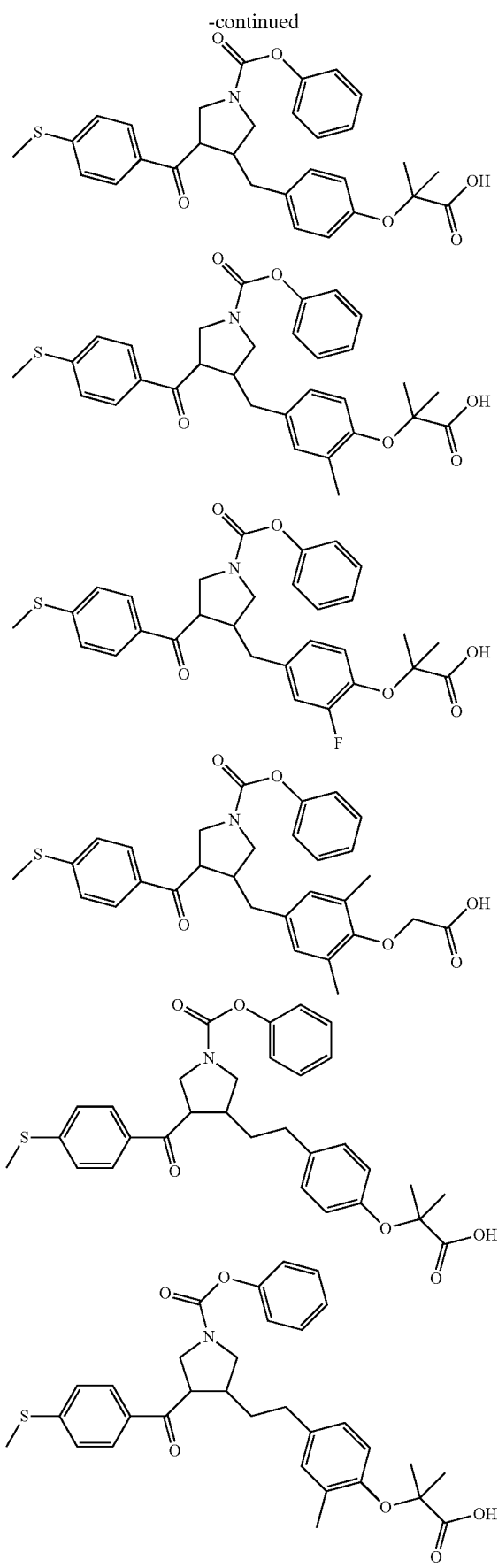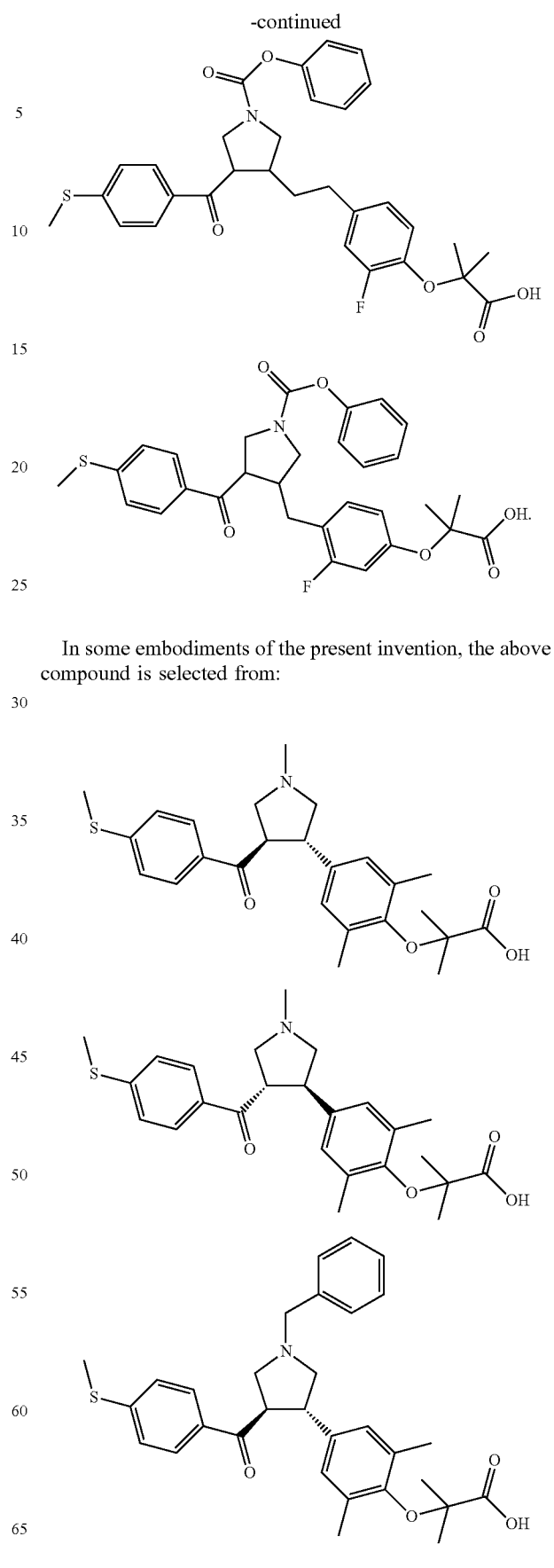
In some embodiments of the present invention, the above compound is selected from:

31
-continued
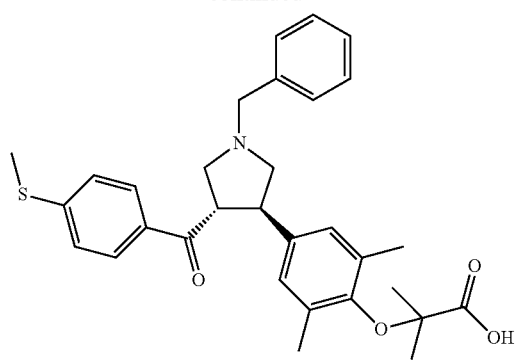
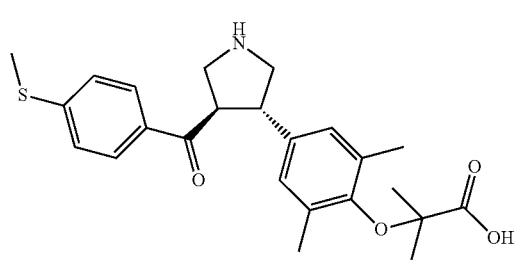
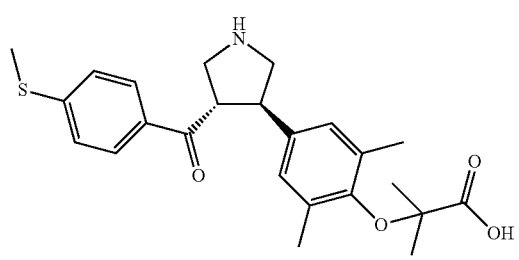
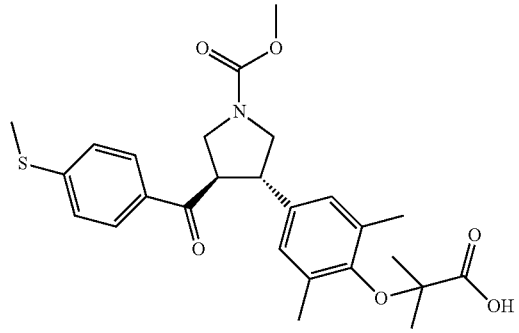
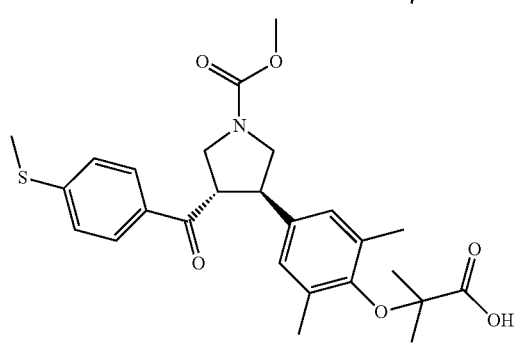
32
-continued
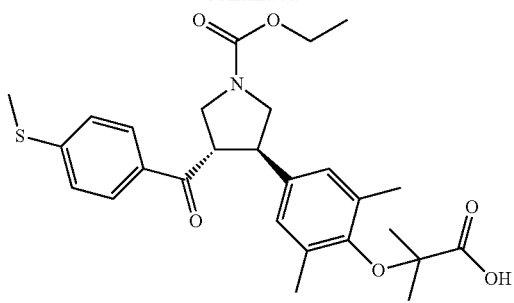
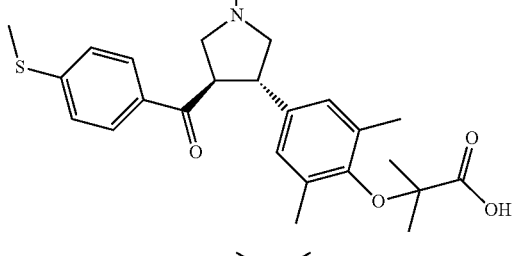
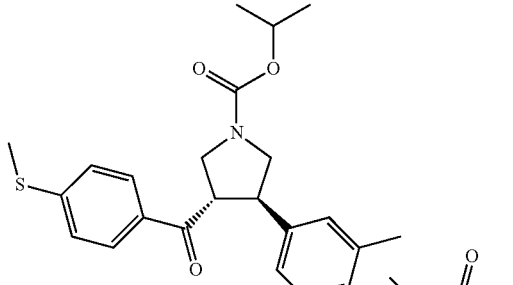
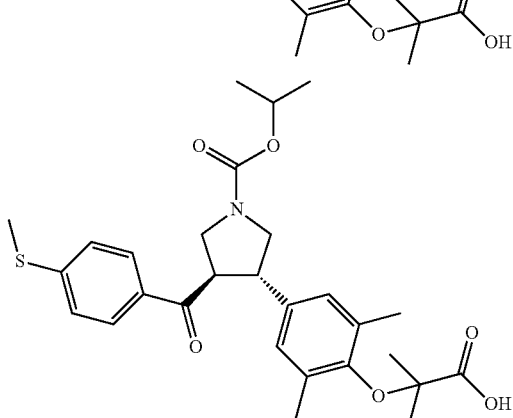
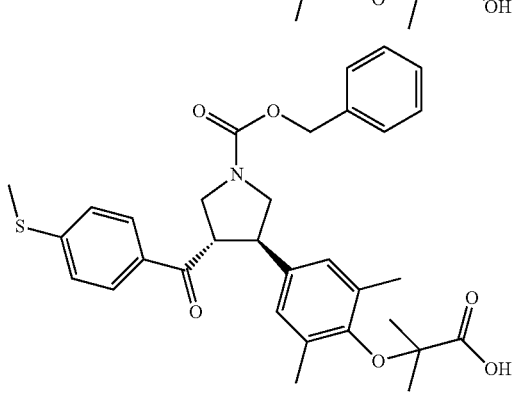

33
-continued
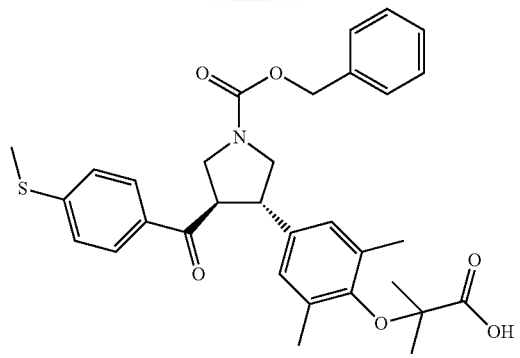
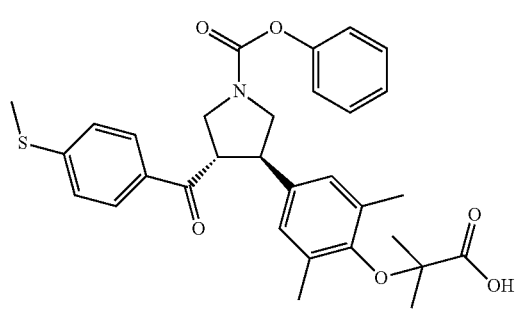
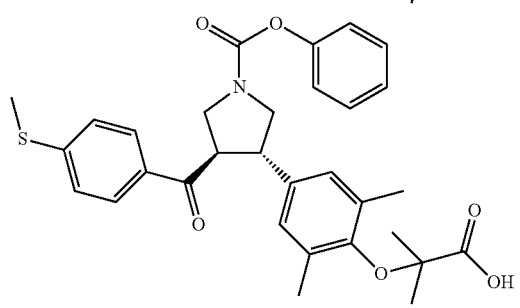
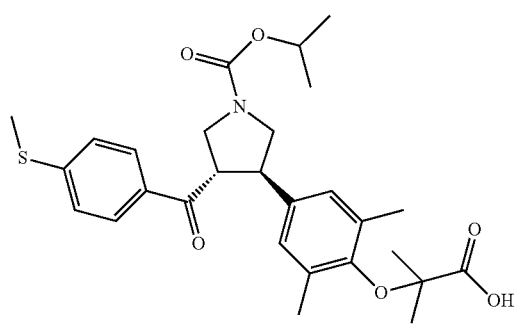
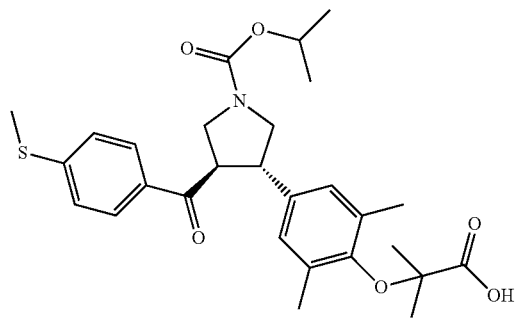
34
-continued
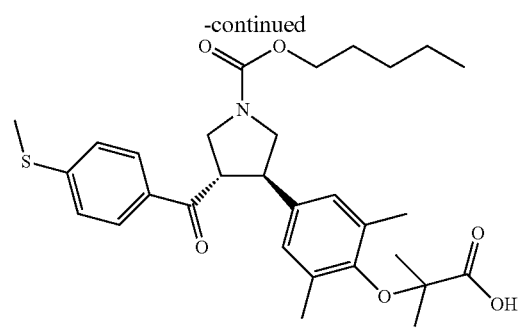
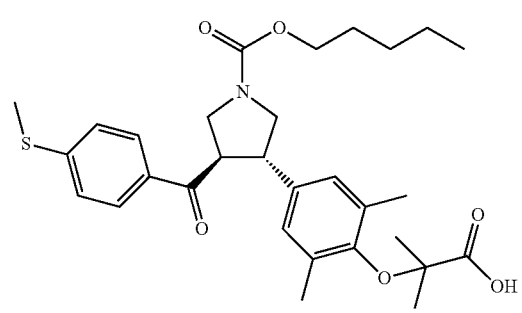
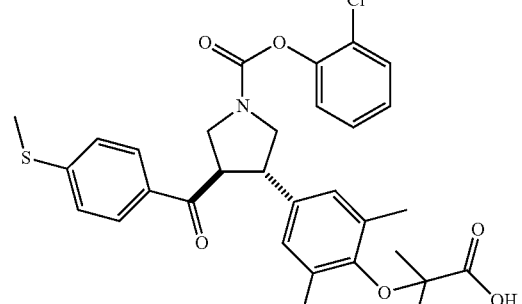
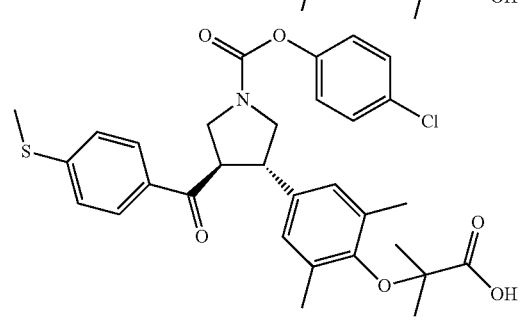
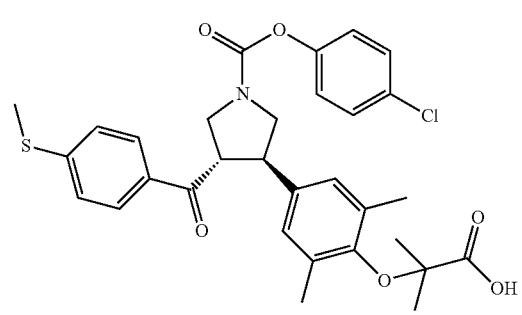

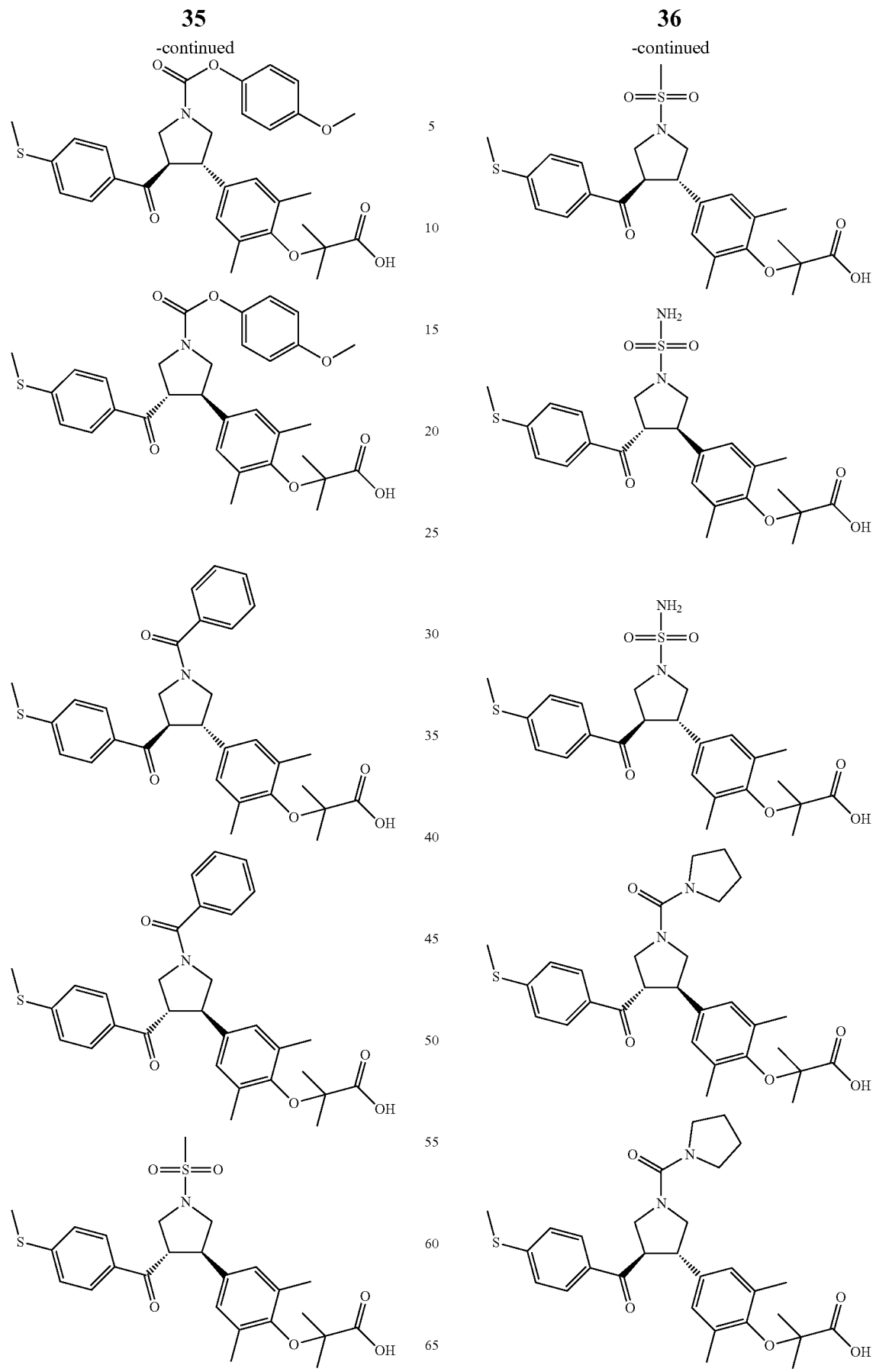

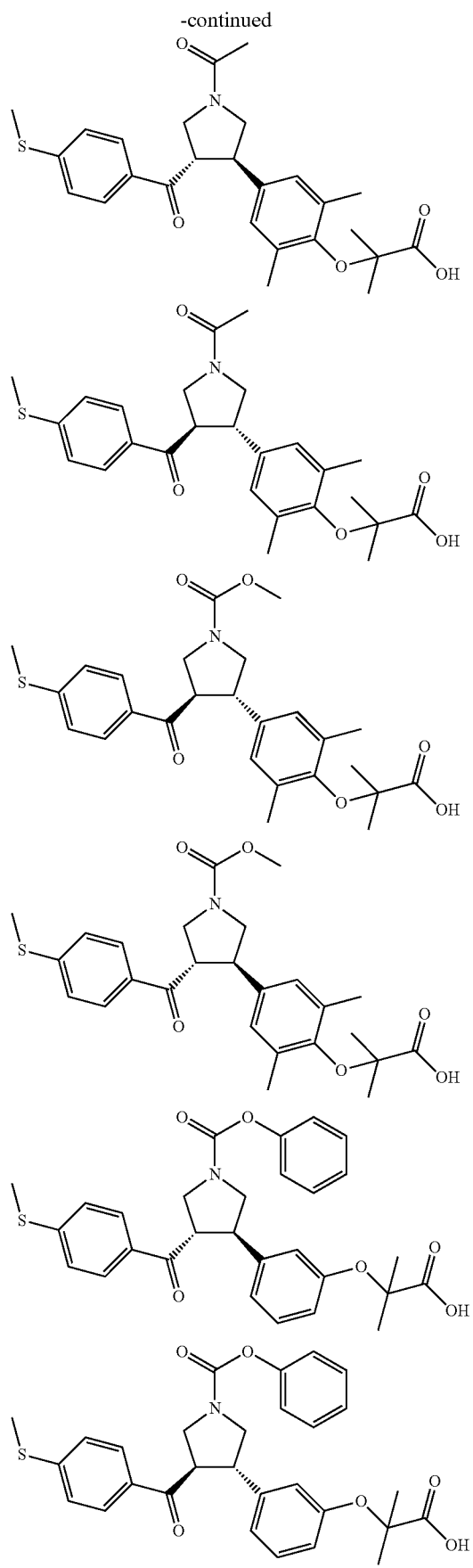
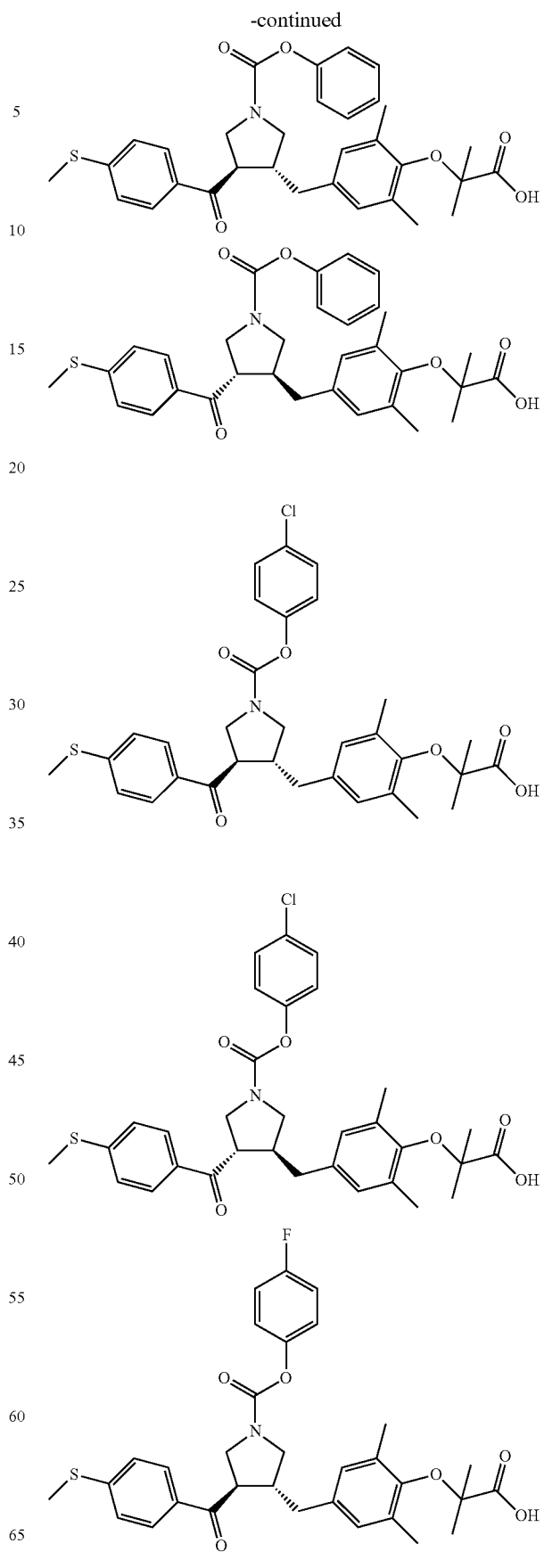

-continued
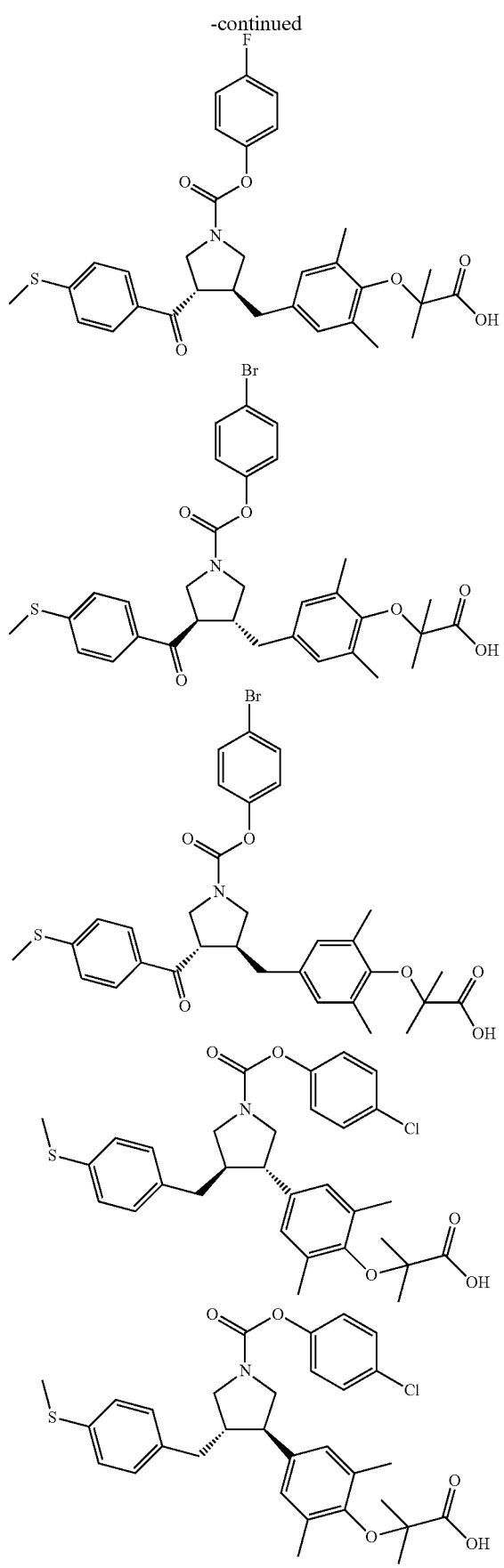
-continued
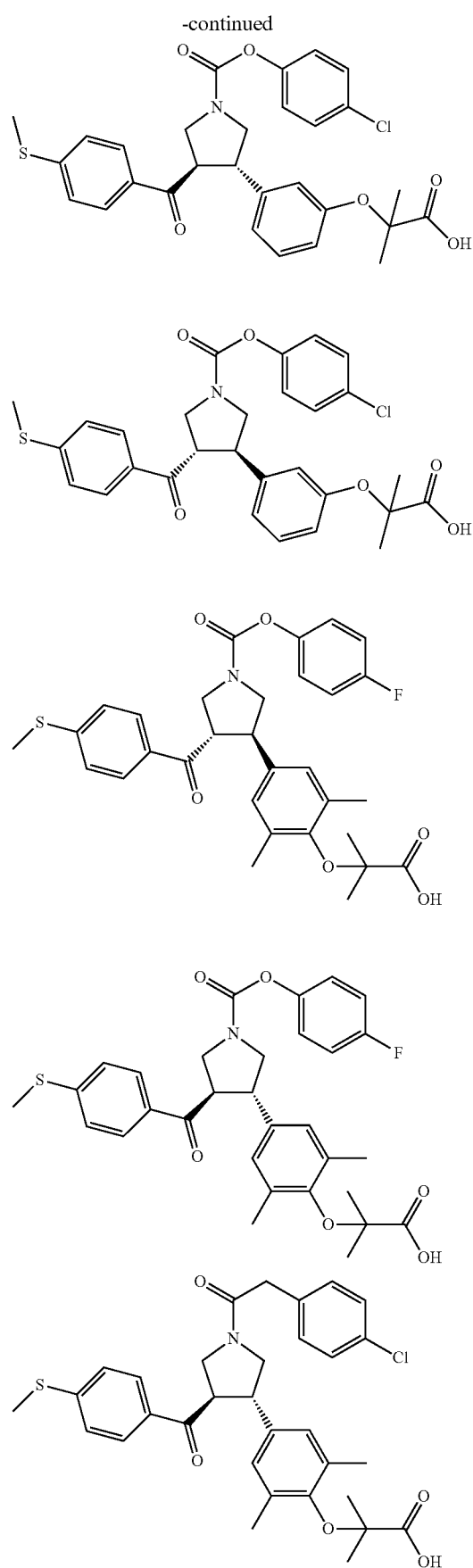

41
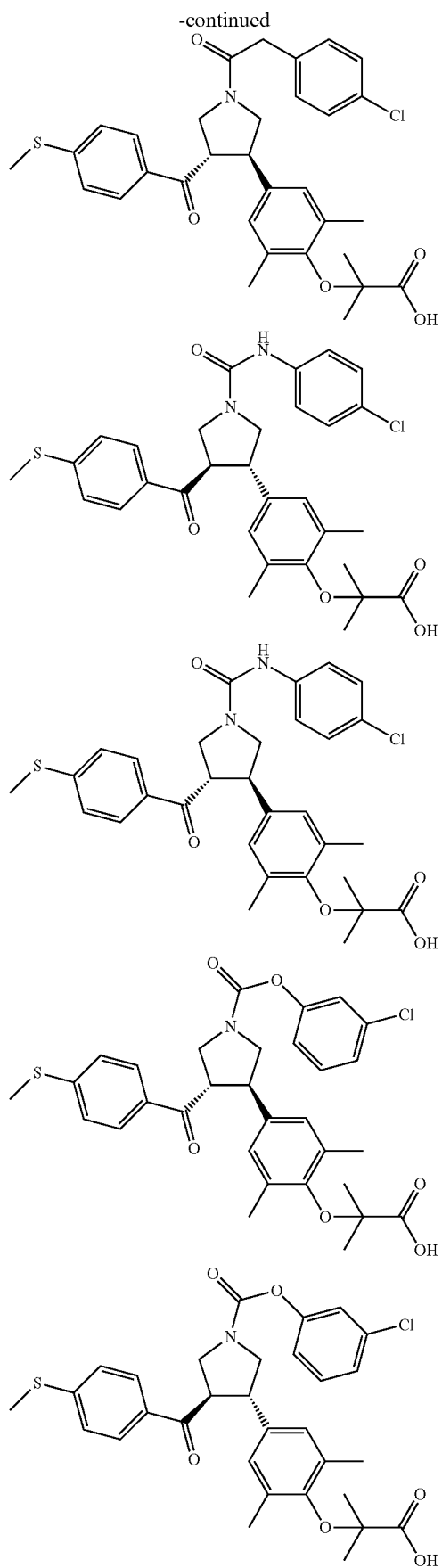
42
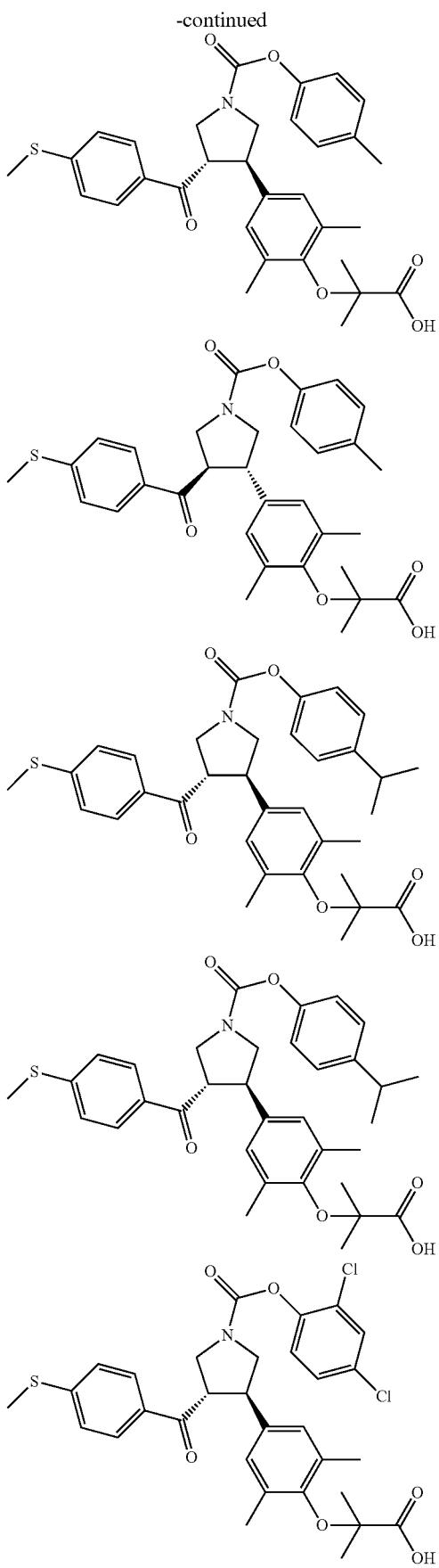

43
-continued
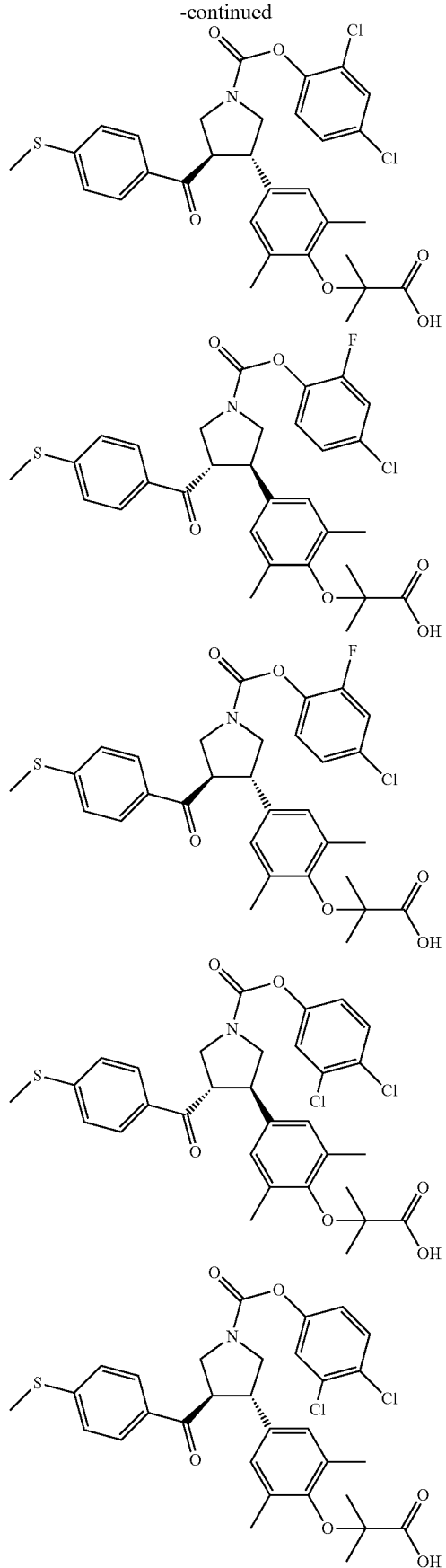
44
-continued
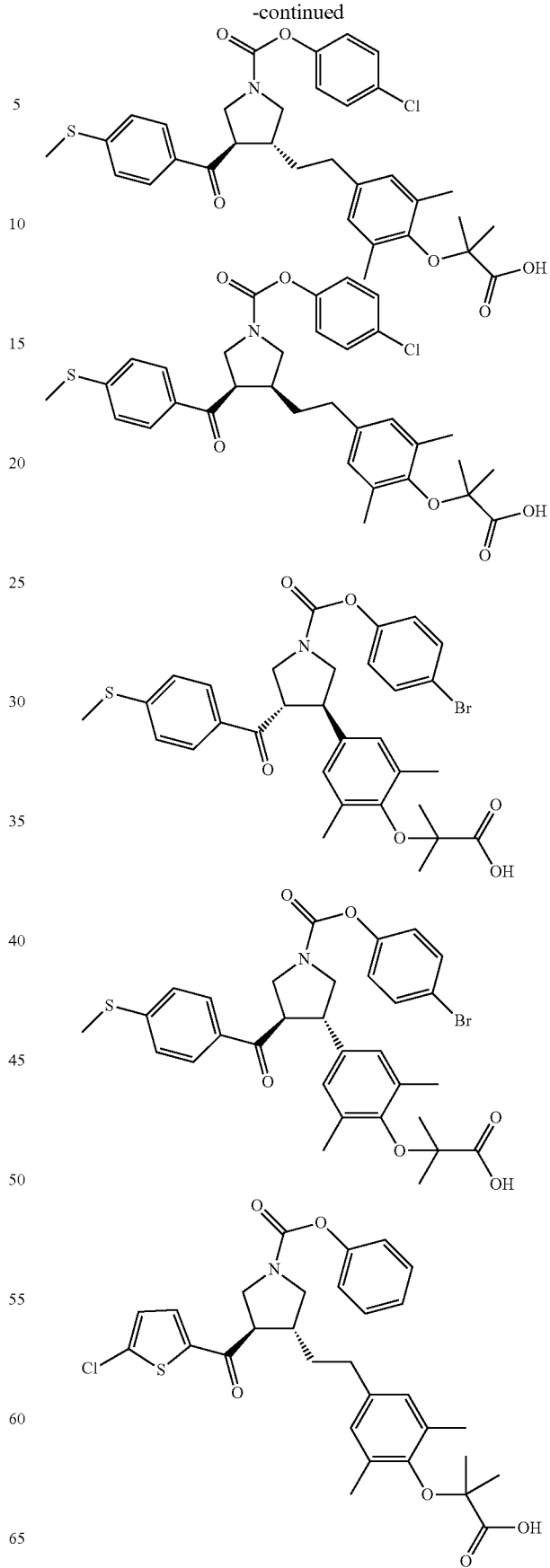

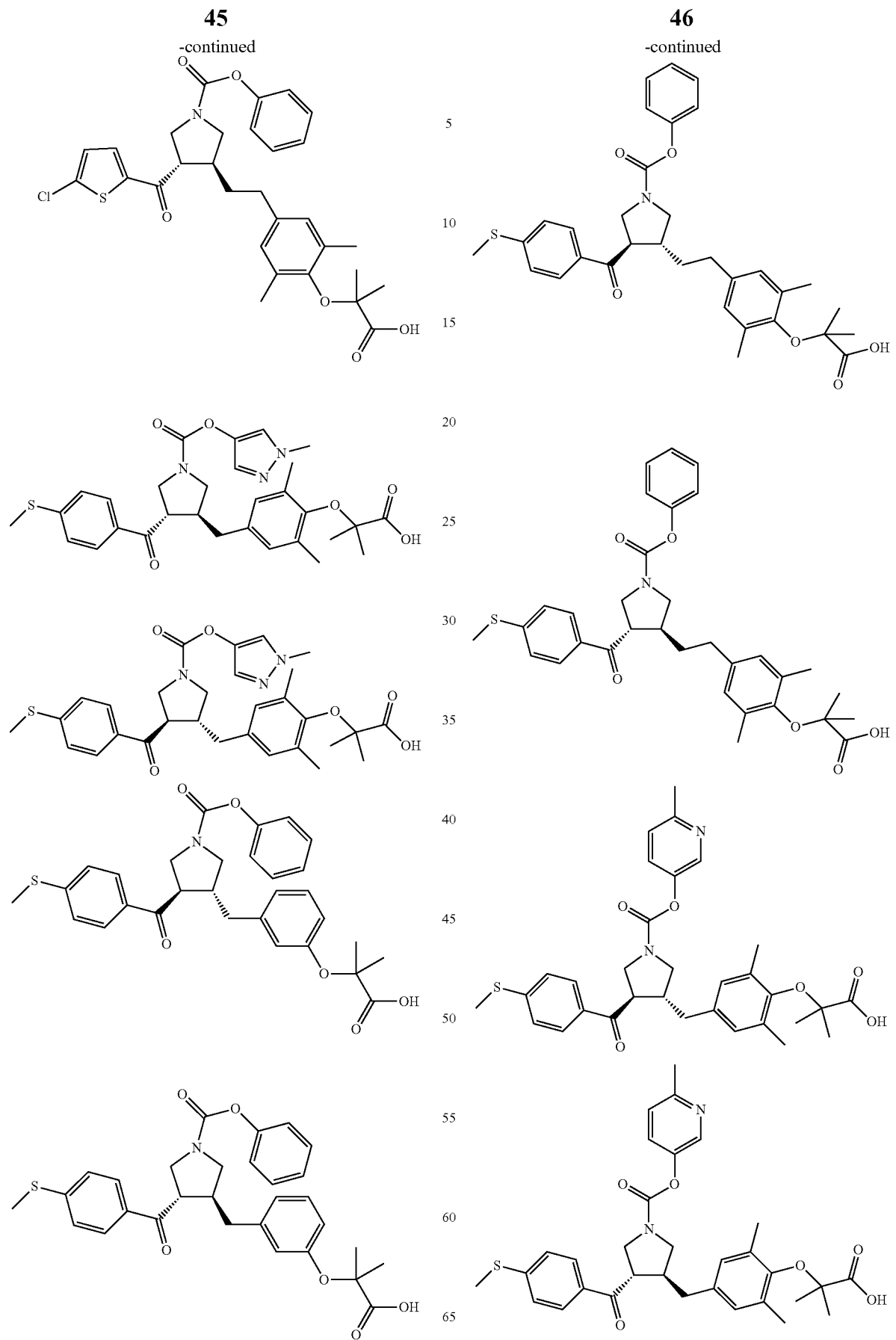

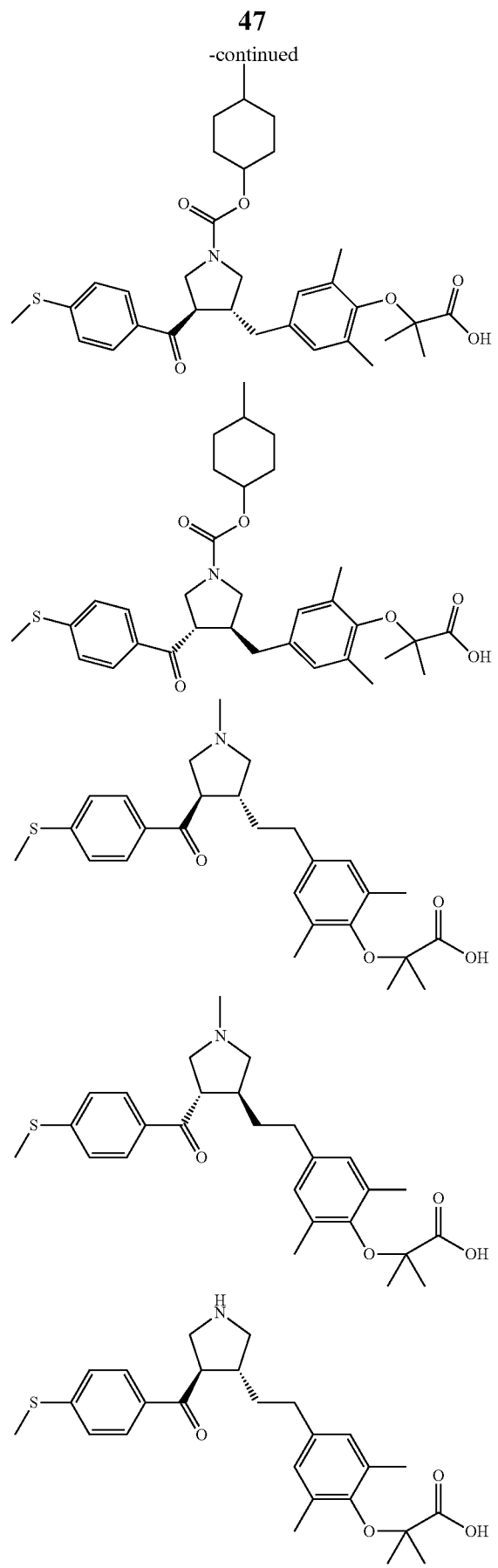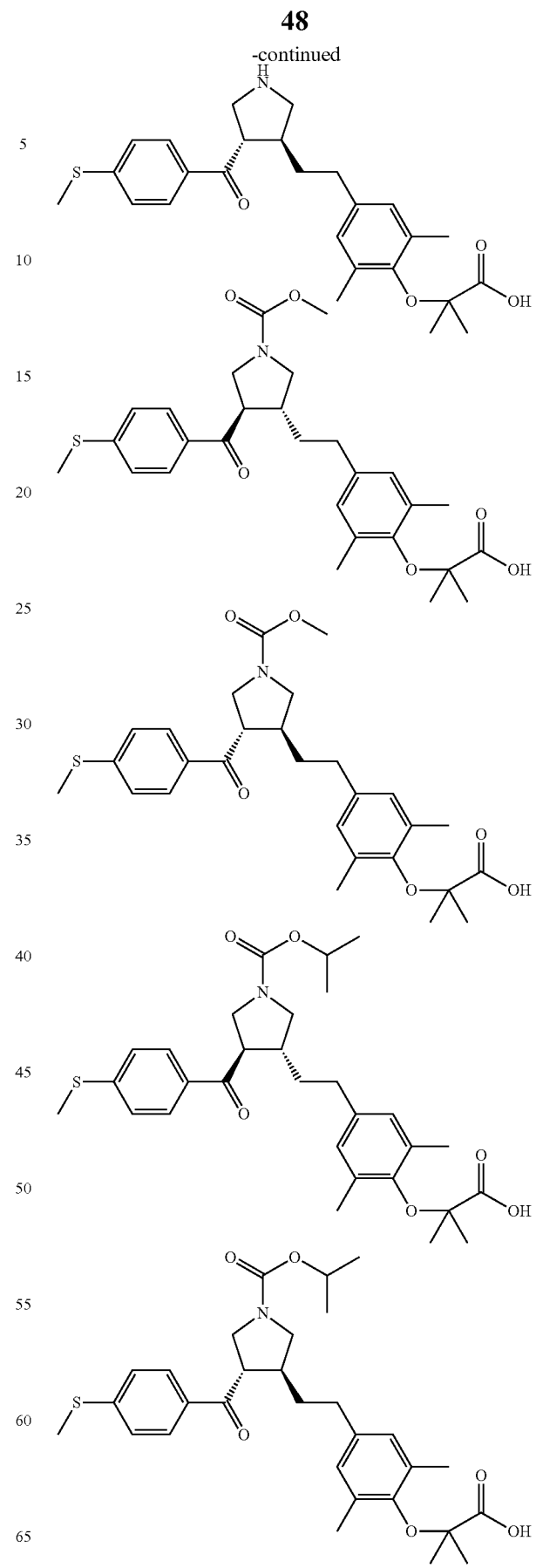

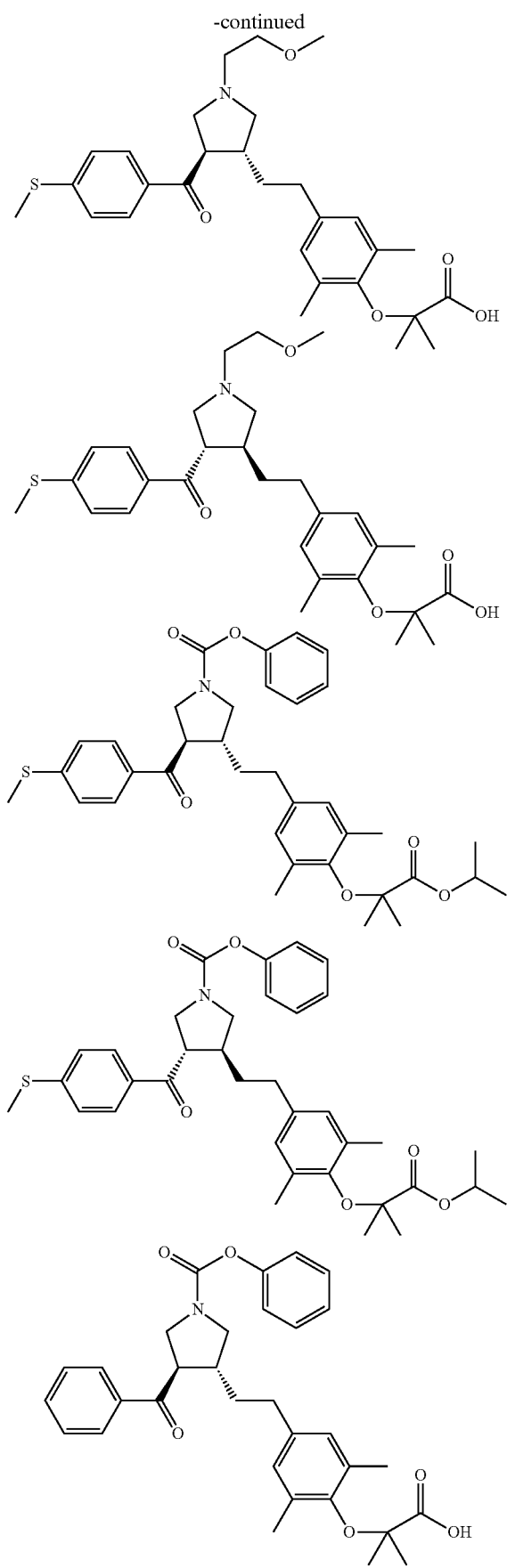
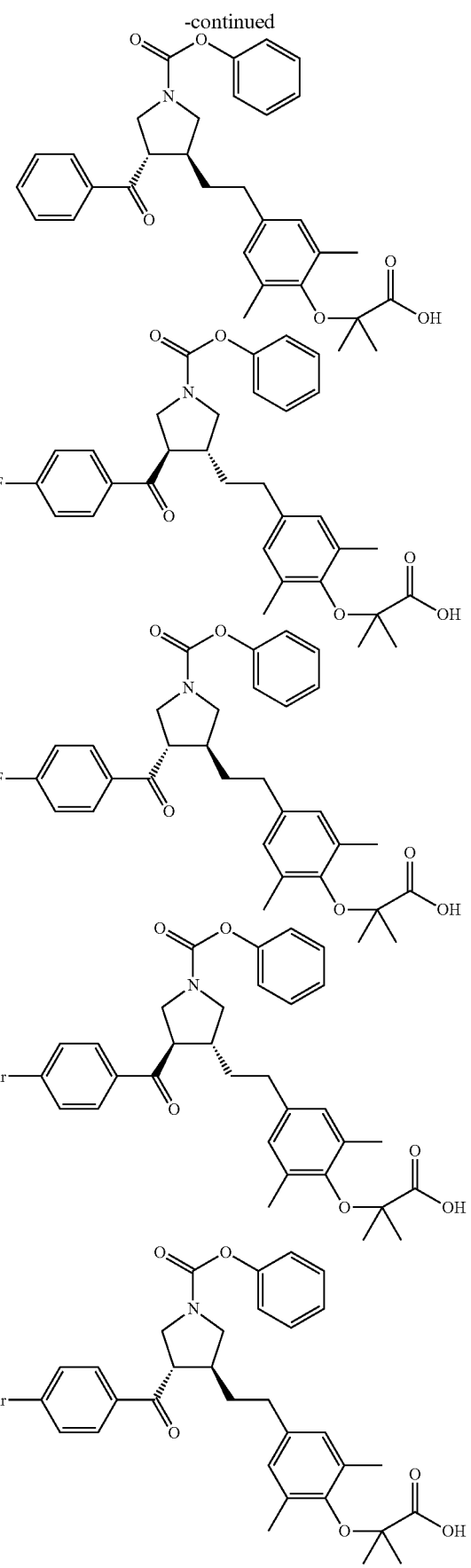

51
-continued
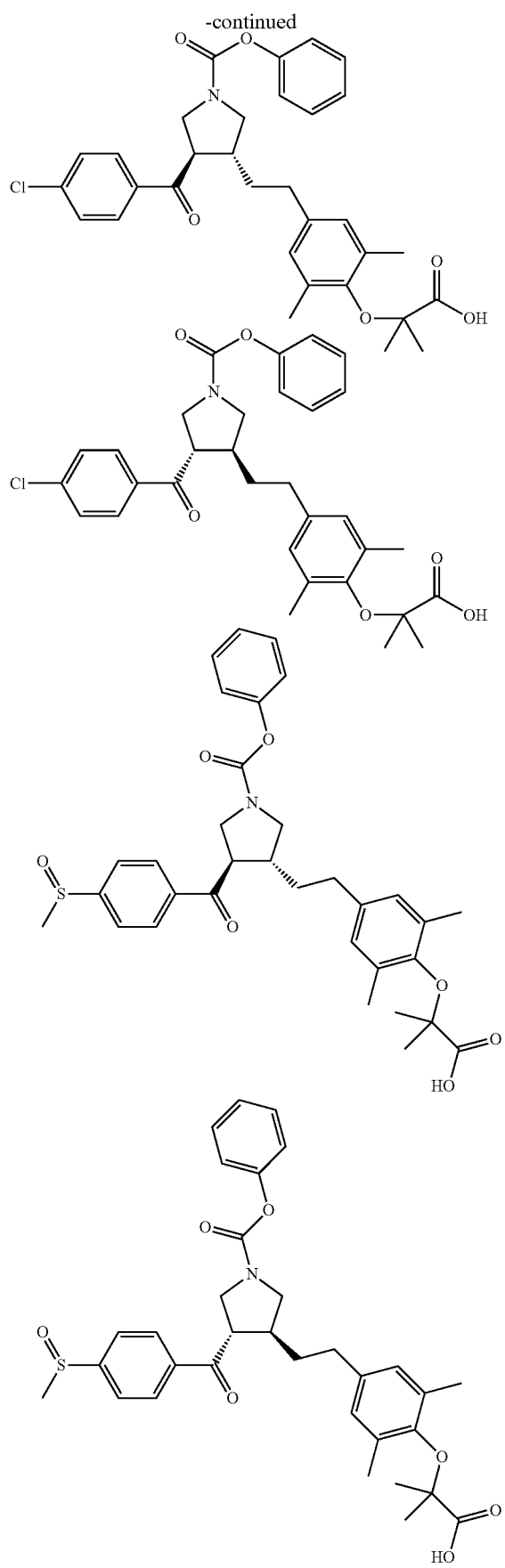
52
-continued
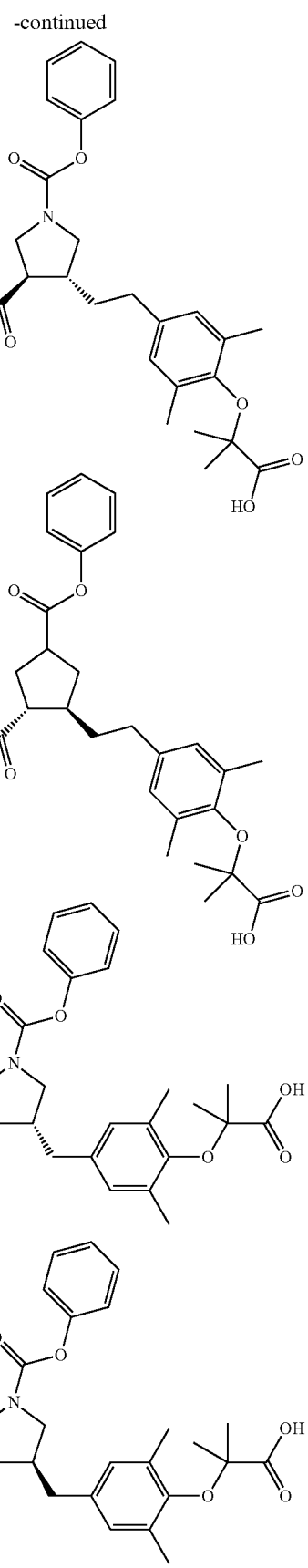

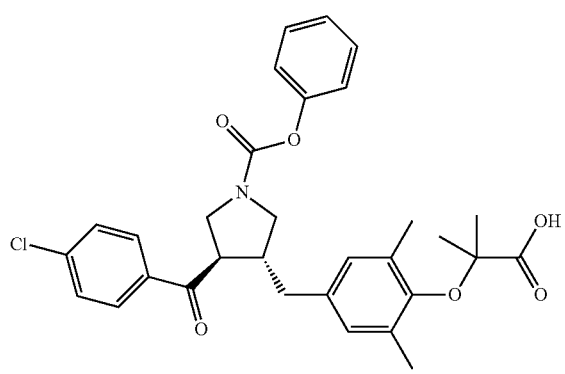
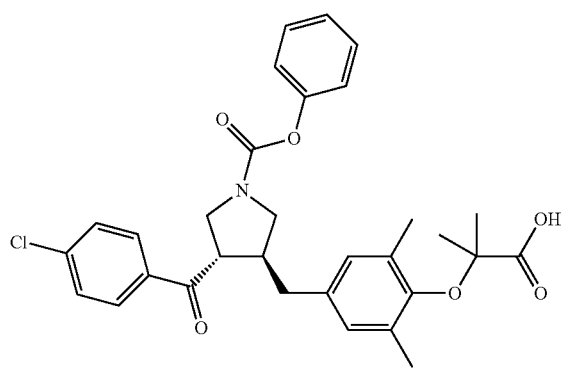
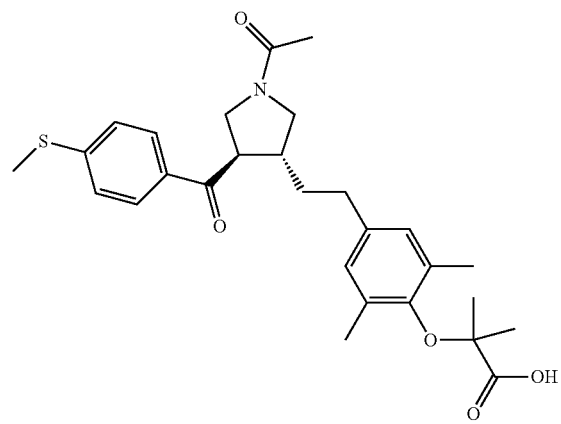
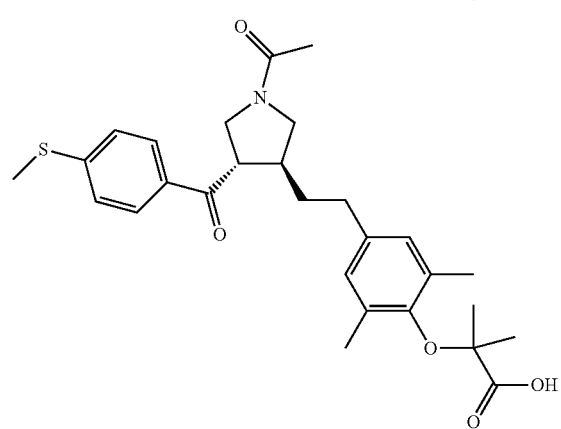
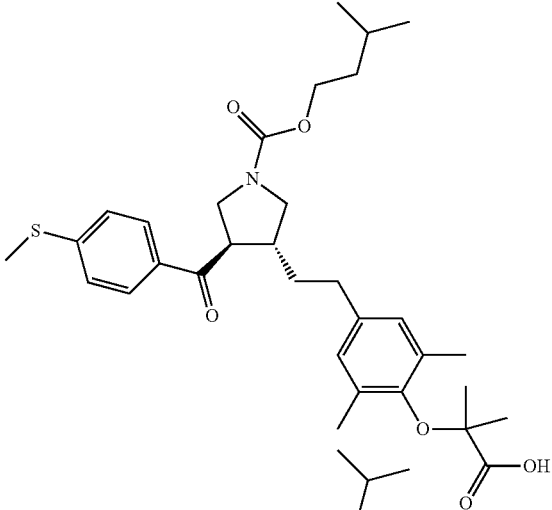
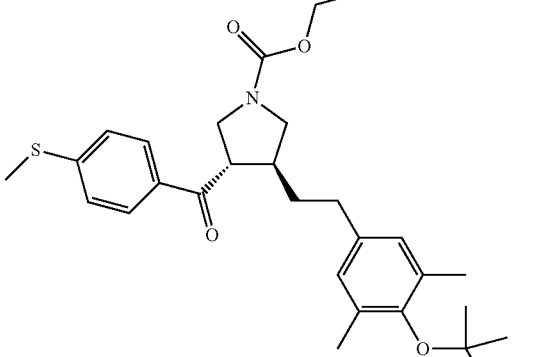
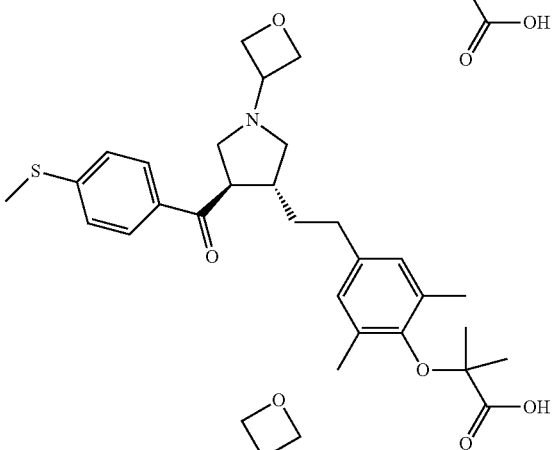
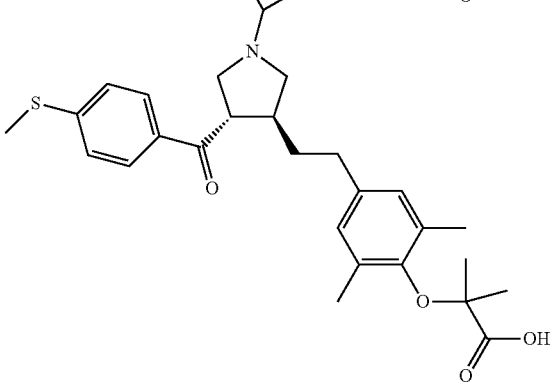

55
-continued
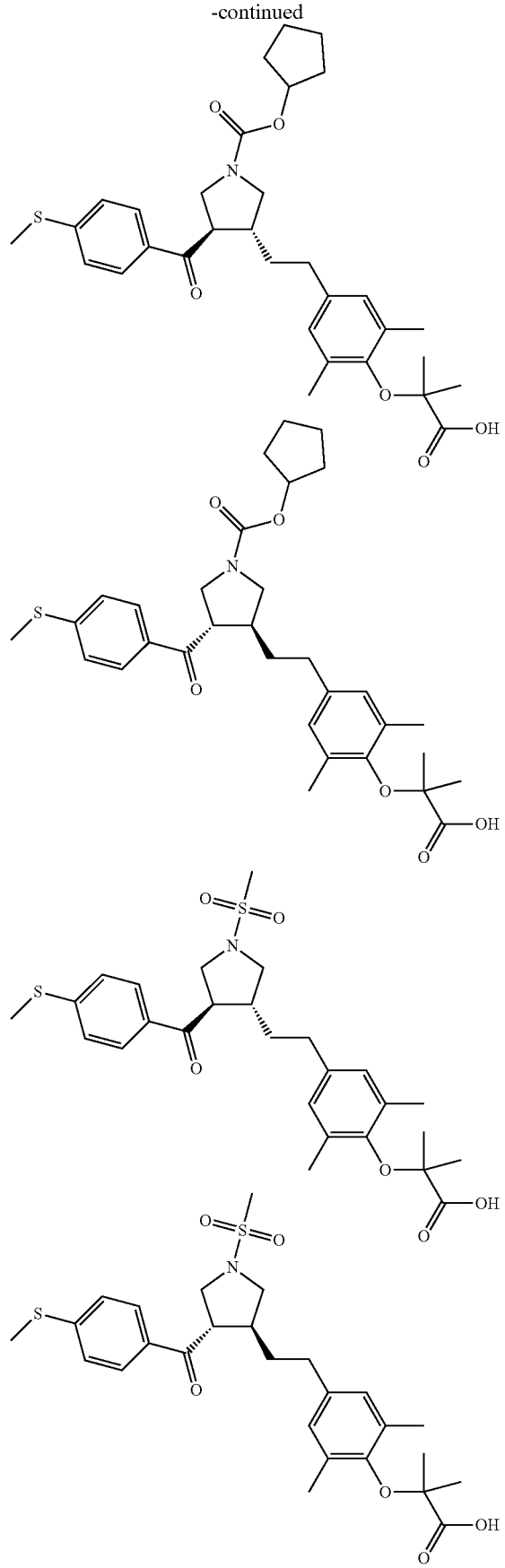
56
-continued
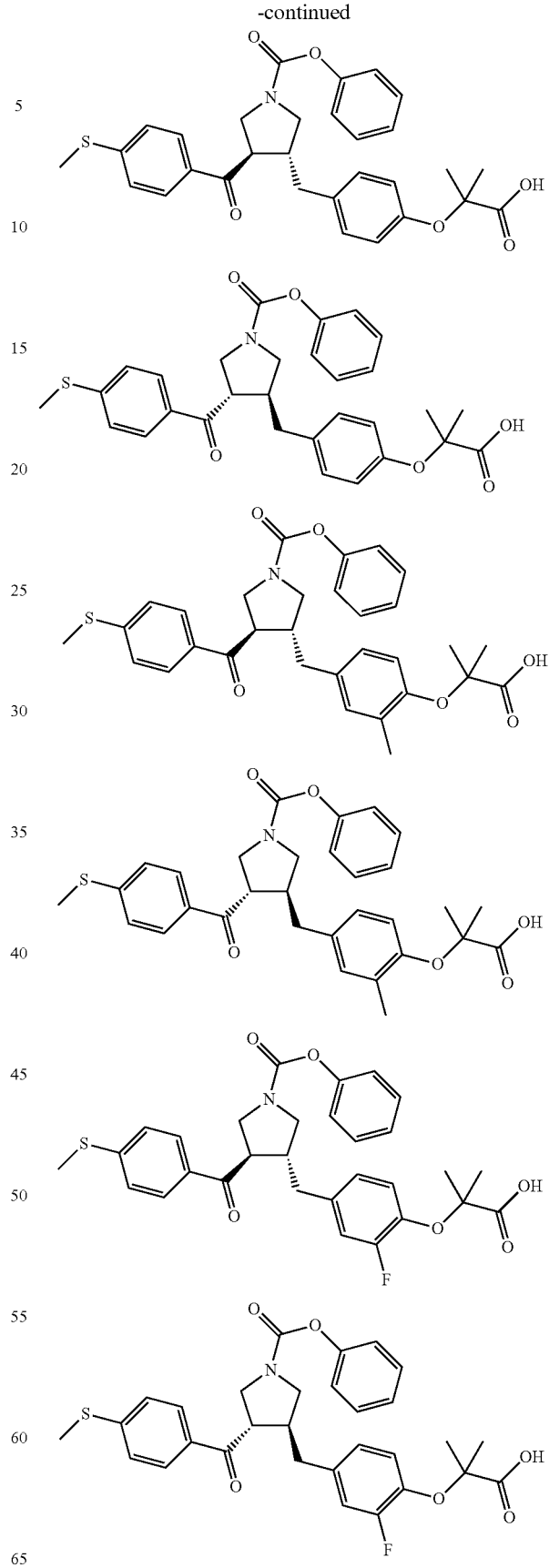

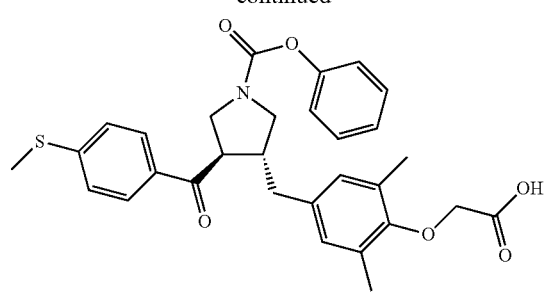
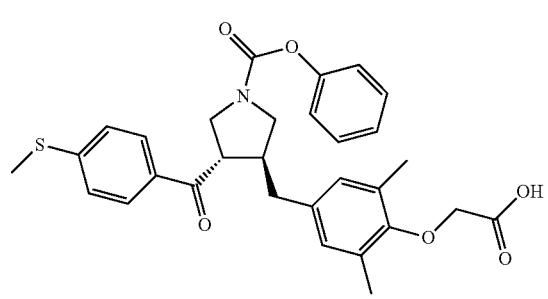
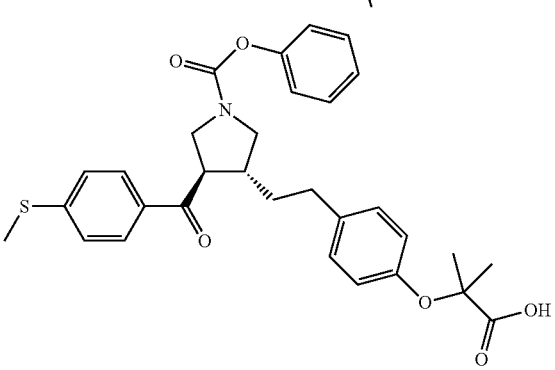
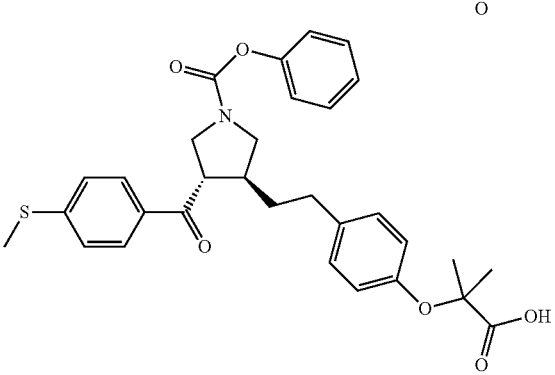
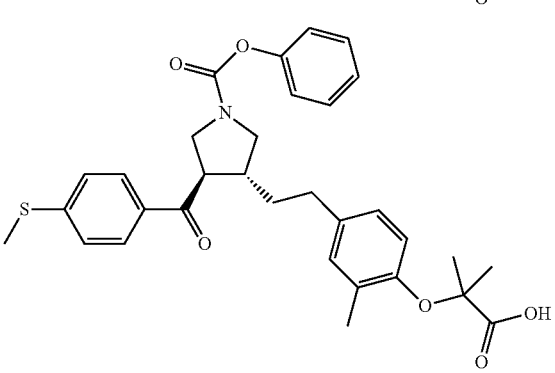
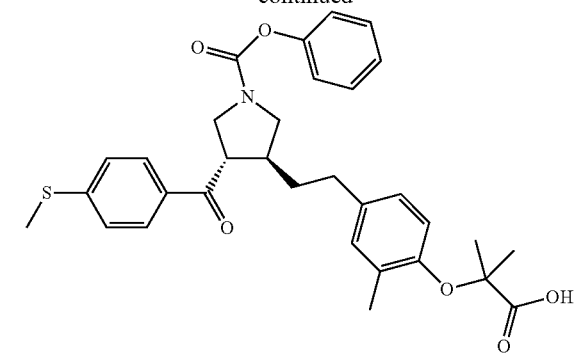
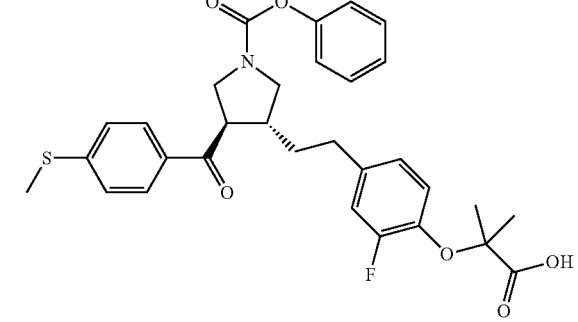
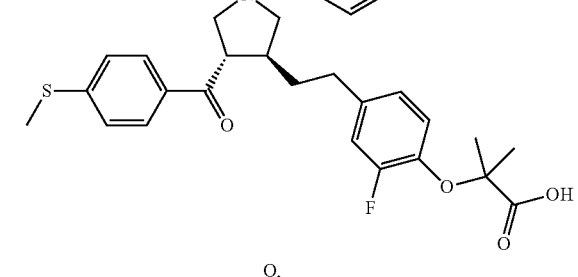
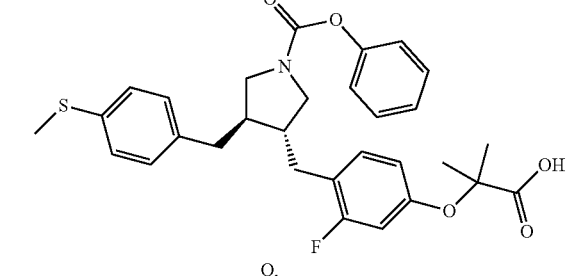
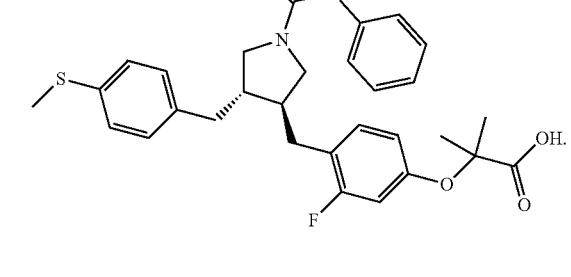
The present invention may further comprise some embodiments which is obtained from any combination of the above variables.
The present invention further provides a pharmaceutical composition comprising a therapeutically effective amount of the above compound or pharmaceutically acceptable salt thereof as an active ingredient, as well as a pharmaceutically acceptable carrier.

The present invention further provides use of the above compound or pharmaceutically acceptable salt thereof, or the above composition for the manufacture of a medicament for treating PPAR receptor-associated disorders.

The present invention further provides use of the above compound or pharmaceutically acceptable salt thereof, or the above composition for manufacture of a medicament for treating nonalcoholic steatohepatitis and concurrent fibrosis, insulin resistance, primary biliary cholangitis, dyslipidemia, hyperlipidemia, hypercholesterolemia, atherosclerosis, hypertriglyceridemia, cardiovascular disease, obesity.

Technical Effect

The present invention discloses a class of pyrrolidine derivatives of Formula (I) as PPAR agonists and a method for preparing the same, wherein this class of compounds can be used to treat some diseases related to PPAR receptor-associated pathways (such as, nonalcoholic steatohepatitis and concurrent fibrosis, insulin resistance, primary biliary cholangitis, dyslipidemia, hyperlipidemia, hypercholesterolemia, atherosclerosis, hypertriglyceridemia, cardiovascular Disease, obesity, and the like). As compared with conventional PPAR agonists, this class of agonists show better activity, higher selectivity, and superior efficacy.

Definition and Explanation

Unless stated otherwise, the following terms and phrases as used herein have the following meanings. A particular term or phrase, without specific definition, should not be deemed to be indefinite or unclear, and should be understood as its common meaning. When a trade name is used herein, it refers to the corresponding commercially available product thereof or the active ingredient thereof. The term "pharmaceutically acceptable" as used herein means that compounds, materials, compositions and/or dosage forms are applicable to use in contact with human and animal tissues as determined by clinically reliable judgements, without excessive toxicities, irritations, allergic reactions or other problems or complications, and having a reasonable benefit/risk ratio.

The term "pharmaceutically acceptable salt" refers to the salts of the compounds of the present invention, and the salts are prepared from the compounds having specific substituent(s) with a relatively non-toxic acid or alkali. When the compounds of the present invention have relatively acidic groups, a alkali addition salt may be obtained by means of contacting a sufficient amount of alkali with a neutral form of such compounds in a pure solution or a suitable inert solvent. Pharmaceutically acceptable alkali additional salts include sodium, potassium, calcium, ammonium, organic amine or magnesium salts, or the like. When the compounds of the present invention have relatively alkaline functional groups, an acid additional salt may be obtained by means of contacting a sufficient amount of acid with a neutral form of such compounds in a pure solution or a suitable inert solvent. Examples of the pharmaceutically acceptable acid addition salts comprise inorganic acid salts, in which the inorganic acid include, e.g., hydrochloric acid, hydrobromic acid, nitric acid, carbonic acid, bicarbonate radical, phosphoric acid, monohydrogen phosphate radical, dihydrogen phosphate radical, sulphuric acid, hydrosulfate radical, hydroiodic acid, phosphorous acid, etc.; and organic acid salts, in which the organic acid include, e.g., acetic acid, propionic acid, isobutyric acid, maleic acid, malonic acid, benzoic acid, succinic acid, suberic acid, fumaric acid, lactic acid, mandelic acid, phthalic acid, benzenesulfonic acid, p-toluenesulfonic acid, citric acid, tartaric acid, methanesulfonic acid and the like; and salts of amino acids such as arginine or the like; as well as salts of organic acids such as glucuronic acid or the like (see Berge et al., "Pharmaceutical Salts", Journal of Pharmaceutical Science 66: 1-19 (1977)). Some particular compounds of the present invention have alkaline and acidic groups, and thus can be converted to any one of alkali or acid additional salt.

Preferably, the neutral form of a compound can be regenerated by conventionally contacting a salt with an alkali or acid, followed by isolating a parent compound. The parent compound of a compound differs from the salt thereof in certain physical properties, e.g., in solubility in a polar solvent.

The term "pharmaceutically acceptable salt" herein belongs to the derivative of the compound of the present invention, wherein the parent compound is modified by forming a salt with an acid or alkali. Examples of the pharmaceutically acceptable salts include, but are not limited to, inorganic or organic acid salts of alkaline groups, such as amines; alkali metal or organic salts of acidic radicals, such as, carboxylic acid. The pharmaceutically acceptable salts comprise common non-toxic salts or quaternary ammonium salts of the parent compound, such as, the salts formed from non-toxic inorganic or organic acids. The common non-toxic salts include, but are not limited to, those derived from inorganic and organic acids selected from 2-acetoxybenzoic acid, 2-hydroxyethanesulfonic acid, acetic acid, ascorbic acid, benzenesulfonic acid, benzoic acid, hydrocarbonate radical, carbonic acid, citric acid, edetic acid, ethanedisulfonic acid, ethanesulfonic acid, fumaric acid, glucoheptose, gluconic acid, glutamic acid, glycolic acid, hydrobromic acid, hydrochloric acid, hydriodate, hydroxyl, hydroxynaphthalene, isethionic acid, lactic acid, lactose, dodecyl sulfonic acid, maleic acid, malic acid, mandelic acid, methanesulfonic acid, nitric acid, oxalic acid, pamoic acid, pantothenic acid, phenylacetic acid, phosphoric acid, polygalactose aldehyde, propionic acid, salicylic acid, stearic acid, folinate, succinic acid, aminosulfonic acid, p-aminobenzenesulfonic acid, sulfuric acid, tannin, tartaric acid and p-toluenesulfonic acid.

The pharmaceutically acceptable salts of the present invention may be synthesized from a parent compound having an acidic or alkaline group via a conventional chemical method. In general, such salts are prepared by reacting these compounds in a form of free acid or alkali with a stoichiometric amount of a suitable alkali or acid in water or an organic solvent or a mixture thereof. Typically, a non-aqueous medium, e.g., ether, ethyl acetate, ethanol, isopropanol, acetonitrile or the like, are preferred.

In addition to the salt form, the compounds provided by the present invention may have a form of prodrug. The prodrug of the compounds as described herein can be easily chemically converted to the compounds of the present invention under physiological conditions. Moreover, the prodrugs may be, in vivo, converted to the compounds of the present invention via a chemical or biochemical process.

Some compounds of the present invention may be present in a form of non-solvate or solvate, including a form of hydrate. In general, the non-solvate form and the solvate form are comparable with each other, both of them are encompassed within the scope of the present invention.

Some compounds of the present invention may have asymmetric carbon atoms (optical center) or double bonds. Racemates, diastereomers, geometric isomers, and individual isomers are all encompassed within the scope of the present invention.

Unless stated otherwise, a wedge bond and dashed bond (⟋ ⟍) are used to indicate the absolute configuration of a stereocenter; a wavy line is used to indicate a wedge or dashed bond (⟋ or ⟍), and ⟋ ⟍ are used to indicate a relative configuration of a stereocenter. When the compounds as described herein comprise an olefinic double bond or other geometrically asymmetric centers, unless defined otherwise, they would comprise E-, Z-geometrical isomers. Similarly, all the tautomers are encompassed within the scope of the present invention.

The compounds of the present invention may be present in a specific geometric or stereoisomeric form. It is expected by present invention that all of such compounds include cis- and trans-isomers, (−)- and (+)-enantiomers, (R)- and (S)-enantiomers, diastereomers, (D)-isomers, (L)-isomers and a racemic mixture thereof, as well as other mixture such as an enantiomer- or diastereomer-enriched mixture, all of the mixtures are encompassed within the scope of the present invention. The substituents, such as alkyl and the like, may have additional asymmetric carbon atoms. All of these isomers and the mixtures thereof are encompassed within the scope of the present invention.

Optically active (R)- and (S)-isomers and D- and L-isomers may be prepared by chiral synthesis or chiral reagents or by other conventional technologies. If one enantiomer of a compound of the present invention is desired, it could be prepared by asymmetric synthesis or derivatization with a chiral auxiliary, in which the resulted mixture of diastereomers would be isolated, and then a pure enantiomer as desired would be provided by cleaving the auxiliary group. Alternatively, if a molecule contains an alkaline (e.g., amino) or acidic (e.g., carboxyl) functional group, it may be reacted with a suitable optically active acid or alkali to form a salt of diastereomers, which are in turn subjected to diastereoisomer resolution via a well-known conventional method in the art, and are then recovered to give a pure enantiomer. Furthermore, the isolation of the enantiomers and diastereoisomers is usually accomplished by chromatography, which may utilize a chiral stationary phase, and optionally be combined with a chemical derivatization method (e.g., producing carbamate from amine).

The compounds of the present invention may comprise a non-naturally occurring ratio of isotope(s) at one or more atoms of the compounds. For instance, the compounds may be labelled with radioisotope(s), such as tritium ($^3$H), iodine-125 ($^{125}$I) or C-14 ($^{14}$C). All isotopic variants of the compounds of the present invention, are encompassed within the scope of the present invention, regardless of their radioactivity.

The term "pharmaceutically acceptable carrier" refers to any preparation or carrier medium which can deliver an effective amount of the active substances of the present invention, without interfering with the bioactivity of the active substances, and without toxic and side effects to subjects or patients. Representative carriers comprise water, oil, vegetables and minerals, cream base, lotion base, ointment base, and the like. These base materials comprise suspending agents, thickening agents, transdermal enhancers, and the like. The preparations thereof are well known by the skilled persons in the cosmetic or topical drug field. Other information for the carriers may refer to Remington: The Science and Practice of Pharmacy, 21 st Ed., Lippincott, Williams & Wilkins (2005), the contents of which are incorporated herein by reference.

The term "excipient" generally refers to carriers, diluents, and/or media required by the formulation of an effective pharmaceutical composition.

With respect to a drug or pharmaceutically active agent, the term "effective amount" or "therapeutically effective amount" refers to a sufficient amount of the drug or medicament which can achieve the desired effect, without producing toxicity. As for the oral dosage form of the present invention, an "effective amount" of one active substance in the composition refers to the amount required to achieve the desired effect, when used in combination with another active substance in the composition. The determination of the effective amount varies from person to person, depending on the age and general conditions of the subject, and on the particular active substance. The appropriate effective amount for an individual case may be determined by a person skilled in the art via conventional experiments.

The term "active ingredient(s)", "therapeutic agent(s)", "active substance(s)" or "active agent(s)" refers to a chemical entity which can effectively treat disorders, diseases, or conditions of the subject.

The phrase "optional" or "optionally" means that the subsequently described event or condition may be not necessarily occur, that is such description includes both the case in which the event or condition occurs and the case in which the event or condition does not occur.

The term "substituted" refers that any one or more hydrogen atom(s) of a particular atom are substituted with a substituent, which may include variants of heavy hydrogen and hydrogen, as long as the valence of the particular atom is normal and the substituted compound is stable. When the substituent is a ketone group (i.e., =O), it means that two hydrogen atoms are substituted. Ketone substitution would not occur on an aromatic group. The term "optionally substituted" means that it may be or not be substituted. Unless defined otherwise, the substituents may be of any type and any number as long as they are chemically achievable.

When any variable (e.g., R) occurs more than once in the composition or structure of a compound, the definition thereof is independent in each case. Thus, as an example, if a group is substituted with 0-2 R, the group may be optionally substituted with at most 2 R, and each R has independent selections in each case. Moreover, a combination of the substituents and/or the variants thereof is allowable only if such combination leads to a stable compound.

When the number of a linking group is zero, such as —(CRR)$_0$—, it means that the linking group is a single bond.

When a variable is selected from a single bond, it means that the two groups linked by this variable are directly linked. For example, when L in a structure A-L-Z represents a single bond, this structure actually is A-Z.

When a substituent is absent, it means that the substituent does not exist. For instance, when X in a structure A-X is absent, it means that the structure actually is A. When a substituent can be linked to more than one atom in a ring, this substituent may be bound to any atom in the ring. For example, a structural unit

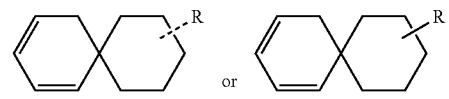

means that the substituent R may be attached to any site of cyclohexyl or cyclohexadiene. When it is not indicated through which atom a recited substituent is attached to a substituted group, the substituent may be bound through any atom therein. For example, pyridyl as a substituent may be attached to a substituted group via any carbon atom of the pyridyl ring. When the linking direction of a recited linking group is not indicated, the linking direction thereof is random. For example, if the linking group L in

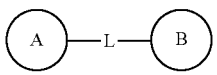

is -M-W—, -M-W— may not only link ring A to ring B in a direction identical to a reading order from left to right so as to form

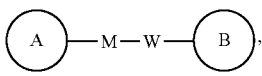, but also link ring A to ring B in a direction opposite to a reading order from left to right so as to form

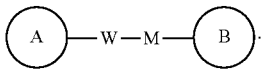.

A combination of the linking groups, substituents and/or variants thereof is allowable only if such combination leads to a stable compound.

Unless defined otherwise, the term "hetero-" refers to a heteroatom or heteroatomic group (i.e., an atomic group containing heteroatom(s)), including atom(s) other than carbon (C) and hydrogen (H) as well as an atomic group containing such heteroatom(s), e.g., oxygen (O), nitrogen (N), sulfur (S), silicon (Si), germanium (Ge), aluminum (Al), boron (B), —O—, —S—, =O, =S, —C(=O)O—, —C(=O)—, —C(=S)—, —S(=O), —S(=O)$_2$—, and optionally substituted —C(=O)N(H)—, —N(H)—, —C(=NH)—, —S(=O)$_2$N(H)— or —S(=O)N(H)—.

Unless defined otherwise, a "ring" refers that substituted or unsubstituted cycloalkyl, heterocycloalkyl, cycloalkylene, heretocycloalkylene, cycloalkynyl, heretocycloalkynyl, aryl or heteroaryl. Said ring comprises a mono ring, linked ring, spiro ring, fused ring, or bridged ring. The number of the atoms in the ring is typically defined as the membered number of the ring. For example, "5-7 membered ring" means that 5-7 atoms are arranged in a circular manner. Unless defined otherwise, the ring optionally contains 1-3 heteroatoms. Thus, "5-7 membered ring" comprises, e.g., phenyl, pyridinyl and piperidyl; and on the other hand, the term "5-7-membered heterocycloalkyl ring" comprises pyridyl and piperidyl, but does not comprise phenyl. The term "cyclo/ring" further comprises a ring system containing at least one ring, in which each "ring" meets independently the above definition.

Unless defined otherwise, the term "heterocycle" or "heterocyclyl" refers to a stable mono-, double-, or triple-ring containing heteroatom(s) or heteroatomic group(s), such ring may be saturated, partially unsaturated or unsaturated (aromatic), and may comprise carbon atom(s) and 1, 2, 3 or 4 ring heteroatom(s) independently selected from N, O and S, wherein any of the above heterocycles may be fused to a phenyl ring to form a double ring. Nitrogen and sulfur heteroatoms may be optionally oxidized (i.e., NO and S (O)$_p$, wherein p is 1 or 2). Nitrogen atom may be substituted or unsubstituted (i.e., N or NR, wherein R is H or another substituent as defined herein). The heterocycle may be attached to a side group of any heteroatom or carbon atom, thereby forming a stable structure. If the resulted compound is stable, the heterocycle as described herein may be substituted at a carbon- or nitrogen-site. Nitrogen atom in the heterocycle is optionally quaternized. In a preferred embodiment, when the total number of S and O atoms in the heterocycle exceeds one, these heteroatoms are not adjacent to each other. In another preferred embodiment, the total number of S and O atoms in the heterocycle is not more than 1. As used herein, the term "aromatic heterocyclyl" or "heteroaryl" refers to a stable 5-, 6-, 7-membered monocyclic or bicyclic, or 7-, 8-, 9- or 10-membered bicyclic heterocyclyl aromatic ring that comprises carbon atoms and 1, 2, 3 or 4 heteroatoms in the ring independently selected from N, O and S. Nitrogen atom may be substituted or unsubstituted (i.e., N or NR, wherein R is H or another substituent as defined herein). Nitrogen and sulfur heteroatoms may be optionally oxidized (i.e., NO and S (O)$_p$, wherein p is 1 or 2). It should be noted that the total number of S and O atoms in the aromatic heretocycle is not more than 1. The bridge ring is also encompassed within the definition of heterocycle. A bridge ring would be formed when one or more atoms (i.e., C, O, N or S) link two non-adjacent carbon or nitrogen atoms. Preferably, the bridge ring includes, but is not limited to, one carbon atom, two carbon atoms, one nitrogen atom, two nitrogen atom, and one carbon-nitrogen bond. It should be noted that one bridge always converts a mono-cycle to a triple-cycle. In a bridge ring, the substituent(s) of the ring may also be attached to the bridge.

Examples of the heterocyclic compounds include, but are not limited to: acridinyl, azocinyl, benzimidazolyl, benzofuryl, benzothiofuryl, benzothiophenyl, benzoxazolyl, benzoxazolinyl, benzothiazolyl, benzotriazolyl, benzotetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolyl, 2H,6H-1,5,2-dithiazinyl, dihydrofuro[2,3-b]tetrahydrofuran, furyl, furazanyl, imidazolidinyl, imidazolinyl, imidazolyl, 1H-indazolyl, indolenyl, indolinyl, indolizinyl, indolyl, 3H-indolyl, isobenzofuryl, isoindolyl, isoindolinyl, isoquinolyl, isothiazolyl, isoxazolyl, methylenedioxyphenyl, morpholinyl, naphthyridinyl, octahydroisoquinolyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, hydroxyindolyl, pyrimidyl, phenanthridinyl, phenanthrolinyl, phenazinyl, phenothiazinyl, benzoxanthinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridyl, pyrrolidinyl, pyrrolinyl, 2H-pyrrolyl, pyrrolyl, quinazolinyl, quinolyl, 4H-quinolizinyl, quinoxalinyl, quinuclidinyl, tetrahydrofuryl, tetrahydroisoquinolyl, tetrahydroquinolyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, isothiazolyl, thienyl, thienooxazolyl, thienothiazolyl, thienoimidazolyl, thiophenyl, triazinyl, 1,2,3-triazolyl, 1,2,4-triazolyl, 1,2,5-triazolyl, 1,3,4-triazolyl, and xanthenyl. Fused ring and spiro ring compounds are also included.

Unless defined otherwise, the term "hydrocarbyl" or its specific terms (e.g., alkyl, alkenyl, alkynyl, aryl, etc.), per se or as a portion of another substituent, represent a linear, branched, or cyclic hydrocarbon radical or a combination thereof, and may: be completely saturated (e.g., alkyl), mono- or multi-unsaturated (e.g., alkenyl, alkynyl, aryl); be mono- or multi-substituted; be monovalent (e.g., methyl), divalent (e.g., methylene) or multivalent (e.g., methine); and comprise divalent or multivalent atomic group(s) having a specified number of carbon atoms (e.g., $C_1$-$C_{12}$ represents 1-12 carbon atoms, $C_{1-12}$ is selected from $C_1$, $C_2$, $C_3$, $C_4$, $C_5$, $C_6$, $C_7$, $C_8$, $C_9$, $C_{10}$, $C_{11}$ and $C_{12}$; $C_{3-12}$ is selected from $C_3$, $C_4$, $C_5$, $C_6$, $C_7$, $C_8$, $C_9$, $C_{10}$, $C_{11}$ and $C_{12}$). The term "hydrocarbyl" comprise, but is not limited to, aliphatic hydrocarbyl and aromatic hydrocarbyl, wherein the aliphatic hydrocarbyl may be linear or cyclic, and in particular include, but are not limited to, alkyl, alkenyl, alkynyl; and the aromatic hydrocarbyl includes, but are not limited to, 6-12 membered aromatic hydrocarbyls, such as, phenyl, naphthyl and the like. In some embodiments, the term "hydrocarbyl" represents linear or branched atomic groups or the combination thereof, and may be completely saturated, mono- or poly-unsaturated, and may comprise divalent and multivalent atomic group(s). Examples of the saturated hydrocarbon atomic group include, but are not limited to, methyl, ethyl, n-propyl, iso-propyl, n-butyl, tert-butyl, iso-butyl, sec-butyl, iso-butyl, cyclohexyl, (cyclohexyl)methyl, cyclopropylmethyl, and homologs or isomers of n-pentyl, n-hexyl, n-heptyl, n-octyl and other atomic groups. The unsaturated hydrocarbyl may have one or more double bond(s) or triple bond(s), and the examples thereof include, but are not limited to, ethenyl, 2-propenyl, butenyl, crotyl, 2-isopentenyl, 2-(butadienyl), 2,4-pentadienyl, 3-(1,4-pentadienyl), ethynyl, 1- and 3-propynyl, 3-butynyl, and higher homologs and isomers.

Unless defined otherwise, the term "hetero-hydrocarbyl" or its specific terms (e.g., heteroalkyl, heteroalkenyl, heteroalkynyl, heteroaryl, etc.), per se or in combination with another term, represents a stable linear, branched or cyclic hydrocarbon atomic group or a combination thereof, and consists of a number of carbon atoms and at least one heteroatom. In some embodiments, the term "heteroalkyl", per se or in combination with another term, represents a stable linear, branched hydrocarbon atomic group or a combination thereof, and consists of a number of carbon atoms and at least one heteroatom. In a typical embodiment, the heteroatom is selected from B, O, N and S, wherein nitrogen and sulfur atoms are optionally oxidized, and the nitrogen heteroatom is optionally quaternized. The heteroatom or heteroatomic group may be located at any site of the hetero-hydrocarbyl, including a site through which the hetero-hydrocarbyl is attached to the remaining moiety of the molecule. However, the term "alkoxy", "alkylamino" and "alkylthio" (or thio-alkoxy) are routine expressions, and refer to those alkyl groups attached to the remaining moiety of the molecule via one oxygen atom, amino, or sulfur atom, respectively. Examples comprise, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —$CH_2$—CH=N—$OCH_3$ and —CH=CH—N($CH_3$)—$CH_3$. At most two heteroatoms may be consecutive, e.g., —$CH_2$—NH—$OCH_3$.

Unless defined otherwise, the term "cyclohydrocarbyl", "heterocyclohydrocarbyl" or their specific terms (e.g., aryl, heteroaryl, cycloalkyl, heterocycloalkyl, cycloalkylene, heretocycloalkylene, cycloalkynyl, heretocycloalkynyl, etc.), per se or in combination with other terms, represent cyclized "hydrocarbyl", "hetero-hydrocarbyl", respectively. Moreover, for hetero-hydrocarbyl or heterocyclohydrocarbyl (e.g., heteroalkyl, heterocycloalkyl), the heteroatom(s) may be located at the site through which the heterocyclyl is attached to the remaining moiety of the molecule. Examples of cyclohydrocarbyl include, but are not limited to, cyclopentyl, cyclohexyl, 1-cyclohexenyl, 3-cyclohexenyl, cycloheptyl, and the like. Non-limiting examples of the heterocyclyl comprise 1-(1,2,5,6-tetrahydropyridyl), 1-piperidyl, 2-piperidyl, 3-piperidyl, 4-morpholinyl, 3-morpholinyl, tetrahydrofuran-2-yl, tetrahydrofuranoindol-3-yl, tetrahydrothiophen-2-yl, tetrahydrothiophen-3-yl, 1-piperazinyl and 2-piperazinyl.

Unless defined otherwise, the term "alkyl" refers to a linear or branched saturated hydrocarbyl, and may be mono-substituted (e.g., —$CH_2F$) or multi-substituted (e.g., —$CF_3$), and may be monovalent (e.g., methyl), divalent (e.g., methylene) or multivalent (e.g., methine). Examples of alkyl comprise methyl (Me), ethyl (Et), propyl (e.g., n-propyl and iso-propyl), butyl (e.g., n-butyl, iso-butyl, s-butyl, t-butyl), pentyl (e.g., n-pentyl, iso-pentyl, neo-pentyl) or the like.

Unless defined otherwise, "alkenyl" refers to an alkyl having one or more carbon-carbon double bond(s) at any site of the chain, and may be mono-substituted or multi-substituted, and may be monovalent, divalent or multivalent. Examples of alkenyl comprise ethenyl, propenyl, butenyl, pentenyl, hexenyl, butadienyl, pentadienyl, hexadienyl, and the like.

Unless defined otherwise, "alkynyl" refers to an alkyl having one or more carbon-carbon triple bond(s) at any site of the chain, and may be mono-substituted or multi-substituted, and may be monovalent, divalent or multivalent. Examples of alkynyl comprise ethynyl, propynyl, butynyl, pentynyl and the like.

Unless defined otherwise, cycloalkyl comprises any stable cyclic or polycyclic hydrocarbyl in which all carbon atoms are saturated, and may be mono-substituted or multi-substituted, and may be monovalent, divalent or multivalent. Examples of these cycloalkyls include, but are not limited to, cyclopropyl, norbornanyl, [2.2.2]bicyclooctyl, [4.4.0]bicyclodecanyl, and the like.

Unless defined otherwise, cycloalkylene comprises any stable cyclic or polycyclic hydrocarbyl which comprises one or more unsaturated carbon-carbon double bond(s) at any site of the ring(s), and may be mono-substituted or multi-substituted, may be monovalent, divalent or multivalent. Examples of these cycloalkylenes comprise, but are not limited to, cyclopentenyl, cyclohexenyl, and the like.

Unless defined otherwise, cycloalkynyl comprises any stable cyclic or polycyclic hydrocarbyl which have one or more carbon-carbon triple bond(s) at any site of the ring(s), and may be mono-substituted or multi-substituted, and may be monovalent, divalent or multivalent.

Unless defined otherwise, the term "halo-" or "halogen", per se or as a part of another substituent, represents fluorine, chlorine, bromine or iodine atom. Moreover, the term "haloalkyl" comprises monohalo-alkyl and polyhalo-alkyl. For example, the term "halo($C_1$-$C_4$) alkyl" comprises, but is not limited to, trifluoromethyl, 2,2,2-trifluoroethyl, 4-chlorobutyl and 3-bromopropyl, etc. Unless defined otherwise, examples of haloalkyl include, but are not limited to, trifluoromethyl, trichloromethyl, pentafluoroethyl, and pentachloroethyl.

"Alkoxy" represents the above alkyl that is attached via an oxygen bridge and has a certain number of carbon atoms.

Unless defined otherwise, $C_{1-6}$ alkoxy comprises $C_1$, $C_2$, $C_3$, $C_4$, $C_5$ and $C_6$ alkoxy. Examples of alkoxy comprise, but are not limited to, methoxy, ethoxy, n-propoxy, iso-propoxy, n-butoxy, sec-butoxy, tert-butoxy, n-pentyloxy and s-pentyloxy.

Unless defined otherwise, the term "aryl" refers to a multi-unsaturated aromatic hydrocarbon substituent, may be mono- or multi-substituted, may be mono-, di-, or polyvalent, and may be mono- or poly-cyclic (e.g., 1-3 ring(s), of which at least one ring is aromatic) fused or covalently bound to each other. The term "heteroaryl" refers to aryl (or ring) containing 1-4 heteroatom(s). In an exemplary embodiment, the heteroatom is selected from B, N, O and S, wherein nitrogen and sulfur atoms are optionally oxidized, and nitrogen atom is optionally quaternized. Heteroaryl may be attached via a heteroatom to the remaining moiety of a molecule. Non-limiting examples of aryl or heteroaryl comprise phenyl, naphthyl, diphenyl, pyrrolyl, pyrazolyl, imidazolyl, pyrazinyl, oxazolyl, phenyl-oxazolyl, isoxazolyl, thiazolyl, furanyl, thienyl, pyridyl, pyrimidyl, benzothiazolyl, purinyl, benzimidazolyl, indolyl, isoquinolyl, quinoxalinyl, quinolyl, 1-naphthyl, 2-naphthyl, 4-diphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furanyl, 3-furanyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl and 6-quinolyl. The substituent of any one of the above aryl and heteroaryl cyclic system is selected from the acceptable substituents as described below.

Unless defined otherwise, when it is used in combination with other terms (e.g., aryloxy, arylthio, aralkyl), aryl comprises the aryl and heteroaryl rings as defined above. Thus, the term "aralkyl" comprises those groups having aryl attached to alkyl (e.g., benzyl, phenylethyl, pyridylmethyl, etc.), and those alkyl groups in which carbon atom(s) (e.g., methylene) have been replaced with oxygen atom(s), such as, phenoxymethyl, 2-pyridyloxymethyl-3-(1-naphthyloxy) propyl and the like.

The term "leaving group" refers to a functional group or atom which can be replaced with another functional or atom via a substitution reaction (e.g., a nucleophilic substitution reaction). For instance, representative leaving groups comprise trifluoromethanesulfonate; chloride, bromide, iodide; sulfonate, e.g., methanesulfonate, tosylate, p-bromobenzenesulfonate, p-toluenesulfonate, and the like; acyloxy, e.g., acetoxy, trifluoroacetoxy, etc.

The term "protective group" include, but are not limited to, a "amino protective group", "hydroxyl protective group" or "mercapto protective group". The term "amino protective group" refers to a protective group adapted to prevent the secondary reaction occurred at the nitrogen site of an amino group. Representative amino protective groups include, but are not limited to: formyl; acyl, such as, alkanoyl (e.g., acetyl, trichloroacetyl or trifluoroacetyl); alkoxycarbonyl, such as, tert-butoxycarbonyl (Boc); arylmethoxycarbonyl, such as, carbobenzoxy (Cbz) and 9-fluorenylmethoxycarbonyl (Fmoc); arylmethyl, such as, benzyl (Bn), trityl (Tr), 1,1-di-(4'-methoxy phenyl) methyl; silyl, such as, trimethylsilyl (TMS) and tert-butyl dimethylsilyl (TBS), etc. The term "hydroxyl protective group" refers to a protective group adapted to prevent the secondary reaction of a hydroxyl group. Representative hydroxyl protective groups include, but are not limited to: alkyl, such as, methyl, ethyl and tert-butyl; acyl, such as, alkanoyl (e,g, acetyl); arylmethyl, such as, benzyl (Bn), p-methoxybenzyl (PMB), 9-fluorenylmethyl (Fm) and benzhydryl (diphenylmethyl, DPM); silyl, such as, trimethylsilyl (TMS) and tert-butyl dimethylsilyl (TBS), etc.

The compounds of the present invention may be prepared by a variety of synthetic methods well known by those persons skilled in the art, including the embodiments as listed below, the embodiments formed by the embodiments as listed below in combination with other chemical synthetic methods, as well as equivalence(s) well known by those persons skilled in the art. Preferred embodiments include, but are not limited to the examples of the present invention.

The solvent as used in the present invention can be commercially available. The follow abbreviations are used in the present invention: aq represents aqueous; HATU represents O-(7-azabenzotriazol-1-yl)-N,N,N',N'-tetramethylureahexafluorophosphate; EDC represents N-(3-dimethylaminopropyl)-N'-ethylcarbodiimide hydrochloride; m-CPBA represents 3-chloroperoxybenzoic acid; eq represents equivalent; CDI represents Carbonyl Diimidazole; DCM represents dichloromethane; PE represents petroleum ether; DIAD represents di-iso-propyl azodicarboxylate; DMF represents N, N-dimethylformamide; DMSO represents dimethylsulfoxide; EtOAc represents ethyl acetate; EtOH represents ethanol; MeOD represents methanol; CBz represents benzyloxycarbonyl, an amino protective group; Boc represents tert-butyloxycarbonyl, an amino protective group; HOAc represents acetic acid; $NaCNBH_3$ represents sodium cyanoborohydride; r.t. represents room temperature; O/N represents overnight; THF represents tetrahydrofuran; $Boc_2O$ represents di-tert-butyl dicarbonate; TFA represents trifluoroacetic acid; DIPEA represents di-iso-propylethylamine; $SOCl_2$ represents sulfoxide chloride; $CS_2$ represents carbon disulfide; TsOH represents p-toluenesulfonic acid; NFSI represents N-fluoro-N-(benzenesulfonyl)benzenesulfonamide; NCS represents 1-chloro pyrrolidine-2,5-dione; n-$Bu_4NF$ represents tetrabutylammonium fluoride; iPrOH represents 2-propanol; mp represents melting point; LDA represents lithium di-iso-propylamide.

The compounds are named manually or by ChemDraw® software, and the commercially available compounds are named based on the supplier's catalog names.

DETAILED DESCRIPTION OF THE EMBODIMENTS

Example 1: Compound 1

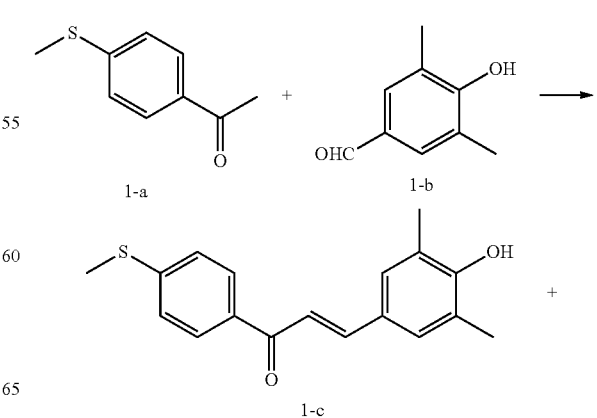

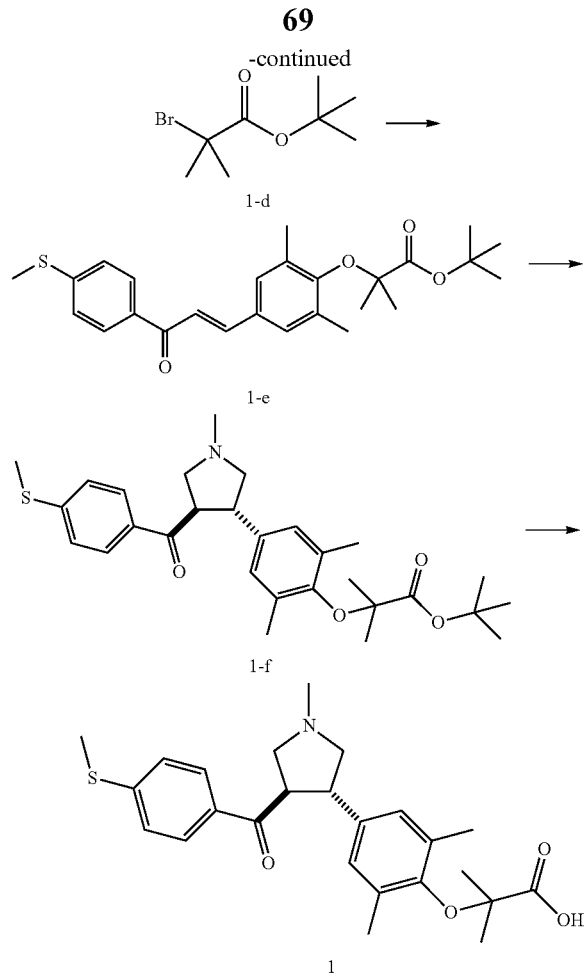

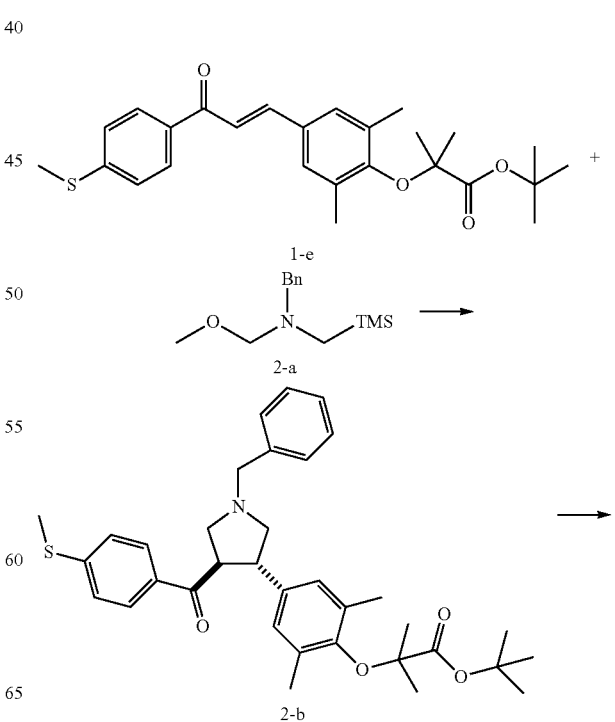

Step 1: Compound 1-c

A solution of Compound 1-a (5.00 g, 30.08 mmol, 1.00 eq) and Compound 1-b (4.52 g, 30.08 mmol, 1.00 eq) in HCl/MeOH (4 N, 40.01 mL, 5.32 eq) was stirred at 20° C. for 16 h. The reaction mixture was concentrated under reduced pressure to give a crude product. The crude product was washed with dichloromethane/MeOH solution (1:1, 50 mL) to give Compound 1-c.

MS m/z (ESI): 298.9 [M+1].

Step 2: Compound 1-e

A solution of Compound 1-c (2.00 g, 6.70 mmol, 1.00 eq), Compound 1-d (2.99 g, 13.40 mmol, 2.49 mL, 2.00 eq), potassium carbonate (1.85 g, 13.40 mmol, 2.00 eq) and potassium iodide (111.26 mg, 670.00 μmol, 0.10 eq) in dimethylsulfoxide (30.00 mL) was stirred under nitrogen protection at 90° C. for 12 h. Water (30 mL) was added into the reaction mixture, and extracted with ethyl acetate (30 mL×3). The combined organic phase was washed with water (20 mL×2) and saturated brine (20 mL×2), dried over anhydrous sodium sulfate, filtered, and concentrated under reduced pressure to give a crude product. The crude product was purified by silica gel chromatography (petroleum ether/ethyl acetate=3/1) to give Compound 1-e.

$^1$H NMR (400 MHz, CDCl$_3$) δ ppm 7.98-7.94 (m, 2H), 7.71 (d, J=15.8 Hz, 1H), 7.42 (d, J=15.8 Hz, 1H), 7.34-7.29 (m, 2H), 7.28 (s, 2H), 2.55 (s, 3H), 2.28 (s, 6H), 1.52 (s, 9H), 1.46 (s, 6H).

Step 3: Compound 1-f

A solution of Compound 1-e (300.00 mg, 680.91 μmol, 1.00 eq), 2-(methylamino)acetic acid (151.65 mg, 1.70 mmol, 2.50 eq) and paraformaldehyde (368.02 mg, 4.09 mmol, 6.00 eq) in toluene (10.00 mL) was stirred under nitrogen protection at 110° C. for 12 h. The mixture was concentrated under reduced pressure. The residue was purified by silica gel column chromatography (petroleum ether/ethyl acetate=1/1) to give Compound 1-f.

MS m/z (ESI): 498.3 [M+1].

$^1$H NMR (400 MHz, CDCl$_3$) δ ppm 7.65 (d, J=8.5 Hz, 2H), 7.14 (d, J=8.5 Hz, 2H), 6.86 (s, 2H), 3.93-3.85 (m, 1H), 3.66 (q, J=7.0 Hz, 1H), 3.03 (t, J=8.7 Hz, 2H), 2.97-2.91 (m, 1H), 2.80-2.73 (m, 1H), 2.48 (s, 3H), 2.42 (s, 3H), 2.18 (s, 6H), 1.51 (s, 9H), 1.41 (s, 6H).

Step 4: Compound 1

Under nitrogen protection, a solution of Compound 1-f (100.00 mg, 200.93 μmol, 1.00 eq) in dichloromethane (5.00 mL) was added dropwise with trifluoroacetic acid (1.50 mL) at 0° C. The mixture was stirred at 20° C. for 1 h. The mixture was concentrated under reduced pressure. The residue was dissolved in ethyl acetate (30 mL). The organic phase was washed with water (10 mL×2) and saturated brine (10 mL×2), dried over anhydrous sodium sulfate, filtered, and concentrated under reduced pressure. The residue was purified by silica gel column chromatography (petroleum ether/ethyl acetate=1:2) to give Compound 1.

MS m/z (ESI): 442.1 [M+1].

$^1$H NMR (400 MHz, DMSO-d$_6$) δ ppm 7.74 (d, J=8.5 Hz, 2H), 7.27 (d, J=8.5 Hz, 2H), 6.91 (s, 2H), 4.02 (td, J=6.7, 9.0 Hz, 1H), 3.63 (q, J=7.4 Hz, 1H), 3.07 (t, J=9.3 Hz, 1H), 2.99 (t, J=8.4 Hz, 1H), 2.77 (dd, J=6.0, 9.3 Hz, 1H), 2.60 (t, J=8.3 Hz, 1H), 2.51 (br. s., 3H), 2.31 (s, 3H), 2.12 (s, 6H), 1.34 (s, 6H).

Example 2: Compound 2

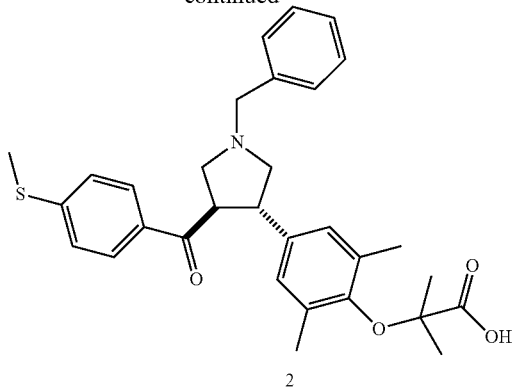

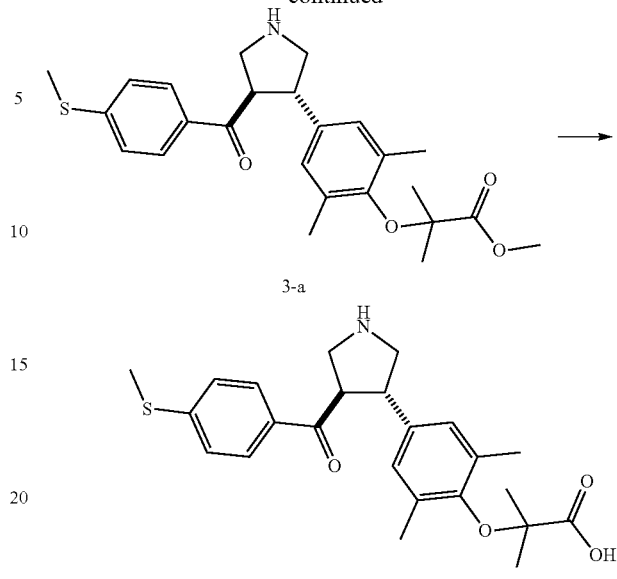

3-a

3

Step 1: Compound 2-b

Under nitrogen protection, a solution of Compounds 1-e (200.00 mg, 453.94 μmol, 1.00 eq) and 2-a (129.32 mg, 544.73 μmol, 1.20 eq) in toluene (3.00 mL) was added dropwise with trifluoroacetic acid (50.00 μL) at 0° C. The mixture was stirred at 20° C. for 1 h. The mixture was adjusted with a saturated solution of sodium bicarbonate to pH-7. The organic phase was concentrated under reduced pressure. The residue was purified by silica gel column chromatography (petroleum ether/ethyl acetate=5:1) to give Compound 2-b.

MS m/z (ESI): 574.3 [M+1].

$^1$H NMR (400 MHz, CDCl$_3$) δ ppm 7.67 (d, J=8.5 Hz, 2H), 7.40-7.36 (m, 2H), 7.32 (t, J=7.3 Hz, 2H), 7.26-7.22 (m, 1H), 7.14 (d, J=8.5 Hz, 2H), 6.88 (s, 2H), 3.93-3.85 (m, 1H), 3.75-3.62 (m, 3H), 3.11 (t, J=8.9 Hz, 1H), 3.01 (t, J=8.7 Hz, 1H), 2.89 (dd, J=6.9, 9.2 Hz, 1H), 2.82 (dd, J=6.3, 9.3 Hz, 1H), 2.48 (s, 3H), 2.18 (s, 6H), 1.50 (s, 9H), 1.41 (s, 6H).

Step 2: Compound 2

A HCl/ethyl acetate solution (4 N, 217.85 μL, 5.00 eq) was added into a solution of Compound 2-b (100.00 mg, 174.28 μmol, 1.00 eq) in ethyl acetate (2.00 mL) at 20° C. The mixture was stirred at 20° C. for 8 h. The mixture was concentrated under reduced pressure, and the residue was purified by preparative High Performance Liquid Chromatography to give Compound 2.

MS m/z (ESI): 518.3 [M+1].

$^1$H NMR (400 MHz, MeOD-d$_4$) δ ppm 7.62-7.55 (m, 4H), 7.53-7.47 (m, 3H), 7.14 (d, J=8.5 Hz, 2H), 6.94 (s, 2H), 4.49 (s, 2H), 4.46-4.40 (m, 1H), 3.90-3.81 (m, 1H), 3.79-3.71 (m, 2H), 3.61-3.50 (m, 2H), 2.49 (s, 3H), 2.19 (s, 6H), 1.42 (s, 6H).

Example 3: Compound 3

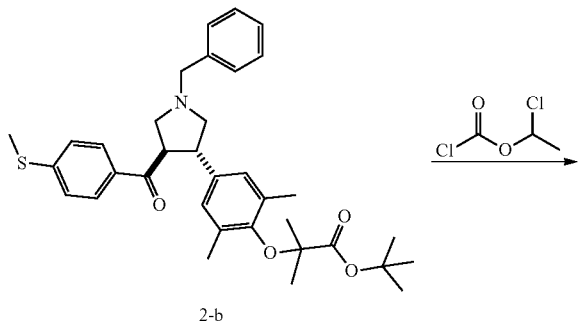

Step 1

Compound 3-a

A solution of Compound 2-b (1.00 g, 1.74 mmol, 1.00 eq) and 1-chloroethyl methylchloroformate (746.30 mg, 5.22 mmol, 3.00 eq) in 1,2-dichloroethane (10.00 mL) was stirred at 80° C. for 8 h. The mixture was concentrated under reduced pressure. Then, methanol (10.00 mL) was added into the residue, heated to 80° C., and stirred for 1 h. The mixture was concentrated under reduced pressure. The residue was purified by silica gel column chromatography (petroleum ether/ethyl acetate=5/1) to give Compound 3-a.

MS m/z (ESI): 442.1 [M+1].

$^1$H NMR (400 MHz, CDCl$_3$) δ ppm 7.57 (d, J=8.5 Hz, 2H), 7.09 (d, J=8.5 Hz, 2H), 6.91 (s, 2H), 4.22 (q, J=8.2 Hz, 1H), 3.94-3.74 (m, 6H), 3.71-3.52 (m, 2H), 2.47 (s, 3H), 2.11 (s, 6H), 1.40 (d, J=4.8 Hz, 6H).

Step 2: Compound 3

A sodium hydroxide solution (2 N, 339.69 μL, 3.00 eq) was added into a solution of Compound 3-a (100.00 mg, 226.46 μmol, 1.00 eq) in ethanol (3.00 mL) at 20° C. The mixture was stirred at 20° C. for 1 h. The mixture was neutralized with a HCl solution (1 N) to pH-7, and then concentrated under reduced pressure. Methanol (20 mL) was added into the residue. The mixture was stirred at 20° C. for 10 min and then filtered. The filtrate was concentrated under reduced pressure. The residue was purified by preparative High Performance Liquid Chromatography to give Compound 3.

MS m/z (ESI): 428.2 [M+1].

$^1$H NMR (400 MHz, MeOD-d$_4$) S ppm 7.64 (d, J=8.5 Hz, 2H), 7.19 (d, J=8.5 Hz, 2H), 6.93 (s, 2H), 4.40 (q, J=7.8 Hz, 1H), 3.87-3.68 (m, 3H), 3.53-3.43 (m, 2H), 2.51 (s, 3H), 2.20 (s, 6H), 1.39 (s, 6H).

Examples 4 and 5: Compounds 4 and 5

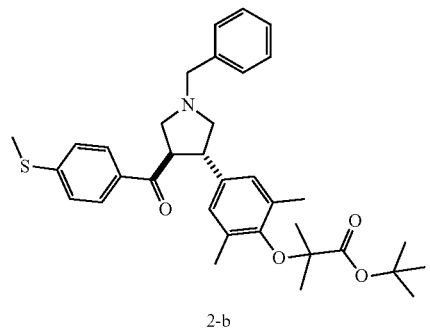
2-b

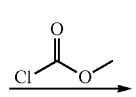

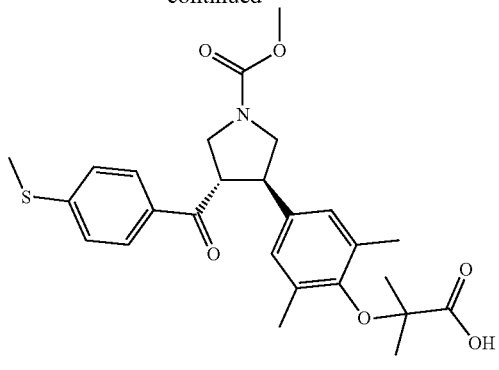
4 or 5

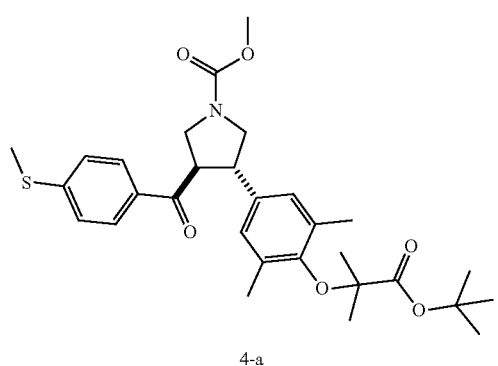
4-a

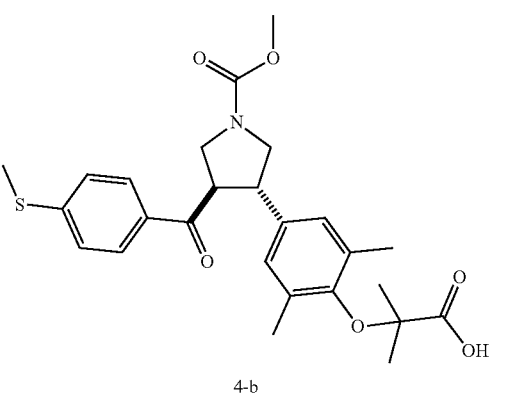
4-b

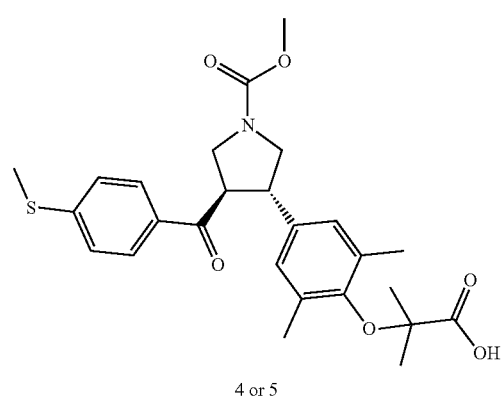 [SMILES: COC(=O)N1C[C@@H](C(=O)c2ccc(SC)cc2)[C@H](c2cc(C)c(OC(C)(C)C(=O)O)c(C)c2)C1]
4 or 5

Step 1: Compound 4-a

Under nitrogen protection, methyl chloroformate (12.35 mg, 130.71 μmol, 1.50 eq) was added into a solution of Compound 2-b (50.00 mg, 87.14 μmol, 1.00 eq) in 1,2-dichloroethane (10.00 mL) at 20° C. The mixture was stirred at 80° C. for 12 h. The mixture was concentrated under reduced pressure. The residue was purified by silica gel column chromatography (petroleum ether/ethyl acetate=5/1) to give Compound 4-a.

MS m/z (ESI): 564.3 [M+23].

$^1$H NMR (400 MHz, CDCl$_3$) δ ppm 7.70 (t, J=8.9 Hz, 2H), 7.18 (d, J=8.0 Hz, 2H), 6.81 (s, 2H), 4.07-3.82 (m, 3H), 3.76-3.50 (m, 6H), 2.50 (s, 3H), 2.16 (s, 6H), 1.49 (s, 9H), 1.39-1.35 (m, 6H).

Step 2: Compound 4-b

Trifluoroacetic acid (500.00 μL) was added into a solution of Compound 4-a (100.00 mg, 184.60 μmol, 1.00 eq) in dichloromethane (2.00 mL) at 20° C. The mixture was stirred at 20° C. for 2 h. The mixture was concentrated under reduced pressure. The residue was purified by silica gel column chromatography (dichloromethane:methanol=20:1) to give Compound 4-b.

MS m/z (ESI): 486.2 [M+1].

$^1$H NMR (400 MHz, MeOD-d$_4$) δ ppm 7.76 (d, J=8.0 Hz, 2H), 7.23 (d, J=8.5 Hz, 2H), 6.93 (s, 2H), 4.39-4.28 (m, 1H), 3.96-3.86 (m, 2H), 3.74 (s, 3H), 3.66 (dd, J=8.9, 10.7 Hz, 1H), 3.60-3.52 (m, 2H), 2.52 (s, 3H), 2.16 (s, 6H), 1.38 (s, 6H).

Step 3: Compounds 4 and 5

Compound 4-b (35 mg) was subjected to chiral separation to give Compound 4; Compound 5.

Compound 4:

MS m/z (ESI): 508.1 [M+23].

$^1$H NMR (400 MHz, CDCl$_3$) δ ppm 7.65 (br. s., 2H), 7.12 (d, J=8.03 Hz, 2H), 6.78 (s, 2H), 3.96-3.84 (m, 3H), 3.66 (s, 3H), 3.60-3.48 (m, 3H), 2.42 (s, 3H), 2.08 (br. s., 6H), 1.33 (br. s., 6H).

Conditions of the chiral resolution: chiral column: Chiralpak AD-3 100×4.6 mm I.D., 3 μm; mobile phase: 40% of methanol (0.05% DEA) in CO$_2$.

Retention time of Compound 4: 4.766 min (peak 1).

Compound 5:
MS m/z (ESI): 508.1 [M+23].
$^1$H NMR (400 MHz, CDCl$_3$) δ ppm 7.65 (br. s., 2H), 7.11 (br. s., 2H), 6.78 (br. s., 2H), 3.93-3.84 (m, 3H), 3.65-3.55 (m, 6H), 2.42 (br. s., 3H), 2.08 (br. s., 6H), 1.34 (br. s., 6H).
Conditions of the chiral resolution: chiral column: Chiralpak AD-3 100×4.6 mm I.D., 3 μm; mobile phase: 40% of methanol (0.05% DEA) in CO$_2$.
Retention time of Compound 5: 5.434 min (peak 2).
Example 6: Compound 6
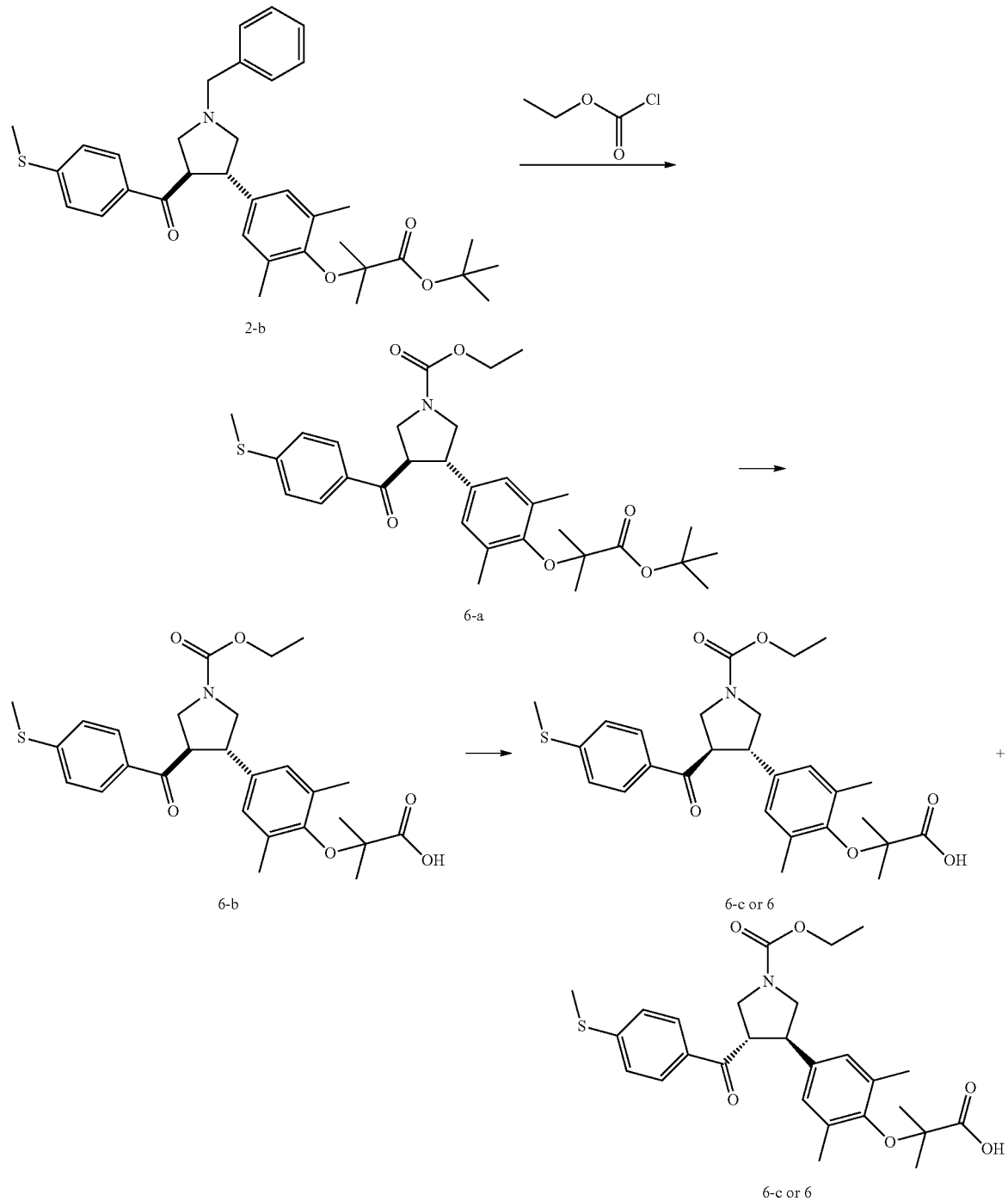

Step 1: Compound 6-a

Ethyl chloroformate (378.26 mg, 3.49 mmol, 331.81 µL, 2.00 eq) was slowly added into a solution of Compound 2-b (1.00 g, 1.74 mmol, 1.00 eq) in dichloromethane (10.00 mL). The mixture was stirred at 25° C. for 16 h. The mixture was concentrated under reduced pressure, and the residue was purified by flash column chromatography to give Compound 6-a.

MS m/z (ESI): 578.2 [M+23].

$^1$H NMR (400 MHz, CDCl$_3$) δ ppm 7.70 (t, J=8.41 Hz, 2H), 7.17 (d, J=8.03 Hz, 2H), 6.81 (s, 2H), 4.16-4.10 (m, 2H), 3.99-3.91 (m, 3H), 3.66-3.53 (m, 3H), 2.49 (s, 3H), 2.15 (br. s., 6H), 1.48 (s, 9H), 1.36 (br. s., 6H), 1.27-1.24 (m, 3H).

Step 2: Compound 6-b

Trifluoroacetic acid (923.40 mg, 8.10 mmol, 599.61 µL, 11.54 eq) was slowly added into a solution of Compound 6-a (390.00 mg, 701.78 µmol, 1.00 eq) in dichloromethane (10.00 mL). The mixture was stirred at 20° C. for 3 h. The mixture was concentrated under reduced pressure, and the residue was purified by preparative High Performance Liquid Chromatography to give Compound 6-b.

MS m/z (ESI): 500.2 [M+1].

$^1$H NMR (400 MHz, CDCl$_3$) δ ppm 7.76-7.72 (m, 2H), 7.20 (d, J=8.28 Hz, 2H), 6.88 (s, 2H), 4.17 (q, J=7.03 Hz, 2H), 4.01-3.92 (m, 3H), 3.61-3.53 (m, 1H), 2.50 (s, 3H), 2.18 (br. s., 6H), 1.46 (s, 6H), 1.27 (t, J=7.03 Hz, 3H).

Step 3: Compound 6

Compound 6-b (100 mg) was subjected to chiral separation to give Compound 6 (24.30 mg, yield: 24.30%).

MS m/z (ESI): 522.1 [M+23].

$^1$H NMR (400 MHz, CDCl$_3$) δ ppm 7.72 (t, J=8.16 Hz, 2H), 7.19 (d, J=8.03 Hz, 2H), 6.86 (br. s., 2H), 4.17 (q, J=7.03 Hz, 2H), 4.01-3.91 (m, 3H), 3.62-3.53 (m, 3H), 2.50 (s, 3H), 2.16 (br. s., 6H), 1.45 (br. s., 6H), 1.27 (t, J=7.03 Hz, 3H).

Conditions of the chiral resolution: chiral column: Chiralpak AD-3 100×4.6 mm I.D., 3 µm; mobile phase: 40% of methanol (0.05% DEA) in CO$_2$.

Retention time of Compound 6: 5.198 min (peak 2).

Example 7: Compound 7

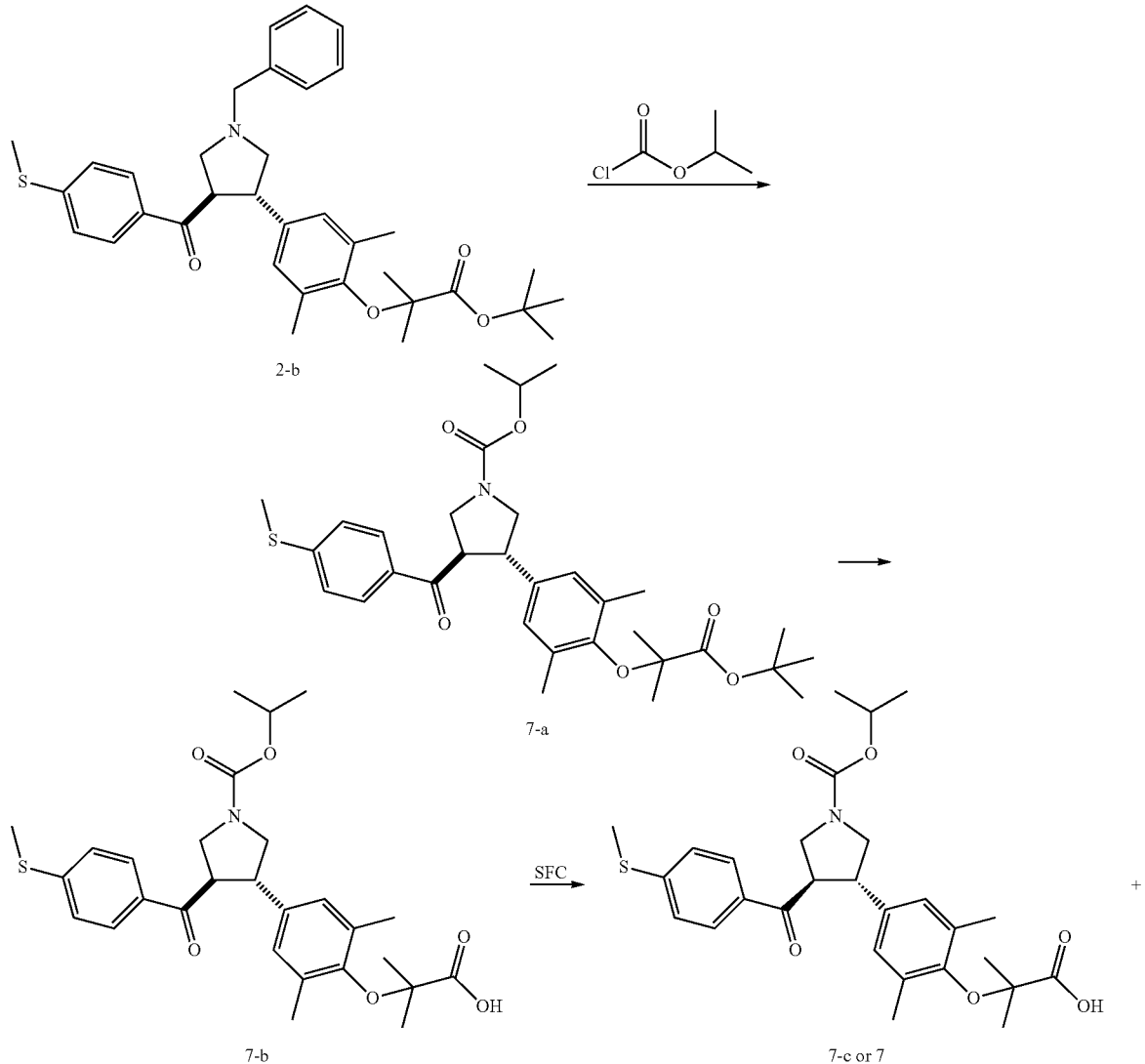

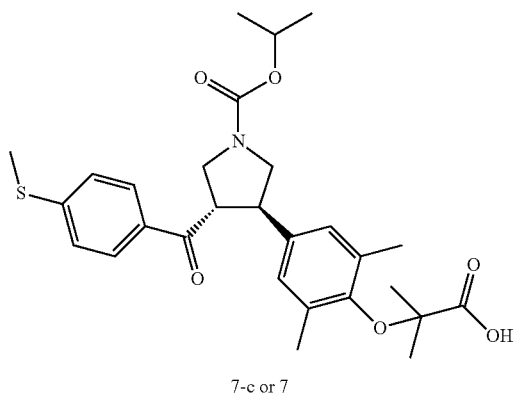

7-c or 7

Step 1: Compound 7-a

Under nitrogen protection, isopropyl chloroformate (426.47 mg, 3.48 mmol, 484.63 μL, 2.00 eq) was added into a solution of Compound 2-b (1.00 g, 1.74 mmol, 1.00 eq) in dichloromethane (10.00 mL) at 20° C. The mixture was stirred at 25° C. for 16 h. The mixture was concentrated under reduced pressure. The residue was purified by flash column chromatography (30.6%, ethyl acetate/petroleum ether) to give Compound 7-a.

MS m/z (ESI): 592.2 [M+23].

$^1$H NMR (400 MHz, CDCl$_3$) δ ppm 7.73-7.68 (m, 2H), 7.18 (d, J=8.28 Hz, 2H), 6.81 (s, 2H), 4.95 (dt, J=12.30, 6.15 Hz, 1H), 4.05-3.88 (m, 3H), 3.71-3.51 (m, 3H), 2.50 (s, 3H), 2.15 (br. s., 6H), 1.48 (s, 9H), 1.37 (d, J=2.76 Hz, 6H), 1.28-1.26 (m, 6H).

Step 2: Compound 7-b

Trifluoroacetic acid (3.09 g, 27.09 mmol, 2.01 mL, 19.29 eq) was added into a solution of Compound 7-a (800.00 mg, 1.40 mmol, 1.00 eq) in dichloromethane (10.00 mL). The mixture was stirred at 25° C. for 3 h. The mixture was concentrated under reduced pressure. The residue was purified by preparative High Performance Liquid Chromatography to give Compound 7-b.

MS m/z (ESI): 514.2 [M+1].

$^1$H NMR (400 MHz, CDCl$_3$) δ ppm 7.76-7.74 (m, 2H), 7.20 (d, J=8.28 Hz, 2H), 6.88 (s, 2H), 4.97-4.94 (m, 1H), 4.02-3.90 (m, 1H), 3.58-3.55 (m, 1H), 2.50 (s, 3H), 2.17 (br. s., 6H), 1.46 (s, 6H), 1.25 (br. s., 6H).

Step 3: Compound 7

Compound 7-b (100 mg) was subjected to chiral separation to give Compound 7.

MS m/z (ESI): 536.1 [M+23].

$^1$H NMR (400 MHz, CDCl$_3$) δ ppm 7.74 (t, J=9.29 Hz, 2H), 7.21 (d, J=8.28 Hz, 2H), 6.88 (br. s., 2H), 4.97 (dt, J=12.30, 6.15 Hz, 1H), 4.07-3.92 (m, 3H), 3.64-3.53 (m, 3H), 2.52 (s, 3H), 2.18 (d, J=4.27 Hz, 6H), 1.47 (br. s., 6H), 1.27 (br. s., 6H).

Conditions of the chiral resolution: chiral column: Chiralpak AD-3 100×4.6 mm I.D., 3 m; mobile phase: 40% of methanol (0.05% DEA) in CO$_2$.

Retention time of Compound 7: 4.639 min (peak 2).

Example 8: Compound 8

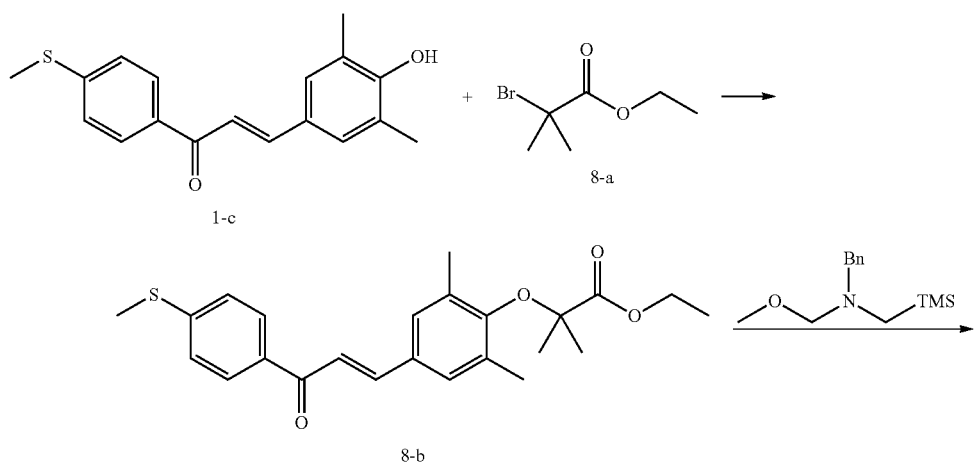

-continued
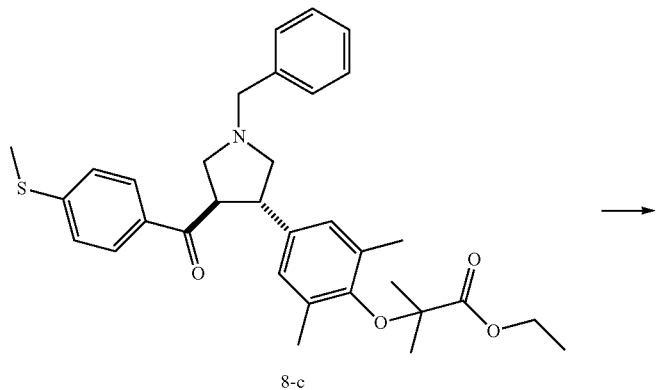
8-c
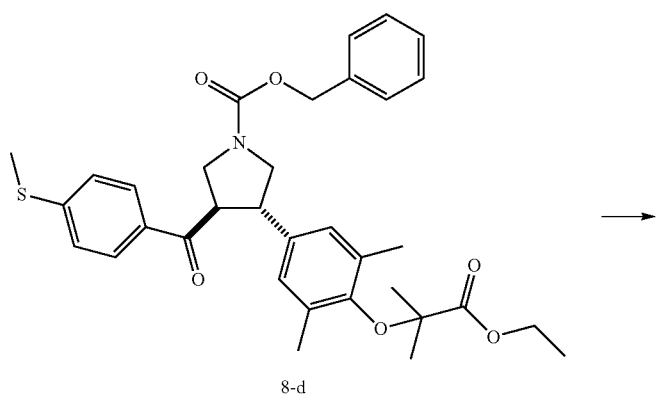
8-d
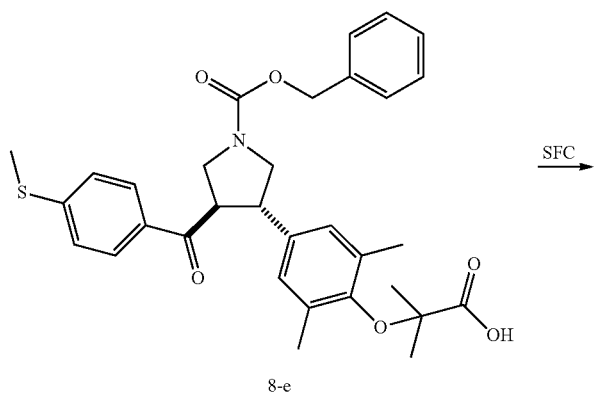
8-e
SFC
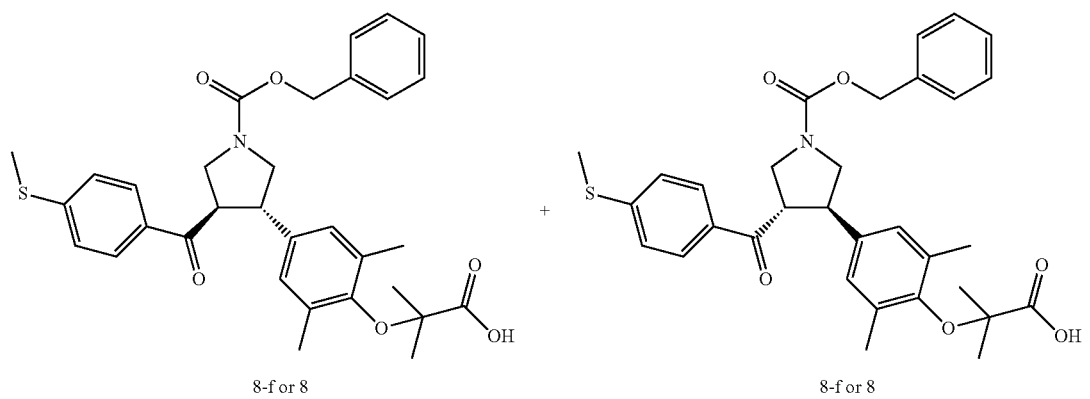
8-f or 8          +          8-f or 8

Step 1: Compound 8-b

A solution of Compound 1-c (7.00 g, 23.46 mmol, 1.00 eq), Compound 8-a (18.30 g, 93.84 mmol, 13.76 mL, 4.00 eq), potassium carbonate (9.73 g, 70.38 mmol, 3.00 eq) and potassium iodide (1.17 g, 7.04 mmol, 0.30 eq) in dimethylsulfoxide (30.00 mL) was stirred under nitrogen protection at 110° C. for 16 h. Ethyl acetate (70.00 mL) was added into the reaction mixture, and washed with water (400 mL×3). The organic phase was dried over anhydrous sodium sulfate, filtered, and concentrated under reduced pressure to give a crude product. The crude product was purified by silica gel column chromatography (petroleum ether/ethyl acetate=15/1) to give Compound 8-b.

MS m/z (ESI): 413.1 [M+1].

$^1$H NMR (400 MHz, CDCl$_3$) δ ppm 7.95 (d, J=8.28 Hz, 2H), 7.71 (d, J=15.56 Hz, 1H), 7.42 (d, J=15.56 Hz, 1H), 7.31-7.28 (m, 4H), 4.30 (q, J=7.28 Hz, 2H), 2.54 (s, 3H), 2.25 (s, 6H), 1.50 (s, 6H), 1.36 (t, J=7.15 Hz, 3H).

Step 2: Compound 8-c

Under nitrogen protection, trifluoroacetic acid (1.53 g, 13.45 mmol, 0.73 eq) was added into a solution of Compound 8-b (7.60 g, 18.42 mmol, 1.00 eq) and N-methoxymethyl-1-phenyl-N-(trimethylsilylethyl)methylamine (5.25 g, 22.10 mmol, 1.20 eq) in dichloromethane (40.00 mL) at 0° C. The mixture was stirred at 25° C. for 16 h. The mixture was neutralized with a saturated solution of sodium bicarbonate to pH=7, and then treated with water and dichloromethane (1:1, 200 mL).

The aqueous phase was extracted with dichloromethane (200 mL×2). The combined organic phase was dried over anhydrous sodium sulfate, filtered, and concentrated under reduced pressure. The residue was purified by flash column chromatography (23.1%, ethyl acetate/petroleum ether) to give Compound 8-c.

MS m/z (ESI): 546.6 [M+1].

$^1$H NMR (400 MHz, CDCl$_3$) δ ppm 7.67 (d, J=8.53 Hz, 2H), 7.39-7.37 (m, 2H), 7.32 (t, J=7.53 Hz, 2H), 7.30-7.24 (m, 1H), 7.14 (d, J=8.53 Hz, 2H), 6.88 (s, 2H), 4.28 (q, J=7.03 Hz, 2H), 3.90-3.88 (m, 1H), 3.71-3.65 (m, 3H), 3.11 (t, J=9.03 Hz, 1H), 3.02 (t, J=8.78 Hz, 1H), 2.90 (dd, J=9.03, 7.03 Hz, 1H), 2.82 (dd, J=9.29, 6.27 Hz, 1H), 2.48 (s, 3H), 2.15 (s, 6H), 1.45 (s, 6H), 1.35 (t, J=7.03 Hz, 3H).

Step 3: Compound 8-d

Compound 8-c (1.00 g, 1.83 mmol, 1.00 eq), 1,2-dichloroethane (2.00 mL) and benzyl chloroformate (937.77 mg, 5.50 mmol, 781.48 µL, 3.00 eq) was added into a dried flask. The mixture was stirred at 80° C. for 16 h, and then concentrated under reduced pressure. The residue was purified by flash column chromatography (32.5%, ethyl acetate/petroleum ether) to give Compound 8-d.

MS m/z (ESI): 590.3 [M+1].

Step 4: Compound 8-e

Compound 8-d (680.00 mg, 1.15 mmol, 1.00 eq) and 1,4-dioxane (5.00 mL) was added into a dried flask. Then, lithium hydroxide (82.63 mg, 3.45 mmol, 3.00 eq) and water (1.00 mL) was added. The mixture was stirred at 25° C. for 16 h. The mixture was adjusted with 1N diluted HCl to pH=3, and treated with water and ethyl acetate (1:1, 50 mL). The aqueous phase was extracted by ethyl acetate (20 mL×2). The combined organic phase was dried over anhydrous sodium sulfate, filtered, and concentrated under reduced pressure. The residue was purified by preparative High Performance Liquid Chromatography to give Compound 8-e.

MS m/z (ESI): 562.2 [M+1].

$^1$H NMR (400 MHz, CDCl$_3$) δ ppm 7.75 (dd, J=15.18, 8.16 Hz, 2H), 7.40-7.35 (m, 5H), 7.21 (t, J=7.65 Hz, 2H), 6.89 (s, 2H), 5.19 (d, J=3.51 Hz, 2H), 4.06-3.98 (m, 2H), 3.75-3.61 (m, 2H), 2.52 (s, 3H), 2.19 (s, 6H), 1.48 (d, J=1.76 Hz, 6H).

Step 5: Compound 8

Compound 8-e (50 mg) was subjected to chiral separation to give Compound 8.

MS m/z (ESI): 584.1 [M+23].

$^1$H NMR (400 MHz, CDCl$_3$) δ ppm 7.72 (dd, J=15.56, 8.28 Hz, 2H), 7.37-7.33 (m, 5H), 7.19 (t, J=7.40 Hz, 2H), 6.86 (s, 2H), 5.17-5.13 (m, 2H), 4.04-3.95 (m, 3H), 3.76-3.59 (m, 3H), 2.50 (s, 3H), 2.16 (s, 6H), 1.45 (br. s., 6H).

Conditions of the chiral resolution: chiral column: Chiralpak AD-3 100×4.6 mm I.D., 3 µm; mobile phase: 40% of ethanol (0.05% DEA) in CO$_2$; flow rate: 2.8 mL/min; column temperature: 40° C.

Retention time of Compound 8: 4.956 min (peak 2).

Example 9: Compound 9

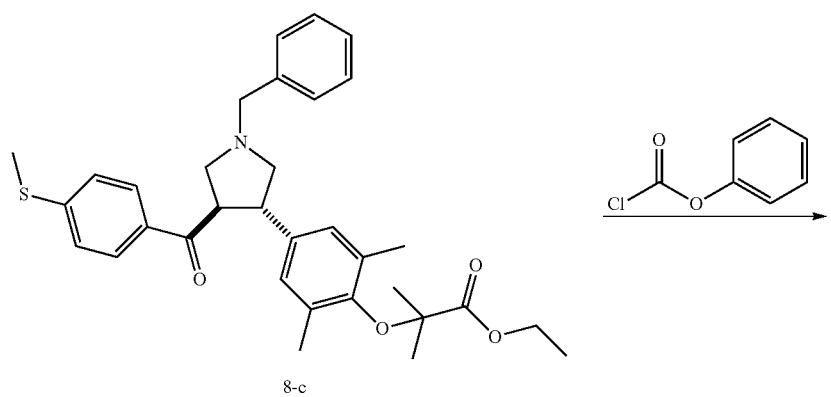

8-c

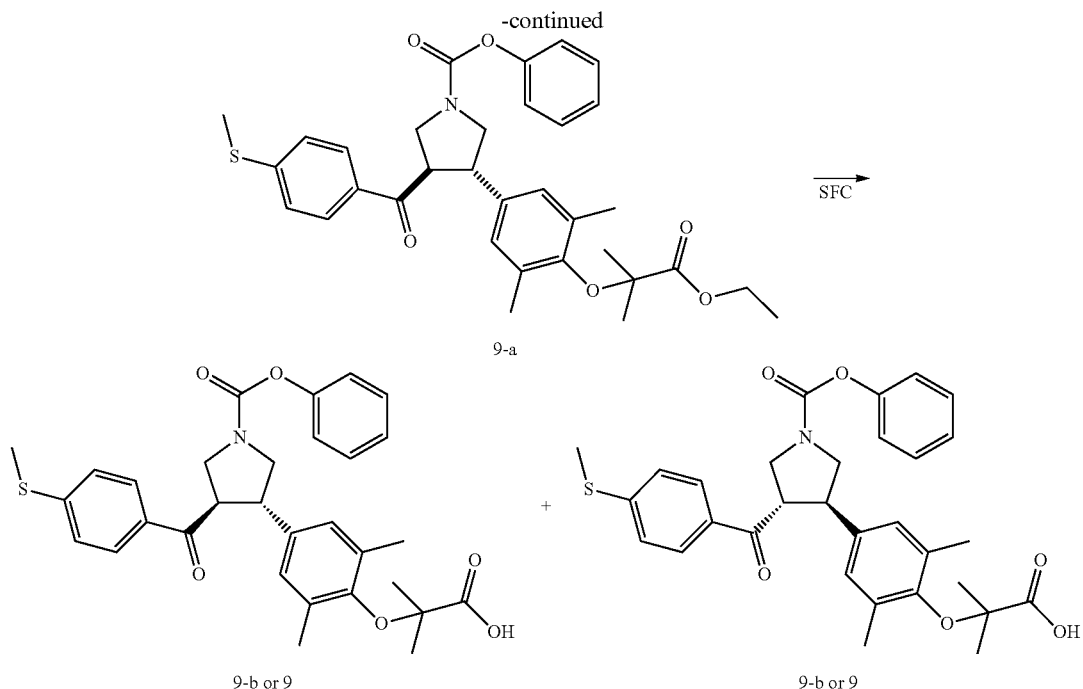

9-a 9-b or 9 + 9-b or 9

Step 1: Compound 9-a

Under nitrogen protection, phenyl chloroformate (294.47 mg, 1.88 mmol, 235.57 μL, 2.00 eq) was slowly added into a solution of Compound 8-c (500.00 mg, 940.36 μmol, 1.00 eq) in dichloromethane (10.00 mL). The mixture was stirred at 25° C. for 16 h. The mixture was concentrated under reduced pressure. The residue was purified by flash column chromatography (40.6%, ethyl acetate/petroleum ether) to give Compound 9-a.

MS m/z (ESI): 576.2 [M+1].

Step 2: Compound 9

Compound 9-a (500.00 mg, 868.48 μmol, 1.00 eq), ethanol (3.00 mL) and 1,4-dioxane (1.00 mL) was added into a flask. Then, lithium hydroxide (62.40 mg, 2.61 mmol, 3.00 eq) and H₂O (1.00 mL) was added. The mixture was stirred at 40° C. for 16 h. The mixture was adjusted with 1N diluted HCl to pH=2, and then treated with water/ethyl acetate (1:1, 50 mL). The aqueous phase was extracted with ethyl acetate (50 mL×2). The combined organic phase was dried over anhydrous sodium sulfate, filtered, and concentrated under reduced pressure. The residue was purified by flash column chromatography (dichloromethane), and the product was subjected to chiral separation to give Compound 9.

MS m/z (ESI): 570.1 [M+23].

¹H NMR (400 MHz, CDCl₃) δ ppm 7.75 (t, J=7.78 Hz, 2H), 7.40-7.36 (m, 2H), 7.24-7.16 (m, 5H), 6.88 (d, J=6.78 Hz, 2H), 4.16-4.10 (m, 3H), 3.88-3.71 (m, 3H), 2.49 (br. s., 3H), 2.12 (br. s., 6H), 1.33 (br. s., 6H).

Conditions of the chiral resolution: chiral column: Chiralpak AD-3 100×4.6 mm I.D., 3 m; mobile phase: 40% of ethanol (0.05% DEA) in CO₂; flow rate: 2.8 mL/min; column temperature: 40° C.

Retention time of Compound 9: 4.709 min (peak 2).

Example 10: Compound 10

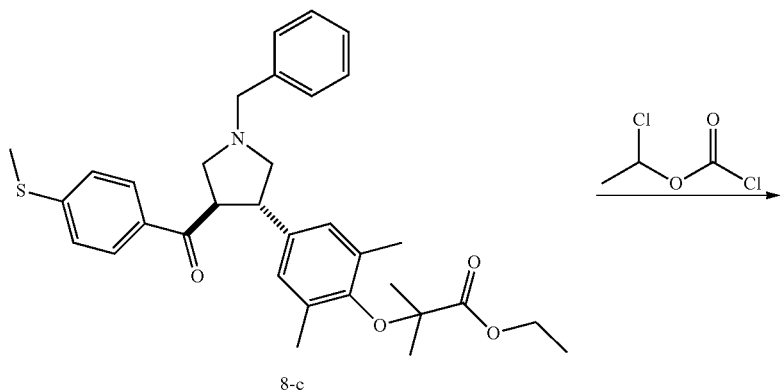

8-c

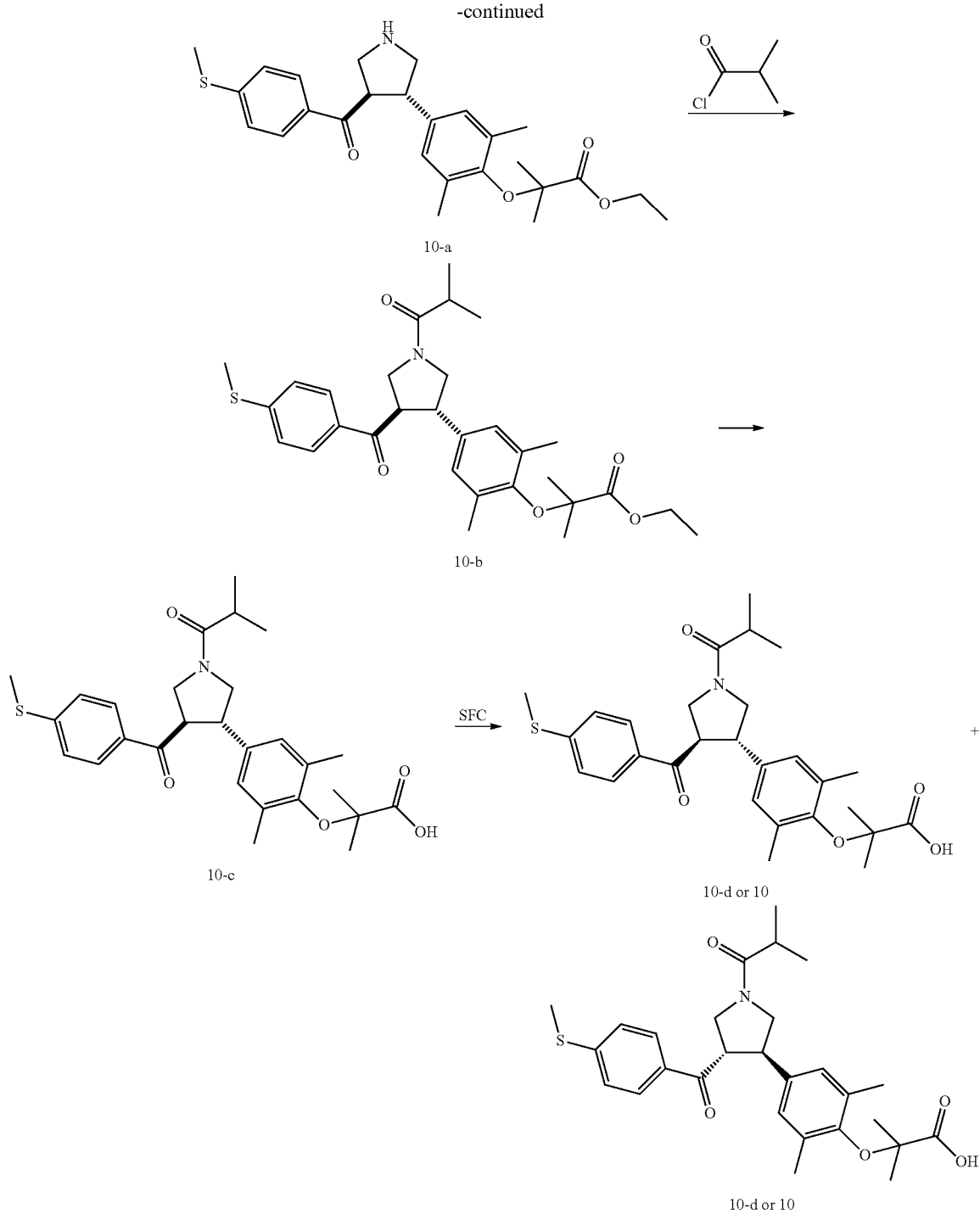

Step 1: Compound 10-a 1-chloroethyl chloroformate (3.93 g, 27.48 mmol, 3.00 eq) was added into a solution of Compound 8-c (5.00 g, 9.16 mmol, 1.00 eq) in toluene (50.00 mL) at 25° C. The mixture was stirred at 80° C. for 16 h. Then, the mixture was concentrated under reduced pressure. The residue was dissolved in methanol (50.00 mL). The solution was stirred at 80° C. for 1 h. The mixture was directly concentrated under reduced pressure. The residue was purified by flash column chromatography (dichloromethane:methanol=100:0-85:15) to give Compound 10-a.

MS m/z (ESI): 456.3 [M+1].

$^1$H NMR (400 MHz, CDCl$_3$) δ ppm 7.59 (d, J=8.53 Hz, 2H), 7.12 (d, J=8.53 Hz, 2H), 6.93 (s, 2H), 4.32-4.26 (m, 2H), 4.23-4.21 (m, 1H), 3.91-3.65 (m, 5H), 2.50 (s, 3H), 2.15 (s, 6H), 1.42 (d, J=5.52 Hz, 6H), 1.36 (t, J=7.03 Hz, 3H).

Step 2: Compound 10-b

Isopropyl chloroformate (140.32 mg, 1.32 mmol, 137.57 µL, 1.50 eq) and triethylamine (177.68 mg, 1.76 mmol, 243.39 µL, 2.00 eq) was added into a solution of Compound 10-a (400.00 mg, 877.94 µmol, 1.00 eq) in dichloromethane (10.00 mL) at 0° C. The mixture was stirred at 20° C. for 2 h. The mixture was concentrated under reduced pressure. The residue was purified by flash column chromatography (dichloromethane:methanol=100:0-80:20) to give Compound 10-b.

MS m/z (ESI): 526.2 [M+1].

1H NMR (400 MHz, CDCl$_3$) δ ppm 7.68 (d, J=8.53 Hz, 1H), 7.58 (d, J=8.53 Hz, 1H), 7.11 (dd, J=8.53, 17.57 Hz, 2H), 6.75 (d, J=9.54 Hz, 2H), 4.11-3.41 (m, 7H), 2.66-2.47 (m, 2H), 2.43 (d, J=1.51 Hz, 3H), 2.06 (d, J=12.05 Hz, 6H), 1.38-1.30 (m, 6H), 1.27 (t, J=7.28 Hz, 3H), 1.15-1.05 (m, 11H).

Step 3: Compound 10-c

Lithium hydroxide (13.67 mg, 570.67 µmol, 3.00 eq) was added into a solution of Compound 10-b (100.00 mg, 190.22 µmol, 1.00 eq) in ethanol (5.00 mL) and water (5.00 mL) at 0° C. The mixture was stirred at 20° C. for 2 h. The mixture was concentrated under reduced pressure. The residue was purified by flash column chromatography (dichloromethane:methanol=100:0-80:20) to give Compound 10-c.

MS m/z (ESI): 498.1 [M+1].

Step 4: Compound 10

The compound was isolated by chiral supercritical chromatography to give Compound 10.

MS m/z (ESI): 498.2 [M+1].

$^1$H NMR (400 MHz, CDCl$_3$) δ ppm 7.77 (d, J=8.28 Hz, 1H), 7.68 (d, J=8.53 Hz, 1H), 7.20 (dd, J=8.53, 17.57 Hz, 2H), 6.86 (d, J=12.30 Hz, 2H), 4.18-3.85 (m, 4H), 3.67-3.62 (m, 2H), 2.69 (qd, J=6.55, 12.99 Hz, 1H), 2.51 (d, J=2.01 Hz, 3H), 2.17 (d, J=13.80 Hz, 6H), 1.46-1.43 (m, 6H), 1.18 (dd, J=6.78, 10.04 Hz, 6H).

Conditions of the chiral resolution: chiral column: Chiralpak AD-3 100×4.6 mm I.D., 3 µm; mobile phase: 40% of methanol (0.05% DEA) in CO$_2$; flow rate: 2.8 mL/min; column temperature: 40° C.

Retention time of Compound 10: 4.188 min (peak 2).

Example 11: Compound 11

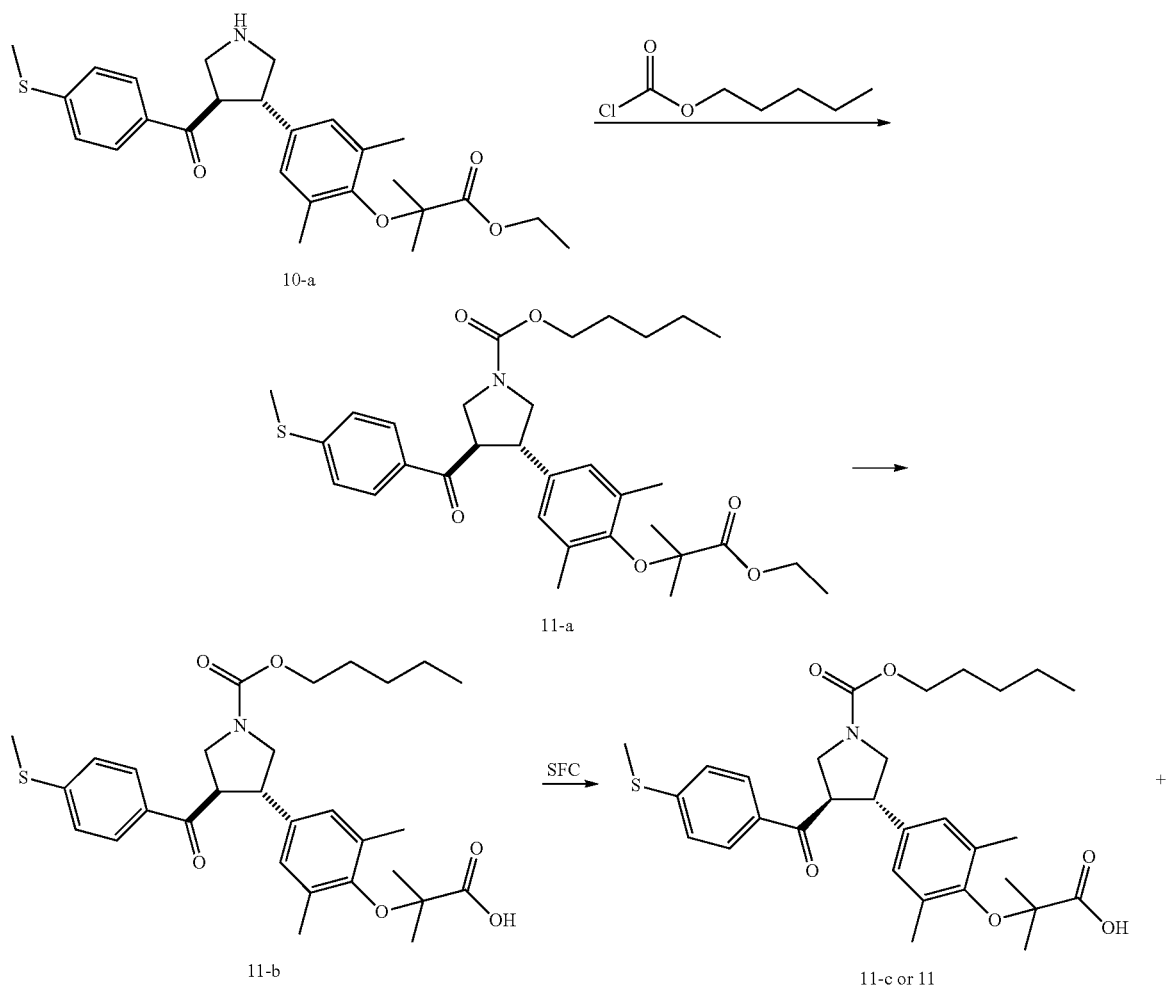

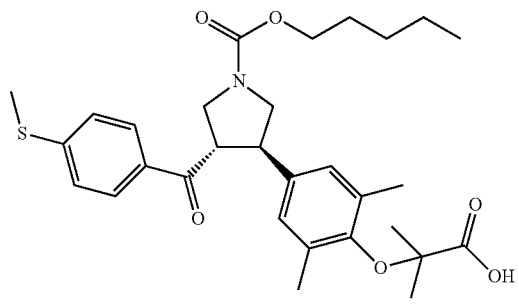

11-c or 11

Step 1: Compound 11-a

Compound 10-a (300.00 mg, 658.46 μmol, 1.00 eq), triethylamine (199.89 mg, 1.98 mmol, 273.82 μL, 3.00 eq) and dichloromethane (10.00 mL) was added into a dried round-bottom flask of 100 mL. Then, n-pentyl chloroformate (247.91 mg, 1.65 mmol, 2.50 eq) was added. The mixture was stirred at 15° C. for 2 h. The mixture was diluted with dichloromethane (20 mL), added with a saturated solution of sodium bicarbonate (10 mL), and then stirred for 10 min. The organic phase was washed with saturated brine (10 mL×2), dried over anhydrous sodium sulfate, and concentrated under reduced pressure. The residue was purified by silica gel column chromatography (petroleum ether:ethyl acetate=10:1-3:1) to give Compound 11-a.

MS m/z (ESI): 592.1 [M+23].

1H NMR (400 MHz, CDCl$_3$) δ 7.63 (t, J=11.2 Hz, 2H), 7.10 (d, J=7.6 Hz, 2H), 6.75 (s, 2H), 4.08-3.44 (m, 10H), 2.43 (s, 3H), 2.06 (br s, 6H), 1.57 (t, J=6.8 Hz, 6H), 1.34-1.25 (m, 7H), 0.83 (t, J=6.4 Hz, 3H).

Step 2: Compound 11-b

Lithium hydroxide (73.65 mg, 1.76 mmol, 5.00 eq) was added into a solution of Compound 11-a (200.00 mg, 351.03 μmol, 1.00 eq) in ethanol (2.00 mL), tetrahydrofuran (2.00 mL) and H$_2$O (1.00 mL). The mixture was stirred at 50° C. for 3 h. The mixture was adjusted with a saturated potassium bisulfate solution to pH=2-3, and then added with ethyl acetate (10 mL) and water (10 mL). The aqueous phase was extracted with ethyl acetate (10 mL×2). The combined organic phase was dried over anhydrous sodium sulfate, and concentrated under reduced pressure. The residue was purified by preparative thin-layer chromatography (petroleum ether:ethyl acetate=15:1) to give Compound 11-b.

MS m/z (ESI): 564.1 [M+23].

1H NMR (400 MHz, CDCl$_3$) δ 7.74 (t, J=8.8 Hz, 2H), 7.20 (d, J=8.0 Hz, 2H), 6.87 (d, J=2.8 Hz, 2H), 4.13-3.14 (m, 8H), 2.51 (s, 3H), 2.18 (d, J=5.2 Hz, 6H), 2.02 (s, 4H), 1.67-1.64 (m, 2H), 1.35-1.27 (m, 6H), 0.92 (br.s., 3H).

Step 3: Compound 11

The compound was isolated by chiral supercritical chromatography to give Compound 11.

MS m/z (ESI): 536.1 [M+23].

1H NMR (400 MHz, CDCl$_3$) δ 7.65 (br s, 2H), 7.11 (br d, J=7.28 Hz, 2H), 6.78 (br s, 2H), 4.08-3.37 (m, 10H), 2.42 (s, 3H), 2.07 (br s, 6H), 1.56 (br d, J=7.04 Hz, 3H), 1.31 (br s, 4H), 0.94-0.67 (m, 6H).

Conditions of the chiral resolution: chiral column: Chiralpak AD-3 100×4.6 mm I.D., 3 m; mobile phase: 40% of ethanol (0.05% DEA) in CO$_2$.

Retention time of Compound 11: 5.294 min (peak 2).

Example 12: Compound 12

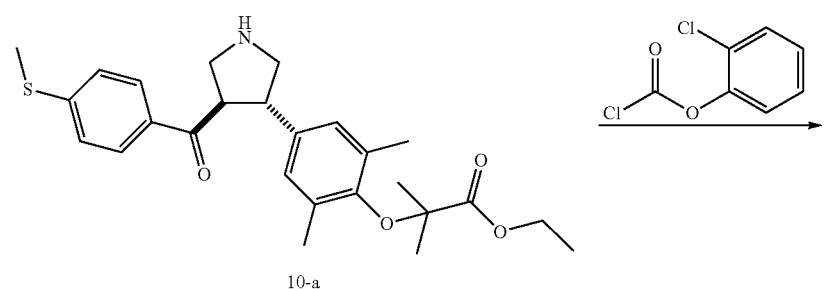

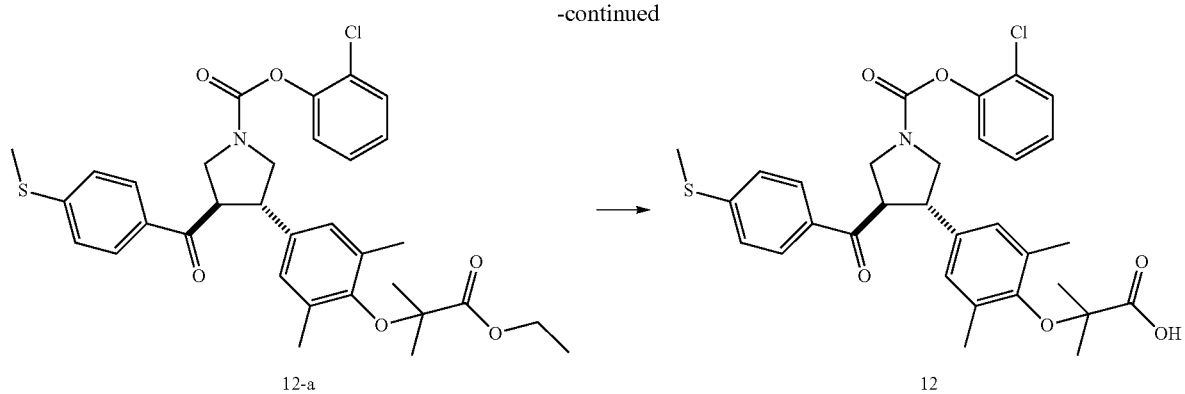

12-a → 12

Step 1

Compound 12-a (2-chlorophenyl) chloroformate (83.85 mg, 438.97 μmol, 61.20 μL, 2.00 eq) and triethylamine (44.42 mg, 438.97 μmol, 60.85 μL, 2.00 eq) was slowly added into a solution of Compound 10-a (100.00 mg, 219.49 μmol, 1.00 eq) in dichloromethane (5.00 mL). The mixture was stirred at 25° C. for 4 h. The mixture was concentrated under reduced pressure. The residue was purified by flash column chromatography (52.6%, ethyl acetate/petroleum ether) to give Compound 12-a.

MS m/z (ESI): 632.1 [M+23].

Step 2: Compound 12

Compound 12-a (180.00 mg, 295.00 μmol, 1.00 eq) and ethanol (6.00 mL) was added into a flask. Then, lithium hydroxide (21.20 mg, 885.00 μmol, 3.00 eq) and water (2.00 mL) were added. The mixture was stirred at 40° C. for 5 h. The mixture was adjusted with 1N diluted HCl to pH=3, and treated with water/ethyl acetate (1:1, 20 mL). The aqueous phase was extracted with ethyl acetate (20 mL×2). The combined organic phase was dried over anhydrous sodium sulfate, filtered, and concentrated under reduced pressure. The residue was purified by preparative High Performance Liquid Chromatography to give Compound 12.

MS m/z (ESI): 604.1 [M+23].

$^1$H NMR (400 MHz, CDCl$_3$) δ ppm 7.69 (dd, J=8.53, 6.78 Hz, 2H), 7.36 (dd, J=8.03, 1.25 Hz, 1H), 7.20 (s, 2H), 7.16-7.13 (m, 3H), 6.86 (d, J=7.28 Hz, 2H), 4.15-4.03 (m, 3H), 3.79-3.65 (m, 3H), 2.44 (s, 3H), 2.12 (d, J=4.77 Hz, 6H), 1.40-1.39 (m, 6H).

Examples 13 and 14: Compounds 13 and 14

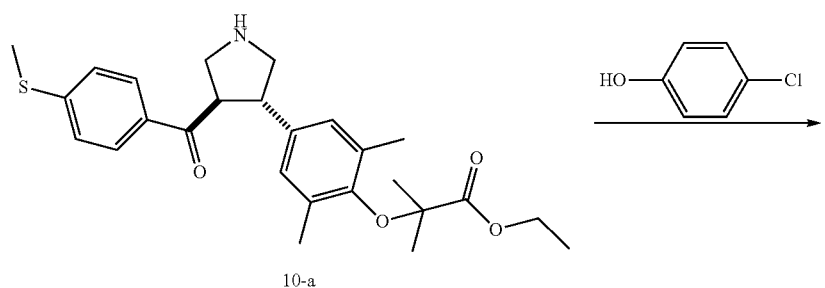

10-a

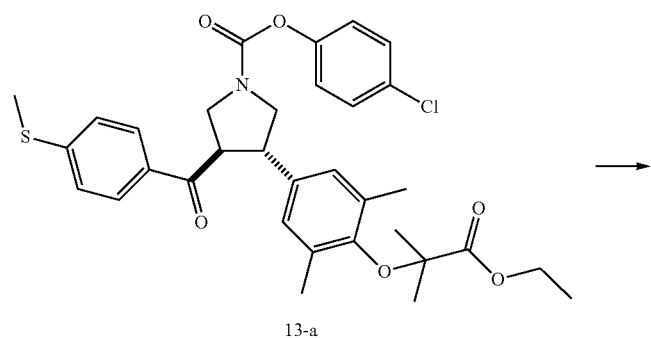

13-a

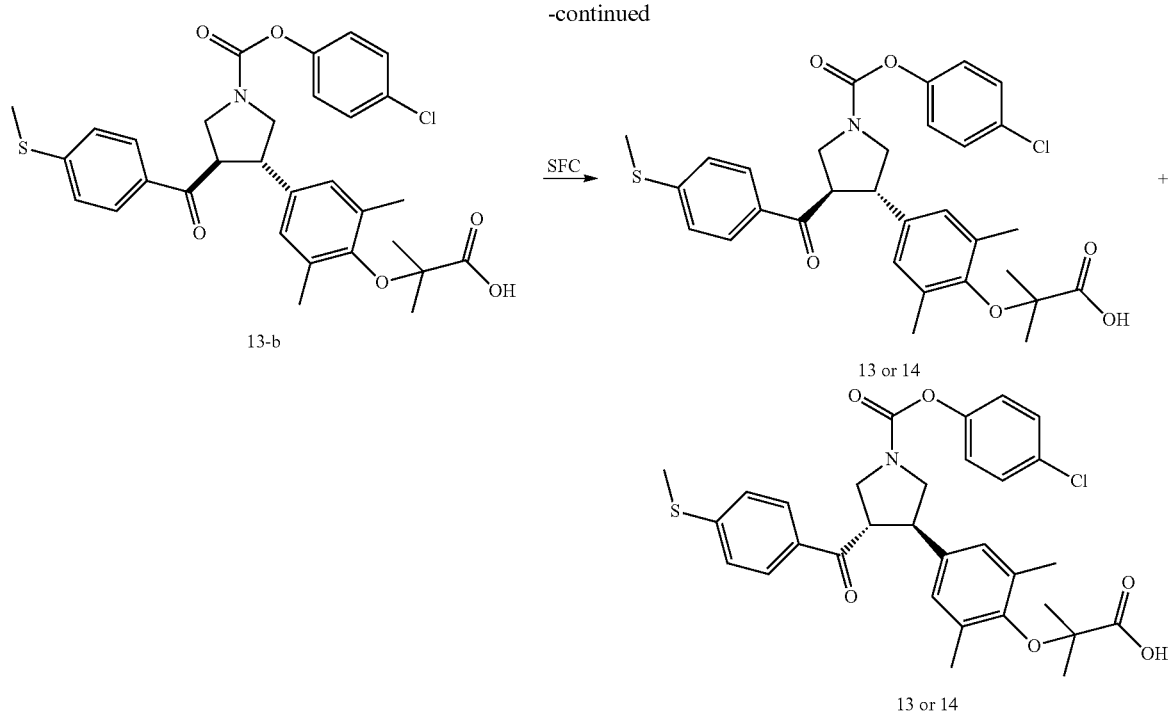

13-b 13 or 14

13 or 14

Step 1: Compound 13-a

Under nitrogen protection, a solution of triphosgene (97.70 mg, 329.23 µmol, 1.00 eq) in tetrahydrofuran (3 mL) was added dropwise into a solution of 4-chlorophenol (42.33 mg, 329.23 µmol, 32.31 µL, 1.00 eq) in tetrahydrofuran (15.00 mL) 0° C., and then triethylamine (33.31 mg, 329.23 µmol, 45.63 µL, 1.00 eq) was slowly added into it. The mixture was stirred at 25° C. for 2 h. After the reaction finished, the mixture was filtered, and the filter cake was washed with tetrahydrofuran (5 mL×2). Compound 10-a (150.00 mg, 329.23 µmol, 1.00 eq) and triethylamine (33.31 mg, 329.23 µmol, 45.63 µL, 1.00 eq) was added into the filtrate at 25° C. The mixture was concentrated under reduced pressure. The residue was purified by flash column chromatography (ethyl acetate/petroleum ether=22.7%) to give Compound 13-a.

MS m/z (ESI): 610.1 [M+1].

Step 2: Compound 13-b

Lithium hydroxide (21.20 mg, 885.00 µmol, 3.00 eq) and H$_2$O (2.00 mL) was added into a solution of Compound 13-a (255.00 mg, 417.92 µmol, 1.00 eq) in ethanol (6.00 mL). The mixture was stirred at 40° C. for 16 h. The mixture was adjusted with 1N diluted HCl to pH=2, and treated with water/ethyl acetate (1:1, 20 mL). The aqueous phase was extracted with ethyl acetate (20 mL×2). The combined organic phase was dried over anhydrous sodium sulfate, filtered, and concentrated under reduced pressure. The residue was purified by preparative High Performance Liquid Chromatography to give Compound 13-b.

MS m/z (ESI): 604.1 [M+23].

$^1$H NMR (400 MHz, CDCl$_3$) δ ppm 7.69 (dd, J=8.53, 6.78 Hz, 2H), 7.36 (dd, J=8.03, 1.25 Hz, 1H), 7.20 (s, 2H), 7.16-7.13 (m, 3H), 6.86 (d, J=7.28 Hz, 2H), 4.15-4.02 (m, 3H), 3.79-3.65 (m, 3H), 2.44 (s, 3H), 2.12 (d, J=4.77 Hz, 6H), 1.40-1.39 (m, 6H).

Step 3: Compounds 13 and 14

Compound 13-b (30.00 mg, 51.54 µmol, 1.00 eq) was isolated and purified by chiral supercritical fluid chromatography to give Compound 13; Compound 14.

Compound 13:

MS m/z (ESI): 582.1 [M+1].

$^1$H NMR (400 MHz, CDCl$_3$) δ ppm 7.67 (t, J=8.66 Hz, 2H), 7.26-7.24 (m, 2H), 7.13 (dd, J=8.53, 4.02 Hz, 2H), 7.03 (d, J=7.94 Hz, 2H), 6.83 (d, J=6.27 Hz, 2H), 4.07-4.00 (m, 3H), 3.79-3.65 (m, 3H), 2.43 (s, 3H), 2.11 (d, J=5.77 Hz, 6H), 1.39 (br s, 6H).

Conditions of the chiral resolution: chiral column: Lux Cellulose-2 150×4.6 mm I.D., 3 µm; mobile phase: 40% of ethanol (0.05% DEA) in CO$_2$; flow rate: 2.5 mL/min; column temperature: 40° C.

Retention time of Compound 13: 5.715 min (peak 1).

Compound 14:

MS m/z (ESI): 582.1 [M+1].

$^1$H NMR (400 MHz, CDCl$_3$) δ ppm 7.68 (t, J=8.41 Hz, 2H), 7.27-7.24 (m, 2H), 7.13 (dd, J=8.53, 4.02 Hz, 2H), 7.03 (d, J=7.94 Hz, 2H), 6.84 (d, J=6.27 Hz, 2H), 4.06-4.00 (m, 3H), 3.79-3.63 (m, 3H), 2.43 (s, 3H), 2.12 (d, J=5.52 Hz, 6H), 1.39-1.38 (m, 6H).

Conditions of the chiral resolution: chiral column: Lux Cellulose-2 150×4.6 mm I.D., 3 µm; mobile phase: 40% of ethanol (0.05% DEA) in CO$_2$; flow rate: 2.5 mL/min; column temperature: 40° C.

Retention time of Compound 14: 9.994 min (peak 2).

Example 15: Compound 15

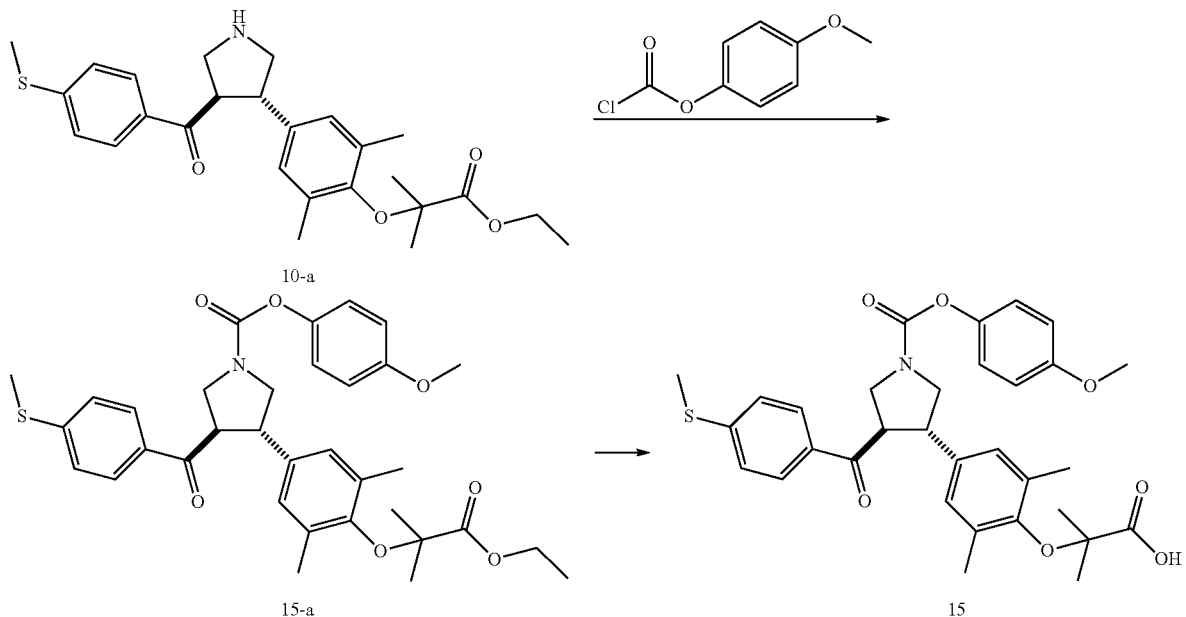

Step 1: Compound 15-a

Compound 10-a (300.00 mg, 658.46 μmol, 1.00 eq), di-iso-propyl ethylamine (170.20 mg, 1.32 mmol, 230.00 μL, 2.00 eq) and trichloromethane (5.00 mL) was added into a 50 mL dried round-bottom flask at 20° C. Then, p-methoxy phenyl chloroformate (184.29 mg, 987.69 μmol, 147.43 μL, 1.50 eq) was added. The mixture was stirred at 20° C. for 2 h. A saturated solution of sodium bicarbonate (5 mL) was added into the mixture, and stirred for 10 min. The aqueous phase was extracted with dichloromethane (10 mL×3). The combined organic phase was washed with saturated brine, dried over anhydrous sodium sulfate, and concentrated under reduced pressure. The residue was purified by silica gel column chromatography (petroleum ether:ethyl acetate=4:1 to 2:1) to give Compound 15-a.

MS m/z (ESI): 606.2 [M+23].

$^1$H NMR (400 MHz, CDCl$_3$) δ ppm 7.65 (dd, J=10.4, 9.2 Hz, 2H), 7.12 (dd, J=8.8, 4.8 Hz, 2H), 6.99 (d, J=8.8 Hz, 2H), 6.81-6.78 (m, 4H), 4.08-3.99 (m, 5H), 3.75-3.59 (m, 7H), 2.43 (s, 3H), 2.08 (s, 3H), 2.07 (s, 3H), 1.55 (b.r.s., 1H), 1.35-1.34 (m, 6H), 1.19 (t, J=6.8 Hz, 1H).

Step 2: Compound 15

Compound 15-a (150.00 mg, 247.63 μmol, 1.00 eq), lithium hydroxide (59.31 mg, 2.48 mmol, 10.00 eq), ethanol (2.00 mL), tetrahydrofuran (2.00 mL) and water (1.00 mL) was added into a reaction flask. The mixture was stirred at 20° C. for 20 h. Lithium hydroxide (59.31 mg, 2.48 mmol, 10.00 eq) was added, and the mixture was stirred at 20° C. for 30 h. The mixture was diluted with water (5 mL), adjusted with a saturated potassium bisulfate solution to pH=2-3, and then added with ethyl acetate (10 mL×3). The organic phase was washed with saturated brine, dried over anhydrous sodium sulfate, and concentrated under reduced pressure. The residue was purified by preparative thin-layer chromatography (ethyl acetate) to give Compound 15.

MS m/z (ESI): 578.2 [M+1].

$^1$H NMR (400 MHz, MeOD-d$_4$) δ ppm 7.64 (dd, J=8.4, 6.8 Hz, 2H), 7.10 (d, J=8.4 Hz, 2H), 6.94 (dd, J=10.0, 8.0 Hz, 2H), 6.85-6.80 (m, 4H), 4.31-4.00 (m, 1H), 3.86-3.85 (m, 1H), 3.84-3.50 (m, 7H), 2.39 (s, 3H), 2.06 (b.r.s, 6H), 1.38-1.36 (m, 6H).

Examples 16 and 17: Compounds 16 and 17

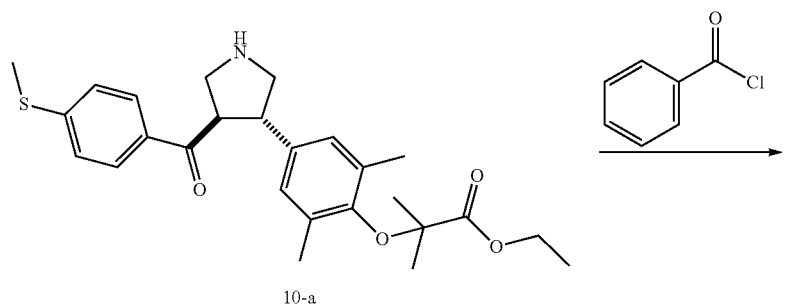

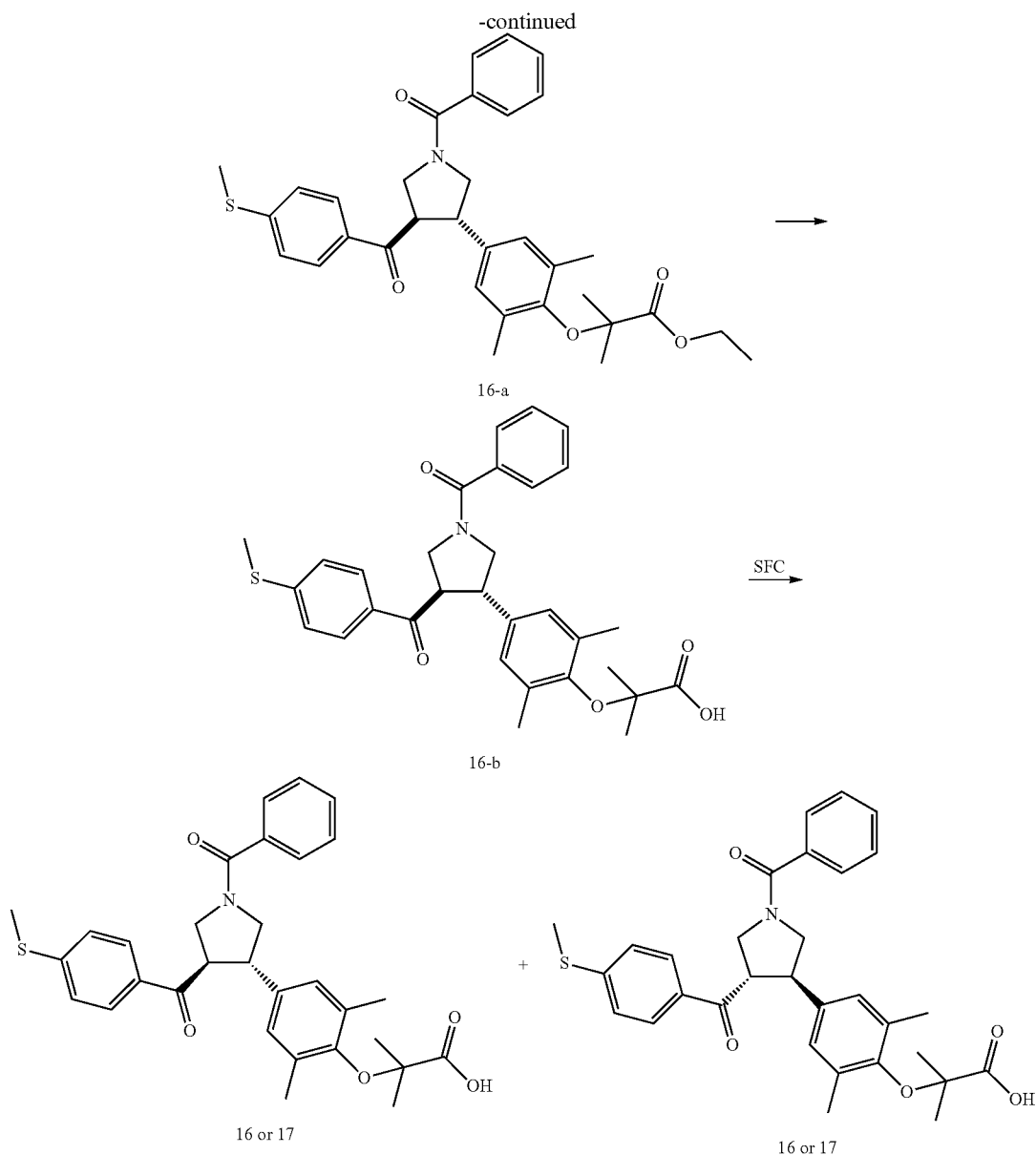

Step 1: Compound 16-a

Benzoyl chloride (185.12 mg, 1.32 mmol, 152.99 μL, 1.50 eq) and triethylamine (177.68 mg, 1.76 mmol, 243.39 μL, 2.00 eq) was added into a solution of Compound 10-a (400.00 mg, 877.94 μmol, 1.00 eq) in dichloromethane (10.00 mL) at 0° C. The mixture was stirred at 20° C. for 2 h. The mixture was concentrated under reduced pressure. The residue was purified by flash column chromatography (dichloromethane:methanol=100:0-80:20) to give Compound 16-a.

MS m/z (ESI): 560.1 [M+1].

$^1$H NMR (400 MHz, CDCl$_3$) δ ppm 7.71 (d, J=8.53 Hz, 1H), 7.58-7.28 (m, 7H), 7.17-6.99 (m, 2H), 6.82-6.68 (m, 2H), 4.19 (br d, J=7.28 Hz, 2H), 4.01-3.51 (m, 5H), 2.42 (d, J=18.57 Hz, 3H), 2.05 (s, 6H), 1.36-1.30 (m, 6H), 1.29-1.23 (m, 3H).

Step 2: Compound 16-b

Lithium hydroxide (213.95 mg, 8.93 mmol, 10.00 eq) was added into a solution of Compound 16-a (500.00 mg, 893.30 μmol, 1.00 eq) in ethanol (10.00 mL) and H$_2$O (5.00 mL) at 20° C. The mixture was stirred at 20° C. for 2 h. The mixture was extracted with dichloromethane (20 mL×3), dried over anhydrous sodium sulfate, filtered, and concentrated under reduced pressure. The residue was purified by flash column chromatography (dichloromethane:methanol=100:0-80:20) to give Compound 16-b.

MS m/z (ESI): 532.1 [M+1].

Step 3: Compounds 16 and 17

Compound 18-b (400 mg, 752.36 μmol, 1.00 eq) was isolated by chiral supercritical chromatography to give Compound 16; Compound 17.

Compound 16:

MS m/z (ESI): 532.5 [M+1].

$^1$H NMR (400 MHz, CDCl$_3$) δ ppm 7.80 (d, J=8.28 Hz, 1H), 7.62-7.55 (m, 3H), 7.44-7.41 (m, 3H), 7.23 (d, J=8.28 Hz, 1H), 7.11 (d, J=8.28 Hz, 1H), 6.89 (s, 1H), 6.82 (s, 1H), 4.31 (dd, J=11.92, 8.91 Hz, 1H), 4.18-4.15 (m, 1H), 3.99-3.93 (m, 3H), 3.77-3.64 (m, 1H), 2.49 (d, J=19.32 Hz, 3H), 2.15 (s, 6H), 1.43 (br. s., 6H).

Conditions of the chiral resolution: chiral column: Chiralpak AD-3 100×4.6 mm I.D., 3 μm; mobile phase: 40% of ethanol (0.05% DEA) in CO$_2$; flow rate: 2.8 mL/min; column temperature: 40° C.

Retention time of Compound 16: 6.673 min (peak 2).

Compound 17:

MS m/z (ESI): 532.1 [M+1].

$^1$H NMR (400 MHz, CDCl$_3$) δ ppm 7.80 (d, J=8.28 Hz, 1H), 7.63-7.54 (m, 3H), 7.44-7.41 (m, 3H), 7.24 (d, J=8.28 Hz, 1H), 7.12 (d, J=8.53 Hz, 1H), 6.87 (d, J=28 Hz, 2H), 4.32-4.15 (m, 2H), 3.96-3.93 (m, 2H), 3.78-3.66 (m, 2H), 2.50 (d, J=19.58 Hz, 3H), 2.16 (s, 6H), 1.44 (br. s., 6H).

Conditions of the chiral resolution: chiral column: Chiralpak AD-3 100×4.6 mm I.D., 3 μm; mobile phase: 40% of ethanol (0.05% DEA) in CO$_2$; flow rate: 2.8 mL/min; column temperature: 40° C.

Retention time of Compound 17: 4.992 min (peak 1).

Example 18: Compound 18

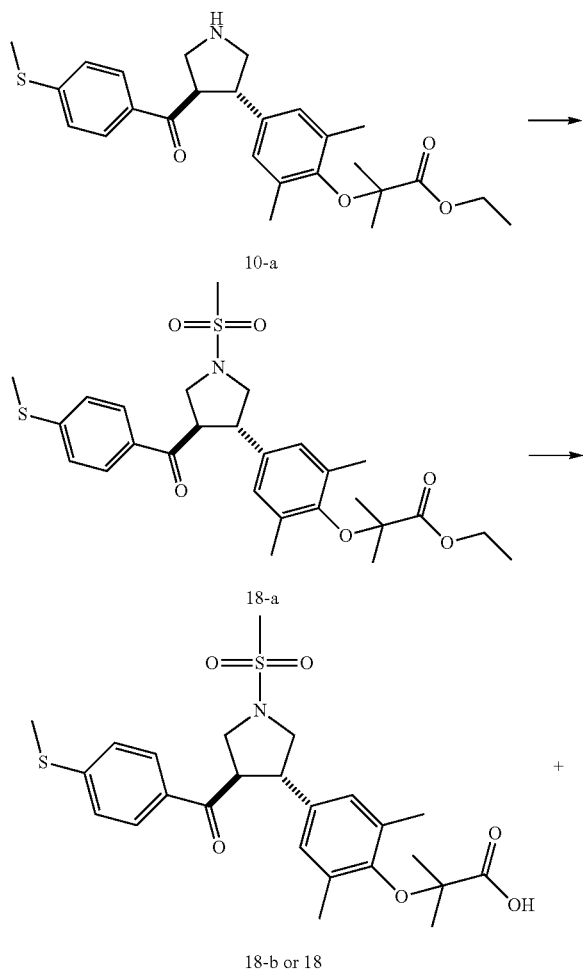

Step 1: Compound 18-a

Mesyl chloride (201.14 mg, 1.76 mmol, 135.91 μL, 2.00 eq) and triethylamine (177.68 mg, 1.76 mmol, 243.40 μL, 2.00 eq) was added into a solution of Compound 10-a (400.00 mg, 877.94 mol, 1.00 eq) in dichloromethane (5.00 mL). The mixture was stirred at 25° C. for 16 h. The mixture was concentrated under reduced pressure. The residue was purified by flash column chromatography (46.1%, ethyl acetate/petroleum ether) to give Compound 18-a.

MS m/z (ESI): 534.1 [M+1].

Step 2: Compound 18

Compound 18-a (110.00 mg, 206.11 μmol, 1.00 eq) and dioxane (1.00 mL) was added into a round-bottom flask. Then, lithium hydroxide (14.81 mg, 618.33 μmol, 3.00 eq) and water (1.00 mL) were added. The mixture was stirred at 40° C. for 16 h. The mixture was adjusted with 1N diluted HCl to pH=3, and was added with water/ethyl acetate (1:1, 50 mL). The aqueous phase was extracted with ethyl acetate (20 mL×2). The combined organic phase was dried over anhydrous sodium sulfate, filtered, and concentrated under reduced pressure. The residue was purified by preparative High Performance Liquid Chromatography. The resulted product was subjected to chiral separation to give Compound 18.

MS m/z (ESI): 528.1 [M+23].

$^1$H NMR □ (400 MHz, MeOD-d$_4$) δ ppm 7.75 (d, J=8.53 Hz, 2H), 7.22 (d, J=8.28 Hz, 2H), 6.95 (s, 2H), 4.62-4.35 (m, 1H), 3.86-3.82 (m, 2H), 3.73-3.68 (m, 1H), 3.57-3.52 (m, 2H), 3.04 (s, 3H), 2.51 (s, 3H), 2.22 (s, 6H), 1.36 (d, J=5.27 Hz, 6H).

Conditions of the chiral resolution: chiral column: Chiralpak OJ-3 100×4.6 mm I.D., 3 μm; mobile phase: 40% of ethanol (0.05% DEA) in CO$_2$.

Retention time of Compound 18: 5.853 min (peak 2).

Example 19: Compound 19

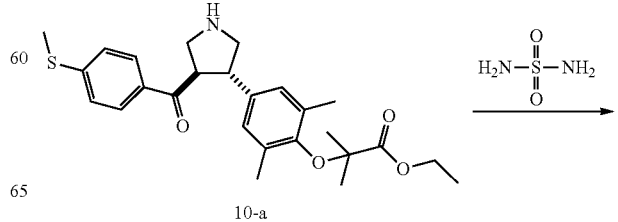

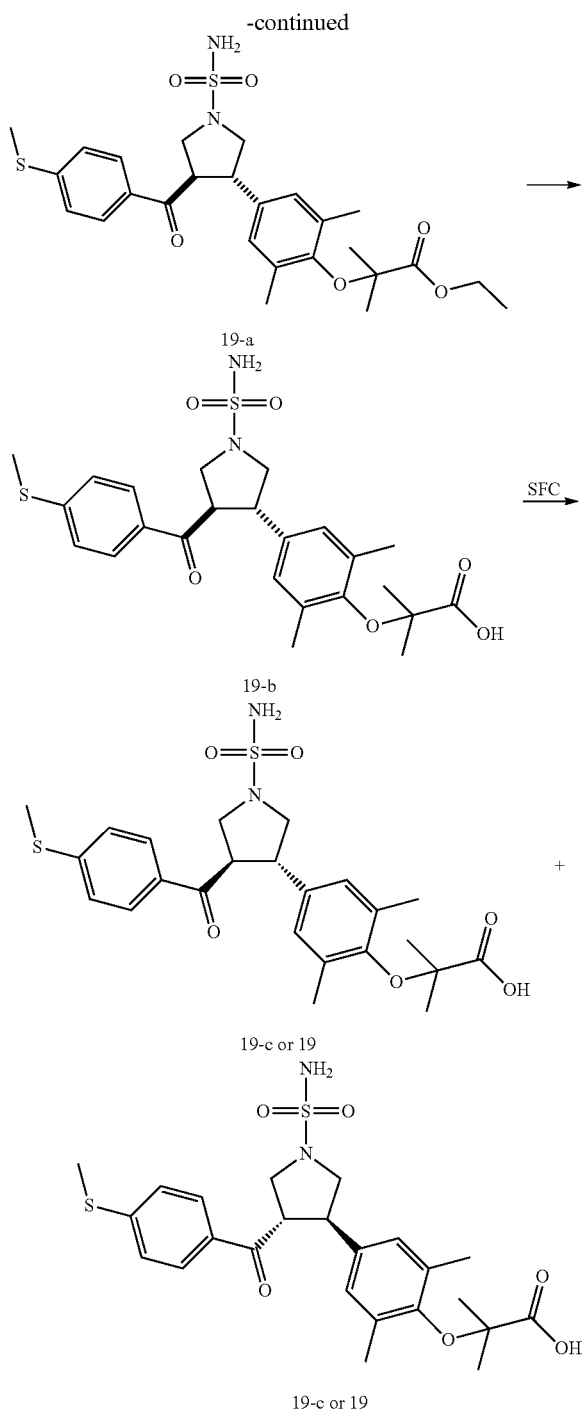

4.48-4.38 (m, 1H), 4.29 (q, J=7.04 Hz, 2H), 3.84-3.56 (m, 9H), 2.52 (s, 3H), 2.17 (s, 6H), 1.45 (d, J=4.02 Hz, 6H), 1.37-1.34 (m, 3H).

Step 2: Compound 19-b

Lithium hydroxide (291.15 mg, 12.16 mmol, 10.00 eq) was added into a solution of Compound 19-a (650.00 mg, 1.22 mmol, 1.00 eq) in ethanol (10.00 mL) and water (5 mL) at 20° C. The mixture was stirred at 20° C. for 2 h. The mixture was extracted with dichloromethane (20 mL×3). The combined organic phase was dried over anhydrous sodium sulfate, filtered, and concentrated under reduced pressure. The residue was purified by flash column chromatography (dichloromethane:methanol=100:0-80:20) to give Compound 19-b.

MS m/z (ESI): 507.1 [M+1].

Step 3: Compound 19

Compound 19-b (400.00 mg, 789.51 µmol, 1.00 eq) was subjected to chiral separation to give Compound 19.

MS m/z (ESI): 507.1 [M+1].

$^1$H NMR (400 MHz, CDCl$_3$) δ ppm 7.71 (d, J=8.04 Hz, 2H), 7.20 (d, J=8.04 Hz, 2H), 6.88 (s, 2H), 4.72 (s, 2H), 4.48-4.38 (m, 1H), 4.29 (q, J=7.04 Hz, 2H), 3.91-3.47 (m, 9H), 2.52 (s, 3H), 2.17 (s, 6H), 1.45 (d, J=4.02 Hz, 6H), 1.38-1.32 (m, 3H).

Conditions of the chiral resolution: chiral column: Chiralpak AD-3 100×4.6 mm I.D., 3 m; mobile phase: 40% of ethanol (0.05% DEA) in CO$_2$; flow rate: 2.8 mL/min; column temperature: 40° C.

Retention time of Compound 19: 4.227 min (peak 2).

Example 20: Compound 20

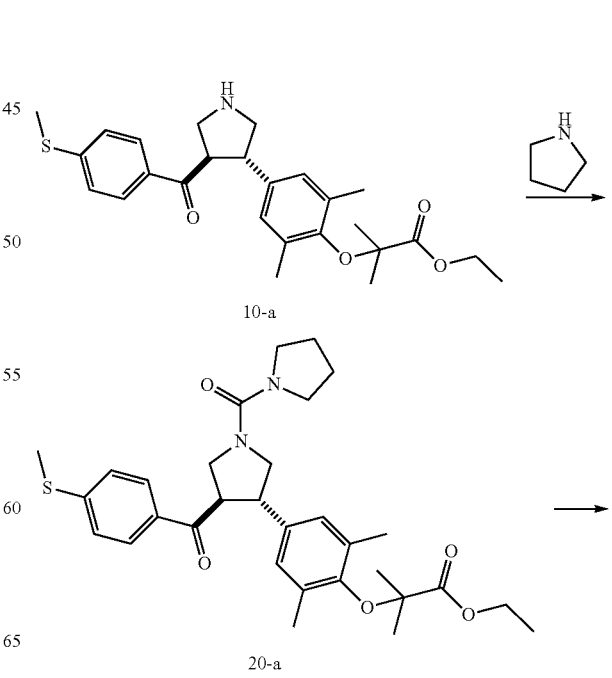

Step 1: Compound 19-a

Compound 10-a (400.03 mg, 878.00 µmol, 1.00 eq) was added into a solution of sulfuryl diamide (421.90 mg, 4.39 mmol, 262.05 µL, 5.00 eq) in dioxane (10.00 mL) at 25° C. The mixture was stirred at 110° C. for 16 h. The mixture was concentrated under reduced pressure. The residue was purified by flash column chromatography (dichloromethane:methanol=100:0-80:20) to give Compound 19-a.

$^1$H NMR (400 MHz, CDCl$_3$) δ ppm 7.71 (d, J=8.04 Hz, 2H), 7.20 (d, J=8.04 Hz, 2H), 6.88 (s, 2H), 4.72 (s, 2H),

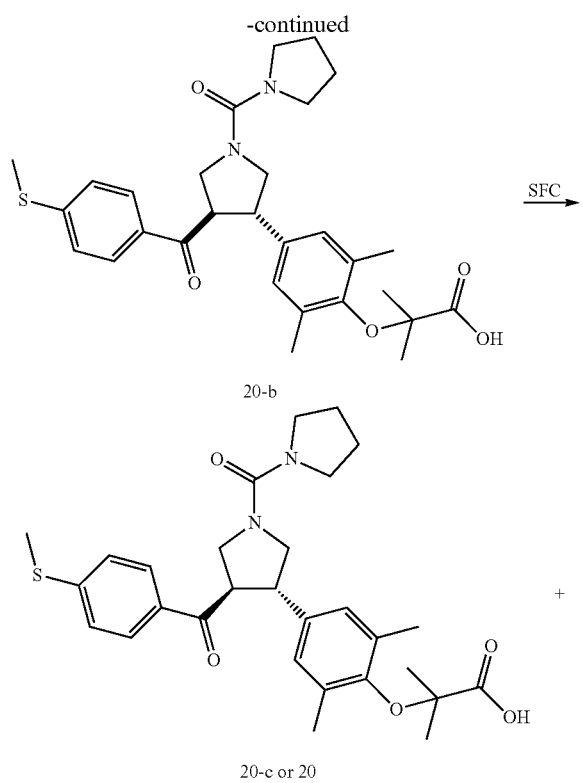

20-b 20-c or 20

20-c or 20

Step 1: Compound 20-a

Triethylamine (177.68 mg, 1.76 mmol, 243.39 μL, 2.00 eq) and carbonyl diimidazole (213.54 mg, 1.32 mmol, 1.50 eq) was added into a solution of Compound 10-a (400.00 mg, 877.94 μmol, 1.00 eq) in toluene (10.00 mL) at 25° C. The mixture was stirred at 80° C. for 16 h. Then, tetrahydropyrrole (93.66 mg, 1.32 mmol, 110.19 μL, 1.50 eq) was added. The mixture was stirred at 80° C. for 2 h. The mixture was concentrated under reduced pressure. The residue was purified by flash column chromatography (dichloromethane:methanol=100:0-75:25) to give Compound 20-a.

MS m/z (ESI): 553.3 [M+1]

Step 2: Compound 20-b

Lithium hydroxide (194.99 mg, 8.14 mmol, 10.00 eq) was added into a solution of Compound 20-a (450.00 mg, 814.16 μmol, 1.00 eq) in ethanol (5.00 mL) and water (5 mL) at 20° C. The mixture was stirred at 45° C. for 16 h. The mixture was extracted with dichloromethane (20 mL×3). The combined organic phase was dried over anhydrous sodium sulfate, filtered, and concentrated under reduced pressure. The residue was purified by flash column chromatography (dichloromethane:methanol=100:0-75:25) to give Compound 20-b.

MS m/z (ESI): 525.1 [M+1].

Step 3: Compound 20

Compound 20-b (100.00 mg, 319.58 μmol, 1.00 eq) was subjected to chiral separation to give Compound 20-c (70.0 mg, yield: 17.50%); Compound 20.

$^1$H NMR (400 MHz, CDCl$_3$) δ 7.72 (d, J=8.54 Hz, 2H), 7.18 (d, J=8.28 Hz, 2H), 6.89 (s, 2H), 4.03-3.85 (m, 3H), 3.75-3.63 (m, 3H), 3.39 (br dd, J=5.52, 10.78 Hz, 4H), 2.49 (s, 3H), 2.15 (s, 6H), 1.85 (br dd, J=5.90, 13.68 Hz, 4H), 1.43 (br s, 6H).

Conditions of the chiral resolution: chiral column: Chiralpak OJ-3 100×4.6 mm I.D., 3 μm; mobile phase: 40% of ethanol (0.05% DEA) in CO$_2$; flow rate: 2.8 mL/min; column temperature: 40° C.

Retention time of Compound 20: 3.362 min (peak 2).

Example 21: Compound 21

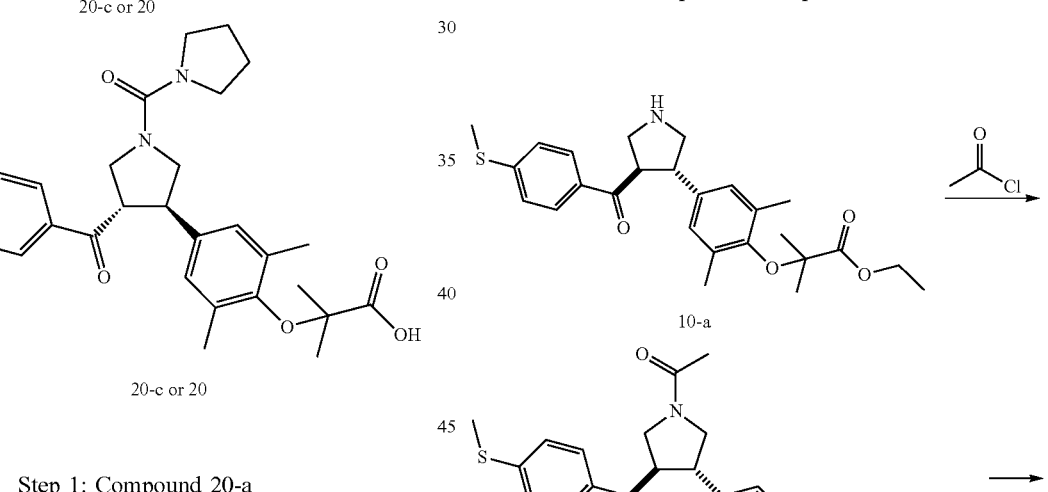

10-a 21-a 21-b or 21

Examples 22 and 23: Compounds 22 and 23

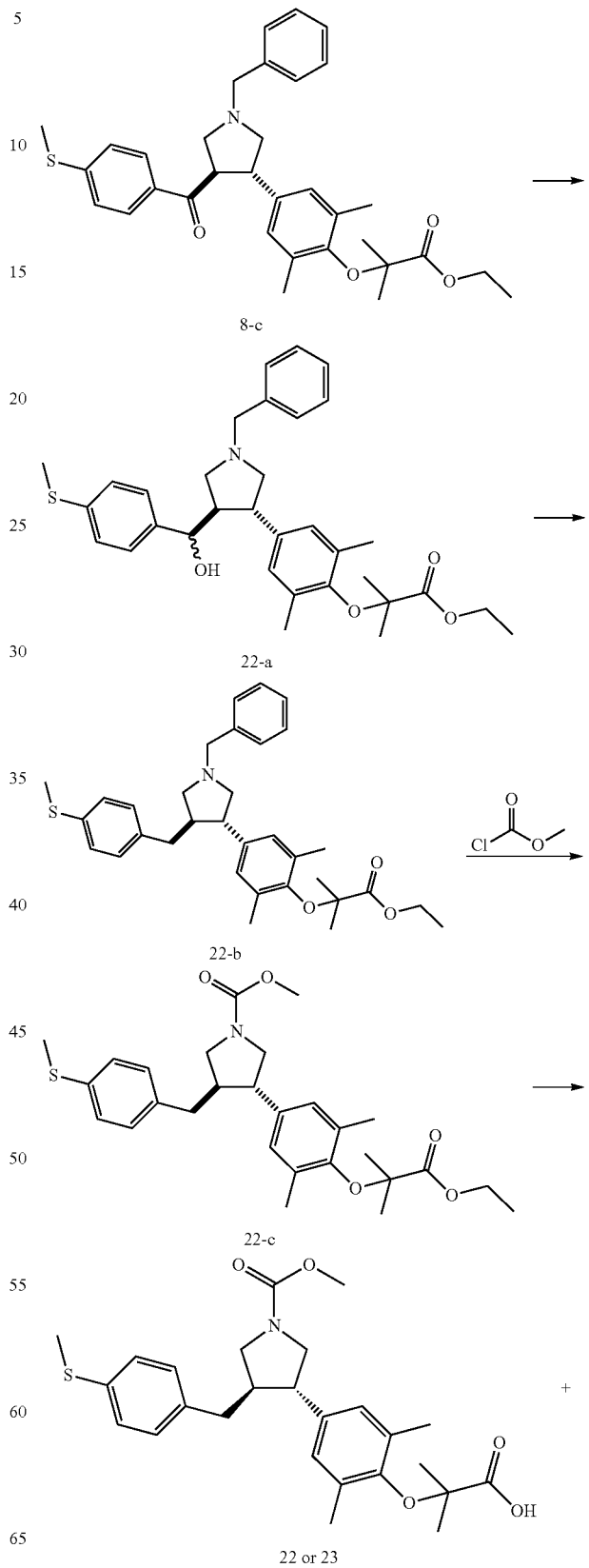

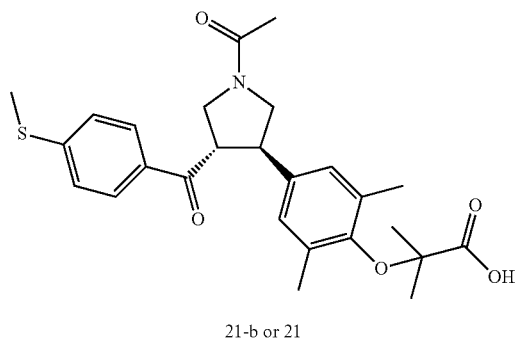

21-b or 21

Step 1: Compound 21-a

Compound 10-a (500.00 mg, 1.10 mmol, 1.00 eq), dichloromethane (5.00 mL), acetylchloride (86.15 mg, 1.10 mmol, 78.32 μL, 1.00 eq) and triethylamine (222.10 mg, 2.19 mmol, 304.24 μL, 2.00 eq) was added into a dried round-bottom flask. The mixture was stirred at 25° C. for 2 h. The mixture was concentrated under reduced pressure. The residue was purified by flash column chromatography (ethyl acetate) to give Compound 21-a.

MS m/z (ESI): 498.1 [M+1].

Step 2: Compound 21

Compound 21-a (130.00 mg, 261.23 μmol, 1.00 eq) and dioxane (1.00 mL) was added into a round-bottom flask. Then, lithium hydroxide (18.77 mg, 783.68 μmol, 3.00 eq) and water (1.00 mL) were added. The mixture was stirred at 40° C. for 16 h. The mixture was adjusted with 1N diluted HCl to pH=3, and was added with water/ethyl acetate (1:1, 20 mL). The aqueous phase was extracted with ethyl acetate (20 mL×2). The combined organic phase was dried over anhydrous sodium sulfate, filtered, and concentrated under reduced pressure. The residue was purified by flash column chromatography (11.3%, dichloromethane/MeOH). The resulted product was subjected to chiral separation to give Compound 21.

MS m/z (ESI): 470.1 [M+1].

$^1$H NMR (400 MHz, CDCl$_3$) δ ppm 7.68 (d, J=8.03 Hz, 1H), 7.61 (d, J=8.03 Hz, 1H), 7.15-7.09 (m, 2H), 6.81-6.77 (m, 2H), 4.11-4.06 (m, 1H), 3.95-3.91 (m, 1H), 3.81-3.79 (m, 2H), 3.58-3.48 (m, 2H), 2.44 (s, 3H), 2.12-2.03 (m, 9H), 1.40-1.38 (m, 6H).

Conditions of the chiral resolution: chiral column: Chiralpak OJ-3 100×4.6 mm I.D., 3 μm; mobile phase: 40% of ethanol (0.05% DEA) in CO$_2$; flow rate: 2.8 mL/min; column temperature: 40° C.

Retention time of Compound 21: 3.430 min (peak 2).

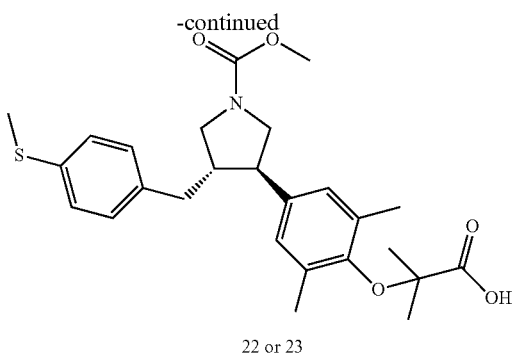

22 or 23

Step 1: Compound 22-a

Sodium borohydride (34.66 mg, 916.20 μmol, 1.00 eq) was added into a solution of Compound 8-c (500.00 mg, 916.20 μmol, 1.00 eq) in ethanol (5.00 mL) at 0° C. The mixture was stirred at 50° C. for 2 h. Ethyl acetate/water (1:1, 50 mL) was added into the mixture. The aqueous phase was extracted with ethyl acetate (20 mL×2). The combined organic phase was dried over anhydrous sodium sulfate, filtered, and concentrated under reduced pressure to give Compound 22-a.

MS m/z (ESI): 548.1 [M+1].

$^1$H NMR (400 MHz, MeOD-d$_4$) δ ppm 7.34 (br d, J=4.27 Hz, 6H), 7.24 (br d, J=8.03 Hz, 2H), 7.18-7.14 (m, 3H), 4.30-4.23 (m, 3H), 3.32-3.18 (m, 3H), 3.03 (br d, J=9.03 Hz, 1H), 2.71-2.69 (m, 1H), 2.46 (s, 3H), 2.42-2.33 (m, 3H), 2.04 (s, 6H), 1.40 (s, 6H), 1.33 (t, J=7.15 Hz, 3H).

Step 2: Compound 22-b

Triethylsilicane (636.86 mg, 5.48 mmol, 872.41 μL, 5.00 eq) was added into a solution of Compound 22-a (600.00 mg, 1.10 mmol, 1.00 eq) in dichloromethane (5.00 mL), and then trifluoroacetic acid (624.48 mg, 5.48 mmol, 405.51 μL, 5.00 eq) was added. The mixture was stirred at 25° C. for 3 h. The mixture was added with a saturated solution of sodium carbonate (30 mL), and was extracted with ethyl acetate (30 mL×3). The combined organic phase was dried over anhydrous sodium sulfate, filtered, and concentrated under reduced pressure. The residue was purified by flash column chromatography to give Compound 22-b.

MS m/z (ESI): 532.1 [M+1].

$^1$H NMR (400 MHz, CDCl$_3$) δ ppm 7.29-7.27 (m, 2H), 7.24-7.17 (m, 3H), 7.03 (d, J=8.28 Hz, 2H), 6.92 (d, J=8.03 Hz, 2H), 6.65 (s, 2H), 4.21 (q, J=7.28 Hz, 2H), 3.63-3.50 (m, 2H), 2.89-2.77 (m, 1H), 2.75-2.68 (m, 3H), 2.58-2.55 (m, 2H), 2.37 (s, 3H), 2.07 (s, 6H), 1.60 (br s, 2H), 1.38 (s, 6H), 1.30-1.27 (m, 3H).

Step 3: Compound 22-c

Compound 22-b (185.00 mg, 347.91 μmol, 1.00 eq), dichloromethane (5.00 mL) and methyl chloroformate (164.39 mg, 1.74 mmol, 134.75 μL, 5.00 eq) was added into a dried round-bottom flask. The mixture was stirred at 25° C. for 16 h. The mixture was concentrated under reduced pressure. The residue was purified by flash column chromatography (34.6%, ethyl acetate/petroleum ether) to give Compound 22-c.

MS m/z (ESI): 522.1 [M+23].

Step 4: Compounds 22 and 23

Compound 22-c (89.00 mg, 178.12 μmol, 1.00 eq) and ethanol (5.00 mL) was added into a dried round-bottom flask. Then, lithium hydroxide (12.80 mg, 534.36 μmol, 3.00 eq) and water (1.00 mL) were added. The mixture was stirred at 40° C. for 16 h. The mixture was adjusted with 1N diluted HCl to pH=3, and then was added with water/ethyl acetate (1:1, 30 mL). The aqueous phase was extracted with ethyl acetate (30 mL×2). The combined organic phase was dried over anhydrous sodium sulfate, filtered, and concentrated under reduced pressure. The residue was purified by flash column chromatography to give a compound, which was subjected to chiral separation to give Compound 22; Compound 23.

Compound 22:

MS m/z (ESI): 472.1 [M+1].

$^1$H NMR (400 MHz, MeOD-d$_4$) δ ppm 7.15 (d, J=8.03 Hz, 2H), 7.03 (br d, J=6.78 Hz, 2H), 6.93 (s, 2H), 3.79 (dd, J=8.28, 10.54 Hz, 1H), 3.68 (s, 3H), 3.56-3.53 (m, 1H), 3.12 (t, J=10.16 Hz, 1H), 2.94-2.92 (m, 1H), 2.69 (br d, J=13.05 Hz, 1H), 2.45-2.43 (m, 5H), 2.27 (s, 6H), 1.43 (s, 6H).

Compound 23:

MS m/z (ESI): 494.1 [M+23].

$^1$H NMR (400 MHz, CDCl$_3$) δ ppm 7.09-7.06 (m, 2H), 6.91 (br d, J=7.03 Hz, 2H), 6.79 (br d, J=2.76 Hz, 2H), 3.79-3.72 (m, 1H), 3.61 (s, 3H), 3.54-3.49 (m, 1H), 3.31-3.25 (m, 1H), 3.07-3.01 (m, 1H), 2.83-2.78 (m, 1H), 2.65 (br d, J=14.05 Hz, 1H), 2.39-2.32 (m, 5H), 2.16 (s, 6H), 1.45 (s, 6H).

Conditions of the chiral resolution: chiral column: Chiralpak OJ-3 100×4.6 mm I.D., 3 μm; mobile phase: 40% of methanol (0.05% DEA) in CO$_2$.

Retention time of Compound 22: 4.092 min (peak 1); retention time of Compound 23: 4.594 min (peak 2)

Example 24: Compound 24

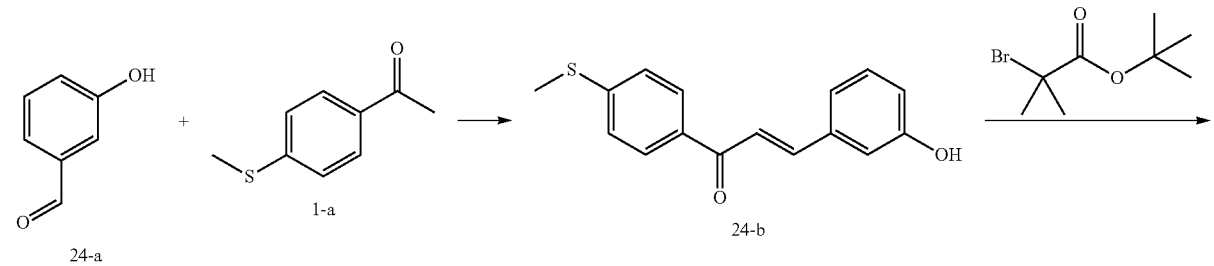

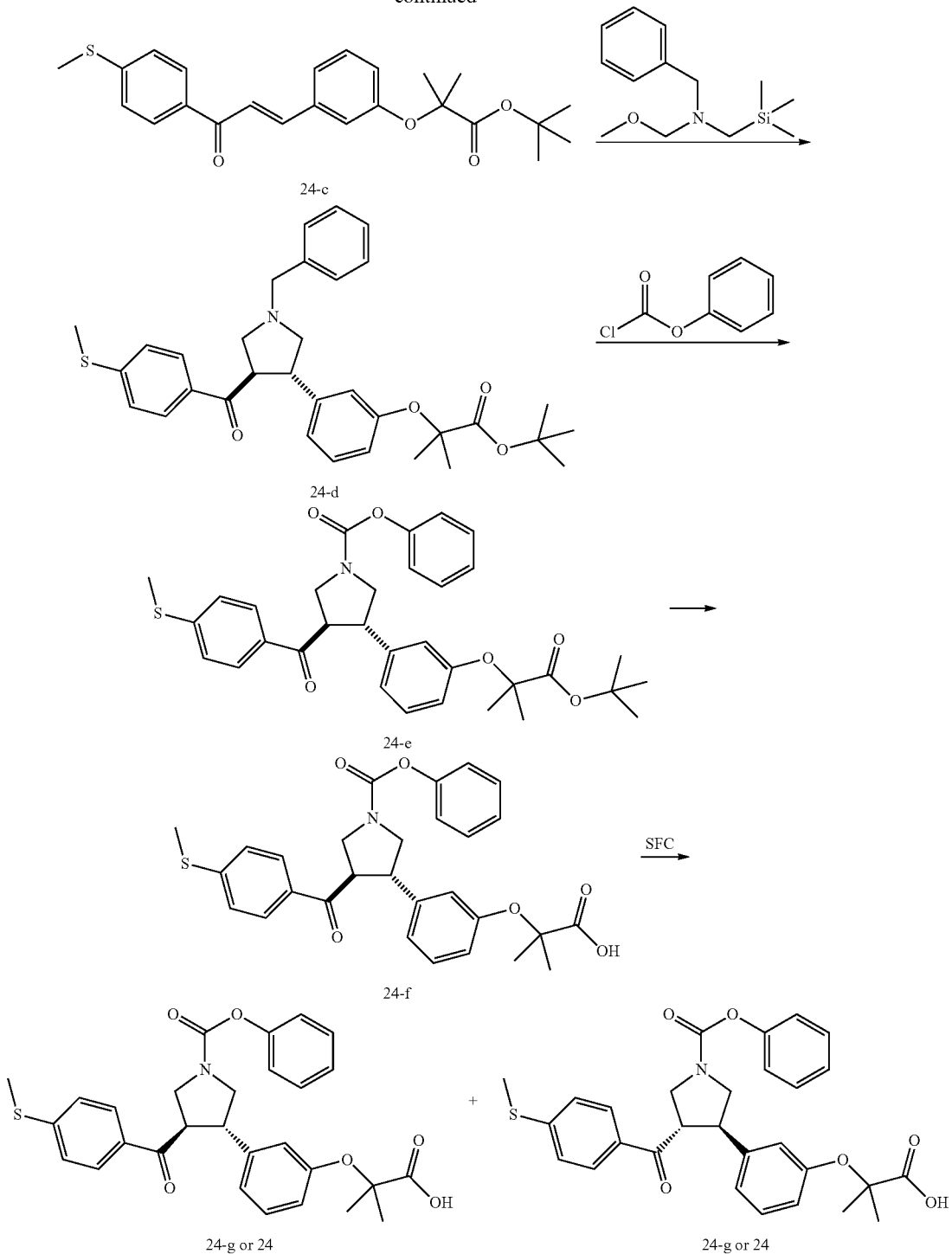

Step 1: Compound 24-b

Compound 1-a (20.42 g, 122.83 mmol, 1.00 eq) was added into a solution of Compound 24-a (15.00 g, 122.83 mmol, 1.00 eq) in HCl/MeOH (4 N, 100.00 mL) at 20° C. The mixture was stirred at 20° C. for 2 h. The mixture was filtered, and the filter cake was dissolved in ethyl acetate (500 mL), added with water (1000 mL), and extracted with ethyl acetate (200 mL×3). The combined organic phase was washed with water (200 mL), dried over anhydrous sodium sulfate, filtered, and concentrated under reduced pressure to give Compound 24-b.

MS m/z (ESI): 270.9 [M+1].

$^1$H NMR (400 MHz, DMSO-d$_6$) δ 8.04 (d, J=8.54 Hz, 2H), 7.71 (d, J=2.26 Hz, 2H), 7.41 (d, J=8.54 Hz, 2H), 7.32-7.21 (m, 2H), 7.16 (s, 1H), 6.89 (d, J=7.78 Hz, 1H), 2.60-2.53 (s, 3H).

Step 2: Compound 24-c

A compound tert-butyl bromo-isopropionate (12.38 g, 55.47 mmol, 3.00 eq) and potassium carbonate (7.67 g, 55.47 mmol, 3.00 eq) was added into a solution of Compound 24-b (5.00 g, 18.49 mmol, 1.00 eq) in acetonitrile (30.00 mL) at 20° C. The mixture was stirred at 80° C. for 16 h. The mixture was filtered, and the filtrate was concentrated under reduced pressure. The crude product was purified by silica gel column chromatography (petroleum ether/ethyl acetate=100:0-80:20) to give Compound 24-c.

MS m/z (ESI): 413.0 [M+1].

$^1$H NMR (400 MHz, CDCl$_3$) δ 7.96 (d, J=8.54 Hz, 2H), 7.75 (d, J=15.56 Hz, 1H), 7.48 (d, J=15.56 Hz, 1H), 7.35-7.27 (m, 3H), 7.26-7.23 (m, 1H), 7.16 (s, 1H), 6.91 (td, J=1.22, 7.84 Hz, 1H), 2.56 (s, 3H), 1.61 (s, 6H), 1.46 (s, 9H).

Step 3: Compound 24-d

N-(methoxymethyl)-1-phenyl-N-(trimethylsilylmethyl) methylamine (6.10 g, 25.70 mmol, 2.00 eq) and TFA (2.20 g, 19.28 mmol, 1.43 mL, 1.50 eq) was added into a solution of Compound 24-c (5.30 g, 12.85 mmol, 1.00 eq) in dichloromethane (25.00 mL) at 0° C. The mixture was stirred at 20° C. for 16 h. The mixture was directly concentrated under reduced pressure. The residue was purified by flash column chromatography (petroleum ether:ethyl acetate=100:0-60:40) to give Compound 24-d.

MS m/z (ESI): 546.1 [M+1].

$^1$H NMR (400 MHz, CDCl$_3$) δ 7.69 (d, J=8.53 Hz, 2H), 7.42-7.36 (m, 2H), 7.32 (t, J=7.40 Hz, 2H), 7.26-7.21 (m, 1H), 7.18-7.08 (m, 3H), 6.94-6.87 (m, 2H), 6.71-6.66 (m, 1H), 3.99-3.89 (m, 1H), 3.80-3.62 (m, 3H), 3.14 (t, J=9.03 Hz, 1H), 3.02 (t, J=8.66 Hz, 1H), 2.89-2.80 (m, 2H), 2.52-2.43 (m, 3H), 1.55 (s, 6H), 1.43 (s, 9H).

Step 4: Compound 24-e

Phenyl chloroformate (3.44 g, 21.99 mmol, 2.75 mL, 3.00 eq) was added into a solution of Compound 24-d (4.00 g, 7.33 mmol, 1.00 eq) in dichloromethane (30.00 mL) at 20° C. The mixture was stirred at 20° C. for 16 h. The mixture was concentrated under reduced pressure. The residue was purified by flash column chromatography (petroleum ether: ethyl acetate=100:0-60:40) to give Compound 24-e.

MS m/z (ESI): 598.0 [M+23].

$^1$H NMR (400 MHz, CDCl$_3$) δ 7.78 (dd, J=5.02, 8.54 Hz, 2H), 7.43-7.35 (m, 2H), 7.26-7.12 (m, 6 h), 6.96-6.82 (m, 2H), 6.72 (dd, J=2.14, 8.16 Hz, 1H), 4.25-4.04 (m, 3H), 3.97-3.67 (m, 3H), 2.52 (s, 3H), 1.55 (d, J=5.02 Hz, 6H), 1.44 (s, 9H).

Step 5: Compound 24-f

Trifluoroacetic acid (11.88 g, 104.22 mmol, 7.72 mL, 20.00 eq) was added into a solution of Compound 24-e (3.00 g, 5.21 mmol, 1.00 eq) in dichloromethane (20.00 mL) at 20° C. The mixture was stirred at 20° C. for 3 h. The mixture was concentrated under reduced pressure. The residue was purified by silica gel column chromatography (dichloromethane:methanol=100:0-90:10) to give Compound 24-f.

MS m/z (ESI): 520.0 [M+1].

Step 6: Compound 24

Compound 24-f (1.00 g, 1.92 mmol, 1.00 eq) was subjected to chiral separation to give Compound 24.

$^1$H NMR (400 MHz, CDCl$_3$) δ ppm 7.70 (t, J=7.54 Hz, 2H), 7.37-7.25 (m, 2H), 7.18-7.05 (m, 6 h), 6.91 (d, J=7.78 Hz, 1H), 6.80 (s, 1H), 6.73 (t, J=5.90 Hz, 1H), 4.15-3.92 (m, 3H), 3.88-3.58 (m, 3H), 2.43 (s, 3H), 1.55-1.40 (m, 6H).

Conditions of the chiral resolution: chiral column: Chiralpak AD-3 100×4.6 mm I.D., 3 μm; mobile phase: 40% of ethanol (0.05% DEA) in CO$_2$; flow rate: 2.8 mL/min; column temperature: 40° C.

Retention time of Compound 24: 6.698 min (peak 2)

Examples 25, 26: Compounds 25, 26

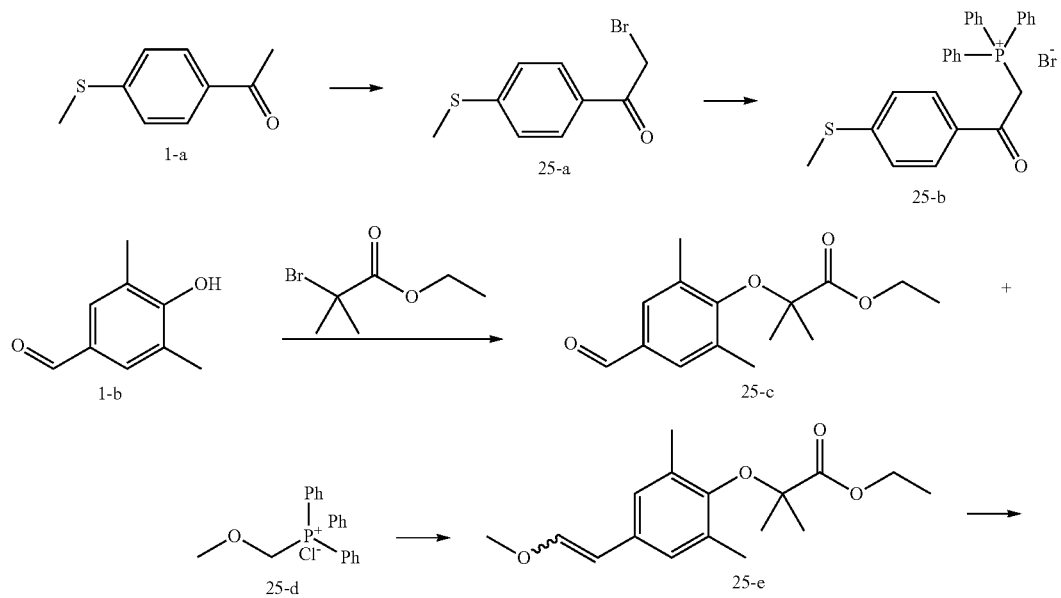

-continued
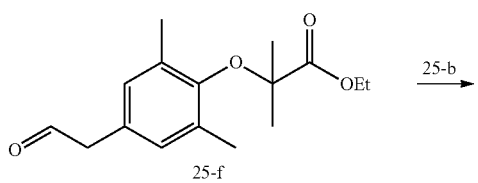
25-f
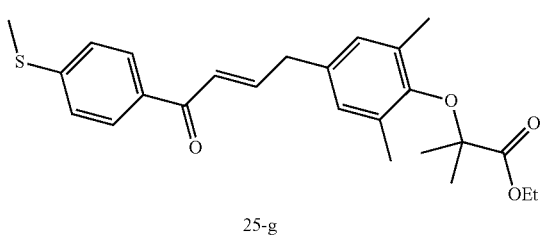
25-g
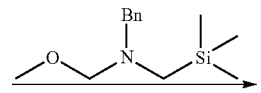
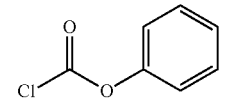
25-h
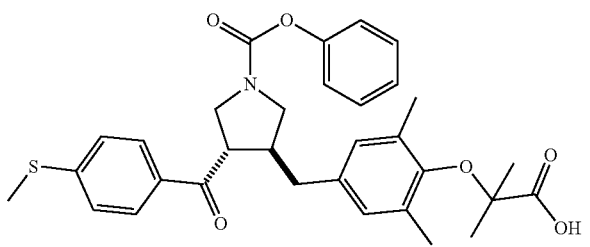
25-i
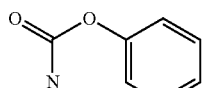
25-j
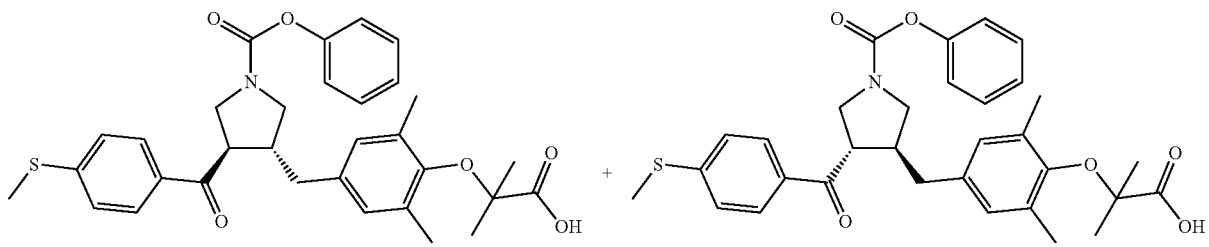
25 or 26    +    25 or 26

Step 1: Compound 25-a

Trimethylchlorosilicane (23.53 g, 216.55 mmol, 27.36 mL, 1.20 eq) was added into a solution of Compound 1-a (30.00 g, 180.46 mmol, 1.00 eq) in dichloromethane (200.00 mL) at 20° C. The mixture was stirred at 20° C. for 1 h. Then, N-bromosuccinimide (38.54 g, 216.55 mmol, 1.20 eq) was added. The mixture was stirred at 20° C. for 1 h. The mixture was concentrated under reduced pressure. The residue was purified by silica gel column chromatography (petroleum ether:ethyl acetate=100/1-100/30) to give Compound 25-a.

$^1$H NMR (400 MHz, CDCl$_3$) δ ppm 7.88-7.85 (m, 2H), 7.27-7.24 (m, 2H), 4.40 (s, 2H), 2.52 (s, 3H).

Step 2: Compound 25-b

Triphenylphosphine (32.10 g, 122.38 mmol, 1.00 eq) was added into a solution of Compound 25-a (30.00 g, 122.38 mmol, 1.00 eq) in toluene (250.00 mL) at 20° C. The mixture was stirred at 80° C. for 17 h. The mixture was filtered, and the filter cake was washed with ethyl acetate (250 mL×3). The organic phases were combined and concentrated to give Compound 25-b.

$^1$H NMR (400 MHz, DMSO-d$_6$) δ ppm 7.99 (d, J=8.5 Hz, 2H), 7.89-7.70 (m, 15H), 7.44 (d, J=8.5 Hz, 2H), 6.17 (d, J=13.1 Hz, 2H), 2.57 (s, 3H).

Step 3: Compound 25-c

Potassium carbonate (110.44 g, 799.05 mmol, 3.00 eq), ethyl 2-bromo-isobutyrate (207.81 g, 1.07 mol, 156.25 mL, 4.00 eq) and potassium iodide (44.21 g, 266.35 mmol, 1.00 eq) was added into a solution of Compound 1-b (40.00 g, 266.35 mmol, 1.00 eq) in dimethylsulfoxide (400.00 mL) at 20° C. The mixture was stirred at 130° C. for 4 h. Water (1 L) was added into the mixture, and extracted with ethyl acetate (200 mL×6). The combined organic phase was washed with water (1 L) and saturated brine (1 L), dried over anhydrous sodium sulfate, filtered, and concentrated under reduced pressure. The residue was purified by flash column chromatography (petroleum ether:ethyl acetate=100:0-100:50) to give Compound 25-c.

$^1$H NMR (400 MHz, CDCl$_3$) δ ppm 9.85 (s, 1H), 7.50 (s, 2H), 4.31-4.23 (m, 2H), 2.25 (s, 6H), 1.45 (s, 6H), 1.33 (t, J=7.2 Hz, 1H).

Step 4: Compound 25-e

Potassium tert-butoxide (19.10 g, 170.25 mmol, 1.50 eq) was added into a solution of Compound 25-d (58.36 g, 170.25 mmol, 1.50 eq) in tetrahydrofuran (50.00 mL) at 0° C. The mixture was stirred at 0° C. for 30 min. Then, Compound 25-c (30.00 g, 113.50 mmol, 1.00 eq) was added. The mixture was stirred at 20° C. for 17 h. The mixture was concentrated under reduced pressure. The residue was purified by silica gel column chromatography petroleum ether/ethyl acetate=100/1-100/20) to give Compound 25-e.

Step 5: Compound 25-f

Camphorsulfonic acid (17.88 g, 76.95 mmol, 3.00 eq) was added to a solution of Compound 25-e (15 g, 51.30 mmol, 1.00 eq) in tetrahydrofuran (200.00 mL) at 20° C. The mixture was stirred at 20° C. for 17 h. A saturated sodium carbonate (500 mL, 4 N) solution was added into the mixture, and extracted with ethyl acetate (500 mL×2). The combined organic phase was washed with saturated brine (500 mL×2), dried over anhydrous sodium sulfate, filtered, and concentrated under reduced pressure to give Compound 25-f.

$^1$H NMR (400 MHz, CDCl$_3$) δ ppm 9.80-9.69 (m, 1H), 9.62 (s, 1H), 6.75 (s, 2H), 4.21 (br d, J=4.0 Hz, 2H), 4.20 (s, 1H), 3.25 (s, 2H), 2.12-2.10 (m, 6H), 1.40-1.38 (m, 6H), 1.28 (d, J=1.8 Hz, 2H), 1.28-1.27 (m, 1H).

Step 6: Compound 25-g

Under nitrogen protection, potassium tert-butoxide (1.11 g, 9.85 mmol, 1.00 eq) was added into a solution of Compound 25-b (5.00 g, 9.85 mmol, 1.00 eq) in tetrahydrofuran (50.00 mL). The mixture was stirred at 20° C. for 1 h. Then, Compound 25-f (2.74 g, 9.85 mmol, 1.00 eq) was added. The mixture was stirred at 50° C. for 16 h. The mixture was concentrated under reduced pressure. The residue was purified by silica gel column chromatography (petroleum ether:ethyl acetate=100/1-100/30) to give Compound 25-g.

$^1$H NMR (400 MHz, CDCl$_3$) δ ppm 7.85 (d, J=8.5 Hz, 2H), 7.28-7.27 (m, 2H), 7.22-7.14 (m, 1H), 7.02 (s, 1H), 6.83 (s, 2H), 4.30 (s, 2H), 3.53 (d, J=6.8 Hz, 2H), 2.55 (s, 3H), 2.21 (s, 6H), 1.49 (s, 6H), 1.38 (s, 3H).

Step 7: Compound 25-h

N-(methoxymethyl)-1-phenyl-N-(trimethylsilyl)methyl-amine (3.33 g, 14.04 mmol, 6.00 eq) and trifluoroacetic acid (1.60 g, 14.04 mmol, 1.04 mL, 6.00 eq) was added into a solution of Compound 25-g (1.00 g, 2.34 mmol, 1.00 eq) in dichloromethane (60.00 mL) at 20° C. The mixture was stirred at 40° C. for 17 h. The mixture was concentrated under reduced pressure. The residue was purified by silica gel column chromatography (petroleum ether/ethyl acetate=100/1-100/30) to give Compound 25-h.

$^1$H NMR (400 MHz, CDCl$_3$) δ ppm 7.71 (d, J=8.5 Hz, 1H), 7.31-7.20 (m, 9H), 6.71 (s, 1H), 4.30-4.23 (m, 2H), 3.76-3.36 (m, 6H), 3.07-2.96 (m, 2H), 2.68 (t, J=7.3 Hz, 2H), 2.51 (s, 3H), 2.10-2.03 (m, 6H), 1.36-1.22 (m, 9H).

Step 8: Compound 25-i

Phenyl chloroformate (375.00 mg, 2.40 mmol, 300.00 μL, 3.12 eq) was added into a solution of Compound 25-h (430.00 mg, 768.19 μmol, 1.00 eq) in dichloromethane (20.00 mL) at 20° C. The mixture was stirred at 20° C. for 17 h. The mixture was concentrated under reduced pressure. The residue was purified by silica gel column chromatography (petroleum ether/ethyl acetate=100/1 to 100/50) to give Compound 25-i.

$^1$H NMR (400 MHz, CDCl$_3$) δ ppm 7.66 (dd, J=4.0, 8.3 Hz, 2H), 7.41-7.33 (m, 2H), 7.23-7.08 (m, 5H), 6.79 (d, J=2.0 Hz, 2H), 4.12 (q, J=7.0 Hz, 2H), 3.93-3.60 (m, 4H), 3.48-3.32 (m, 1H), 2.97-2.84 (m, 1H), 2.67 (d, J=7.8 Hz, 2H), 2.57-2.49 (m, 3H), 2.25-2.13 (m, 6H), 1.46 (s, 6H), 1.36 (t, J=7.2 Hz, 3H).

Step 9: Compound 25-j

Water (8.00 mL) and lithium hydroxide (81.22 mg, 3.39 mmol, 20.00 eq) was added into a solution of Compound 25-i (100.00 mg, 169.57 μmol, 1.00 eq) in ethanol (8.00 mL) at 20° C. The mixture was stirred at 20° C. for 17 h. A diluted HCl (1N, 10 mL) was added into the mixture, and extracted with dichloromethane (50 mL×3). The combined organic phase was washed with saturated brine (50 mL×2), dried over anhydrous sodium sulfate, filtered, and concentrated under reduced pressure. The residue was purified by preparative High Performance Liquid Chromatography to give Compound 25-j.

MS m/z (ESI): 584.1 [M+23].

$^1$H NMR (400 MHz, MeOD-d$_4$) δ ppm 7.65 (d, J=6.8 Hz, 2H), 7.43-7.37 (m, 2H), 7.29-7.22 (m, 3H), 7.16 (t, J=7.2 Hz, 2H), 6.87 (s, 2H), 4.13-3.92 (m, 2H), 3.89-3.80 (m, 1H), 3.69 (dd, J=5.4, 10.7 Hz, 1H), 3.58-3.49 (m, 1H), 2.81 (d, J=14.1 Hz, 2H), 2.71-2.63 (m, 1H), 2.55 (s, 3H), 2.23 (s, 6H), 1.43 (s, 6H).

Step 10: Compounds 25 and 26

Compound 25-j (25.00 mg, 44.51 μmol, 1.00 eq) was subjected to chiral separation to give Compound 25; Compound 26.

Compound 25: $^1$H NMR (400 MHz, CDCl$_3$) δ 7.73 (d, J=8.28 Hz, 2H), 7.41-7.33 (m, 2H), 7.27-7.18 (m, 3H), 7.15 (d, J=8.28 Hz, 2H), 6.83 (d, J=5.52 Hz, 2H), 4.02-3.64 (m, 4H), 3.50-3.32 (m, 1H), 3.08-2.88 (m, 1H), 2.81-2.61 (m, 2H), 2.55 (s, 3H), 2.20 (d, J=3.51 Hz, 6H).

Compound 26: $^1$H NMR (400 MHz, CDCl$_3$) δ 7.73 (d, J=8.28 Hz, 2H), 7.42-7.34 (m, 2H), 7.27-7.18 (m, 3H), 7.15 (d, J=8.54 Hz, 2H), 6.83 (d, J=5.78 Hz, 2H), 4.05-3.64 (m, 4H), 3.50-3.32 (m, 1H), 3.07-2.88 (m, 1H), 2.83-2.62 (m, 2H), 2.55 (s, 3H), 2.20 (d, J=3.52 Hz, 6H).

Conditions of the chiral resolution: chiral column: Chiralpak AD-3 100×4.6 mm I.D., 3 μm; mobile phase: 40% of methanol (0.05% DEA) in CO$_2$; flow rate: 2.8 mL/min; column temperature: 40° C.

Retention time of Compound 25: 2.018 min (peak 1); Retention time of Compound 26: 2.410 min (peak 2).

Example 27: Compound 27

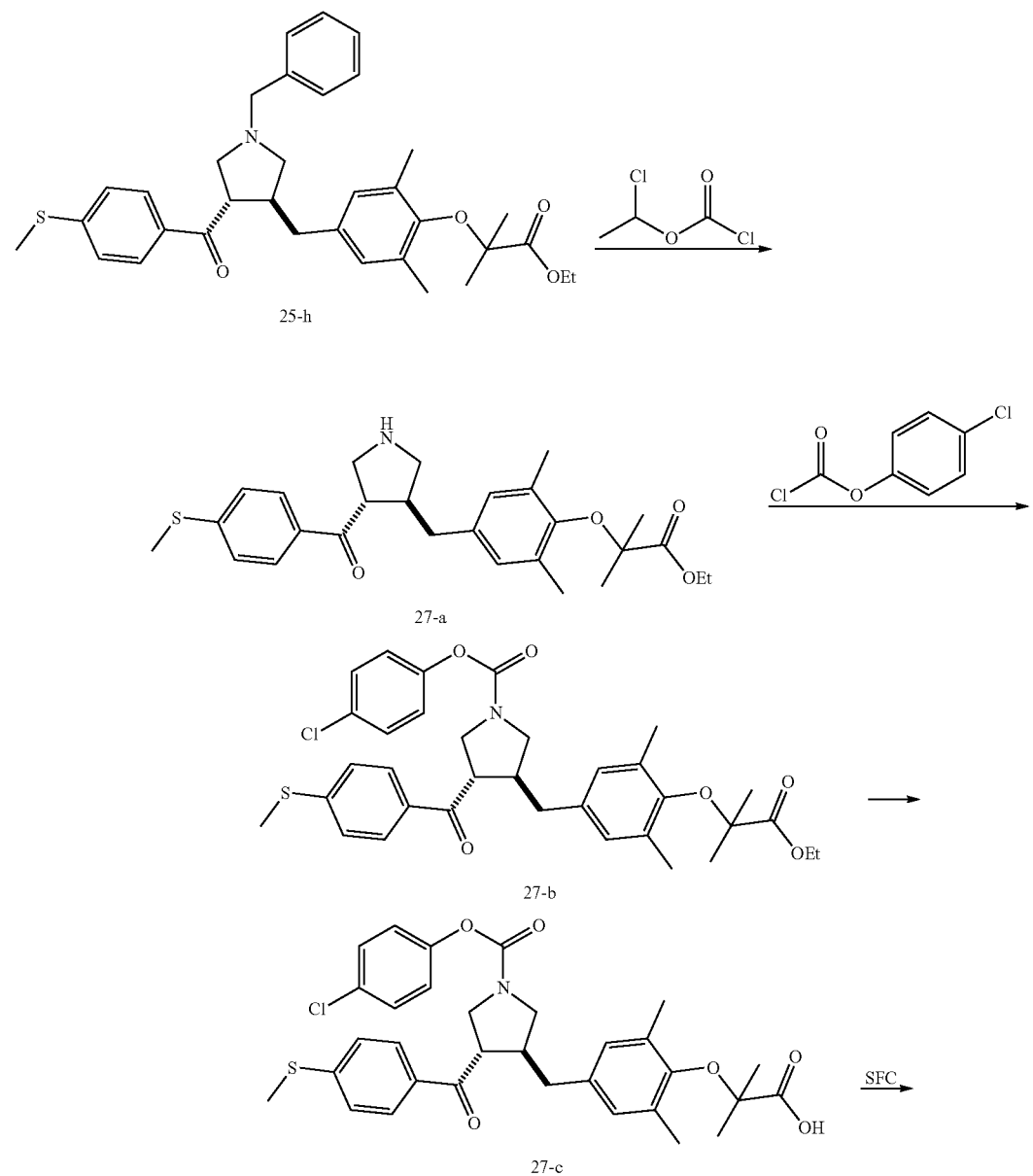

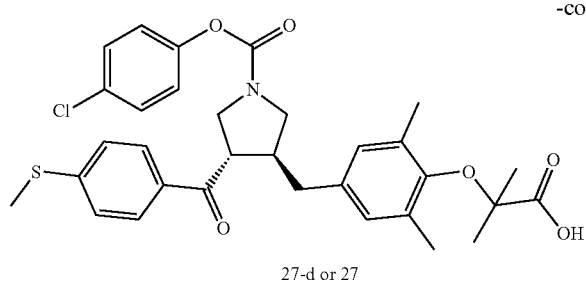

27-d or 27

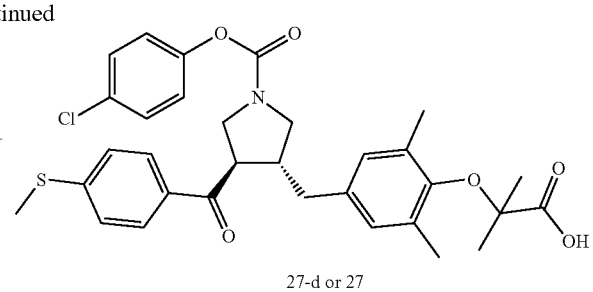

27-d or 27

Step 1: Compound 27-a

Chloromethyl 1-chloroformate (3.32 g, 23.22 mmol, 2.00 eq) was added into a solution of Compound 25-h (6.50 g, 11.61 mmol, 1.00 eq) in toluene (60.00 mL) at 25° C. The mixture was stirred under nitrogen protection at 100° C. for 8 h. The mixture was concentrated under reduced pressure. Methanol (50.00 mL) was added into the residue. The mixture was stirred at 70° C. for 1 h. The mixture was concentrated under reduced pressure. The residue was purified by silica gel column chromatography (dichloromethane:methanol=10:1) to give Compound 27-a.

$^1$H NMR (400 MHz, CDCl$_3$) δ ppm 7.57 (d, J=8.8 Hz, 2H), 7.15 (d, J=8.5 Hz, 2H), 6.77 (s, 2H), 4.27 (q, J=7.2 Hz, 2H), 3.96-3.86 (m, 1H), 3.74 (dd, J=3.3, 7.0 Hz, 1H), 3.69-3.59 (m, 1H), 3.53-3.36 (m, 1H), 3.32-3.20 (m, 1H), 2.88 (br d, J=7.0 Hz, 1H), 2.76 (dd, J=2.6, 7.9 Hz, 2H), 2.52-2.49 (m, 3H), 2.14-2.09 (m, 6H), 1.42 (d, J=2.8 Hz, 6H), 1.34 (t, J=7.2 Hz, 3H).

Step 2: Compound 27-b

A solution of Compound 27-a (250.00 mg, 532.32 μmol, 1.00 eq), di-iso-propyl ethylamine (137.59 mg, 1.06 mmol, 185.93 μL, 2.00 eq) and dichloromethane (5.00 mL) was added into a 50 mL reaction flask. Then, (4-chlorophenyl) methyl chloroformate (152.52 mg, 798.48 μmol, 1.50 eq) was added. The mixture was stirred at 25° C. for 2 h. A saturated solution of sodium bicarbonate (5 mL) was added into the mixture. The aqueous phase was extracted with dichloromethane (3×10 mL). The combined organic phase was washed with a saturated aqueous solution of potassium bisulfate (10 mL) and saturated brine (10 mL), dried over anhydrous sodium sulfate, and concentrated under reduced pressure. The residue was purified by silica gel column chromatography (petroleum ether:ethyl acetate=8:1 to 5:1) to give Compound 27-b.

$^1$H NMR (400 MHz, CDCl$_3$) δ ppm 7.56 (dd, J=8.8, 4.0 Hz, 2H), 7.24 (d, J=8.4 Hz, 2H), 7.13 (d, J=8.4 Hz, 2H), 7.02 (dd, J=9.2, 4.0 Hz, 2H), 6.70 (d, J=2.4 Hz, 2H), 4.22 (q, J=7.2 Hz, 2H), 3.82-3.53 (m, 4H), 3.38-3.30 (m, 1H), 2.85-2.77 (m, 1H), 2.59-2.46 (m, 2H), 2.46 (s, 3H), 2.10 (s, 6H), 1.39 (s, 6H), 1.29 (t, J=7.2 Hz, 3H).

Step 3: Compound 27-c

Lithium hydroxide (29.93 mg, 1.25 mmol, 3.00 eq) was added into a solution of Compound 27-b (260.00 mg, 416.54 μmol, 1.00 eq) in ethanol (2.00 mL), tetrahydrofuran (2.00 mL) and water (1.00 mL). The mixture was stirred at 25° C. for 60 h. The mixture was adjusted with a saturated aqueous solution of potassium bisulfate to pH=2-3, and extracted with ethyl acetate (10 mL×3). The combined organic phase was washed with saturated brine, dried over anhydrous sodium sulfate, and concentrated under reduced pressure. The residue was purified by silica gel column chromatography (petroleum ether:ethyl acetate=1:2) to give Compound 27-c.

MS m/z (ESI): 618.0 [M+23].

Step 4: Compound 27

Compound 27-c (100.00 mg) was subjected to chiral separation to give Compound 27.

MS m/z (ESI): 618.0 [M+23].

$^1$H NMR (400 MHz, MeOD-d$_4$) δ ppm 7.65 (d, J=8.4 Hz, 2H), 7.39 (d, J=8.8 Hz, 2H), 7.13 (d, J=8.4 Hz, 2H), 7.17 (t, J=8.8 Hz, 2H), 6.87 (s, 2H), 4.01-3.96 (m, 2H), 3.82-3.81 (m, 1H), 3.70-3.67 (m, 1H), 3.53-3.51 (m, 1H), 2.82-2.68 (m, 3H), 2.67 (s, 3H), 2.24 (s, 6H), 1.42 (s, 6H).

Conditions of the chiral resolution: chiral column: Chiralpak AD-3 50×4.6 mm I.D., 3 μm; mobile phase: 40% of ethanol (0.05% DEA) in CO$_2$; flow rate: 4 mL/min; column temperature: 40° C.

Retention time of Compound 27: 1.148 min (peak 1)

Example 28: Compound 28

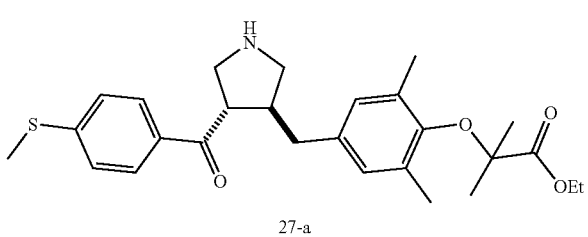

27-a

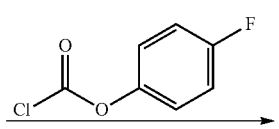

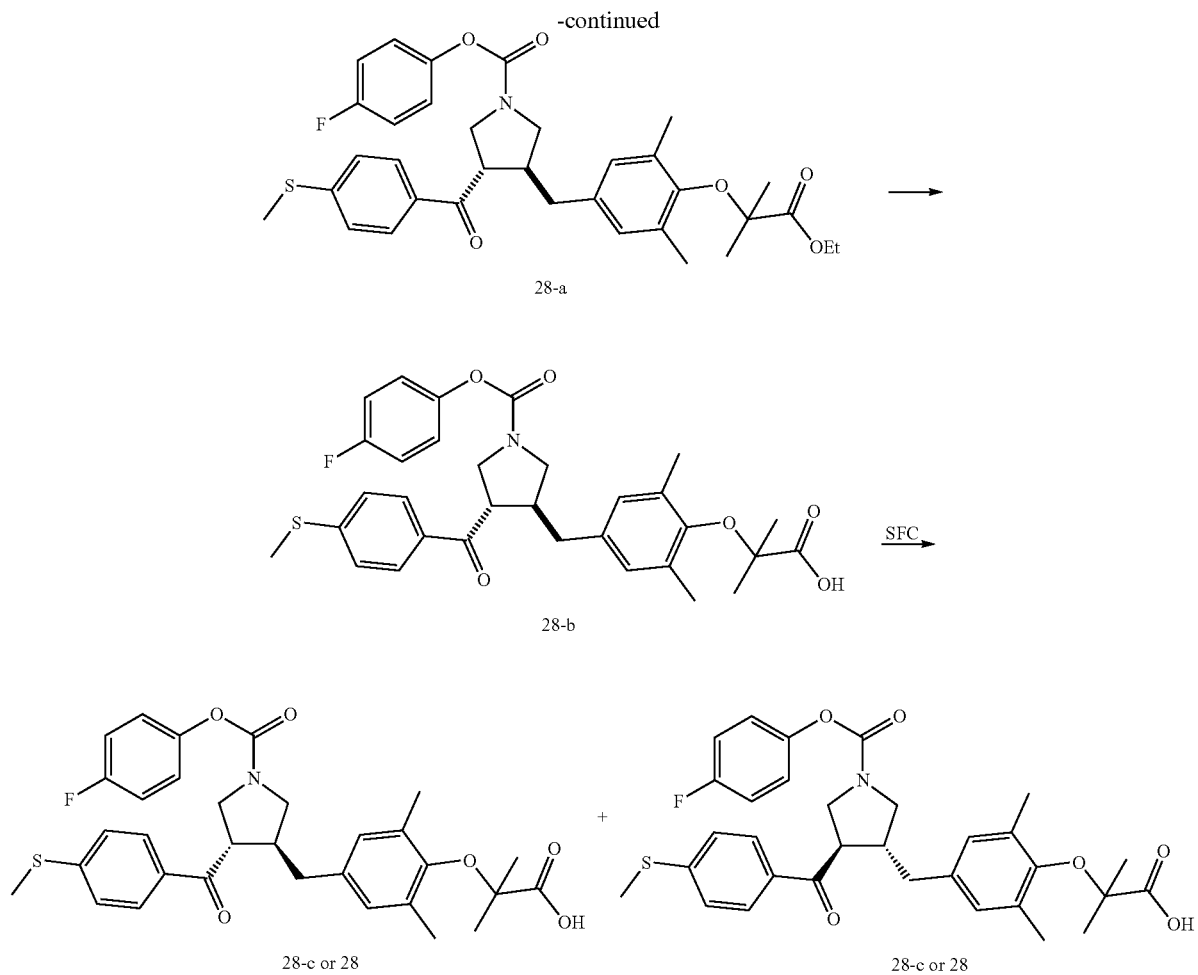

Step 1: Compound 28-a

A solution of Compound 27-a (250.00 mg, 532.32 μmol, 1.00 eq), di-iso-propyl ethylamine (137.59 mg, 1.06 mmol, 185.93 μL, 2.00 eq) and dichloromethane (5.00 mL) was added into a 50 mL reaction flask. Then, (4-fluorophenyl) methyl chloroformate (139.38 mg, 798.48 μmol, 104.80 μL, 1.50 eq) was added. The mixture was stirred at 25° C. for 2 h. A saturated solution of sodium bicarbonate (5 mL) was added into the mixture. The aqueous phase was extracted with dichloromethane (3×10 mL), and the combined organic phase was washed with a saturated aqueous solution of potassium bisulfate (10 mL) and saturated brine (10 mL), dried over anhydrous sodium sulfate, and concentrated under reduced pressure. The residue was purified by silica gel column chromatography (petroleum ether:ethyl acetate=10:1-5:1) to give Compound 28-a.

$^1$H NMR (400 MHz, CDCl$_3$) δ ppm 7.57 (dd, J=8.4, 4.4 Hz, 2H), 7.13 (d, J=8.0 Hz, 2H), 7.03-6.96 (m, 4H), 6.71 (d, J=2.8 Hz, 2H), 4.22 (q, J=7.2 Hz, 2H), 3.83-3.66 (m, 4H), 3.64-3.36 (m, 1H), 2.78-2.76 (m, 1H), 2.61-2.56 (m, 2H), 2.46 (s, 3H), 2.09 (s, 6H), 1.39 (s, 6H), 1.29 (t, J=7.2 Hz, 3H).

Step 2: Compound 28-b

Lithium hydroxide (30.74 mg, 1.28 mmol, 3.00 eq) was added into a solution of Compound 28-a (260.00 mg, 416.54 μmol, 1.00 eq) in ethanol (2.00 mL), tetrahydrofuran (2.00 mL) and water (1.00 mL). The mixture was stirred at 25° C. for 60 h. The mixture was adjusted with a saturated aqueous solution of potassium bisulfate to pH=2-3, and extracted with ethyl acetate (10 mL×3). The combined organic phase was washed with saturated brine, dried over anhydrous sodium sulfate, and concentrated under reduced pressure. The residue was purified by silica gel column chromatography (petroleum ether:ethyl acetate=1:2) to give Compound 28-b.

MS m/z (ESI): 602.1 [M+23].

Step 3: Compound 28

Compound 28-b (100.00 mg) was subjected to chiral separation to give Compound 28.

MS m/z (ESI): 602.1 [M+23].

$^1$H NMR (400 MHz, MeOD-d$_4$) δ ppm 7.65 (dd, J=8.4, 2.4 Hz, 2H), 7.26 (d, J=8.4 Hz, 2H), 7.17-7.13 (m, 4H), 6.88 (s, 2H), 4.02-3.97 (m, 2H), 3.82-3.80 (m, 1H), 3.67-3.65 (m, 1H), 3.53-3.50 (m, 1H), 2.84-2.67 (m, 3H), 2.56 (s, 3H), 2.19 (s, 6H), 1.45 (s, 6H).

Conditions of the chiral resolution: chiral column: Chiralpak AD-3 50×4.6 mm I.D., 3 μm; mobile phase: 40% of methanol (0.05% DEA) in CO$_2$; flow rate: 4 mL/min; column temperature: 40° C.

Retention time of Compound 28: 1.867 min (peak 1)

Examples 29 and 30: Compounds 29 and 30

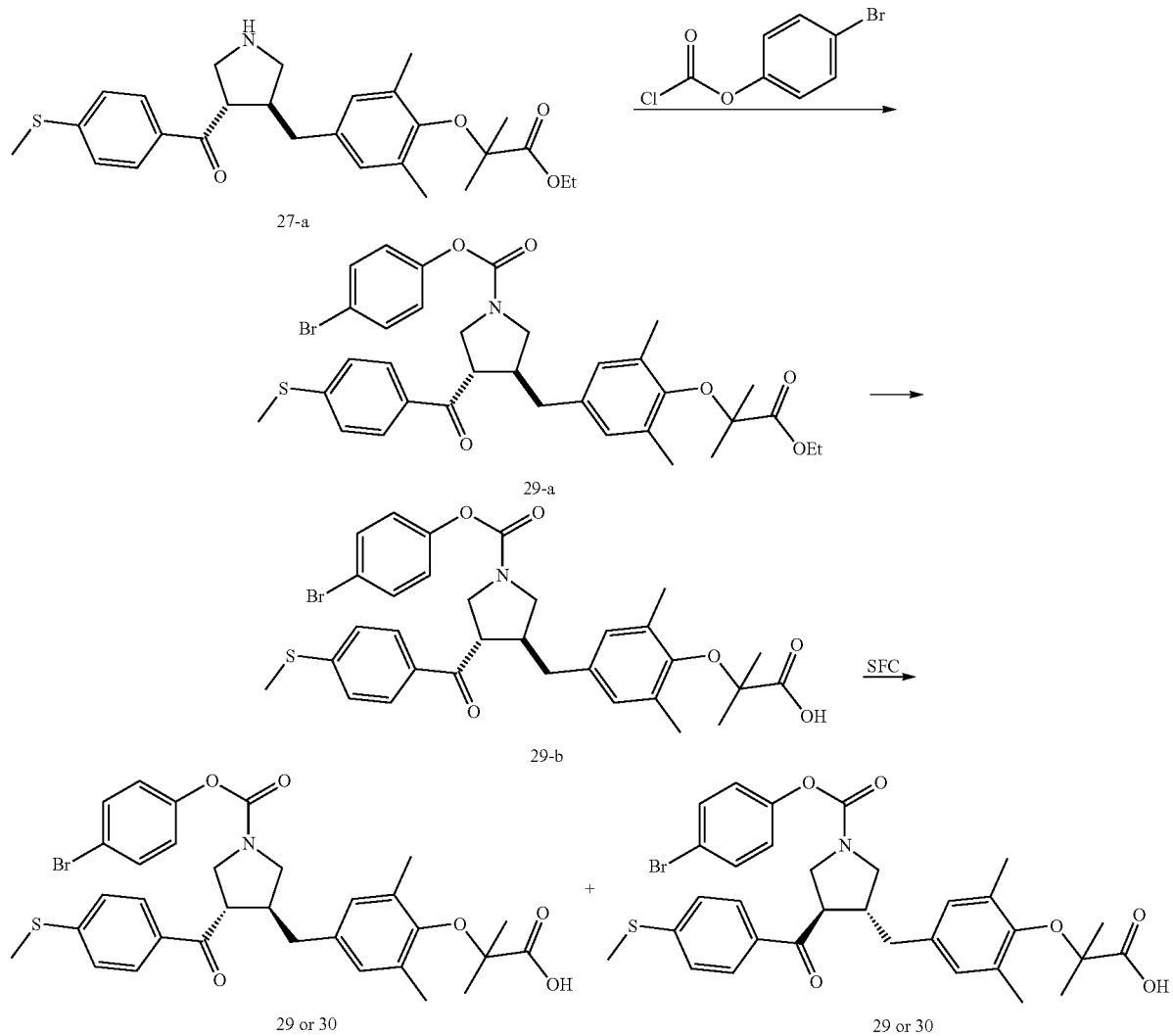

Step 1: Compound 29-a

A solution of Compound 27-a (250.00 mg, 532.32 µmol, 1.00 eq), di-iso-propyl ethylamine (137.60 mg, 1.06 mmol, 2.00 eq) and trichloromethane (5.00 mL) was added into a 50 mL reaction flask. Then, (4-bromo phenyl) methyl chloroformate (188.02 mg, 798.50 µmol, 113.95 µL, 1.50 eq) was added. The mixture was stirred at 25° C. for 18 h. A saturated solution of sodium bicarbonate (5 mL) was added into the mixture. The aqueous phase was extracted with dichloromethane (2*10 mL), and the combined organic phase was washed with a saturated aqueous solution of potassium bisulfate (10 mL) and saturated brine (10 mL), dried over anhydrous sodium sulfate, and concentrated under reduced pressure. The residue was purified by silica gel column chromatography (petroleum ether:ethyl acetate=8:1) to give Compound 29-a.

$^1$H NMR (400 MHz, CDCl$_3$) δ ppm 7.55 (dd, J=8.8, 3.2 Hz, 2H), 7.39 (d, J=8.4 Hz, 2H), 7.13 (d, J=8.8 Hz, 2H), 6.71 (d, J=2.4 Hz, 2H), 4.22 (q, J=7.6 Hz, 2H), 3.82-3.66 (m, 4H), 3.37-3.30 (m, 1H), 2.85-2.80 (m, 1H), 2.77 (d, J=6.4 Hz, 2H), 2.45 (s, 3H), 2.09 (s, 6H), 1.39 (s, 6H), 1.29 (t, J=7.6 Hz, 1H).

Step 2: Compound 29-b

Lithium hydroxide (29.01 mg, 1.21 mmol, 3.00 eq) was added into a solution of Compound 29-a (270.00 mg, 403.80 µmol, 1.00 eq) in ethanol (2.00 mL), tetrahydrofuran (2.00 mL) and water (1.00 mL). The mixture was stirred at 25° C. for 60 h. The mixture was adjusted with a saturated aqueous solution of potassium bisulfate to pH=2-3, and extracted with ethyl acetate (10 mL×3). The combined organic phase was washed with saturated brine, dried over anhydrous sodium sulfate, and concentrated under reduced pressure. The residue was purified by silica gel column chromatography (petroleum ether:ethyl acetate=1:3) to give Compound 29-b.

MS m/z (ESI): 664.0 [M+23].

Step 3: Compounds 29 and 30

Compound 29-b (100.00 mg) was subjected to chiral separation to give Compound 29; Compound 30.

Compound 29:

MS m/z (ESI): 664.0 [M+23].

¹H NMR (400 MHz, MeOD-d₄) δ ppm 7.65 (dd, J=8.0, 2.0 Hz, 2H), 7.53 (d, J=9.2 Hz, 2H), 7.26 (d, J=8.0 Hz, 2H), 7.12 (dd, J=8.8, 2.4 Hz, 2H), 6.88 (s, 2H), 3.98-3.95 (m, 2H), 3.84-3.80 (m, 1H), 3.69-3.67 (m, 1H), 3.53-3.51 (m, 1H), 2.82-2.66 (m, 3H), 2.55 (s, 3H), 2.23 (s, 6H), 1.42 (s, 6H).

Compound 30:

MS m/z (ESI): 664.0 [M+23].

¹H NMR (400 MHz, MeOD-d₄) S ppm 7.66 (d, J=6.4 Hz, 2H), 7.54 (d, J=8.4 Hz, 2H), 7.26 (d, J=8.4 Hz, 2H), 7.12 (dd, J=8.8, 2.8 Hz, 2H), 6.88 (s, 2H), 4.02-3.84 (m, 2H), 3.84-3.82 (m, 1H), 3.69-3.66 (m, 1H), 3.53-3.51 (m, 1H), 2.83-2.79 (m, 4H), 2.67 (s, 3H), 2.23 (s, 6H), 1.43 (s, 6H).

Conditions of the chiral resolution: chiral column: Chiralpak AD-3 50×4.6 mm I.D., 3 μm; mobile phase: 40% of ethanol (0.05% DEA) in CO₂; flow rate: 4 mL/min; column temperature: 40° C.

Retention time of Compound 29: 1.376 min (peak 1); Retention time of Compound 30: 2.462 min (peak 2).

Examples 31 and 32: Compounds 31 and 32

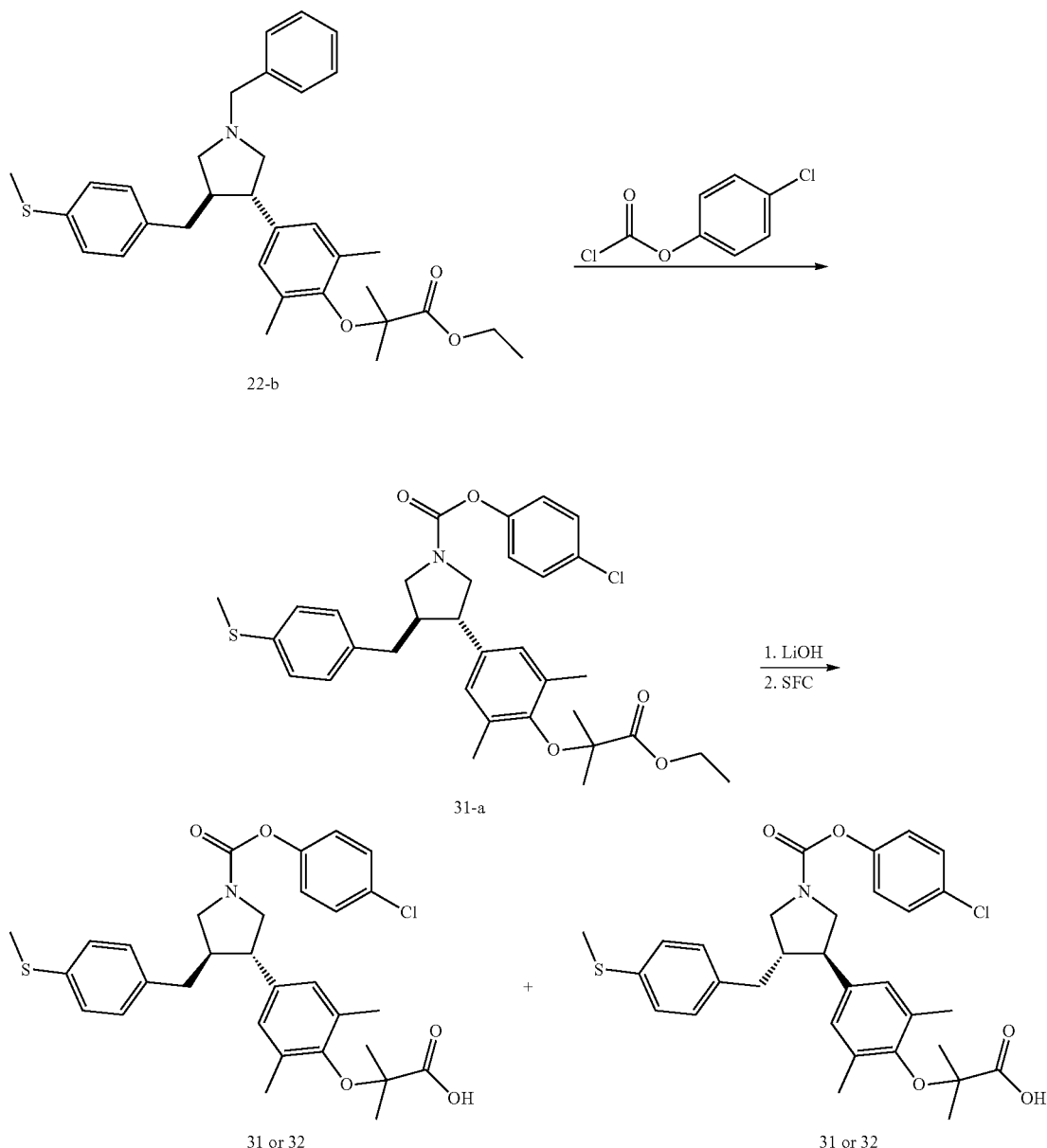

Step 1: Compound 31-a

Compound 22-b (850.00 mg, 1.60 mmol, 1.00 eq) and dichloromethane (10.00 mL) was added into a dried round-bottom flask. Then, (4-chlorophenyl)chloroformate (610.66 mg, 3.20 mmol, 445.74 µL, 2.00 eq) was added. The mixture was stirred at 25° C. for 16 h. The mixture was concentrated under reduced pressure. The residue was purified by flash column chromatography (40.6%, ethyl acetate/petroleum ether) to give Compound 31-a.

MS m/z (ESI): 596.1 [M+1].

Step 2: Compounds 31 and 32

Lithium hydroxide (8.03 mg, 335.47 µmol, 1.00 eq) and water (1.00 mL) was added into a solution of Compound 31-a (200.00 mg, 335.47 µmol, 1.00 eq) in tetrahydrofuran (3 mL) and ethanol (2.00 mL). The mixture was stirred at 25° C. for 16 h. The mixture was adjusted with 1N diluted HCl to pH=2, and then water/ethyl acetate (1:1, 50 mL) was added. The aqueous phase was extracted with ethyl acetate (50 mL×2). The combined organic phase was dried over anhydrous sodium sulfate, filtered, and concentrated under reduced pressure. The residue was purified by flash column chromatography (50.7%, ethyl acetate/petroleum ether) to give a compound, which was subjected to chiral separation to give Compound 31; Compound 32.

Compound 31:

MS m/z (ESI): 590.1 [M+23].

$^1$H NMR (400 MHz, CDCl$_3$) δ ppm 7.24-7.21 (m, 2H), 7.08 (t, J=6.7 Hz, 2H), 6.99-6.94 (m, 4H), 6.83 (s, 2H), 3.94-3.85 (m, 1H), 3.70-3.69 (m, 1H), 3.45-3.38 (m, 1H), 3.21-3.15 (m, 1H), 2.90-2.88 (m, 1H), 2.70-2.67 (m, 1H), 2.52-2.50 (m, 2H), 2.39 (d, J=1.5 Hz, 3H), 2.18 (s, 6H), 1.45 (s, 6H).

Compound 32:

MS m/z (ESI): 590.1 [M+23].

$^1$H NMR (400 MHz, CDCl$_3$) δ ppm 7.23 (dd, J=2.0, 8.8 Hz, 2H), 7.08 (t, J=6.8 Hz, 2H), 6.99-6.94 (m, 4H), 6.83 (s, 2H), 3.94-3.85 (m, 1H), 3.70-3.69 (m, 1H), 3.45-3.39 (m, 1H), 3.21-3.15 (m, 1H), 2.90-2.88 (m, 1H), 2.70-2.67 (m, 1H), 2.52-2.50 (m, 2H), 2.39 (d, J=1.5 Hz, 3H), 2.18 (s, 6H), 1.45 (s, 6H).

Conditions of the chiral resolution: chiral column: Chiralpak AD-3 150×4.6 mm I.D., 3 µm; mobile phase: 40% of ethanol (0.05% DEA) in CO$_2$; flow rate: 2.5 mL/min; column temperature: 40° C.

Retention time of Compound 31: 2.644 min (peak 1);
Retention time of Compound 32: 3.026 min (peak 2).

Examples 33 and 34: Compounds 33 and 34

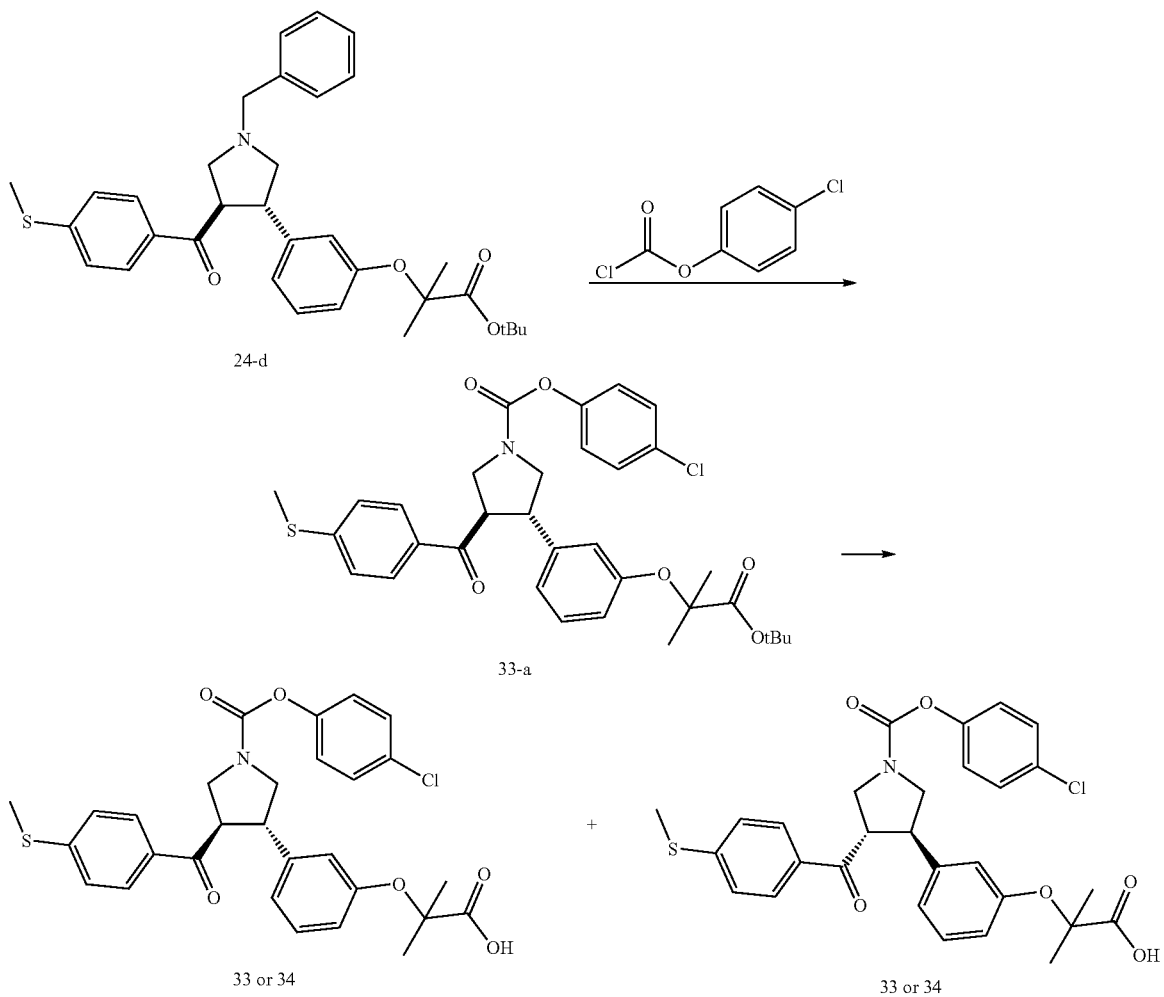

Step 1: Compound 33-a

Under nitrogen protection, (4-chlorophenyl)chloroformate (5.25 g, 27.48 mmol, 3.83 mL, 2.00 eq) was slowly added into a solution of Compound 2-b (7.50 g, 13.74 mmol, 1.00 eq) in dichloromethane (60.00 mL). The mixture was stirred at 25° C. for 16 h. The mixture was concentrated under reduced pressure. The residue was purified by flash column chromatography (41.5%, ethyl acetate/petroleum ether) to give Compound 33-a.

$^1$H NMR (400 MHz, CDCl$_3$) δ ppm 7.68 (dd, J=5.3, 8.5 Hz, 2H), 7.26-7.24 (m, 2H), 7.15-7.03 (m, 5H), 6.87-6.82 (m, 2H), 6.63 (dd, J=2.3, 8.3 Hz, 1H), 4.11-3.96 (m, 3H), 3.82-3.70 (m, 1H), 3.68-3.60 (m, 2H), 2.43 (s, 3H), 1.46 (d, J=4.8 Hz, 6H), 1.35 (s, 9H)

Step 2: Compounds 33 and 34

In a flask, trifluoroacetic acid (23.10 g, 202.60 mmol, 15.00 mL, 16.94 eq) was slowly added into a solution of Compound 33-a (7.30 g, 11.96 mmol, 1.00 eq) in dichloromethane (60.00 mL). The mixture was stirred at 25° C. for 16 h. The mixture was concentrated under reduced pressure. The residue was purified by flash column chromatography (40.6%, ethyl acetate/petroleum ether), and the resulted product was subjected to chiral separation to give Compound 33, yield: 3.65%; Compound 34.

Compound 33:
MS m/z (ESI): 576.0 [M+23].
$^1$H NMR (400 MHz, CDCl$_3$) δ ppm 7.78-7.75 (m, 2H), 7.33-7.31 (m, 2H), 7.23-7.12 (m, 5H), 6.93-6.86 (m, 2H), 6.79 (t, J=7.1 Hz, 1H), 4.08-3.97 (m, 3H), 3.81-3.77 (m, 3H), 2.50 (s, 3H), 1.56-1.53 (m, 6H)

Compound 34:
MS m/z (ESI): 576.0 [M+23].
$^1$H NMR (400 MHz, CDCl$_3$) δ ppm 7.69 (dd, J=6.0, 8.3 Hz, 2H), 7.24 (d, J=8.8 Hz, 2H), 7.15-7.03 (m, 5H), 6.83 (br t, J=6.5 Hz, 1H), 6.78 (s, 1H), 6.75-6.72 (m, 1H), 4.01-3.91 (m, 3H), 3.73-3.69 (m, 3H), 2.42 (s, 3H), 1.47-1.45 (m, 6H)

Conditions of the chiral resolution: chiral column: Chiralpak AD-3 100×4.6 mm I.D., 3 μm; mobile phase: 40% of ethanol (0.05% DEA) in CO$_2$.

Retention time of Compound 33: 5.039 min (peak 1); Retention time of Compound 34: 6.986 min (peak 2).

Example 35: Compound 35

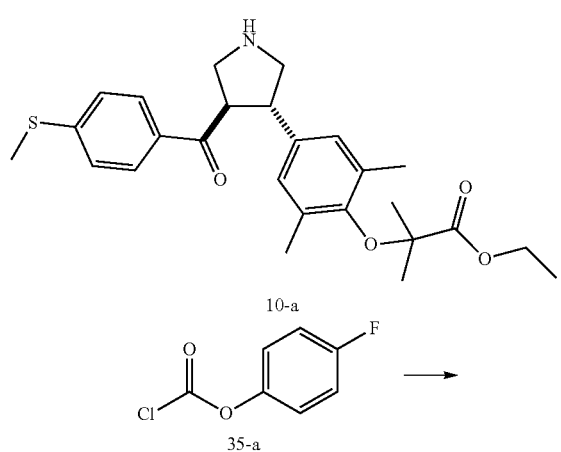

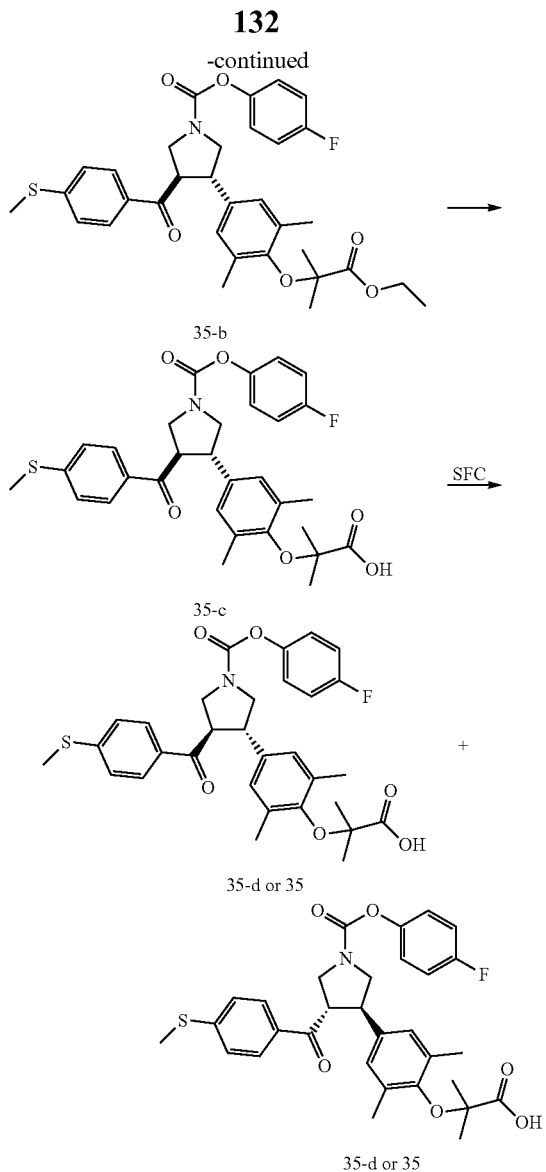

Step 1: Compound 35-b

Under nitrogen protection, Compound 10-a (150.00 mg, 329.23 μmol, 1.00 eq), di-iso-propyl ethylamine (85.10 mg, 658.46 μmol, 115.00 μL, 200 eq) and 35-a (68.96 mg, 395.07 μmol, 51.85 μL, 1.20 eq) were stirred at 20° C. for 12 h. The reaction solution was concentrated to give a crude product which was purified by silica gel column chromatography (petroleum ether/ethyl acetate=4/1) to give Compound 35-b.

$^1$H NMR (400 MHz, CDCl$_3$) δ ppm 7.77-7.72 (m, 2H), 7.23-7.21 (m, 2H), 7.13-7.12 (m, 2H), 7.08-7.06 (m, 2H), 6.88-6.87 (m, 2H), 4.32-4.17 (m, 2H), 4.15-4.09 (m, 3H), 3.84-3.77 (m, 3H), 2.53 (s, 3H), 2.16 (t, J=6.53 Hz, 6H), 1.44 (s, 6H), 1.38-1.34 (m, 3H).

Step 2: Compound 35-c

A solution of Compound 35-b (180.00 mg, 303.18 μmol, 1.00 eq) and lithium hydroxide (127.22 mg, 3.03 mmol, 10.00 eq) in ethanol (9.00 mL) and water (3.00 mL) was stirred at 25° C. for 12 h. The mixture was adjusted with 1N diluted HCl to pH=3, and treated with water and ethyl acetate (1:1, 50 mL). The aqueous phase was extracted with ethyl acetate (50 mL×3). The combined organic phase was washed with saturated brine (20 mL×1), dried over anhydrous sodium sulfate, filtered, and concentrated under reduced pressure to give a crude product. The crude product was purified by silica gel column chromatography (petroleum ether/ethyl acetate=2/1) to give Compound 35-c.

$^1$H NMR (400 MHz, MeOD-d$_4$) δ ppm 7.67-7.65 (m, 2H), 7.45-7.39 (m, 1H), 7.13-7.02 (m, 5H), 6.87-6.86 (m, 2H), 4.35-4.31 (m, 1H), 4.06-4.03 (m, 1H), 3.88-3.78 (m, 2H), 3.54-3.51 (m, 2H), 2.40 (s, 3H), 2.06-2.05 (m, 6H), 1.26 (d, J=2.80 Hz, 6H).

Step 3: Compound 35

Compound 35-c (120 mg) was subjected to chiral separation to give Compound 35.

MS m/z (ESI): 588.1 [M+23].

$^1$H NMR (400 MHz, CDCl$_3$) δ ppm 7.68 (t, J=8.41 Hz, 2H), 7.13 (dd, J=4.02, 8.53 Hz, 2H), 7.03-7.02 (m, 2H), 6.99-6.97 (m, 2H), 6.84 (d, J=6.53 Hz, 2H), 4.08-4.01 (m, 3H), 3.70-3.65 (m, 3H), 2.44 (s, 3H), 2.12 (d, J=5.52 Hz, 6H), 1.40 (s, 6H).

Conditions of the chiral resolution: chiral column: Chiralpak AD-3 100×4.6 mm I.D., 3 μm; mobile phase: 40% of methanol (0.05% DEA) in CO$_2$; flow rate: 2.8 mL/min; column temperature: 40° C.

Retention time of Compound 35: 2.429 min (peak 2).

Example 36: Compound 36

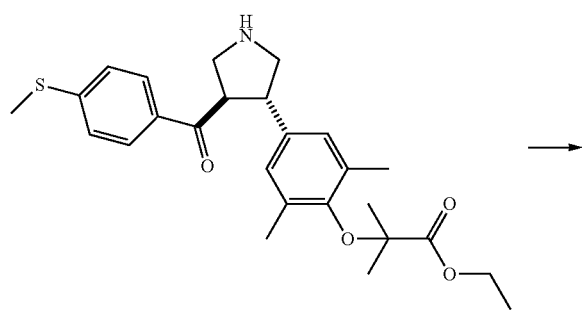

10-a

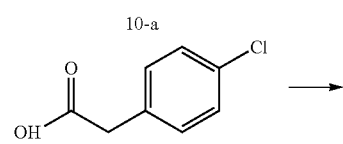

36-a

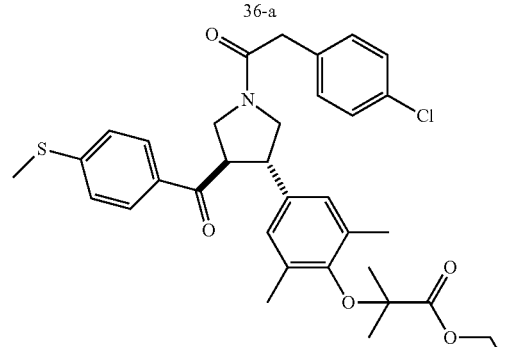

36-b

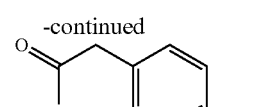

36-c

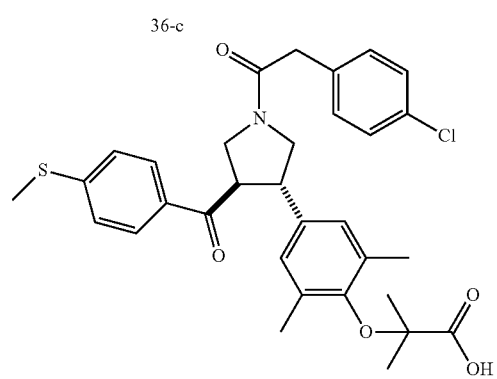

36

Step 1: Compound 36-b

Under nitrogen protection, a solution of Compound 10-a (150.00 mg, 329.23 μmol, 1.00 eq), triethylamine (66.63 mg, 658.46 μmol, 91.27 μL, 2.00 eq), oxy-(7-azabenzotriazol-1-yl)-N,N,N',N'-tetramethylureahexafluorophosphonate (187.77 mg, 493.85 μmol, 1.50 eq) and 36-a (84.25 mg, 493.85 μmol, 1.50 eq) in dichloromethane (10.00 mL) was stirred at 20° C. for 12 h. The reaction solution was concentrated to give a crude product which was purified by silica gel column chromatography (petroleum ether/ethyl acetate=4/1) to give Compound 36-b.

$^1$H NMR (400 MHz, CDCl$_3$) δ ppm 7.65 (d, J=8.4 Hz, 2H), 7.53-7.52 (m, 1H), 7.24-7.09 (m, 6H), 6.67 (d, J=4.8 Hz, 2H), 3.97-3.89 (m, 3H), 3.60-3.58 (m, 5H), 2.43 (s, 3H), 2.03 (d, J=8.0 Hz, 6H), 1.34-1.31 (m, 6H), 1.29-1.25 (m, 3H).

Step 2: Compound 36-c

A solution of Compound 36-b (120.00 mg, 197.31 μmol, 1.00 eq) and lithium hydroxide (82.79 mg, 1.97 mmol, 10.00 eq) in ethanol (9.00 mL) and water (3.00 mL) was stirred at 25° C. for 12 h. The mixture was adjusted with 1N diluted HCl to pH=3, and treated with water and ethyl acetate (1:1, 50 mL). The aqueous phase was extracted with ethyl acetate (50 mL×3). The combined organic phase was washed with saturated brine (20 mL×1), dried over anhydrous sodium sulfate, filtered, and concentrated under reduced pressure to give a crude product. The crude product was purified by silica gel column chromatography (petroleum ether/ethyl acetate=2/1) to give Compound 36-c.

$^1$H NMR (400 MHz, MeOD-d$_4$) δ ppm 7.78-7.75 (m, 2H), 7.36-7.31 (m, 4H), 7.24-7.21 (m, 2H), 6.89 (s, 2H), 4.09-3.91 (m, 3H), 3.77-3.50 (m, 5H), 2.51 (d, J=2.8 Hz, 3H), 2.16 (s, 6H), 1.36 (s, 6H).

Step 3: Compound 36

Compound 36-c (80 mg) was separated by High Performance Liquid Chromatography to give Compound 36.

MS m/z (ESI): 602.1 [M+23].

$^1$H NMR (400 MHz, CDCl$_3$) δ ppm 7.67 (d, J=8.53 Hz, 1H), 7.56 (d, J=8.53 Hz, 1H), 7.22-7.21 (m, 2H), 7.18-7.09 (m, 4H), 6.70 (d, J=5.02 Hz, 2H), 4.03-3.98 (m, 1H), 3.91-3.89 (m, 1H), 3.80 (d, J=8.03 Hz, 1H), 3.72 (d, J=7.78 Hz, 1H), 3.61-3.60 (m, 3H), 3.59-3.56 (m, 1H), 2.43 (s, 3H), 2.07 (d, J=9.54 Hz, 6H), 1.39-1.35 (m, 6H).

Example 37: Compound 37

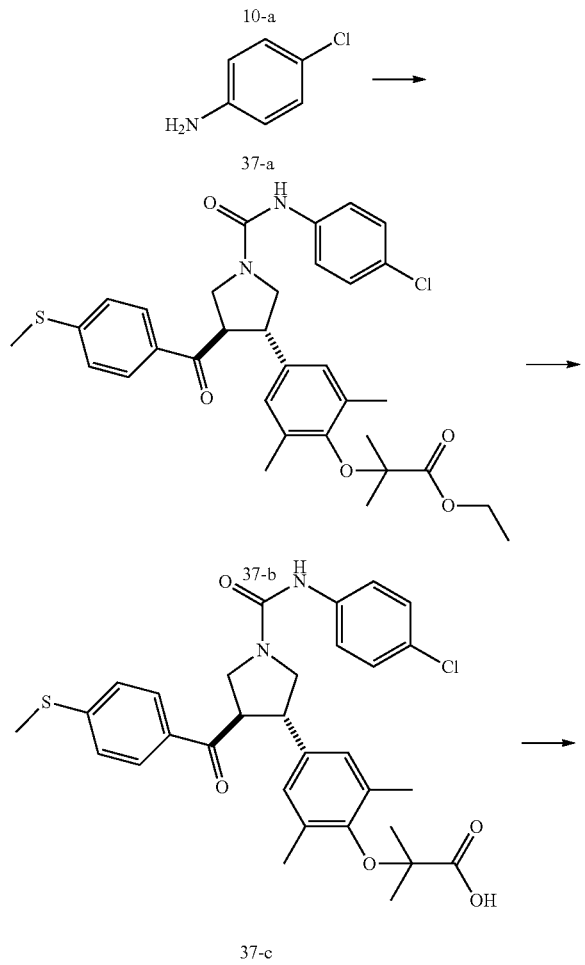

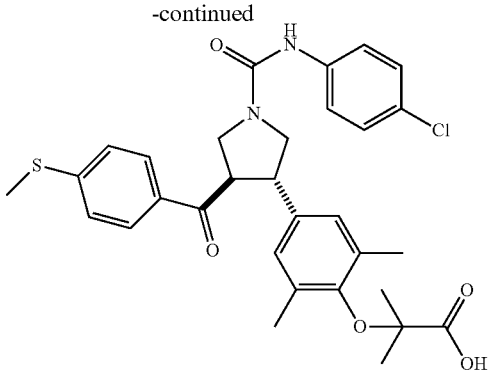

Step 1: Compound 37-b

Under nitrogen protection, a solution of Compound 10-a (400.00 mg, 877.94 μmol, 1.00 eq), triphosgene (208.42 mg, 702.35 μmol, 0.80 eq), di-iso-propyl ethylamine (226.93 mg, 1.76 mmol, 306.66 μL, 2.00 eq) and 37-a (134.40 mg, 1.05 mmol, 1.20 eq) in tetrahydrofuran (20.00 mL) was stirred at 25° C. for 12 h. The reaction mixture was concentrated to give a crude product which was purified by silica gel column chromatography (petroleum ether/ethyl acetate=4/1) to give Compound 37-b.

$^1$H NMR (400 MHz, CDCl$_3$) δ ppm 7.65-7.62 (m, 2H), 7.30-7.27 (m, 3H), 7.17-7.10 (m, 3H), 6.79 (d, J=6.4 Hz, 2H), 4.22-4.05 (m, 5H), 3.93-3.58 (m, 3H), 2.43 (s, 3H), 2.05 (s, 6H), 1.33-1.25 (m, 8H).

Step 2: Compound 37-c

A solution of Compound 37-b (200.00 mg, 328.32 μmol, 1.00 eq) and lithium hydroxide (13.78 mg, 328.32 mol, 1.00 eq) in ethanol (6.00 mL) and water (3.00 mL) was stirred at 25° C. for 12 h. The mixture was adjusted with 1N diluted HCl to pH=3, and treated with water and ethyl acetate (1:1.50 mL). The aqueous phase was extracted with ethyl acetate (50 mL×3). The combined organic phase was washed with saturated brine (20 mL×1), dried over anhydrous sodium sulfate, filtered, and concentrated under reduced pressure to give a crude product. The crude product was purified by silica gel column chromatography (petroleum ether/ethyl acetate=2/1) to give Compound 37-c.

$^1$H NMR (400 MHz, DMSO-d$_6$) δ ppm 7.82 (d, J=8.8 Hz, 2H), 7.54 (d, J=8.8 Hz, 2 Hz), 7.46 (d, J=8.8 Hz, 1H), 7.32-7.27 (m, 4H), 6.97 (s, 1H), 4.49-4.45 (m, 1H), 4.02-3.93 (m, 2H), 3.62-3.60 (m, 1H), 3.49-3.45 (m, 2H), 2.56 (s, 3H), 2.08 (s, 6H), 1.25 (d, J=3.6 Hz, 6H).

Step 3: Compound 37

Compound 37-c (110 mg) was separated by HPLC to give Compound 37.

MS m/z (ESI): 603.0 [M+23].

$^1$H NMR (400 MHz, DMSO-d$_6$) δ ppm 8.35 (s, 1H), 7.82 (d, J=8.53 Hz, 2H), 7.54 (d, J=7.70 Hz, 2H), 7.28-7.23 (m, 4H), 6.96 (s, 2H), 4.47-4.43 (m, 3H), 3.98-3.90 (m, 3H), 2.48 (br s, 3H), 2.08 (s, 6H), 1.26 (d, J=3.51 Hz, 6H).

Example 38: Compound 38

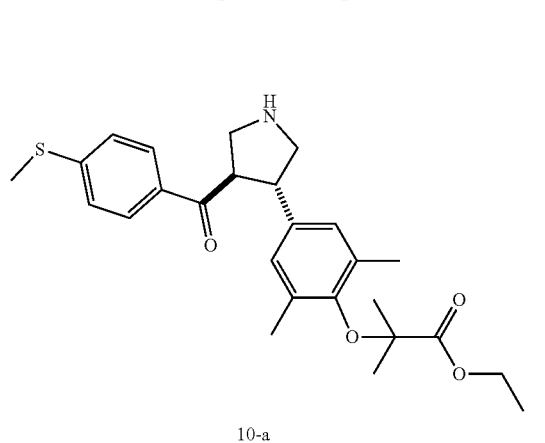

10-a

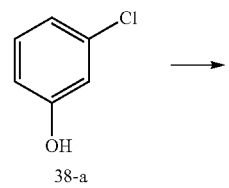

38-a

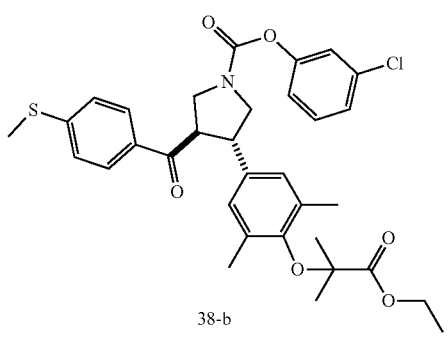

38-b

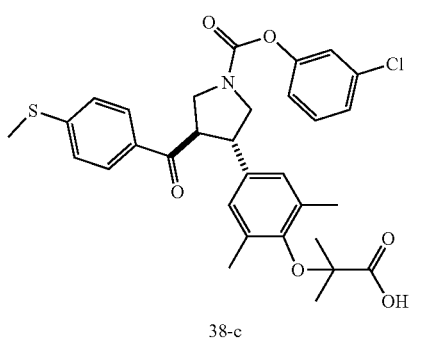

38-c

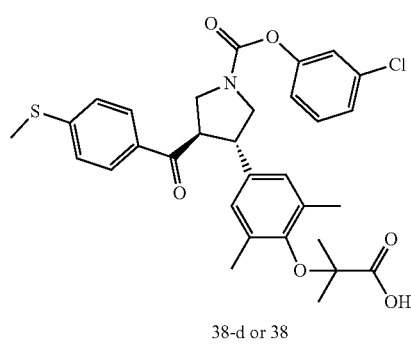

38-d or 38

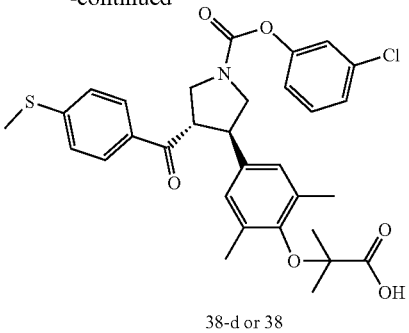

38-d or 38

Step 1: Compound 38-a

Under nitrogen protection, a solution of Compound 38-a (1.00 g, 7.78 mmol, 819.67 μL, 1.00 eq), triphosgene (1.85 g, 6.22 mmol, 0.80 eq) and triethylamine (787.26 mg, 7.78 mmol, 1.08 mL, 1.00 eq) in tetrahydrofuran (20.00 mL) was stirred at 0° C. for 15 min, warmed to 20° C., and stirred for 1 h. The reaction solution was filtered and concentrated, and the resulted crude product was dissolved in tetrahydrofuran (5.00 mL), and then 10-a (1.00 g, 2.19 mmol, 1.00 eq) and di-iso-propyl ethylamine (424.55 mg, 3.29 mmol, 573.72 μL, 1.50 eq) were added and stirred at 20° C. for 1 h. The reaction solution was concentrated to give a crude product which was purified by silica gel column chromatography (petroleum ether/ethyl acetate=4/1) to give Compound 38-b.

MS m/z (ESI): 610.2 [M+1].

$^1$H NMR (400 MHz, CDCl$_3$) δ ppm 7.78 (dd, J=3.52, 8.54 Hz, 2H), 7.44-7.38 (m, 1H), 7.32-7.24 (m, 4H), 7.18-7.12 (m, 1H), 6.97 (d, J=2.76 Hz, 2H), 4.55-4.38 (m, 1H), 4.13 (q, J=7.28 Hz, 2H), 3.97-3.84 (m, 1H), 3.67-3.43 (m, 3H), 2.50 (s, 3H), 2.04 (s, 6H), 1.28 (s, 6H), 1.20 (t, J=7.04 Hz, 3H)

Step 2: Compound 38-c

A solution of Compound 38-b (1.00 g, 1.64 mmol, 1.00 eq) and lithium hydroxide (117.83 mg, 4.92 mmol, 3.00 eq) in ethanol (20.00 mL) and water (5.00 mL) was stirred at 20° C. for 16 h. The mixture was adjusted with 1N diluted HCl to pH=4, and treated with water and ethyl acetate (1:1.50 mL). The aqueous phase was extracted with ethyl acetate (10 mL×3). The combined organic phase was dried over anhydrous sodium sulfate, filtered, and concentrated under reduced pressure to give a crude product. The crude product was purified by silica gel column chromatography (petroleum ether/ethyl acetate=1/1) to give Compound 38-c.

MS m/z (ESI): 582.2 [M+1].

Step 3: Compound 38

Compound 38-c (200 mg) was subjected to chiral separation to give Compound 38.

MS m/z (ESI): 604.0 [M+23].

$^1$H NMR (400 MHz, CDCl$_3$) δ ppm 7.74 (t, J=8.66 Hz, 2H), 7.32-7.27 (m, 1H), 7.23-7.15 (m, 4H), 7.09-7.03 (m, 1H), 6.90 (br d, J=5.52 Hz, 2H), 4.19-4.02 (m, 3H), 3.90-3.64 (m, 3H), 2.50 (s, 3H), 2.19 (br d, J=5.52 Hz, 6H), 1.46 (br s, 6H).

Conditions of the chiral resolution: chiral column: Chiralpak AD-3 50×4.6 mm I.D., 3 μm; mobile phase: 40% of methanol (0.05% DEA) in CO$_2$; flow rate: 4.0 mL/min; column temperature: 40° C.

Retention time of Compound 38: 1.667 min (peak 2).

Example 39: Compound 39

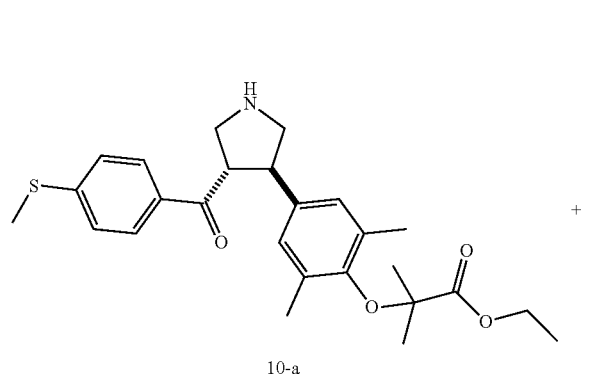

10-a

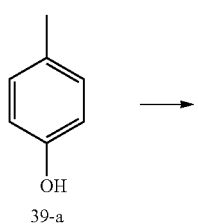

39-a

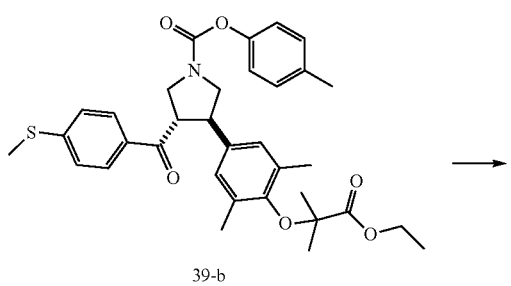

39-b

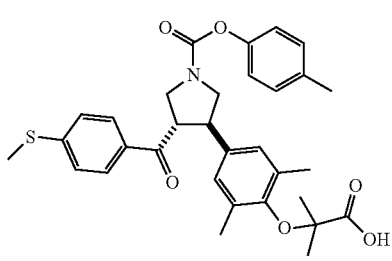

39-c

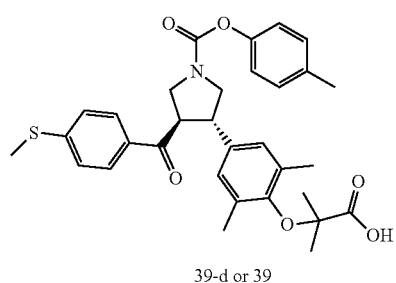

39-d or 39

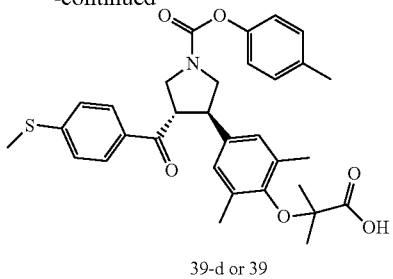

39-d or 39

Step 1: Compound 39-b

Under nitrogen protection, a solution of Compound 39-a (1.00 g, 9.25 mmol, 1.00 eq), triphosgene (2.20 g, 7.40 mmol, 0.80 eq) and triethylamine (1.12 g, 11.10 mmol, 1.54 mL, 1.20 eq) in tetrahydrofuran (20.00 mL) was stirred at 0° C. for 15 min, warmed to 20° C. and stirred for 1 h. The reaction solution was filtered and concentrated, and the resulted crude product was dissolved in tetrahydrofuran (20.00 mL), 10-a (1.00 g, 2.19 mmol, 1.00 eq) and di-isopropyl ethylamine (424.55 mg, 3.29 mmol, 573.72 μL, 1.50 eq) were added and stirred at 20° C. for 1 h. The reaction solution was concentrated to give a crude product which was purified by silica gel column chromatography (petroleum ether/ethyl acetate=4/1) to give Compound 39-b.

MS m/z (ESI): 612.1 [M+23].

Step 2: Compound 39-c

A solution of Compound 39-b (200.00 mg, 339.13 μmol, 1.00 eq) and lithium hydroxide (81.22 mg, 3.39 mmol, 10.00 eq) in ethanol (20.00 mL) and water (5.00 mL) was stirred at 20° C. for 16 h. The mixture was adjusted with 1N diluted HCl to pH=4, and treated with water and ethyl acetate (1:1, 50 mL). The aqueous phase was extracted with ethyl acetate (10 mL×3). The combined organic phase was dried over anhydrous sodium sulfate, filtered, and concentrated under reduced pressure to give a crude product. The crude product was purified by silica gel column chromatography (petroleum ether/ethyl acetate=1/1) to give Compound 39-c.

MS m/z (ESI): 562.2 [M+1].

Step 3: Compound 39

Compound 39-c (200 mg) was subjected to chiral separation to give Compound 39.

MS m/z (ESI): 562.2 [M+1].

$^1$H NMR (400 MHz, CDCl$_3$) δ ppm 7.77 (t, J=8.16 Hz, 2H), 7.25-7.15 (m, 4H), 7.04 (d, J=8.28 Hz, 2H), 6.93 (d, J=6.54 Hz, 2H), 4.21-4.05 (m, 3H), 3.92-3.65 (m, 3H), 2.53 (s, 3H), 2.21 (br d, J=5.52 Hz, 6H), 1.49 (s, 6H)

Conditions of the chiral resolution: chiral column: Chiralpak AD-3 100×4.6 mm I.D., 3 μm; mobile phase: 40% of methanol (0.05% DEA) in CO$_2$; flow rate: 2.8 mL/min; column temperature: 40° C.

Retention time of Compound 39: 3.697 min (peak 2).

Example 40: Compound 40

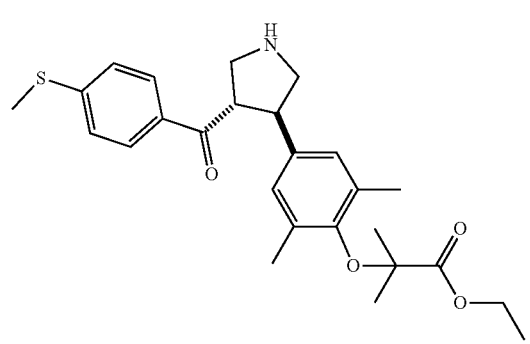

10-a

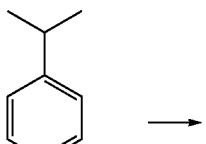

40-a

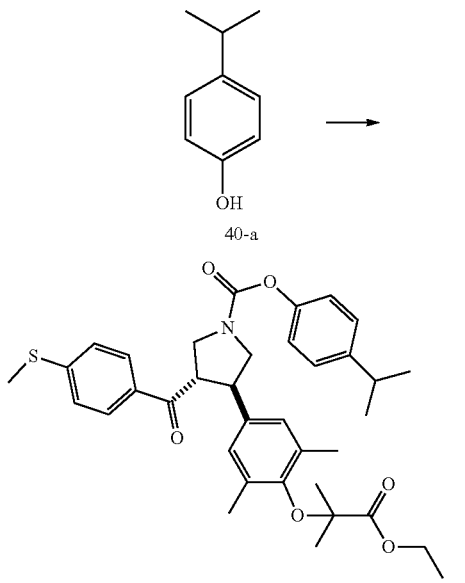

40-b 40-c

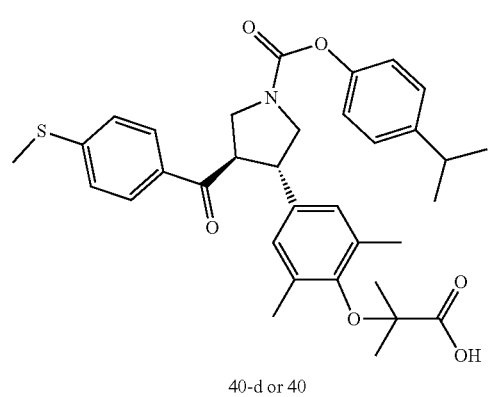 [SMILES: CSc1ccc(C(=O)[C@@H]2CN(C(=O)Oc3ccc(C(C)C)cc3)C[C@H]2c2cc(C)c(OC(C)(C)C(=O)O)c(C)c2)cc1]

40-d or 40

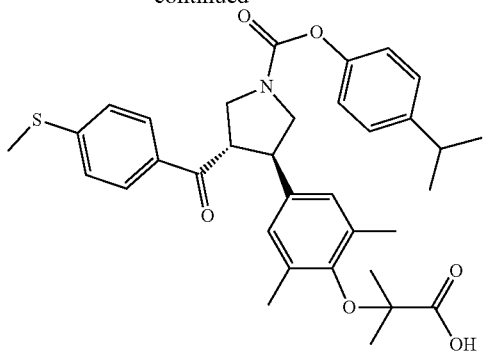

40-d or 40

Step 1: Compound 40-a

Under nitrogen protection, a solution of Compound 40-a (1.00 g, 7.34 mmol, 1.00 eq), triphosgene (1.74 g, 5.87 mmol, 0.80 eq) and triethylamine (891.28 mg, 8.81 mmol, 1.22 mL, 1.20 eq) in tetrahydrofuran (20.00 mL) was stirred at 0° C. for 15 min, warmed to 20° C. and stirred for 1 h. The reaction solution was filtered and concentrated, and the resulted crude product was dissolved in tetrahydrofuran (20.00 mL), and then 10-a (1.00 g, 2.19 mmol, 1.00 eq) and di-iso-propyl ethylamine (424.55 mg, 3.29 mmol, 573.72 μL, 1.50 eq) were added and stirred at 20° C. for 1 h. The reaction solution was concentrated to give a crude product which was purified by silica gel column chromatography (petroleum ether/ethyl acetate=4/1) to give Compound 40-b.

$^1$H NMR (400 MHz, CDCl$_3$) δ ppm 7.81 (d, J=7.54 Hz, 2H), 7.26 (dd, J=8.54, 13.30 Hz, 4H), 7.11-6.94 (m, 4H), 4.58-4.41 (m, 1H), 4.20-4.09 (m, 2H), 3.99-3.82 (m, 1H), 3.43-3.72 (m, 3H), 2.89 (q, J=6.74, 13.69 Hz, 1H), 2.50-2.48 (m, 3H), 2.14-2.01 (m, 6H), 1.30 (s, 6H), 1.25-1.18 (m, 9H).

Step 2: Compound 40-c

A solution of Compound 40-b (1.00 g, 1.62 mmol, 1.00 eq) and lithium hydroxide (387.67 mg, 16.20 mmol, 10.00 eq) in ethanol (20.00 mL) and water (5.00 mL) was stirred at 20° C. for 16 h. The mixture was adjusted with 1N diluted HCl to pH=4, and treated with water and ethyl acetate (1:1.50 mL). The aqueous phase was extracted with ethyl acetate (10 mL×3). The combined organic phase was dried over anhydrous sodium sulfate, filtered, and concentrated under reduced pressure to give a crude product. The crude product was purified by silica gel column chromatography (petroleum ether/ethyl acetate=1/1) to give Compound 40-c.

MS m/z (ESI): 612.2 [M+23].

Step 3: Compound 40

Compound 40-c (200 mg) was subjected to chiral separation to give Compound 40.

MS m/z (ESI): 612.1 [M+23].

$^1$H NMR (400 MHz, CDCl$_3$) δ ppm 7.66 (br t, J=8.78 Hz, 2H), 7.15-7.08 (m, 4H), 6.98 (d, J=8.54 Hz, 2H), 6.82 (br d, J=7.28 Hz, 2H), 4.13-3.95 (m, 3H), 3.84-3.56 (m, 3H), 2.88-2.77 (m, 1H), 2.41 (s, 3H), 2.10 (br d, J=6.54 Hz, 6H), 1.37 (br s, 6H), 1.16 (d, J=6.78 Hz, 6H).

Conditions of the chiral resolution: chiral column: Chiralpak AD-3 100×4.6 mm I.D., 3 μm; mobile phase: 40% of iso-propanol (0.05% DEA) in CO$_2$; flow rate: 2.8 mL/min; column temperature: 40° C.

Retention time of Compound 40: 2.240 min (peak 2).

Example 41: Compound 41

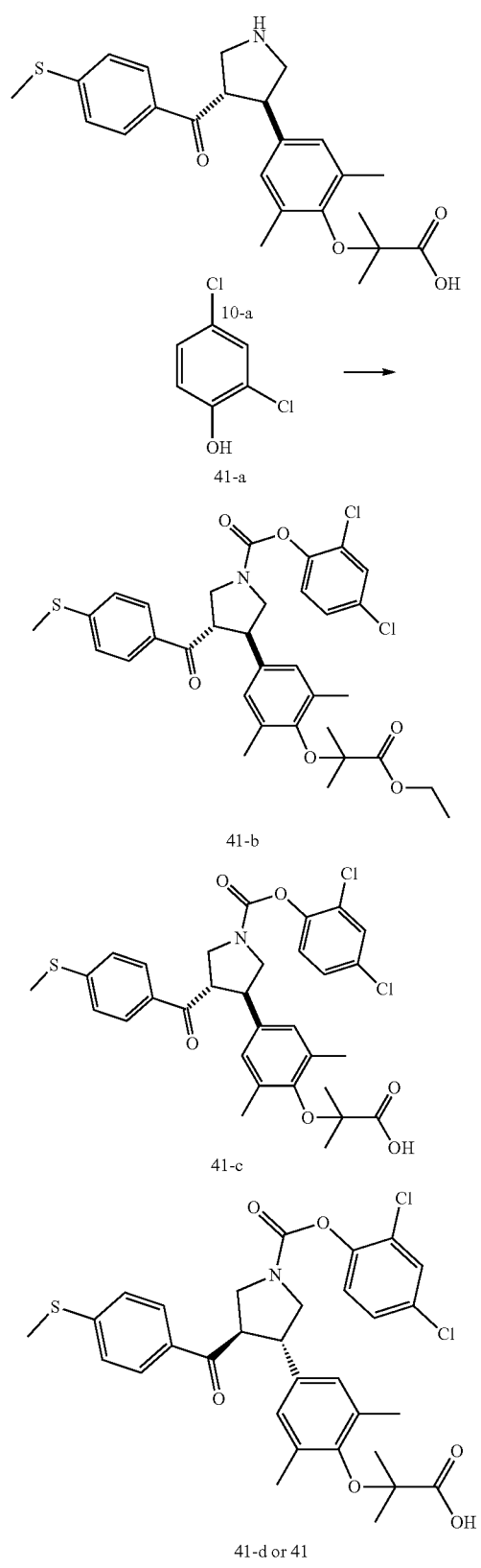

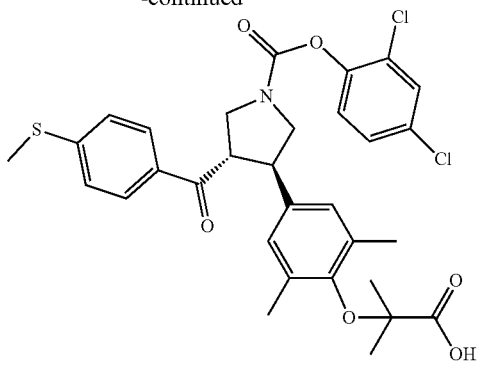

41-d or 41

Step 1: Compound 41-b

Under nitrogen protection, a solution of Compound 41-a (1.00 g, 6.13 mmol, 1.00 eq), triphosgene (1.46 g, 4.90 mmol, 0.80 eq) and triethylamine (620.80 mg, 6.13 mmol, 850.41 µL, 1.00 eq) in tetrahydrofuran (20.00 mL) was stirred at 0° C. for 15 min, warmed to 20° C. and stirred for 1 h. The reaction solution was filtered and concentrated, and the resulted crude product was dissolved in tetrahydrofuran (20.00 mL), and then 10-a (1.00 g, 2.19 mmol, 1.00 eq) and di-iso-propyl ethylamine (424.55 mg, 3.29 mmol, 573.72 µL, 1.50 eq) were added and stirred at 20° C. for 1 h. The reaction solution was concentrated to give a crude product which was purified by silica gel column chromatography (petroleum ether/ethyl acetate=4/1) to give Compound 41-b.
MS m/z (ESI): 644.1 [M+1].
$^1$H NMR (400 MHz, CDCl$_3$) δ ppm 7.82-7.73 (m, 3H), 7.45 (dt, J=2.51, 8.66 Hz, 1H), 7.40-7.36 (m, 1H), 7.27 (d, J=8.28 Hz, 2H), 6.97 (d, J=3.52 Hz, 2H), 4.56-4.42 (m, 1H), 4.13 (q, J=7.04 Hz, 2H), 3.96-3.83 (m, 1H), 3.42-3.79 (m, 4H), 2.06-2.02 (m, 6H), 1.28 (d, J=1.76 Hz, 6H), 1.20 (t, J=7.16 Hz, 3H)

Step 2: Compound 41-c

A solution of Compound 41-b (1.00 g, 1.55 mmol, 1.00 eq) and lithium hydroxide (111.46 mg, 4.65 mmol, 3.00 eq) in ethanol (20.00 mL) and water (5.00 mL) was stirred at 20° C. for 16 h. The mixture was adjusted with 1N diluted HCl to pH=4, and treated with water and ethyl acetate (1:1, 50 mL). The aqueous phase was extracted with ethyl acetate (10 mL×3). The combined organic phase was dried over anhydrous sodium sulfate, filtered, and concentrated under reduced pressure to give a crude product. The crude product was purified by silica gel column chromatography (petroleum ether/ethyl acetate=1/1) to give Compound 41-c.
MS m/z (ESI): 616.1 [M+1].

Step 3: Compound 41

Compound 41-c (200 mg) was subjected to chiral separation to give Compound 41.
MS m/z (ESI): 616.1 [M+1].
$^1$H NMR (400 MHz, CDCl$_3$) δ ppm 7.69 (t, J=8.16 Hz, 2H), 7.37 (d, J=2.26 Hz, 1H), 7.18 (d, J=2.26 Hz, 1H), 7.16-7.11 (m, 3H), 6.84 (d, J=7.28 Hz, 2H), 4.15-3.62 (m, 6 h), 2.44 (s, 3H), 2.12 (d, J=5.02 Hz, 6H), 1.44-1.35 (m, 6H)

Conditions of the chiral resolution: chiral column: Chiralpak AD-3 50×4.6 mm I.D., 3 µm; mobile phase: 40% of iso-propanol (0.05% DEA) in $CO_2$; flow rate: 4.0 mL/min; column temperature: 40° C.

Retention time of Compound 41: 1.899 min (peak 2).

Example 42: Compound 42

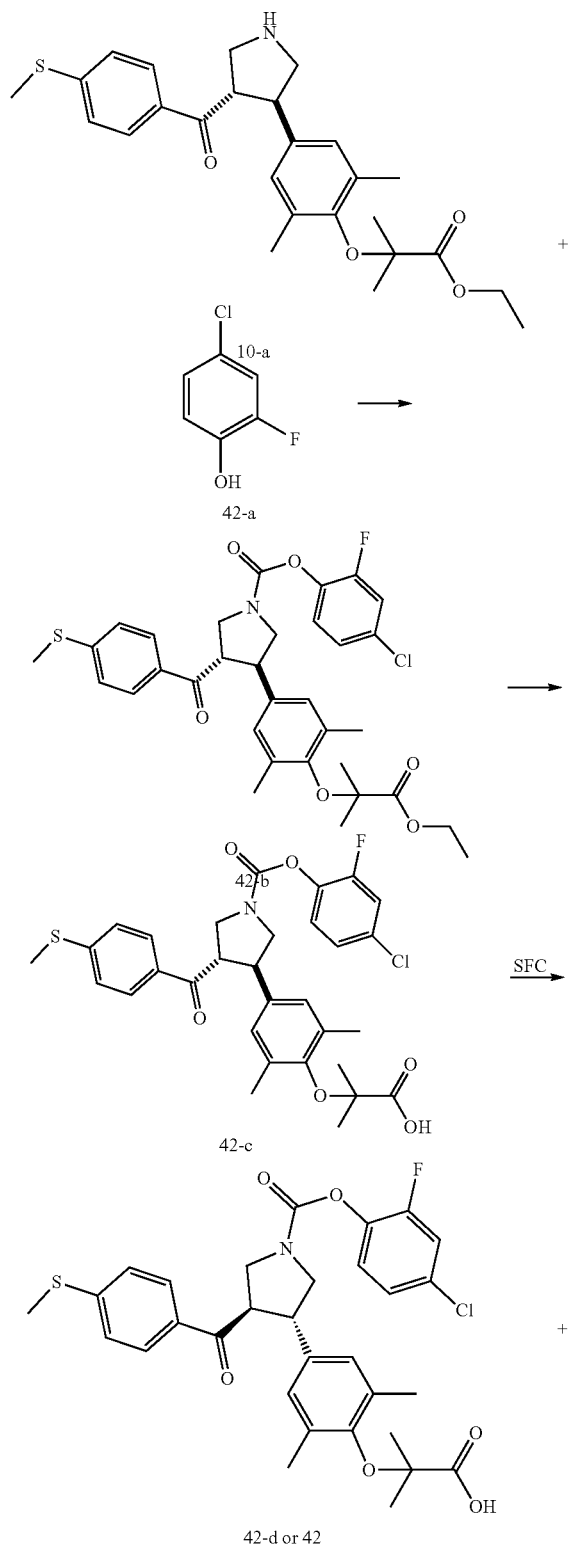

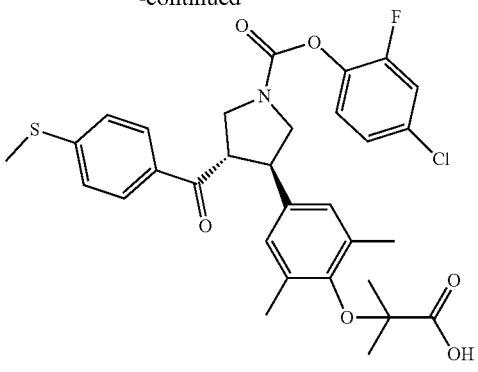

Step 1: Compound 42-b

Under nitrogen protection, a solution of Compound 42-a (1.00 g, 6.82 mmol, 1.00 eq), triphosgene (1.62 g, 5.46 mmol, 0.80 eq) and triethylamine (690.48 mg, 6.82 mmol, 945.86 µL, 1.00 eq) in tetrahydrofuran (20.00 mL) was stirred at 0° C. for 15 min, warmed to 20° C. and stirred for 1 h. The reaction solution was filtered and concentrated, and the resulted crude product was dissolved in tetrahydrofuran (20.00 mL), and then 10-a (1.00 g, 2.19 mmol, 1.00 eq) and di-iso-propyl ethylamine (424.55 mg, 3.29 mmol, 573.72 µL, 1.50 eq) were added and stirred at 20° C. for 1 h. The reaction solution was concentrated to give a crude product which was purified by silica gel column chromatography (petroleum ether/ethyl acetate=4/1) to give Compound 42-b.

MS m/z (ESI): 628.1 [M+1].

$^1$H NMR (400 MHz, DMSO-$d_6$) δ ppm 7.78 (d, J=7.28 Hz, 2H), 7.60 (dd, J=2.38, 10.16 Hz, 1H), 7.41-7.21 (m, 5H), 6.97 (d, J=3.76 Hz, 2H), 4.56-4.41 (m, 1H), 4.13 (q, J=7.18 Hz, 2H), 3.97-3.81 (m, 1H), 3.74-3.40 (m, 4H), 2.51-2.50 (m, 3H), 2.06-2.01 (m, 6H), 1.28 (d, J=1.52 Hz, 6H), 1.20 (t, J=7.16 Hz, 3H).

Step 2: Compound 42-c

A solution of Compound 42-b (1.00 g, 1.59 mmol, 1.00 eq) and lithium hydroxide (114.24 mg, 4.77 mmol, 3.00 eq) in ethanol (20.00 mL) and water (5.00 mL) was stirred at 20° C. for 16 h. The mixture was adjusted with 1N diluted HCl to pH=4, and treated with water and ethyl acetate (1:1.50 mL). The aqueous phase was extracted with ethyl acetate (10 mL×3). The combined organic phase was dried over anhydrous sodium sulfate, filtered, and concentrated under reduced pressure to give a crude product. The crude product was purified by silica gel column chromatography (petroleum ether/ethyl acetate=1/1) to give Compound 42-c.

MS m/z (ESI): 622.1 [M+23].

Step 3: Compound 42

Compound 42-c (200 mg) was subjected to chiral separation to give Compound 42.

MS m/z (ESI): 600.1 [M+1].

$^1$H NMR (400 MHz, CDCl$_3$) δ ppm 7.72 (d, J=7.54 Hz, 2H), 7.21-7.12 (m, 5H), 6.89 (s, 2H), 4.21-4.00 (m, 3H), 3.83-3.64 (m, 3H), 2.49 (s, 3H), 2.18 (s, 6H), 1.25 (s, 6H)

Conditions of the chiral resolution: chiral column: Chiralpak AD-3 100×4.6 mm I.D., 3 µm; mobile phase: 40% of iso-propanol (0.05% DEA) in $CO_2$; flow rate: 2.8 mL/min; column temperature: 40° C.

Example 43: Compound 43

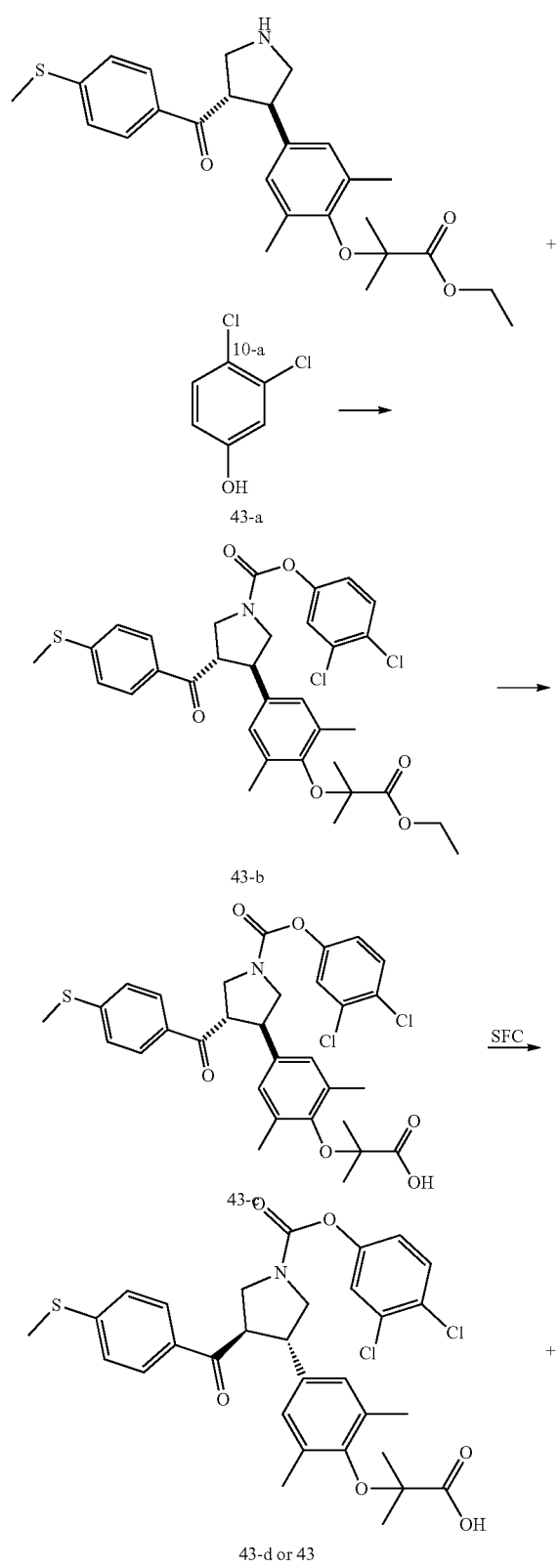

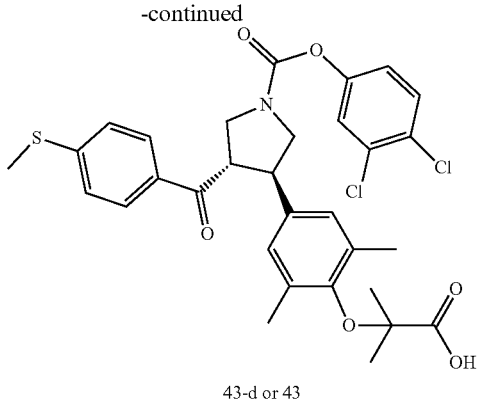

43-d or 43

Step 1: Compound 43-b

Under nitrogen protection, a solution of Compound 43-a (1.00 g, 6.13 mmol, 1.00 eq), triphosgene (1.46 g, 4.90 mmol, 0.80 eq) and triethylamine (620.80 mg, 6.13 mmol, 850.41 μL, 1.00 eq) in tetrahydrofuran (20.00 mL) was stirred at 0° C. for 15 min, warmed to 20° C. and stirred for 1 h. The reaction solution was filtered and concentrated, and the resulted crude product was dissolved in tetrahydrofuran (20.00 mL), and then 10-a (1.00 g, 2.19 mmol, 1.00 eq) and di-iso-propyl ethylamine (424.55 mg, 3.29 mmol, 573.72 μL, 1.50 eq) were added and stirred at 20° C. for 1 h. The reaction solution was concentrated to give a crude product which was purified by silica gel column chromatography (petroleum ether/ethyl acetate=4/1) to give Compound 43-b.

MS m/z (ESI): 644.1 [M+1].

$^1$H NMR (400 MHz, CDCl$_3$) δ ppm 7.78 (dd, J=4.02, 8.54 Hz, 2H), 7.65 (d, J=8.78 Hz, 1H), 7.55 (d, J=2.52 Hz, 1H), 7.38 (d, J=8.78 Hz, 1H), 7.29-7.18 (m, 3H), 6.96 (d, J=2.52 Hz, 3H), 6.75 (dd, J=2.76, 8.78 Hz, 1H), 4.55-4.39 (m, 1H), 4.12 (q, J=7.20 Hz, 2H), 3.84-3.97 (m, 1H), 3.45-3.67 (m, 3H), 2.50-2.50 (m, 3H), 2.02-2.07 (m, 6H), 1.28 (s, 6H), 1.20 (t, J=7.04 Hz, 3H)

Step 2: Compound 43-c

A solution of Compound 43-b (1.00 g, 1.55 mmol, 1.00 eq) and lithium hydroxide (111.37 mg, 4.65 mmol, 3.00 eq) in ethanol (20.00 mL) and water (5.00 mL) was stirred at 20° C. for 16 h. The mixture was adjusted with 1N diluted HCl to pH=4, and treated with water and ethyl acetate (1:1.50 mL). The aqueous phase was extracted with ethyl acetate (10 mL×3). The combined organic phase was dried over anhydrous sodium sulfate, filtered, and concentrated under reduced pressure to give a crude product. The crude product was purified by silica gel column chromatography (petroleum ether/ethyl acetate=1/1) to give Compound 43-c.

MS m/z (ESI): 616.1 [M+1].

Step 3: Compound 43

Compound 43-c (200 mg) was subjected to chiral separation to give Compound 43.

MS m/z (ESI): 616.0 [M+1].

$^1$H NMR (400 MHz, CDCl$_3$) δ ppm 7.71-7.62 (m, 2H), 7.35 (d, J=8.78 Hz, 1H), 7.24 (br s, 1H), 7.12 (br s, 2H), 6.97 (br d, J=8.78 Hz, 1H), 6.81 (br s, 2H), 4.01 (br s, 3H), 3.81-3.56 (m, 3H), 2.43 (s, 3H), 2.11 (br s, 6H), 1.18 (s, 6H).

Conditions of the chiral resolution: chiral column: Chiralpak AD-3 50×4.6 mm I.D., 3 μm; mobile phase: 40% of methanol (0.05% DEA) in $CO_2$; flow rate: 4.0 mL/min; column temperature: 40° C.
Retention time of Compound 43: 4.876 min (peak 2).
Examples 44 and 45: Compounds 44 and 45
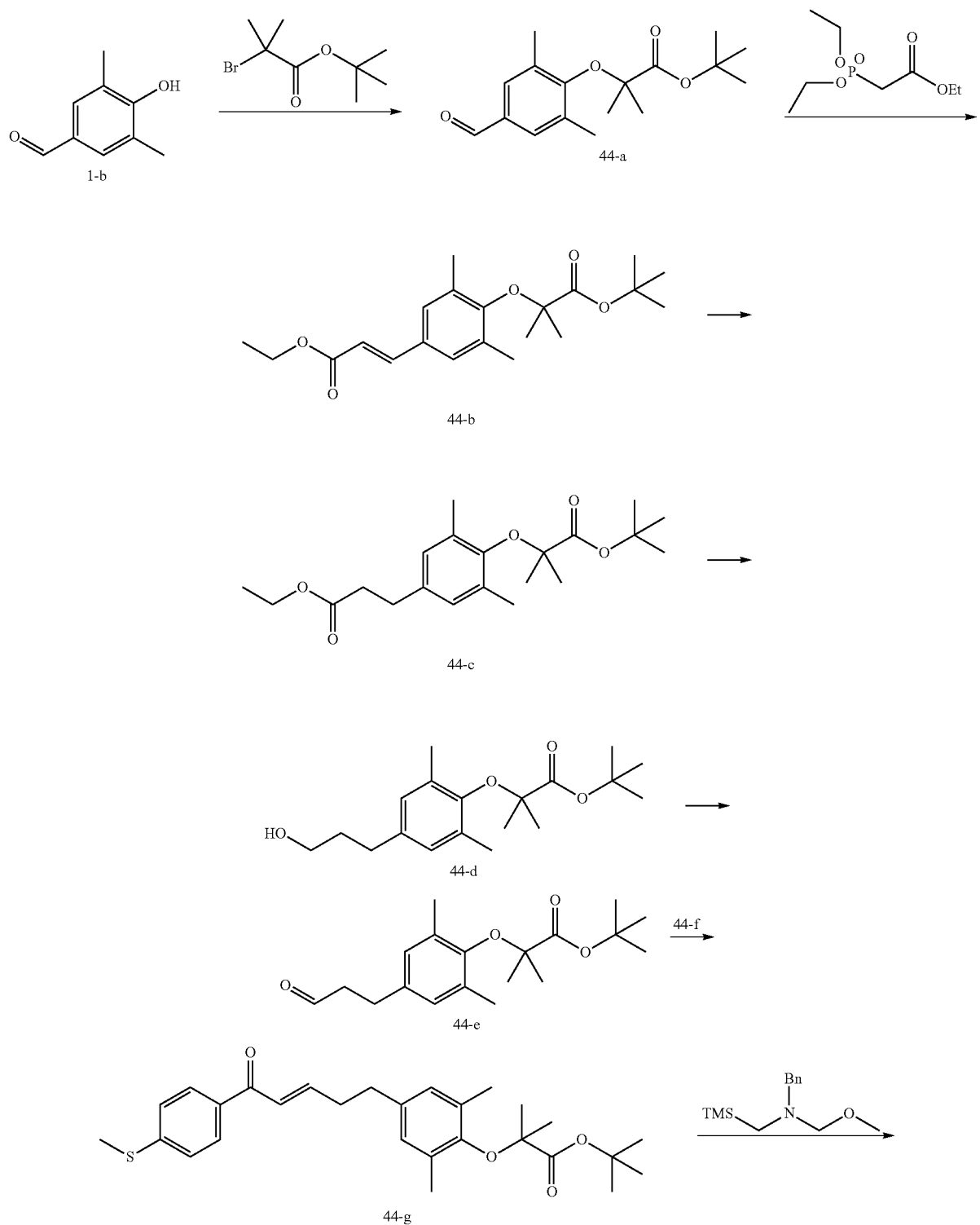

-continued
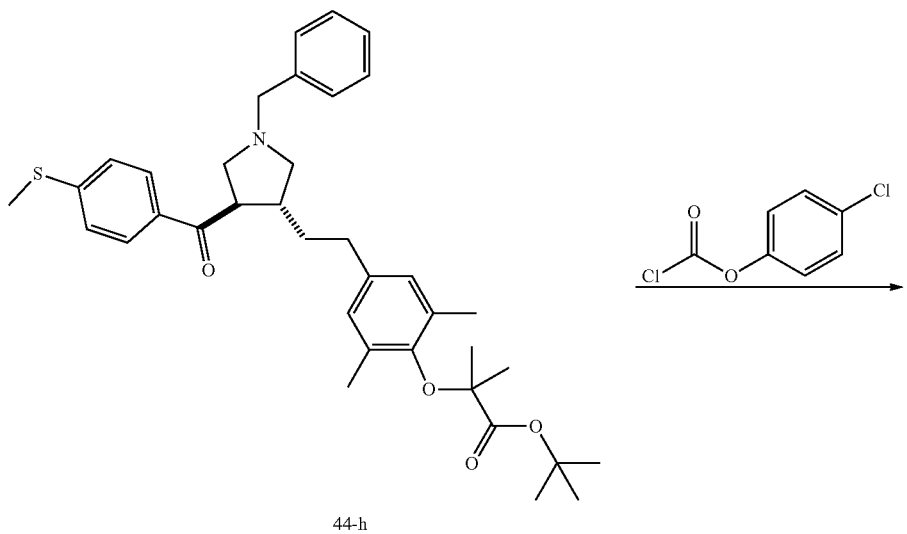
44-h
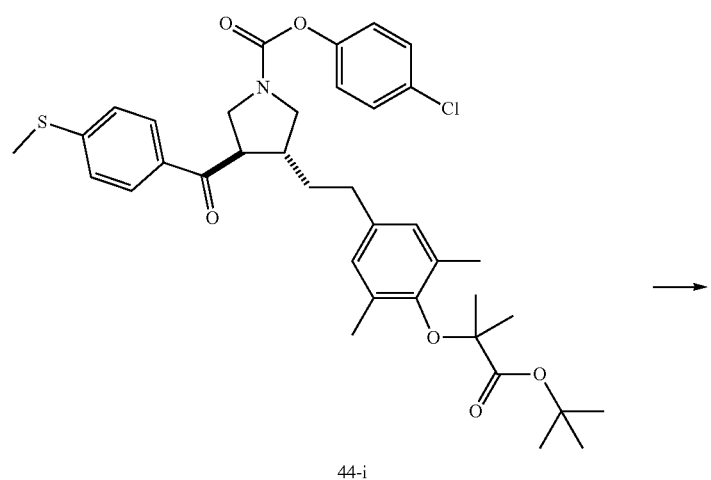
44-i
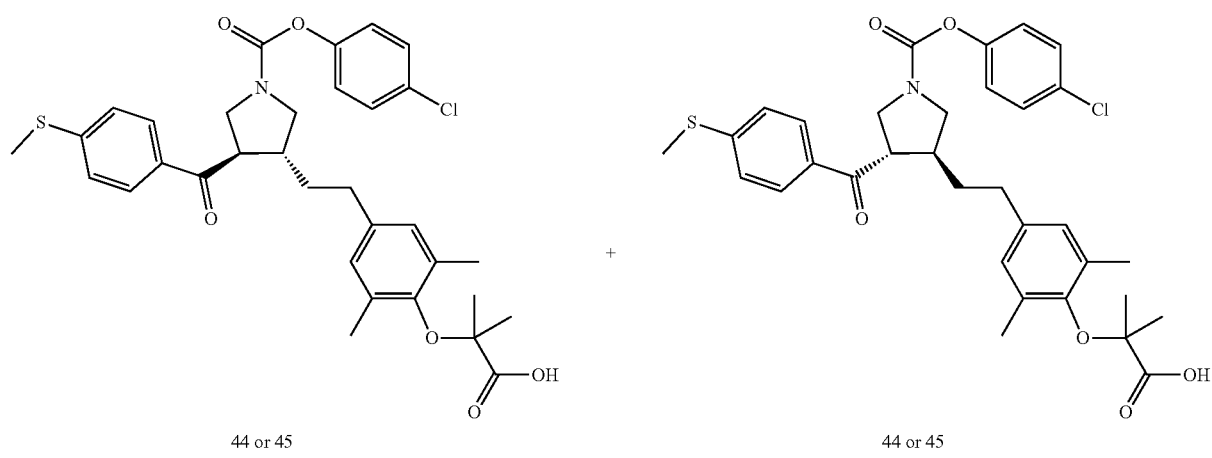
44 or 45                44 or 45

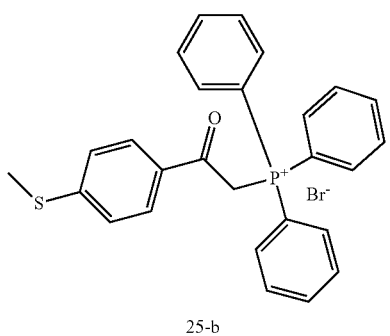

25-b

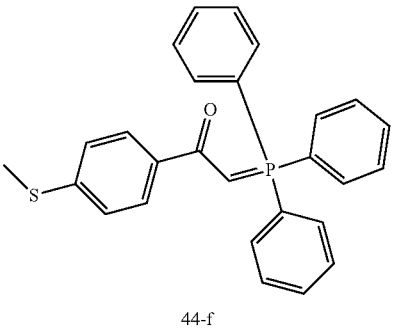

44-f

Step 1: Compound 44-a

Under nitrogen protection, a solution of Compound 1-b (20.00 g, 133.18 mmol, 1.00 eq), tert-butyl 2-bromo-isobutyrate (118.86 g, 532.72 mmol, 99.05 mL, 4.00 eq), potassium carbonate (55.22 g, 399.54 mmol, 3.00 eq) and potassium iodide (2.21 g, 13.32 mmol, 0.10 eq) in dimethylsulfoxide (250.00 mL) was stirred at 110° C. for 16 h. The mixture was filtered, and ethyl acetate/water (1:1, 300 mL) was added into the filtrate. The organic phase was washed with water (2×300 mL), dried over anhydrous sodium sulfate, and concentrated under reduced pressure. The residue was purified by flash column chromatography (11.8%, ethyl acetate/petroleum ether) to give Compound 44-a.

$^1$H NMR (400 MHz, CDCl$_3$) δ ppm 9.89 (s, 1H), 7.48 (s, 2H), 2.26 (s, 6H), 1.47 (s, 9H), 1.42 (s, 6H).

Step 2: Compound 44-b

A solution of triethyl phosphonoacetate (2.30 g, 10.26 mmol, 2.04 mL, 1.50 eq) in tetrahydrofuran (5 m) was added into a solution of sodium hydride (547.25 mg, 13.68 mmol, 60% purity, 2.00 eq) in tetrahydrofuran (15.00 mL) at 0° C. The mixture was stirred at 25° C. for 1 h, and then a solution of Compound 44-a (2.00 g, 6.84 mmol, 1.00 eq) in tetrahydrofuran (10 mL) was added. The mixture was stirred for additional 4 h. Water (50 mL) was added into the mixture, and extracted with ethyl acetate (50 mL×3). The combined organic phase was dried over anhydrous sodium sulfate, filtered, and concentrated under reduced pressure to give Compound 44-b.

MS m/z (ESI): 363.0 [M+1].

$^1$H NMR (400 MHz, CDCl$_3$) δ ppm 7.50 (d, J=15.81 Hz, 1H), 7.09 (s, 2H), 6.25 (d, J=15.81 Hz, 1H), 4.11-4.05 (m, 2H), 2.17 (s, 6 h), 1.44 (s, 9H), 1.37 (s, 6H), 1.27-1.25 (m, 3H).

Step 3: Compound 44-c

Palladium-carbon (300.00 mg, 10% purity) and anhydrous ethanol (50 mL) was added into hydrogenation flask under argon protection. Then, a solution of Compound 44-b (2.00 g, 5.52 mmol, 1.00 eq) in ethanol (50 mL) was added. The mixture was stirred at 25° C. for 4 h in hydrogen (50 psi) atmosphere. The mixture was filtered, and the filtrate was concentrated under reduced pressure to give Compound 44-c.

MS m/z (ESI): 387.1 [M+23].

$^1$H NMR (400 MHz, CDCl$_3$) δ ppm 6.71 (s, 2H), 4.03 (q, J=7.19 Hz, 2H), 2.74 (br t, J=7.78 Hz, 2H), 2.50-2.46 (m, 2H), 2.12 (s, 6H), 1.43 (s, 9H), 1.34 (s, 6H), 1.27 (t, J=7.03 Hz, 6H), 1.21 (br t, J=7.03 Hz, 3H).

Step 4: Compound 44-d

Under nitrogen protection, a solution of Compound 44-c (200.00 mg, 548.73 μmol, 1.00 eq) in tetrahydrofuran (5 mL) was added into a solution of aluminum lithium hydride (41.65 mg, 1.10 mmol, 2.00 eq) in tetrahydrofuran (5.00 mL) at 0° C. The mixture was stirred at 0° C. for 3 h. Water (100 mL) was added into the reaction mixture, and extracted with ethyl acetate (100 mL×3). The combined organic phase was dried over anhydrous sodium sulfate, filtered, and concentrated under reduced pressure to give Compound 44-d.

MS m/z (ESI): 345.0 [M+23].

Step 5: Compound 44-e

Oxalyl chloride (1.42 g, 11.16 mmol, 976.92 μL, 2.00 eq) was added into a solution of dimethylsulfoxide (1.74 g, 22.32 mmol, 1.74 mL, 4.00 eq) in dichloromethane (15.00 mL) at −78° C. The mixture was stirred at −78° C. for 5 min. Then, Compound 44-d (1.80 g, 5.58 mmol, 1.00 eq) was added, and the mixture was stirred at −78° C. for 40 min. Then, triethylamine (3.39 g, 33.48 mmol, 4.64 mL, 6.00 eq) was added at −78° C., and the mixture was stirred at 0° C. for 30 min. The mixture was quenched by water (50 mL), and extracted with ethyl acetate (50 mL×3). The combined organic phase was washed with saturated brine (50 mL), dried over anhydrous sodium sulfate, filtered, and concentrated under reduced pressure. The residue was purified by flash column chromatography (24.3%, ethyl acetate/petroleum ether) to give Compound 44-e.

MS m/z (ESI): 343.2 [M+23].

Step 6: Compound 44-f

Sodium tert-butoxide (1.36 g, 14.18 mmol, 1.20 eq) was added into a solution of Compound 25-b (6.00 g, 11.82 mmol, 1.00 eq) in tetrahydrofuran (50.00 mL) at 20° C. The mixture was stirred at 20° C. for 30 min. Water (50 mL) was added into the reaction mixture, and extracted with ethyl acetate (30 mL×3). The combined organic phase was dried over anhydrous sodium sulfate, filtered, and concentrated under reduced pressure to give Compound 44-f.

Step 7: Compound 44-g

Compound 44-f (2.06 g, 4.84 mmol, 1.00 eq) was added into a solution of Compound 44-e (1.55 g, 4.84 mmol, 1.00 eq) in tetrahydrofuran (10 mL). The mixture was stirred at 50° C. for 16 h. Water/ethyl acetate (1:1, 50 mL) was added into the mixture, and the aqueous phase was extracted with ethyl acetate (50 mL×2). The combined organic phase was concentrated under reduced pressure. The residue was purified by flash column chromatography (16.5%, ethyl acetate/petroleum ether) to give Compound 44-g.

Step 8: Compound 44-h

Under nitrogen protection, trifluoroacetic acid (1.00 mL) was added into a solution of Compound 44-g (1.60 g, 3.41 mmol, 1.00 eq) and N-(methoxymethyl)-1-phenyl-N-(trimethylsilylmethyl)methylamine (972.64 mg, 4.10 mmol, 1.20 eq) in dichloromethane (150.00 mL) at 0° C. The mixture was stirred at 25° C. for 16 h. Water/dichloromethane (1:1, 100 mL) was added into the mixture, and the aqueous phase was extracted with dichloromethane (100 mL×2). The combined organic phase was concentrated under reduced pressure. The residue was purified by flash column chromatography (27.3%, ethyl acetate/petroleum ether) to give Compound 44-h.
MS m/z (ESI): 602.3 [M+1].

Step 9: Compound 44-i (4-chlorophenyl) methyl chloroformate (952.13 mg, 4.98 mmol, 694.99 µL, 2.00 eq) was slowly added into a solution of Compound 44-h (1.50 g, 2.49 mmol, 1.00 eq) in dichloromethane (15.00 mL). The mixture was stirred at 25° C. for 20 h. The mixture was concentrated under reduced pressure. The residue was purified by flash column chromatography (25.6%, ethyl acetate/petroleum ether) to give Compound 44-i.

MS m/z (ESI): 610.2 [M+1].

Step 10: Compounds 44 and 45

A solution of Compound 44-i (220.00 mg, 330.20 µmol, 1.00 eq) and trifluoroacetic acid (1.54 g, 13.51 mmol, 1.00 mL, 40.90 eq) in dichloromethane (5.00 mL) was stirred at 25° C. for 16 h. The mixture was concentrated under reduced pressure. The residue was purified by flash column chromatography (54.2%, ethyl acetate/petroleum ether), and the resulted product was subjected to chiral separation to give Compound 44; Compound 45.
Compound 44:
MS m/z (ESI): 632.1 [M+23].
$^1$H NMR (400 MHz, CDCl$_3$) δ ppm 7.86 (dd, J=5.8, 8.5 Hz, 2H), 7.31-7.27 (m, 4H), 7.09-7.05 (m, 2H), 6.76 (d, J=5.3 Hz, 2H), 3.96-3.91 (m, 1H), 3.77-3.59 (m, 3H), 3.20-3.16 (m, 1H), 2.80-2.67 (m, 1H), 2.55-2.52 (m, 5H), 2.19 (d, J=4.5 Hz, 6H), 1.93-1.85 (m, 1H), 1.74-1.63 (m, 1H), 1.51-1.47 (m, 6H).
Compound 45:
MS m/z (ESI): 632.1 [M+23].
$^1$H NMR (400 MHz, CDCl$_3$) δ ppm 7.86 (dd, J=5.6, 8.4 Hz, 2H), 7.33-7.26 (m, 4H), 7.07-7.05 (m, 2H), 6.77-6.75 (m, 2H), 3.93 (dt, J=2.6, 10.6 Hz, 1H), 3.80-3.59 (m, 3H), 3.39-3.20 (m, 1H), 2.84-2.64 (m, 1H), 2.55-2.51 (m, 5H), 2.18 (d, J=3.5 Hz, 6H), 1.95-1.85 (m, 1H), 1.70 (br dd, J=3.8, 8.8 Hz, 1H), 1.51-1.47 (m, 6H).
Conditions of the chiral resolution: chiral column: Chiralpak IC-3 150×4.6 mm I.D., 3 µm; mobile phase: 40% of methanol (0.05% DEA) in CO$_2$; flow rate: 2.5 mL/min; column temperature: 40° C.
Retention time of Compound 44: 5.592 min (peak 1); Retention time of Compound 45: 7.585 min (peak 1)

Example 46: Compound 46

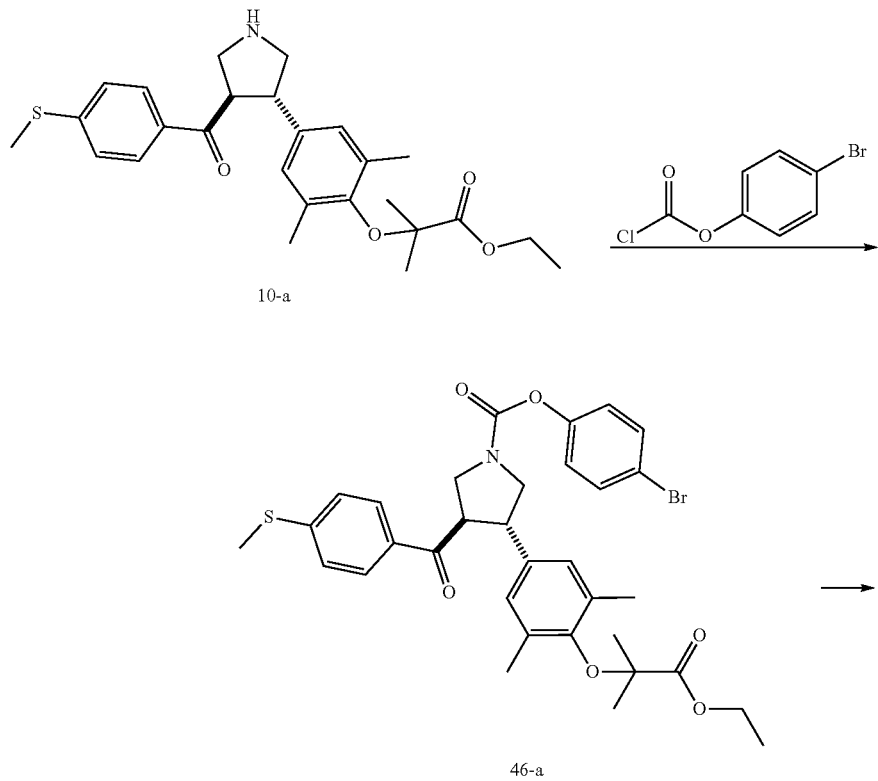

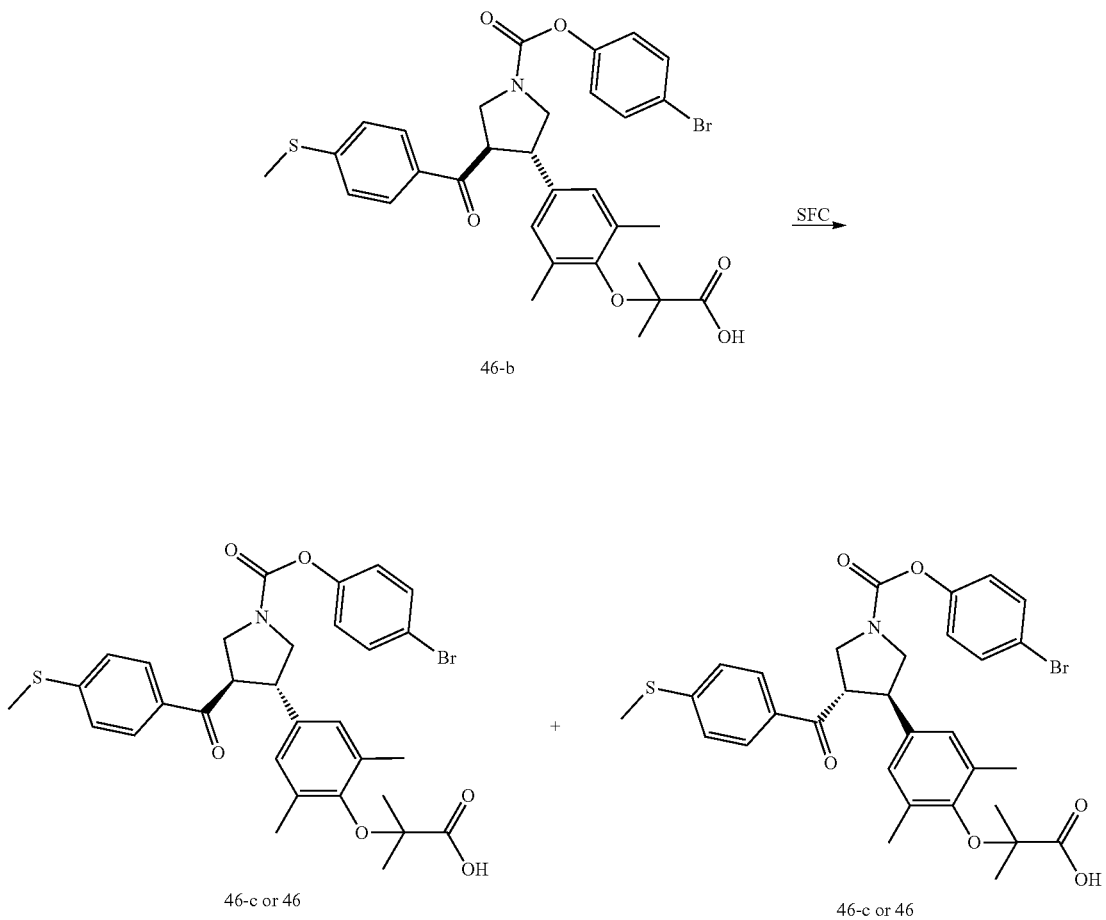

Step 1: Compound 46-a

Under nitrogen protection, a solution of Compound 10-a (150.00 mg, 329.23 μmol, 1.00 eq), di-iso-propyl ethylamine (85.10 mg, 658.46 μmol, 115.00 μL, 2.00 eq) and 4-bromo phenyl chloroformate (93.02 mg, 395.08 μmol, 56.38 μL, 1.20 eq) in dichloromethane (10 mL) was stirred at 20° C. for 12 h. The reaction solution was concentrated to give a crude product which was purified by silica gel column chromatography (petroleum ether/ethyl acetate=4/1) to give Compound 46-a.

$^1$H NMR (400 MHz, CDCl$_3$) δ ppm 7.76-7.71 (m, 2H), 7.49 (d, J=8.8 Hz, 2H), 7.21 (d, J=5.2 Hz, 2H), 7.07 (d, J=8.8 Hz, 2H), 6.86 (d, J=5.6 Hz, 2H), 4.17-4.09 (m, 5H), 3.84-3.77 (m, 3H), 2.52 (s, 3H), 2.15 (s, 6H), 1.44-1.42 (m, 6H), 1.38-1.36 (m, 3H).

Step 2: Compound 46-b

A solution of Compound 46-a (140.00 mg, 213.87 μmol, 1.00 eq) and lithium hydroxide (89.74 mg, 2.14 mmol, 10.00 eq) in ethanol (9.00 mL) and water (3.00 mL) was stirred at 25° C. for 12 h. The mixture was adjusted with 1N diluted HCl to pH=3, and treated with water and ethyl acetate (1:1, 50 mL). The aqueous phase was extracted with ethyl acetate (50 mL×3). The combined organic phase was washed with saturated brine (20 mL×1), dried over anhydrous sodium sulfate, filtered, and concentrated under reduced pressure to give a crude product. The crude product was purified by silica gel column chromatography (petroleum ether/ethyl acetate=2/1) to give Compound 46-b.

$^1$H NMR (400 MHz, MeOD-d$_4$) δ ppm 7.78 (d, J=8.0 Hz, 2H), 7.55 (d, J=8.0 Hz, 2H), 7.23 (d, J=8.8 Hz, 2H), 7.15-7.12 (m, 2H), 6.98 (d, J=4.0 Hz, 2H), 4.17-4.14 (m, 1H), 4.00-3.97 (m, 2H), 3.92-3.90 (m, 1H), 3.66-3.64 (m, 2H), 2.52 (s, 3H), 2.17 (d, J=5.6 Hz, 6H), 1.38 (s, 6H).

Step 3: Compound 46

Compound 46-b (50 mg) was subjected to chiral separation to give Compound 46.

MS m/z (ESI): 650.0 [M+23].

$^1$H NMR (400 MHz, CDCl$_3$) δ ppm 7.67 (t, J=8.5 Hz, 2H), 7.41-7.39 (m, 2H), 7.13 (dd, J=4.3, 8.5 Hz, 2H), 6.99-6.97 (m, 2H), 6.83 (d, J=6.3 Hz, 2H), 4.09-4.00 (m, 3H), 3.70-3.60 (m, 3H), 2.43 (s, 3H), 2.12 (d, J=5.5 Hz, 6H), 1.39-1.38 (m, 6H).

Conditions of the chiral resolution: chiral column: Chiralpak AD-3 100×4.6 mm I.D., 3 μm; mobile phase: 40% of methanol (0.05% DEA) in CO$_2$; flow rate: 2.8 mL/min; column temperature: 40° C.

Retention time of Compound 46: 7.984 min (peak 2).

Example 47: Compound 47
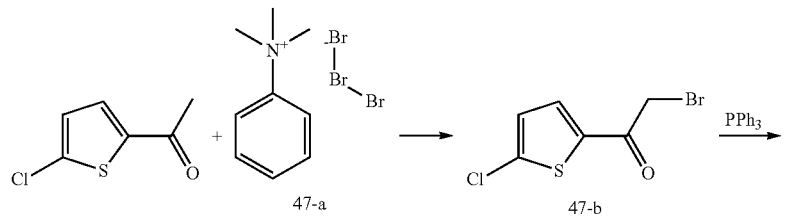
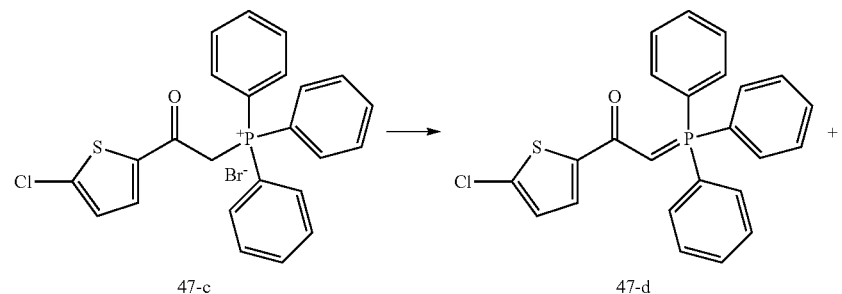
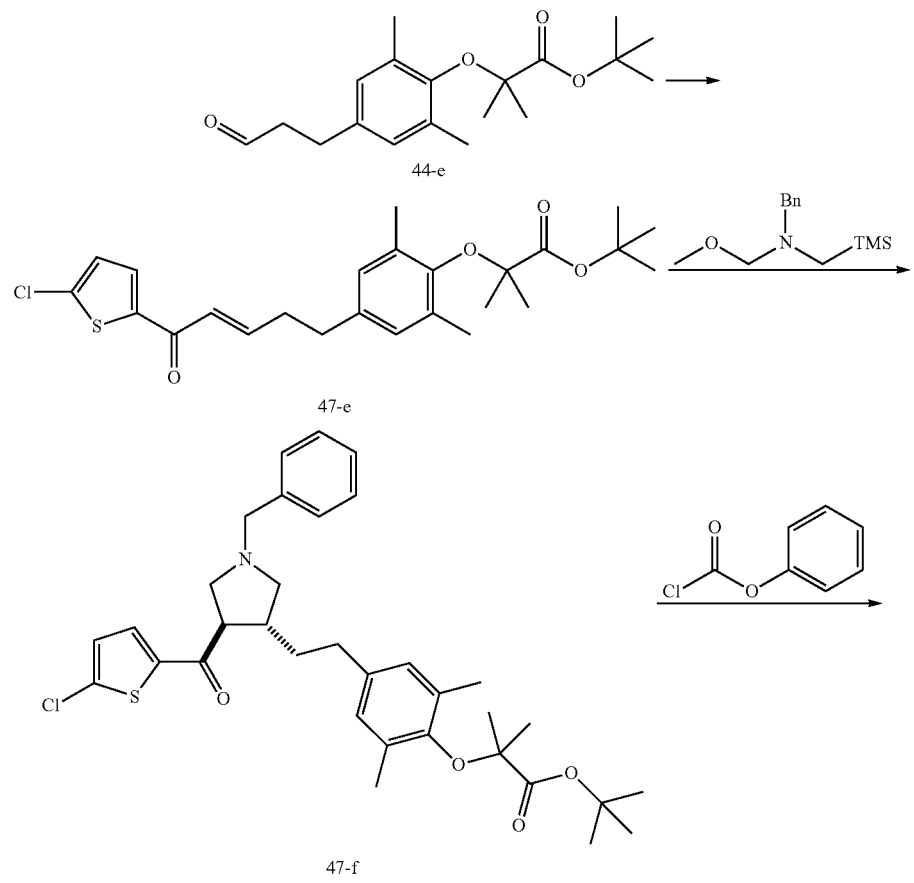

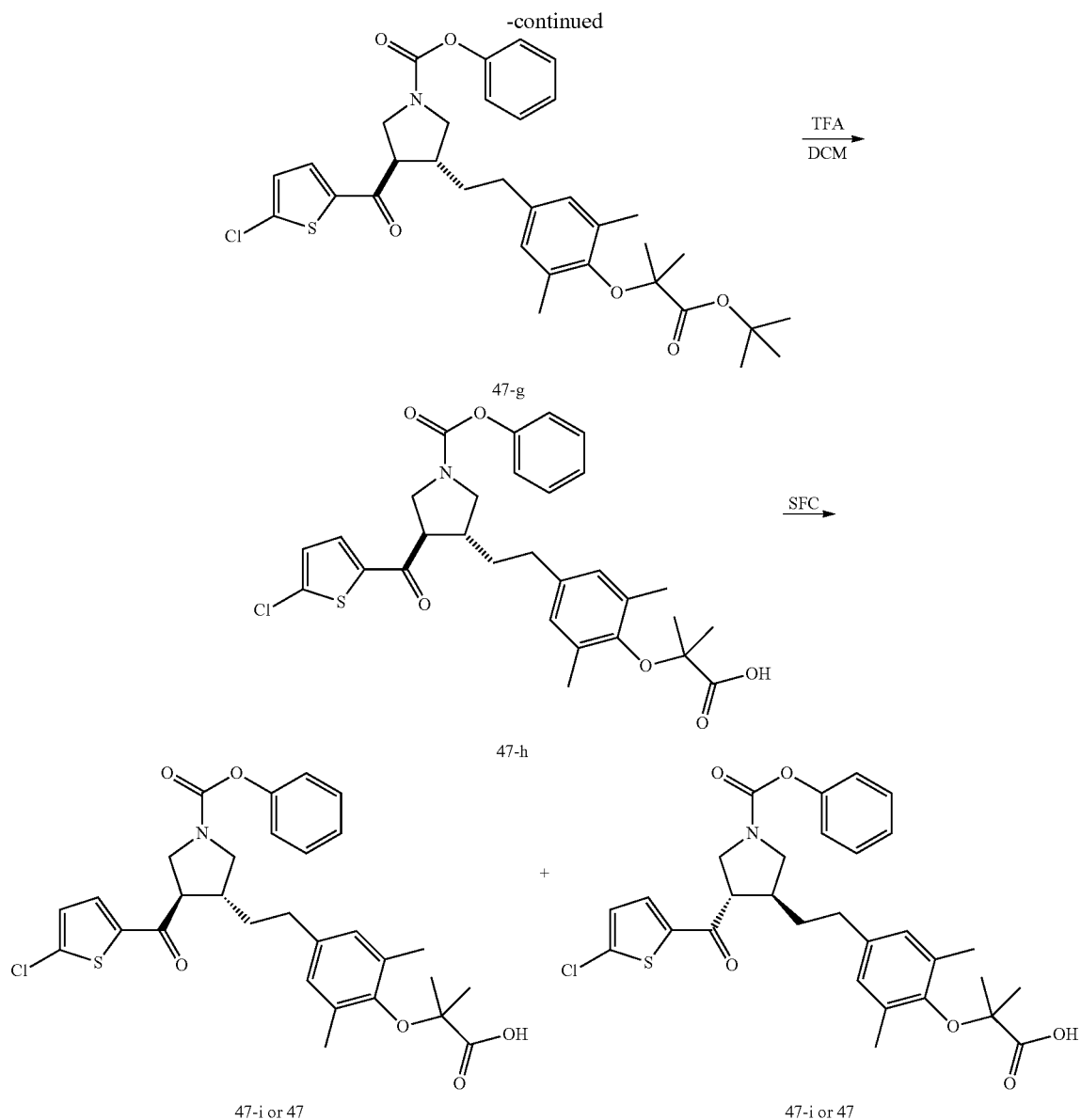

Step 1: Compound 47-b

Compound 1-(5-chlorothien-2-yl)-ethanone (10.00 g, 62.26 mmol, 1.00 eq), 47-a (23.40 g, 62.26 mmol, 1.00 eq) and dichloromethane (200.00 mL) was added into a dried round-bottom flask, and the resulted clear solution was stirred at 20° C. for 16 h. The mixture was concentrated under reduced pressure to give a residue. The residue was purified by flash column chromatography (petroleum ether: ethyl acetate=100:0-80:20) to give 47-b.

MS m/z (ESI): 240.7 [M+1].

$^1$H NMR (400 MHz, CDCl$_3$) δ ppm 7.60 (d, J=4.0 Hz, 1H), 7.00 (d, J=4.0 Hz, 1H), 4.28 (s, 1H).

Step 2: Compound 47-c

At 20° C., Compound 47-b (13.00 g, 54.28 mmol, 1.00 eq), triphenylphosphine (14.24 g, 54.28 mmol, 1.00 eq) and toluene (100.00 mL) was added into a dried round-bottom flask, the resulted suspension was stirred at 20° C. for 2 h. The reaction system was cooled to room temperature, and produced a yellow precipitate, which was filtered. The filter cake was washed with ethyl acetate (3×50 mL) to give Compound 47-c.

$^1$H NMR (CDCl$_3$) δ ppm 8.91 (d, J=4.0 Hz, 1H), 7.92-7.87 (m, 6H), 7.75-7.72 (m, 2H), 7.66-7.60 (m, 6H), 7.00 (d, J=4.0 Hz, 1H), 6.13 (d, J=12.8 Hz, 1H).

Step 3: Compound 47-d

At 20° C., Compound 47-c (5.00 g, 10.27 mmol, 1.00 eq), potassium tert-butoxide (1.73 g, 15.41 mmol, 1.50 eq) and tetrahydrofuran (30.00 mL) was added into a dried round-bottom flask and the resulted suspension was stirred at 20° C. for 1 h. The reaction system was cooled to room temperature, and diluted with water (50 mL) and ethyl acetate (20 mL). After phase separation, the organic phase was collected, and the aqueous phase was extracted with ethyl acetate (3×20 mL). The organic phases were combined, dried over anhydrous sodium sulfate, and concentrated under reduced pressure to give a residue so as to give Compound 47-d.

$^1$H NMR (400 MHz, CDCl$_3$) δ ppm 7.71-7.68 (m, 6H), 7.66-7.63 (m, 3H), 7.51-7.48 (m, 7H), 7.26 (s, 1H), 6.82 (d, J=4.0 Hz, 1H).

Step 4: Compound 47-e

At 20° C., Compound 44-e (2.00 g, 6.24 mmol, 1.00 eq), 47-d (2.63 g, 6.24 mmol, 1.00 eq) and tetrahydrofuran (20.00 mL) was added into a dried round-bottom flask, the resulted clear solution was stirred at 65° C. for 16 h. The reaction solution was concentrated under reduced pressure to give a residue. The residue was purified by flash column chromatography (petroleum ether:ethyl acetate=100:0-60:40) to give Compound 47-e.

$^1$H NMR (400 MHz, CDCl$_3$) δ ppm 7.45 (d, J=4.0 Hz, 1H), 7.10 (td, J=6.8, 15.2 Hz, 1H), 6.98-6.94 (m, 1H), 6.78 (br s, 2H), 6.66 (d, J=15.3 Hz, 1H), 2.83 (s, 2H), 2.72 (s, 2H), 2.21-2.20 (m, 6H), 1.51-1.50 (m, 9H), 1.41-1.40 (m, 6H).

Step 5: Compound 47-f

At 20° C., Compound 47-e (1.00 g, 2.16 mmol, 1.00 eq), trifluoroacetic acid (12.31 mg, 108.00 μmol, 7.99 μL, 0.05 eq) was added into a dried round-bottom flask. The reaction mixture was heated to 80° C., and N-benzyl-1-methoxy-N-((trimethylsilyl)methyl)methylamine (1.54 g, 6.48 mmol, 1.66 mL, 3.00 eq) was slowly added dropwise to the reaction system, which was stirred at 80° C. for 30 min. The reaction mixture was concentrated under reduced pressure, and the residue was purified by flash column chromatography (gradient elution: petroleum ether:ethyl acetate=100:0-60:40) to give Compound 47-f.

MS m/z (ESI): 596.3 [M+1].

$^1$H NMR (400 MHz, CDCl$_3$) δ ppm 7.38-7.33 (m, 2H), 7.38-7.21 (m, 4H), 6.78 (s, 2H), 4.41-4.28 (m, 2H), 4.08-3.94 (m, 1H), 3.74-3.69 (m, 2H), 3.08 (dd, J=6.5, 11.0 Hz, 1H), 2.77-2.48 (m, 3H), 2.20 (s, 6H), 1.96-1.84 (m, 1H), 1.81-1.66 (m, 2H), 1.53-1.51 (m, 9H), 1.41 (s, 6H).

Step 6: Compound 47-g

At 20° C., Compound 47-f (1.10 g, 1.84 mmol, 1.00 eq), phenyl chloroformate (1.44 g, 9.20 mmol, 1.15 mL, 5.00 eq) and chloroform (10.00 mL) was added into a dried round-bottom flask, the resulted clear solution was stirred at 80° C. for 16 h. The reaction solution was concentrated under reduced pressure. The residue was purified by flash column chromatography (petroleum ether:ethyl acetate=100:0-60:40) to give Compound 47-g.

MS m/z (ESI): 648.1 [M+23].

Step 7: Compound 47-h

Compound 47-g (220.00 mg, 348.20 μmol, 1.00 eq) and dichloromethane (6.00 mL), and then trifluoroacetic acid (397.02 mg, 3.48 mmol, 257.81 μL, 10.00 eq) was added into a 100 mL reaction flask. The mixture was stirred at 25° C. for 2 h. The reaction mixture was concentrated under reduced pressure to give a crude product. The residue was purified by thin-layer chromatography silica gel plate (dichloromethane:methanol=10:1) to give Compound 47-h.

Step 8: Compound 47

Compound 47-h (17.00 mg, 29.82 μmol, 1.00 eq) was isolated by chiral supercritical chromatography to give Compound 47.

MS m/z (ESI): 570.3 [M+1].

$^1$H NMR (400 MHz, CDCl$_3$) δ ppm 7.55 (br d, J=6.0 Hz, 1H), 7.38-7.33 (m, 2H), 7.21 (br d, J=6.5 Hz, 1H), 7.15-7.11 (m, 2H), 7.02 (br d, J=4.5 Hz, 1H), 6.78 (br d, J=5.0 Hz, 2H), 3.97 (br d, J=7.5 Hz, 2H), 3.73 (br d, J=8.0 Hz, 1H), 3.39-3.34 (m, 1H), 3.16 (br d, J=10.0 Hz, 1H), 2.54 (br s, 2H), 2.21 (br d, J=4.5 Hz, 6 h), 1.86 (br s, 1H), 1.68 (br s, 2H), 1.51 (br d, J=19.6 Hz, 6H)

Conditions of the chiral resolution: chiral column: OJ (250 mm×30 mm, 10 μm); mobile phase: 50% of methanol (0.05% DEA) in CO$_2$; flow rate: 80 mL/min; column temperature: 40° C.

Retention time of Compound 47: 3.760 min (peak 1).

Example 48: Compound 48

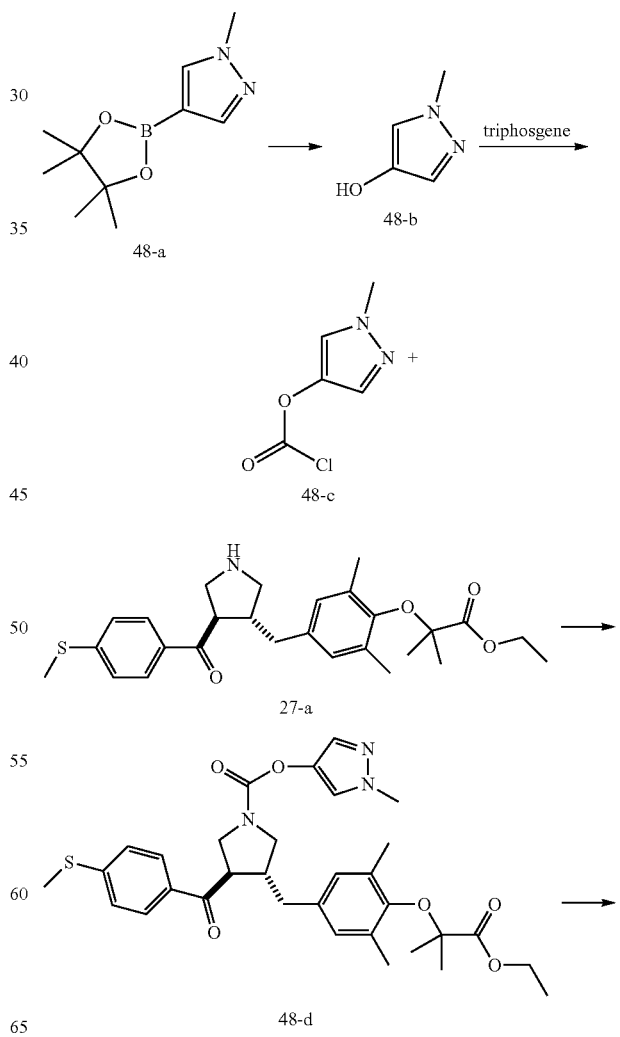

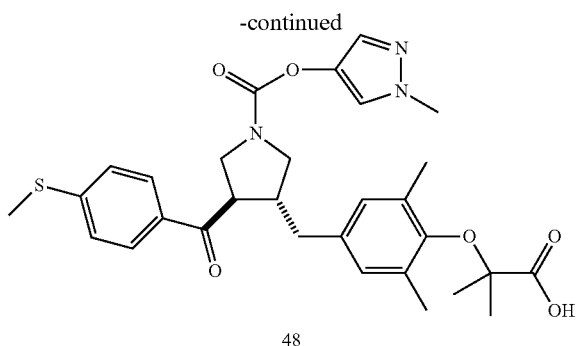

48

Step 1: Compound 48-b

At 20° C., hydrogen peroxide (599.71 mg, 5.29 mmol, 508.23 µL, 30% purity, 1.10 eq) and sodium hydroxide (211.64 mg, 5.29 mmol, 1.10 eq) was added into a solution of Compound 48-a (1.00 g, 4.81 mmol, 1.00 eq) in tetrahydrofuran (30.00 mL). The mixture was stirred at 20° C. for 2 h. The reaction mixture was quenched by adding a saturated solution of sodium sulfite (10 mL), and extracted with ethyl acetate (5 mL×3). The combined organic phase was washed with water (5 mL), dried over anhydrous sodium sulfate, filtered, and concentrated under reduced pressure to give Compound 48-b.

$^1$H NMR (400 MHz, CDCl$_3$) δ ppm 7.13 (s, 1H) 7.03 (s, 1H) 3.78 (s, 3H) 1.25 (s, 8H).

Step 2: Compound 48-c

At 0° C., Compound 48-b (400.00 mg, 4.08 mmol, 1.00 eq) and triethylamine (412.60 mg, 4.08 mmol, 565.20 µL, 1.00 eq) was added into a solution of triphosgene (967.99 mg, 3.26 mmol, 0.80 eq) in tetrahydrofuran (10.00 mL). The mixture was stirred at 20° C. for 2 h. After filtration, the filtrate was concentrated under reduced pressure to give Compound 48-c.

Step 3: Compound 48-d

At 20° C., Compound 27-a (1.00 g, 2.13 mmol, 1.00 eq) and DIEA (550.38 mg, 4.26 mmol, 743.76 µL, 2.00 eq) was added into a solution of 48-c (410.25 mg, 2.56 mmol, 1.20 eq) in dichloromethane (50.00 mL). The mixture was stirred at 20° C. for 1 h. The mixture was concentrated under reduced pressure, and the residue was purified by flash column chromatography (petroleum ether:ethyl acetate=100/0-40/60) to give Compound 48-d.

MS m/z (ESI): 594.3 [M+1].

Step 4: Compound 48

At 20° C., lithium hydroxide (201.69 mg, 8.42 mmol, 10.00 eq) was added into a solution of Compound 48-d (500.00 mg, 842.13 µmol, 1.00 eq) in ethanol (20.00 mL) and water (5.00 mL). The mixture was stirred at 20° C. for 16 h. The mixture was acidized by 1N diluted HCl (5 mL), and then extracted with ethyl acetate (10 mL×3). The combined organic phase was dried over anhydrous sodium sulfate, filtered by suction, and concentrated under reduced pressure. The residue was separated by High Performance Liquid Chromatography to give Compound 48.

MS m/z (ESI): 566.4 [M+1].

$^1$H NMR (400 MHz, CDCl$_3$) δ ppm 7.61 (br t, J=7.92 Hz, 2H) 7.41 (s, 1H) 7.29 (s, 1H) 7.10-7.17 (m, 2H) 6.72 (br s, 2H) 3.77 (s, 3H) 3.67 (br d, J=11.54 Hz, 2H) 3.28 (br s, 2H) 2.84 (br d, J=14.56 Hz, 2H) 2.59 (br s, 2H) 2.45 (s, 3H) 2.10 (br s, 6H) 1.41 (br s, 6H).

Examples 49 and 50: Compounds 49 and 50

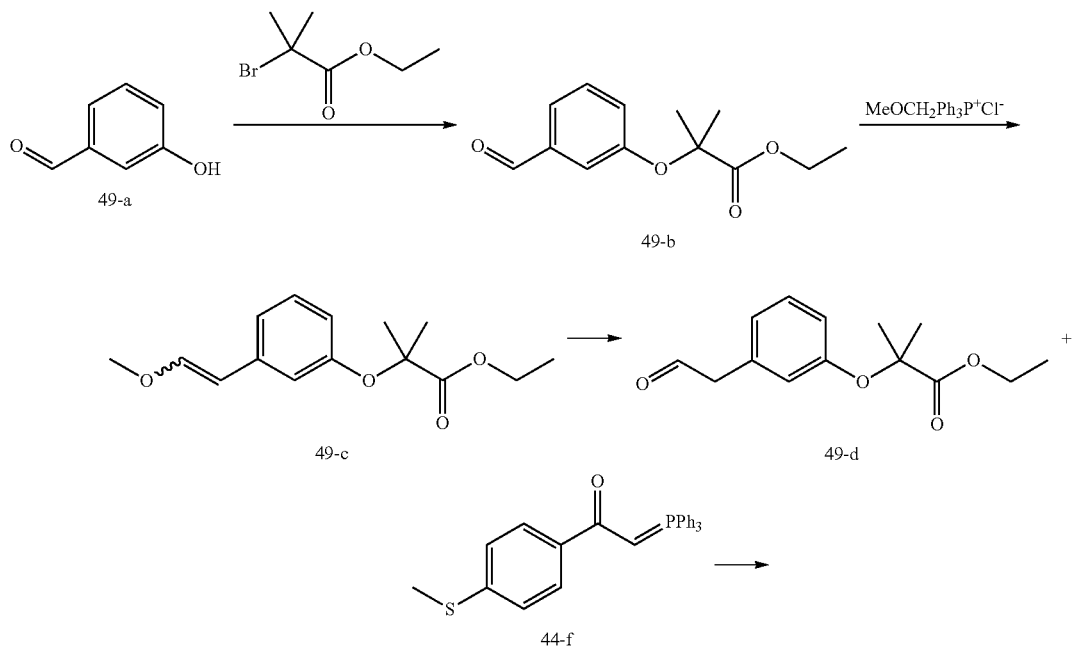

-continued
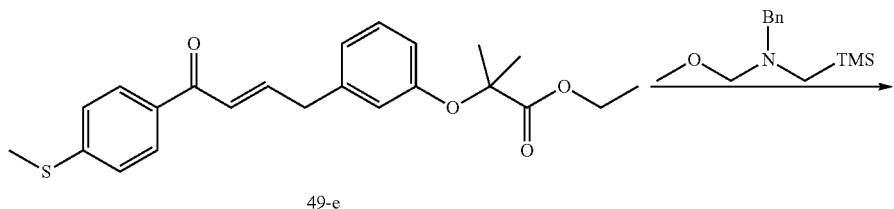
49-e
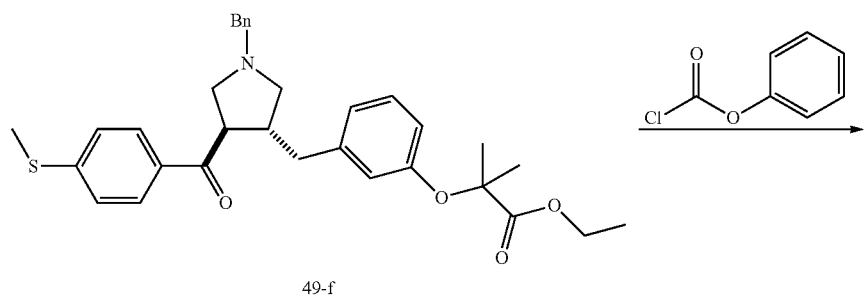
49-f
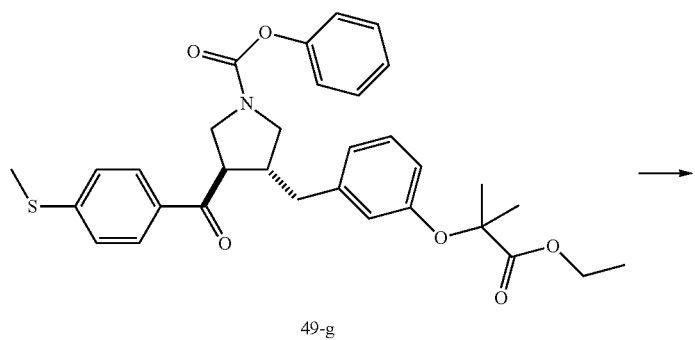
49-g
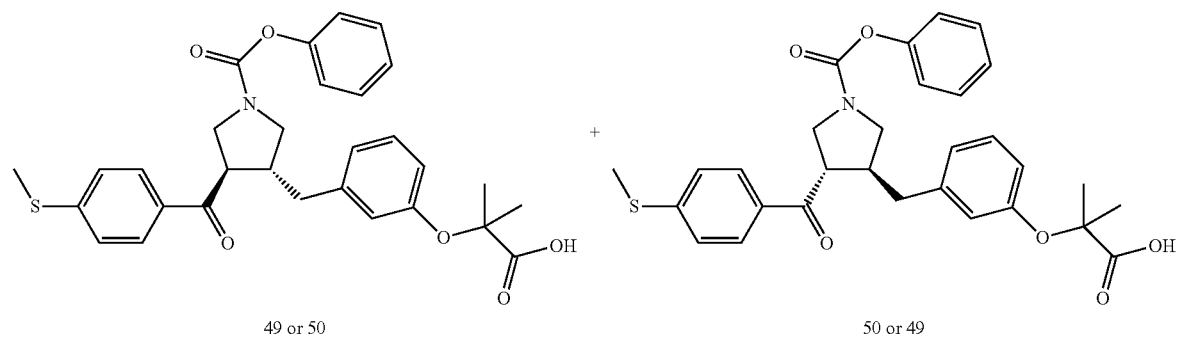 [SMILES: CSc1ccc(C(=O)[C@H]2CN(C(=O)Oc3ccccc3)C[C@@H]2Cc2cccc(OC(C)(C)C(=O)O)c2)cc1 ; CSc1ccc(C(=O)[C@@H]2CN(C(=O)Oc3ccccc3)C[C@H]2Cc2cccc(OC(C)(C)C(=O)O)c2)cc1]
49 or 50       50 or 49

Step 1: Compound 49-b

A solution of sodium ethoxide (9.19 g, 135.11 mmol, 1.10 eq) in ethanol (50.00 mL) was added into a solution of Compound 49-a (15.00 g, 122.83 mmol, 1.00 eq) and ethyl 2-bromo-isobutyrate (31.15 g, 159.68 mmol, 23.42 mL, 1.30 eq) in ethanol (100.00 mL). Under nitrogen protection, the mixture was stirred at 90° C. for 8 h. The mixture was acidized by diluted HCl (1N) to pH=6-7, and then extracted with ethyl acetate (100 mL×3). The combined organic phase was washed with water (100 mL×3) and saturated brine (100 mL×2), dried over anhydrous sodium sulfate, filtered by suction, and concentrated under reduced pressure. The residue was isolated by silica gel column chromatography (petroleum ether:ethyl acetate=20/1) to give Compound 49-b.

$^1$H NMR (400 MHz, CDCl$_3$) δ ppm 9.95 (s, 1H), 7.52 (d, J=6.4 Hz, 1H), 7.43 (t, J=8.0 Hz, 1H), 7.34 (t, J=1.2 Hz, 1H), 7.15 (s, 1H), 4.29-4.24 (q, J=7.2 Hz, 2H), 1.64 (s, 6H), 1.27 (t, J=7.2 Hz, 3H).

Step 2: Compound 49-c

Under nitrogen protection, potassium tert-butoxide (8.55 g, 76.16 mmol, 1.20 eq) was added into a solution of a compound methoxymethyl triphenylphosphine chloride (28.29 g, 82.54 mmol, 1.30 eq) in tetrahydrofuran (100.00 mL) at 0° C., and the mixture was stirred at 0° C. for 30 min. Then, a solution of Compound 49-b (15.00 g, 63.49 mmol, 1.00 eq) in tetrahydrofuran (50.00 mL) was added dropwise. The mixture was quenched by adding water (100 mL), and then extracted with ethyl acetate (100 mL×3). The combined organic phase was washed with water (100 mL) and saturated brine (100 mL×2), dried over anhydrous sodium sulfate, filtered by suction, and concentrated under reduced pressure. The residue was isolated by silica gel column chromatography (petroleum ether:ethyl acetate=20/1) to give Compound 49-c.

$^1$H NMR (400 MHz, CDCl$_3$) δ ppm 7.10-7.04 (m, 2H), 6.93 (d, J=13.2 Hz, 1H), 6.67-6.56 (m, 1H), 6.04 (d, J=6.8 Hz, 1H), 5.68-5.07 (m, 1H), 4.19-4.13 (q, J=7.2 Hz, 2H), 3.70-3.60 (m, 3H), 1.52 (s, 6H), 1.20-1.15 (m, 3H)

Step 3: Compound 49-d

Under nitrogen protection, oxalyl chloride (19.10 g, 150.50 mmol, 13.17 mL, 2.00 eq), and then ethanol (6.93 g, 150.50 mmol, 8.77 mL, 2.00 eq) and water (2.71 g, 150.50 mmol, 2.00 eq) were added into a solution of Compound 49-c (22.00 g, 75.25 mmol, 1.00 eq) in chloroform (200.00 mL) at 0° C. The mixture was stirred 0° C. for 0.5 h. The mixture was adjusted with a saturated solution of sodium carbonate to pH 7-8. The organic phase was washed with water (50 mL×2) and saturated brine (50 mL×2), dried over anhydrous sodium sulfate, filtered, and concentrated under reduced pressure. The residue was isolated by silica gel column chromatography (petroleum ether:ethyl acetate=30/1-10/1) to give Compound 49-d.

$^1$H NMR (400 MHz, CDCl$_3$) δ ppm 9.64 (t, J=2.3 Hz, 1H), 7.16 (t, J=7.8 Hz, 1H), 6.77 (d, J=7.5 Hz, 1H), 6.70-6.66 (m, 2H), 4.32-4.26 (m, 2H), 3.55 (d, J=2.3 Hz, 2H), 1.53 (s, 6H), 1.31 (t, J=7.2 Hz, 3H).

Step 4: Compound 49-e

Under nitrogen protection, a solution of Compound 49-d (22.00 g, 87.90 mmol, 1.00 eq) and 44-f (37.49 g, 87.90 mmol, 1.00 eq) in tetrahydrofuran (400.00 mL) was stirred at 50° C. for 12 h.

The mixture was concentrated under reduced pressure. The residue was purified by silica gel column (chromatography petroleum ether:ethyl acetate=30/1-10/1) to give Compound 49-e.

MS m/z (ESI): 399.2 [M+1].

Step 5: Compound 49-f

Under nitrogen protection, N-methoxymethyl-1-phenyl-N-(trimethyldisilanyl)methylamine (8.94 g, 37.64 mmol, 1.50 eq) was added dropwise into a solution of Compound 49-e (10.00 g, 25.09 mmol, 1.00 eq) and trifluoroacetic acid (143.05 mg, 1.25 mmol, 92.89 μL, 0.05 eq) in dioxane (50.00 mL) solution at 90° C. The mixture was stirred at 90° C. for 0.5 h. The mixture was diluted with water (500 mL), and extracted with ethyl acetate (300 mL×3). The combined organic phase was washed with water (300 mL×3) and saturated brine (300 mL×2), dried over anhydrous sodium sulfate, filtered, and concentrated under reduced pressure. The residue was purified by flash column chromatography (petroleum ether:ethyl acetate=20/1-5/1) to give Compound 49-f.

MS m/z (ESI): 532.2 [M+1].

Step 6: Compound 49-g

Under nitrogen protection, a solution of Compound 49-f (6.00 g, 11.28 mmol, 1.00 eq) and phenyl chloroformate (3.53 g, 22.57 mmol, 2.83 mL, 2.00 eq) in chloroform (40.00 mL) was stirred at 70° C. for 3 h. The mixture was concentrated under reduced pressure. The residue was purified by flash column chromatography (petroleum ether:ethyl acetate=5/1) to give Compound 49-g.

$^1$H NMR (400 MHz, CDCl$_3$) δ ppm 7.66 (d, J=8.5 Hz, 1H), 7.61 (br d, J=8.5 Hz, 1H), 7.35 (t, J=7.6 Hz, 2H), 7.27-7.11 (m, 6H), 6.83 (br d, J=7.5 Hz, 1H), 6.78-6.66 (m, 2H), 4.26-4.17 (m, 2H), 3.95-3.57 (m, 4H), 3.52-3.35 (m, 1H), 2.98-2.65 (m, 3H), 2.52 (s, 3H), 1.59 (d, J=2.3 Hz, 6H), 1.26-1.21 (m, 3H).

Step 7: Compounds 49 and 50

At 25° C., a solution of lithium hydroxide monohydrate (448.97 mg, 10.70 mmol, 5.00 eq) in water (2.00 mL) was added into a solution of Compound 49-g (1.20 g, 2.14 mmol, 1.00 eq) in ethanol (5.00 mL) and tetrahydrofuran (5.00 mL). The mixture was stirred at 25° C. for 8 h. The mixture was neutralized with diluted HCl (1N) to pH=5-6, and then extracted with ethyl acetate (20 mL×3). The combined organic phase was washed with water (20 mL×3) and saturated brine (20 mL×2), dried over anhydrous sodium sulfate, filtered, and concentrated under reduced pressure. The residue was purified by flash column chromatography (petroleum ether:ethyl acetate=3/1-1/1), and then the purified product was subjected to chiral separation to give Compound 49; Compound 50.

Compound 49: MS m/z (ESI): 534.3 [M+1].

$^1$H NMR (400 MHz, CDCl$_3$) δ ppm 7.70-7.55 (m, 2H), 7.27 (d, J=8.0 Hz, 2H), 7.20-7.04 (m, 6H), 6.79-6.63 (m, 3H), 3.93-3.26 (m, 5H), 2.88-2.49 (m, 3H), 2.47-2.40 (m, 3H), 1.56-1.45 (m, 6 h).

Compound 50: MS m/z (ESI): 534.3 [M+1].

$^1$H NMR (400 MHz, CDCl$_3$) δ ppm 7.72-7.59 (m, 2H), 7.30-7.07 (m, 9H), 6.80-6.60 (m, 3H), 3.91-3.73 (m, 3H), 3.42-3.27 (m, 1H), 2.81-2.54 (m, 4H), 2.47-2.44 (m, 3H), 1.55-1.50 (m, 6H).

Conditions of the chiral resolution: chiral column: Chiralpak AD-50 mm×4.6 mm I.D., 3 μm; mobile phase: 40% of ethanol (0.05% DEA) in $CO_2$; flow rate: 4 mL/min; column temperature: 40° C.
Retention time of Compound 49: 1.904 min (peak 1); Retention time of Compound 50: 2.071 min (peak 2).
Examples 51 and 52: Compounds 51 and 52
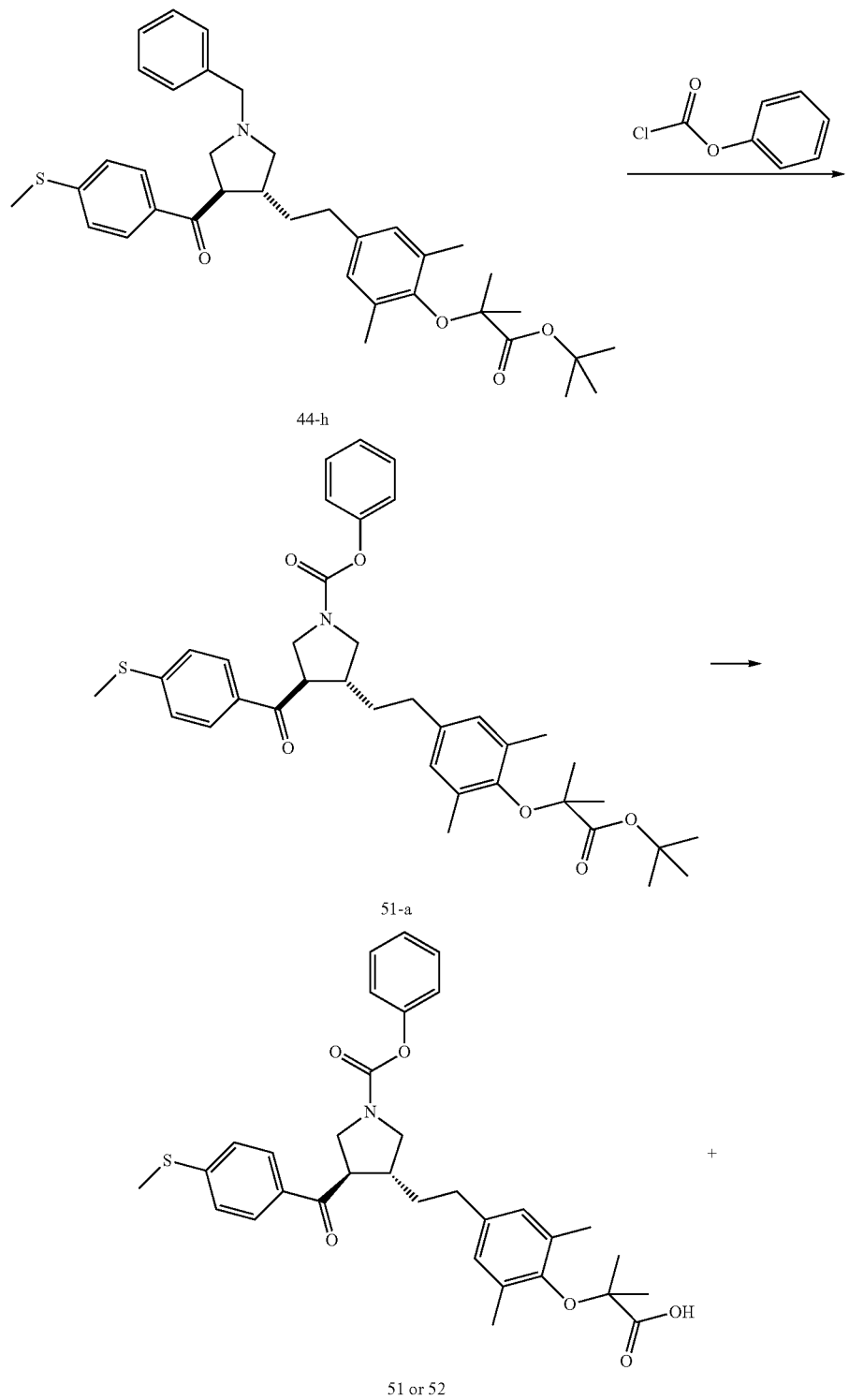

-continued

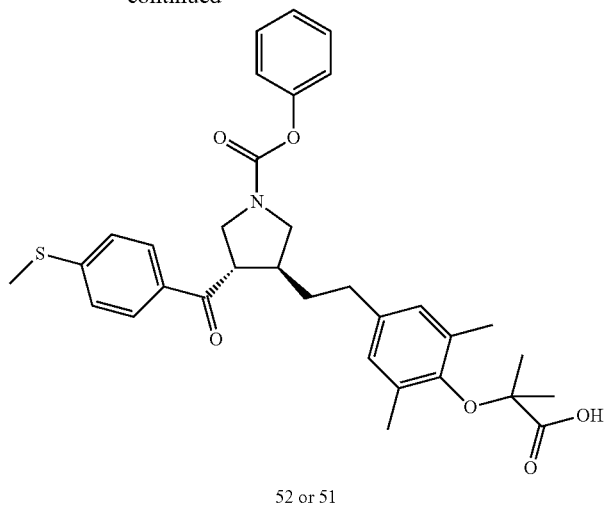

52 or 51

Step 1: Compound 51-a

Phenyl chloroformate (156.09 mg, 996.94 mol, 124.87 μL, 1.00 eq) was slowly added into a solution of Compound 44-h (600.00 mg, 996.94 μmol, 1.00 eq) in chloroform (10.00 mL). The mixture was stirred at 70° C. for 4 h. The mixture was concentrated under reduced pressure. The residue was purified by flash column chromatography (51.6%, ethyl acetate/petroleum ether) to give Compound 51-a.

MS m/z (ESI): 654.4 [M+23].

Step 2: Compounds 51 and 52

A solution of Compound 51-a (360.00 mg, 569.78 μmol, 1.00 eq) and trifluoroacetic acid (2.66 g, 23.30 mmol, 1.73 mL, 40.90 eq) in dichloromethane (5.00 mL) was stirred at 25° C. for 16 h. The mixture was concentrated under reduced pressure. The residue was purified by flash column chromatography (54.2%, ethyl acetate/petroleum ether), and the resulted product was subjected to chiral separation to give Compound 51; Compound 52.

Compound 51: MS m/z (ESI): 598.1 [M+23].

$^1$H NMR (400 MHz, CDCl$_3$) δ ppm 7.80 (dd, J=6.3, 8.3 Hz, 2H), 7.29-7.20 (m, 4H), 7.05-7.03 (m, 3H), 6.69 (d, J=5.3 Hz, 2H), 3.89-3.86 (m, 1H), 3.70-3.63 (m, 2H), 3.51-3.31 (m, 1H), 3.12 (br dd, J=8.5, 10.8 Hz, 1H), 2.80-2.60 (m, 1H), 2.49-2.45 (m, 5H), 2.12 (d, J=4.8 Hz, 6H), 1.80-1.78 (m, 1H), 1.61-1.60 (m, 1H), 1.41 (br d, J=16.8 Hz, 6H).

Compound 52: MS m/z (ESI): 598.1 [M+23].

$^1$H NMR (400 MHz, CDCl$_3$) δ ppm 7.80 (dd, J=6.0, 8.3 Hz, 2H), 7.29-7.20 (m, 4H), 7.07-7.05 (m, 3H), 6.70 (d, J=5.3 Hz, 2H), 3.89-3.86 (m, 1H), 3.70-3.63 (m, 2H), 3.52-3.24 (m, 1H), 3.12 (dd, J=8.5, 11.0 Hz, 1H), 2.77-2.62 (m, 1H), 2.49-2.45 (m, 5H), 2.12 (d, J=4.8 Hz, 6H), 1.80-1.78 (m, 1H), 1.61-1.52 (m, 1H), 1.42 (d, J=15.8 Hz, 6H).

Conditions of the chiral resolution: chiral column: Lux Cellulose-2 150×4.6 mm I.D., 3 μm; mobile phase: 40% of methanol (0.05% DEA) in CO$_2$; flow rate: 2.5 mL/min; column temperature: 40° C.

Retention time of Compound 51: 8.092 min (peak 1); Retention time of Compound 52: 13.834 min (peak 2).

Example 53: Compound 53

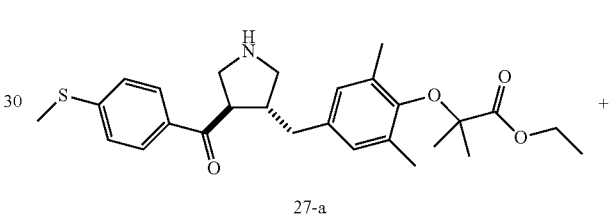

27-a

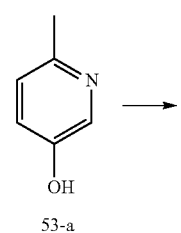

53-a

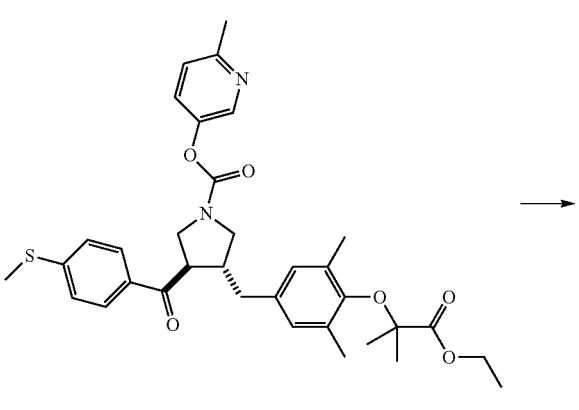

53-b

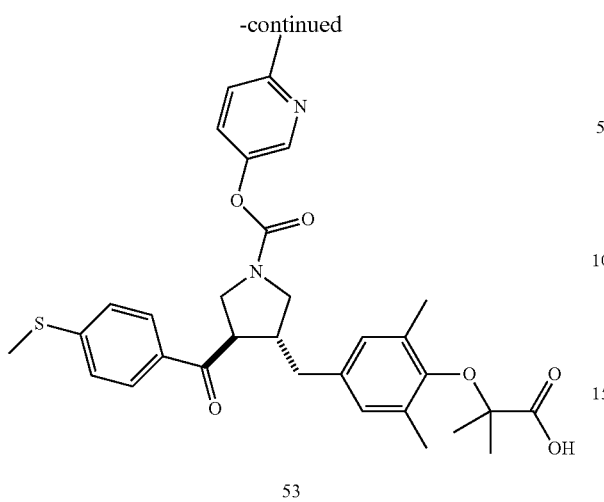

53

Step 1: Compound 53-b

Under nitrogen protection, triphosgene (2.17 g, 7.33 mmol, 0.80 eq) was slowly added into a solution of Compound 53-a (1.00 g, 9.16 mmol, 1.00 eq) and triethylamine (926.90 mg, 9.16 mmol, 1.27 mL, 1.00 eq) in tetrahydrofuran (20.00 mL) at 0° C. The mixture was stirred at 20° C. for 1 h. The mixture was filtered, and the filtrate was concentrated under reduced pressure to give a residue. Compound 27-a (1.00 g, 2.13 mmol, 1.00 eq) and N,N-di-iso-propyl ethylamine (550.38 mg, 4.26 mmol, 743.76 μL, 2.00 eq) was added into a solution of the residue (365.47 mg, 2.13 mmol, 1.00 eq) in dichloromethane (50.00 mL) at 20° C. The mixture was stirred at 20° C. for 1 h. The mixture was concentrated under reduced pressure. The residue was purified by flash column chromatography (petroleum ether:ethyl acetate=100/0-40/60) to give Compound 53-b.

MS m/z (ESI): 605.3 [M+1].

Step 2: Compound 53

At 20° C., lithium hydroxide (118.81 mg, 4.96 mmol, 10.00 eq) was added into a solution of Compound 53-b (300.00 mg, 496.06 μmol, 1.00 eq) in ethanol (20.00 mL) and water (5.00 mL). The mixture was stirred at 20° C. for 16 h. The mixture was acidized by adding 1N diluted HCl (5 mL), and then extracted with ethyl acetate (10 mL×3). The combined organic phase was dried over anhydrous sodium sulfate, filtered, and concentrated under reduced pressure. The residue was separated by High Performance Liquid Chromatography to give Compound 53

MS m/z (ESI): 577.4 [M+1].

$^1$H NMR (400 MHz, CDCl$_3$) δ ppm 8.32 (t, J=2.76 Hz, 1H), 7.59 (dd, J=8.54, 2.76 Hz, 2H), 7.38-7.45 (m, 1H), 7.06-7.16 (m, 3H), 6.73 (s, 2H), 3.58-3.88 (m, 5H), 3.27-3.40 (m, 1H), 2.58-2.64 (m, 2H), 2.50 (s, 3H), 2.45 (s, 3H), 2.14 (br d, J=2.26 Hz, 6H), 1.42 (br d, J=3.26 Hz, 6H).

Example 54: Compound 54

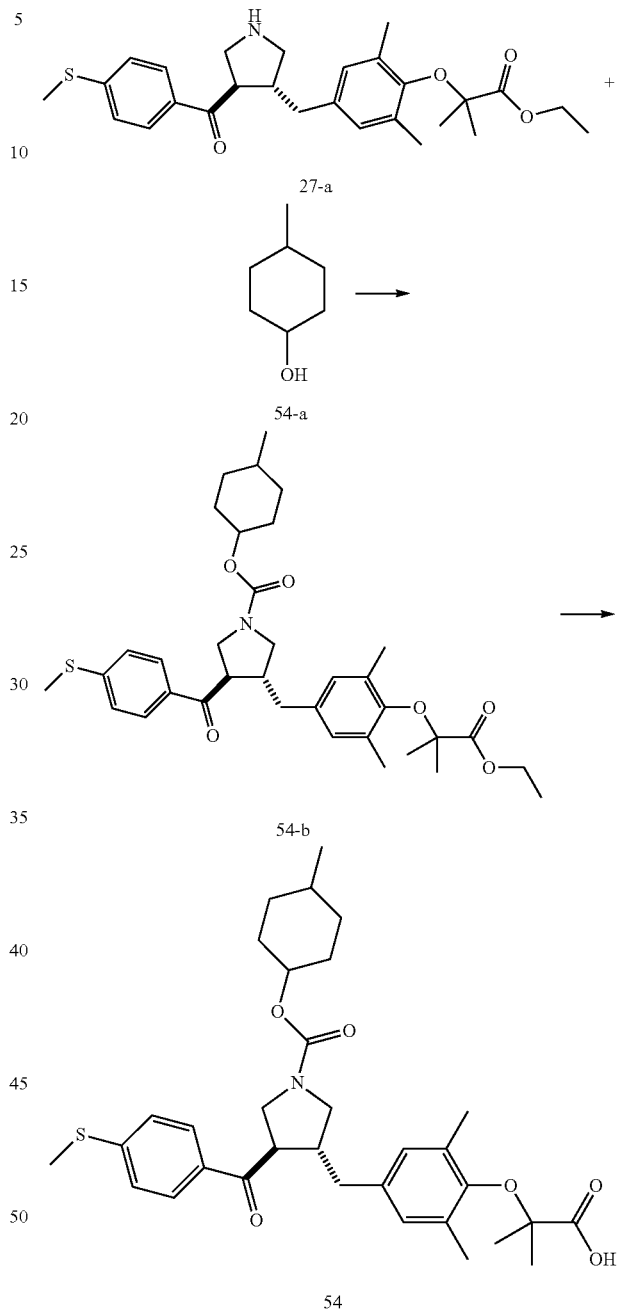

Step 1: Compound 54-b

Under nitrogen protection, triphosgene (2.08 g, 7.01 mmol, 0.80 eq) was slowly added dropwise into a solution of Compound 54-a (1.00 g, 8.76 mmol, 1.08 mL, 1.00 eq) and triethylamine (886.42 mg, 8.76 mmol, 1.21 mL, 1.00 eq) in tetrahydrofuran (10.00 mL) at 0° C. The mixture was stirred at 20° C. for 2 h. The mixture was filtered, and the filtrate was concentrated under reduced pressure to give a residue. The residue (752.49 mg, 4.26 mmol, 2.00 eq) and N,N-di-iso-propyl ethylamine (550.38 mg, 4.26 mmol, 743.76 μL, 2.00 eq) was added into a solution of Compound 27-a (1.00 g, 2.13 mmol, 1.00 eq) in dichloromethane (50.00 mL) at 20° C. The mixture was stirred at 20° C. for 1 h. The mixture was concentrated under reduced pressure. The residue was purified by flash column chromatography (petroleum ether:ethyl acetate=100/0-40/60) to give Compound 54-b.

MS m/z (ESI): 610.3 [M+1].

$^1$H NMR (400 MHz, CDCl$_3$) δ ppm 7.61-7.71 (m, 2H), 7.22 (br dd, J=5.28, 2.76 Hz, 2H), 6.72-6.80 (m, 2H), 4.50-4.64 (m, 1H), 4.25-4.37 (m, 2H), 3.43-3.79 (m, 4H), 3.17-3.31 (m, 1H), 2.84 (br s, 1H), 2.58-2.67 (m, 2H), 2.54 (s, 3H), 2.16 (br d, J=4.02 Hz, 6H), 1.69-2.03 (m, 4H), 1.46 (s, 6H), 1.37 (t, J=7.16 Hz, 3H).

Step 2: Compound 54

At 20° C., lithium hydroxide (479.14 mg, 20.01 mmol, 10.00 eq) was added into a solution of Compound 54-b (1.22 g, 2.00 mmol, 1.00 eq) in ethanol (20.00 mL) and water (4.00 mL). The mixture was stirred at 20° C. for 2 h. The mixture was acidized by adding 1N diluted HCl (5 mL), and then extracted with ethyl acetate (10 mL×3). The combined organic phase was dried over anhydrous sodium sulfate, filtered, and concentrated under reduced pressure. The residue was separated by High Performance Liquid Chromatography to give Compound 54.

MS m/z (ESI): 582.4 [M+1].

$^1$H NMR (400 MHz, CDCl$_3$) δ ppm 7.56-7.65 (m, 2H), 7.09-7.17 (m, 2H), 6.67 (br s, 2H), 3.34-3.78 (m, 5H), 3.08-3.23 (m, 1H), 2.77 (br s, 1H), 2.49-2.59 (m, 2H), 2.43 (br s, 3H), 2.06 (br s, 6H), 1.90 (br s, 1H), 1.77 (br d, J=10.04 Hz, 1H), 1.63 (br d, J=13.06 Hz, 1H), 1.36 (br s, 6H), 1.06-1.26 (m, 4H), 0.89-1.02 (m, 2H), 0.80 (br d, J=6.54 Hz, 3H).

Example 55: Compound 55

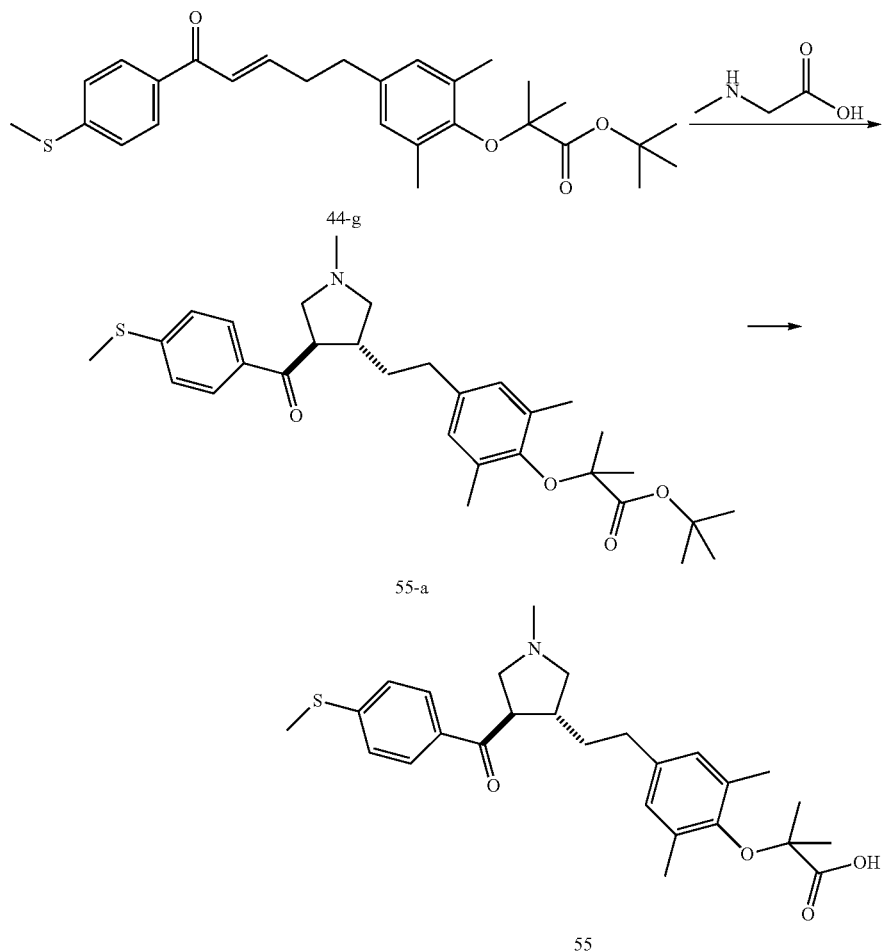

Step 1: Compound 55-a

A solution of Compound 44-g (900.00 mg, 1.92 mmol, 1.00 eq), sarcosine (427.72 mg, 4.80 mmol, 2.50 eq) and paraformaldehyde (1.04 g, 11.52 mmol, 6.00 eq) in toluene (10.00 mL) was stirred at 110° C. for 16 h under nitrogen protection. The mixture was concentrated under reduced pressure. The residue was purified by flash column chromatography (70.2%, ethyl acetate/petroleum ether) to give Compound 55-a.

MS m/z (ESI): 526.2 [M+1].

Step 2: Compound 55

Trifluoroacetic acid (1.30 g, 11.41 mmol, 844.16 μL, 30.00 eq) was added into a solution of Compound 55-a (200.00 mg, 380.42 μmol, 1.00 eq) in dichloromethane (10.00 mL). The mixture was stirred at 25° C. for 4 h. The mixture was concentrated under reduced pressure. The residue was purified by flash column chromatography (80.3%, ethyl acetate/petroleum ether), and then isolated by High Performance Liquid Chromatography to give Compound 55.

MS m/z (ESI): 470.1 [M+1].

$^1$H NMR (400 MHz, CDCl$_3$) δ ppm 7.95 (d, J=8.8 Hz, 2H), 7.29 (d, J=8.5 Hz, 2H), 6.67 (s, 2H), 4.06-3.99 (m, 2H), 3.44 (dd, J=3.5, 10.8 Hz, 1H), 2.92-2.83 (m, 3H), 2.72 (s, 3H), 2.51 (s, 3H), 2.49-2.29 (m, 2H), 2.15 (s, 6 h), 1.83-1.80 (m, 2H), 1.42 (d, J=8.3 Hz, 6H)

Example 56: Compound 56 was concentrated, and methanol (50.00 mL) was added and stirred at 80° C. for additional 1 h. The reaction mixture was concentrated under reduced pressure, the crude product was purified by flash column chromatography (76.3%, ethyl acetate/petroleum ether) to give Compound 56-a.

$^1$H NMR (400 MHz, CDCl$_3$) δ ppm 7.39 (br s, 2H), 7.22 (br d, J=6.5 Hz, 2H), 6.63 (br d, J=11.0 Hz, 2H), 4.38-4.19 (m, 2H), 3.87 (br s, 1H), 3.78 (s, 3H), 3.69 (br s, 1H), 3.34 (br s, 1H), 3.18-3.02 (m, 2H), 2.65 (br s, 1H), 2.49 (d, J=3.5 Hz, 3H), 2.42-2.35 (m, 2H), 2.06 (d, J=7.5 Hz, 6H), 1.38 (d, J=4.8 Hz, 6H).

Step 2: Compound 56

Compound 56-a (500.00 mg, 1.06 mmol, 1.00 eq), lithium hydroxide (76.16 mg, 3.18 mmol, 3.00 eq), water (2.00 mL)

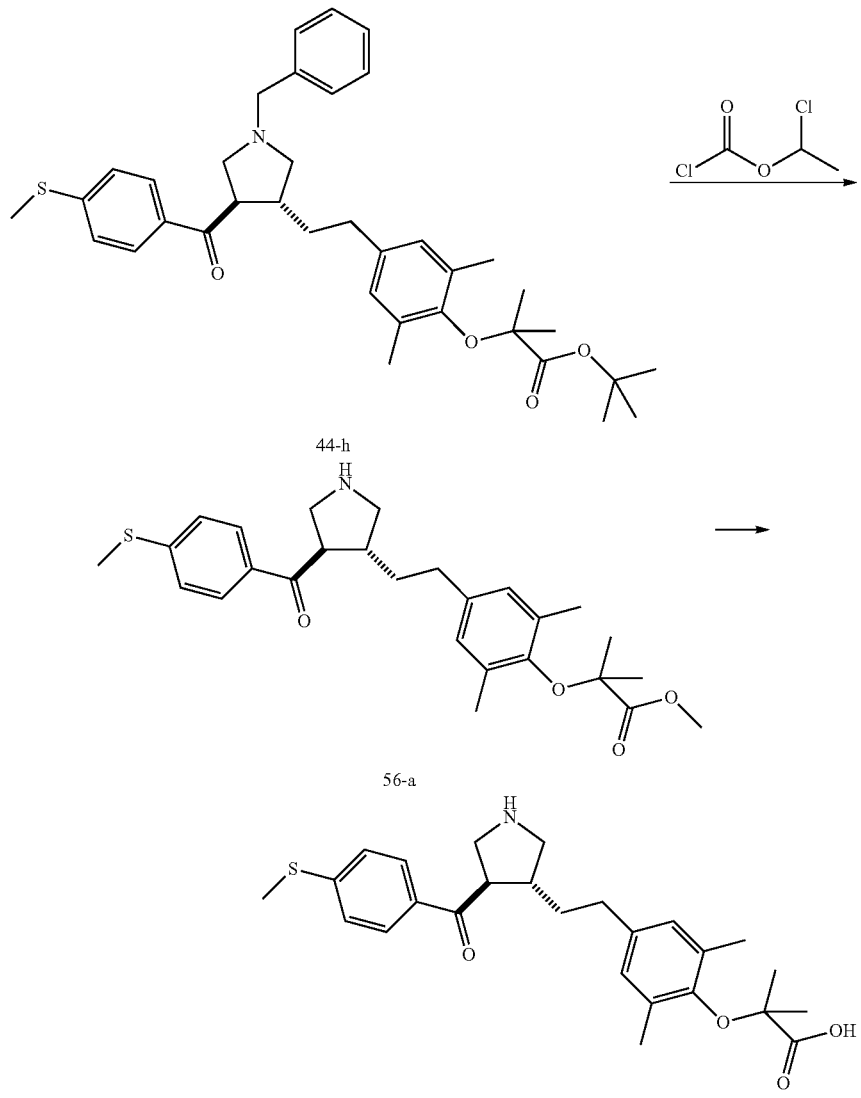

Step 1: Compound 56-a

α-chloroethyl chloroformate (3.56 g, 24.93 mmol, 3.00 eq) was added into a solution of Compound 44-h (5.00 g, 8.31 mmol, 1.00 eq) in toluene (50.00 mL). The reaction solution was stirred at 80° C. for 16 h. The reaction solution and methanol (6.00 mL) was added into a dried reaction flask. The reaction solution was stirred at 40° C. for 16 h. The reaction solution was adjusted by 1N diluted HCl to pH=6, and treated by water and ethyl acetate (1:1, 20 mL), the aqueous phase was extracted with ethyl acetate (2*20 mL). The combined organic phase was dried over anhydrous sodium sulfate, filtered, concentrated to give a crude product. The crude product was purified by preparative High Performance Liquid Chromatography to give Compound 56.

MS m/z (ESI): 456.1 [M+1].

¹H NMR (400 MHz, MeOD-d₄) δ ppm 8.52 (s, 1H), 7.89 (d, J=8.5 Hz, 2H), 7.35 (d, J=8.5 Hz, 2H), 6.74 (s, 2H), 4.06-4.04 (m, 1H), 3.61-3.56 (m, 2H), 3.40 (dd, J=7.3, 11.5 Hz, 1H), 3.14-3.12 (m, 1H), 2.56-2.45 (m, 6H), 2.19 (s, 6H), 1.87-1.83 (m, 1H), 1.75-1.70 (m, 1H), 1.37 (d, J=12.0 Hz, 6H).

Example 57: Compound 57

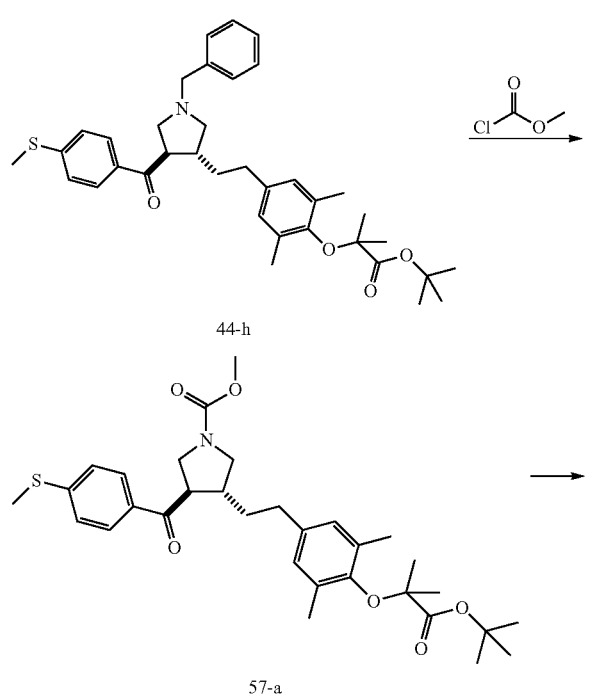

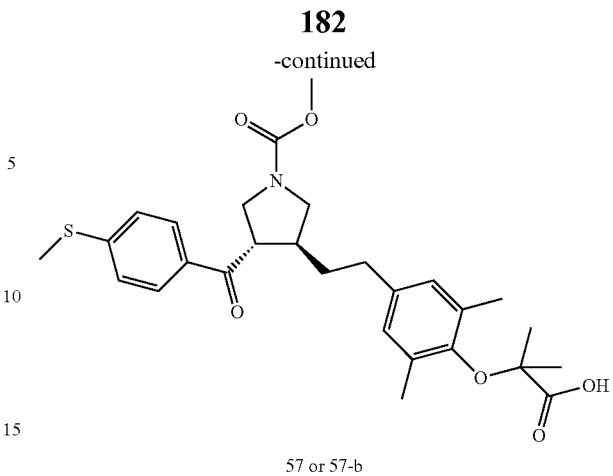

57 or 57-b

Step 1: Compound 57-a

Methyl chloroformate (785.10 mg, 8.31 mmol, 643.52 μL, 10.00 eq) was slowly added into a solution of Compound 44-h (500.00 mg, 830.79 μmol, 1.00 eq) in chloroform (10 mL). The mixture was stirred at 70° C. for 32 h. The reaction solution was concentrated under reduced pressure, the crude product was purified by flash column chromatography (26.6%, ethyl acetate/petroleum ether) to give Compound 57-a.

MS m/z (ESI): 592.2 [M+23].

Step 2: Compound 57

Trifluoroacetic acid (1.86 g, 16.32 mmol, 1.21 mL, 30.00 eq) was added into a solution of Compound 57-a (310.00 mg, 544.10 μmol, 1.00 eq) in dichloromethane (30.00 mL). The reaction solution was stirred at 25° C. for 4 h. The reaction solution was concentrated under reduced pressure to give a crude product which was purified by flash column chromatography (73.3%, ethyl acetate/petroleum ether) to give a product. The product was subjected to chiral separation to give Compound 57.

MS m/z (ESI): 536.1 [M+23].

¹H NMR (400 MHz, CDCl₃) δ ppm 7.77 (d, J=8.3 Hz, 2H), 7.21-7.19 (m, 2H), 6.67 (s, 2H), 3.79-3.55 (m, 6H), 3.37-3.35 (m, 1H), 3.13-2.98 (m, 1H), 2.70-2.51 (m, 1H), 2.46-2.41 (m, 5H), 2.11 (br d, J=7.0 Hz, 6H), 1.73 (br s, 1H), 1.57-1.53 (m, 1H), 1.45-1.40 (m, 6H).

Conditions of the chiral resolution: chiral column: AD (250 mm×30 mm, 5 um); mobile phase: 40% of methanol (0.1% NH₃H₂O) in CO₂; flow rate: 60 mL/min; column temperature: 40° C.

Retention time of Compound 57: 2.964 min (peak 1).

Example 58: Compound 58
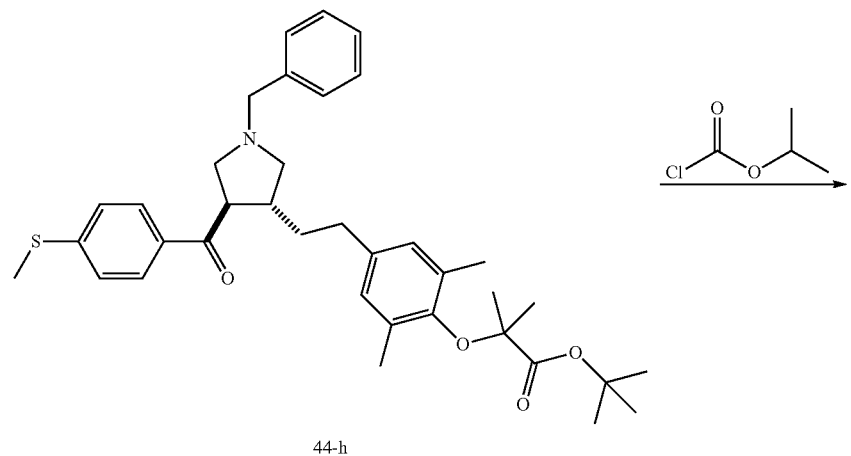
44-h
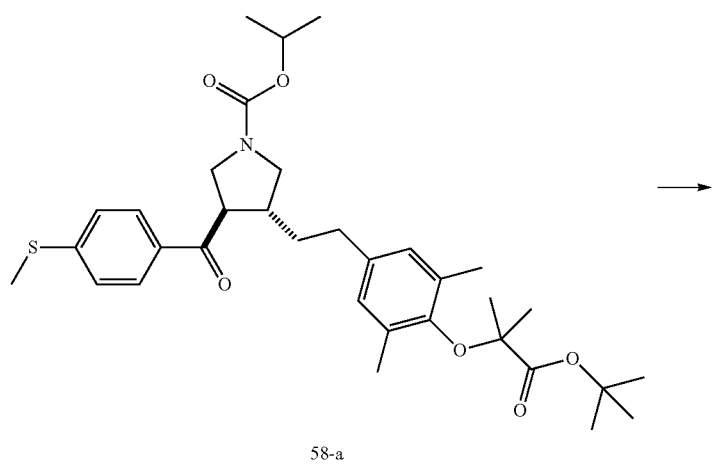
58-a
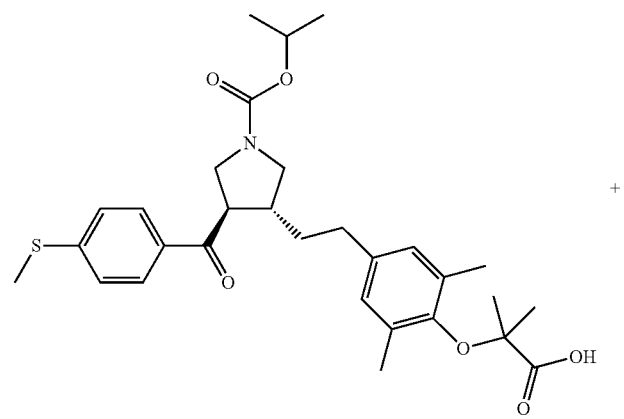
58-b or 58

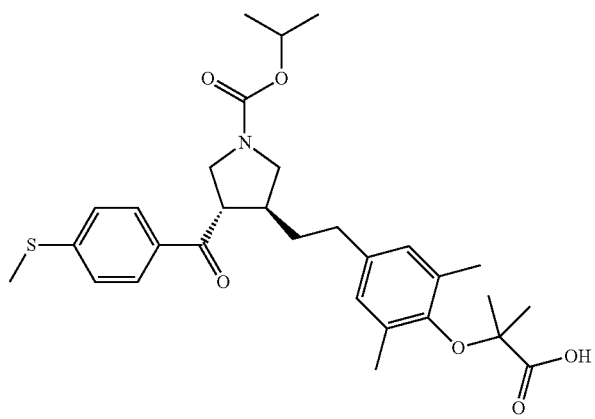

58 or 58-b

Step 1: Compound 58-a

Isopropyl chloroformate (1.02 mg, 8.31 mmol, 1.16 μL, 10.00 eq) was slowly added into a solution of Compound 44-h (500.00 mg, 830.79 μmol, 1.00 eq) in chloroform (10.00 mL). The reaction solution was stirred at 70° C. for 32 h. The reaction solution was concentrated under reduced pressure to give a crude product which was purified by flash column chromatography (47.6%, ethyl acetate/petroleum ether) to give Compound 58-a.

MS m/z (ESI): 620.3 [M+23].

Step 2: Compound 58

Trifluoroacetic acid (801.08 mg, 7.03 mmol, 520.18 μL, 30.00 eq) was added into a solution of Compound 58-a (140.00 mg, 234.19 μmol, 1.00 eq) in dichloromethane (30.00 mL). The reaction solution was stirred at 25° C. for 4 h. The reaction solution was concentrated under reduced pressure, and the crude product was purified by flash column chromatography (73.3%, ethyl acetate/petroleum ether) to give a product. The product was subjected to chiral separation to give Compound 58.

MS m/z (ESI): 564.1 [M+23].

$^1$H NMR (400 MHz, CDCl$_3$) δ ppm 7.78 (br d, J=8.3 Hz, 2H), 7.23-7.21 (m, 2H), 6.68 (s, 2H), 4.85-4.82 (m, 1H), 3.82-3.59 (m, 2H), 3.44-3.29 (m, 2H), 3.11-2.89 (m, 1H), 2.76-2.54 (m, 1H), 2.47-2.40 (m, 5H), 2.14-2.11 (m, 6H), 1.74 (br s, 1H), 1.56-1.41 (m, 7H), 1.20-1.12 (m, 6H).

Conditions of the chiral resolution: chiral column: AD (250 mm×30 mm, 5 um); mobile phase: 40% of methanol (0.1% NH$_3$H$_2$O) in CO$_2$; flow rate: 60 mL/min; column temperature: 40° C.

Retention time of Compound 58: 6.217 min (peak 1).

Examples 59 and 60: Compounds 59 and 60

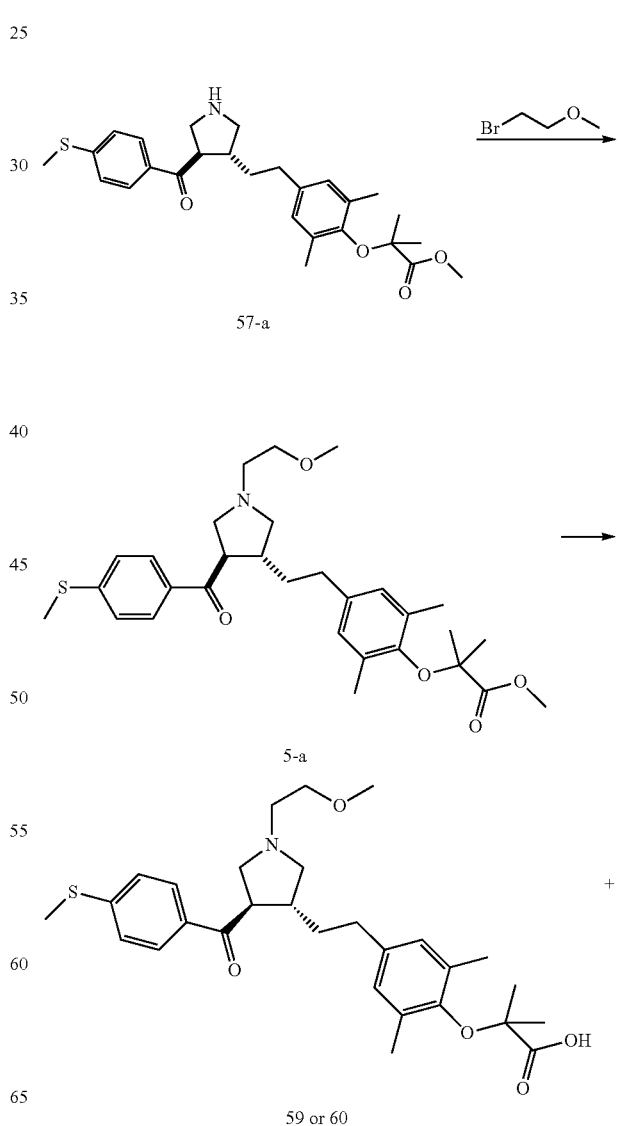

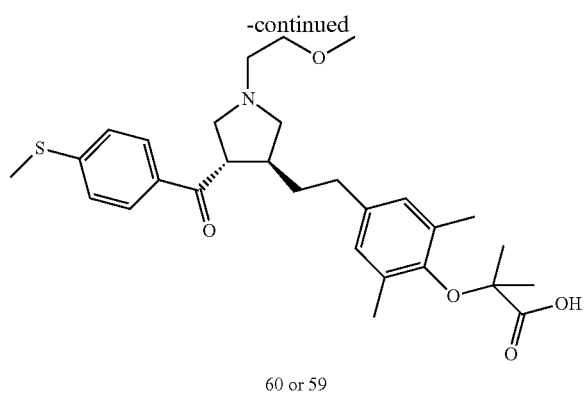

60 or 59

Step 1: Compound 59-a 1-bromo-2-methoxyethane (441.99 mg, 3.18 mmol, 298.64 µL, 3.00 eq) and triethylamine (321.78 mg, 3.18 mmol, 440.79 µL, 3.00 eq) was added into a solution of Compound 57-a (500.00 mg, 1.06 mmol, 1.00 eq) in acetonitrile (10.00 mL). The reaction solution was stirred at 25° C. for 16 h. The reaction solution was concentrated under reduced pressure, and the crude product was purified by flash column chromatography (80.3%, ethyl acetate/petroleum ether) to give Compound 59-a.

MS m/z (ESI): 528.4 [M+1].

Step 2: Compounds 59 and 60

Lithium hydroxide (21.10 mg, 881.16 µmol, 3.00 eq) and water (2.00 mL) was added into a solution of Compound 59-a (155.00 mg, 293.72 µmol, 1.00 eq) in methanol (6.00 mL). The reaction solution was stirred at 40° C. for 16 h. The reaction solution was adjusted by 1N diluted HCl to pH=6, and treated with water and ethyl acetate (1:1, 15 mL). After phase separation, the aqueous phase was extracted with ethyl acetate (2×15 mL). The combined organic phase was dried over anhydrous sodium sulfate, filtered, concentrated to give a crude product which was purified by flash column chromatography (82.3%, ethyl acetate/petroleum ether) to give a product. The product was subjected to chiral separation to give Compound 59 and Compound 60.

Compound 59:
$^1$H NMR (400 MHz, CDCl$_3$) δ ppm 7.99 (br d, J=8.3 Hz, 2H), 7.29 (br d, J=8.5 Hz, 2H), 6.67 (s, 2H), 3.95 (br s, 2H), 3.62 (br s, 1H), 3.38-3.29 (m, 5H), 3.07 (br s, 1H), 2.98 (br t, J=9.4 Hz, 2H), 2.86 (br s, 1H), 2.75 (s, 1H), 2.51 (s, 3H), 2.39 (br dd, J=5.1, 11.9 Hz, 1H), 2.35-2.26 (m, 1H), 2.17 (s, 6H), 1.84-1.70 (m, 2H), 1.47-1.38 (m, 6H).

Compound 60:
$^1$H NMR (400 MHz, CDCl$_3$) δ ppm 7.99 (d, J=8.5 Hz, 2H), 7.29 (d, J=8.5 Hz, 2H), 6.67 (s, 2H), 3.97 (br s, 2H), 3.62 (br d, J=4.5 Hz, 1H), 3.40-3.28 (m, 5H), 3.15-3.07 (m, 1H), 2.98 (br t, J=10.2 Hz, 2H), 2.87 (br s, 1H), 2.79-2.69 (m, 1H), 2.51 (s, 3H), 2.45-2.35 (m, 1H), 2.34-2.23 (m, 1H), 2.17 (s, 6H), 1.89-1.68 (m, 2H), 1.48-1.37 (m, 6H).

Conditions of the chiral resolution: chiral column: AD (250 mm×30 mm, 5 um); mobile phase: 40% of EtOH (0.1% NH$_3$H$_2$O) in CO$_2$; flow rate: 60 mL/min; column temperature: 40° C.

Retention time of Compound 59: 5.564 min (peak 1);
Retention time of Compound 60: 5.981 min (peak 2).

Example 61: Compound 61

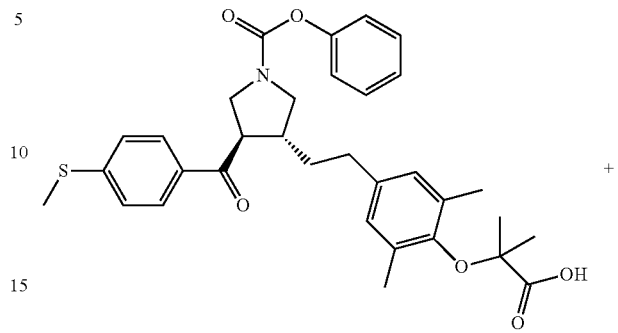

52

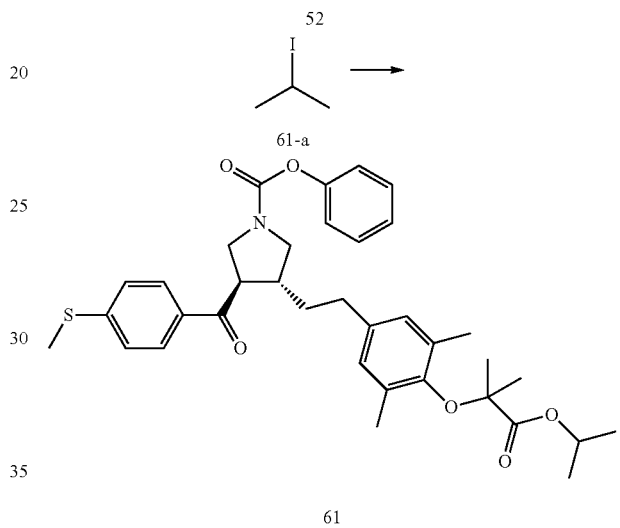

61

Step 1: Compound 61

At 20° C., Compound 61-a (59.05 mg, 347.40 µmol, 34.74 µL, 2.00 eq) and anhydrous potassium carbonate (72.02 mg, 521.10 µmol, 3.00 eq) was added into a solution of Compound 52 (100.00 mg, 173.70 µmol, 1.00 eq) in N,N-dimethylformamide (10.00 mL). The mixture was stirred at 20° C. for 16 h. The mixture was diluted with water (10 mL), and then extracted with ethyl acetate (10 mL×3). The combined organic phase was dried over anhydrous sodium sulfate, filtered, and concentrated under reduced pressure to give a crude product. The crude product was separated by High Performance Liquid Chromatography to give Compound 61.

MS m/z (ESI): 618.2 [M+1].
$^1$H NMR (400 MHz, CDCl$_3$) δ ppm 7.79 (dd, J=3.26, 8.53 Hz, 2H), 7.32-7.24 (m, 2H), 7.23-7.18 (m, 2H), 7.14-7.09 (m, 1H), 7.06 (dd, J=4.89, 7.40 Hz, 2H), 6.65 (d, J=6.27 Hz, 2H), 5.04 (spt, J=6.27 Hz, 1H), 3.96-3.47 (m, 4H), 3.33-3.19 (m, 1H), 2.79-2.57 (m, 1H), 2.53-2.34 (m, 5H), 2.08 (s, 6H), 1.85-1.71 (m, 1H), 1.66-1.60 (m, 1H), 1.34 (d, J=3.26 Hz, 6H), 1.24 (d, J=6.27 Hz, 6H).

Conditions of the chiral resolution: chiral column: Chiralpak AD-3 50*4.6 mm I.D., 3 µm; mobile phase: ethanol (0.05% DEA); flow rate: 4 mL/min; column temperature: 40° C.

Retention time of Compound 61: 1.790 min (peak 1).

Example 62: Compound 62
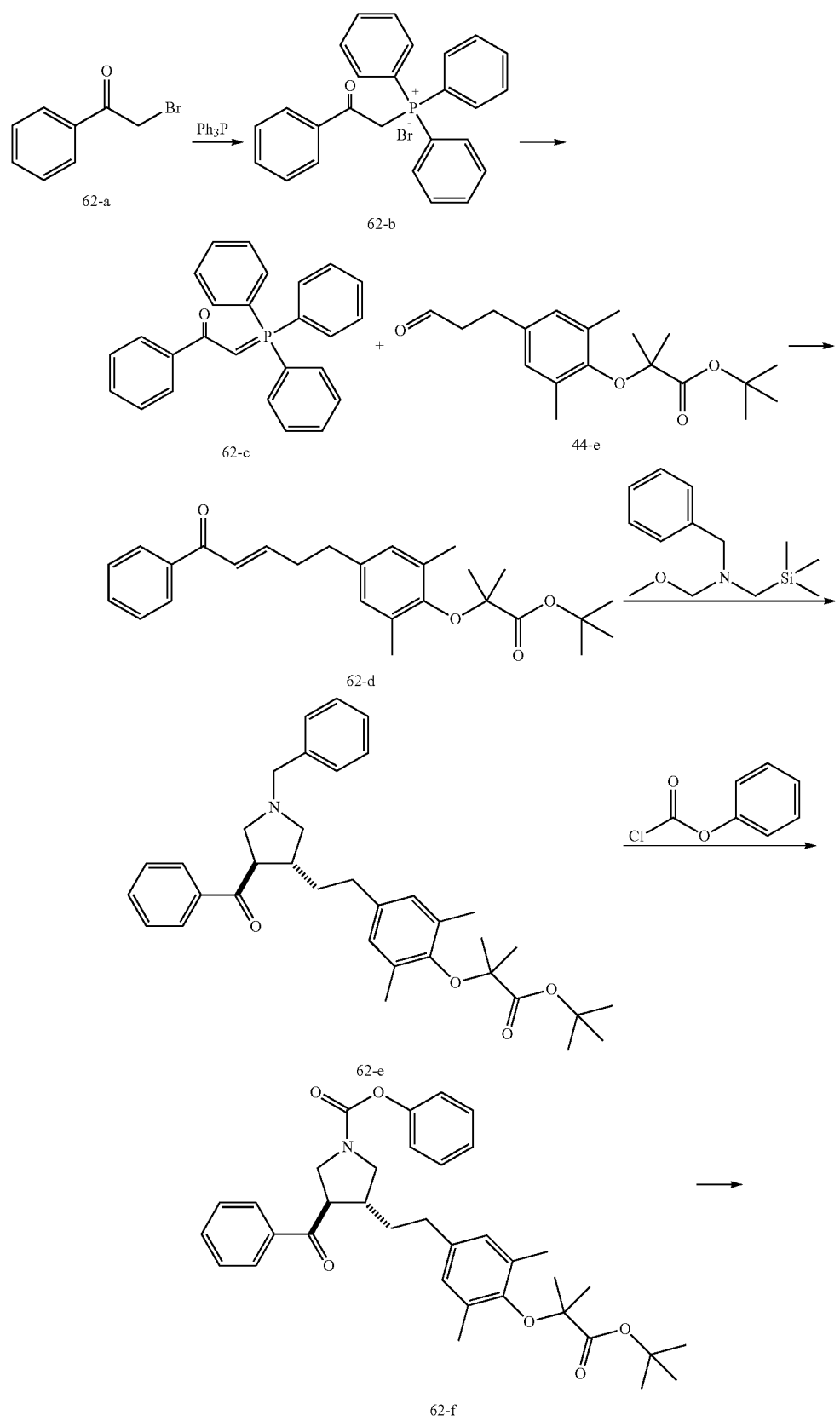

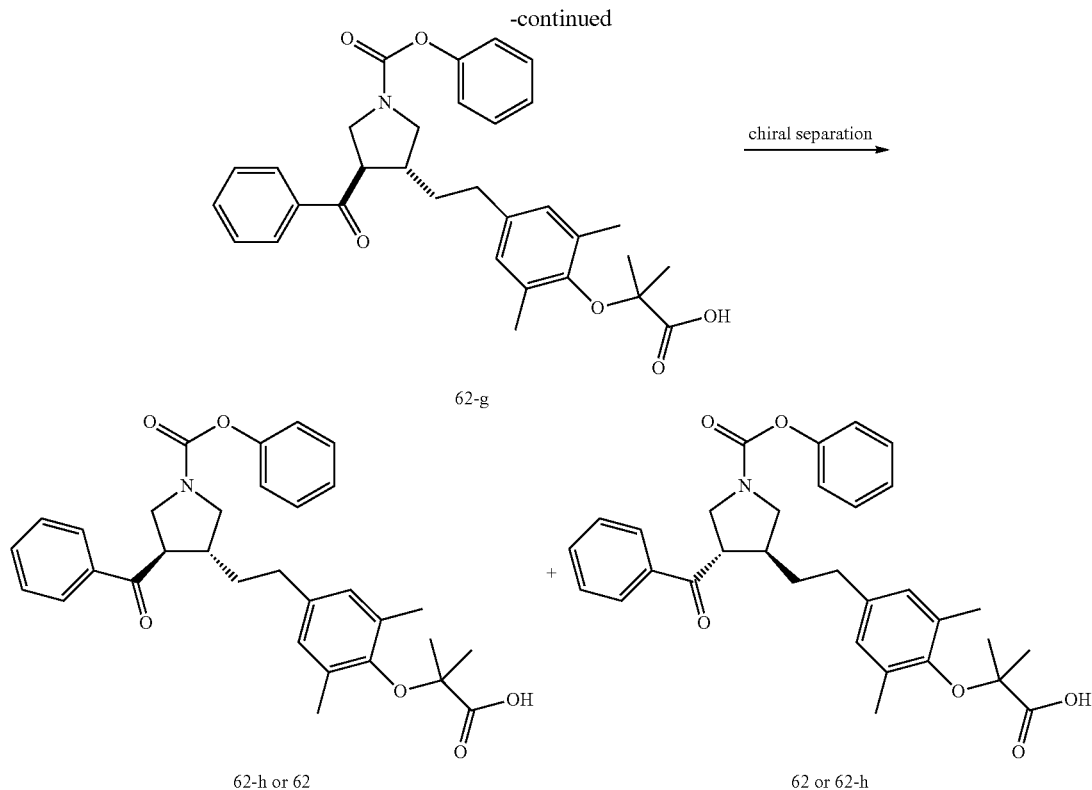

62-g 62-h or 62

62 or 62-h

Step 1: Compound 62-b

At 25° C., triphenylphosphine (37.37 g, 142.48 mmol, 1.00 eq) was added into a solution of Compound 62-a (28.36 g, 142.48 mmol, 1.00 eq) in toluene (300.00 mL). The mixture was stirred at 25° C. for 4 h. The reaction solution was filtered, and the filter cake was washed with dichloromethane (200 mL) and dried under reduced pressure to give Compound 62-b.

$^1$H NMR (400 MHz, CDCl$_3$) δ ppm 8.09 (d, J=7.6 Hz, 2H), 7.88-7.86 (m, 9H), 7.83-7.82 (m, 7H), 7.78-7.76 (m, 2H), 6.22 (d, J=13.2 Hz, 2H).

Step 2: Compound 62-c

At 20° C., potassium tert-butoxide (3.65 g, 32.52 mmol, 1.50 eq) was added into a solution of Compound 62-b (10.00 g, 21.68 mmol, 1.00 eq) in tetrahydrofuran (100 mL). The mixture was stirred at 20° C. for 0.5 h. The reaction solution was filtered, and the filtrate was extracted with ethyl acetate (100 mL×3). The combined organic phase was washed with water (100 mL), dried over anhydrous sodium sulfate, filtered, and concentrated under reduced pressure to give Compound 62-c.

MS m/z (ESI): 381.1 [M+1].

$^1$H NMR (400 MHz, CDCl$_3$) δ ppm 8.01 (d, J=7.2 Hz, 2H), 7.83 (t, J=5.2 Hz, 4H), 7.51-7.49 (m, 2H), 7.48-7.38 (m, 13H).

Step 3: Compound 62-d

At 20° C., Compound 44-e (850 mg, 2.65 mmol, 1.00 eq) was slowly added into a solution of Compound 62-c (1.01 g, 2.65 mmol, 1.00 eq) in tetrahydrofuran (10.00 mL). The reaction solution was stirred at 50° C. for 5 h. The reaction solution was concentrated under reduced pressure. The residue was purified by silica gel column chromatography (petroleum ether:ethyl acetate=100:0-70:30) to give Compound 62-d.

MS m/z (ESI): 445.2 [M+23].

$^1$H NMR (400 MHz, CDCl$_3$) δ ppm 9.80 (t, J=1.4 Hz, 2H), 7.90-7.83 (m, 1H), 7.61-7.41 (m, 2H), 7.09-6.77 (m, 4H), 6.77-6.76 (m, 2H), 2.83-2.81 (m, 2H), 2.72 (s, 2H), 2.20 (br s, 6H), 1.51-1.50 (m, 9H), 1.42-1.41 (m, 6H)

Step 4: Compound 62-e

At 0° C., N-(methoxymethyl)-1-phenyl-N-(trimethylsilylmethyl)methylamine (264.06 mg, 1.11 mmol, 1.00 eq) and trifluoroacetic acid (12.68 mg, 111.23 μmol, 0.10 eq) was added into a solution of Compound 62-d (470.00 mg, 1.11 mmol, 1.00 eq) in dichloromethane (20.00 mL). The reaction solution was stirred at 25° C. for 16 h. The reaction solution was concentrated under reduced pressure to give a crude product. The crude product was purified by flash column chromatography (petroleum ether:ethyl acetate=100:0-40:60) to give Compound 62-e.

MS m/z (ESI): 556.3 [M+1].

$^1$H NMR (400 MHz, CDCl$_3$) δ ppm 7.95 (d, J=7.2 Hz, 2H), 7.49 (d, J=7.6 Hz, 2H), 7.45-7.31 (m, 6H), 6.66 (s, 2H), 4.41-4.33 (m, 1H), 3.74-3.72 (m, 1H), 2.81-2.70 (m, 4H), 2.48-2.38 (m, 4H), 2.14 (s, 6H), 2.13-2.10 (m, 2H), 1.51 (s, 9H), 1.38 (s, 6H).

Step 5: Compound 62-f

Methyl phenyl chloroformate (394.42 mg, 2.52 mmol, 5.00 eq) was slowly added into a solution of Compound 62-e (280.00 mg, 503.82 μmol, 1.00 eq) in chloroform (30.00 mL). The reaction solution was stirred at 70° C. for 4 h. The reaction solution was concentrated under reduced pressure to give a crude product. The crude product was purified by flash column chromatography (petroleum ether:ethyl acetate=100:0-30:70) to give Compound 62-f.

MS m/z (ESI): 608.4 [M+23].

$^1$H NMR (400 MHz, CDCl$_3$) δ ppm 7.91-7.89 (m, 2H), 7.44-7.42 (m, 2H), 7.30-7.27 (m, 3H), 7.09-7.06 (m, 3H), 6.66 (d, J=7.2 Hz, 2H), 3.92-3.80 (m, 2H), 3.35-3.32 (m, 2H), 2.95-2.83 (m, 2H), 2.50-2.46 (m, 2H), 2.16 (s, 6H), 1.68-1.63 (m, 2H), 1.44 (s, 9H), 1.36 (s, 6H).

Step 6: Compound 62-g

At 20° C., trifluoroacetic acid (778.65 mg, 6.83 mmol, 505.62 μL, 40.00 eq) was added into a solution of Compound 62-f (100.00 mg, 170.73 μmol, 1.00 eq) in dichloromethane (20.00 mL). The mixture was stirred at 20° C. for 1 h. The reaction solution was concentrated to give a crude product. The crude product was purified by flash column chromatography (petroleum ether:ethyl acetate=100:0-60:40) to give Compound 62-g.

MS m/z (ESI): 530.4 [M+1].

Step 7: Compound 62

Compound 62-g (20.00 mg) was isolated by chiral supercritical chromatography to give Compound 62.

MS m/z (ESI): 530.1 [M+1].

$^1$H NMR (400 MHz, CDCl$_3$) δ ppm 7.96-7.76 (m, 1H), 7.57-7.15 (m, 5H), 7.03 (br d, J=11.54 Hz, 1H), 6.24 (s, 1H), 5.29-5.16 (m, 6H), 3.42 (s, 1H), 2.13-1.48 (m, 10H), 1.33 (br t, J=7.15 Hz, 1H), 1.21-1.17 (m, 6H).

Conditions of the chiral resolution: chiral column: Chiralpak AD-3 50*4.6 mm I.D., 3 μm; mobile phase: ethanol (0.05% DEA); flow rate: 4 mL/min; column temperature: 40° C.

Retention time of Compound 62: 1.651 min (peak 1).

Example 63: Compound 63

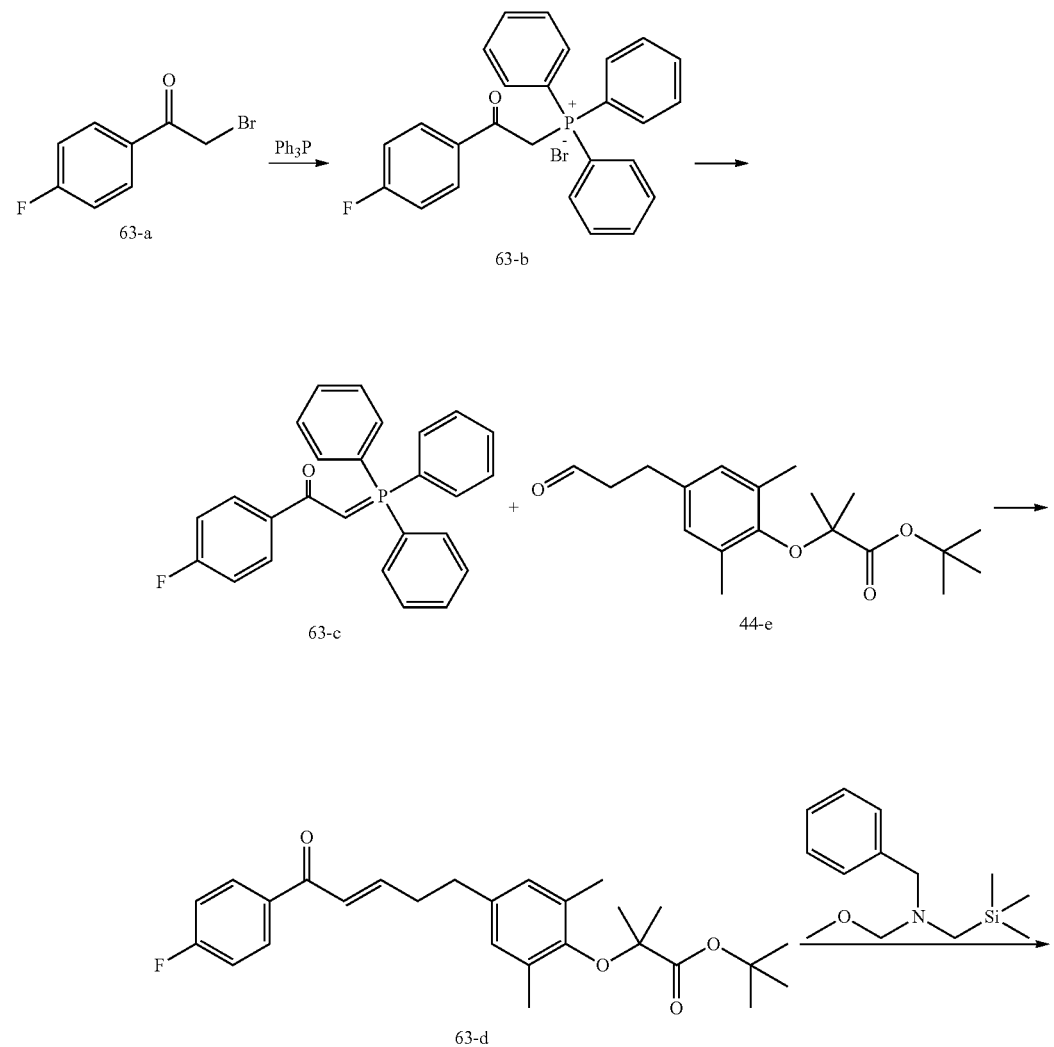

-continued
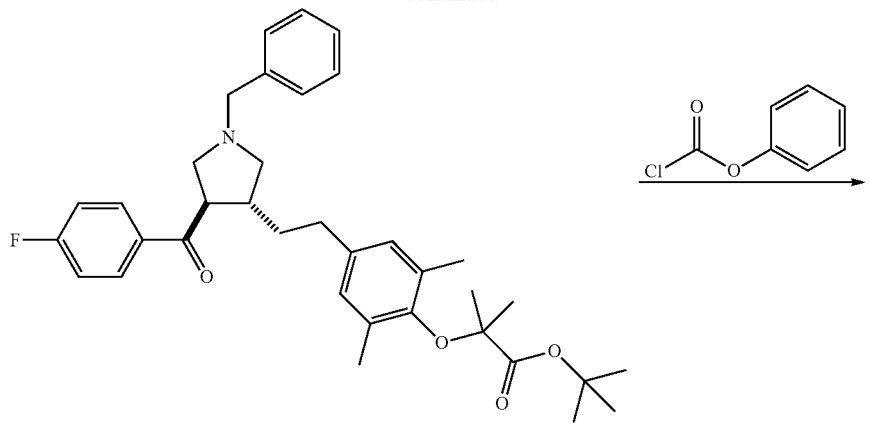
63-e
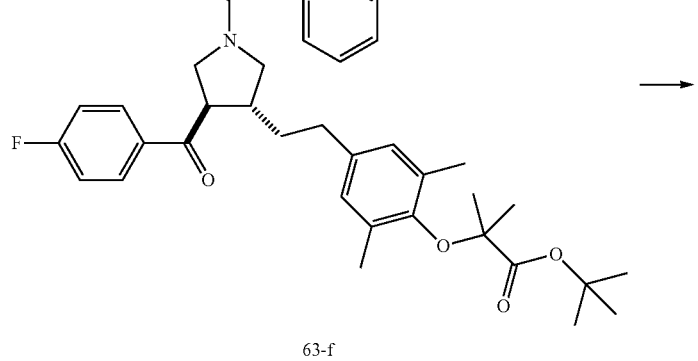
63-f
chiral separation
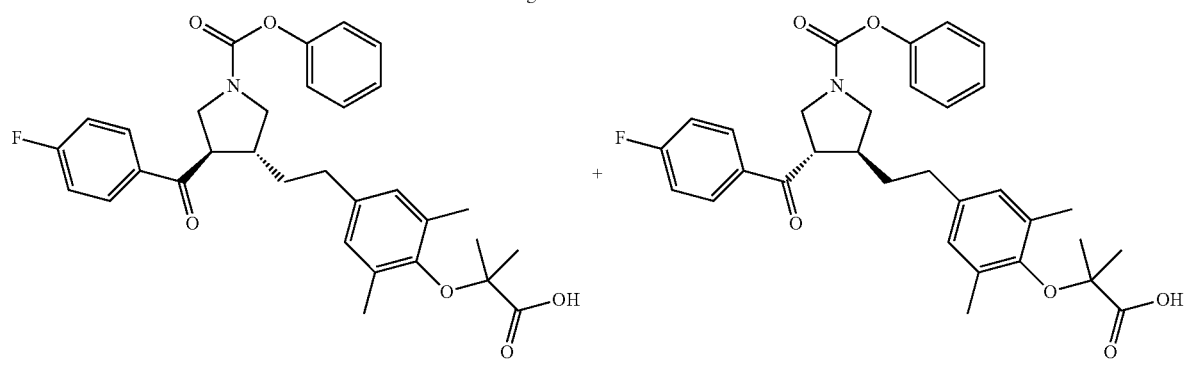
64-g
63-h or 63
63 or 63-h

Step 1: Compound 63-b

At 25° C., triphenylphosphine (60.43 g, 230.38 mmol, 1.00 eq) was added into a solution of Compound 63-a (50.00 g, 230.38 mmol, 1.00 eq) in toluene (300.00 mL). The mixture was stirred at 25° C. for 4 h. The reaction solution was filtered, and the filter cake was washed with dichloromethane (300 mL) and then dried under reduced pressure to give Compound 63-b.

MS m/z (ESI): 399.1 [M+1].

$^1$H NMR (400 MHz, CDCl$_3$) δ ppm 8.51 (dd, J=5.3, 8.8 Hz, 2H), 7.96 (dd, J=7.3, 13.3 Hz, 6H), 7.82-7.76 (m, 3H), 7.72-7.64 (m, 6H), 7.20 (t, J=8.5 Hz, 2H), 6.38 (d, J=12.0 Hz, 2H).

Step 2: Compound 63-c

At 20° C., potassium tert-butoxide (3.51 g, 31.29 mmol, 1.50 eq) was added into a solution of Compound 63-b (10.00 g, 20.86 mmol, 1.00 eq) in tetrahydrofuran (100.00 mL). The mixture was stirred at 20° C. for 0.5 h. The reaction solution was filtered, and the filtrate was extracted with ethyl acetate (100 mL×3). The organic phase was washed with water (100 mL), dried over anhydrous sodium sulfate, filtered, and concentrated under reduced pressure to give Compound 63-c.

MS m/z (ESI): 399.1 [M+1].

$^1$H NMR (400 MHz, CDCl$_3$) δ ppm 8.00-7.94 (m, 2H), 7.77-7.68 (m, 6H), 7.59-7.44 (m, 10H), 7.06-6.98 (m, 2H).

Step 3: Compound 63-d

At 50° C., Compound 44-e (1.00 g, 3.26 mmol, 1.00 eq) was slowly added into a solution of Compound 63-c (1.30 g, 3.26 mmol, 1.00 eq) in tetrahydrofuran (20.00 mL). Under nitrogen protection, the reaction solution was stirred at 50° C. for 16 h. The reaction solution was concentrated under reduced pressure a residue. The residue was purified by silica gel column chromatography (petroleum ether:ethyl acetate=70:1) to give Compound 63-d.

MS m/z (ESI): 463.2 [M+23].

$^1$H NMR (400 MHz, CDCl$_3$) δ ppm 7.85-7.80 (m, 2H), 7.07-7.02 (m, 2H), 6.73-6.69 (m, 4H), 2.78-2.73 (m, 2H), 2.55-2.48 (m, 2H), 2.13 (s, 6H), 1.43 (s, 9H), 1.34 (s, 6H)

Step 4: Compound 63-e

At 0° C., N-(methoxymethyl)-1-phenyl-N-(trimethylsilylmethyl)methylamine (538.93 mg, 2.27 mmol, 1.00 eq) and trifluoroacetic acid (258.83 mg, 2.27 mmol, 168.07 μL, 1.00 eq) was added into a solution of Compound 63-d (999.00 mg, 2.27 mmol, 1.00 eq) in dichloromethane (20.00 mL). The reaction solution was stirred at 25° C. for 16 h. The reaction solution was concentrated under reduced pressure to give a crude product. The crude product was purified by flash column chromatography (petroleum ether:ethyl acetate=100:0-70:30) to give Compound 63-e.

MS m/z (ESI): 574.3 [M+1].

$^1$H NMR (400 MHz, CDCl$_3$) δ ppm 8.04-7.98 (m, 2H), 7.45-7.42 (m, 5H), 7.21-7.16 (m, 1H), 7.18 (t, J=8.5 Hz, 1H), 6.63 (s, 2H), 4.37-4.30 (m, 1H), 4.28-4.22 (m, 1H), 3.92 (br s, 1H), 3.50 (br s, 1H), 3.15 (br s, 2H), 2.51-2.30 (m, 4H), 2.14 (s, 5H), 1.87 (br d, J=7.0 Hz, 1H), 1.92-1.85 (m, 1H), 1.52-1.50 (m, 9H), 1.38 (s, 6H)

Step 5: Compound 63-f

At 20° C., methyl phenyl chloroformate (559.43 mg, 3.57 mmol, 447.55 μL, 5.00 eq) was slowly added into a solution of Compound 63-e (410.00 mg, 714.61 μmol, 1.00 eq) in chloroform (30.00 mL). The reaction solution was stirred at 70° C. for 4 h. The reaction solution was concentrated under reduced pressure to give a crude product. The crude product was purified by flash column chromatography (petroleum ether:ethyl acetate=100:0-30:70) to give Compound 63-f.

MS m/z (ESI): 548.3 [M-56].

$^1$H NMR (400 MHz, DMSO-d$_6$) δ ppm 8.15 (dd, J=5.77, 7.78 Hz, 2H), 7.44-7.37 (m, 5H), 7.16 (br d, J=8.03 Hz, 2H), 6.82 (s, 2H), 4.14 (br dd, J=7.78, 15.81 Hz, 2H), 3.84-3.76 (m, 2H), 3.68-3.57 (m, 4H), 2.12 (s, 6H), 1.87-1.68 (m, 2H), 1.45 (d, J=1.51 Hz, 9H), 1.33 (d, J=5.02 Hz, 6H).

Step 6: Compound 63-g

At 25° C., trifluoroacetic acid (1.51 g, 13.25 mmol, 980.52 μL, 40.00 eq) was added into a solution of Compound 63-f (200.00 mg, 331.28 μmol, 1.00 eq) in dichloromethane (10.00 mL). The reaction solution was stirred at 25° C. for 4 h. The reaction solution was concentrated under reduced pressure to give a crude product. The crude product was purified by flash column chromatography (petroleum ether:ethyl acetate=100:0-40:60) to give Compound 63-g.

MS m/z (ESI): 548.3 [M+1].

Step 7: Compound 63

Compound 63-g (85 mg) was subjected to chiral separation to give Compound 63.

MS m/z (ESI): 548.0 [M+1].

$^1$H NMR (400 MHz, CDCl$_3$) δ ppm 8.01 (td, J=6.0, 8.7 Hz, 2H), 7.36 (q, J=8.0 Hz, 2H), 7.24-7.10 (m, 5H), 6.78 (br d, J=5.5 Hz, 2H), 4.02-3.93 (m, 1H), 3.57 (dd, J=8.0, 11.0 Hz, 1H), 3.39 (dd, J=8.0, 10.5 Hz, 1H), 3.23-3.18 (m, 1H), 2.83 (br dd, J=7.8, 13.3 Hz, 1H), 2.73 (td, J=4.4, 8.3 Hz, 1H), 2.55 (br t, J=7.8 Hz, 2H), 2.20 (br d, J=3.5 Hz, 6H), 1.92-1.81 (m, 1H), 1.75-1.64 (m, 1H), 1.55-1.41 (m, 6H).

Conditions of the chiral resolution: chiral column: Lux Cellulose-2 150×4.6 mm I.D., 3 μm; mobile phase: 40% of methanol (0.05% DEA) in CO$_2$; flow rate: 2.5 mL/min; column temperature: 40° C.

Retention time of Compound 63: 3.626 min (peak 1).

Example 64: Compound 64
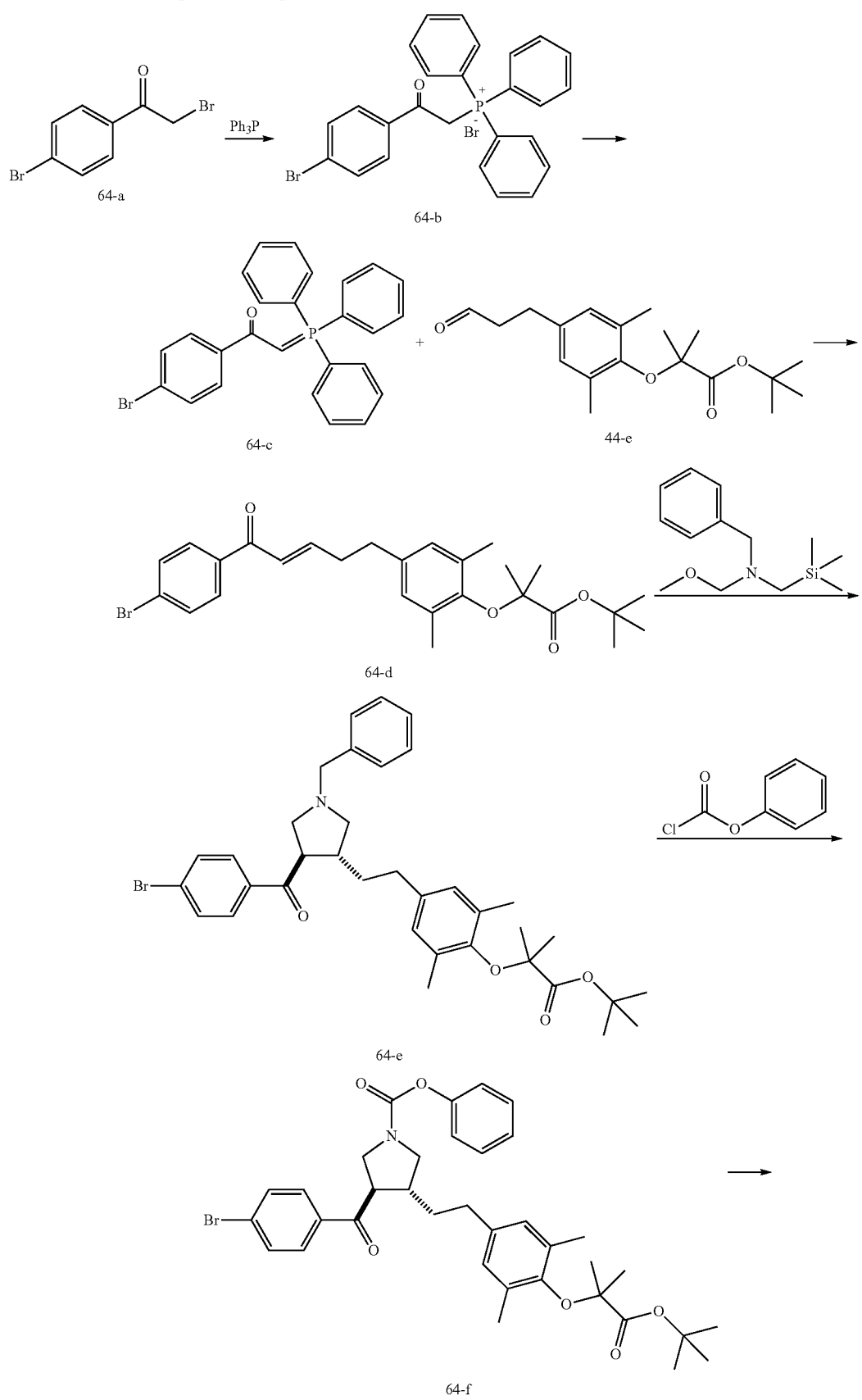

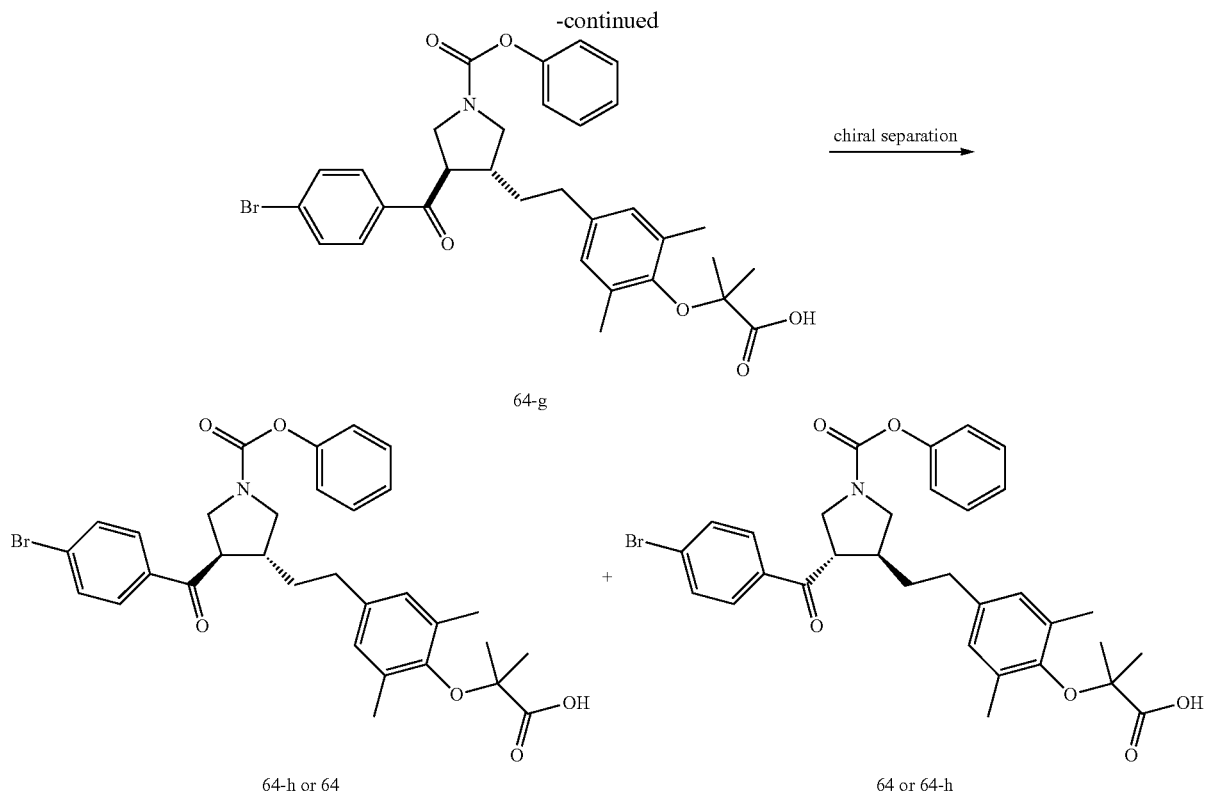

64-g chiral separation →

64-h or 64

+

64 or 64-h

Step 1

Compound 64-b

At 25° C., triphenylphosphine (49.54 g, 188.88 mmol, 1.05 eq) was added into a solution of Compound 64-a (50.00 g, 179.89 mmol, 1.00 eq) in toluene (500.00 mL). The reaction solution was stirred at 25° C. for 12 h. The reaction solution was filtered, and the filter cake was washed with dichloromethane (200 mL), and then dried under reduced pressure to give Compound 64-b.

MS m/z (ESI): 461 [M+1].

$^1$H NMR (400 MHz, CDCl$_3$) δ ppm 8.01 (d, J=8.5 Hz, 2H), 7.88-7.84 (m, 11H), 7.82-7.76 (m, 6H), 6.23 (d, J=13.1 Hz, 2H).

Step 2: Compound 64-c

At 20° C., potassium tert-butoxide (3.12 g, 27.77 mmol, 1.50 eq) was added into a solution of Compound 64-b (10.00 g, 18.51 mmol, 1.00 eq) in tetrahydrofuran (100.00 mL). The reaction solution was stirred at 20° C. for 0.5 h. The reaction solution was extracted with ethyl acetate (100 mL×3). The combined organic phase was washed with saturated brine (200 mL), dried over anhydrous sodium sulfate, filtered, and concentrated under reduced pressure to give Compound 64-C.

$^1$H NMR (400 MHz, CDCl$_3$) δ ppm 7.90-7.77 (m, 4H), 7.73-7.68 (m, 4H), 7.59-7.54 (m, 4H), 7.51-7.45 (m, 8H).

Step 3: Compound 64-d

At 50° C., Compound 44-e (1.00 g, 3.12 mmol, 1.00 eq) was slowly added into a solution of Compound 64-c (1.43 g, 3.12 mmol, 1.00 eq) in tetrahydrofuran (20.00 mL). The reaction solution was stirred at 50° C. for 24 h. The reaction solution was concentrated under reduced pressure to give a crude product. The crude product was purified by flash column chromatography (petroleum ether:ethyl acetate=100:0-90:10) to give Compound 64-d.

$^1$H NMR (400 MHz, CDCl$_3$) δ ppm 7.79-7.72 (m, 2H), 7.61 (d, J=8.5 Hz, 2H), 6.84-6.81 (m, 2H), 6.80-6.79 (m, 2H), 2.87-2.85 (m, 2H), 2.74-2.72 (m, 2H), 2.22 (s, 6H), 1.53 (s, 9H), 1.44 (s, 6H).

Step 4: Compound 64-e

At 0° C., N-(methoxymethyl)-1-phenyl-N-(trimethylsilyl-methyl)methylamine (467.22 mg, 1.97 mmol, 1.20 eq) and trifluoroacetic acid (187.00 mg, 1.64 mmol, 121.43 µL, 1.00 eq) was added into a solution of Compound 64-d (824.00 mg, 1.64 mmol, 1.00 eq) in dichloromethane (20.00 mL). The reaction solution was stirred at 25° C. for 16 h. The reaction solution was concentrated under reduced pressure to give a crude product which was purified by flash column chromatography (petroleum ether:ethyl acetate=100:0-20:80) to give Compound 64-e.

$^1$H NMR (400 MHz, CDCl$_3$) δ ppm 7.81 (br d, J=8.3 Hz, 2H), 7.65 (d, J=8.5 Hz, 2H), 7.45-7.40 (m, 5H), 6.62 (s, 2H), 4.35-4.23 (m, 2H), 3.16 (br s, 2H), 2.66 (br s, 2H), 2.47-2.35 (m, 4H), 2.13 (s, 6H), 1.94-1.83 (m, 2H), 1.50 (s, 9H), 1.37 (d, J=3.0 Hz, 6H).

Step 5: Compound 64-f

At 25° C., phenyl chloroformate (356.49 mg, 2.28 mmol, 285.19 µL, 5.00 eq) was added into a solution of Compound 64-e (289.00 mg, 455.38 µmol, 1.00 eq) in chloroform (20.00 mL). The reaction solution was heated to 70° C. and stirred for 48 h. The reaction solution was concentrated under reduced pressure to give a crude product which was purified by flash column chromatography (petroleum ether: ethyl acetate=100:0-40:60) to give Compound 64-f.

$^1$H NMR (400 MHz, CDCl$_3$) δ ppm 7.78-7.72 (m, 2H), 7.57 (dd, J=3.0, 8.5 Hz, 2H), 7.30 (br d, J=2.0 Hz, 2H), 7.11-7.03 (m, 3H), 6.66 (d, J=6.5 Hz, 2H), 3.85-3.55 (m, 4H), 3.40-3.25 (m, 1H), 2.76-2.58 (m, 1H), 2.56-2.36 (m, 2H), 2.12 (s, 6H), 1.79-1.62 (m, 2H), 1.44 (s, 9H), 1.36-1.33 (m, 6H).

Step 6: Compound 64-g

At 25° C., trifluoroacetic acid (686.22 mg, 6.02 mmol, 445.60 µL, 40.00 eq) was added into a solution of Compound 64-f (100.00 mg, 150.46 µmol, 1.00 eq) in dichloromethane (10.00 mL). The reaction solution was stirred at 25° C. for 1 h. The reaction solution was concentrated under reduced pressure to give a crude product which was purified by flash column chromatography (petroleum ether:ethyl acetate=100:0-40:60) to give Compound 64-g.

MS m/z (ESI): 610.1 [M+1].

Step 7: Compound 64

Compound 64-g (85.00 mg, 155.22 µmol, 1.00 eq) was subjected to chiral separation to give Compound 64.

MS m/z (ESI): 610.0 [M+1].

$^1$H NMR (400 MHz, CDCl$_3$) δ ppm 7.86-7.78 (m, 2H), 7.64 (dd, J=5.3, 8.3 Hz, 2H), 7.35 (q, J=8.0 Hz, 2H), 7.23-7.17 (m, 1H), 7.12 (br t, J=8.8 Hz, 2H), 6.77 (d, J=5.5 Hz, 2H), 4.02-3.88 (m, 2H), 3.81-3.67 (m, 2H), 3.43-3.34 (m, 1H), 3.23-3.15 (m, 1H), 2.54 (br t, J=7.8 Hz, 2H), 2.19 (d, J=5.0 Hz, 6H), 1.86 (br d, J=7.5 Hz, 2H), 1.50 (d, J=17.6 Hz, 6H).

Conditions of the chiral resolution: chiral column: AD (250 mm×30 mm, 5 um); mobile phase: 0.1% NH$_3$H$_2$O IPA; flow rate: 60 mL/min; column temperature: 40° C.

Retention time of Compound 64: 1.915 min (peak 1).

Examples 65 and 66: Compounds 65 and 66

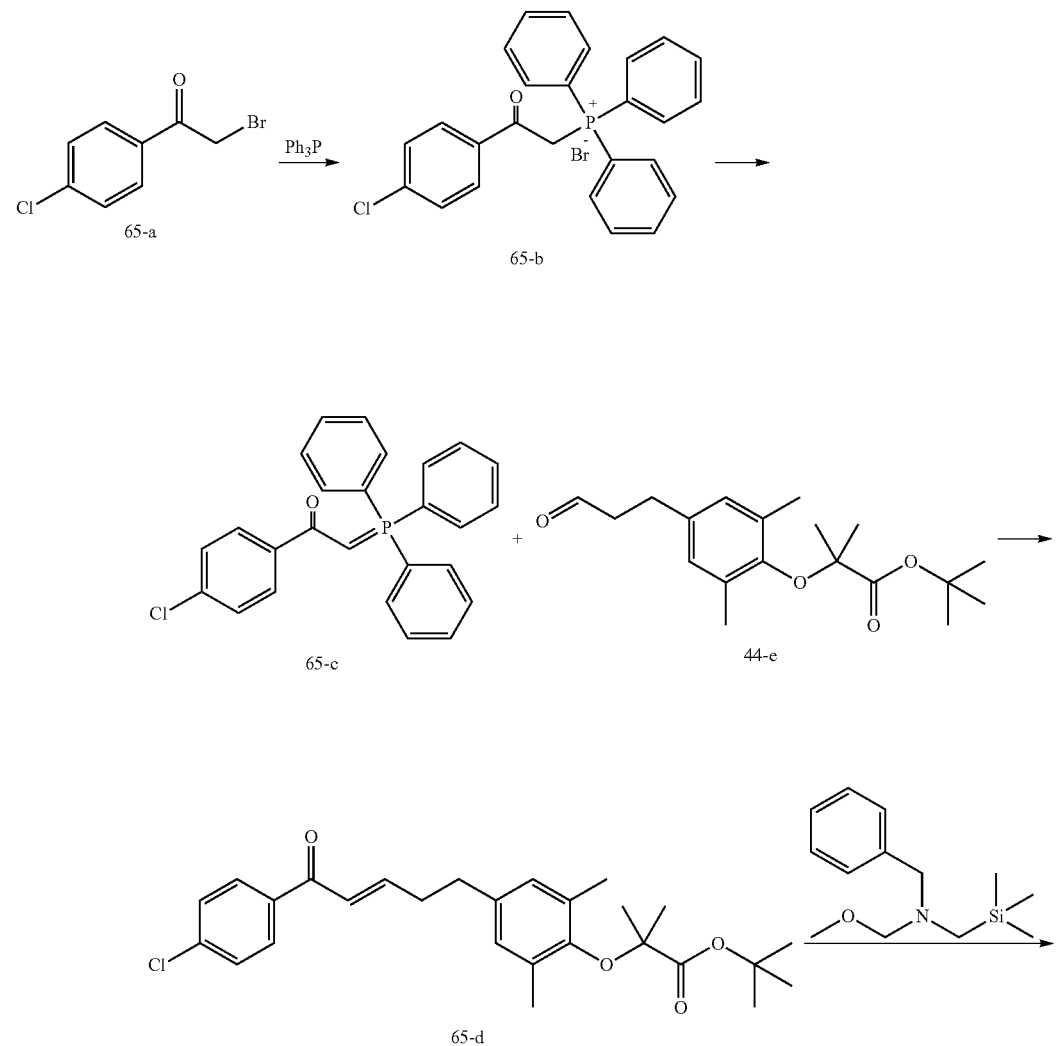

205                                    206
-continued
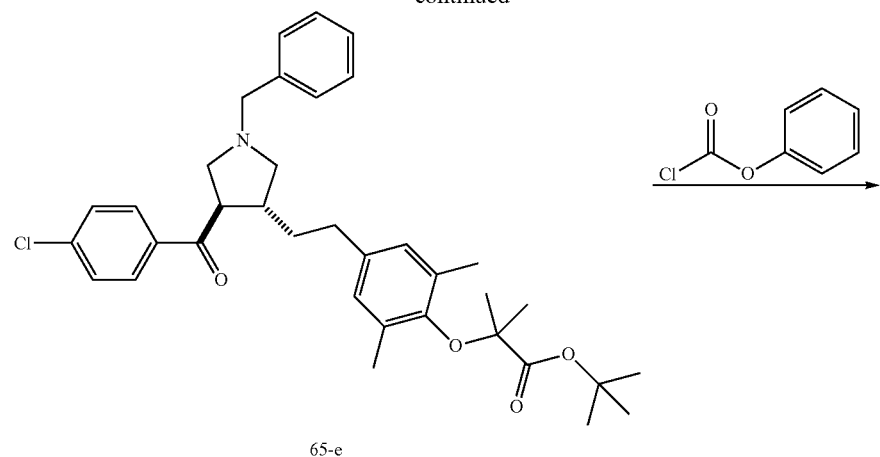
65-e
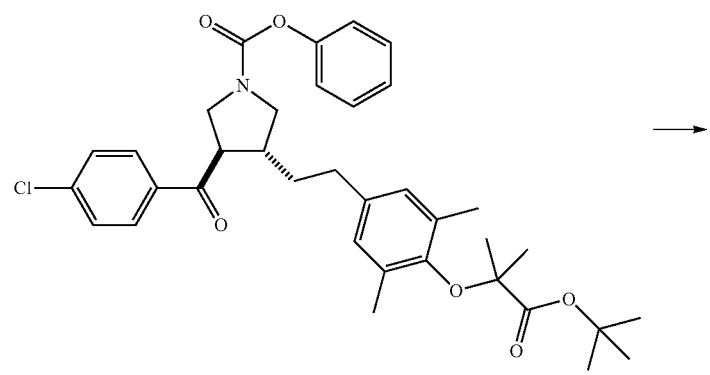
65-f
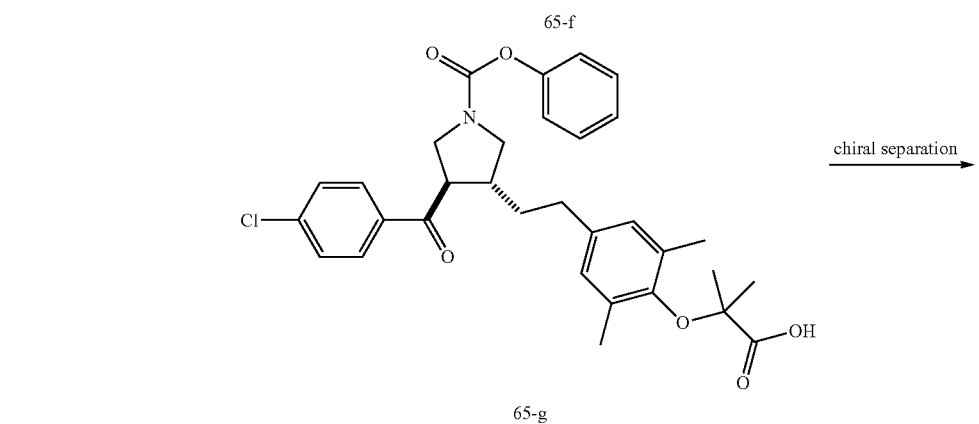
65-g
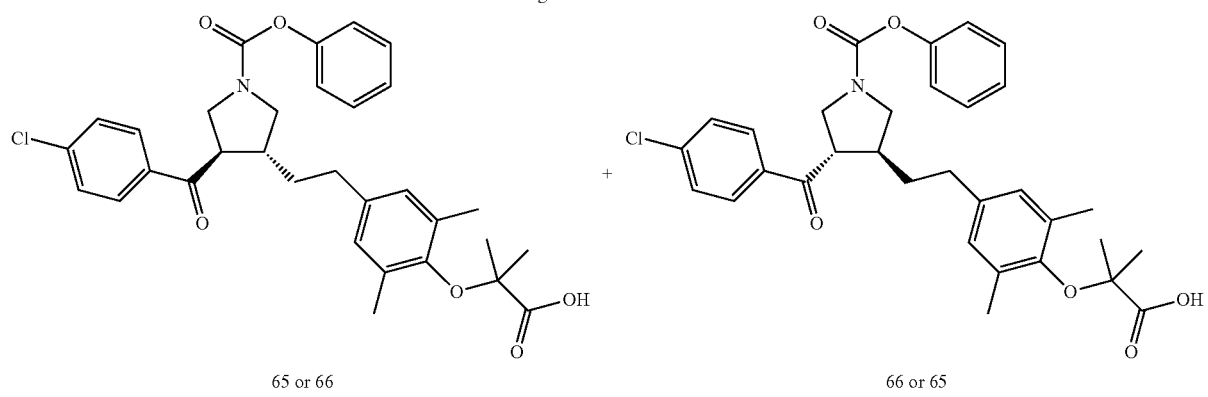
65 or 66                                    66 or 65

Step 1: Compound 65-b

At 25° C., triphenylphosphine (58.97 g, 224.85 mmol, 1.05 eq) was added into a solution of Compound 65-a (50.00 g, 214.14 mmol, 1.00 eq) in toluene (500.00 mL). The reaction solution was stirred at 25° C. for 48 h under nitrogen protection. The reaction solution was filtered, and the filter cake was washed with dichloromethane (200 mL), and dried under reduced pressure to give Compound 65-b.

MS m/z (ESI): 415.0 [M+1].

$^1$H NMR (400 MHz, DMSO-$d_6$) δ ppm 8.10 (d, J=8.8 Hz, 2H), 7.91-7.81 (m, 9H), 7.80-7.74 (m, 6H), 7.72 (d, J=8.8 Hz, 2H), 6.20 (d, J=13.1 Hz, 2H).

Step 2: Compound 65-c

At 20° C., potassium tert-butoxide (3.40 g, 30.26 mmol, 1.50 eq) was added into a solution of Compound 65-b (10.00 g, 20.17 mmol, 1.00 eq) in tetrahydrofuran (100.00 mL). The reaction solution was stirred at 20° C. for 0.5 h. The reaction solution was extracted with ethyl acetate (100 mL×3). The organic phases were combined and washed with saturated brine, dried over anhydrous sodium sulfate, filtered, and concentrated under reduced pressure to give Compound 65-c.

$^1$H NMR (400 MHz, CDCl$_3$) δ ppm 7.92-7.87 (m, 2H), 7.84-7.76 (m, 2H), 7.74-7.67 (m, 6H), 7.57-7.54 (m, 2H), 7.51-7.48 (m, 6H), 7.33-7.29 (m, 2H).

Step 3: Compound 65-d

At 50° C., Compound 44-e (1.00 g, 3.12 mmol, 1.00 eq) was slowly added into a solution of Compound 65-c (1.29 g, 3.12 mmol, 1.00 eq) in tetrahydrofuran (20.00 mL). The reaction solution was stirred at 50° C. for 24 h. The reaction solution was concentrated under reduced pressure to give a crude product which was purified by flash column chromatography (petroleum ether:ethyl acetate=100:0-90:10) to give Compound 65-d.

$^1$H NMR (400 MHz, CDCl$_3$) δ ppm 7.76-7.71 (m, 2H), 7.35 (d, J=8.5 Hz, 2H), 6.77-6.74 (m, 2H), 6.72 (s, 2H), 2.78-2.76 (m, 2H), 2.68-2.67 (m, 2H), 2.13 (s, 6H), 1.44 (s, 9H), 1.35 (s, 6H)

Step 4: Compound 65-e

At 0° C., N-(methoxymethyl)-1-phenyl-N-(trimethylsilylmethyl)methylamine (441.99 mg, 1.86 mmol, 1.20 eq) and trifluoroacetic acid (176.89 mg, 1.55 mmol, 114.87 μL, 1.00 eq) was added into a solution of Compound 65-d (709.00 mg, 1.55 mmol, 1.00 eq) in dichloromethane (20.00 mL). The reaction solution was warmed to 25° C. and stirred for 16 h. The reaction solution was concentrated under reduced pressure to give a crude product which was purified by flash column chromatography (petroleum ether:ethyl acetate=100:0-20:80) to give Compound 65-e.

$^1$H NMR (400 MHz, CDCl$_3$) δ ppm 7.89 (br d, J=8.3 Hz, 2H), 7.49-7.42 (m, 7H), 6.62 (s, 2H), 4.38-4.22 (m, 2H), 3.15 (br d, J=8.8 Hz, 2H), 2.67 (br s, 2H), 2.50-2.28 (m, 4H), 2.13 (s, 4H), 2.14-2.11 (m, 1H), 2.14-2.11 (m, 1H), 1.93-1.82 (m, 2H), 1.50 (s, 9H), 1.37 (s, 6 h).

Step 5: Compound 65-f

At 25° C., phenyl chloroformate (332.94 mg, 2.13 mmol, 266.35 μL, 5.00 eq) was added into a solution of Compound 65-e (251.00 mg, 425.29 μmol, 1.00 eq) in chloroform (20.00 mL). The reaction solution was warmed to 70° C. and stirred for 48 h. The reaction solution was concentrated under reduced pressure to give a crude product which was purified by flash column chromatography (petroleum ether: ethyl acetate=100:0-40:60) to give Compound 65-f.

MS m/z (ESI): 642.4 [M+1].

Step 6: Compound 65-g

At 25° C., trifluoroacetic acid (588.33 mg, 5.16 mmol, 382.03 μL, 40.00 eq) was added into a solution of Compound 65-f (80.00 mg, 129.00 μmol, 1.00 eq) in dichloromethane (10.00 mL). The reaction solution was stirred at 25° C. for 1 h. The reaction solution was concentrated under reduced pressure to give a crude product which was purified by flash column chromatography (petroleum ether:ethyl acetate=100:0-50:50) to give Compound 65-g.

MS m/z (ESI): 564.1 [M+1].

Step 7: Compounds 65 and 66

Compound 65-g (60.00 mg, 106.37 μmol, 1.00 eq) was subjected to chiral separation to give Compound 65 and Compound 66.

Compound 65:

MS m/z (ESI): 564.1 [M+1].

$^1$H NMR (400 MHz, CDCl$_3$) δ ppm 7.90 (dd, J=6.0, 8.5 Hz, 2H), 7.48 (dd, J=5.5, 8.5 Hz, 2H), 7.40-7.31 (m, 2H), 7.20 (q, J=7.5 Hz, 1H), 7.12 (br t, J=8.8 Hz, 2H), 6.77 (d, J=6.0 Hz, 2H), 4.03-3.89 (m, 2H), 3.81-3.65 (m, 2H), 3.41-3.35 (m, 1H), 3.22-3.15 (m, 1H), 2.54 (br t, J=7.5 Hz, 2H), 2.19 (d, J=5.0 Hz, 6H), 1.90-1.81 (m, 2H), 1.50 (d, J=17.6 Hz, 6H).

Compound 66:

MS m/z (ESI): 564.1 [M+1].

$^1$H NMR (400 MHz, CDCl$_3$) δ ppm 7.90 (dd, J=6.0, 8.5 Hz, 2H), 7.48 (dd, J=5.0, 8.5 Hz, 2H), 7.35 (q, J=8.0 Hz, 2H), 7.19 (q, J=7.4 Hz, 1H), 7.12 (t, J=8.8 Hz, 2H), 6.77 (d, J=5.5 Hz, 2H), 4.04-3.89 (m, 2H), 3.80-3.64 (m, 2H), 3.38 (dd, J=7.8, 10.8 Hz, 1H), 3.19 (dd, J=8.0, 11.0 Hz, 1H), 2.60-2.48 (m, 2H), 2.19 (d, J=5.0 Hz, 6H), 1.91-1.80 (m, 2H), 1.49 (d, J=16.6 Hz, 6H).

Conditions of the chiral resolution: chiral column: AD (250 mm×30 mm, 5 um); mobile phase: 0.1% NH$_3$H$_2$O IPA; flow rate: 60 mL/min; column temperature: 40° C.

Retention time of Compound 65: 1.835 min (peak 1). Retention time of Compound 66: 1.905 min (peak 2).

Example 67: Compound 67

Example 68: Compound 68

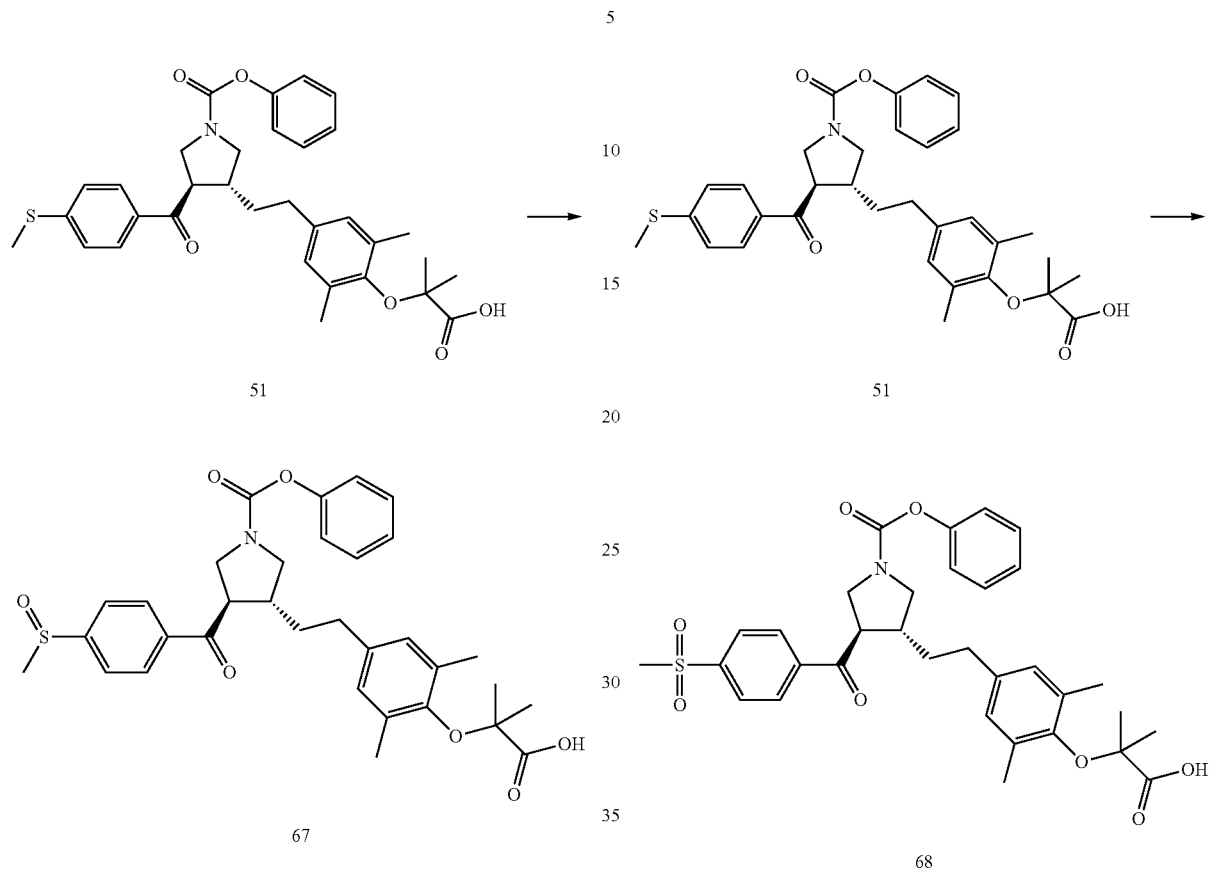

Step 1: Compound 67

Compound 51 (50.00 mg, 86.85 μmol, 1.00 eq) and chloroform (5.00 mL) was added into a dried reaction flask. The mixture was cooled to 0° C. in an ice-water bath, and then m-chloroperbenzoic acid (14.11 mg, 69.48 μmol, 0.80 eq) was slowly added. After removing the ice-water bath, the mixture was naturally warmed to 20° C., and stirred for 1 h. A saturated solution of sodium thiosulfate was added dropwise into the reaction system, which was monitored with potassium iodide test paper until the test paper did not change color. Then, the mixture was extracted with ethyl acetate (20 mL). The organic phases were collected, dried over anhydrous sodium sulfate, filtered, and concentrated to give a crude product. The crude product was purified with preparative High Performance Liquid Chromatography to give Compound 67.

MS m/z (ESI): 592.2 [M+1].

$^1$H NMR (400 MHz, CDCl$_3$) δ ppm 8.00-7.92 (m, 2H), 7.71 (t, J=8.5 Hz, 2H), 7.40-7.33 (m, 2H), 7.24-7.17 (m, 1H), 7.14 (br dd, J=5.5, 7.0 Hz, 2H), 6.78-6.72 (m, 2H), 3.99-3.61 (m, 4H), 3.44 (ddd, J=3.8, 6.9, 10.9 Hz, 0.5H), 3.34-3.26 (m, 0.5H), 2.83-2.79 (m, 3H), 2.68-2.61 (m, 1H), 2.56-2.45 (m, 1H), 2.21-2.11 (m, 6H), 1.93-1.78 (m, 2H), 1.57-1.41 (m, 6H).

Step 1: Compound 68

Compound 51 (50.00 mg, 86.85 μmol, 1.00 eq) and chloroform (5.00 mL) was added into a dried reaction flask. Then, m-chloroperbenzoic acid (35.26 mg, 173.70 μmol, 2.00 eq) was slowly added. The mixture was stirred at 20° C. for additional 1 h. A saturated solution of sodium thiosulfate was added dropwise to the reaction system, which was monitored with potassium iodide test paper until the test paper did not change color. Then, the mixture was extracted with ethyl acetate (3×20 mL). The organic phases were collected, and dried over anhydrous sodium sulfate, filtered, and concentrated to give a crude product. The crude product was purified by preparative High Performance Liquid Chromatography to give Compound 68.

MS m/z (ESI): 608.2 [M+1].

$^1$H NMR (400 MHz, CDCl$_3$) δ ppm 8.05 (d, J=4.5 Hz, 4H), 7.36 (q, J=7.5 Hz, 2H), 7.24-7.17 (m, 1H), 7.13 (t, J=7.8 Hz, 2H), 6.77 (d, J=3.5 Hz, 2H), 4.02-3.91 (m, 1H), 3.85-3.70 (m, 2.5H), 3.59 (dd, J=7.5, 11.0 Hz, 0.5H), 3.43 (dd, J=7.5, 10.5 Hz, 0.5H), 3.28 (dd, J=8.0, 11.0 Hz, 0.5H), 3.10 (s, 3H), 2.87-2.68 (m, 1H), 2.59-2.49 (m, 1H), 2.17 (d, J=4.5 Hz, 6H), 1.93-1.72 (m, 2H), 1.48 (d, J=13.6 Hz, 6H).

Example 69: Compound 69
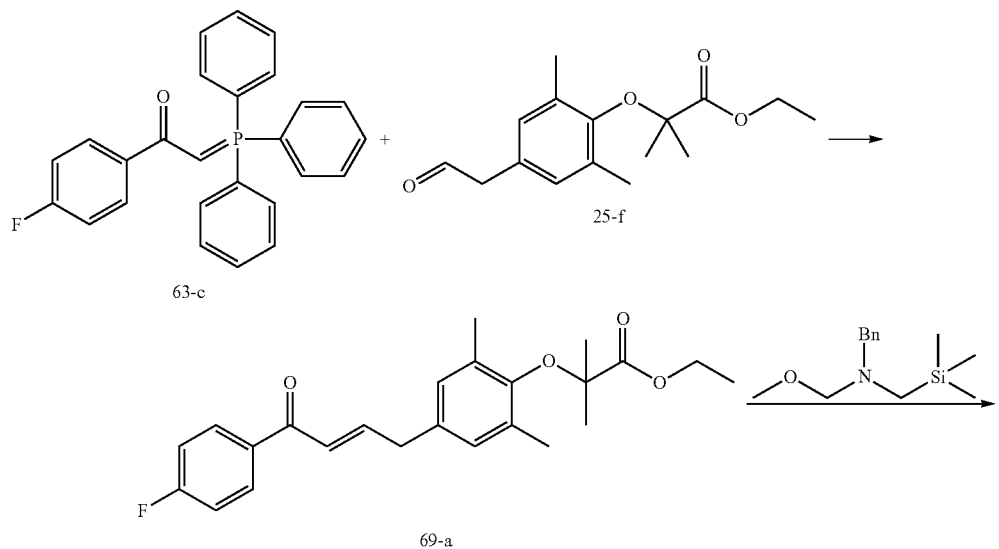
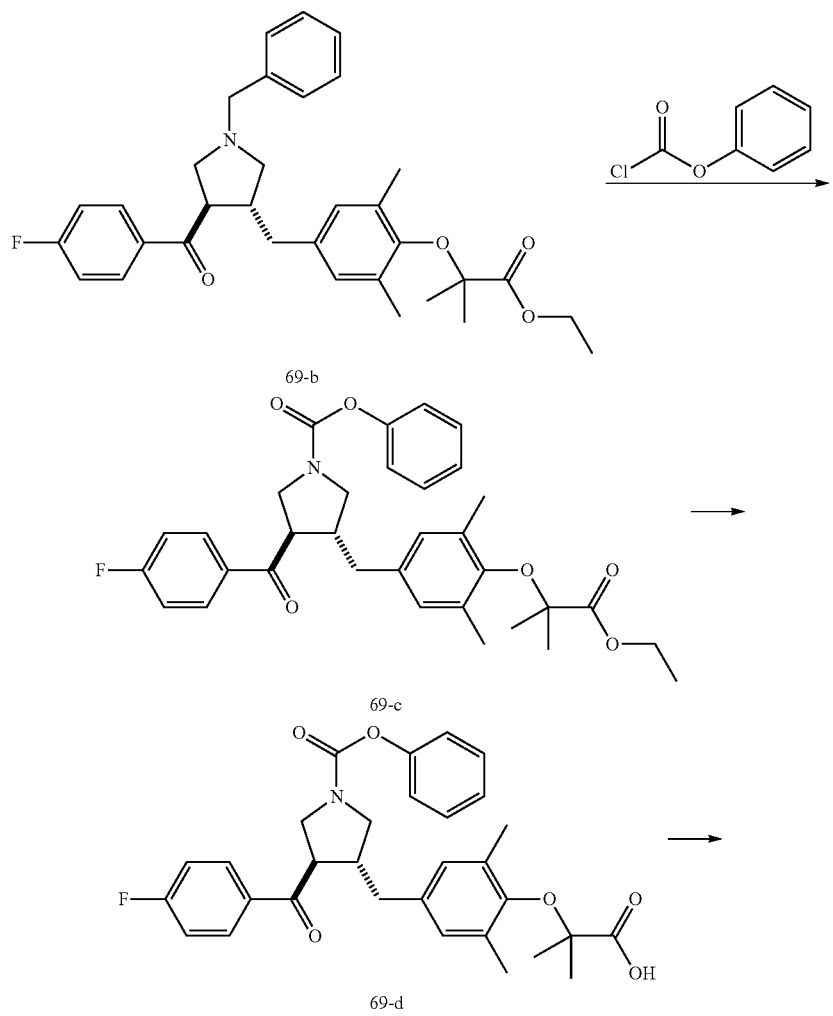

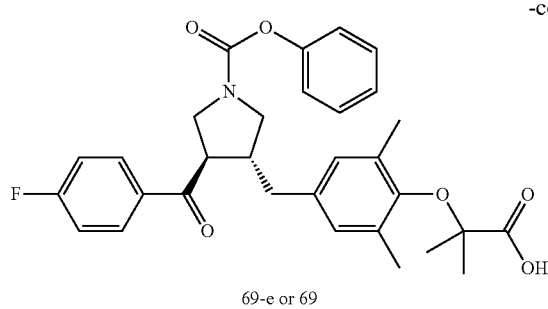

69-e or 69

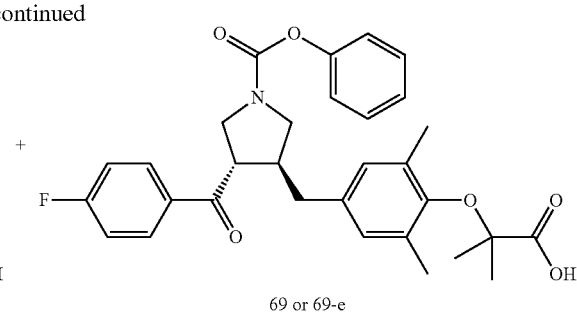

69 or 69-e

Step 1: Compound 69-a

Compound 25-f (8.70 g, 31.26 mmol, 1.00 eq) and tetrahydrofuran (100.00 mL) was added into a pre-dried flask of 250 mL. And then 63-c (12.45 g, 31.26 mmol, 1.00 eq) was added into the reaction system. The mixture was stirred at 50° C. for 16 h. The reaction mixture was concentrated under reduced pressure to give a residue. The residue was purified by flash column chromatography (petroleum ether:ethyl acetate=100:0-20:80) to give pure Compound 69-a.

$^1$H NMR (400 MHz, CDCl$_3$) δ ppm 7.96-7.92 (m, 2H), 7.17-7.11 (m, 3H), 7.01 (s, 1H), 6.81 (s, 2H), 4.37-4.34 (m, 2H), 3.52 (dd, J=1.0, 6.8 Hz, 2H), 2.19 (s, 6H), 1.48-1.47 (m, 6H), 1.38-1.36 (m, 3H).

Step 2: Compound 69-b

Compound 69-a (3.30 g, 8.28 mmol, 1.00 eq) and dioxane (100.00 mL) was added into a pre-dried flask of 1000 mL, purged with nitrogen gas three times followed by adding trifluoroacetic acid (83.01 mg, 728.00 µmol, 53.90 µL, 0.05 eq). Subsequently, the resulted clear reaction solution was heated and stirred at 80° C. for 5 min, and then a solution of N-(methoxymethyl)-1-phenyl-N-(trimethylsilylmethyl) methylamine (5.90 g, 24.84 mmol, 3.00 eq) in dioxane (10.00 mL) was slowly added, while keeping the reaction system at 80° C. After 30 min the feeding was completed, the reaction system was stirred at 80° C. for 1 h. The reaction system was cooled to room temperature, and concentrated under reduced pressure to give a residue. The crude product was purified by flash column chromatography (petroleum ether:ethyl acetate=100:0-20:80) to give the product, pure Compound 69-b.

$^1$H NMR (400 MHz, CDCl$_3$) δ ppm 7.75 (dd, J=5.5, 9.0 Hz, 2H), 7.23-7.12 (m, 5H), 7.02-6.94 (m, 2H), 6.64 (s, 2H), 4.19 (q, J=7.4 Hz, 2H), 3.63-3.54 (m, 2H), 3.04-2.94 (m, 2H), 2.66-2.61 (m, 2H), 2.17-2.06 (m, 2H), 2.01-1.98 (m, 6H), 1.60-1.52 (m, 2H), 1.36 (s, 6H), 0.84-0.77 (m, 3H).

Step 3: Compound 69-c

Compound 69-b (1.53 g, 2.88 mmol, 1.00 eq) and chloroform (10.00 mL) was added into a pre-dried round-bottom flask of 50 mL. Then, phenyl chloroformate (2.25 g, 14.39 mmol, 1.80 mL, 5.00 eq) was added. Under nitrogen protection, the reaction vessel was placed in an oil bath at 70° C., and stirred for 6 h. The reaction system was cooled to room temperature, and concentrated under reduced pressure to give a residue. The crude product was purified by flash column chromatography (petroleum ether:ethyl acetate=100:0-90:10) to give the product, pure Compound 69-c.

$^1$H NMR (400 MHz, CDCl$_3$) δ ppm 7.76 (td, J=5.9, 8.3 Hz, 2H), 7.38-7.34 (m, 2H), 7.21-7.07 (m, 5H), 6.79 (s, 2H), 4.30 (q, J=7.0 Hz, 2H), 3.97-3.83 (m, 2H), 3.77-3.62 (m, 2H), 3.51-3.36 (m, 1H), 2.97-2.83 (m, 1H), 2.73-2.60 (m, 2H), 2.17 (s, 6H), 1.47 (s, 6H), 1.37 (t, J=6.8 Hz, 3H)

Step 4: Compound 69-d

Compound 69-c (1.24 g, 2.21 mmol, 1.00 eq) was added into a pre-dried flask of 100 mL, and then was dissolved by adding ethanol (9.00 mL) and water (3.00 mL). Subsequently, lithium hydroxide (925.35 mg, 38.64 mmol, 17.50 eq) was added into the reaction system, and the mixture was stirred at 40° C. for 16 h. A saturated aqueous solution of potassium bisulfate was added dropwise to the reaction system until pH=5-6. Then the mixture was extracted with ethyl acetate (3×10 mL). The organic phases were combined, and successively washed with water (20 mL) and saturated brine (20 mL), dried over anhydrous sodium sulfate, and concentrated under reduced pressure to give a residue. The residue was purified by flash column chromatography (petroleum ether:ethyl acetate=100:0-50:50) to give a crude product. The crude product was purified by preparative High Performance Liquid Chromatography to give Compound 69-d.

MS m/z (ESI): 534.3 [M+1].

Step 5: Compound 69

Compound 69-d (145.00 mg, 271.74 mmol, 1.00 eq) was isolated by chiral supercritical chromatography to give Compound 70.

MS m/z (ESI): 534.3 [M+1].

$^1$H NMR (400 MHz, CDCl$_3$) δ ppm 7.75 (dd, J=5.5, 8.5 Hz, 2H), 7.32-7.25 (m, 2H), 7.16-7.00 (m, 5H), 6.75 (d, J=5.0 Hz, 2H), 3.95-3.81 (m, 1H), 3.79-3.64 (m, 2H), 3.59 (br dd, J=7.5, 11.0 Hz, 1H), 3.42-3.26 (m, 1H), 2.96-2.82 (m, 1H), 2.69-2.55 (m, 2H), 2.12 (d, J=3.0 Hz, 6H), 1.43 (s, 6H).

Chiral Analysis Conditions: chiral column: AS (250 mm×30 mm, 10 µm); mobile phase: 0.1% NH$_3$H$_2$O EtOH; flow rate: 80 mL/min; column temperature: 40° C.

Retention time of Compound 70: 3.561 min (peak 1).

Example 70: Compound 70
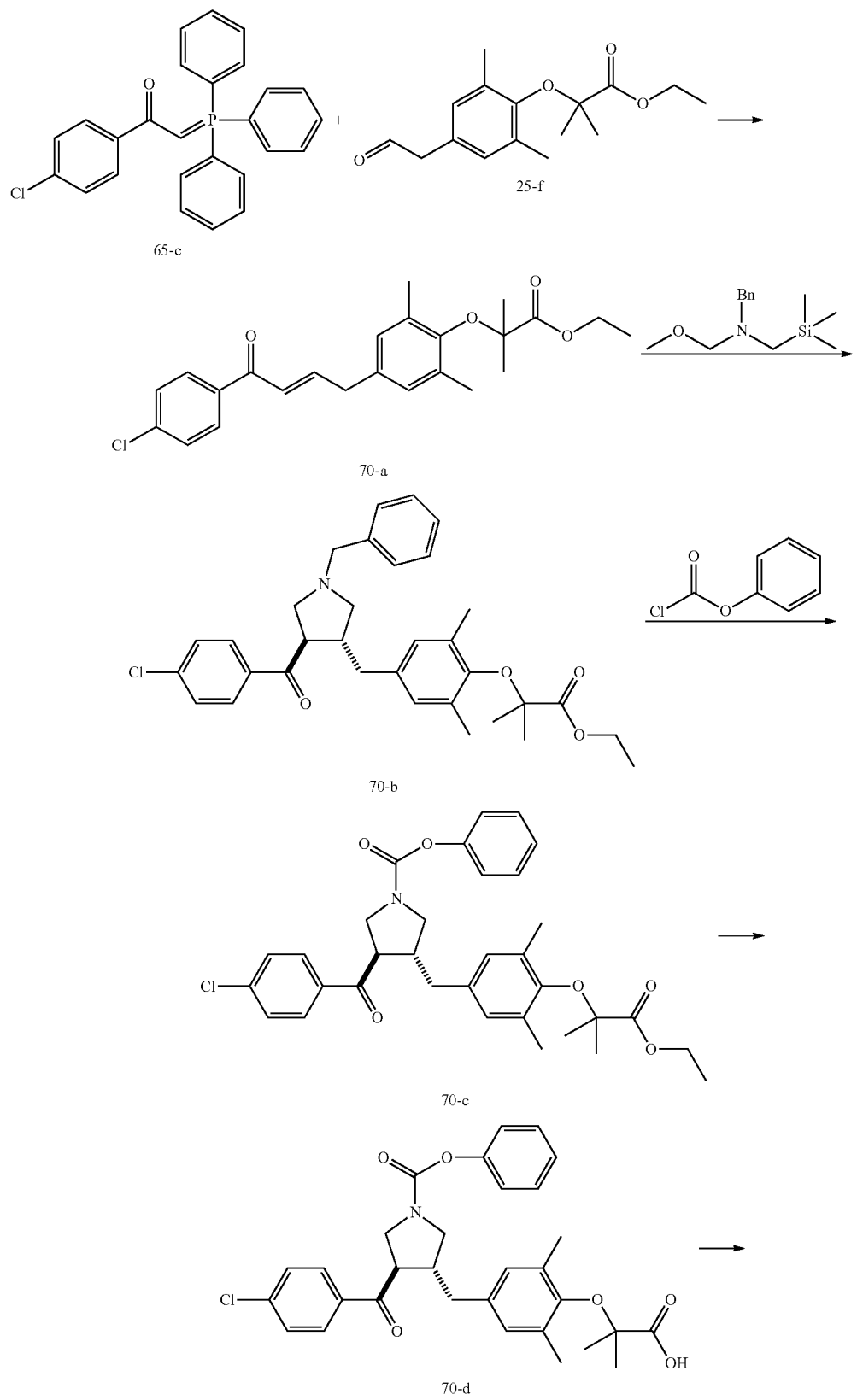

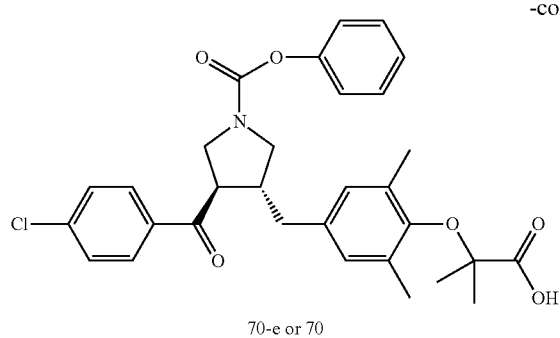

70-e or 70

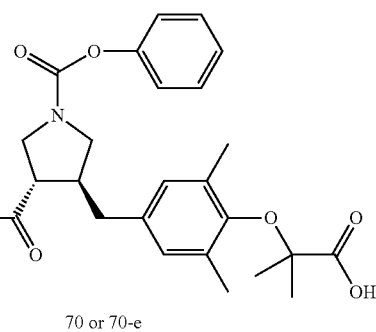

70 or 70-e

Step 1: Compound 70-a

Compound 25-f (18.00 g, 64.67 mmol, 1.00 eq) and tetrahydrofuran (100.00 mL) was added into a pre-dried flask of 250 mL. Then, 65-c (26.83 g, 64.67 mmol, 1.00 eq) was added into the reaction system, and the mixture was stirred at 50° C. for 16 h. The reaction mixture was concentrated under reduced pressure to give a residue. The residue was purified by flash column chromatography (petroleum ether:ethyl acetate=100:0-90:10) to give Compound 70-a.

$^1$H NMR (400 MHz, CDCl$_3$) δ ppm 7.86 (d, J=8.5 Hz, 2H), 7.44 (d, J=8.5 Hz, 2H), 7.28 (s, 0.5H), 7.24-7.15 (m, 1H), 7.02 (s, 0.5H), 6.82 (s, 2H), 4.41-4.35 (m, 2H), 3.53 (d, J=6.5 Hz, 2H), 2.20 (s, 6H), 1.49 (s, 6H), 1.39-1.37 (m, 3H).

Step 2: Compound 70-b

Compound 70-a (4.00 g, 9.64 mmol, 1.00 eq) and dioxane (120.00 mL) was added into a dried flask, and then trifluoroacetic acid (83.01 mg, 728.00 μmol, 53.90 μL, 0.05 eq) was added. The solution was heated and stirred at 80° C. for 5 min, followed by slowly adding dropwise a solution of N-(methoxymethyl)-1-phenyl-N-(trimethylsilylmethyl)methylamine (6.87 g, 28.92 mmol, 3.00 eq) in dioxane (120.00 mL). After the completion of the feeding, the reaction mixture was stirred at 80° C. for 1 h. The reaction mixture was concentrated under reduced pressure. The crude product was purified by flash column chromatography (petroleum ether:ethyl acetate=100:0-90:10) to give Compound 70-b.

$^1$H NMR (400 MHz, CDCl$_3$) δ ppm 7.66 (d, J=8.5 Hz, 2H), 7.26-7.23 (m, 7H), 6.63 (s, 2H), 4.22-4.18 (m, 2H), 3.71-3.61 (m, 2H), 3.54-3.44 (m, 2H), 3.05-2.96 (m, 2H), 2.69-2.59 (m, 2H), 2.11 (d, J=12.0 Hz, 2H), 2.02-1.97 (m, 6H), 1.41-1.34 (m, 6H), 0.93-0.75 (m, 3H)

Step 3: Compound 70-c

Compound 70-b (1.00 g, 1.82 mmol, 1.00 eq) and chloroform (10.00 mL) was added into a pre-dried round-bottom flask of 50 mL. Then, phenyl chloroformate (1.43 g, 9.12 mmol, 1.14 mL, 5.00 eq) was added. Under nitrogen protection, the reaction vessel was placed in an oil bath at 70° C., and stirred for 6 h. The reaction system was cooled to room temperature, and concentrated under reduced pressure to give a residue. The crude product was purified by flash column chromatography (petroleum ether:ethyl acetate=100:0-90:10) to give Compound 70-c.

$^1$H NMR (400 MHz, CDCl$_3$) δ ppm 7.68 (dd, J=6.3, 8.3 Hz, 2H), 7.43-7.35 (m, 4H), 7.25-7.13 (m, 3H), 6.80 (s, 2H), 4.32 (q, J=7.0 Hz, 2H), 3.98-3.68 (m, 4H), 3.52-3.38 (m, 1H), 2.98-2.84 (m, 1H), 2.75-2.63 (m, 2H), 2.20-2.16 (m, 6H), 1.59 (d, J=1.0 Hz, 6H), 1.42-1.35 (m, 3H).

Step 4: Compound 70-d

Compound 70-c (560.00 mg, 968.69 μmol, 1.00 eq) was added into a dried flask, and then was dissolved by adding ethanol (6.00 mL) and water (2.00 mL). Subsequently, lithium hydroxide (406.46 mg, 16.97 mmol, 17.52 eq) was added into the reaction system, and the mixture was stirred at 40° C. for 16 h. A saturated aqueous solution of potassium bisulfate was added dropwise to the reaction system until pH=5-6. Then the mixture was extracted with ethyl acetate (3×10 mL). The organic phases were combined, and successively washed with water (20 mL) and saturated brine (20 mL), dried over anhydrous sodium sulfate, and concentrated under reduced pressure to give a residue. The residue was purified by flash column chromatography (petroleum ether:ethyl acetate=100:0-50:50) to give a crude product. The crude product was purified by preparative High Performance Liquid Chromatography to give Compound 70-d.

MS m/z (ESI): 550.3 [M+1].

Step 5: Compound 70

Compound 70-d (100.00 mg, 181.80 μmol, 1.00 eq) was isolated by chiral supercritical chromatography to give Compound 70.

MS m/z (ESI): 572.3 [M+23].

$^1$H NMR (400 MHz, CDCl$_3$) δ ppm 7.66 (d, J=8.5 Hz, 2H), 7.34 (d, J=8.5 Hz, 2H), 7.32-7.26 (m, 2H), 7.16-7.09 (m, 1H), 7.06 (br d, J=7.5 Hz, 2H), 6.75 (d, J=5.0 Hz, 2H), 3.95-3.82 (m, 1H), 3.76-3.65 (m, 2H), 3.60 (br dd, J=7.0, 11.0 Hz, 1H), 3.39-3.27 (m, 1H), 2.94-2.81 (m, 1H), 2.65-2.57 (m, 2H), 2.12 (d, J=3.0 Hz, 6H), 1.43 (s, 6H).

Chiral Analysis Conditions: chiral column: AS (250 mm×30 mm, 10 μm); mobile phase: 0.1% NH$_3$H$_2$O EtOH; flow rate: 80 mL/min; column temperature: 40° C.

Retention time of Compound 70: 3.827 min (peak 1).

Example 71: Compound 71
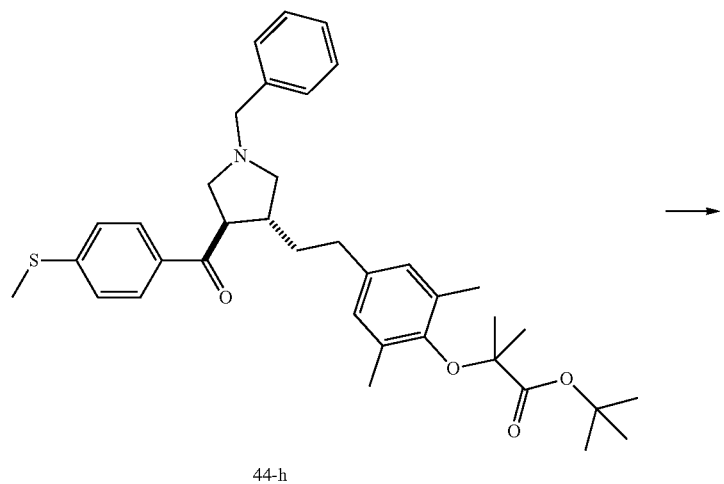
44-h
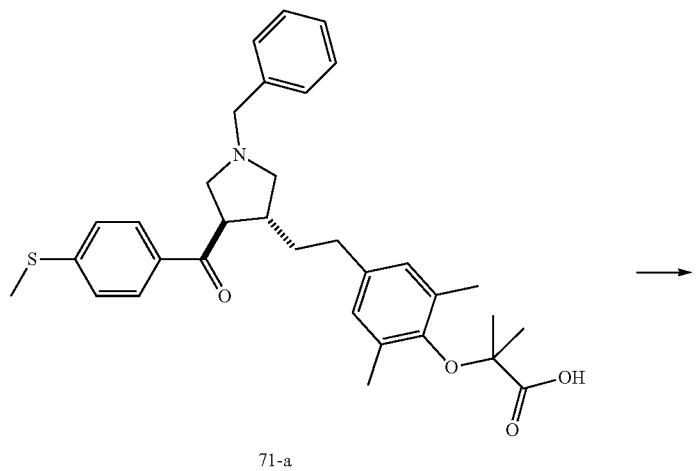
71-a
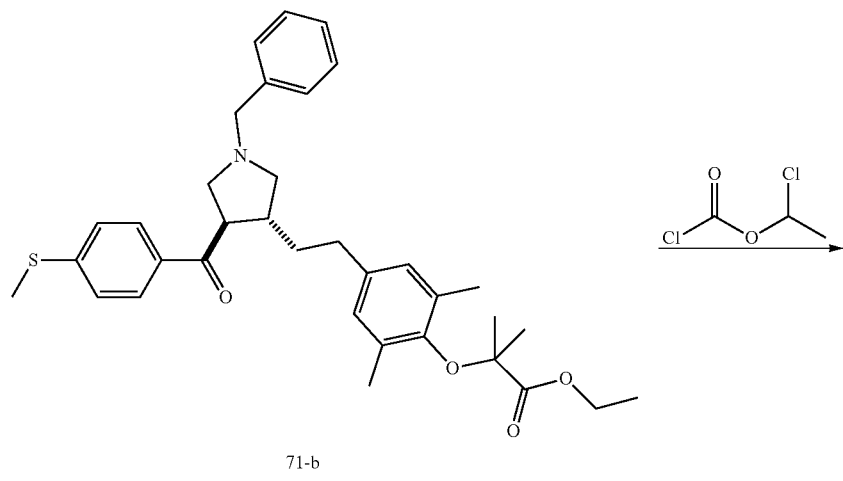
71-b

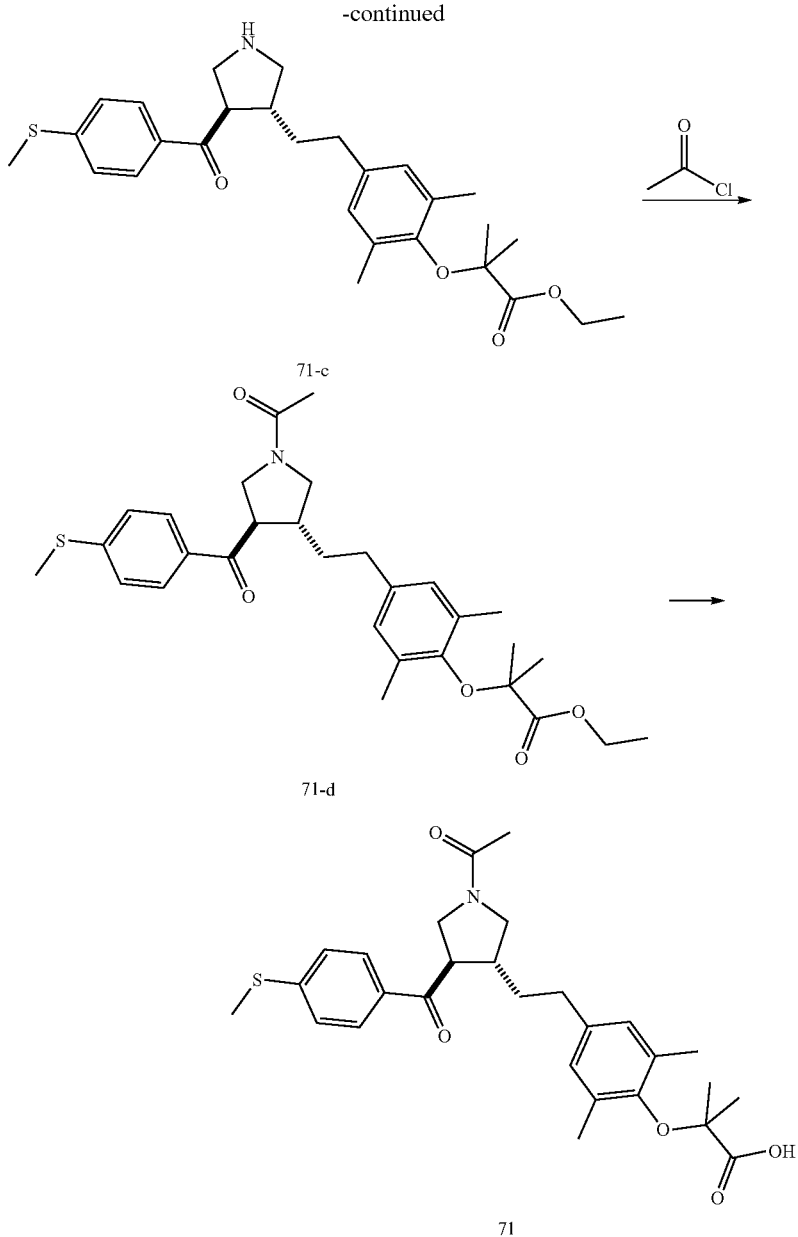

Step 1: Compound 71-a

Compound 44-h (5.00 g, 8.31 mmol, 1.00 eq), trifluoroacetic acid (9.47 g, 83.08 mmol, 6.15 mL, 10.00 eq) and dichloromethane (50.00 mL) was added into a dried round-bottom flask, and the resulted clear solution was stirred at 20° C. for 3 h. The reaction solution was concentrated under reduced pressure. The residue was isolated by flash column chromatography (petroleum ether:ethyl acetate=100:0-10:90) to give Compound 71-a.

MS m/z (ESI): 546.3 [M+1].

$^1$H NMR (400 MHz, CDCl$_3$) δ ppm 7.87 (d, J=8.4 Hz, 2H), 7.49-7.42 (m, 6H), 7.31 (s, 1H), 6.69 (s, 2H), 4.46-4.22 (m, 2H), 3.89 (s, 1H), 3.46 (s, 1H), 3.17-3.10 (m, 2H), 2.72-2.70 (m, 1H), 2.54 (s, 3H), 2.48-2.44 (m, 2H), 2.17 (s, 6H), 1.92-1.87 (m, 2H), 1.51 (s, 6H).

Step 2: Compound 71-b 71-a (4.10 g, 7.51 mmol, 1.00 eq), oxalyl chloride (9.53 g, 75.10 mmol, 6.57 mL, 10.00 eq) and dichloromethane (40.00 mL) was added into a dried round-bottom flask, and the resulted clear solution was stirred at 20° C. for 1 h. The reaction system was concentrated under reduced pressure, and then ethanol (20.00 mL) was added. The solution was stirred at 20° C. for 1 h. A saturated aqueous solution of sodium carbonate was added dropwise into the reaction system until pH=8-9. The reaction system was extracted with ethyl acetate (100 mL) and water (100 mL). After phase separation, the organic phases were collected, and dried over anhydrous sodium sulfate, and concentrated under reduced pressure to give Compound 71-b.

MS m/z (ESI): 574.3 [M+1].

$^1$H NMR (400 MHz, CDCl$_3$) δ ppm 7.85 (t, J=8.4 Hz, 2H), 7.31-7.22 (m, 7H), 6.68 (s, 2H), 4.31-4.24 (m, 2H), 3.59-3.53 (m, 2H), 2.99-2.65 (m, 4H), 2.51 (s, 3H), 2.49-2.39 (m, 3H), 2.11 (s, 6H), 1.76-1.74 (m, 3H), 1.42 (s, 6H), 1.34 (t, J=7.2 Hz, 3H).

Step 3: Compound 71-c

At 20° C., α-chloroethyl chloroformate (7.48 g, 52.30 mmol, 10.00 eq), Compound 71-b (3.00 g, 5.23 mmol, 1.00 eq) and anhydrous toluene (30.00 mL) was added into a pre-dried round-bottom flask of 100 mL, and the mixture was stirred at 80° C. for 16 h. The reaction solution was concentrated under reduced pressure, and was added with methanol (30.00 mL) and stirred at 80° C. for hours. The reaction solution was concentrated under reduced pressure. The residue was purified by flash column chromatography (petroleum ether:ethyl acetate=100:0-10:90) to give Compound 71-c.

MS m/z (ESI): 484.2 [M+1].

$^1$H NMR (400 MHz, CDCl$_3$) δ ppm 7.84 (d, J=4.8 Hz, 2H), 7.28-7.25 (m, 2H), 6.66 (d, J=12.8 Hz, 2H), 4.29-4.24 (m, 2H), 3.89-3.51 (m, 4H), 3.18-3.02 (m, 1H), 2.53 (s, 1H), 2.49-2.46 (m, 2H), 2.12-2.08 (d, J=7.5 Hz, 6H), 1.40-1.32 (d, J=4.8 Hz, 6H).

Step 4: Compound 71-d

At 20° C., Compound 71-c (100.00 mg, 206.76 μmol, 1.00 eq) was added into a pre-dried round-bottom flask of 100 mL, and then acetylchloride (12.98 mg, 165.41 mol, 11.80 μL, 0.80 eq) and triethylamine (20.92 mg, 206.76 μmol, 28.66 μL, 1.00 eq) were added. The reaction system produced a substantial amount of white smoke. The reaction solution was stirred at 20° C. for 3 h. The reaction solution was concentrated under reduced pressure to give a crude product. The crude product was purified by flash column chromatography (dichloromethane:methanol=100:0-30:70) to give Compound 71-d.

MS m/z (ESI): 526.3 [M+1].

Step 5: Compound 71

71-d (50.00 mg, 95.11 μmol, 1.00 eq), and then ethanol (6.00 mL) were added into a pre-dried flask of 50 mL. Next, lithium hydroxide (22.78 mg, 951.10 μmol, 10.00 eq) and water (2.00 mL) were added into the reaction system. The reaction solution was stirred at 40° C. for 16 h. A saturated aqueous solution of potassium bisulfate was added dropwise to the reaction system until pH=6. The reaction mixture was extracted with ethyl acetate and water (1:1, 20 mL). After phase separation, the organic phases were collected, and the aqueous phase was extracted with ethyl acetate (3×10 mL). The organic phases were combined and dried over anhydrous sodium sulfate, and concentrated under reduced pressure to give a residue. The residue was purified by thin layer chromatography (dichloromethane:methanol=10:1) to give a crude product which was further purified by preparative High Performance Liquid Chromatography to give Compound 71.

MS m/z (ESI): 498.3 [M+1].

$^1$H NMR (400 MHz, CDCl$_3$) δ ppm 7.85 (br d, J=4.8 Hz, 2H), 7.30 (br d, J=8.3 Hz, 2H), 6.75 (br d, J=10.8 Hz, 2H), 3.83-3.70 (m, 3H), 3.50 (br s, 2H), 2.54 (d, J=6.0 Hz, 3H), 2.46 (br s, 3H), 2.20 (br d, J=16.8 Hz, 6H), 2.02 (br s, 3H), 1.83 (br s, 2H), 1.64-1.41 (m, 6H).

Example 72: Compound 72

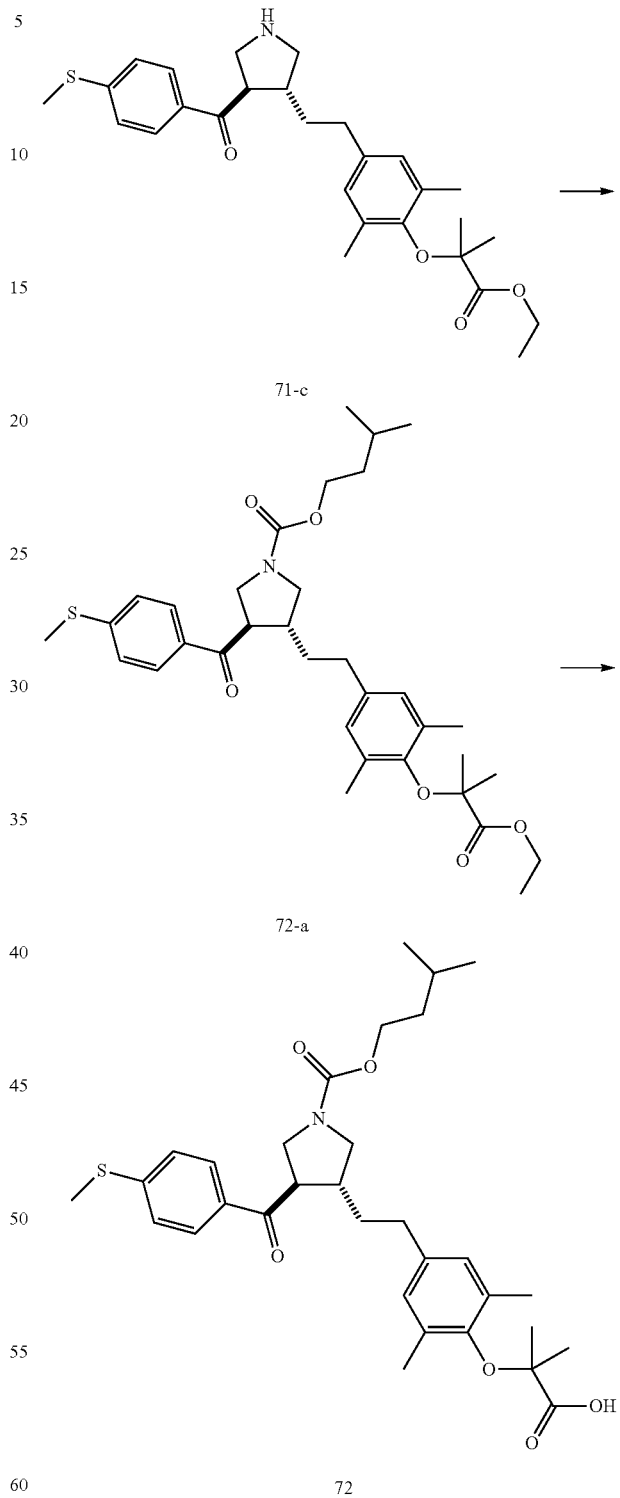

71-c 72-a

72

Step 1: Compound 72-a

Iso-pentyl chloroformate (31.14 mg, 206.76 μmol, 1.00 eq) and triethylamine (41.84 mg, 413.52 μmol, 57.32 μL, 2.00 eq) was added into a solution of Compound 71-c (100.00 mg, 206.76 mol, 1.00 eq) in dichloromethane (10.00 mL) The resulted clear solution was stirred at 20° C. for 1 h. The reaction solution was concentrated under reduced pressure. The residue was isolated and purified by flash column chromatography (petroleum ether:ethyl acetate=100:0-50:50) to give Compound 72-a.

Step 2: Compound 72

Lithium hydroxide (20.03 mg, 836.40 µmol, 10.00 eq) and water (2.00 mL) was added into a solution of Compound 72-a (50.00 mg, 83.64 µmol, 1.00 eq) in ethanol solution (6.00 mL). The mixed solution was stirred at 40° C. for 16 h. The mixture was adjusted with a saturated aqueous solution of potassium bisulfate to pH=6, and treated by water and ethyl acetate (1:1, 20 mL). The aqueous phase was extracted with ethyl acetate (10 mL×3). The combined organic phase was dried over anhydrous sodium sulfate, filtered, and concentrated under reduced pressure to give a residue. The residue was purified by silica gel column chromatography (dichloromethane:methanol=10/1) to give a crude product which further was isolated by High Performance Liquid Chromatography to give Compound 72.

MS m/z (ESI): 570.4 [M+1].

$^1$H NMR (400 MHz, CDCl$_3$) δ ppm 7.88-7.84 (m, 2H), 7.30 (br s, 2H), 6.74 (br s, 2H), 3.96 (br s, 2H), 3.77-3.62 (m, 4H), 2.98 (br d, J=9.3 Hz, 1H), 2.54 (s, 3H), 2.50 (br s, 2H), 2.19 (br d, J=13.1 Hz, 6H), 2.03 (br s, 2H), 1.53 (br s, 6H), 1.45 (br s, 4H), 0.89 (br d, J=3.8 Hz, 6H)

Example 73: Compound 73

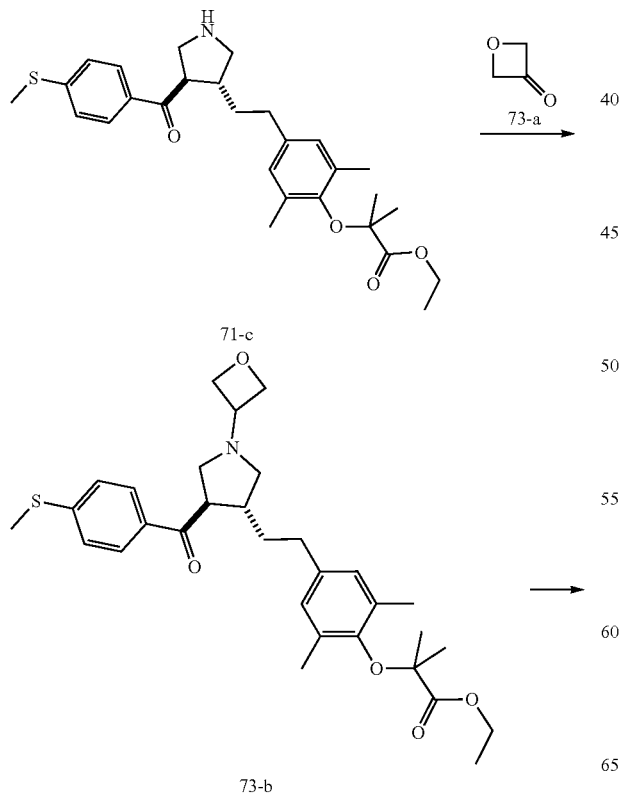

71-c 73-b

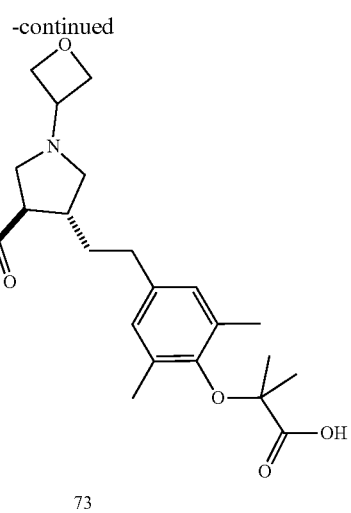

73

Step 1: Compound 73-b 73-a (22.35 mg, 310.14 µmol, 1.50 eq) and acetic acid (1.24 mg, 20.68 µmol, 1.18 µL, 0.10 eq) was added into a solution of Compound 71-c (100.00 mg, 206.76 µmol, 1.00 eq) in methanol (10.00 mL). The resulted clear solution was stirred at 20° C. for 1 h. Then, sodium cyanoborohydride (19.49 mg, 310.14 µmol, 1.50 eq) was added into the reaction system and stirred at 20° C. for 16 h. The reaction solution was concentrated under reduced pressure. The residue was isolated and purified by flash column chromatography (petroleum ether:ethyl acetate=100:0-10:90) to give Compound 73-b.

MS m/z (ESI): 540.3 [M+1].

Step 2: Compound 73

Lithium hydroxide (124.25 mg, 5.19 mmol, 20.00 eq) was added into a mixed solution of Compound 73-b (140.00 mg, 259.39 µmol, 1.00 eq) in ethanol (10.00 mL) and water (5.00 mL). The resulted clear solution was stirred at 50° C. for 16 h. An 1N aqueous HCl solution was added dropwise to the reaction system until pH=6. The reaction system was diluted with 10 mL ethyl acetate/10 mL water. After phase separation, the organic phases were collected, and the aqueous phase was extracted with ethyl acetate (10 mL×3). The organic phases were combined and dried over anhydrous sodium sulfate, and concentrated under reduced pressure to give a residue. The residue was purified by thin-layer chromatography silica gel plate (dichloromethane:methanol=10:1) to give a colorless oil crude product. The crude product was isolated and purified by preparative High Performance Liquid Chromatography to give Compound 73.

MS m/z (ESI): 512.3 [M+1].

$^1$H NMR (400 MHz, CDCl$_3$) δ ppm 7.92 (d, J=8.5 Hz, 2H), 7.29 (d, J=8.5 Hz, 2H), 6.72 (s, 2H), 4.79-4.71 (m, 4H), 3.97 (br s, 1H), 3.83 (br s, 1H), 3.54 (br s, 1H), 2.96 (br s, 1H), 2.84 (br s, 2H), 2.71-2.61 (m, 1H), 2.53 (s, 3H), 2.41-2.33 (m, 1H), 2.17 (s, 6H), 1.81 (br d, J=5.3 Hz, 3H), 1.48 (d, J=8.8 Hz, 6H)

Example 74: Compound 74

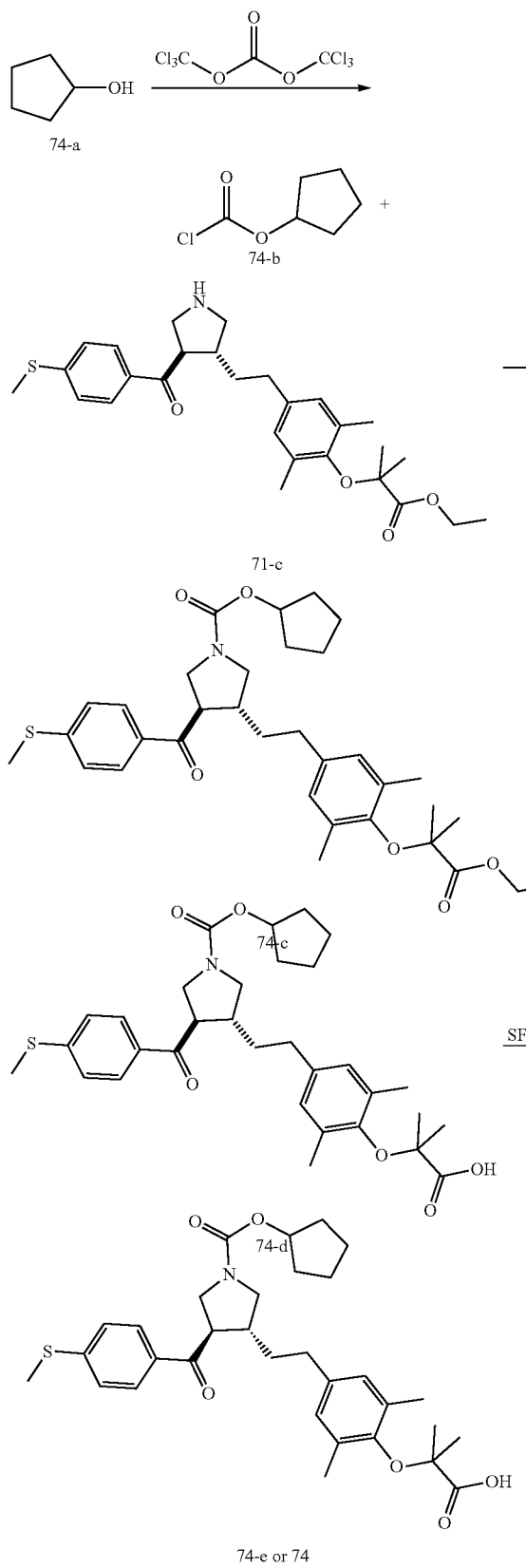

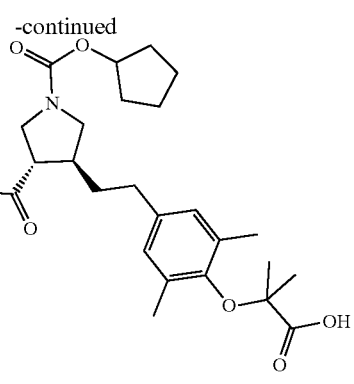

74 or 74-e

Step 1: Compound 74-b

At 20° C., Compound 74-a (200.00 mg, 2.32 mmol, 210.53 μL, 1.00 eq), triethylamine (704.91 mg, 6.97 mmol, 965.63 μL, 3.00 eq) and tetrahydrofuran (10.00 mL) was added into a dried round-bottom flask, and then triphosgene (551.26 mg, 1.86 mmol, 0.80 eq) was added. The resulted suspension was stirred at 20° C. for 1 h. The mixture was filtered, and the filtrate was concentrated under reduced pressure to give Compound 74-b.

Step 2: Compound 74-c

At 20° C., Compound 74-b (46.08 mg, 310.14 μmol, 1.50 eq), Compound 71-c (100.00 mg, 206.76 μmol, 1.00 eq), triethylamine (41.84 mg, 413.52 μmol, 57.32 μL, 2.00 eq) and dichloromethane (10.00 mL) was added into a dried round-bottom flask, and the resulted clear solution was stirred at 20° C. for 1 h. The reaction solution was concentrated under reduced pressure. The residue was purified by flash column chromatography (petroleum ether:ethyl acetate=100:0-60:40) to give Compound 74-c.

MS m/z (ESI): 596.4 [M+1].

Step 3: Compound 74-d

Compound 74-c (100.00 mg, 167.84 μmol, 1.00 eq) and ethanol (6.00 mL) was added into a reaction flask and then lithium hydroxide (40.20 mg, 1.68 mmol, 10.00 eq) and water (2.00 mL) were added. The mixture was stirred at 40° C. for 16 h. An 1N aqueous HCl solution was added dropwise to the reaction system to pH=6. The reaction system was extracted with ethyl acetate (20 mL) and water (20 mL). After phase separation, the organic phases were collected, and the aqueous phase was extracted with ethyl acetate (3×10 mL). The combined organic phase was dried over anhydrous sodium sulfate, and concentrated under reduced pressure. The residue was purified by thin-layer chromatography silica gel plate (dichloromethane:methanol=10:1) to give Compound 74-d.

MS m/z (ESI): 590.2 [M+23].

Step 4: Compound 74

Compound 74-d (14.00 mg, 24.66 μmol, 1.00 eq) was isolated by chiral supercritical chromatography to give Compound 74.

MS m/z (ESI): 568.4 [M+1].

¹H NMR (400 MHz, CDCl₃) δ ppm 7.85 (br s, 2H), 7.28-7.27 (m, 2H), 6.64 (br s, 2H), 3.89 (s, 1H), 3.70 (br s, 2H), 3.41 (br s, 1H), 3.12 (br s, 1H), 2.62 (s, 1H), 2.51 (br s, 5H), 2.03 (br s, 6H), 1.76-1.65 (m, 11H), 1.35-1.28 (m, 6H).

Chiral column: AS (250 mm×30 mm, 10 μm); mobile phase: 35% of methanol (0.05% DEA) in CO₂; flow rate: 80 mL/min; column temperature: 40° C.

Retention time of Compound 74: 4.120 min (peak 1).

Example 75: Compound 75

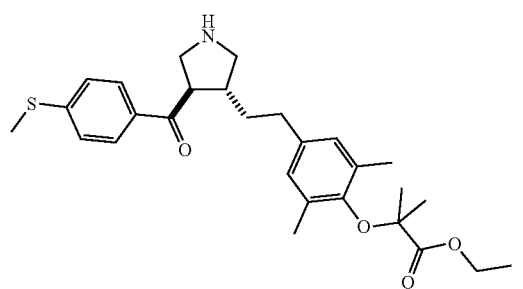

71-c

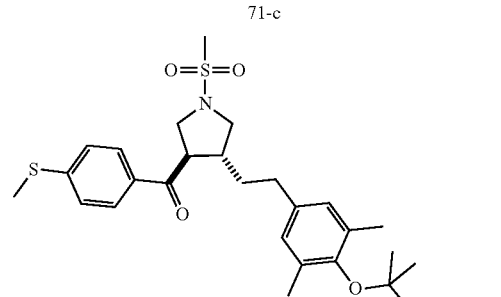

75-a

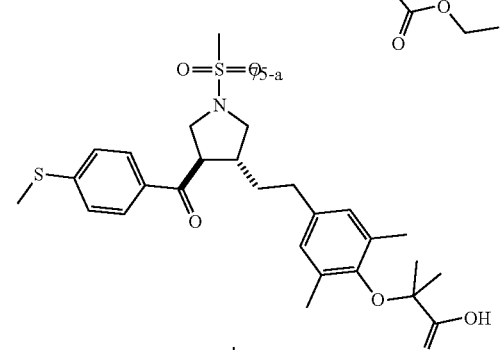

75-c or 75

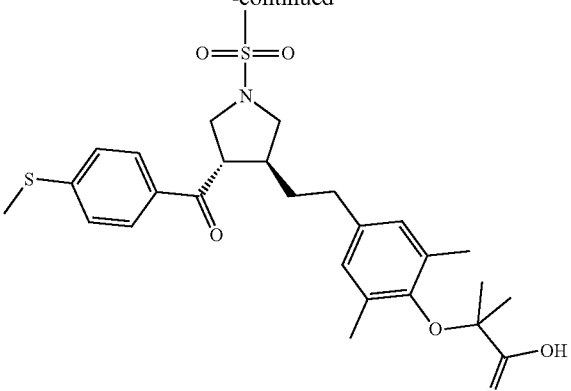

75 or 75-c

Step 1: Compound 75-a

At 20° C., Compound 71-c (200.00 mg, 413.51 μmol, 1.00 eq), mesyl chloride (71.05 mg, 620.27 μmol, 48.01 μL, 1.50 eq), triethylamine (125.53 mg, 1.24 mmol, 171.96 μL, 3.00 eq) and dichloromethane (10.00 mL) was added into a dried round-bottom flask, and the resulted clear solution was stirred at 20° C. for 1 h. The reaction solution was concentrated under reduced pressure. The residue was purified by flash column chromatography (petroleum ether:ethyl acetate=100:0-60:40) to give Compound 75-a.

MS m/z (ESI): 584.2 [M+23].

¹H NMR (400 MHz, CDCl₃) δ ppm 7.89-7.81 (m, 2H), 7.30 (s, 2H), 6.74 (s, 2H), 4.33-4.27 (m, 2H), 3.84-3.77 (m, 2H), 3.56-3.50 (m, 1H), 3.33-3.31 (m, 2H), 2.96 (s, 3H), 2.65-2.47 (m, 6H), 2.19 (s, 6H), 1.90-1.79 (m, 2H), 1.49 (d, J=2.0 Hz, 6H), 1.37-1.35 (m, 3H).

Step 2: Compound 75-b

Compound 75-a (51.00 mg, 90.79 μmol, 1.00 eq) and ethanol (6.00 mL) was added into a reaction flask of 100 mL, and then lithium hydroxide (21.74 mg, 907.88 μmol, 10.00 eq) and water (2.00 mL) were added. The mixture was stirred at 40° C. for 16 h. A saturated aqueous solution of potassium bisulfate was added dropwise into the reaction system to pH=6. The reaction system was extracted with ethyl acetate (20 mL) and water (20 mL). After phase separation, the organic phases were collected, and the aqueous phase was extracted with ethyl acetate (3×10 mL). The combined organic phase was dried over anhydrous sodium sulfate, and concentrated under reduced pressure. The residue was purified by thin-layer chromatography silica gel plate (dichloromethane:methanol=10:1) to give Compound 75-b.

MS m/z (ESI): 534.3 [M+1].

Step 3: Compound 75

Compound 75-b (16.00 mg, 29.98 μmol, 1.00 eq) was isolated by chiral supercritical chromatography to give Compound 75.

MS m/z (ESI): 534.3 [M+1].

¹H NMR (400 MHz, CDCl₃) δ ppm 7.81 (d, J=8.5 Hz, 2H), 7.29 (s, 2H), 6.77 (s, 2H), 3.80-3.71 (m, 2H), 3.55-3.50 (m, 1H), 3.40 (dd, J=6.8, 9.8 Hz, 1H), 3.28 (dd, J=5.3, 9.8

Hz, 1H), 2.94 (s, 3H), 2.65-2.56 (m, 2H), 2.55 (s, 3H), 2.54-2.47 (m, 1H), 2.19 (s, 6H), 1.90-1.79 (m, 2H), 1.49 (d, J=2.0 Hz, 6H)

Conditions of the chiral resolution: chiral column: AD (250 mm×30 mm, 5 um); mobile phase: 40% of methanol (0.05% DEA) in $CO_2$; flow rate: 60 mL/min; column temperature: 40° C.

Retention time of Compound 75: 4.725 min (peak 1).

Example 76: Compound 76

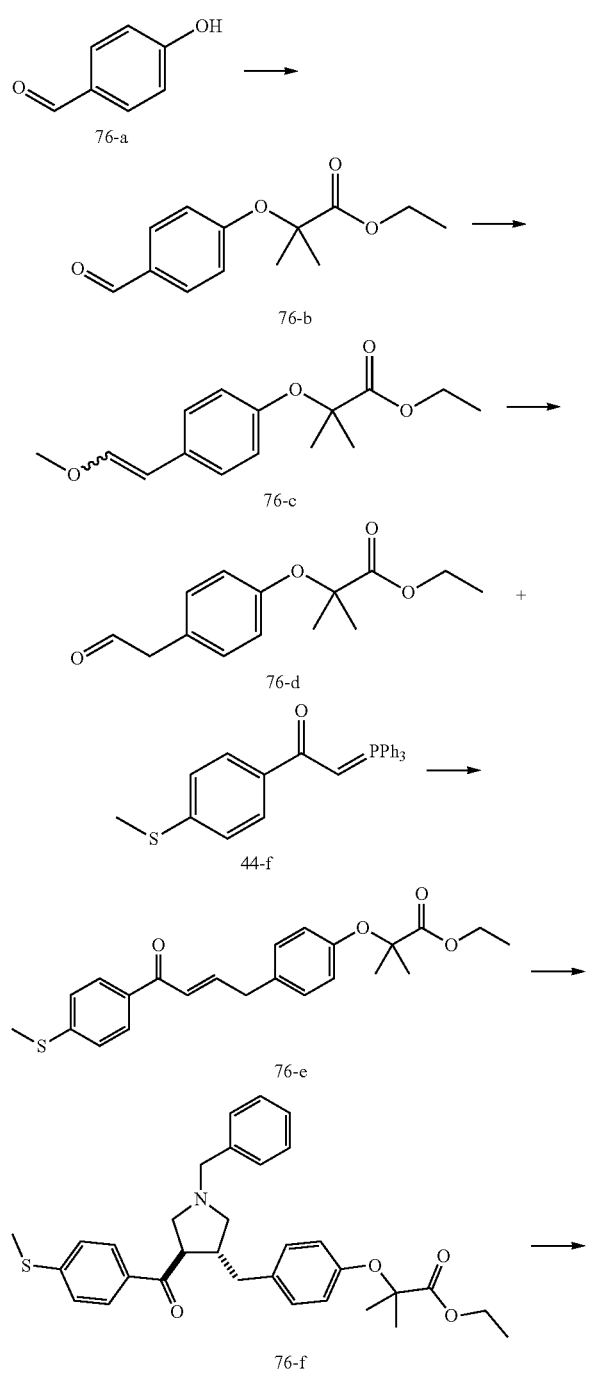

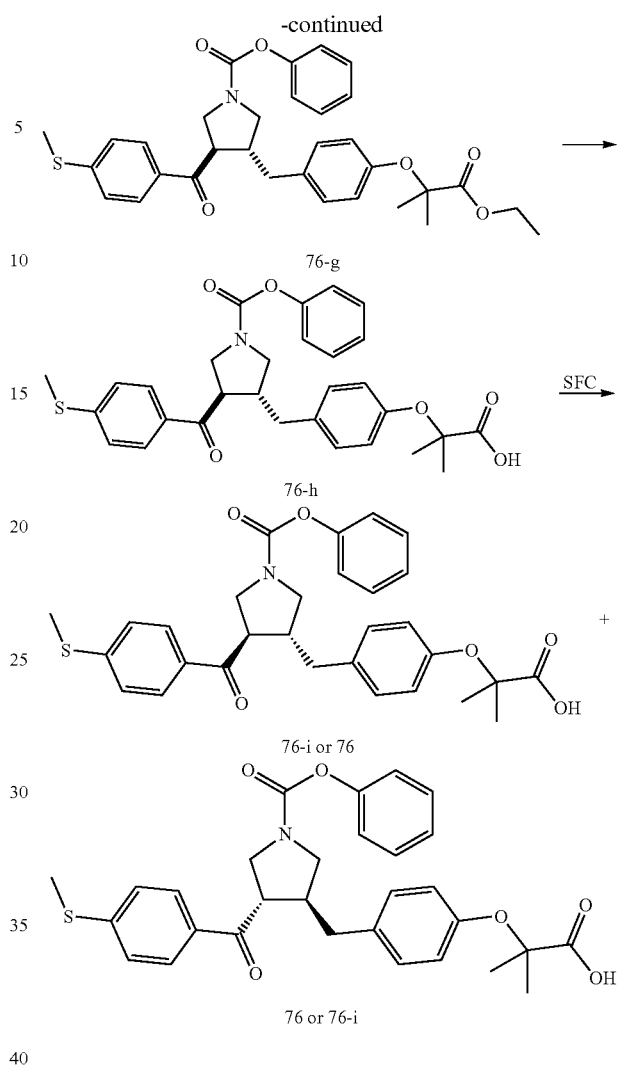

Step 1: Compound 76-b

Cesium carbonate (388.20 g, 1.19 mol, 3.00 eq) and ethyl 2-bromo-isobutyrate (154.93 g, 794.30 mmol, 2.00 eq) was added into a solution of Compound 76-a (48.50 g, 397.15 mmol, 1.00 eq) in 1,4-dioxane (500.00 mL). The mixture was stirred at 90° C. for 1 h. The reaction mixture was filtered, and the filter cake was washed with ethanol (200 mL×3). The combined filtrate was concentrated under reduced pressure to give Compound 76-b.

$^1$H NMR (400 MHz, $CDCl_3$) δ ppm 9.89 (s, 1H), 7.83-7.78 (m, 2H), 6.94-6.89 (m, 2H), 4.25-4.21 (m, 2H), 1.68 (s, 6H), 1.22 (t, J=7.2 Hz, 3H).

Step 2: Compound 76-c

Methoxymethyl triphenylphosphine chloride (28.29 g, 82.53 mmol, 1.50 eq) and tetrahydrofuran (200.00 mL) was added into a dried reaction flask, and then potassium tert-butoxide (10.69 g, 95.27 mmol, 1.73 eq) was added in batches at 20° C. After reacting for 1 hour, Compound 76-b (13.00 g, 55.02 mmol, 1.00 eq) was added into the reaction solution. The mixture was stirred at 20° C. for 1 h, and concentrated under reduced pressure. The crude product was purified by flash column chromatography (petroleum ether: ethyl acetate=100:0-70:30) to give Compound 76-c.

¹H NMR (400 MHz, CDCl₃) δ ppm 7.48-7.44 (m, 1H), 7.36-7.35 (m, 1H), 7.14-6.91 (m, 2H), 6.80-6.77 (m, 1H), 6.09-5.73 (m, 1H), 4.16-4.10 (m, 2H), 3.77-3.66 (m, 3H), 1.58 (s, 6H), 1.29-1.27 (m, 3H).

Step 3: Compound 76-d

Oxalyl chloride (15.99 g, 125.98 mmol, 11.03 mL, 2.00 eq) was slowly added into a solution of Compound 76-c (16.65 g, 62.99 mmol, 1.00 eq) in chloroform (200.00 mL) at 0° C., and then ethanol (5.80 g, 125.98 mmol, 7.34 mL, 2.00 eq) and water (2.27 g, 125.98 mmol, 2.27 mL, 2.00 eq) were added. The mixed solution was stirred at 0° C. for 1 h. A saturated aqueous sodium carbonate solution was added dropwise to the reaction system to pH 7-8. The reaction system was extracted with dichloromethane (20 mL) and water (20 mL). After phase separation, the organic phases were collected, and the aqueous phase was extracted with ethyl acetate (3×20 mL). The organic phases were combined and successively washed with water (3×20 mL) and saturated brine (3×20 mL), dried over anhydrous sodium sulfate, and concentrated under reduced pressure to give Compound 76-d.

¹H NMR (400 MHz, CDCl₃) δ ppm 9.71 (t, J=2.4 Hz, 1H), 7.08 (d, J=8.5 Hz, 2H), 6.87-6.81 (m, 2H), 4.23 (q, J=7.1 Hz, 2H), 3.92-3.90 (m, 2H), 1.59 (s, 6H), 1.40-1.37 (m, 3H).

Step 4: Compound 76-e

Compound 44-f (23.79 g, 55.78 mmol, 1.00 eq) was added into a solution of Compound 76-d (13.96 g, 55.78 mmol, 1.00 eq) in tetrahydrofuran (150.00 mL). The mixture was stirred at 50° C. for 16 h. The reaction solution was concentrated under reduced pressure, and the crude product was purified by flash column chromatography (petroleum ether:ethyl acetate=100:0-60:40) to give Compound 76-e.

MS m/z (ESI): 399.1 [M+1].

¹H NMR (400 MHz, CDCl₃) δ ppm 7.93-7.83 (m, 2H), 7.30-7.27 (m, 3H), 7.21-7.06 (m, 2H), 6.85-6.76 (m, 3H), 4.27-4.21 (m, 2H), 3.84 (dd, J=1.0, 6.8 Hz, 1H), 3.57 (d, J=5.8 Hz, 1H), 2.53 (d, J=2.0 Hz, 3H), 1.59 (d, J=1.5 Hz, 6H), 1.27-1.25 (m, 3H)

Step 5: Compound 76-f

Trifluoroacetic acid (90.27 mg, 791.50 μmol, 58.62 μL, 0.05 eq) was added into a solution of Compound 76-e (6.31 g, 15.83 mmol, 1.00 eq) in 1,4-dioxane (350.00 mL), and then N-benzyl-1-methoxy-N-((trimethylsilyl)methyl)methylamine (11.28 g, 47.49 mmol, 3.00 eq) was slowly added. The mixture was stirred at 80° C. for 2 h. The reaction solution was concentrated under reduced pressure to give a crude product. The crude product was purified by flash column chromatography (petroleum ether:ethyl acetate=100:0-60:40) to give Compound 76-f.

MS m/z (ESI): 532.2 [M+1].

¹H NMR (400 MHz, CDCl₃) δ ppm 7.89-7.83 (m, 1H), 7.70 (d, J=8.8 Hz, 1H), 7.33-7.29 (m, 5H), 7.22-7.18 (m, 2H), 6.99 (d, J=8.3 Hz, 2H), 6.72-6.66 (m, 2H), 4.21-4.15 (m, 2H), 4.09-4.00 (m, 1H), 3.67-3.62 (m, 2H), 3.11-2.99 (m, 2H), 2.88-2.82 (m, 1H), 2.75-2.57 (m, 4H), 2.52-2.50 (m, 3H), 1.55-1.50 (m, 6H), 1.23-1.18 (m, 3H)

Step 6: Compound 76-g

Phenyl chloroformate (6.37 g, 40.70 mmol, 5.10 mL, 5.00 eq) was slowly added into a solution of Compound 76-f (4.33 g, 8.14 mmol, 1.00 eq) in chloroform (50.00 mL), and the mixture was stirred at 70° C. for 16 h. The mixture was concentrated under reduced pressure to give a crude product. The crude product was purified by flash column chromatography (petroleum ether:ethyl acetate=100:0-60:40) to give Compound 76-g.

MS m/z (ESI): 562.0 [M+1].

¹H NMR (400 MHz, CDCl₃) δ ppm 7.92-7.82 (m, 1H), 7.65-7.62 (m, 1H), 7.39-7.29 (m, 3H), 7.26-7.11 (m, 6H), 7.08-7.05 (m, 1H), 6.81-6.78 (m, 1H), 4.29-4.20 (m, 2H), 4.00-3.90 (m, 1H), 3.88-3.80 (m, 1H), 3.77-3.70 (m, 2H), 3.49-3.35 (m, 1H), 2.95-2.80 (m, 1H), 2.74 (dd, J=2.6, 7.7 Hz, 1H), 2.55-2.53 (m, 3H), 2.51-2.49 (m, 1H), 1.61-1.59 (m, 6H), 1.27-1.25 (m, 3H).

Step 7: Compound 76-h

Lithium hydroxide (766.40 mg, 32.00 mmol, 10.00 eq) and water (5.00 mL) was added into a solution of Compound 76-g (1.80 g, 3.20 mmol, 1.00 eq) in ethanol (15.00 mL), and the mixture was stirred at 40° C. for 4 h. A saturated aqueous solution of potassium bisulfate was added dropwise into the reaction system to pH=6. The reaction system was extracted with ethyl acetate (20 mL) and water (20 mL). After phase separation, the organic phases were collected. The aqueous phase was extracted with ethyl acetate (3×10 mL). The organic phases were combined and dried over anhydrous sodium sulfate, and concentrated under reduced pressure to give a residue. The crude product was purified by flash column chromatography (petroleum ether:ethyl acetate=100:0-0:100) to give a crude product, which was further purified by High Performance Liquid Chromatography to give Compound 76-h.

MS m/z (ESI): 534.2 [M+1].

¹H NMR (400 MHz, CDCl₃) δ ppm 7.68 (d, J=7.5 Hz, 2H), 7.39-7.33 (m, 2H), 7.26-7.18 (m, 3H), 7.16-7.09 (m, 4H), 6.91-6.85 (m, 2H), 4.00-3.87 (m, 1H), 3.84-3.73 (m, 2H), 3.67 (dd, J=6.5, 10.8 Hz, 1H), 3.51-3.35 (m, 1H), 3.02-2.91 (m, 1H), 2.78 (td, J=6.8, 13.9 Hz, 2H), 2.53 (s, 3H), 1.59 (br s, 6H).

Step 8: Compound 76

Compound 76-h (200.00 mg, 374.78 μmol, 1.00 eq) was isolated by chiral supercritical chromatography to give Compound 76.

MS m/z (ESI): 534.1 [M+1].

¹H NMR (400 MHz, CDCl₃) δ ppm 7.65 (br dd, J=4.9, 7.9 Hz, 2H), 7.38-7.32 (m, 2H), 7.23-7.17 (m, 3H), 7.15-7.11 (m, 2H), 7.08-7.01 (m, 2H), 6.84 (br s, 2H), 3.98-3.85 (m, 1H), 3.84-3.69 (m, 2H), 3.68-3.60 (m, 1H), 3.47-3.30 (m, 1H), 2.95-2.81 (m, 1H), 2.80-2.65 (m, 2H), 2.51 (s, 3H), 1.53 (br s, 6H).

Conditions of the chiral resolution: chiral column: AD (250 mm×30 mm, 10 μm); mobile phase: 55% of methanol (0.05% DEA) in $CO_2$; flow rate: 80 mL/min; column temperature: 40° C. Retention time of Compound 76: 0.729 min (peak 1).

Example 77: Compound 77
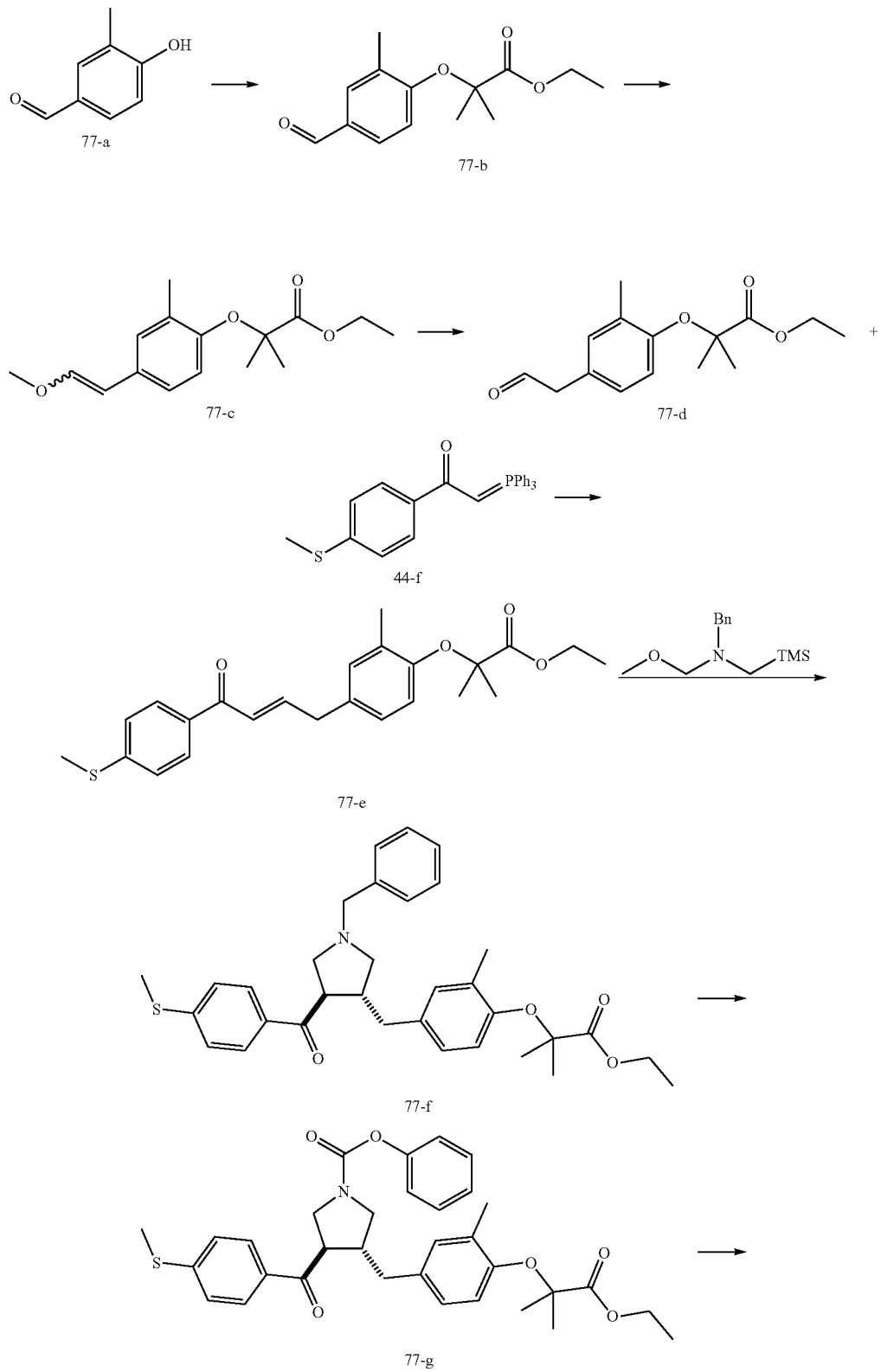

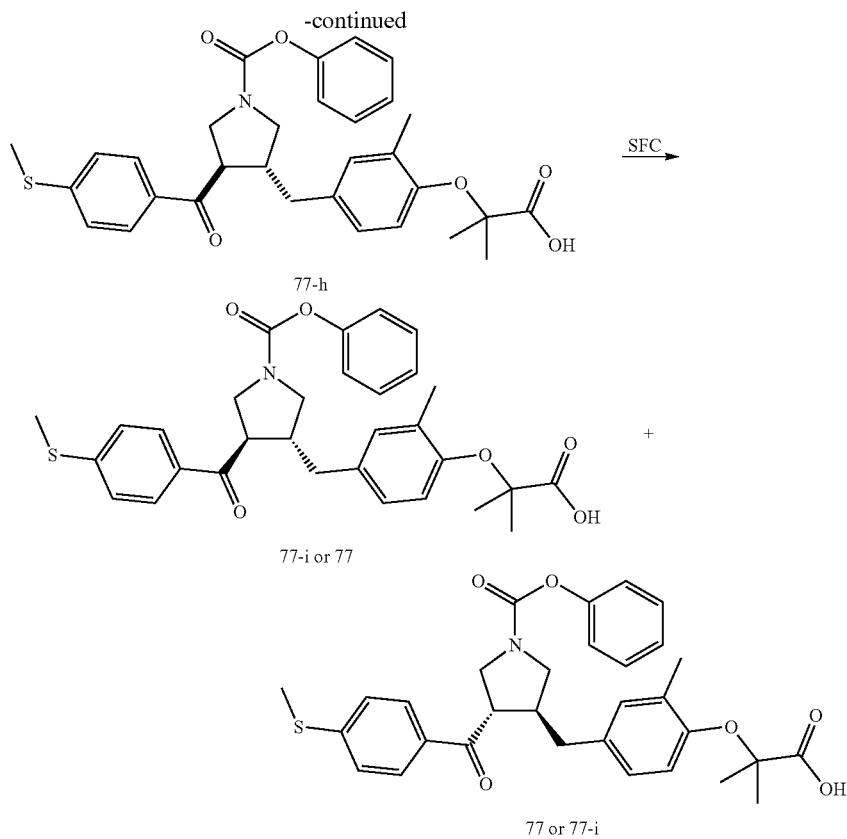

Step 1: Compound 77-b

Cesium carbonate (179.48 g, 550.86 mmol, 3.00 eq) and ethyl 2-bromo-isobutyrate (71.63 g, 367.24 mmol, 53.86 mL, 2.00 eq) was added into a solution of Compound 77-a (25.00 g, 183.62 mmol, 1.00 eq) in 1,4-dioxane (500.00 mL), and stirred at 90° C. for 1 h. The reaction system was diluted with ethyl acetate (500 mL) and water (500 mL). The organic phase was washed with saturated brine (3×500 mL), dried over anhydrous sodium sulfate, and concentrated under reduced pressure to give Compound 77-b.

$^1$H NMR (400 MHz, CDCl$_3$) δ☐ ppm 9.83 (s, 1H), 7.68 (d, J=1.5 Hz, 1H), 7.58 (dd, J=2.0, 8.5 Hz, 1H), 6.66 (d, J=8.3 Hz, 1H), 4.23-4.17 (m, 2H), 2.27 (s, 3H), 1.66 (s, 6H), 1.20 (t, J=7.2 Hz, 3H).

Step 2: Compound 77-c

Methoxymethyl triphenylphosphine chloride (35.61 g, 103.88 mmol, 1.30 eq) and tetrahydrofuran (200.00 mL) was added into a dried reaction flask, and then potassium tert-butoxide (13.45 g, 119.87 mmol, 1.50 eq) was added in batches at 20° C. After reacting for 1 hour, Compound 77-b (20.00 g, 79.91 mmol, 1.00 eq) was added into the reaction solution. The mixture was stirred at 20° C. for 1 h, and concentrated under reduced pressure. The crude product was purified by flash column chromatography (petroleum ether: ethyl acetate=100:0-15:1) to give Compound Compound 77-c.

$^1$H NMR (400 MHz, CDCl$_3$) δ ppm 7.30-7.18 (m, 1H), 6.98-6.81 (m, 2H), 6.53 (dd, J=5.6, 8.4 Hz, 1H), 5.99-5.63 (m, 1H), 4.17 (dq, J=1.3, 7.1 Hz, 2H), 3.69-3.57 (m, 3H), 2.14 (d, J=3.5 Hz, 3H), 1.50 (s, 6H), 1.21-1.17 (m, 3H)

Step 3: Compound 77-d

Oxalyl chloride (12.51 g, 98.58 mmol, 8.63 mL, 2.00 eq) was slowly added into a solution of Compound 77-c (13.72 g, 49.29 mmol, 1.00 eq) in chloroform (150.00 mL) at 0° C., and then ethanol (4.54 g, 98.58 mmol, 5.75 mL, 2.00 eq) and water (1.78 g, 98.58 mmol, 1.78 mL, 2.00 eq) were added. The mixed solution was stirred 0° C. for 1 h. A saturated aqueous sodium carbonate solution was added dropwise into the reaction system to pH 7-8. Dichloromethane (20 mL) and water (20 mL) were added. After phase separation, the organic phases were collected, and the aqueous phase was extracted with ethyl acetate (3×20 mL). The organic phases were combined and successively washed with water (3×20 mL) and saturated brine (3×20 mL), dried over anhydrous sodium sulfate, and concentrated under reduced pressure to give Compound 77-d.

$^1$H NMR (400 MHz, CDCl$_3$) δ ppm 9.69 (t, J=2.5 Hz, 1H), 6.99 (d, J=2.0 Hz, 1H), 6.89 (dd, J=2.0, 8.3 Hz, 1H), 6.64 (d, J=8.3 Hz, 1H), 4.24 (q, J=7.2 Hz, 2H), 3.56 (d, J=2.5 Hz, 2H), 2.23 (s, 3H), 1.59 (s, 6H), 1.27-1.24 (m, 3H).

Step 4: Compound 77-e

Compound 44-f (21.75 g, 51.00 mmol, 1.00 eq) was added into a solution of Compound 77-d (13.48 g, 51.00 mmol, 1.00 eq) in tetrahydrofuran (150.00 mL). The mixture was stirred at 50° C. for 16 h. The reaction solution was concentrated under reduced pressure, and the crude product was purified by flash column chromatography (petroleum ether:ethyl acetate=100:0-60:40) to give Compound 77-e.

MS m/z (ESI): 413.0 [M+1].

¹H NMR (400 MHz, CDCl₃) δ ppm 7.78-7.74 (m, 2H), 7.21-7.17 (m, 2H), 7.08 (td, J=6.8, 15.3 Hz, 1H), 6.91 (d, J=1.8 Hz, 1H), 6.83-6.72 (m, 2H), 6.56 (d, J=8.3 Hz, 1H), 4.18 (q, J=7.0 Hz, 2H), 3.45 (d, J=6.8 Hz, 2H), 2.44 (s, 3H), 2.14 (s, 3H), 1.51 (s, 6H), 1.20-1.17 (m, 3H).

Step 5: Compound 77-f

Trifluoroacetic acid (141.37 mg, 1.24 mmol, 91.80 μL, 0.05 eq) was added into a solution of Compound 77-e (10.23 g, 24.80 mmol, 1.00 eq) in 1,4-dioxane (350.00 mL), and then N-benzyl-1-methoxy-N-((trimethylsilyl)methyl)methylamine (17.66 g, 74.39 mmol, 3.00 eq) was slowly added dropwise. The mixture was stirred at 80° C. for 2 h. The reaction solution was concentrated under reduced pressure to give a crude product. The crude product was purified by flash column chromatography (petroleum ether:ethyl acetate=100:0-60:40) to give Compound 77-f.

MS m/z (ESI): 546.3 [M+1].

¹H NMR (400 MHz, CDCl₃) δ ppm 7.27-7.20 (m, 3H), 7.17-7.15 (m, 3H), 7.10-7.07 (m, 4H), 6.58 (td, J=6.8, 10.7 Hz, 2H), 5.85 (d, J=10.5 Hz, 2H), 5.23 (s, 2H), 4.63-4.36 (m, 8H), 3.33 (br s, 3H), 2.94 (br s, 3H), 1.39-1.38 (m, 6H), 1.35-1.35 (m, 3H).

Step 6: Compound 77-g

Phenyl chloroformate (4.30 g, 27.49 mmol, 3.44 mL, 5.00 eq) was slowly added into a solution of Compound 77-f (3.00 g, 5.50 mmol, 1.00 eq) in chloroform (50.00 mL), and the mixture was stirred at 70° C. for 4 h. The mixture was concentrated under reduced pressure to give a crude product.

The crude product was purified by flash column chromatography (petroleum ether:ethyl acetate=100:0-60:40) to give Compound 77-g.

MS m/z (ESI): 576.1 [M+1].

¹H NMR (400 MHz, CDCl₃) δ ppm 7.61 (t, J=8.9 Hz, 2H), 7.38-7.33 (m, 2H), 7.22-7.18 (m, 3H), 7.16-7.12 (m, 2H), 6.96 (br s, 1H), 6.87 (br d, J=8.3 Hz, 1H), 6.61 (dd, J=2.0, 8.3 Hz, 1H), 4.25 (dq, J=2.0, 7.1 Hz, 2H), 3.94-3.88 (m, 1H), 3.86-3.78 (m, 1H), 3.76-3.58 (m, 2H), 3.49-3.36 (m, 1H), 2.91-2.78 (m, 1H), 2.72-2.67 (m, 2H), 2.52 (s, 3H), 2.19 (d, J=2.0 Hz, 3H), 1.60 (s, 6H), 1.26 (s, 3H).

Step 7: Compound 77-h

Lithium hydroxide (1.04 g, 43.40 mmol, 10.00 eq) and water (7.00 mL) was added into a solution of Compound 77-g (2.50 g, 4.34 mmol, 1.00 eq) in ethanol (21.00 mL), and the mixture was stirred at 30° C. for 1 h. A saturated aqueous solution of potassium bisulfate was added dropwise to the reaction system to pH=6. The reaction system was extracted with ethyl acetate (20 mL) and water (20 mL). After phase separation, the organic phases were collected. The aqueous phase was extracted with ethyl acetate (3×10 mL). The organic phases were combined and dried over anhydrous sodium sulfate, and concentrated under reduced pressure to give a residue of 1.5 g. A crude product of 0.5 g was taken from the residue, and purified by High Performance Liquid Chromatography to give Compound 77-h.

MS m/z (ESI): 548.3 [M+1].

¹H NMR (400 MHz, CDCl₃) δ ppm 7.59 (br d, J=7.8 Hz, 2H), 7.27 (br d, J=7.3 Hz, 2H), 7.14 (br d, J=7.8 Hz, 3H), 7.06 (br d, J=7.3 Hz, 2H), 6.92 (br s, 1H), 6.82 (br s, 1H), 6.69 (br s, 1H), 3.91-3.80 (m, 1H), 3.73 (br s, 1H), 3.68-3.55 (m, 2H), 3.40-3.26 (m, 1H), 2.92-2.79 (m, 1H), 2.63 (br s, 2H), 2.45 (s, 3H), 2.11 (br s, 3H), 1.51 (br s, 6H).

Step 8: Compound 77

Compound 77-h (100.00 g, 182.60 mmol, 1.00 eq) was isolated by chiral supercritical chromatography to give Compound 77.

MS m/z (ESI): 548.1 [M+1].

¹H NMR (400 MHz, CDCl₃) δ ppm 7.65 (br s, 2H), 7.33 (br d, J=7.5 Hz, 2H), 7.18 (br s, 3H), 7.13 (br s, 2H), 7.06-7.01 (m, 1H), 6.95 (br s, 1H), 6.85 (br s, 1H), 3.88-3.54 (m, 5H), 2.84 (br s, 1H), 2.68 (br s, 2H), 2.50 (br s, 3H), 2.15 (br s, 3H), 1.52 (br s, 6H).

Conditions of the chiral resolution: chiral column: AD (250 mm×30 mm, 10 m); mobile phase: 50% of methanol (0.05% DEA) in CO₂; flow rate: 80 mL/min; column temperature: 40° C.

Retention time of Compound 77: 0.564 min (peak 1).

Example 78: Compound 78

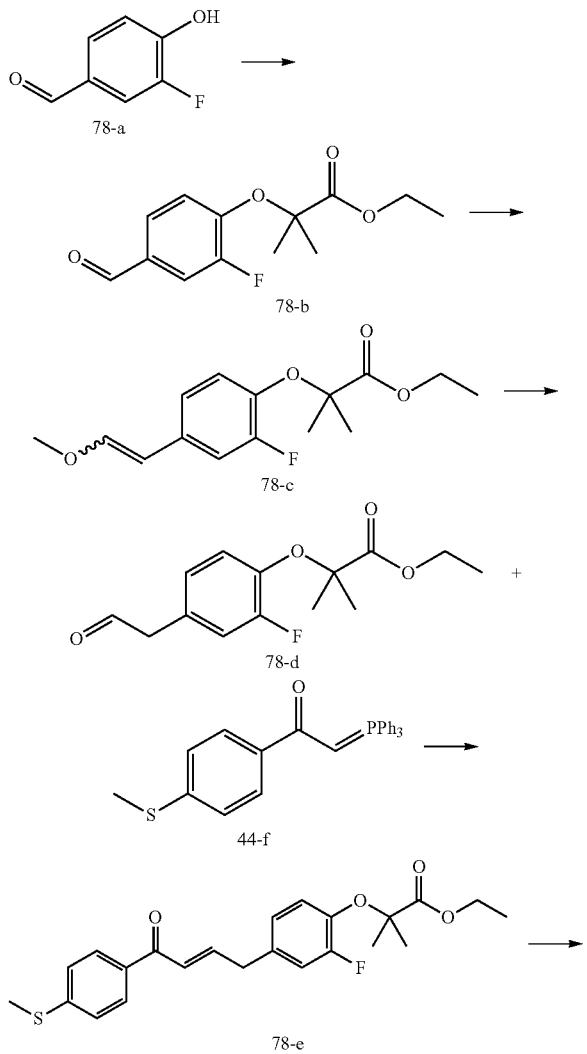

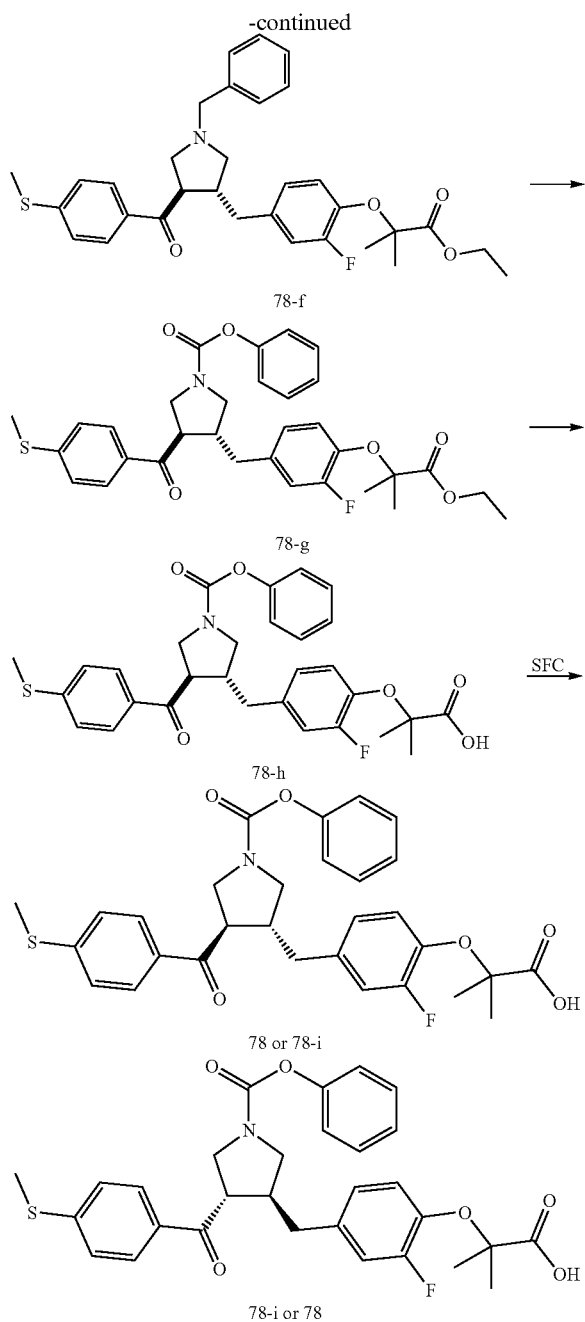

78-f 78-g 78-h 78 or 78-i 78-i or 78

Step 1: Compound 78-b

Cesium carbonate (345.33 g, 10.71 mmol, 3.00 eq) and ethyl 2-bromo-isobutyrate (137.82 g, 706.58 mmol, 2.00 eq) was added into a solution of Compound 78-a (49.5 g, 353.29 mmol, 1.00 eq) in 1,4-dioxane (500.00 mL) and N,N-dimethylformamide (200 mL) at 25° C. The mixture was stirred at 90° C. for 16 h. Water (800 mL) was added into the reaction mixture, and extracted with ethyl acetate (300 mL×3). The combined organic phase was washed with water (300 mL×3) and saturated brine (300 mL×2), dried over anhydrous sodium sulfate, filtered, and concentrated under reduced pressure to give a crude product, so as to give Compound 78-b.

$^1$H NMR (400 MHz, CDCl$_3$) δ ppm 9.79 (d, J=2.0 Hz, 1H), 7.54 (dd, J=2.0, 10.8 Hz, 1H), 7.51-7.44 (m, 1H), 7.51-7.44 (m, 1H), 6.89 (t, J=8.0 Hz, 1H), 4.19-4.15 (m, 2H), 1.61 (s, 6H), 1.18 (t, J=7.2 Hz, 3H)

Step 2: Compound 78-c

Under nitrogen protection, methoxymethyl triphenylphosphine chloride (26.29 g, 76.70 mmol, 1.30 eq) and tetrahydrofuran (120 mL) was added into a reaction flask, and then potassium tert-butoxide (7.94 g, 70.80 mmol, 1.20 eq) was added in batches at 0° C. The reaction system was stirred at 0° C. for 1 h. Then, a solution of Compound 78-b (15.00 g, 59.00 mmol, 1.00 eq) in tetrahydrofuran (30 mL) was added dropwise to the reaction solution. The reaction system was stirred at 0° C. for additional 30 min. The reaction mixture was quenched with a saturated solution of ammonium chloride (30 mL), and extracted with ethyl acetate (100 mL×3). The combined organic phase was washed with water (100 mL×3) and saturated brine (100 mL×3), dried over anhydrous sodium sulfate, filtered, and concentrated under reduced pressure. The residue was purified by flash column chromatography (gradient elution: petroleum ether:ethyl acetate=100:0-80:20) to give Compound 78-c.

MS m/z (ESI): 283.0 [M+1].

$^1$H NMR (400 MHz, CDCl$_3$) δ ppm 7.36 (dd, J=2.1, 12.9 Hz, 1H), 7.02 (d, J=8.5 Hz, 1H), 7.05-6.75 (m, 3H), 6.04 (d, J=6.8 Hz, 1H), 5.63 (d, J=13.1 Hz, 1H), 5.06 (d, J=7.0 Hz, 1H), 4.21-4.14 (m, 2H), 3.72-3.56 (m, 3H), 1.49 (s, 6H), 1.22 (dt, J=1.3, 7.2 Hz, 3H)

Step 3: Compound 78-d

Oxalyl chloride (10.79 g, 7.44 mL, 85.02 mmol, 2.00 eq) was slowly added dropwise into a solution of Compound 78-c (12 g, 42.51 mmol, 1.00 eq) in chloroform (100 mL) at 15° C., and then ethanol (3.92 g, 4.96 mL, 85.02 mmol, 2.00 eq) and water (1.53 g, 85.02 mmol, 2.00 eq) were successively added dropwise. The reaction mixture was stirred at 15° C. for additional 30 min. The mixture was adjusted with a saturated solution of sodium bicarbonate to pH=7-8. The organic phase was washed with water (50 mL×2) and saturated brine (50 mL×2), dried over anhydrous sodium sulfate, filtered, and concentrated under reduced pressure to give a crude product, so as to give Compound 78-d.

$^1$H NMR (400 MHz, CDCl$_3$) δ ppm 9.66 (t, J=2.3 Hz, 1H), 6.93-6.85 (m, 2H), 6.85-6.72 (m, 1H), 4.18 (q, J=7.1 Hz, 2H), 3.56 (d, J=2.0 Hz, 2H), 1.51 (s, 6H), 1.21 (t, J=7.2 Hz, 3H)

Step 4: Compound 78-e

Compound 44-f (19.08 g, 44.73 mmol, 1.00 eq) was added into a solution of Compound 78-d (12 g, 44.73 mmol, 1.00 eq) in tetrahydrofuran (120 mL). The mixture was stirred at 55° C. for 12 h. The mixture was concentrated under reduced pressure to give a crude product. The residue was purified by flash column chromatography (gradient elution: petroleum ether:ethyl acetate=100:0-80:20) to give Compound 78-e.

MS m/z (ESI): 417.0 [M+1].

$^1$H NMR (400 MHz, CDCl$_3$) δ ppm 7.85-7.73 (m, 2H), 7.23-7.17 (m, 2H), 7.11-6.29 (m, 5H), 4.18 (dq, J=3.6, 7.2 Hz, 2H), 3.77 (d, J=6.3 Hz, 1H), 3.49 (d, J=6.0 Hz, 1H), 2.45 (d, J=1.5 Hz, 3H), 1.50 (d, J=1.8 Hz, 6H), 1.21 (dt, J=4.5, 7.2 Hz, 3H).

Step 5: Compound 78-f

Trifluoroacetic acid (134.14 mg, 1.18 mmol, 0.05 eq) was added into a solution of Compound 78-e (9.8 g, 23.53 mmol, 1.00 eq) in 1,4-dioxane (250 mL), and then the reaction system was warmed to 80° C. Then, a solution of N-benzyl-1-methoxy-N-((trimethylsilyl)methyl)methylamine (16.76 g, 70.59 mmol, 3.00 eq) in 1,4-dioxane (50 mL) was added dropwise into the reaction solution. The reaction mixture was stirred at 80° C. for additional 30 min. The mixture was concentrated under reduced pressure. The residue was purified by flash column chromatography (gradient elution: petroleum ether:ethyl acetate=100:0-80:20) to give Compound 78-f.

MS m/z (ESI): 550.1 [M+1].

Step 6: Compound 78-g

Phenyl chloroformate (3.85 g, 24.57 mmol, 3.00 eq) was added into a solution of Compound 78-f (4.5 g, 8.19 mmol, 1.00 eq) in chloroform (50 mL) at 15° C. The reaction system was reacted at 70° C. for 12 h. The reaction mixture was concentrated under reduced pressure to give a crude product. The residue was purified by flash column chromatography (gradient elution: petroleum ether:ethyl acetate=100:0-80:20) to give Compound 78-g.

MS m/z (ESI): 580.1 [M+23].

$^1$H NMR (400 MHz, CDCl$_3$) δ ppm 7.62 (dd, J=6.4, 8.4 Hz, 2H), 7.31-7.26 (m, 2H), 7.19-7.04 (m, 5H), 6.89-6.73 (m, 3H), 4.18 (dq, J=1.8, 7.1 Hz, 2H), 3.93-3.83 (m, 1H), 3.78-3.54 (m, 3H), 3.41-3.22 (m, 1H), 2.98-2.77 (m, 1H), 2.75-2.55 (m, 2H), 2.46 (s, 3H), 1.50 (s, 6H), 1.22-1.19 (m, 3H).

Step 7: Compound 78-h

A solution of lithium hydroxide monohydrate (434.29 mg, 10.35 mmol, 3.00 eq) in water (4.00 mL) was slowly added into a solution of Compound 78-g (2.00 g, 3.45 mmol, 1.00 eq) in tetrahydrofuran (10 mL) and ethanol (10 mL). The reaction mixture was stirred at 25° C. for 6 h. The reaction system was adjusted with a saturated aqueous solution of potassium bisulfate to pH=5-6, and extracted with ethyl acetate (20 mL×3). The combined organic phase was washed with water (10 mL×3) and saturated brine (10 mL×3), dried over anhydrous sodium sulfate, filtered, and concentrated under reduced pressure. The residue was purified by preparative High Performance Liquid Chromatography to give Compound 78-h.

MS m/z (ESI): 552.1 [M+23].

$^1$H NMR (400 MHz, CDCl$_3$) δ ppm 7.66 (d, J=8.5 Hz, 2H), 7.33-7.24 (m, 2H), 7.19-7.16 (m, 2H), 7.15-7.09 (m, 1H), 7.05 (d, J=7.5 Hz, 2H), 6.96-6.85 (m, 2H), 6.84-6.78 (m, 1H), 3.96-3.84 (m, 1H), 3.79-3.51 (m, 3H), 3.44-3.23 (m, 1H), 3.00-2.82 (m, 1H), 2.78-2.69 (m, 1H), 2.65-2.57 (m, 1H), 2.46 (s, 3H), 1.51-1.46 (m, 6H).

Step 8: Compound 78

Compound 78-h (220 mg, 398.83 mmol, 1.00 eq) was isolated by chiral supercritical chromatography to give Compound 78.

MS m/z (ESI): 574.1 [M+23].

$^1$H NMR (400 MHz, CDCl$_3$) δ ppm 7.65 (dd, J=2.5, 8.5 Hz, 2H), 7.31-7.23 (m, 2H), 7.19-7.08 (m, 3H), 7.04 (d, J=7.8 Hz, 2H), 6.96-6.70 (m, 3H), 3.99-3.81 (m, 1H), 3.77-3.47 (m, 3H), 3.39-3.18 (m, 1H), 2.99-2.81 (m, 1H), 2.76-2.52 (m, 2H), 2.45 (s, 3H), 1.44 (br s, 6H).

Conditions of the chiral resolution: chiral column: AD (250 mm×30 mm, 10 μm); mobile phase: [0.1% NH$_3$H$_2$O EtOH]; flow rate: 80 mL/min; column temperature: 40° C.

Retention time of Compound 78: 0.651 min (peak 1).

Example 79: Compound 79

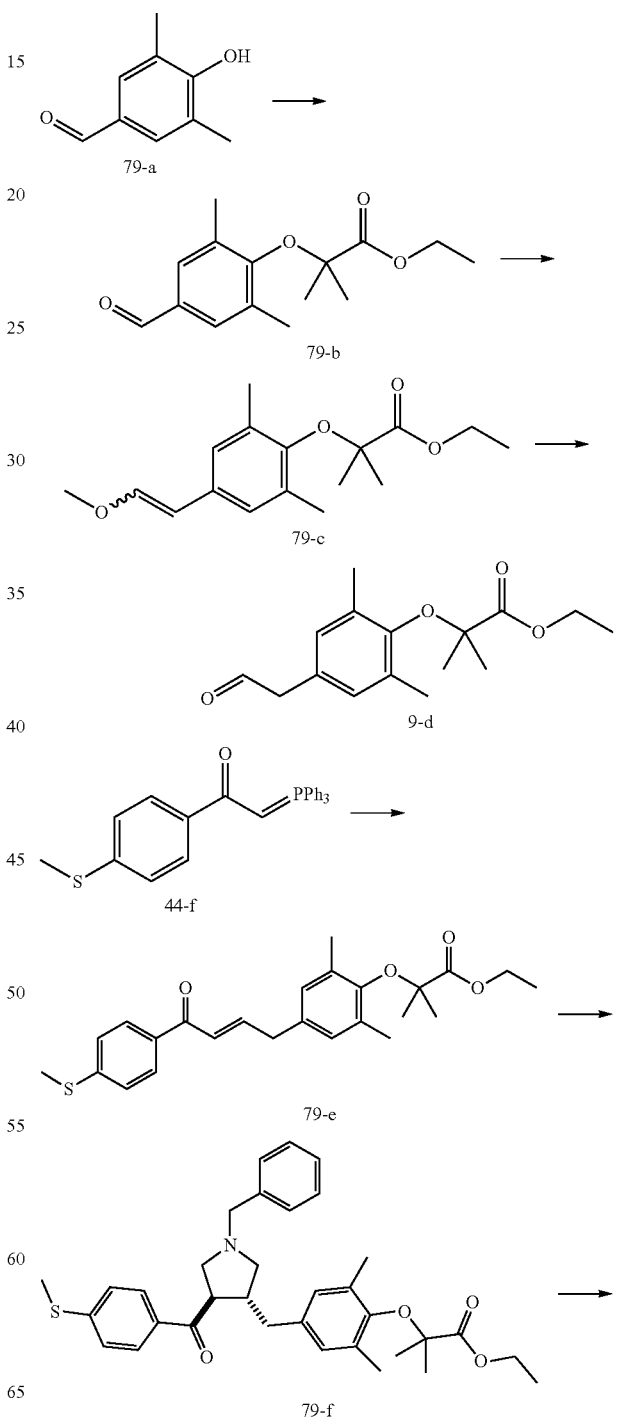

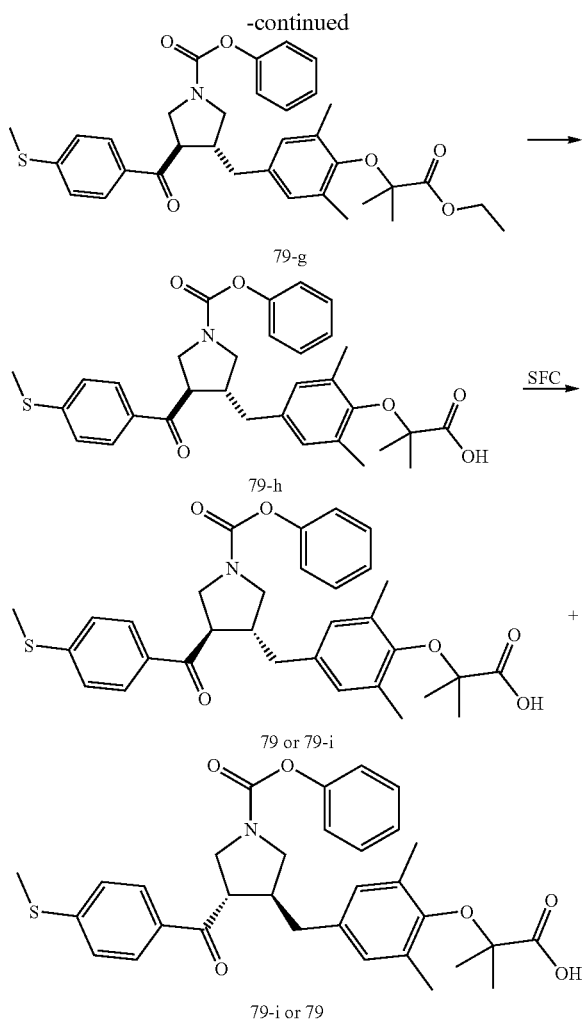

79-g 79-h 79 or 79-i 79-i or 79

Step 1: Compound 79-b

Cesium carbonate (65.08 g, 10.71 mmol, 1.50 eq) and bromoethyl acetate (33.36 g, 199.75 mmol, 1.50 eq) was added into a solution of Compound 79-a (20 g, 133.17 mmol, 1.00 eq) in acetone (200.00 mL). The mixture was stirred at 60° C. for 1 h. The reaction mixture was filtered, and the filtrate was concentrated under reduced pressure to give Compound 79-b.

$^1$H NMR (400 MHz, CDCl$_3$) δ ppm 9.91-9.85 (m, 1H), 7.56 (s, 2H), 4.46 (s, 2H), 4.34-4.27 (m, 2H), 2.37 (s, 6H), 1.33 (t, J=7.2 Hz, 3H).

Step 2: Compound 79-c

Sodium ethoxide (5.62 g, 82.54 mmol, 1.30 eq) was added into a solution of methoxymethyl triphenylphosphine chloride (32.65 g, 95.23 mmol, 1.50 eq) in tetrahydrofuran (120 mL) in batches at 0° C., and then a solution of 79-b (15.00 g, 63.49 mmol, 1.00 eq) in tetrahydrofuran (30 mL) was added dropwise. The reaction mixture was stirred at 20° C. for additional 12 h, and then quenched with water (100 mL), extracted with ethyl acetate (200 mL×3). The combined organic phase was washed with water (100 mL×3) and saturated brine (100 mL×3), dried over anhydrous sodium sulfate, filtered, and concentrated under reduced pressure to give a crude product. The crude product was purified by silica gel column chromatography (petroleum ether:ethyl acetate=100:0-80:20) to give Compound 79-c.

MS m/z (ESI): 265.1 [M+1].

$^1$H NMR (400 MHz, CDCl$_3$) δ ppm 7.25 (s, 1H), 6.97 (d, J=13.1 Hz, 1H), 6.90 (s, 1H), 6.09 (d, J=7.0 Hz, 1H), 5.73 (d, J=13.1 Hz, 1H), 5.13 (d, J=7.0 Hz, 1H), 4.40 (s, 2H), 4.32 (q, J=7.0 Hz, 2H), 3.80-3.67 (m, 3H), 2.29 (d, J=3.5 Hz, 6H), 1.36 (t, J=7.2 Hz, 3H).

Step 3: Compound 79-d

Oxalyl chloride (3.36 g, 2.32 mL, 26.48 mmol, 2.00 eq) was added dropwise into a solution of Compound 79-c (3.5 g, 13.24 mmol, 1.00 eq) in chloroform (35 mL) at 0° C. After completion of the addition, ethanol (1.22 g, 1.54 mL, 26.48 mmol, 2.00 eq) and water (477.22 mg, 26.48 mmol, 2.00 eq) were successively added dropwise into the reaction solution. The mixture was stirred at 0° C. for additional 30 min. The mixture was adjusted with a saturated solution of sodium bicarbonate to pH=7-8. The organic phase was washed with water (200 mL×2) and saturated brine (200 mL×2), dried over anhydrous sodium sulfate, filtered, and concentrated under reduced pressure to give a crude product, so as to give Compound 79-d.

$^1$H NMR (400 MHz, CDCl$_3$) δ ppm 9.64 (t, J=2.4 Hz, 1H), 6.79 (s, 2H), 4.33 (s, 2H), 4.23 (q, J=7.0 Hz, 2H), 3.50 (d, J=2.3 Hz, 2H), 2.22 (s, 6H), 1.31 (t, J=7.2 Hz, 3H)

Step 4: Compound 79-e 1-(4-(methylthio) phenyl-2-(triphenylphosphoranyl)) ethanone 44-f (5.96 g, 12.57 mmol, 1.00 eq) was added into a solution of Compound 79-d (3.50 g, 13.98 mmol, 1.00 eq) in tetrahydrofuran (50 mL). The mixture was stirred at 55° C. for 12 h. The mixture was concentrated under reduced pressure to give a crude product. The residue was purified by flash column chromatography (petroleum ether:ethyl acetate=100:0-80:20) to give Compound 79-e.

MS m/z (ESI): 399.1 [M+1].

$^1$H NMR (400 MHz, CDCl$_3$) δ ppm 7.88-7.73 (m, 2H), 7.24-7.18 (m, 2H), 7.11-7.03 (m, 0.5H), 6.83-6.73 (m, 2H), 6.39-6.21 (m, 0.5H), 4.33-4.29 (m, 2H), 4.27-4.18 (m, 2H), 2.45 (s, 2H), 2.23-2.19 (m, 6H), 1.29-1.23 (m, 3H).

Step 5: Compound 79-f

Trifluoroacetic acid (48.64 mg, 426.58 μmol, 0.05 eq) was added into a solution of Compound 79-e (3.4 g, 8.53 mmol, 1.00 eq) in 1,4-dioxane (170 mL), and warmed to 80° C. Then, a solution of N-benzyl-1-methoxy-N-((trimethylsilyl) methyl)methylamine (5.68 g, 25.59 mmol, 3.00 eq) in 1,4-dioxane (30 mL) was slowly added dropwise to the reaction system. The mixture was stirred for additional 30 min. The mixture was concentrated under reduced pressure. The residue was purified by flash column chromatography (petroleum ether:ethyl acetate=100:0-80:20) to give Compound 79-f.

MS m/z (ESI): 532.3 [M+1].

$^1$H NMR (400 MHz, CDCl$_3$) δ ppm 7.55 (d, J=8.5 Hz, 2H), 7.19-7.14 (m, 5H), 7.04 (d, J=8.5 Hz, 2H), 6.59 (s, 2H), 4.14 (q, J=7.2 Hz, 2H), 4.10 (s, 2H), 3.58-3.45 (m, 3H), 2.99-2.79 (m, 2H), 2.59-2.41 (m, 5H), 2.37 (s, 3H), 2.00 (s, 6H), 1.18 (t, J=7.2 Hz, 3H)

Step 6: Compound 79-g

Phenyl chloroformate (2.30 g, 14.67 mmol, 3.00 eq) was added into a solution of Compound 79-f (2.60 g, 4.89 mmol, 1.00 eq) in chloroform (30 mL), and the reaction system was reacted at 70° C. for 1 h. The mixture was concentrated under reduced pressure to give a crude product. The residue was purified by flash column chromatography (gradient elution: petroleum ether:ethyl acetate=100:0-80:20) to give Compound 79-g.

MS m/z (ESI): 562.3 [M+1].

$^1$H NMR (400 MHz, CDCl$_3$) δ ppm 7.59 (dd, J=5.5, 8.5 Hz, 2H), 7.32-7.24 (m, 2H), 7.16-7.09 (m, 3H), 7.09-7.03 (m, 2H), 6.73 (d, J=4.8 Hz, 2H), 4.29 (d, J=2.3 Hz, 2H), 4.23 (dq, J=1.1, 7.2 Hz, 2H), 3.91-3.80 (m, 1H), 3.78-3.72 (m, 1H), 3.61-3.55 (m, 1H), 3.40-3.25 (m, 1H), 2.93-2.76 (m, 1H), 2.60 (br d, J=7.3 Hz, 1H), 2.45 (s, 3H), 2.17 (d, J=3.0 Hz, 6H), 1.28-1.24 (m, 3H).

Step 7: Compound 79-h

A solution of lithium hydroxide monohydrate (402.82 mg, 10.35 mmol, 3.00 eq) in water (4.00 mL) was added into a solution of Compound 79-g (1.80 g, 3.20 mmol, 1.00 eq) in tetrahydrofuran (10 mL) and ethanol (10 mL) at 0° C. The reaction mixture was stirred at 25° C. for 2 h. The reaction system was adjusted with a saturated aqueous solution of potassium bisulfate to pH=5-6, and extracted with ethyl acetate (20 mL×3). The combined organic phase was washed with water (10 mL×3) and saturated brine (10 mL×3), dried over anhydrous sodium sulfate, filtered, and concentrated under reduced pressure. The residue was purified by flash column chromatography (petroleum ether:ethyl acetate=100:0-80:20) to give Compound 79-h.

MS m/z (ESI): 534.1 [M+1].

$^1$H NMR (400 MHz, CDCl$_3$) δ ppm 7.63 (dd, J=1.5, 8.5 Hz, 2H), 7.33-7.25 (m, 2H), 7.18-7.02 (m, 5H), 6.75 (d, J=6.3 Hz, 1H), 6.79-6.72 (m, 1H), 4.34 (d, J=3.0 Hz, 2H), 3.93-3.83 (m, 1H), 3.75-3.56 (m, 3H), 3.40-3.23 (m, 1H), 2.98-2.78 (m, 1H), 2.71-2.52 (m, 2H), 2.46 (s, 3H), 2.16 (d, J=4.3 Hz, 6H).

Step 8: Compound 79

The raw material 79-h (250 mg, 468.48 mmol, 1.00 eq) was isolated by chiral supercritical chromatography to give Compound 79.

MS m/z (ESI): 534.1 [M+1].

$^1$H NMR (400 MHz, CDCl$_3$) δ ppm 7.62 (d, J=8.5 Hz, 2H), 7.30-7.22 (m, 2H), 7.16-7.08 (m, 3H), 7.04 (br d, J=8.0 Hz, 2H), 4.19 (br s, 1H), 4.27-4.07 (m, 1H), 3.93-3.78 (m, 1H), 3.74-3.48 (m, 3H), 3.37-3.17 (m, 1H), 2.95-2.74 (m, 1H), 2.68-2.46 (m, 2H), 2.43 (s, 3H), 2.09 (br d, J=5.0 Hz, 6H).

Conditions of the chiral resolution: chiral column: AD (250 mm×30 mm, 10 μm); mobile phase: [0.1% NH$_3$H$_2$O EtOH]; flow rate: 80 mL/min; column temperature: 40° C.

Retention time of Compound 79: 0.600 min (peak 1).

Example 80: Compound 80

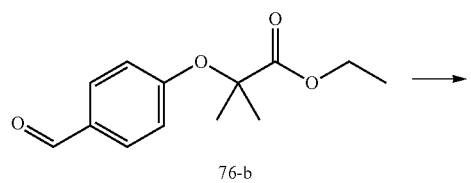

76-b

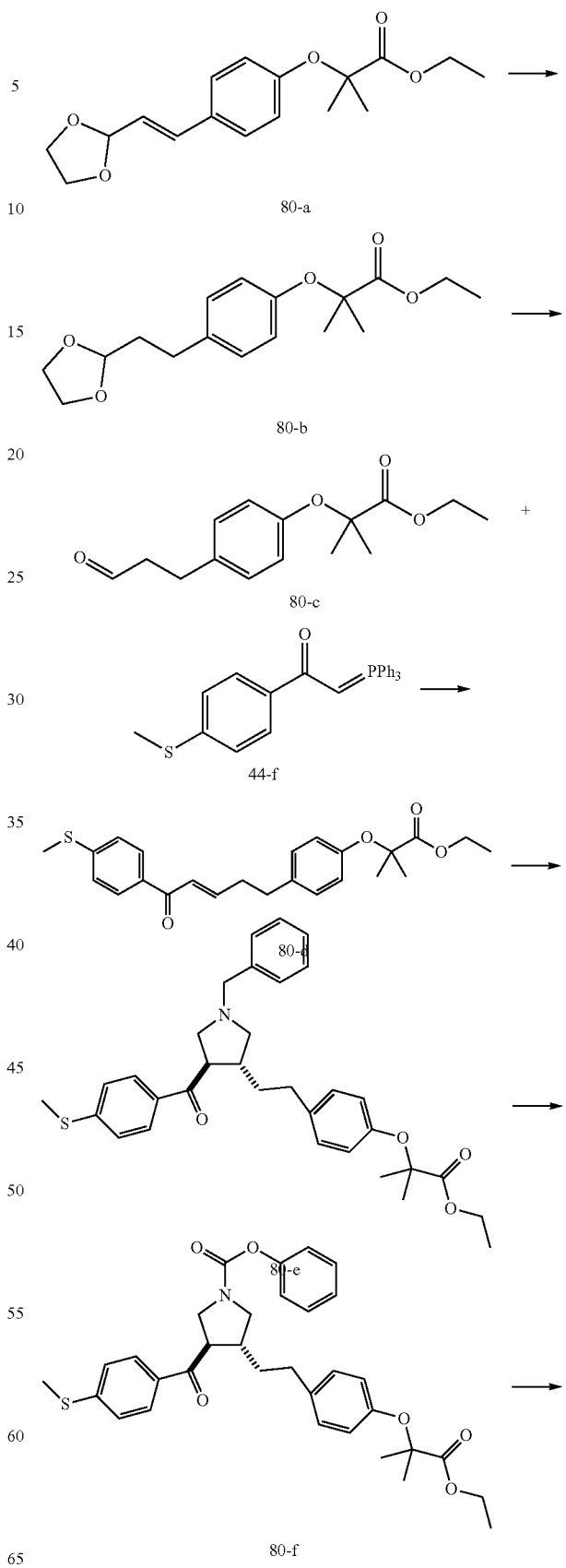

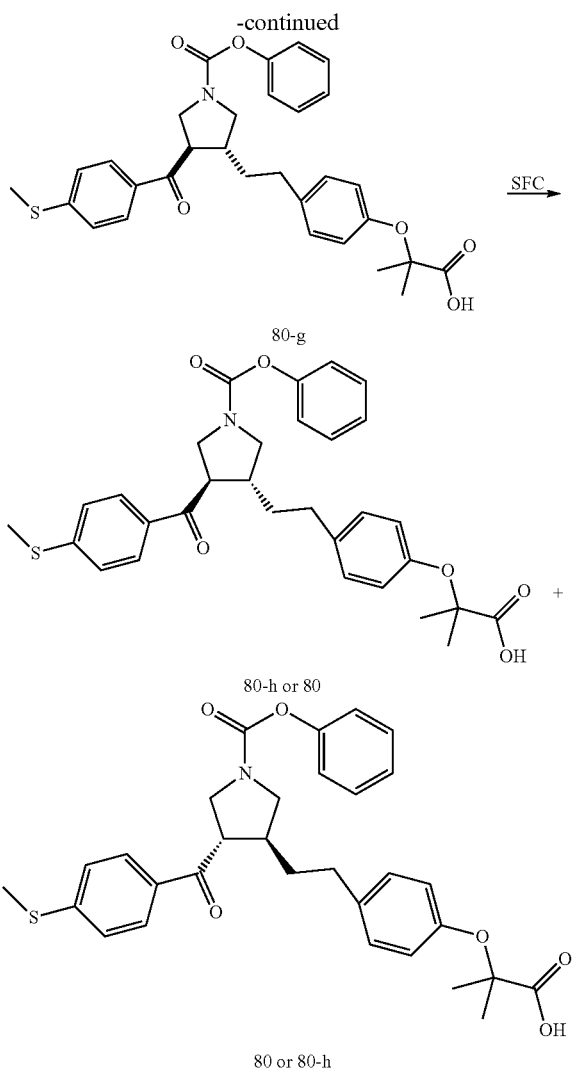

Step 1: Compound 80-a

A saturated aqueous solution of potassium carbonate (63.49 mmol, 100.00 mL, 1.00 eq) was added into a solution of Compound 76-b (15.00 g, 63.49 mmol, 1.00 eq), ((1,3-dioxolan-2-yl)methyl)triphenylphosphine bromide (35.43 g, 82.54 mmol, 1.30 eq), 2-(2-methoxyethoxy)-N,N-di[2-(2-methoxyethoxy) ethyl]ethylamine (14.37 g, 44.44 mmol, 0.70 eq) in dichloromethane (100.00 mL). The reaction system was stirred at 40° C. for 20 h. The reaction system was diluted with (dichloromethane/water=1:1, 200 mL). The aqueous phase was extracted with dichloromethane (300 mL×3), and the combined organic phase was washed with saturated brine (300 mL×1), dried over anhydrous sodium sulfate, filtered, and concentrated under reduced pressure. The residue was purified by flash column chromatography (petroleum ether:ethyl acetate=100:0-80:20) to give Compound 80-a.

$^1$H NMR (400 MHz, CDCl$_3$) δ ppm 7.24-7.17 (m, 2H), 6.75-6.69 (m, 2H), 6.67-6.59 (m, 1H), 6.00-5.53 (m, 1H), 5.47-5.30 (m, 1H), 4.15 (dq, J=4.0, 7.1 Hz, 2H), 4.07-3.82 (m, 4H), 1.53 (d, J=2.8 Hz, 6H), 1.20-1.12 (m, 3H).

Step 2: Compound 80-b

Under argon protection, palladium hydroxide (458.43 mg, 653.00 μmol, 20% purity, 0.05 eq) was added into a solution of Compound 80-a (4.00 g, 13.06 mmol, 1.00 eq) in ethanol (50.00 mL). The reaction system was stirred at 50° C. for 5 h in hydrogen (50 psi) atmosphere. The reaction mixture was filtered, and the filter cake was washed with ethyl acetate (3×100 mL). The combined organic phase was concentrated under reduced pressure to give Compound 80-b.

$^1$H NMR (400 MHz, CDCl$_3$) δ ppm 7.06 (d, J=8.5 Hz, 2H), 6.79-6.74 (m, 2H), 4.23 (q, J=7.3 Hz, 2H), 4.03-3.83 (m, 4H), 2.72-2.64 (m, 2H), 1.98-1.88 (m, 2H), 1.57 (s, 6H), 1.25 (t, J=7.2 Hz, 3H).

Step 3: Compound 80-c

A 2N aqueous HCl solution (18.00 mL) was added into a solution of Compound 80-b (3.00 g, 9.73 mmol, 1.00 eq) in tetrahydrofuran (18.00 mL). The reaction system was stirred at 70° C. for 3 h. Water (50 mL) was added into the mixture, and extracted with ethyl acetate (100 mL×3). The combined organic phase was washed with water (100 mL×3) and saturated brine (100 mL×3), dried over anhydrous sodium sulfate, filtered, and concentrated under reduced pressure to give Compound 80-c.

$^1$H NMR (400 MHz, CDCl$_3$) δ ppm 9.73 (s, 1H), 7.00-6.96 (m, 2H), 6.72-6.68 (m, 2H), 4.16 (q, J=7.0 Hz, 2H), 2.86-2.78 (m, 2H), 2.70-2.62 (m, 2H), 1.50 (s, 6H), 1.18 (t, J=7.2 Hz, 3H).

Step 4: Compound 80-d

Compound 44-f (3.07 g, 7.19 mmol, 1.00 eq) was added into a solution of Compound 80-c (1.90 g, 7.19 mmol, 1.00 eq) in tetrahydrofuran (20.00 mL), and the mixture was stirred at 50° C. for 16 h. The mixture was concentrated under reduced pressure, and the residue was purified by flash column chromatography (gradient elution: petroleum ether:ethyl acetate=100:0-90:10) to give Compound 80-d.

$^1$H NMR (400 MHz, CDCl$_3$) δ ppm 7.85-7.79 (m, 2H), 7.29-7.26 (m, 2H), 7.10-7.02 (m, 3H), 6.87-6.77 (m, 3H), 4.26-4.20 (m, 2H), 2.81-2.76 (m, 2H), 2.64-2.57 (m, 2H), 2.53 (s, 3H), 1.58 (s, 6H), 1.25 (t, J=7.2 Hz, 3H).

Step 5: Compound 80-e

Trifluoroacetic acid (23.49 mg, 206.04 μmol, 15.26 μL, 0.05 eq) was added into a solution of Compound 80-d (1.7 g, 4.12 mmol, 1.00 eq) and 1,4-dioxane (100 mL), and warmed to 80° C. Then, a solution of N-benzyl-1-methoxy-N-((trimethylsilyl)methyl)methylamine (2.93 g, 12.36 mmol, 3.00 eq) in 1,4-dioxane (10 mL) was slowly added dropwise into the reaction solution. After the completion of the addition, the reaction solution was stirred at 80° C. for 1 h. The mixture was concentrated under reduced pressure. The crude product was purified by flash column chromatography (petroleum ether:ethyl acetate=100:0-80:20) to give Compound 80-e.

$^1$H NMR (400 MHz, CDCl$_3$) δ ppm 7.87 (d, J=8.8 Hz, 2H), 7.34-7.29 (m, 5H), 7.26-7.24 (m, 2H), 6.96 (d, J=8.5 Hz, 2H), 6.72 (d, J=8.5 Hz, 2H), 4.13 (q, J=7.0 Hz, 2H), 3.71-3.53 (m, 4H), 3.05-2.98 (m, 1H), 2.92-2.78 (m, 2H), 2.69-2.61 (m, 1H), 2.52 (s, 3H), 2.48-2.40 (m, 2H), 1.81-1.71 (m, 2H), 1.56 (s, 6H), 1.26-1.22 (m, 3H).

Step 6: Compound 80-f

Phenyl chloroformate (2.30 g, 14.66 mmol, 1.84 mL, 5.00 eq) was added into a solution of Compound 80-e (1.60 g, 2.93 mmol, 1.00 eq) in chloroform (20.00 mL), and stirred at 70° C. for 16 h. The mixture was concentrated under reduced pressure, and the crude product was purified by flash column chromatography (petroleum ether:ethyl acetate=100:0-80:20) to give Compound 80-f.

¹H NMR (400 MHz, CDCl₃) δ ppm 7.88 (br dd, J=3.4, 8.4 Hz, 2H), 7.43-7.28 (m, 4H), 7.25-7.11 (m, 3H), 7.06-6.98 (m, 2H), 6.82-6.74 (m, 2H), 4.28-4.19 (m, 2H), 4.03-3.54 (m, 4H), 3.43-3.27 (m, 1H), 2.89-2.71 (m, 1H), 2.67-2.51 (m, 5H), 1.93-1.65 (m, 2H), 1.60-1.54 (m, 6H), 1.30-1.26 (m, 3H).

Step 7: Compound 80-g

A solution of lithium hydroxide (270.40 mg, 11.29 mmol, 5.00 eq) in water (2.00 mL) was added into a solution of Compound 80-f (1.30 g, 2.26 mmol, 1.00 eq) in ethanol (6.00 mL) and tetrahydrofuran (6.00 mL). The mixture was stirred at 40° C. for 4 h. The reaction system was adjusted with a saturated aqueous solution of potassium bisulfate to pH=5-6, and then was extracted with ethyl acetate (3×10 mL). The combined organic phase was successively washed with water (20 mL) and saturated brine (20 mL), dried over anhydrous sodium sulfate, and concentrated under reduced pressure to give a residue. The crude product was purified by High Performance Liquid Chromatography to give Compound 80-g.

MS m/z (ESI): 548.1 [M+1].

Step 8: Compound 80

Compound 80-g (400.00 mg, 0.73 mmol, 1.00 eq) was isolated by chiral supercritical chromatography to give Compound 80.

MS m/z (ESI): 548.1 [M+1].

¹H NMR (400 MHz, CDCl₃) δ ppm 7.87 (dd, J=5.4, 8.4 Hz, 2H), 7.39-7.27 (m, 4H), 7.23-7.10 (m, 3H), 7.08-7.02 (m, 2H), 6.86 (d, J=8.3 Hz, 2H), 4.03-3.53 (m, 4H), 3.42-3.15 (m, 1H), 2.87-2.66 (m, 1H), 2.64-2.56 (m, 2H), 2.53 (d, J=1.8 Hz, 3H), 1.93-1.62 (m, 2H), 1.57 (d, J=9.3 Hz, 6H).

Conditions of the chiral resolution: chiral column: AD (250 mm×30 mm, 10 μm); mobile phase: [0.1% NH₃H₂O EtOH]; flow rate: 80 mL/min; column temperature: 40° C.

Retention time of Compound 80: 2.054 min (peak 1).

Example 81: Compound 81

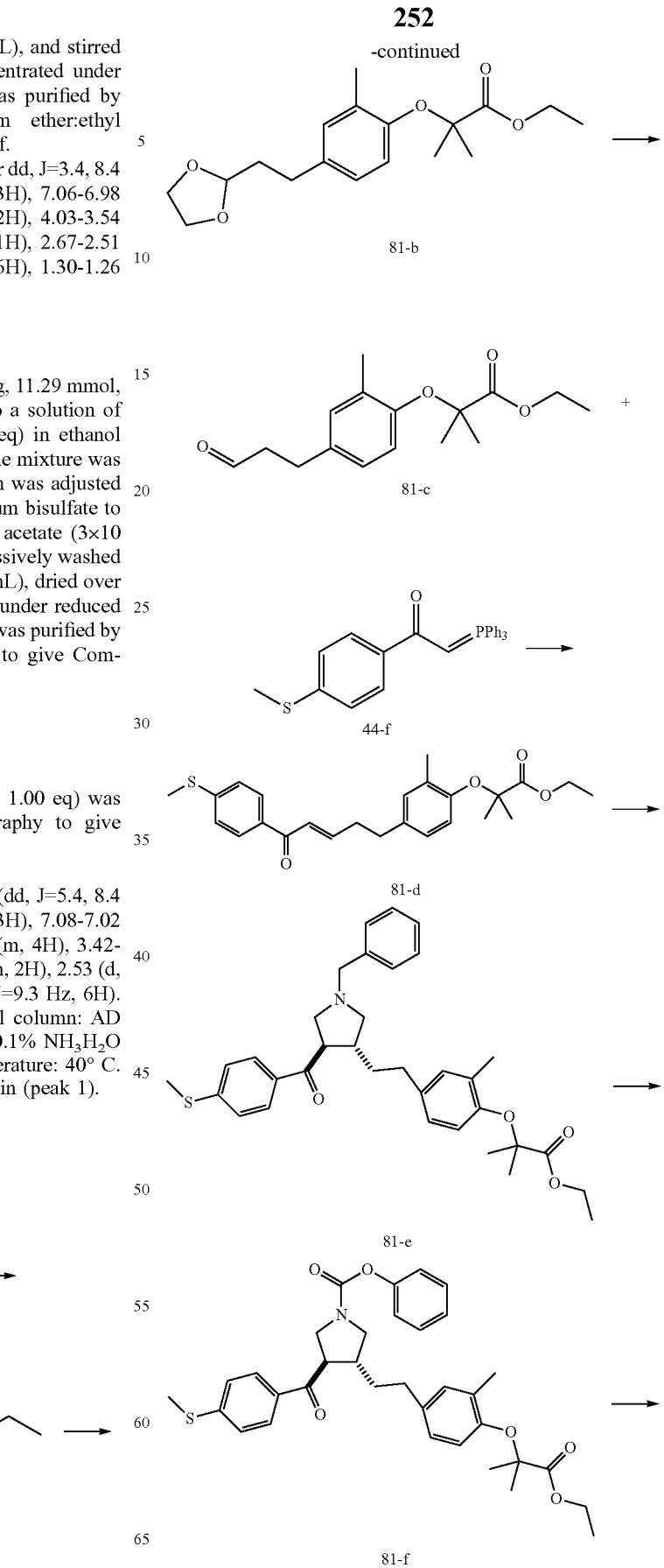

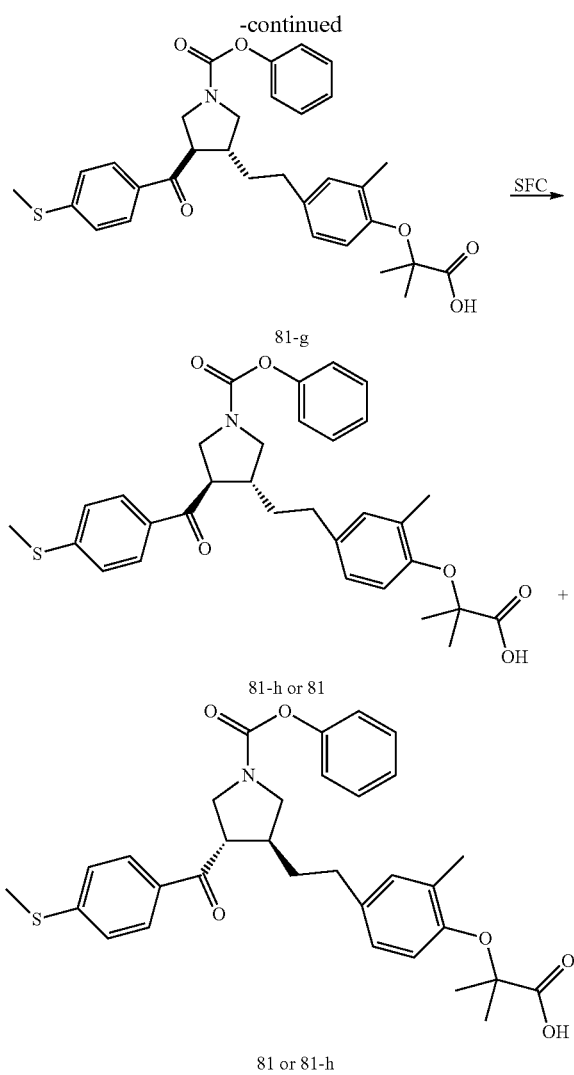

81-g 81-h or 81

81 or 81-h

Step 1: Compound 81-a

A saturated aqueous solution of potassium carbonate (79.91 mmol, 100.00 mL, 1.00 eq) was added into a solution of Compound 77-b (20.00 g, 79.91 mmol, 1.00 eq), ((1,3-dioxolan-2-yl)methyl)triphenylphosphine bromide (44.59 g, 103.88 mmol, 1.30 eq) and 2-(2-methoxyethoxy)-N,N-di[2-(2-methoxyethoxy) ethyl]ethylamine (8.09 g, 55.94 mmol, 17.91 mL, 0.70 eq) in dichloromethane (100.00 mL). The reaction system was stirred at 40° C. for 20 h. The reaction system was diluted with (dichloromethane/water=1:1, 200 mL). The aqueous phase was extracted with dichloromethane (300 mL×3), and the combined organic phase was washed with saturated brine (300 mL×1), dried over anhydrous sodium sulfate, filtered, and concentrated under reduced pressure. The residue was purified by flash column chromatography (petroleum ether:ethyl acetate=100:0-80:20) to give Compound 81-a.

$^1$H NMR (400 MHz, CDCl$_3$) δ ppm 7.24-7.08 (m, 2H), 6.73-6.57 (m, 2H), 6.11-5.35 (m, 2H), 4.30-4.22 (m, 2H), 4.07-3.91 (m, 4H), 2.22 (d, J=5.0 Hz, 3H), 1.60 (d, J=2.8 Hz, 6H), 1.29-1.24 (m, 3H).

Step 2: Compound 81-b

Under argon protection, palladium hydroxide (657.53 mg, 936.39 µmol, 20% purity, 0.05 eq) was added into a solution of Compound 81-a (6.00 g, 18.73 mmol, 1.00 eq) in ethanol (50.00 mL). The reaction system was stirred at 50° C. for 5 h in hydrogen (50 psi) atmosphere. The reaction mixture was filtered, and the filter cake was washed with ethyl acetate (3×100 mL). The combined organic phase was concentrated under reduced pressure to give Compound 81-b.

$^1$H NMR (400 MHz, CDCl$_3$) δ ppm 6.98 (d, J=1.8 Hz, 1H), 6.87 (dd, J=2.0, 8.3 Hz, 1H), 6.59 (d, J=8.3 Hz, 1H), 4.87 (t, J=4.8 Hz, 1H), 4.25 (q, J=7.1 Hz, 2H), 4.02-3.84 (m, 4H), 2.68-2.61 (m, 2H), 2.21 (s, 3H), 1.96-1.90 (m, 2H), 1.57 (s, 6H), 1.26 (t, J=7.2 Hz, 3H).

Step 3: Compound 81-c

An aqueous HCl solution (2 M, 24.00 mL) was added into a solution of Compound 81-b (4.50 g, 13.96 mmol, 1.00 eq) in tetrahydrofuran (24.00 mL) at 25° C. The mixture was stirred at 70° C. for 2 h. Water (50 mL) was added into the reaction system, and was extracted with ethyl acetate (100 mL×3). The combined organic phase was washed with water (100 mL) and saturated brine (100 mL), dried over anhydrous sodium sulfate, filtered, and concentrated under reduced pressure to give Compound 81-c.

$^1$H NMR (400 MHz, CDCl$_3$) δ ppm 9.81 (t, J=1.4 Hz, 1H), 6.97 (d, J=2.0 Hz, 1H), 6.85 (dd, J=2.0, 8.3 Hz, 1H), 6.59 (d, J=8.3 Hz, 1H), 4.28-4.23 (m, 2H), 2.89-2.82 (m, 2H), 2.76-2.70 (m, 2H), 2.21 (s, 3H), 1.58 (s, 6H), 1.26 (t, J=7.2 Hz, 3H).

Step 4: Compound 81-d

Compound 44-f (4.75 g, 11.14 mmol, 1.00 eq) was added into a solution of Compound 81-c (3.10 g, 11.14 mmol, 1.00 eq) in tetrahydrofuran (30.00 mL), and then was stirred at 50° C. for 16 h. The mixture was concentrated under reduced pressure, and the residue was purified by flash column chromatography (petroleum ether:ethyl acetate=100:0-90:10) to give Compound 81-d.

$^1$H NMR (400 MHz, CDCl$_3$) δ ppm 7.74 (d, J=8.3 Hz, 2H), 7.21-7.17 (m, 2H), 7.02-6.89 (m, 2H), 6.82-6.72 (m, 2H), 6.53 (d, J=8.3 Hz, 1H), 4.16 (q, J=7.1 Hz, 2H), 2.70-2.62 (m, 2H), 2.51 (q, J=7.3 Hz, 2H), 2.45 (s, 3H), 2.14 (s, 3H), 1.50 (s, 6H), 1.20-1.16 (m, 3H).

Step 5: Compound 81-e

Trifluoroacetic acid (40.09 mg, 351.50 µmol, 26.03 µL, 0.05 eq) was added into a solution of Compound 81-d (3.00 g, 7.03 mmol, 1.00 eq) in 1,4-dioxane (200 mL), and warmed to 80° C. Then, a solution of N-benzyl-1-methoxy-N-(((trimethylsilyl)methyl)methylamine (5.01 g, 21.09 mmol, 3.00 eq) in 1,4-dioxane (20 mL) was slowly added dropwise, and stirred at 80° C. for additional 1 h. The reaction mixture was concentrated under reduced pressure, and the crude product was purified by flash column chromatography (petroleum ether:ethyl acetate=100:0-80:20) to give Compound 81-e.

$^1$H NMR (400 MHz, CDCl$_3$) δ ppm 7.81 (d, J=8.5 Hz, 2H), 7.27-7.18 (m, 7H), 6.82 (d, J=1.8 Hz, 1H), 6.71 (dd, J=2.0, 8.3 Hz, 1H), 6.49 (d, J=8.3 Hz, 1H), 4.19 (q, J=7.0 Hz, 2H), 3.73-3.53 (m, 4H), 3.00-2.93 (m, 1H), 2.85-2.70

(m, 2H), 2.60 (dd, J=7.0, 9.3 Hz, 1H), 2.50-2.39 (m, 5H), 2.11 (s, 3H), 1.75-1.67 (m, 2H), 1.50 (s, 6H), 1.26-1.20 (m, 3H).

Step 6: Compound 81-f

Phenyl chloroformate (5.03 g, 32.15 mmol, 4.02 mL, 5.00 eq) was added into a solution of Compound 81-e (3.60 g, 6.43 mmol, 1.00 eq) in chloroform (40.00 mL), and stirred at 70° C. for 16 h. The reaction mixture was concentrated under reduced pressure. The crude product was purified by flash column chromatography (petroleum ether:ethyl acetate=100:0-80:20) to give Compound 81-f.
$^1$H NMR (400 MHz, CDCl$_3$) δ ppm 7.87 (dd, J=3.3, 8.5 Hz, 2H), 7.40-7.33 (m, 2H), 7.31-7.27 (m, 2H), 7.24-7.11 (m, 3H), 6.94-6.89 (m, 1H), 6.84-6.78 (m, 1H), 6.57 (dd, J=2.8, 8.3 Hz, 1H), 4.29-4.20 (m, 2H), 4.03-3.55 (m, 4H), 3.46-3.27 (m, 1H), 2.89-2.69 (m, 1H), 2.62-2.47 (m, 5H), 2.19 (s, 3H), 1.91-1.64 (m, 2H), 1.56 (s, 6H), 1.29-1.26 (m, 3H).

Step 7: Compound 81-g

A solution of lithium hydroxide (467.03 mg, 19.50 mmol, 5.00 eq) in water (3.00 mL) was added into a solution of Compound 81-f (2.30 g, 3.90 mmol, 1.00 eq) in ethanol (9.00 mL) and tetrahydrofuran (9.00 mL), and then was stirred at 40° C. for 4 h. The reaction system was adjusted with a saturated aqueous solution of potassium bisulfate to pH=5-6, and then the mixture was extracted with ethyl acetate (3×10 mL). The combined organic phase was successively washed with water (20 mL) and saturated brine (20 mL), dried over anhydrous sodium sulfate, and concentrated under reduced pressure to give a residue. The crude product was purified by High Performance Liquid Chromatography to give Compound 81-g.
MS m/z (ESI): 562.1 [M+1].

Step 8: Compound 81

Compound 81-g (400.00 mg, 712.14 μmol, 1.00 eq) was isolated by chiral supercritical chromatography to give Compound 81.
MS m/z (ESI): 562.1 [M+1].
$^1$H NMR (400 MHz, CDCl$_3$) δ ppm 7.91-7.85 (m, 2H), 7.40-7.28 (m, 4H), 7.24-7.08 (m, 3H), 6.99-6.73 (m, 3H), 4.01-2.98 (m, 6H), 2.87-2.61 (m, 2H), 2.54 (d, J=1.5 Hz, 3H), 2.21 (d, J=3.5 Hz, 3H), 1.94-1.67 (m, 2H), 1.65-1.54 (m, 6H).
Conditions of the chiral resolution: chiral column: AD (250 mm×30 mm, 10 μm); mobile phase: [0.1% NH$_3$H$_2$O EtOH]; flow rate: 60 mL/min; column temperature: 40° C.
Retention time of Compound 81: 1.187 min (peak 1).

Example 82: Compound 82

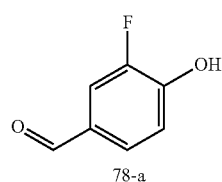
78-a

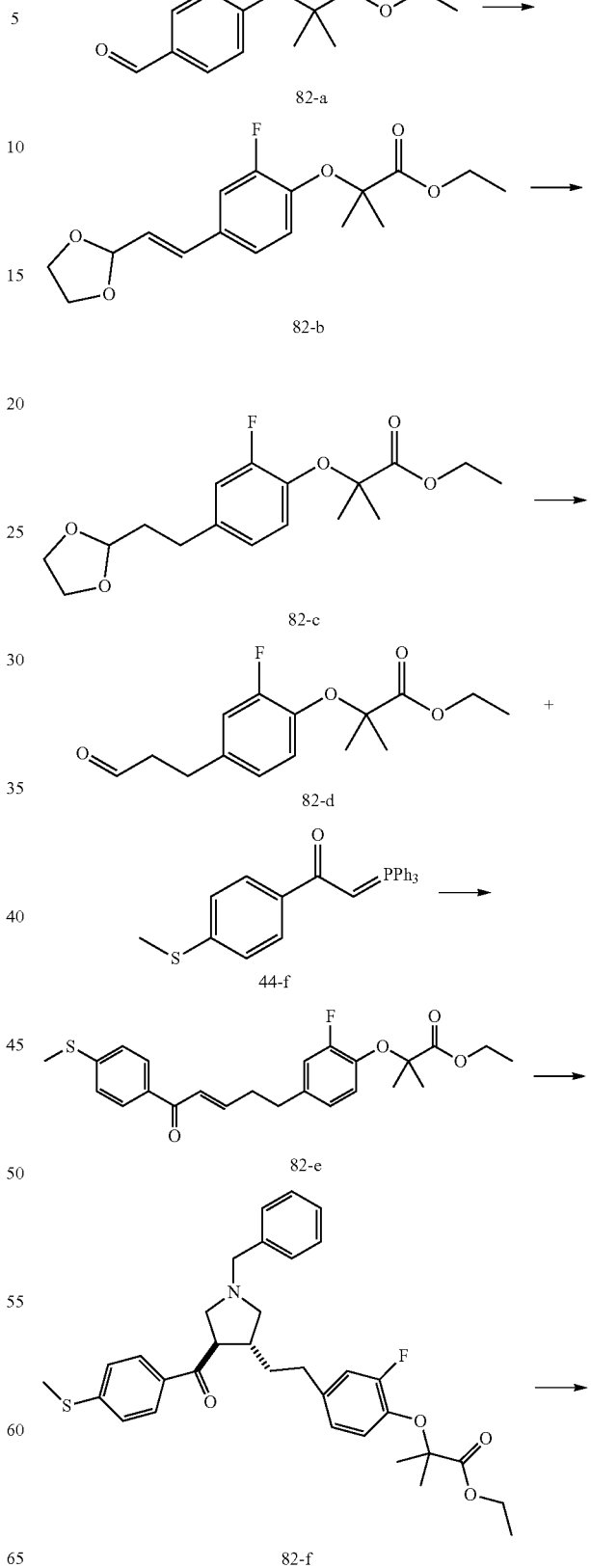

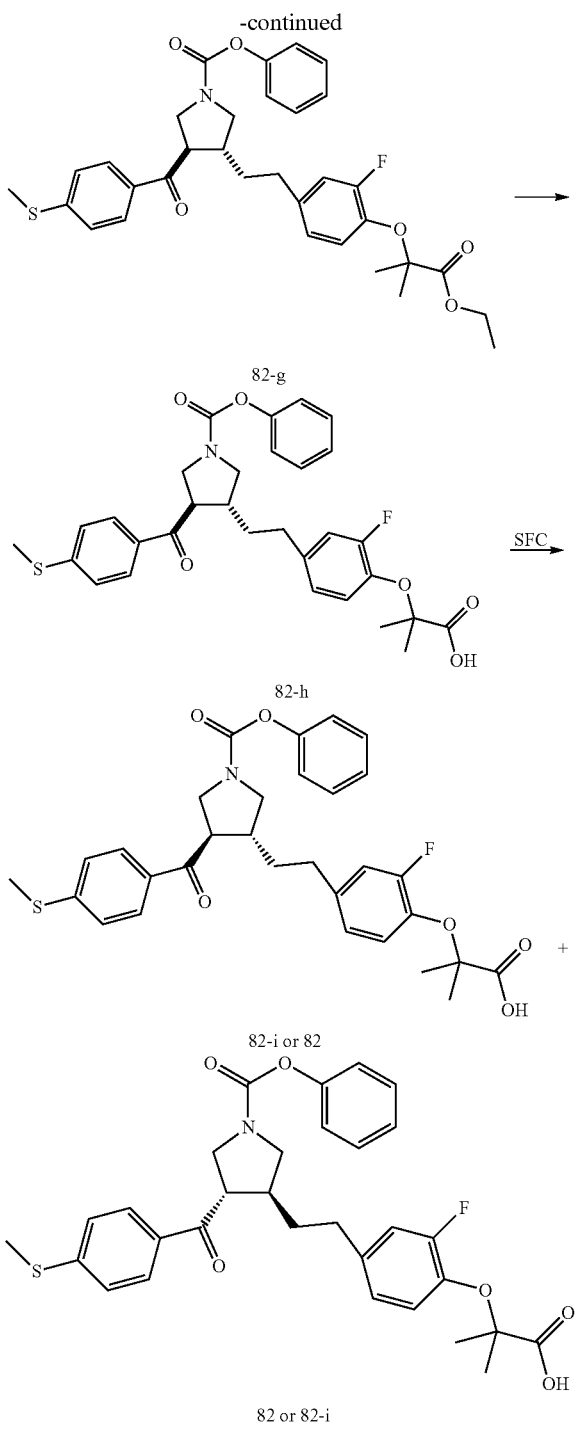

82-g 82-h 82-i or 82

82 or 82-i

Step 1: Compound 82-a

A saturated potassium carbonate solution (83.00 mL) was added into a solution of Compound 78-a (40.00 g, 157.33 mmol, 1.00 eq), ((1,3-dioxolan-2-yl)methyl)triphenylphosphine bromide (33.77 g, 78.67 mmol, 0.50 eq) and 2-(2-methoxyethoxy)-N,N-di[2-(2-methoxyethoxy) ethyl]ethylamine (17.81 g, 55.07 mmol, 17.63 mL, 0.35 eq) in dichloromethane (83.00 mL). The mixture was stirred at 40° C. for 20 h. The reaction system was diluted with (dichloromethane/water=1:1, 500 mL). The aqueous phase was extracted with dichloromethane (100 mL×3), and the combined organic phase was washed with saturated brine (100 mL×1), dried over anhydrous sodium sulfate, filtered, and concentrated under reduced pressure. The residue was purified by flash column chromatography (petroleum ether:ethyl acetate=100:0-80:20) to give Compound 82-a.

MS m/z (ESI): 325.1 [M+1].

$^1$H NMR (400 MHz, CDCl$_3$) δ 7.04-7.11 (m, 1H), 6.93-6.98 (m, 1H), 6.84 (q, J=8.28 Hz, 1H), 6.54-6.63 (m, 1H), 5.57-6.01 (m, 1H), 5.29-5.44 (m, 1H), 4.17 (dq, J=3.51, 7.11 Hz, 2H), 3.95-4.01 (m, 2H), 3.83-3.89 (m, 2H), 1.52 (d, J=3.51 Hz, 6H), 1.19-1.24 (m, 3H)

Step 2: Compound 82-b

Under argon protection, palladium hydroxide (1.30 g, 1.85 mmol, 20% purity, 0.10 eq) was added into a solution of Compound 82-a (6.00 g, 18.50 mmol, 1.00 eq) in ethanol (30.00 mL). The mixture was stirred at 50° C. for 16 h in hydrogen (50 psi) atmosphere. The reaction mixture was filtered, and the filter cake was washed with ethyl acetate (3×10 mL). The combined filtrate was concentrated under reduced pressure to give Compound 82-b.

MS m/z (ESI): 349.1 [M+23].

$^1$H NMR (400 MHz, CDCl$_3$) δ 6.72-6.89 (m, 3H), 4.80 (t, J=4.64 Hz, 1H), 4.17 (q, J=7.28 Hz, 2H), 3.88-3.93 (m, 2H), 3.76-3.82 (m, 2H), 2.56-2.66 (m, 2H), 1.81-1.91 (m, 2H), 1.43-1.53 (m, 6H), 1.21 (t, J=7.03 Hz, 3H).

Step 3: Compound 82-c

An aqueous HCl solution (2 M, 28.34 mL, 3.70 eq) was added into a solution of Compound 82-b (5.00 g, 15.32 mmol, 1.00 eq) in tetrahydrofuran (28.34 mL). The mixture was stirred at 70° C. for 3 h. Water (50 mL) was added into the mixture, and extracted with ethyl acetate (100 mL×3). The combined organic phase was washed with water (100 mL) and saturated brine (100 mL), dried over anhydrous sodium sulfate, filtered, and concentrated under reduced pressure to give Compound 82-c.

$^1$H NMR (400 MHz, CDCl$_3$) δ 9.73 (t, J=1.13 Hz, 1H), 6.79-6.87 (m, 2H), 6.73-6.77 (m, 1H), 4.17 (q, J=7.11 Hz, 2H), 2.79-2.84 (m, 2H), 2.66-2.72 (m, 2H), 1.49 (s, 6H), 1.19-1.24 (m, 3H).

Step 4: Compound 82-d

Compound 44-f (6.65 g, 15.59 mmol, 1.00 eq) was added into a solution of Compound 82-c (4.40 g, 15.59 mmol, 1.00 eq) in tetrahydrofuran (40.00 mL), and then was stirred at 50° C. for 5 h. The reaction mixture was concentrated under reduced pressure, and the residue was purified by flash column chromatography (petroleum ether:ethyl acetate=100:0-60:40) to give Compound 82-d.

MS m/z (ESI): 431.1 [M+1].

$^1$H NMR (400 MHz, CDCl$_3$) δ 7.70-7.77 (m, 2H), 7.15-7.22 (m, 2H), 6.96 (td, J=6.78, 15.31 Hz, 1H), 6.72-6.88 (m, 4H), 4.17 (q, J=7.28 Hz, 2H), 2.66-2.72 (m, 2H), 2.48-2.57 (m, 2H), 2.45 (s, 3H), 1.49 (s, 6H), 1.18-1.23 (m, 3H).

Step 5: Compound 82-e

Trifluoroacetic acid (58.26 mg, 511.00 μmol, 37.83 μL, 0.05 eq) was added into a solution of Compound 82-d (4.40 g, 10.22 mmol, 1.00 eq) in 1,4-dioxane (120 mL), and warmed to 80° C. Then, a solution of N-benzyl-1-methoxy-N-((trimethylsilyl)methyl)methylamine (7.28 g, 30.66 mmol, 7.84 mL, 3.00 eq) was added dropwise into the reaction mixture, followed by stirring for additional 30 min. The mixture was concentrated under reduced pressure, and the residue was purified by flash column chromatography (petroleum ether:ethyl acetate=100:0-60:40) to give Compound 82-e.

MS m/z (ESI): 564.1 [M+1].

$^1$H NMR (400 MHz, CDCl$_3$) δ 7.72 (d, J=8.53 Hz, 2H), 7.01-7.17 (m, 7H), 6.53-6.76 (m, 3H), 4.09 (q, J=7.19 Hz, 2H), 3.37-3.46 (m, 2H), 2.83-2.91 (m, 1H), 2.62-2.74 (m, 2H), 2.49 (dd, J=7.15, 9.16 Hz, 1H), 2.36-2.40 (m, 1H), 2.37 (s, 2H), 2.22-2.34 (m, 2H), 1.58-1.66 (m, 2H), 1.36-1.42 (m, 6H), 1.14 (t, J=7.15 Hz, 3H).

Step 6: Compound 82-f

Phenyl chloroformate (1.25 g, 7.98 mmol, 999.54 μL, 3.00 eq) was added into a solution of Compound 82-e (1.50 g, 2.66 mmol, 1.00 eq) in chloroform (10.00 mL), and then was stirred at 70° C. for 16 h. The reaction solution was concentrated under reduced pressure, and the residue was purified by flash column chromatography (petroleum ether: ethyl acetate=100:0-70:30) to give Compound 82-f.

MS m/z (ESI): 594.2 [M+1].

Step 7: Compound 82-g

Compound 82-f (1.10 g, 1.85 mmol, 1.00 eq), lithium hydroxide (443.08 mg, 18.50 mmol, 10.00 eq) and ethanol (10.00 mL), water (5.00 mL) was added into a round-bottom flask at 20° C., and then stirred at 30° C. for 3 h. A saturated aqueous solution of potassium bisulfate was added dropwise into the reaction system to pH=5. Water (10 mL) was added into the mixture, and extracted with ethyl acetate (10 mL×3). The organic phases were combined and washed with saturated brine (10 mL×3), dried over anhydrous sodium sulfate, and concentrated under reduced pressure. The residue was purified by preparative High Performance Liquid Chromatography to give Compound 82-g.

MS m/z (ESI): 566.2 [M+1].

Step 8: Compound 82

Compound 82-g (500.00 mg, 883.94 μmol, 1.00 eq) was isolated by chiral supercritical chromatography to give Compound 82.

MS m/z (ESI): 566.0 [M+1].

$^1$H NMR (400 MHz, CDCl$_3$) δ 7.74-7.83 (m, 2H), 6.98-7.32 (m, 8H), 6.63-6.90 (m, 3H), 3.61-3.95 (m, 3H), 3.39-3.60 (m, 1H), 3.04-3.32 (m, 1H), 2.56-2.79 (m, 1H), 2.37-2.53 (m, 5H), 1.49-1.82 (m, 2H), 1.39 (br d, J=7.53 Hz, 6H).

Conditions of the chiral resolution: chiral column: Chiralpak AD-3 100×4.6 mm I.D., 3 μm; mobile phase: 40% of iso-propanol (0.05% DEA) in CO$_2$; flow rate: 2.8 mL/min; column temperature: 40° C.

Retention time of Compound 82: 2.772 min (peak 1).

Example 83: Compound 83

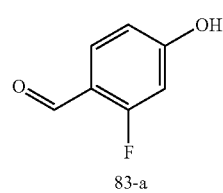

83-a

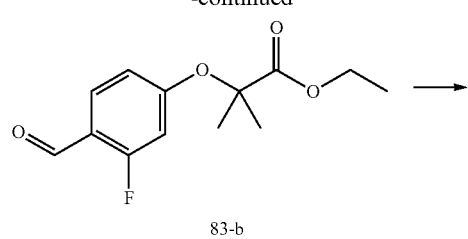

83-b

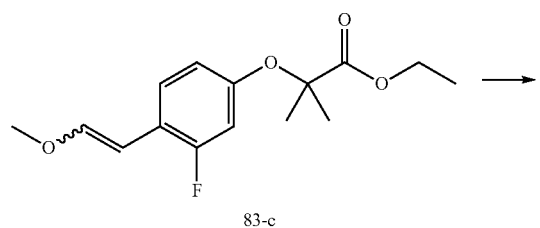

83-c

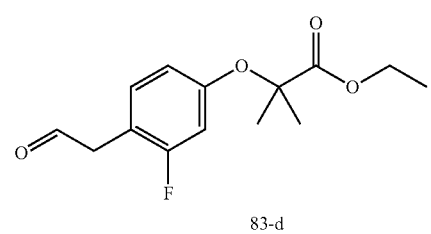

83-d

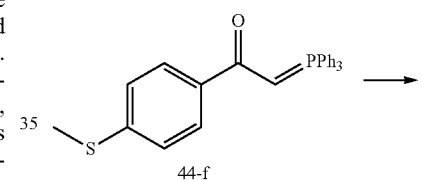

44-f

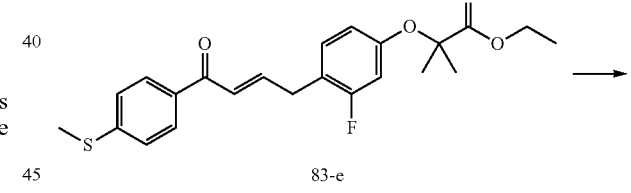

83-e

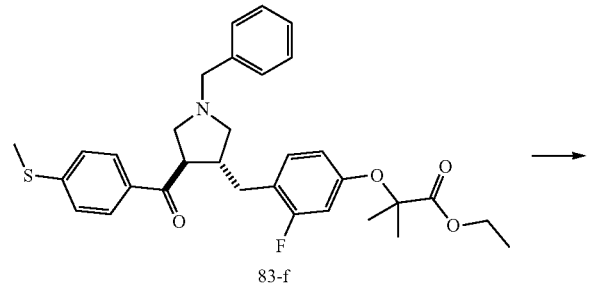

83-f

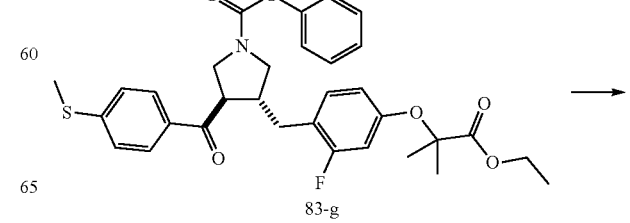

83-g

-continued

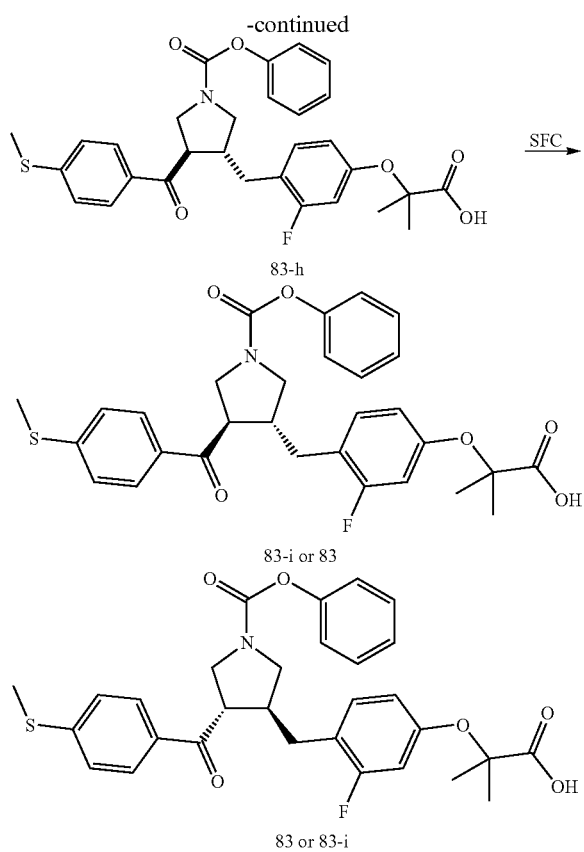

83-h 83-i or 83

83 or 83-i

Step 1: Compound 83-b

Cesium carbonate (52.32 g, 160.59 mmol, 1.50 eq) and ethyl 2-bromo-isoburtrate (52.21 g, 267.65 mmol, 39.25 mL, 2.50 eq) was added into a solution of Compound 83-a (15.00 g, 107.06 mmol, 1.00 eq) in N,N-dimethylformamide (150.00 mL). The mixture was stirred at 90° C. for 2 h. The reaction mixture was extracted with ethyl acetate (200 mL) and water (300 mL). After phase separation, the organic phases were collected, and the aqueous phase was extracted with ethyl acetate (100 mL×3), and the combined organic phase was washed with an 1N solution of sodium hydroxide (100 mL) and a saturated solution of potassium bisulfate (50 mL), dried over anhydrous sodium sulfate, and concentrated under reduced pressure to give Compound 83-b.

MS m/z (ESI): 254.9 [M+1].
$^1$H NMR (400 MHz, CDCl$_3$) δ ppm 10.20 (s, 1H), 7.77 (t, J=8.5 Hz, 1H), 6.66 (dd, J=2.5, 8.8 Hz, 1H), 6.55 (dd, J=2.3, 12.3 Hz, 1H), 4.24 (q, J=7.0 Hz, 2H), 1.67 (s, 6H), 1.23 (t, J=7.2 Hz, 3H).

Step 2: Compound 83-c

Potassium tert-butoxide (10.29 g, 91.74 mmol, 1.50 eq) was added into a solution of methoxymethyl triphenylphosphine chloride (27.26 g, 79.51 mmol, 1.30 eq) in tetrahydrofuran (200.00 mL) in batches at 20° C. The mixed solution was reacted for 1 h, and Compound 83-b (15.55 g, 61.16 mmol, 1.00 eq) was added. The mixture was stirred at 20° C. for 1 h. Sodium borohydride (2.00 g, 52.87 mmol, 0.86 eq) was added into the reaction system, which was subsequently quenched by adding water (50 ml). Next, the reaction system was extracted with ethyl acetate (100 ml) and water (100 ml). After phase separation, the organic phases were collected, and the aqueous phase was extracted with ethyl acetate (3×50 mL). The organic phases were combined and dried over anhydrous sodium sulfate, and concentrated under reduced pressure to give a residue. The crude product was purified by flash column chromatography (petroleum ether:ethyl acetate=100:0-70:30) to give Compound 83-c.

MS m/z (ESI): 282.9 [M+1].
$^1$H NMR (400 MHz, CDCl$_3$) δ ppm 7.95-7.32 (m, 1H), 7.15-7.03 (m, 1H), 6.61-6.15 (m, 2H), 5.81-5.36 (m, 1H), 4.24 (dq, J=2.1, 7.2 Hz, 2H), 3.79-3.67 (m, 3H), 1.59 (s, 6H), 1.26 (dt, J=1.5, 7.2 Hz, 3H).

Step 3: Compound 83-d

Compound 83-c (8.84 g, 31.31 mmol, 1.00 eq) was added into a dry reaction flask, and then chloroform (100.00 mL) was added. Next, oxalyl chloride (7.95 g, 62.62 mmol, 5.48 mL, 2.00 eq) was slowly added into the reaction system under nitrogen protection at 0° C., and then ethanol (2.88 g, 62.62 mmol, 3.65 mL, 2.00 eq), water (1.13 g, 62.62 mmol, 1.13 mL, 2.00 eq) were added into the mixture solution. The mixed solution was stirred 0° C. for 1 h. A saturated aqueous sodium carbonate solution was added dropwise into the reaction system to pH=7-8. The reaction system was extracted with dichloromethane (100 ml) and water (100 ml). After phase separation, the organic phases were collected, and the aqueous phase was extracted with ethyl acetate (3×50 mL). The organic phases were combined and were successively washed with water (3×50 mL) and saturated brine (3×50 mL), dried over anhydrous sodium sulfate, and concentrated under reduced pressure to give Compound 83-d.

$^1$H NMR (400 MHz, CDCl$_3$) δ ppm 9.71 (q, J=1.8 Hz, 1H), 7.72-7.42 (m, 1H), 7.07-7.00 (m, 1H), 6.65-6.61 (m, 1H), 4.24 (q, J=7.1 Hz, 2H) 3.65 (s, 2H), 1.61 (s, 6H), 1.25 (t, J=7.2 Hz, 3H)

Step 4: Compound 83-e

Compound 83-d (6.86 g, 25.57 mmol, 1.00 eq), Compound 44-f (10.91 g, 25.57 mmol, 1.00 eq) was added into a dried reaction flask, and then tetrahydrofuran (100.00 mL) was added. The mixture was stirred at 50° C. for 16 h. The reaction solution was concentrated under reduced pressure to give a crude product. The crude product was purified by flash column chromatography (petroleum ether:ethyl acetate=100:0-60:40) to give Compound 83-e.

MS m/z (ESI): 417.1 [M+1].
$^1$H NMR (400 MHz, CDCl$_3$) δ ppm 7.85-7.72 (m, 2H), 7.29-7.16 (m, 3H), 7.08-6.94 (m, 1H), 6.76 (d, J=15.3 Hz, 1H), 6.57-6.47 (m, 2H), 4.19-4.14 (m, 2H), 3.82-3.77 (m, 1H), 3.50 (d, J=6.5 Hz, 1H), 2.46-2.43 (m, 3H), 1.54-1.51 (m, 6H), 1.21-1.16 (m, 3H).

Step 5: Compound 83-f

Compound 83-e (3.69 g, 8.86 mmol, 1.00 eq) was added into a dried reaction flask, and then 1,4-dioxane (150.00 mL) was added. Next, trifluoroacetic acid (50.51 mg, 443.00 μmol, 0.05 eq) was added into the reaction system, and then N-benzyl-1-methoxy-N-((trimethylsilyl)methyl)methylamine (6.31 g, 26.58 mmol, 3.00 eq) dissolved in 1,4-dioxane (30.00 mL) was added into the mixed solution at a rate of 1 drop per two seconds. The mixed solution was stirred at 100° C. for 2 h. The reaction mixture was concentrated under reduced pressure to give a crude product. The crude product was purified by flash column chromatography (petroleum ether:ethyl acetate=100:0-60:40) to give Compound 83-f.

MS m/z (ESI): 550.1 [M+1].

$^1$H NMR (400 MHz, CDCl$_3$) δ ppm 7.65 (d, J=8.5 Hz, 2H), 7.25 (br d, J=2.0 Hz, 2H), 7.19-7.11 (m, 5H), 6.93-6.84 (m, 1H), 6.41-6.35 (m, 2H), 4.05 (q, J=7.0 Hz, 2H), 3.61-3.52 (m, 3H), 3.04-2.95 (m, 2H), 2.71-2.59 (m, 3H), 2.55-2.46 (m, 2H), 2.43 (s, 3H), 1.44 (d, J=4.0 Hz, 6H), 1.20-1.17 (m, 3H).

Step 6: Compound 83-g

Compound 83-f (1.85 g, 3.37 mmol, 1.00 eq) and chloroform (30.00 mL) was added into a dried reaction flask. Then, phenyl chloroformate (2.64 g, 16.85 mmol, 2.11 mL, 5.00 eq) was slowly added. The mixed solution was stirred at 70° C. for 16 h. The reaction solution was concentrated under reduced pressure to give a crude product. The crude product was purified by flash column chromatography (petroleum ether:ethyl acetate=100:0-85:15) to give Compound 83-g.

MS m/z (ESI): 580.2 [M+1].

$^1$H NMR (400 MHz, CDCl$_3$) δ ppm 7.68 (t, J=7.8 Hz, 2H), 7.39-7.33 (m, 2H), 7.25-7.13 (m, 5H), 7.04 (t, J=8.8 Hz, 1H), 6.61-6.53 (m, 2H), 4.24 (dq, J=2.0, 7.1 Hz, 2H), 3.99-3.90 (m, 1H), 3.85-3.61 (m, 3H), 3.51-3.36 (m, 1H), 3.01-2.86 (m, 1H), 2.79 (br d, J=5.8 Hz, 2H), 2.53 (s, 3H), 1.60 (d, J=4.3 Hz, 6H), 1.26 (s, 3H)

Step 7: Compound 83-h

Compound 83-g (328.00 mg, 565.83 μmol, 1.00 eq) was added into a dried reaction flask, and then ethanol (15.00 mL) was added. Next, lithium hydroxide (135.52 mg, 5.66 mmol, 10.00 eq) and water (5.00 mL) were added into the reaction system, and the mixed solution was stirred at 20° C. for 16 h. A saturated aqueous solution of potassium bisulfate was added dropwise into the reaction system to pH=6. The reaction mixture was extracted with ethyl acetate (20 mL) and water (20 mL). After phase separation, the organic phases were collected, and the aqueous phase was extracted with ethyl acetate (3×10 mL). The organic phases were combined and dried over anhydrous sodium sulfate, and concentrated under reduced pressure to give a residue. The crude product was purified by flash column chromatography (petroleum ether:ethyl acetate=100:0-60:40) to give Compound 83-h.

MS m/z (ESI): 552.1 [M+1].

Step 8: Compound 83

Compound 83-h (195.00 mg, 353.50 μmol, 1.00 eq) was isolated by chiral supercritical chromatography to give Compound 83.

MS m/z (ESI): 552.1 [M+1].

$^1$H MR (400 MHz, CDCl$_3$) δ ppm 7.66 (br dd, J=5.4, 8.2 Hz, 2H), 7.39-7.32 (m, 2H), 7.25-7.18 (m, 3H), 7.13 (br d, J=7.8 Hz, 2H), 7.08-7.00 (m, 1H), 6.63 (br s, 2H), 4.00-3.62 (m, 4H), 3.51-3.32 (m, 1H), 2.97-2.86 (m, 1H), 2.81-2.69 (m, 2H), 2.51 (s, 3H), 1.57 (br s, 6H)

Conditions of the chiral resolution: chiral column: AD (250 mm×30 mm, 10 μm); mobile phase: 40% of methanol (0.05% DEA) in CO$_2$; flow rate: 80 mL/min; column temperature: 40° C.

Retention time of Compound 83: 0.546 min (peak 1).

Experimental Example 1: In Vitro Evaluation

In Vitro Testing Principles of PPAR Agonist Activity
Cell Nuclear Hormon Receptor (NHR) Test PathHunter's NHR protein interaction and nuclear translocation test is used to detect the activation ability of a cell nuclear hormone receptor in uniform, non-imaging experiments. This technology is called Enzyme Fragmentation Complementation (ETC), and developed by DiscoverX.

NHR protein test is based on the detection of protein-protein interaction between a standard-length of NHR protein in an activated state, and a nuclear fusion protein containing a steroid receptor co-activation peptide (SRCP) region and one or more standard LXXLL acting sequence(s).

NHR is labeled on the ProLink™ component of the EFC test system, meanwhile the SRCP region and the enzyme acceptor (EA) component are fused and expressed in a nucleus. When bound with a ligand, NHR will be translocated to the nucleus and obtain the SRCP region, in which a complementatory effect would be produced, resulting in one equivalent of activated galactosidase (-Gal), accompanied with chemiluminescent signals. The benefits associated with this pathway include reduced incubation time of compounds, direct test of NHR targets, use of a standard length of human NHR sequences, and selection of some novel types of compounds based on disrupting protein-protein interaction.

NHR NT test detects the translocation of NHR between cytoplasm and nuclear compartments. The receptor is labeled on the ProLink™ component of the EFC test system, meanwhile EA is fused with nuclear sequences, thereby limiting the expression of EA in nuclei. The translocation of NHR to nuclei results in the complementation with EA, which produces one equivalent of activated galactosidase, accompanied with the generation of chemiluminescent signals.

Treatment of Cells:
1. A PathHunter NHR cell strain was expanded from a frozen stock in accordance with a standard procedure.
2. Cells were seeded in a white 384-well plate at 20 μL/well, and incubated at 37° C. for a proper period of time followed by the test. The culture medium contained activated Charcoal/Dextran in which serum was filtered and removed to decrease the level of hormone expression.

Agonist Experiment Procedure:
1. For testing the agonist activity, the cells were required to be incubated with a compound to induce a response.
2. The compound was formulated with a buffer solution to obtain a stock solution, which would be diluted 5×.
3. 5 μL of 5×-diluted solution of the compound was added to the cells, and then the cells were incubated at 37° C. (or room temperature) for 3-16 h. The final medium concentration should be ensured to be 1%.

Inhibitor Experiment Procedure:
1. For testing the inhibitor activity, cells were required to be pre-incubated with an antagonist, and then challenged with an agonist at the EC$_{80}$ concentration.
2. The compound was formulated with a buffer solution to obtain a stock solution, which would be diluted 5×.
3. 5 μL of 5×-diluted solution of the compound was added to the cells, and then the cells were incubated at 37° C. (or room temperature) for 60 min. The final medium concentration should be ensured to be 1%.

4. 5 μL of $EC_{80}$ agonist, which was 6× diluted with a buffer solution, was added to the cells, and incubated at 37° C. (or room temperature) for 3-16 h.

Test of Signals:

1. Experimental signals were generated by 12.5 μL or 15 μL of (50% v/v) a PathHunter test reagent mixture which was added at one time and subsequently incubated at room temperature for 1 h.
2. The chemiluminescent signals generated in the microplate was detected by a PerkinElmer Envision Instrument.

Data Analysis:

1. The activity of compounds is analyzed by CIBS Data Analysis Software (ChemInnovation, CA).
2. With respect to the experiments of the agonist procedure, the percent activity is calculated in accordance with the following equation:

% Activity=100%×(RLU mean of the tested compound−Background RLU mean of medium)/(Maximum control mean of the ligand−Background RLU mean of the medium)

3. For the experiments of antagonist procedure, the percent activity is calculated in accordance with the following equation:

% Inhibition=100%×(1−(RLU mean of the tested compound−Background RLU mean of the medium)/(RLU mean of $EC_{80}$ control compound−Background RLU mean of medium))

4. It should be noted that the response of the ligand will cause a reduced activity of the receptor (inverse agonists having a continuously active target). The activity of these inverse agonists is calculated in accordance with the following equation:

% inverse agonist activity=100%×((Background RLU mean of the medium−RLU mean of the tested compound)/(Background RLU mean of the medium−Maximum control RLU mean of the ligand))

The experimental results are shown in Table 1:

TABLE 1

Results of in vitro screening experiments of the compounds of the present invention

| Compounds | PPAR Alpha | | PPAR Delta | | PPAR Gamma | |
|---|---|---|---|---|---|---|
| | $EC_{50}$ nM | Maximum Activation Response % | $EC_{50}$ nM | Maximum Activation Response % | $EC_{50}$ nM | Maximum Activation Response % |
| GW7647 | A | 100% | / | / | / | / |
| L-165,041 | / | / | A | 100% | / | / |
| Troglitazone | / | / | / | / | E | 100% |
| GFT-505 (Elafibranor) | E | I | C | II | E | II |
| Compound 1 (rac-) | E | III | / | / | / | / |
| Compound 2 (rac-) | E | III | / | / | / | / |
| Compound 3 (rac-) | E | III | / | / | / | / |
| Compound 4 (*) | E | III | / | / | / | / |
| Compound 5 (*) | E | I | B | II | E | III |
| Compound 6 (*) | E | II | / | / | / | / |
| Compound 7 (*) | E | II | E | II | / | / |
| Compound 8 (*) | E | II | / | / | / | / |
| Compound 9 (*) | E | I | / | / | / | / |
| Compound 10 (*) | E | III | / | / | / | / |
| Compound 11 (*) | D | I | C | II | E | I |
| Compound 12 (rac-) | C | I | E | II | | |
| Compound 13 (*) | A | II | A | II | E | I |
| Compound 14 (*) | A | II | A | II | E | I |
| Compound 15 (rac-) | C | I | D | II | / | / |
| Compound 16 (*) | E | I | / | / | / | / |
| Compound 17 (*) | E | I | / | / | / | / |
| Compound 18 (*) | D | I | E | II | / | / |
| Compound 19 (*) | D | I | E | II | / | / |
| Compound 20 (*) | D | II | E | II | / | / |
| Compound 21 (*) | E | I | E | II | / | / |
| Compound 22 (*) | E | III | / | / | / | / |
| Compound 23 (*) | E | III | / | / | / | / |
| Compound 24 (*) | E | I | E | I | / | / |
| Compound 25 (*) | A | I | A | II | E | I |
| Compound 26 (*) | A | I | A | II | E | I |
| Compound 27 (*) | A | I | A | II | / | / |
| Compound 28 (*) | A | I | A | II | / | / |
| Compound 29 (*) | A | I | A | I | / | / |
| Compound 30 (*) | A | I | A | I | / | / |
| Compound 31 (*) | C | I | E | I | / | / |
| Compound 32 (*) | A | I | E | II | / | / |
| Compound 33 (*) | D | I | E | II | / | / |
| Compound 34 (*) | A | I | E | III | E | I |
| Compound 35 (*) | D | I | C | II | / | / |

TABLE 1-continued

Results of in vitro screening experiments of the compounds of the present invention

| Compounds | PPAR Alpha | | PPAR Delta | | PPAR Gamma | |
|---|---|---|---|---|---|---|
| | $EC_{50}$ nM | Maximum Activation Response % | $EC_{50}$ nM | Maximum Activation Response % | $EC_{50}$ nM | Maximum Activation Response % |
| Compound 36 (rac-) | A | I | E | II | / | / |
| Compound 37 (rac-) | A | I | D | II | / | / |
| Compound 38 (*) | A | I | C | II | / | / |
| Compound 39 (*) | A | I | B | I | / | / |
| Compound 40 (*) | A | I | B | I | / | / |
| Compound 41 (*) | A | I | A | I | / | / |
| Compound 42 (*) | A | I | A | I | / | / |
| Compound 43 (*) | A | I | A | I | / | / |
| Compound 44 (*) | A | I | D | III | E | I |
| Compound 45 (*) | A | I | C | II | E | I |
| Compound 46 (*) | A | I | A | I | E | I |
| Compound 47 (*) | A | I | A | I | C | I |
| Compound 48 (rac-) | A | II | B | II | / | / |
| Compound 49 (*) | C | II | B | II | D | II |
| Compound 50 (*) | C | III | C | II | / | / |
| Compound 51 (*) | A | I | A | I | D | I |
| Compound 52 (*) | A | I | A | I | C | I |
| Compound 53 (rac-) | B | I | B | II | E | I |
| Compound 54 (rac-) | A | I | B | I | D | I |
| Compound 55 (rac-) | E | III | D | II | E | III |
| Compound 56 (rac-) | E | III | D | II | E | III |
| Compound 57 (*) | A | I | A | II | D | II |
| Compound 58 (*) | B | I | A | II | D | II |
| Compound 59 (*) | D | II | D | II | / | / |
| Compound 60 (*) | D | II | D | II | / | / |
| Compound 61 (*) | E | III | E | III | / | / |
| Compound 62 (*) | B | I | B | I | / | / |
| Compound 63 (*) | A | I | A | I | D | I |
| Compound 64 (*) | A | I | A | I | D | I |
| Compound 65 (*) | A | I | A | I | D | I |
| Compound 66 (*) | A | I | A | I | C | I |
| Compound 67 (rac-) | E | I | E | I | E | I |
| Compound 68 (rac-) | E | I | E | I | E | I |
| Compound 69 (*) | A | I | A | I | C | I |
| Compound 70 (*) | A | I | A | I | C | I |
| Compound 71 (rac-) | D | I | C | I | / | / |
| Compound 72 (rac-) | A | I | B | I | / | / |
| Compound 73 (rac-) | D | I | E | I | / | / |
| Compound 74 (*) | A | I | B | I | / | / |
| Compound 75 (*) | E | I | D | I | / | / |
| Compound 76 (*) | B | I | B | I | E | I |
| Compound 77 (*) | C | I | C | I | E | I |
| Compound 78 (*) | B | I | B | I | E | I |
| Compound 79 (*) | B | I | C | I | D | I |
| Compound 80 (*) | A | I | C | I | E | I |
| Compound 81 (*) | A | I | B | I | D | I |

TABLE 1-continued

Results of in vitro screening experiments of the compounds of the present invention

| Compounds | PPAR Alpha | | PPAR Delta | | PPAR Gamma | |
|---|---|---|---|---|---|---|
| | $EC_{50}$ nM | Maximum Activation Response % | $EC_{50}$ nM | Maximum Activation Response % | $EC_{50}$ nM | Maximum Activation Response % |
| Compound 82 (*) | A | I | B | I | D | I |
| Compound 83 (*) | B | I | D | I | / | / |

Note 1:
The maximum activation response values, determined in in vitro platform, of a known PPARα agonist GW7647, PPARδ agonist L-165,041 and PPARγ agonist Troglitazone are indicated to be 100%. The maximum response values of other compound are compared with the maximum activation responses of the known agonists, to obtain the corresponding maximum activation response values. In general, a compound having a maximum activation response value of greater than 80% is considered to be a full agonist, a compound having a maximum activation response value of greater than 50% and less than 80% is considered to be a partial agonist, and a compound having a maximum activation response value of less than 50% is considered to be an agonist with insufficient effect.

Note 2:
A ≤ 100 nM; 100 nM < B ≤ 150 nM; 150 nM < C ≤ 200 nM; 200 nM < D ≤ 250 nM; E > 250 nM.

Note 3:
100% ≥ I ≥ 80%; 80% ≥ II ≥ 50%; III < 50%.

Note 4:
"*" refers to be optically pure compounds.

Note 5:
"rac-" refers to be trans-racemic compounds.

Conclusion: the compounds of the present invention activate significantly PPAR Alpha and Delta receptors, and activate selectively PPAR Gamma receptor.

What is claimed is:

1. A compound of Formula (I),

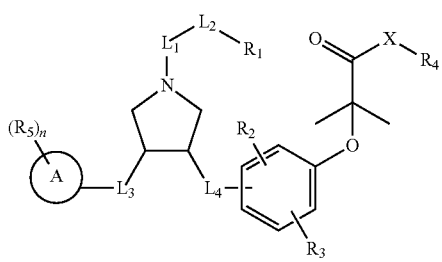

or a pharmaceutically acceptable salt thereof,
wherein
$R_1$ is selected from H, $NH_2$, or from $C_{1-6}$ alkyl, $C_{1-6}$ heteroalkyl, $C_{3-6}$ cycloalkyl, 3-6-membered heterocycloalkyl, phenyl, or 5-6-membered heteroaryl each of which is optionally substituted with 1, 2, or 3 R;
$R_2$, $R_3$ are independently selected from H, halogen, OH, $NH_2$, or from $C_{1-3}$ alkyl optionally substituted with 1, 2, or 3 R;
X is selected from NH, O, or S;
when X is selected from O or S, $R_4$ is selected from H or from $C_{1-6}$ alkyl optionally substituted with 1, 2, or 3 R;
when X is selected from NH, $R_4$ is selected from H, $C_{1-6}$ alkyl, or from $C_{1-6}$ alkyl-S(=O)$_2$—, or —$C_{1-6}$ alkyl-S(=O)$_2$OH optionally substituted with 1, 2, or 3 R;
or,
a structural unit $R_4$—X— is selected from:

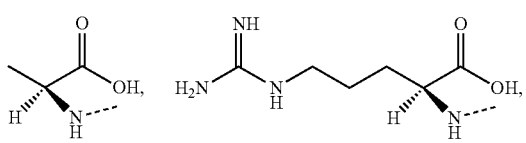

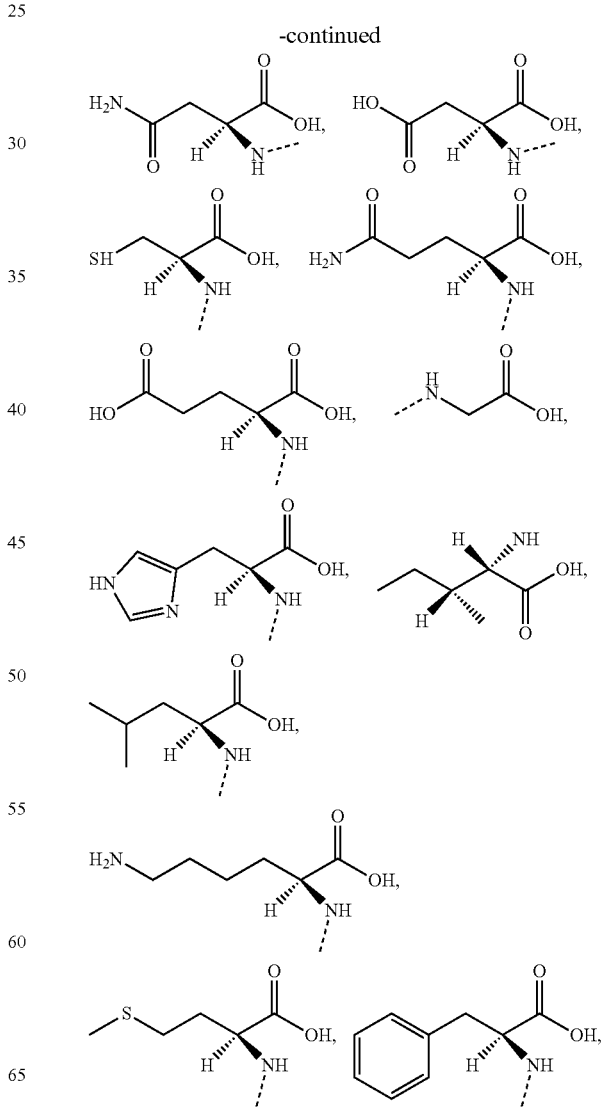

-continued

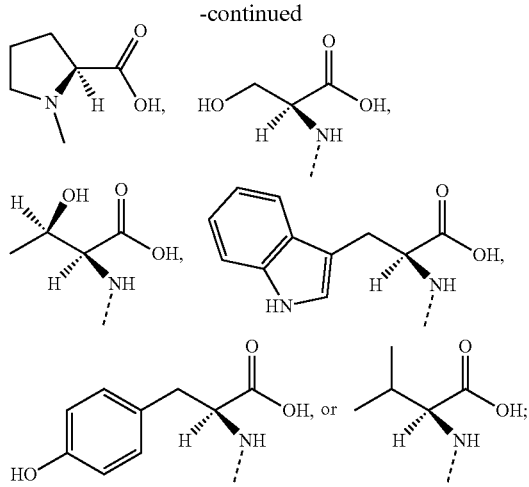

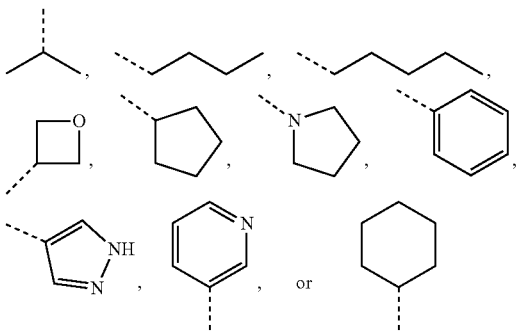

each of which is optionally substituted with 1, 2, or 3 R.

$R_5$ is selected from H, halogen, OH, $NH_2$, CN, COOH, or from $C_{1-6}$ alkyl, $C_{1-6}$ alkyl-S(=O)—, $C_{1-6}$ alkyl-S(=O)$_2$—, $C_{1-6}$ alkoxy, or $C_{1-6}$ alkylthio each of which is optionally substituted with 1, 2, or 3 R;

n is selected from 0, 1, 2 or 3;

a ring A is selected from phenyl, naphthyl, or 5-6-membered heteroaryl;

$L_1$ is selected from a single bond, —C(=O)—, —O—, —NH—, —C(=O)O—, —C(=O)NH—, —S(=O)$_2$—, —S(=O)—, or —(CRR)$_{1-3}$—;

$L_2$ is selected from a single bond, —(CRR)$_{1-3}$—, —C(=O)—, —O—, —S—, —NH—, —C(=O)O—, —C(=O)NH—, —S(=O)$_2$—, —S(=O)—;

$L_3$ is selected from —(CRR)—, or —C(=O)—;

$L_4$ is selected from a single bond, —(CRR)$_{1-3}$—;

R is selected from H, F, Cl, Br, I, OH, CN, $NH_2$, COOH, C(=O)$NH_2$, or from $C_{1-6}$ alkyl, or $C_{1-6}$ heteroalkyl each of which is optionally substituted with 1, 2, or 3 R';

R' is selected from F, Cl, Br, I, OH, CN, $NH_2$, COOH, Me, Et, $CF_3$, $CHF_2$, $CH_2F$, $NHCH_3$, or $N(CH_3)_2$;

"hetero-" refers to a heteroatom or a heteroatomic group, and is selected from —C(=O)NH—, —NH—, —C(=NH)—, —S(=O)$_2$NH—, —S(=O) NH—, —O—, —S—, =O, =S, —O—N=, —C(=O)O—, —C(=O)—, —C(=S)—, —S(=O)—, —S(=O)$_2$— and —NHC(=O)NH—;

in any one of the cases defined above, the number of the heteroatoms or heteroatomic groups is independently selected from 1, 2 or 3.

2. The compound or pharmaceutically acceptable salt thereof according to claim 1, wherein R is selected from H, F, Cl, Br, I, OH, CN, $NH_2$, COOH, C(=O)$NH_2$, or from $C_{1-3}$ alkyl, $C_{1-3}$ alkoxy, $C_{1-3}$ alkylthio, $C_{1-3}$ alkylamino, or N,N'-di($C_{1-3}$ alkyl)amino each of which is optionally substituted with 1, 2, or 3 R'.

3. The compound or pharmaceutically acceptable salt thereof according to claim 1, wherein $R_1$ is selected from H, $NH_2$, or from $C_{1-6}$ alkyl, cyclopentyl, azetidinyl, pyrrolidinyl, tetrahydrothienyl, tetrahydrofuranyl, piperidyl, morpholinyl, piperazinyl, phenyl, pyrazolyl, pyridyl, or cyclohexyl each of which is optionally substituted with 1, 2, or 3 R.

4. The compound or pharmaceutically acceptable salt thereof according to claim 1, wherein $R_1$ is selected from H, $NH_2$, or from Me, Et, 5. The compound or pharmaceutically acceptable salt thereof according to claim 1, wherein $R_2$, $R_3$ are independently selected from H, F, Cl, Br, I, OH, $NH_2$, or from Me, or Et each of which is optionally substituted with 1, 2, or 3 R.

6. The compound or pharmaceutically acceptable salt thereof according to claim 1, wherein when X is selected from O or S, $R_4$ is selected from H, or from Me, Et,

each of which is optionally substituted with 1, 2, or 3 R.

7. The compound or pharmaceutically acceptable salt thereof according to claim 1, wherein when X is selected from NH, $R_4$ is selected from H, $C_{1-4}$ alkyl, or from $C_{1-4}$ alkyl-S(=O)$_2$—, or —$C_{1-3}$ alkyl-S(=O)$_2$OH each of which is optionally substituted with 1, 2, or 3 R.

8. The compound or pharmaceutically acceptable salt thereof according to claim 1, wherein $R_5$ is selected from H, F, Cl, Br, I, OH, $NH_2$, CN, COOH, or from Me, Et,

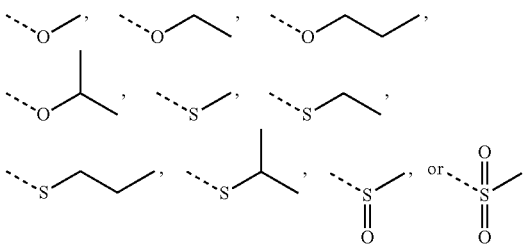

each of which is optionally substituted with 1, 2, or 3 R.

9. The compound or pharmaceutically acceptable salt thereof according to claim 1, wherein the structural unit

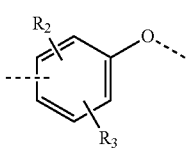

is selected from:

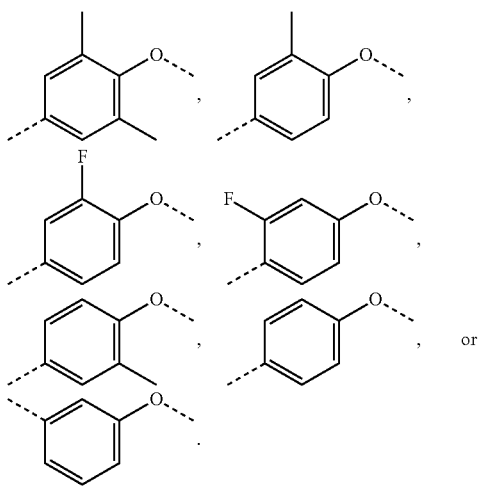

10. The compound or pharmaceutically acceptable salt thereof according to claim 1, wherein the ring A is selected from: phenyl, naphthyl, pyridyl, pyrimidyl, pyrazinyl, pyridazinyl, thienyl, pyrazolyl, imidazolyl, oxazolyl, thiazolyl, isoxazolyl, or isothiazolyl.

11. The compound or pharmaceutically acceptable salt thereof according to claim 1, wherein the structural unit

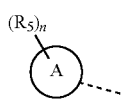

is selected from

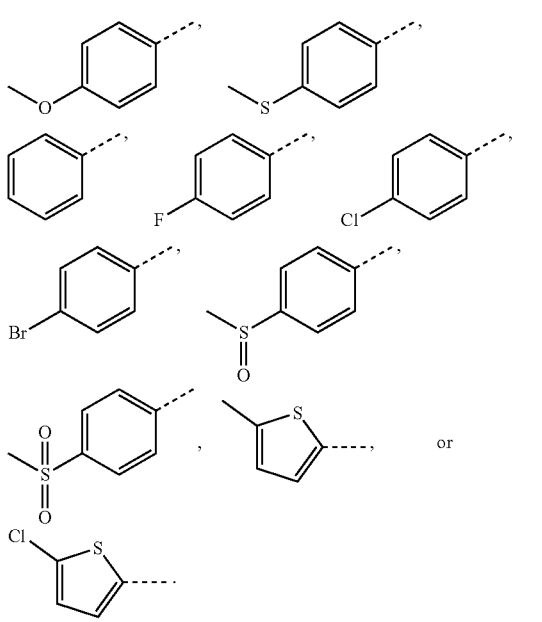

12. The compound or pharmaceutically acceptable salt thereof according to claim 1, wherein $L_3$ is selected from —$CH_2$—, or —C(=O)—.

13. The compound or pharmaceutically acceptable salt thereof according to claim 1, wherein a structural unit -$L_1$-$L_2$- is selected from: a single bond, —$CH_2$—, —C(=O)—, —S(=O)$_2$—, —C(=O)O—, —C(=O)NH—, —C(=O)—$CH_2$—, —C(=O)O—$CH_2$—, or —$CH_2CH_2O$—.

14. The compound or pharmaceutically acceptable salt thereof according to claim 1, wherein $L_4$ is selected from a single bond, —$CH_2$—, or —$CH_2CH_2$—.

15. The compound or pharmaceutically acceptable salt thereof according to claim 1, which is selected from:

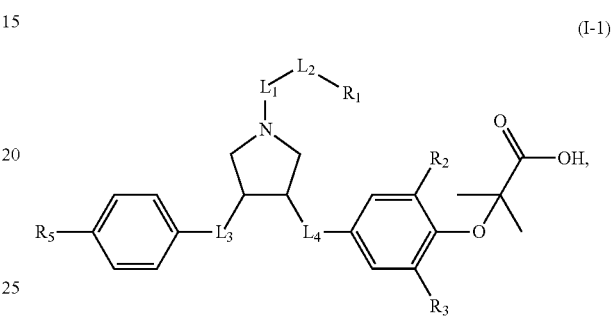

(I-1)

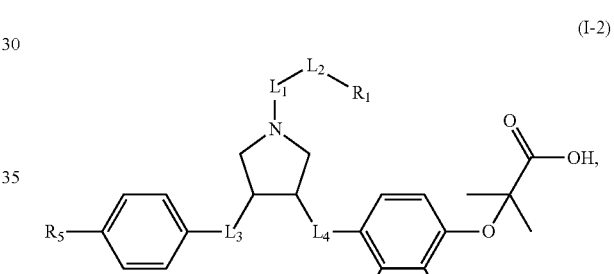

(I-2)

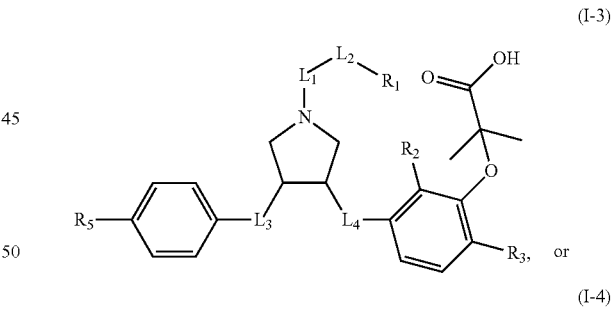

(I-3)

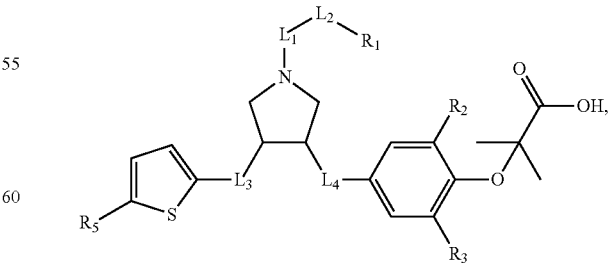

(I-4)

wherein $R_1$, $R_2$, $R_3$, $R_5$, $L_1$, $L_2$, $L_3$, $L_4$ are as defined in claim 1.

16. The compound according to claim 1, which is selected from:
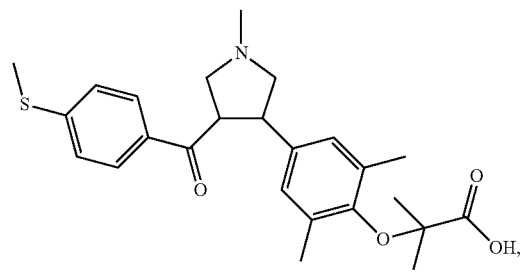
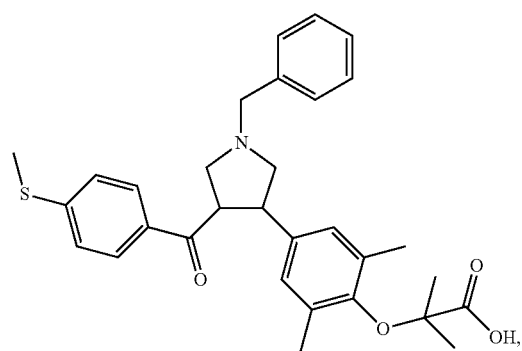
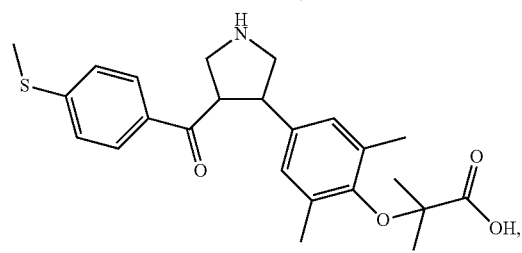
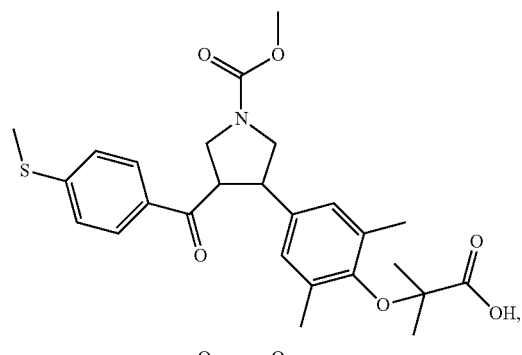
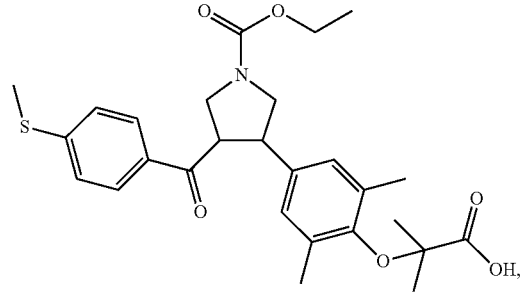
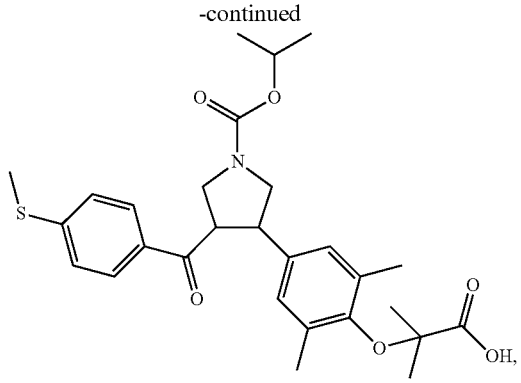
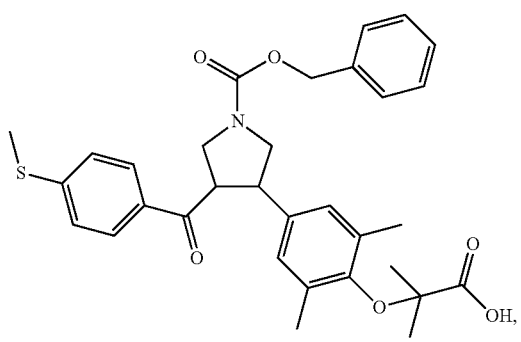
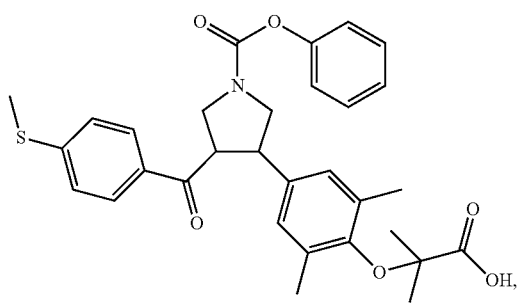
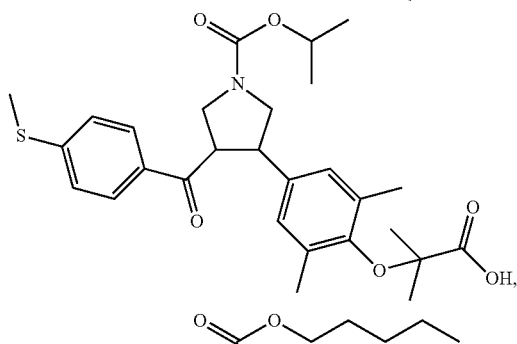
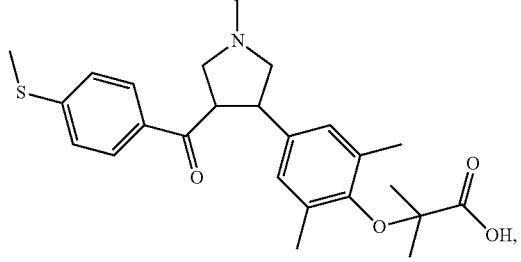

277
-continued
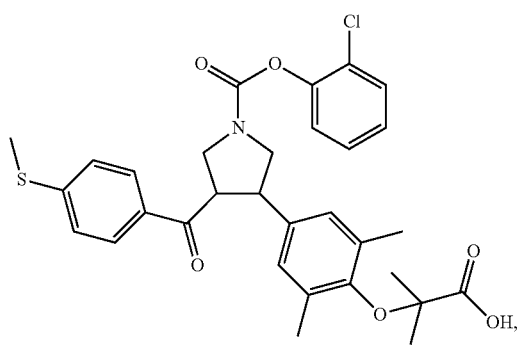
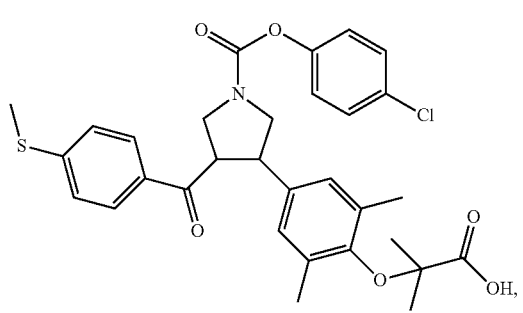
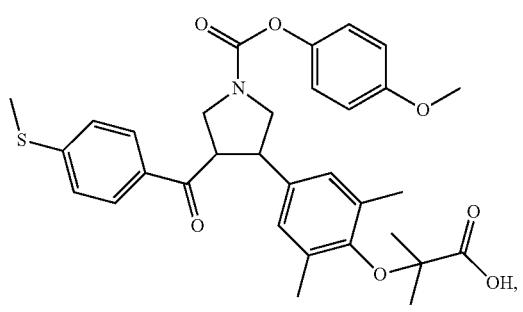
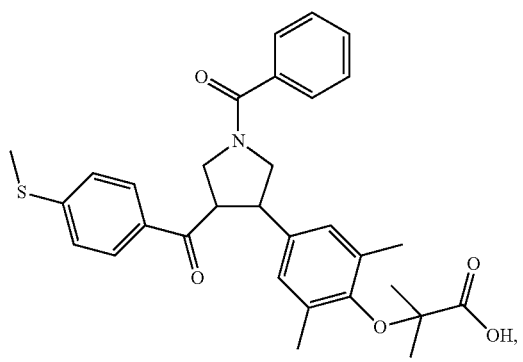
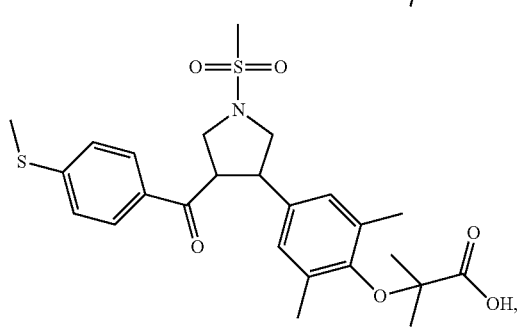
278
-continued
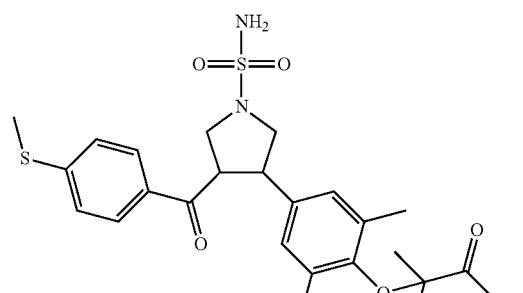
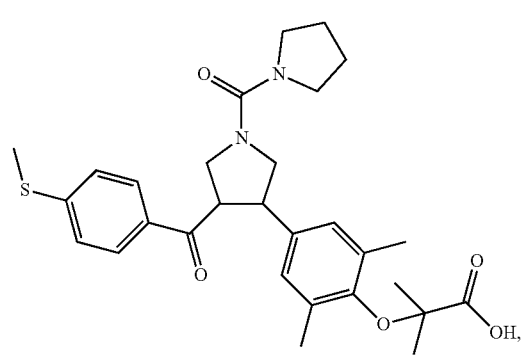
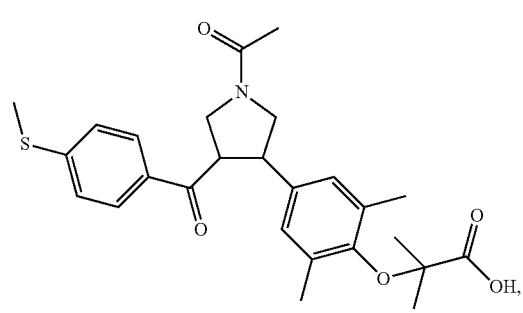
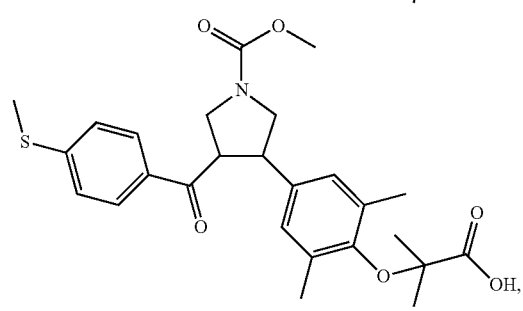
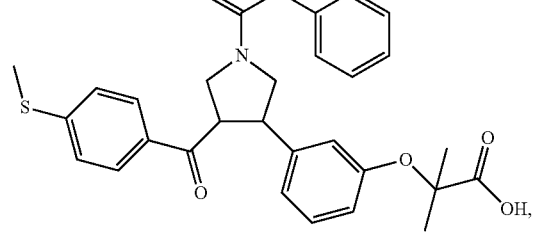

-continued
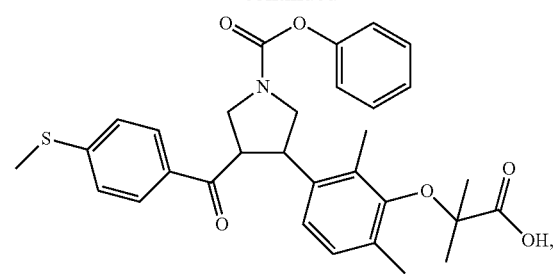
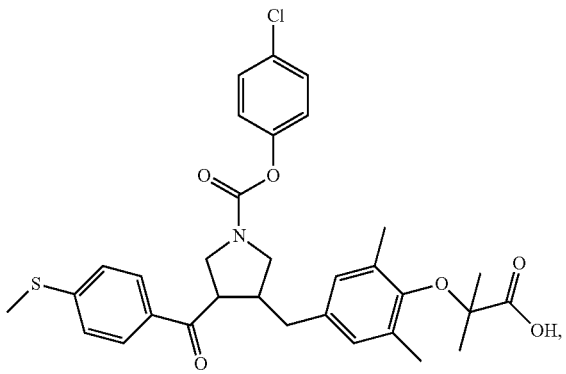
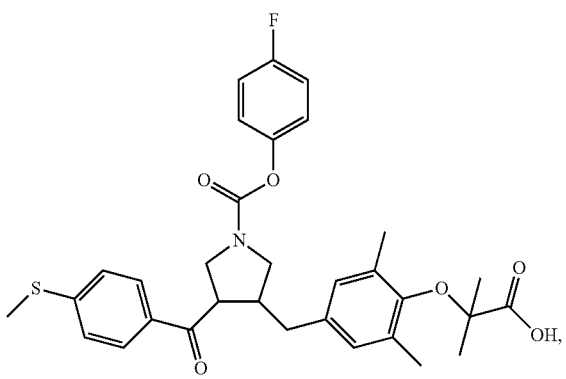
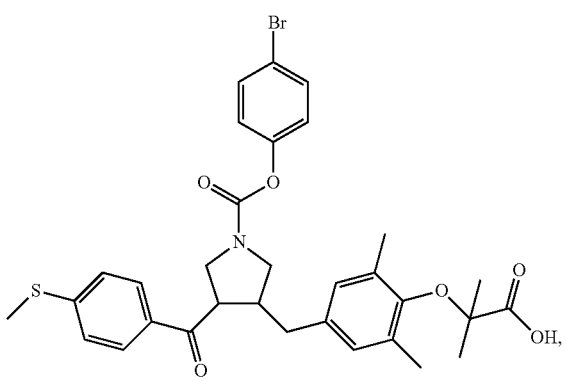
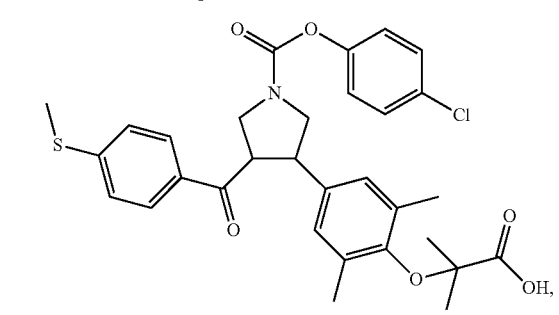
-continued
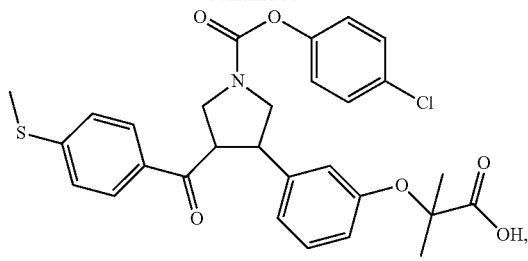
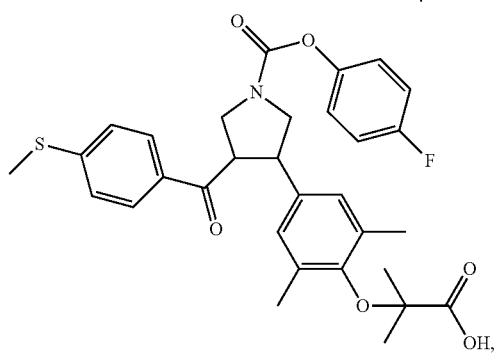
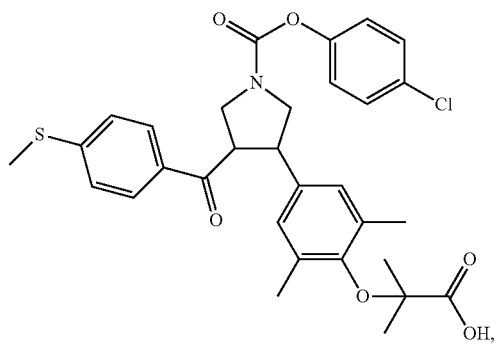
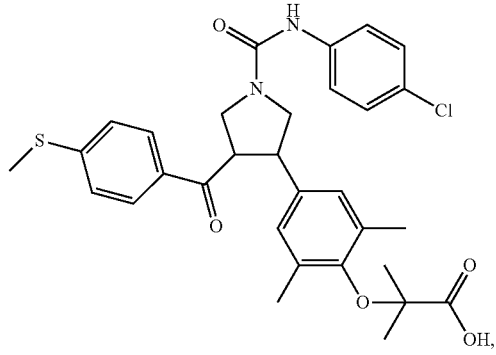
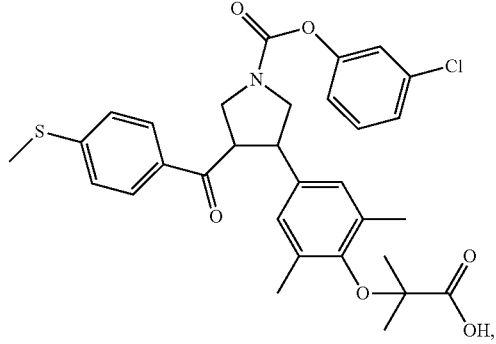

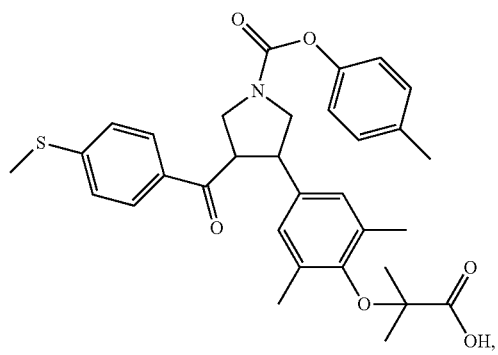
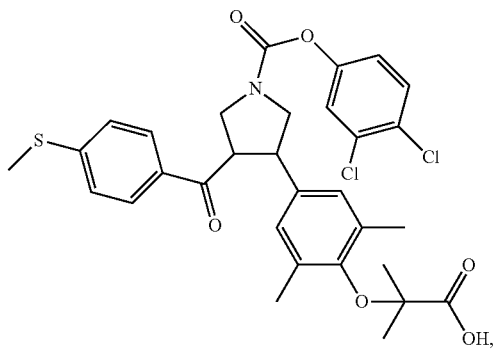

283
-continued
284
-continued
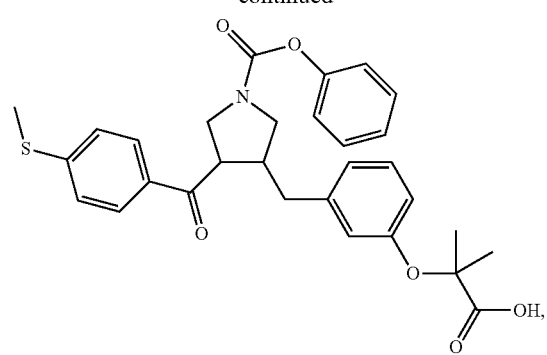
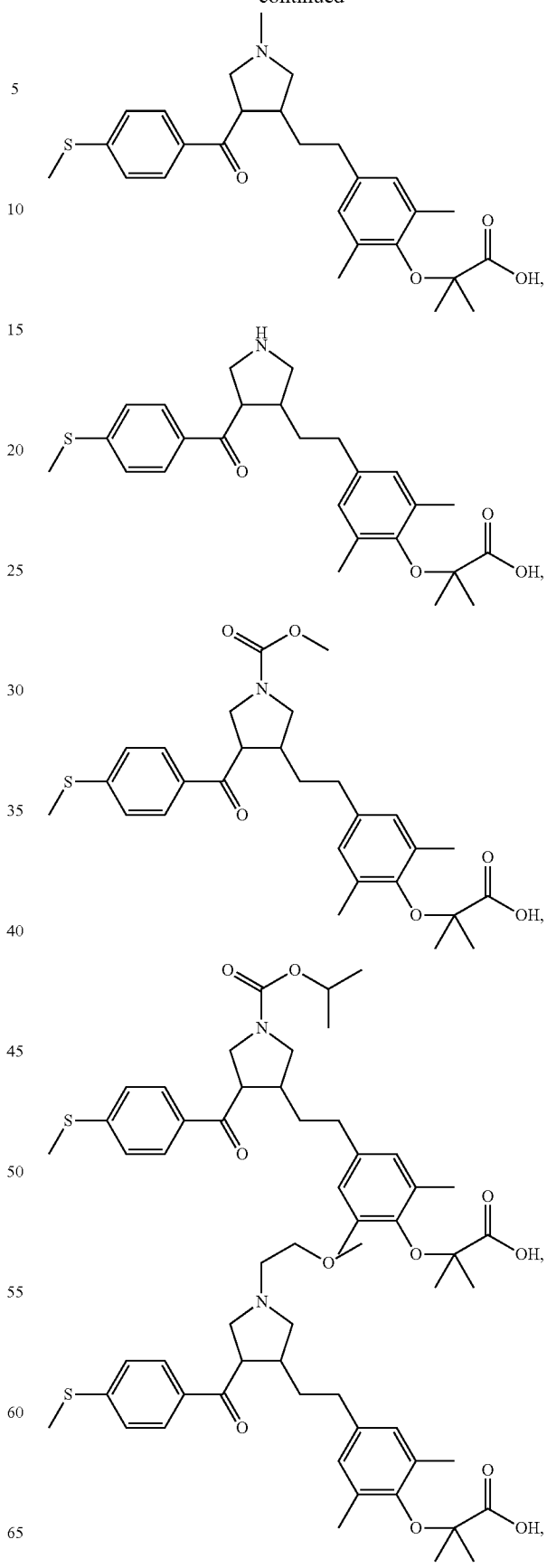

285
-continued
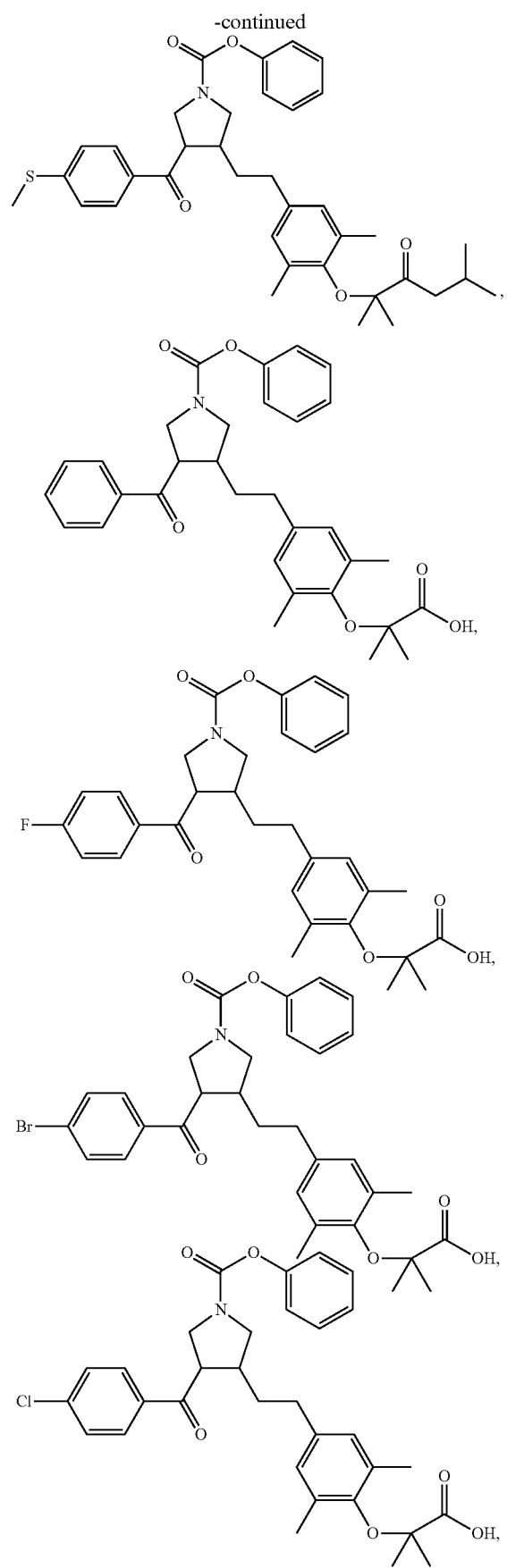
286
-continued
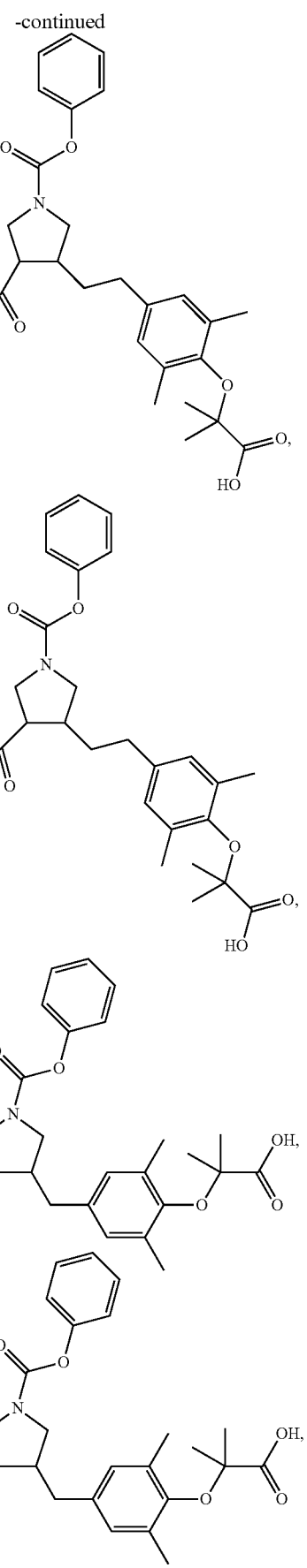

287
-continued
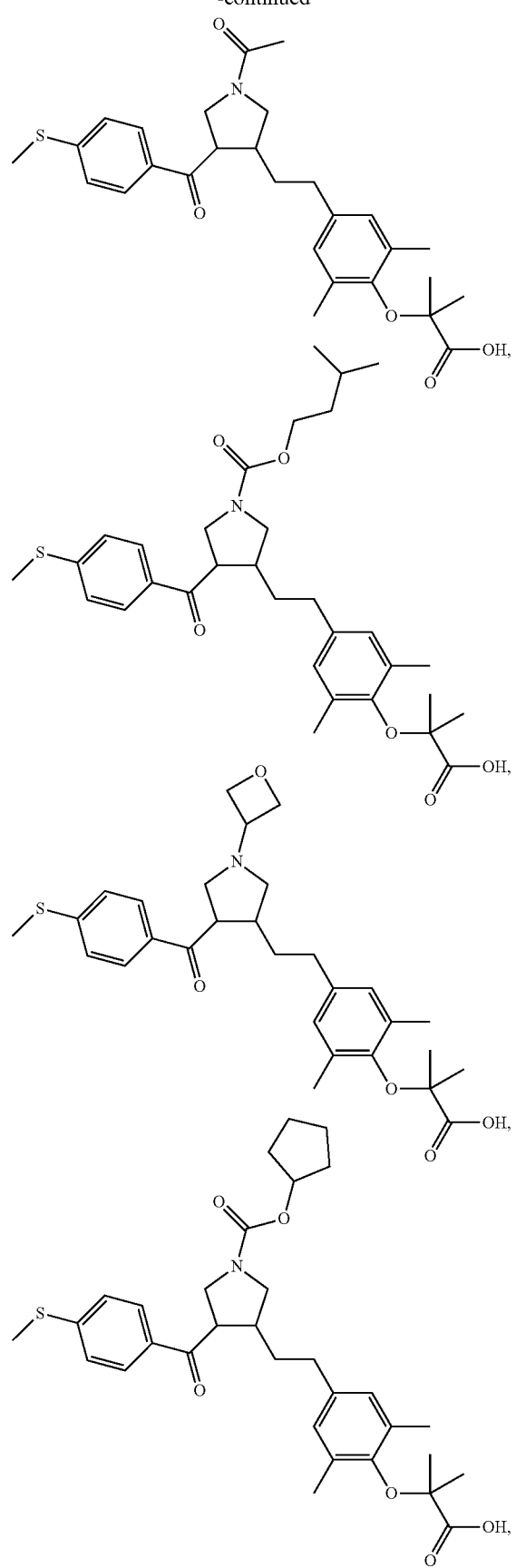
288
-continued
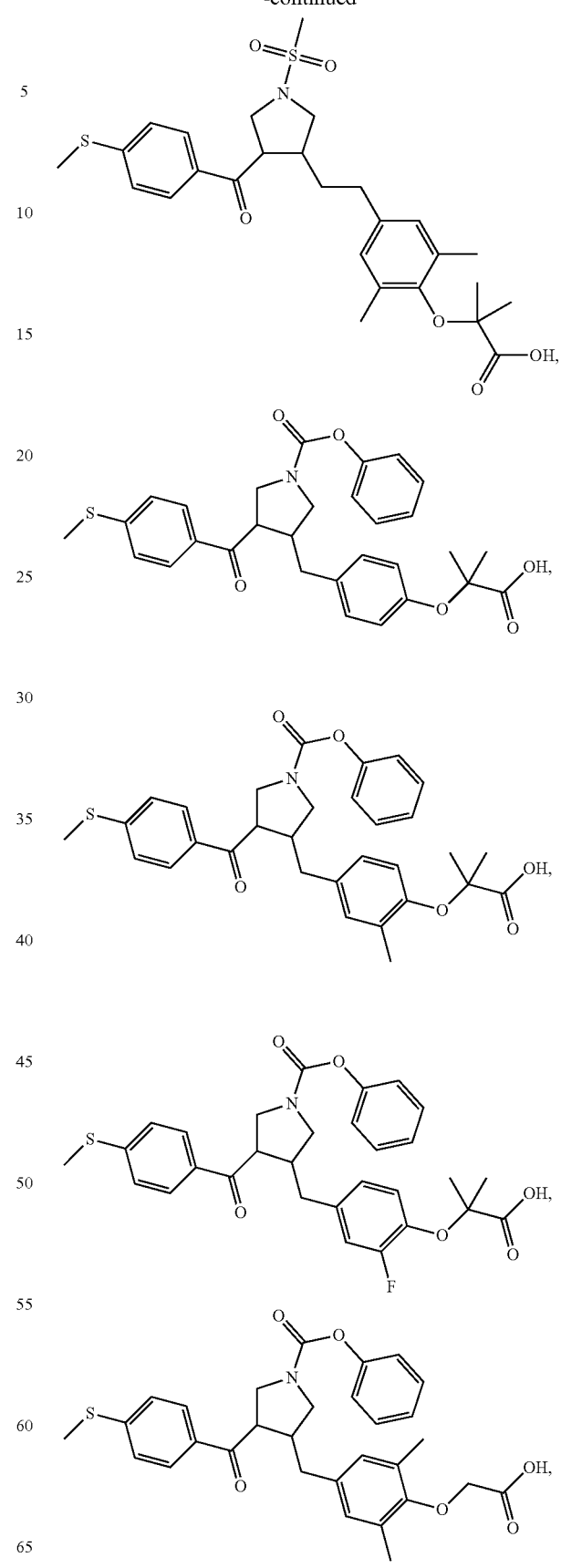

289
-continued
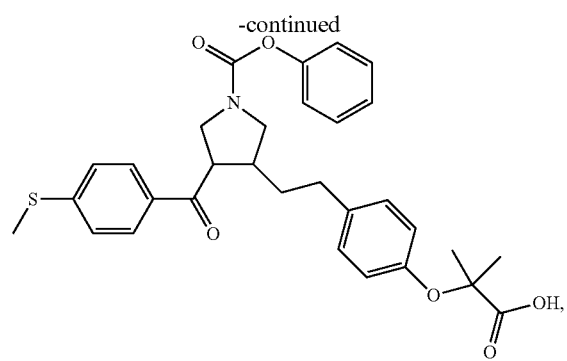
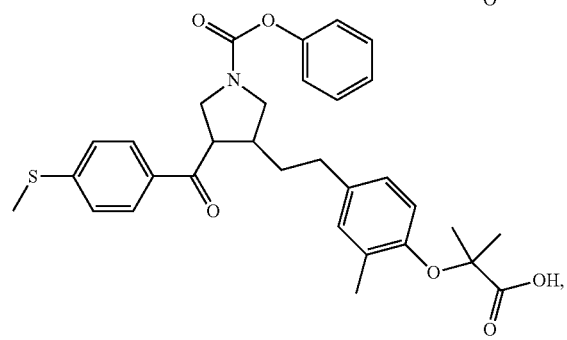
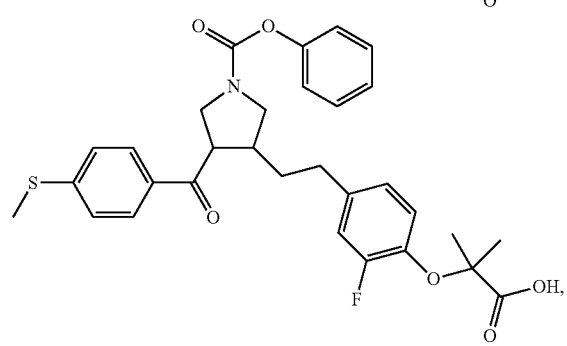
or
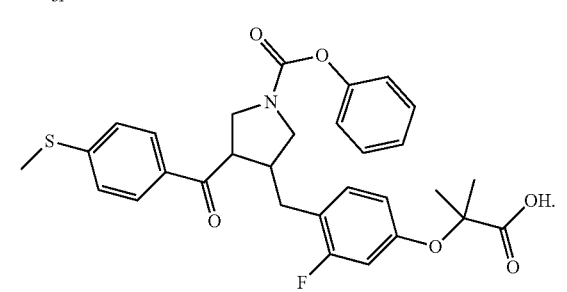
17. The compound according to claim 1, which is selected from:
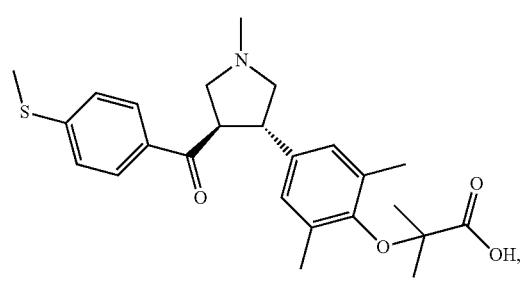
290
-continued
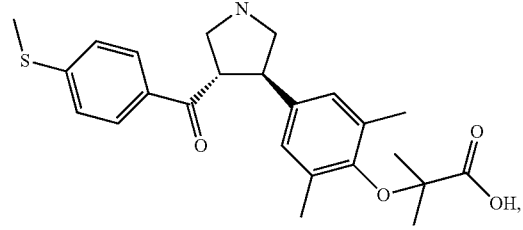
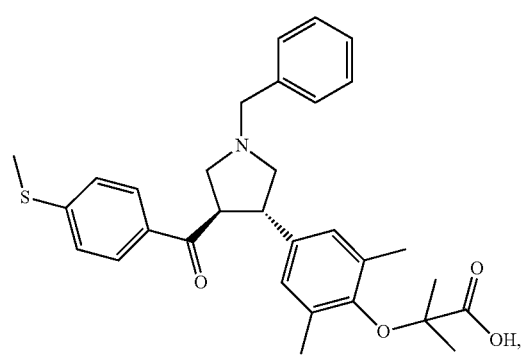
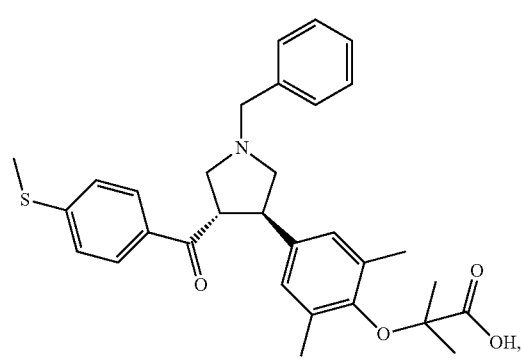
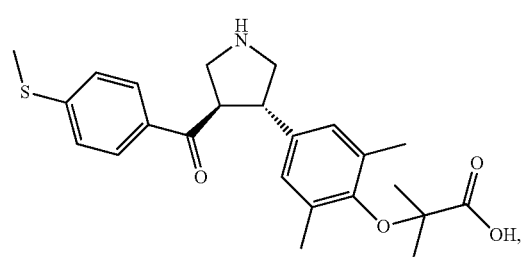
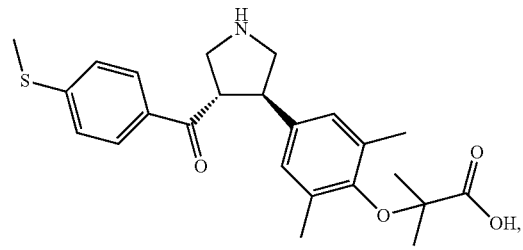

291
-continued
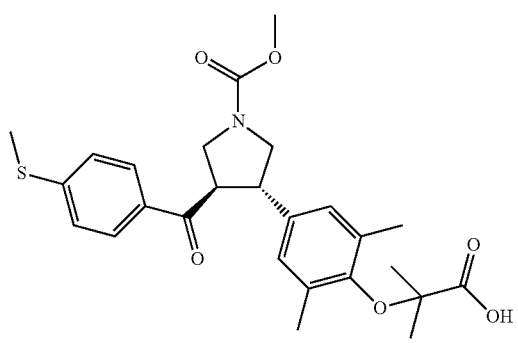
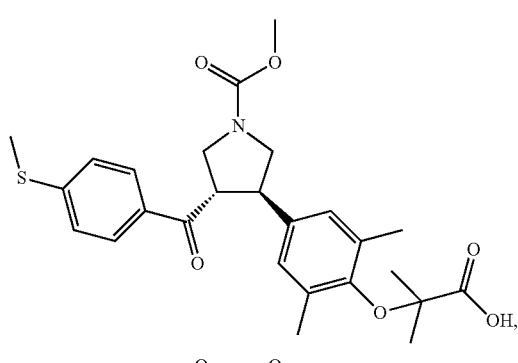
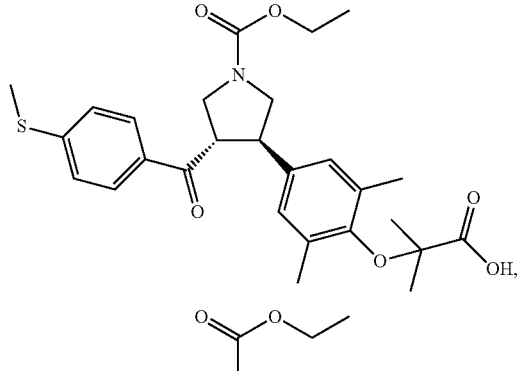
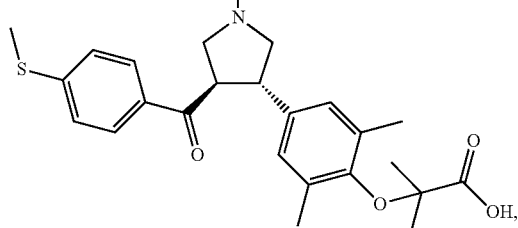
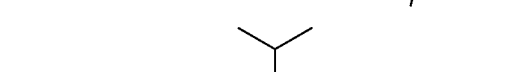
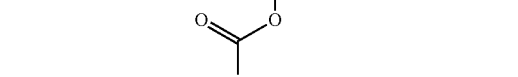
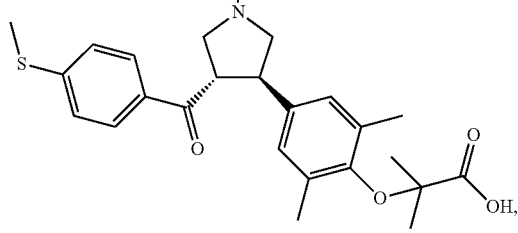
292
-continued
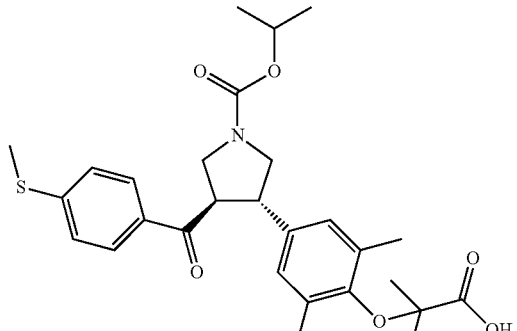
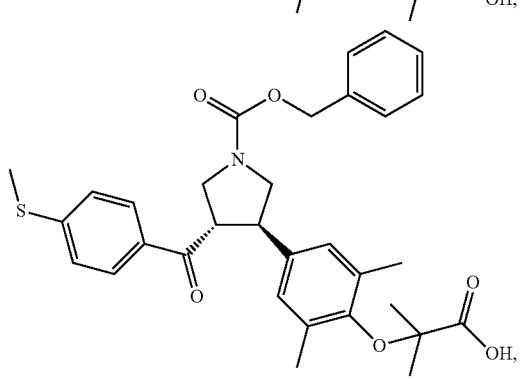
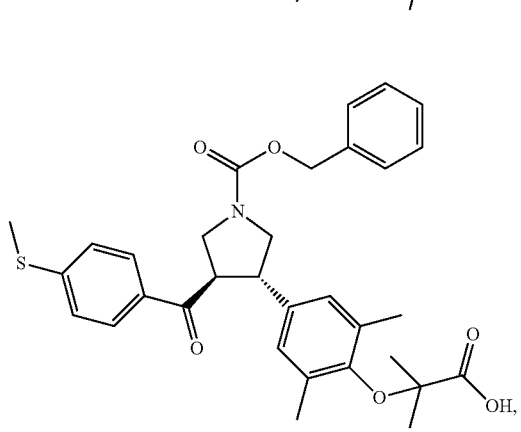
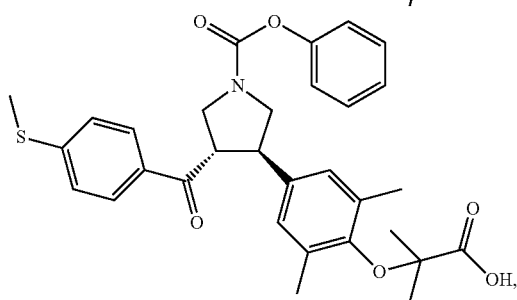
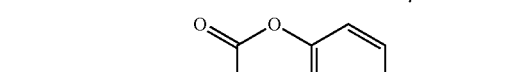
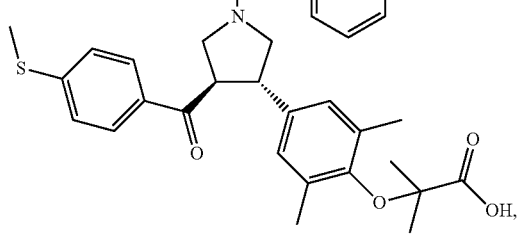

293
-continued
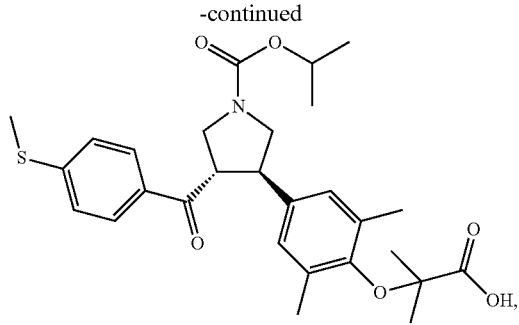
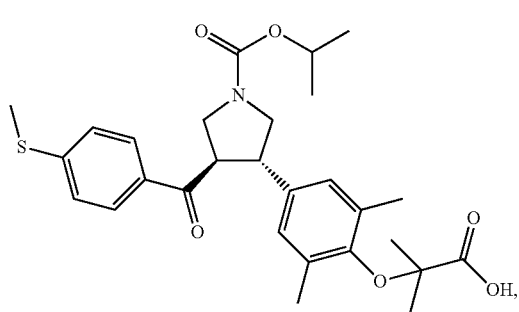
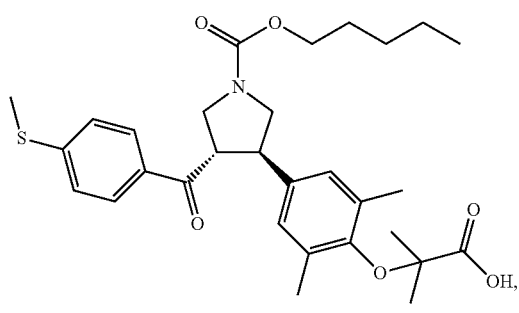
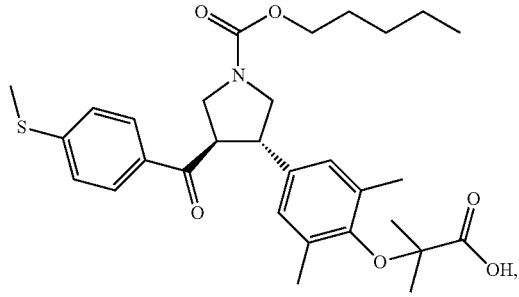
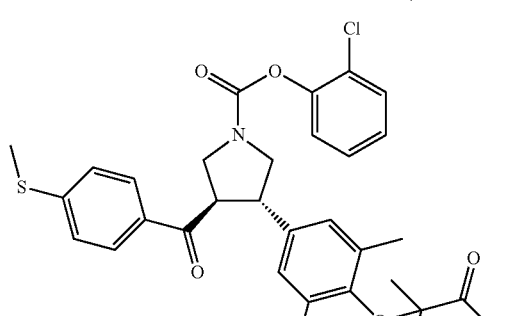
294
-continued
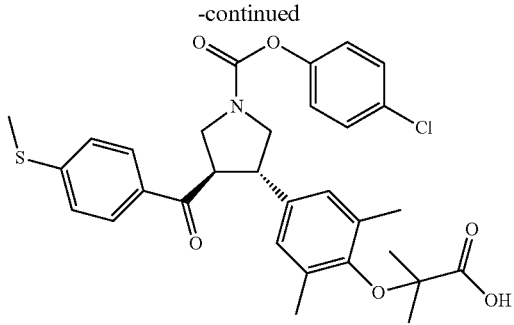
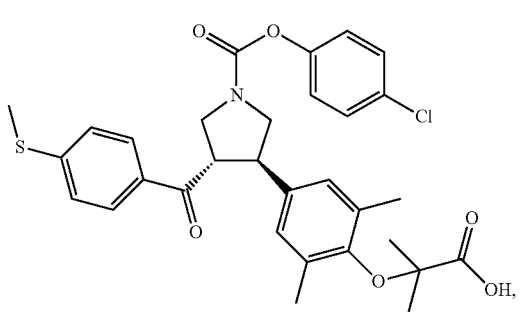
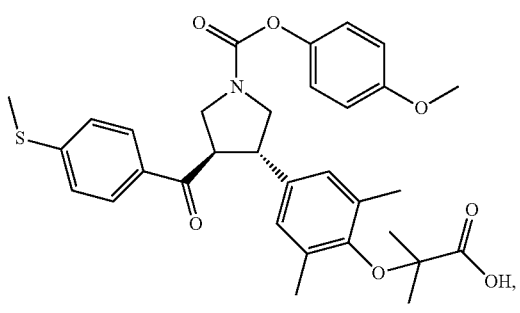
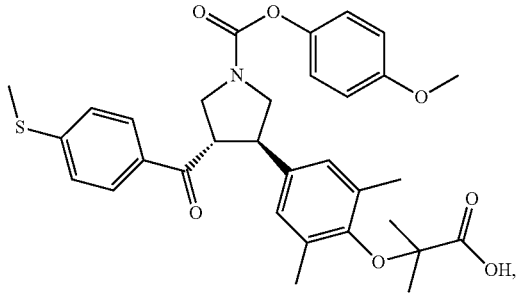
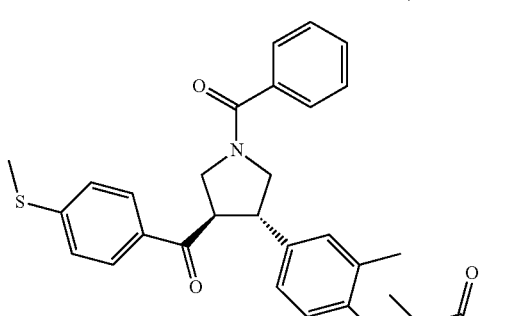

295
-continued
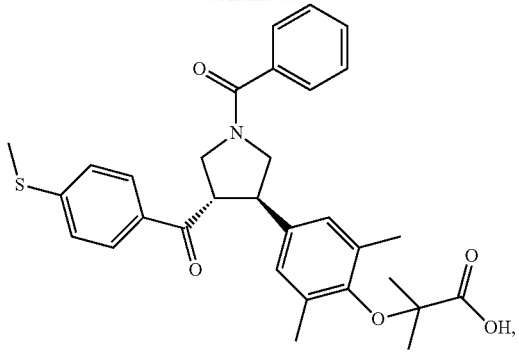
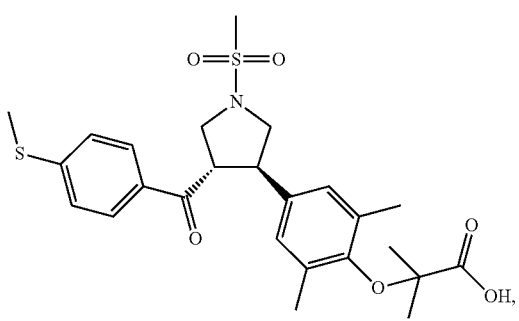
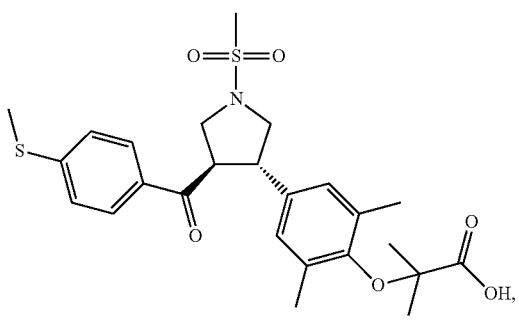
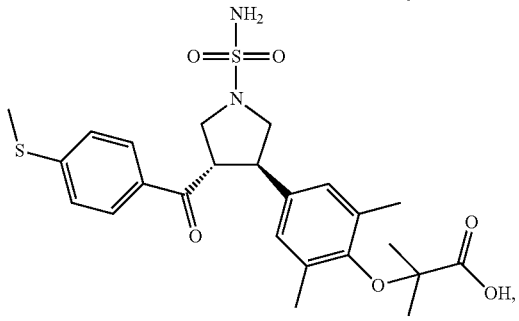
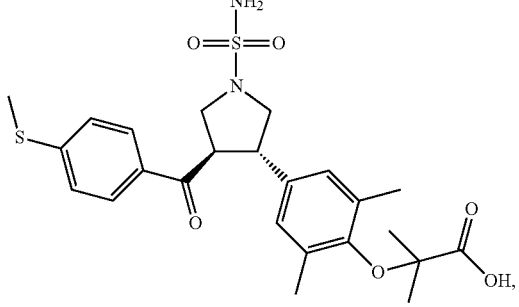
296
-continued
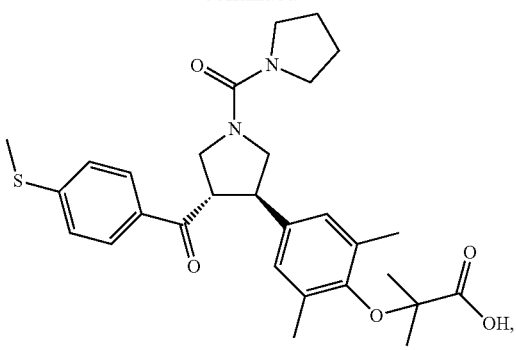
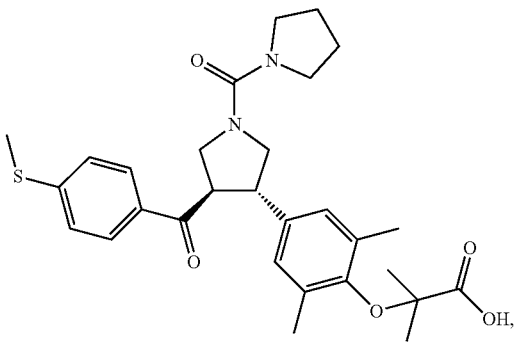
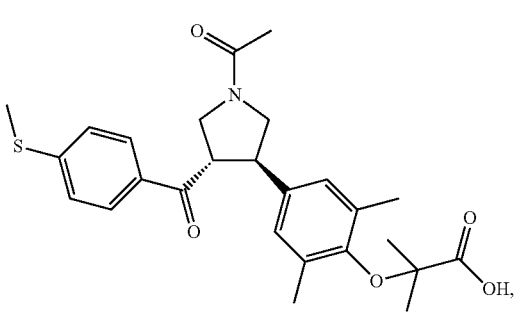
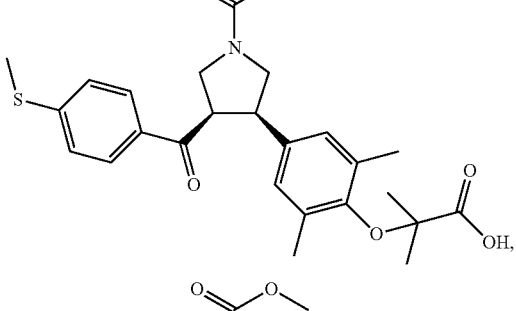
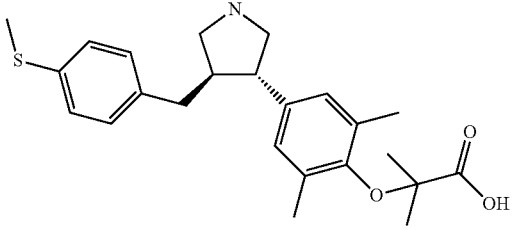

297
-continued
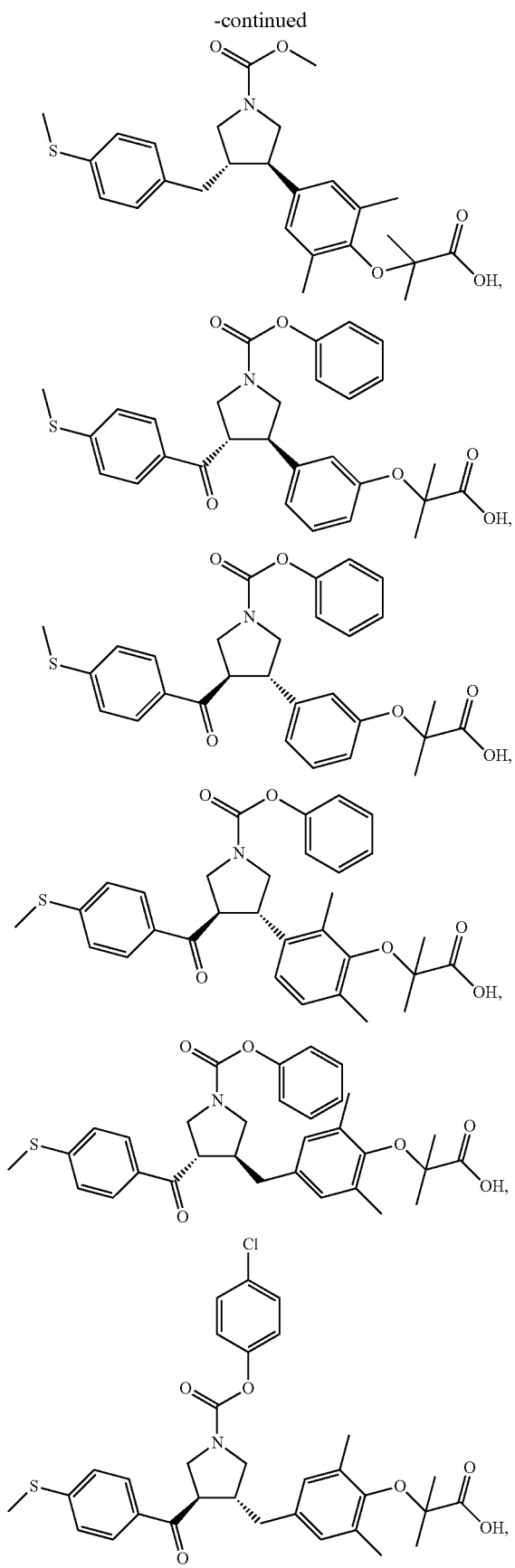
298
-continued
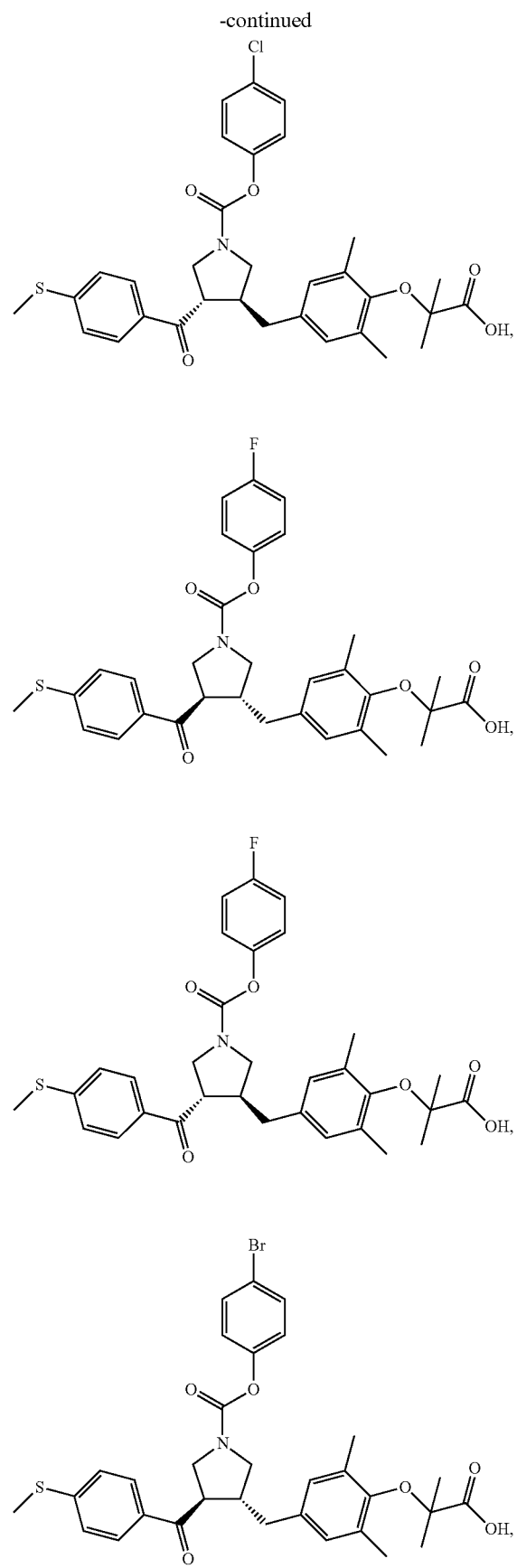

299
-continued
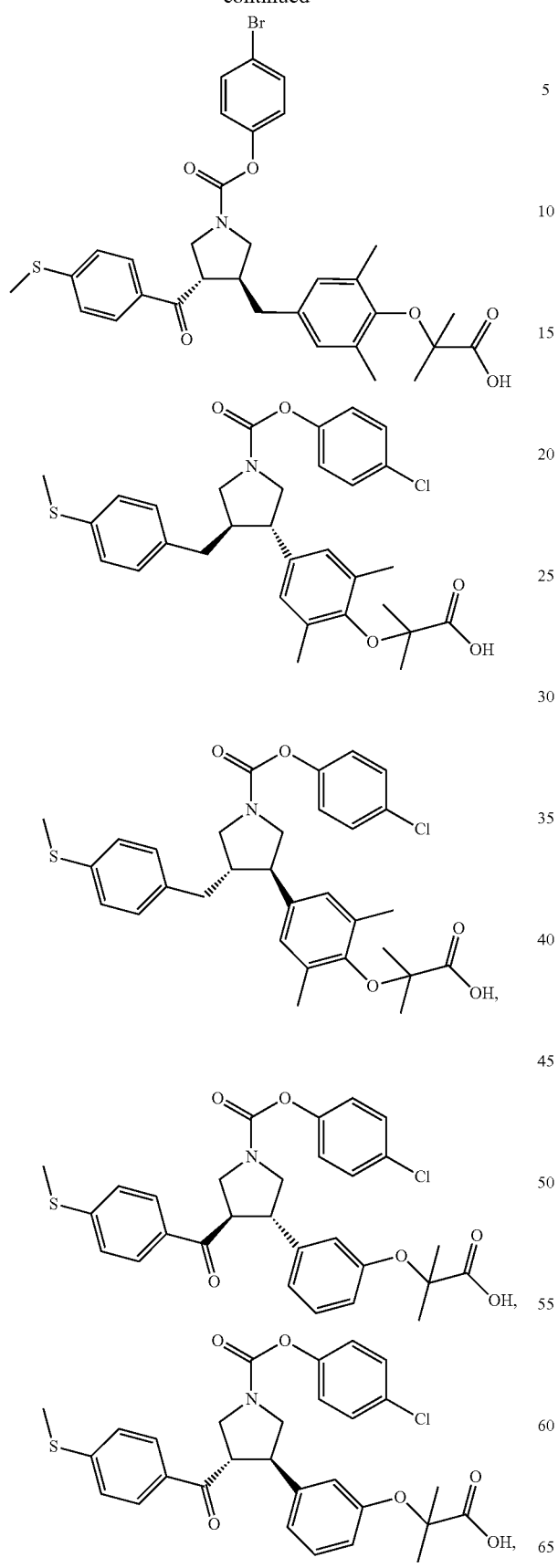
300
-continued
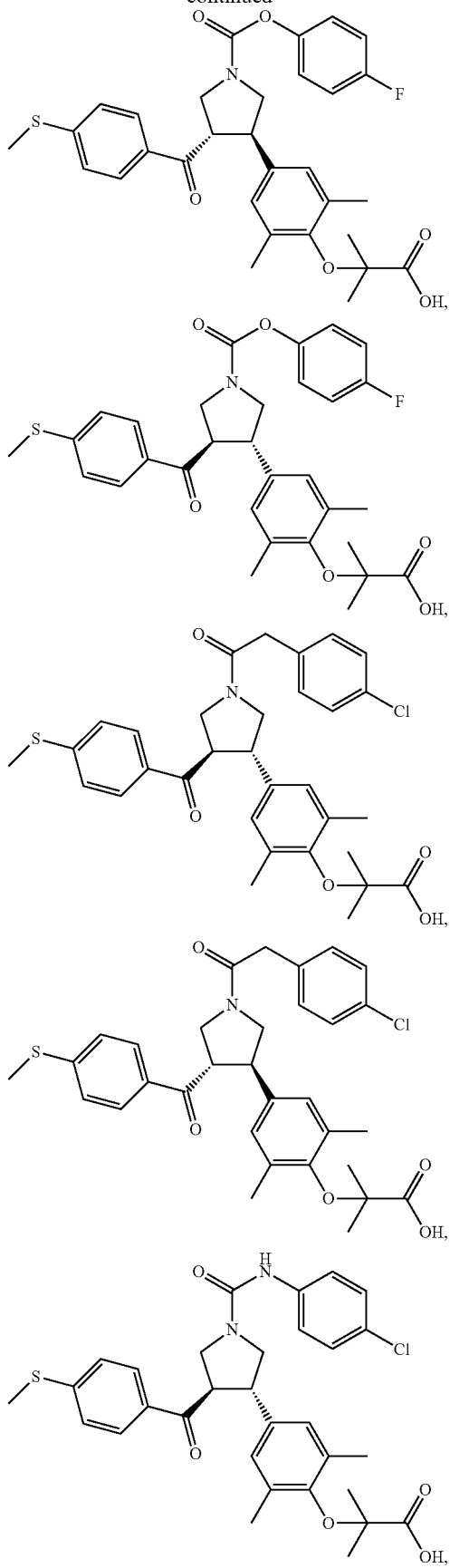

301
-continued
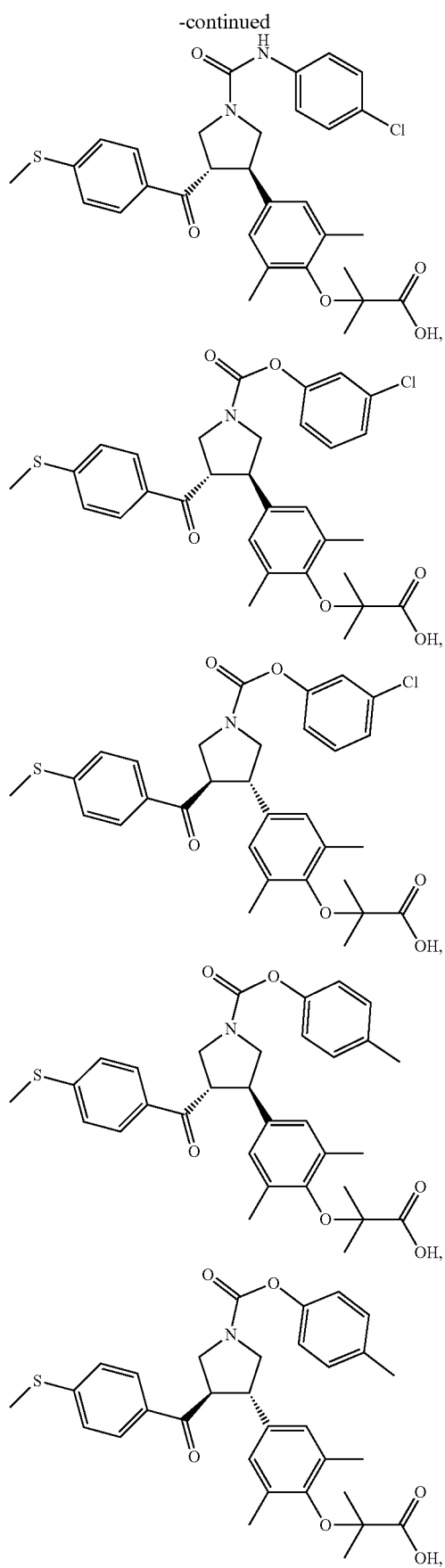
302
-continued
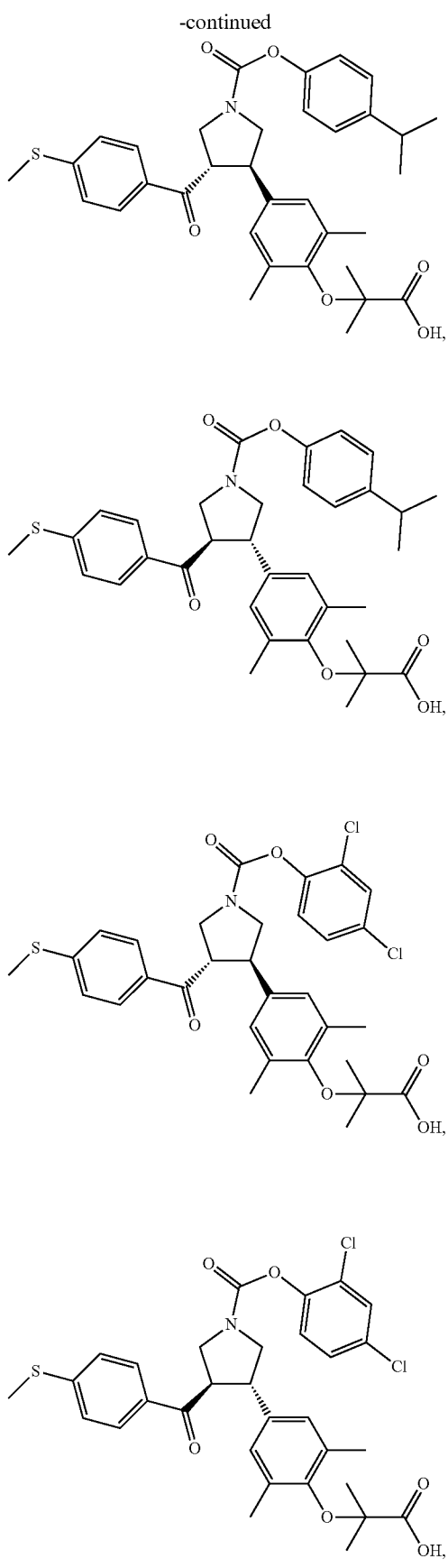

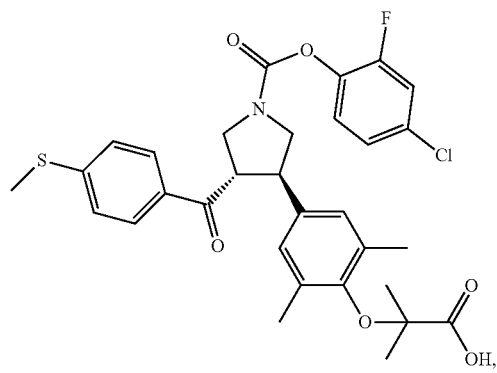
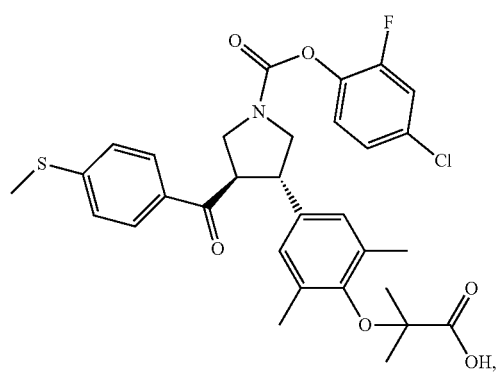
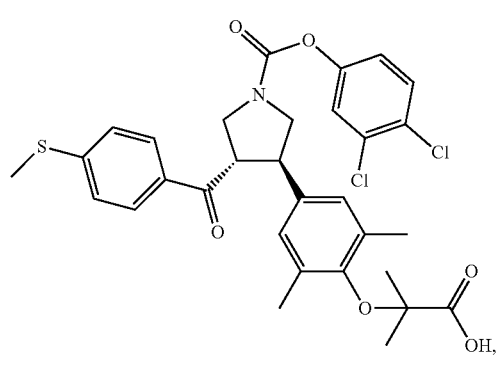
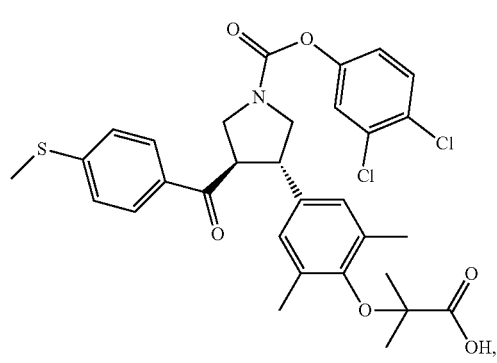
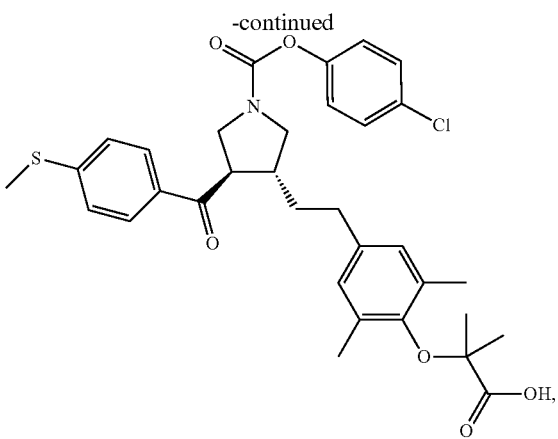
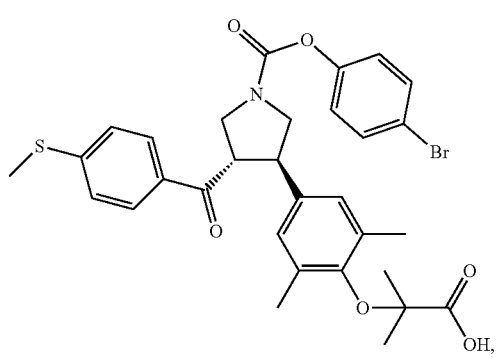
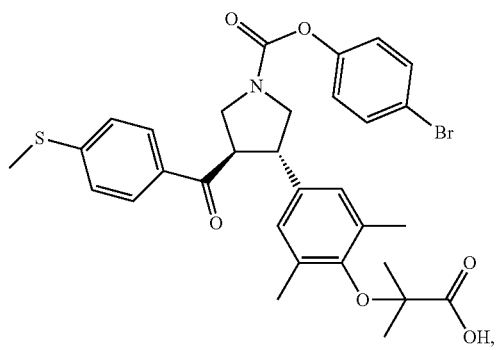

-continued
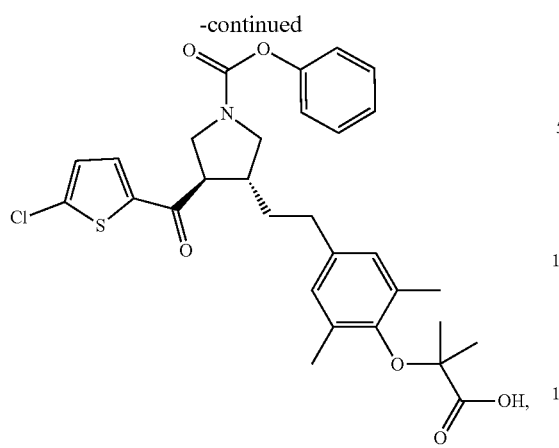
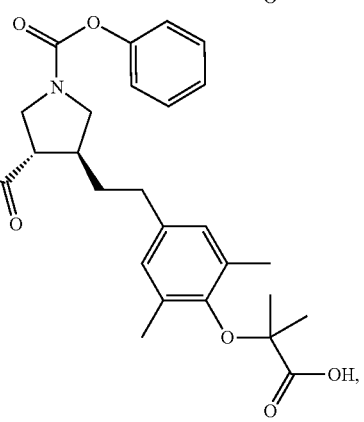
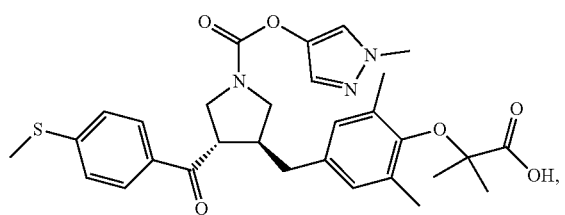
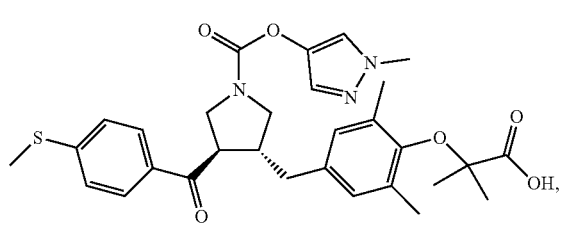
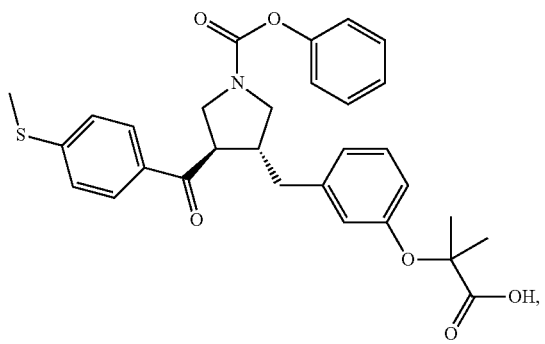
-continued
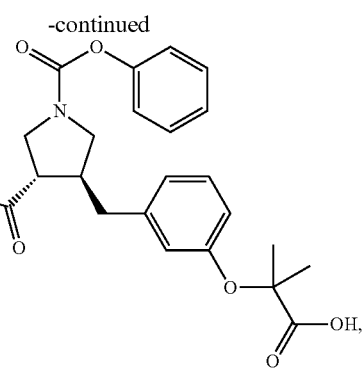
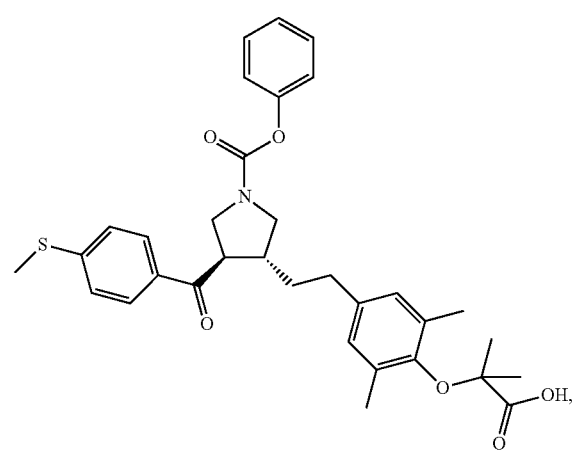
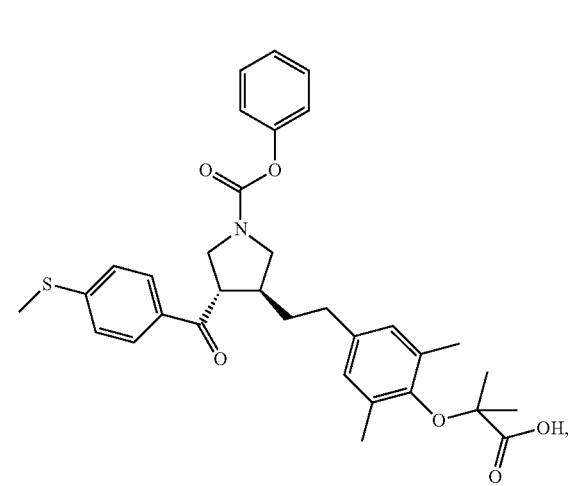
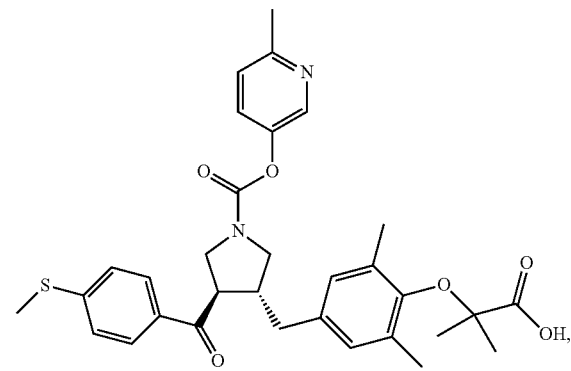

307
-continued
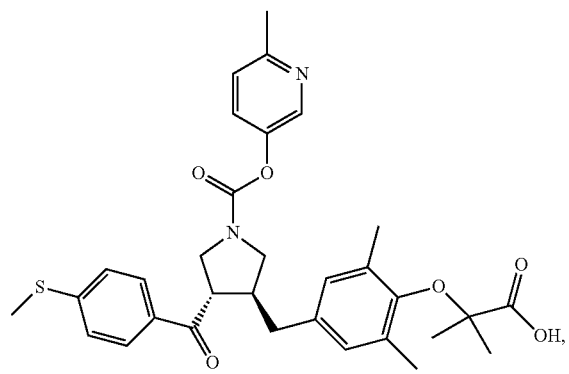
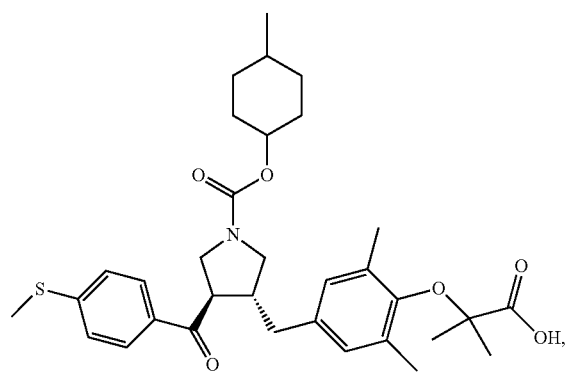
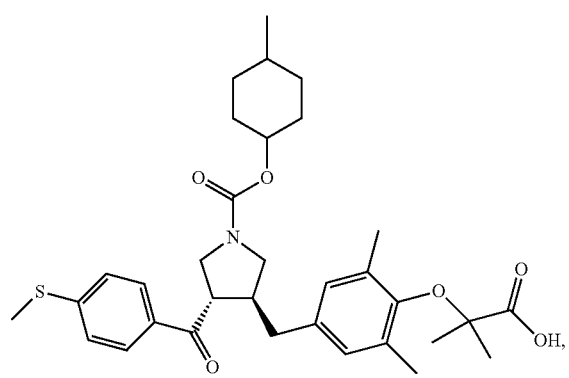
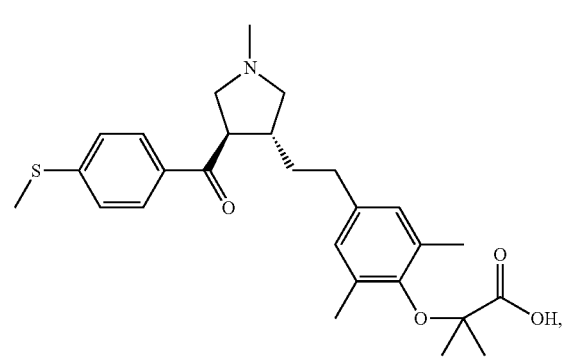
308
-continued
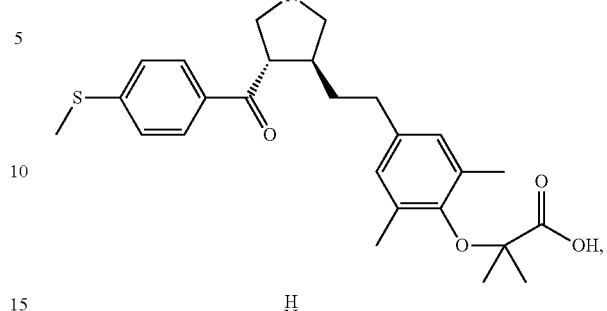
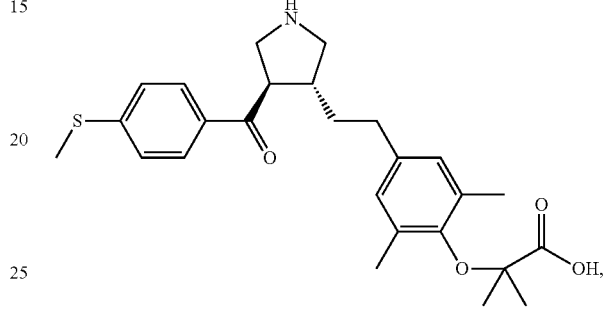
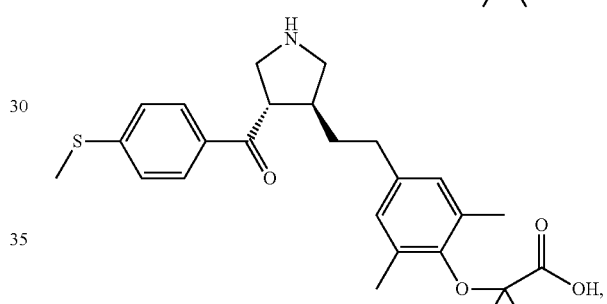
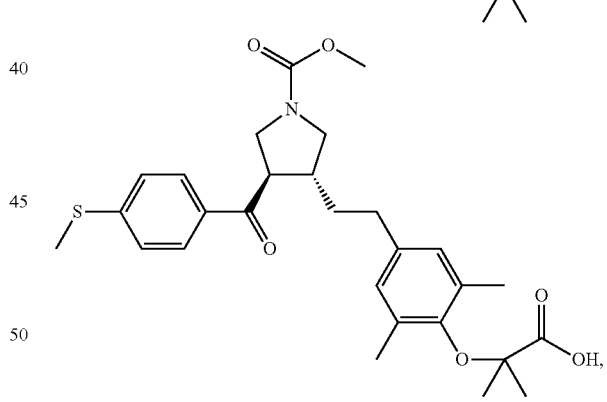
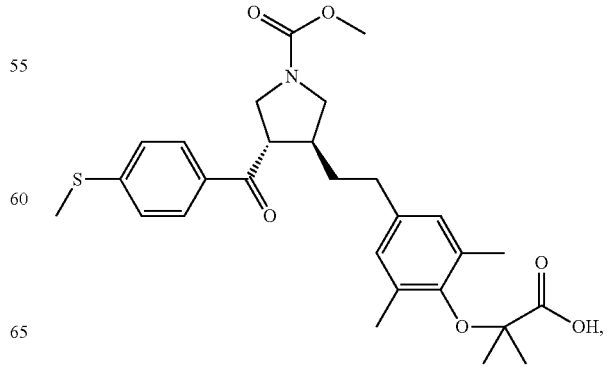

309
-continued
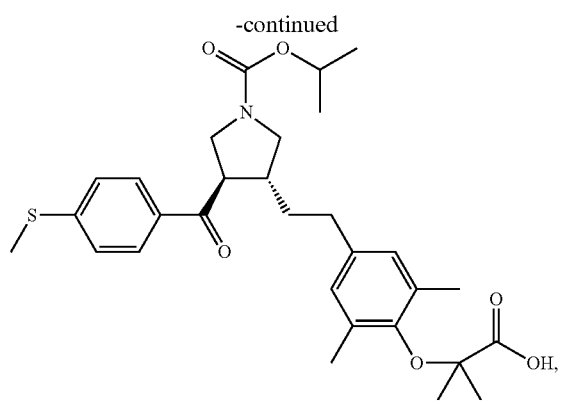
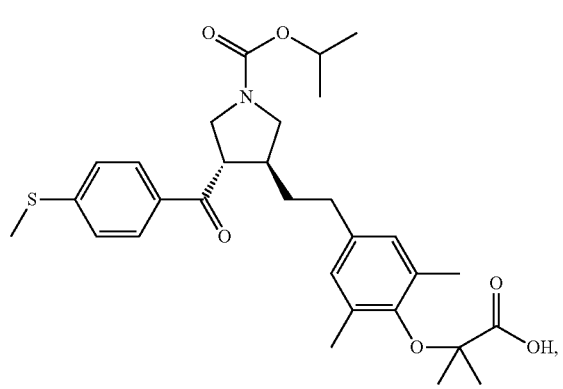
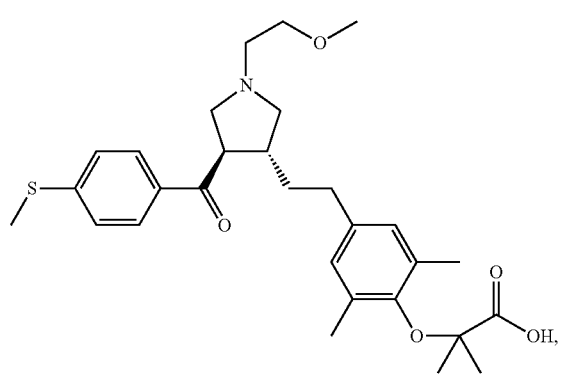
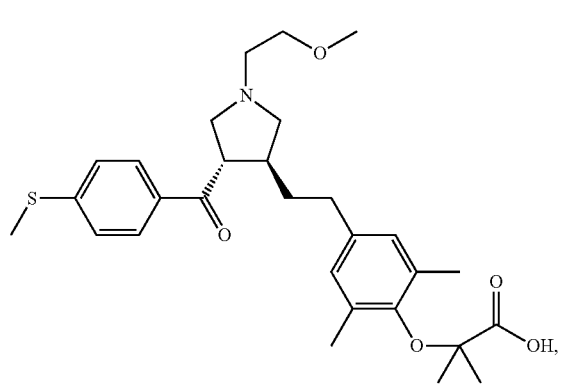
310
-continued
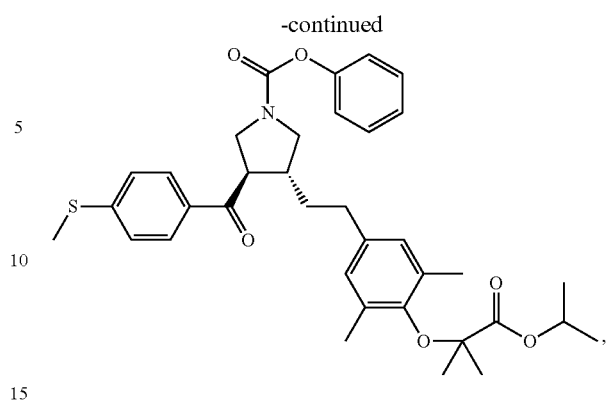
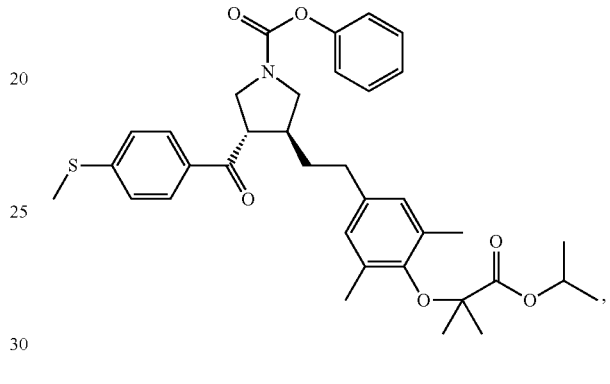
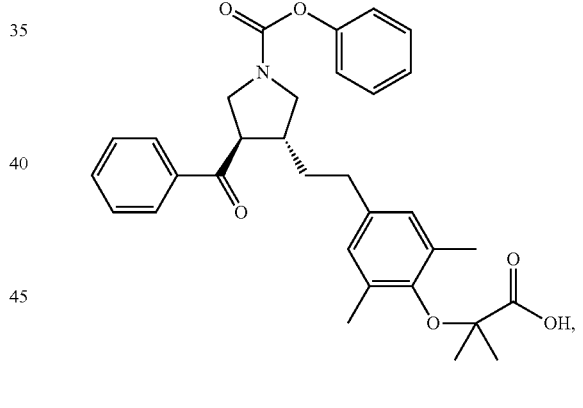
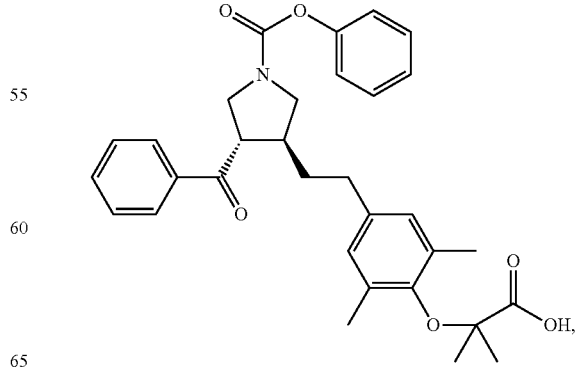

311
-continued
312
-continued
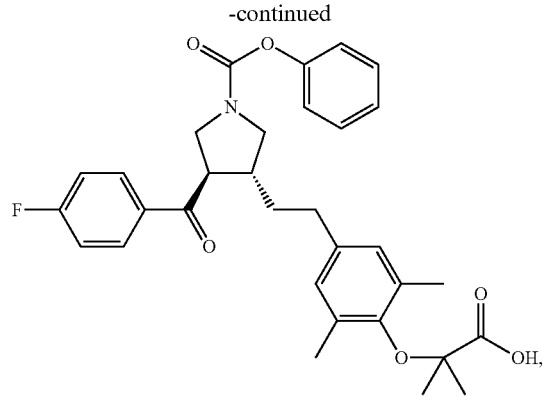
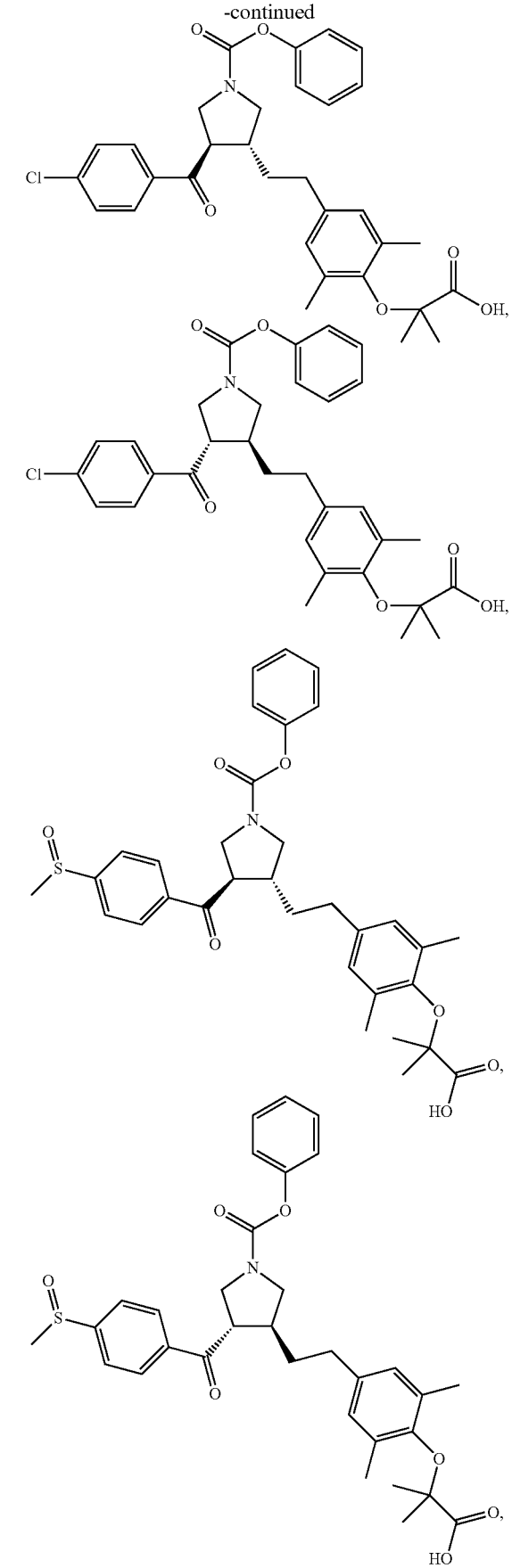

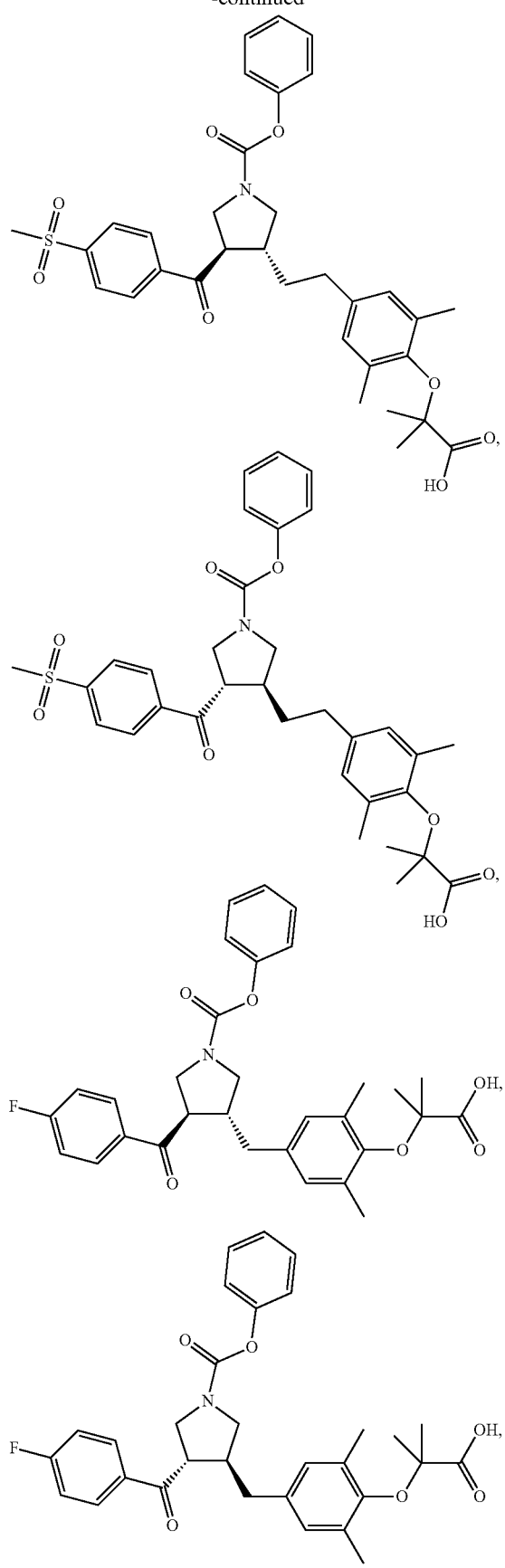

315
-continued
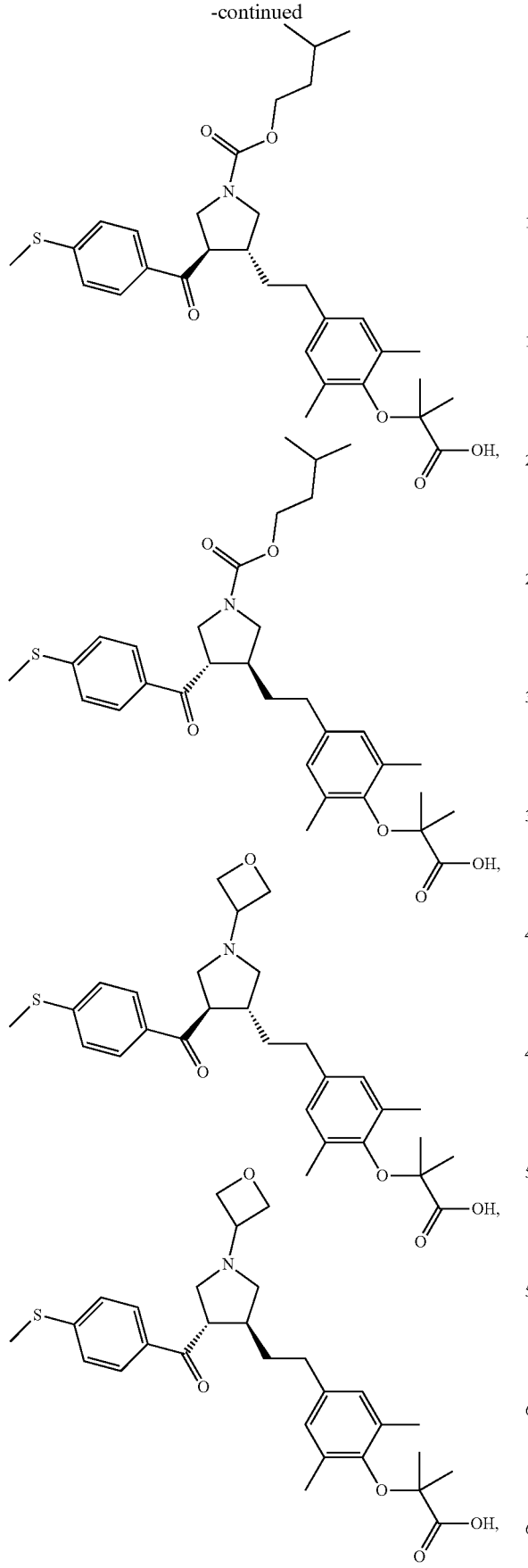
316
-continued
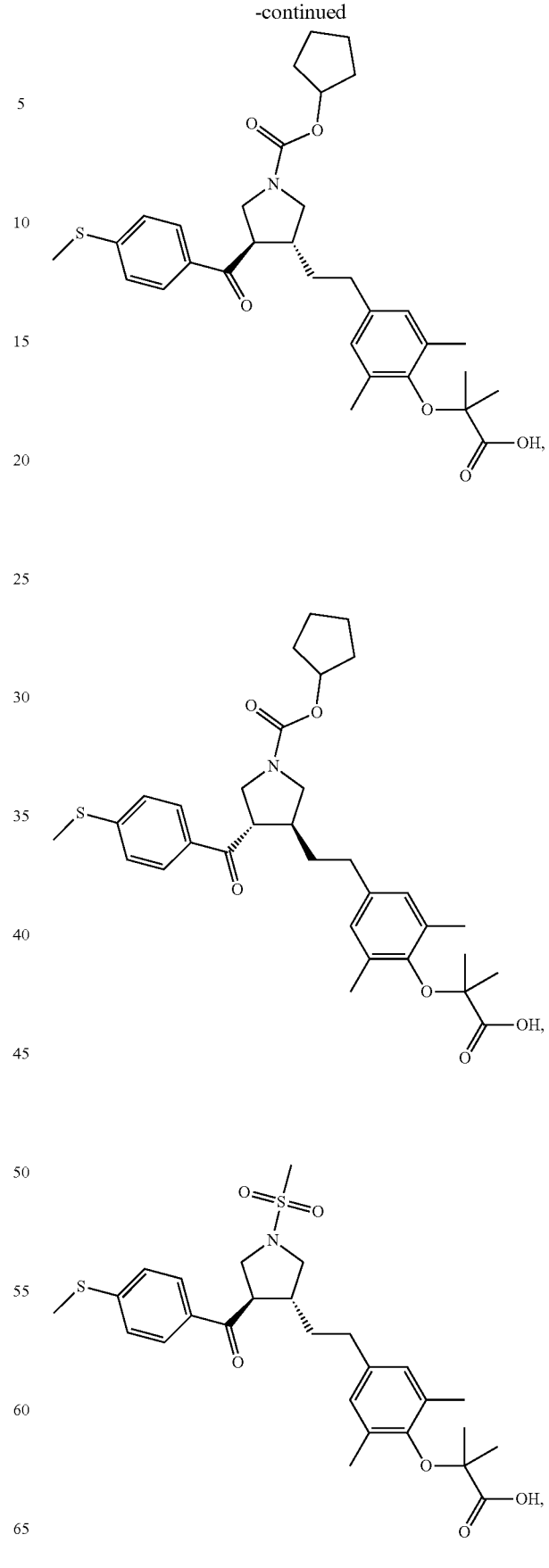

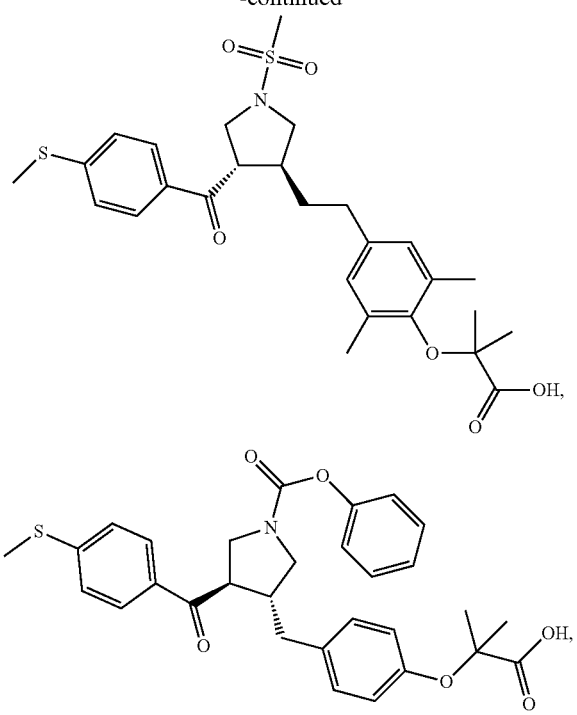
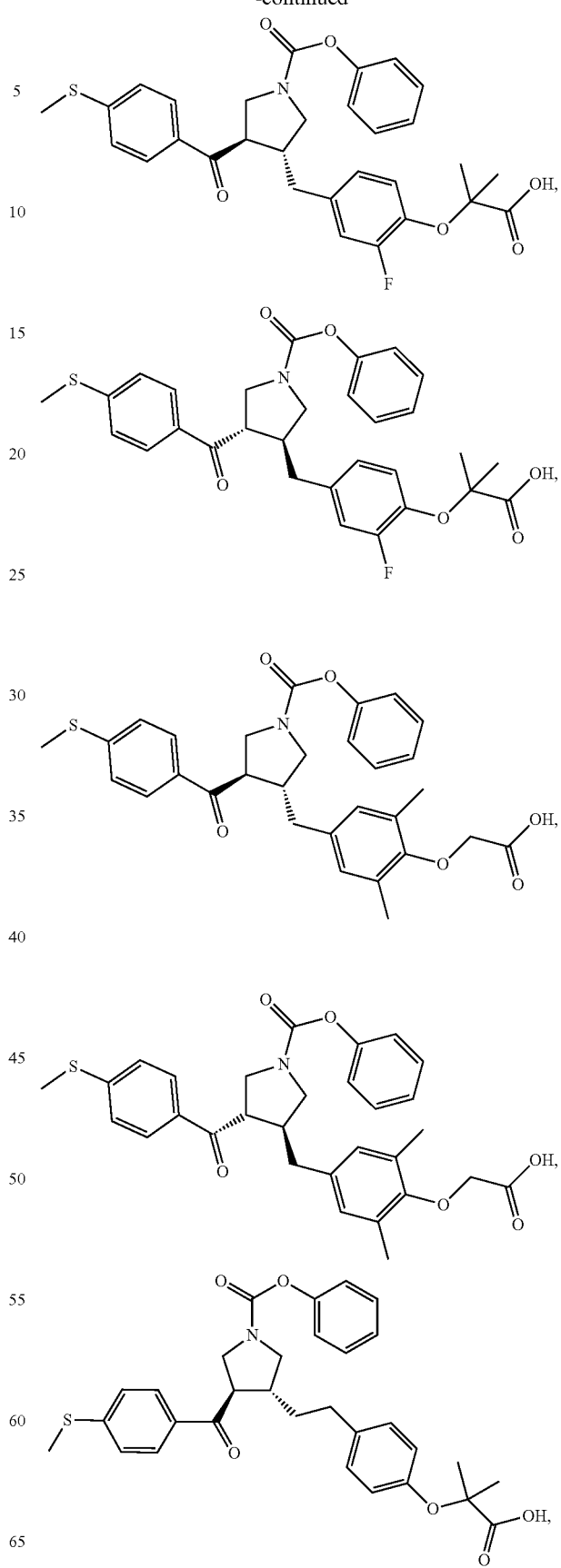

-continued

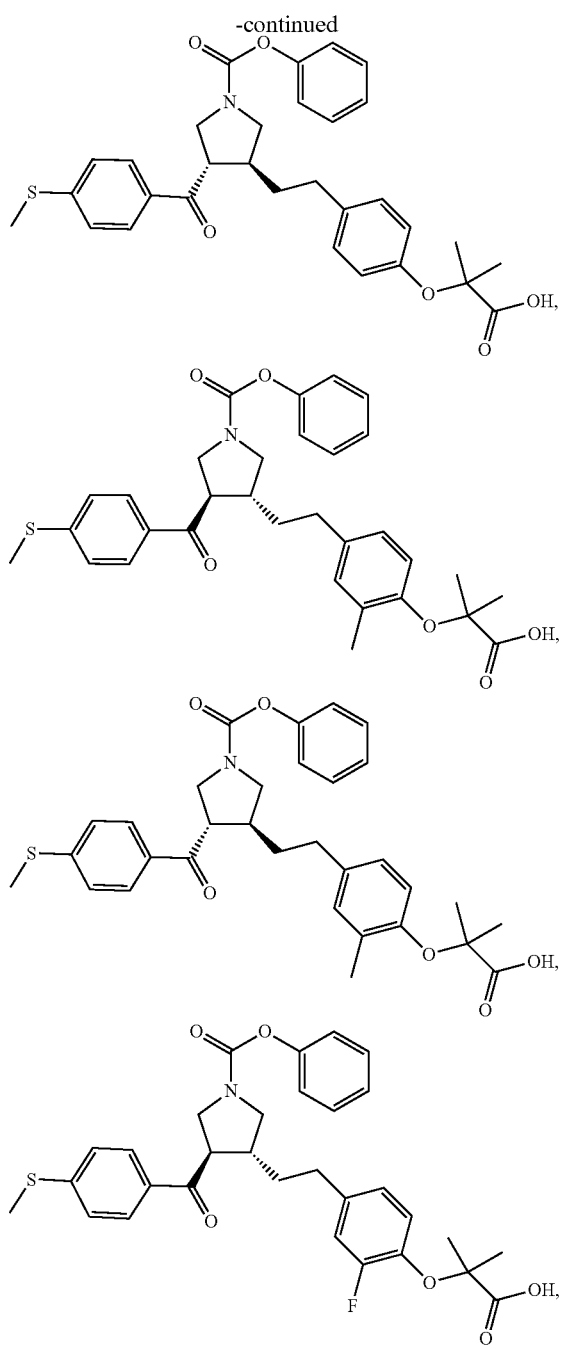

-continued

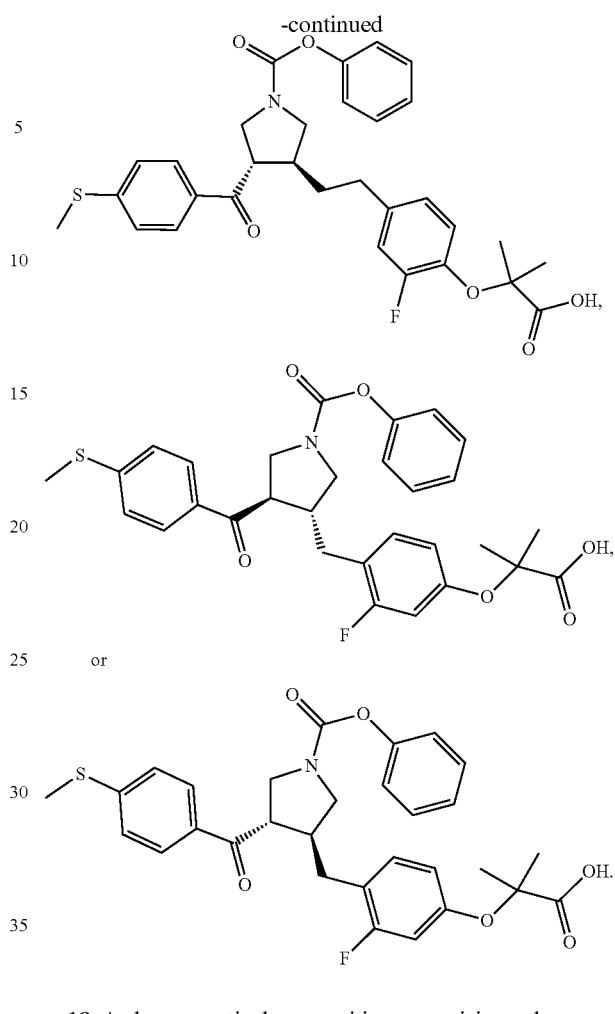

or

18. A pharmaceutical composition comprising a therapeutically effective amount of the compound of claim 1 or a pharmaceutically acceptable salt thereof as an active ingredient, as well as a pharmaceutically acceptable carrier.

19. A method of treating a PPAR receptor-associated disorder, comprising administrating a compound of claim 1, or a pharmaceutically acceptable salt thereof to a subject.

20. The method according to claim 19, wherein the disorder is selected from nonalcoholic steatohepatitis and concurrent fibrosis, insulin resistance, primary biliary cholangitis, dyslipidemia, hyperlipidemia, hypercholesterolemia, atherosclerosis, hypertriglyceridemia, cardiovascular disease, or obesity.

* * * * *

UNITED STATES PATENT AND TRADEMARK OFFICE
CERTIFICATE OF CORRECTION

Page 1 of 4

PATENT NO. : 10,526,320 B2
APPLICATION NO. : 16/317510
DATED : January 7, 2020
INVENTOR(S) : Zhiliang Yuan et al.

It is certified that error appears in the above-identified patent and that said Letters Patent is hereby corrected as shown below:

In the Claims

Column 270, the formula beginning at Line 45-50 reading - 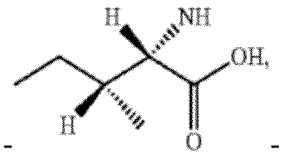 -

Should be read as -- 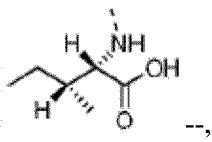 --,

Column 278, the formula beginning at Line 45 reading - 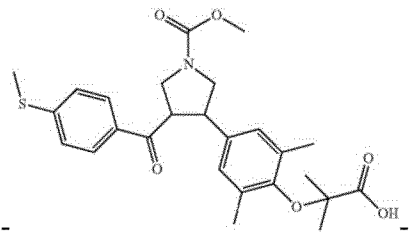 -

Should be read as -- 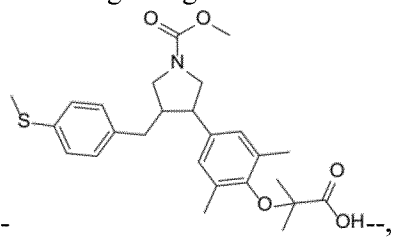 --,

Signed and Sealed this
Fifth Day of July, 2022

Katherine Kelly Vidal

Katherine Kelly Vidal
*Director of the United States Patent and Trademark Office*

Column 279, the formula beginning at Line 5 reading - 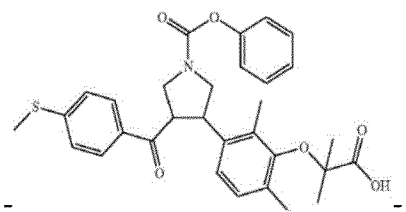
Should be read as -- 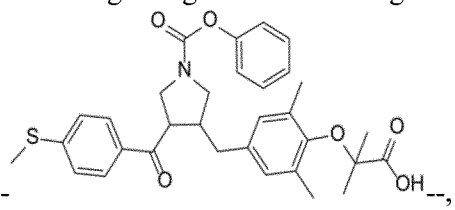 --,
Column 279, the formula beginning at Line 55-65 reading - 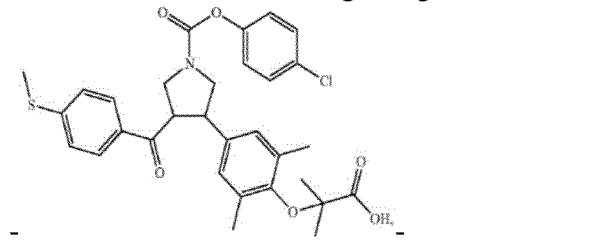 -
Should be read as -- 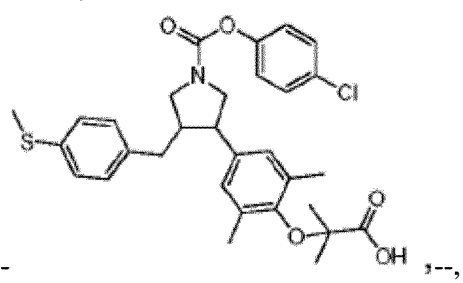 ,--,
Column 280, the formula beginning at Line 25 reading - 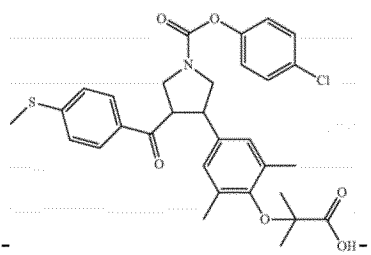
Should be read as -- 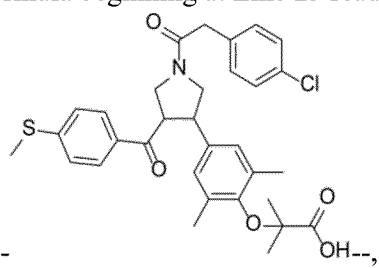 --,

CERTIFICATE OF CORRECTION (continued)
U.S. Pat. No. 10,526,320 B2

Column 285, the formula beginning at Line 5 reading - 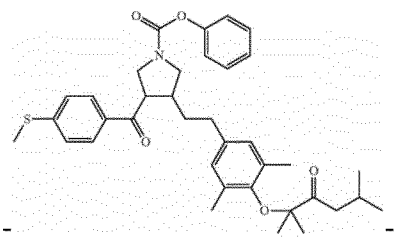

Should be read as -- 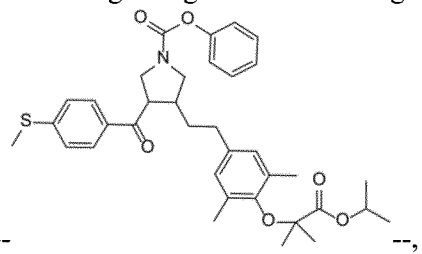 --,

Column 296, the formula beginning at Line 45 reading - 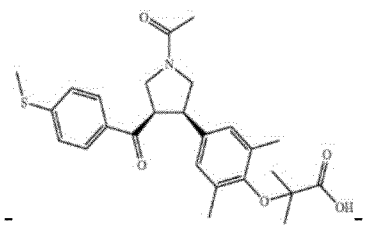

Should be read as -- 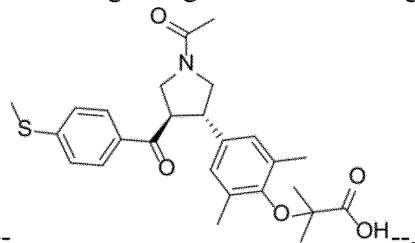 --,

Column 297, the formula beginning at Line 35 reading - 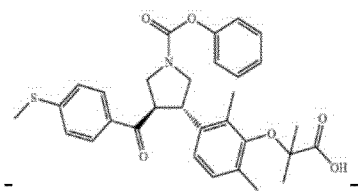

Should be read as -- 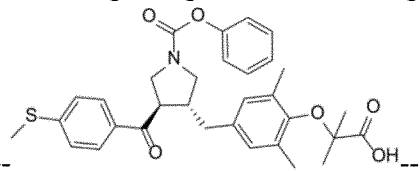 --,

Column 318, the formula beginning at Line 40-55 reading - 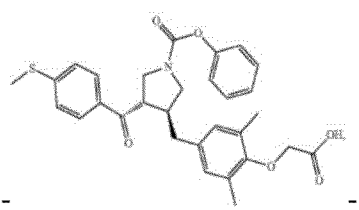 -

CERTIFICATE OF CORRECTION (continued)
U.S. Pat. No. 10,526,320 B2

Should be read as -- 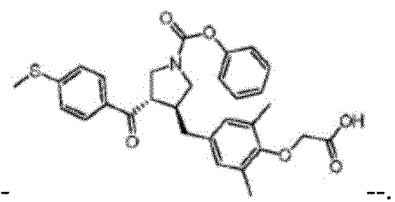 --.